United States Patent
Ledbetter et al.

(10) Patent No.: US 12,180,521 B2
(45) Date of Patent: Dec. 31, 2024

(54) PARAOXONASE FUSION POLYPEPTIDES AND RELATED COMPOSITIONS AND METHODS

(71) Applicant: Theripion, Inc., Shoreline, WA (US)

(72) Inventors: Jeffrey A. Ledbetter, Shoreline, WA (US); Martha S. Hayden-Ledbetter, Shoreline, WA (US)

(73) Assignee: Theripion, Inc., Shoreline, WA (US)

( * ) Notice: Subject to any disclaimer, the term of this patent is extended or adjusted under 35 U.S.C. 154(b) by 0 days.

(21) Appl. No.: 18/546,413

(22) PCT Filed: Feb. 17, 2022

(86) PCT No.: PCT/US2022/016723
§ 371 (c)(1),
(2) Date: Aug. 14, 2023

(87) PCT Pub. No.: WO2022/178078
PCT Pub. Date: Aug. 25, 2022

(65) Prior Publication Data
US 2024/0101982 A1  Mar. 28, 2024

Related U.S. Application Data

(60) Provisional application No. 63/151,236, filed on Feb. 19, 2021, provisional application No. 63/151,272, filed on Feb. 19, 2021.

(51) Int. Cl.
| | |
|---|---|
| *C12N 9/22* | (2006.01) |
| *A61P 11/00* | (2006.01) |
| *C07K 16/24* | (2006.01) |
| *C12N 9/16* | (2006.01) |
| *A61K 38/00* | (2006.01) |

(52) U.S. Cl.
CPC ............. *C12N 9/22* (2013.01); *A61P 11/00* (2018.01); *C07K 16/241* (2013.01); *C12N 9/16* (2013.01); *C12Y 301/08001* (2013.01); *A61K 38/00* (2013.01); *C07K 2317/31* (2013.01); *C07K 2317/622* (2013.01); *C07K 2319/01* (2013.01); *C07K 2319/30* (2013.01); *C12Y 301/21001* (2013.01)

(58) Field of Classification Search
CPC .. C12N 9/22; C12N 9/16; A61P 11/00; C07K 16/241; C07K 2317/31; C07K 2317/622; C07K 2319/01; C07K 2319/30; C07K 2319/00; C12Y 301/08001; C12Y 301/21001; C12Y 308/01; C12Y 301/01; A61K 38/00
See application file for complete search history.

(56) References Cited

U.S. PATENT DOCUMENTS

| | | | |
|---|---|---|---|
| 8,735,124 B2 | 5/2014 | Tawfik | |
| 2003/0092059 A1* | 5/2003 | Salfeld | A61P 29/00 435/7.1 |
| 2003/0118592 A1* | 6/2003 | Ledbetter | A61K 39/001124 530/391.1 |
| 2010/0098693 A1 | 4/2010 | Pardridge | |
| 2012/0213834 A1* | 8/2012 | Tawfik | C12N 9/16 435/320.1 |
| 2014/0120091 A1* | 5/2014 | Ledbetter | C07K 14/70578 435/69.6 |
| 2018/0201664 A1 | 7/2018 | Hayden-Ledbetter | |
| 2019/0241878 A1* | 8/2019 | Posada | A61P 1/16 |

FOREIGN PATENT DOCUMENTS

| | | | | |
|---|---|---|---|---|
| WO | WO-2011084714 A2 * | 7/2011 | ........... | C07K 16/241 |
| WO | 2014115084 A2 | 7/2014 | | |
| WO | WO-2018136163 A2 * | 7/2018 | ........... | C07K 14/775 |

OTHER PUBLICATIONS

Gaidukov, L., et al., "High Affinity, Stability, and Lactonase Activity of Serum Paraoxonase PON1 Anchored on HDL with ApoA-I," Biochemistry 2005, 44: 11843-11854.
Chen, W.-Q., et al., "Influences of PON1 on airway inflammation and remodeling in bronchial asthma," J. Cell. Biochem. 119:793-805, 2018.
Dahl, M., et al., "Protection against inhaled oxidants through scavenging of oxidized lipids by macrophage receptors MARCO and SR-AI/II," J. Clin. Invest. 117:757-764, 2007, DOI:10.1172/JCI29968.
Emin, O., et al., "Plasma paraoxonase, oxidative status level, and their relationship with asthma control test in children with asthma," Allergol. Immunopathol. (Madr). 43:346-352, 2015.

(Continued)

*Primary Examiner* — Nelson B Moseley, II
*Assistant Examiner* — Alyssa Rae Stonebraker
(74) *Attorney, Agent, or Firm* — CHRISTENSEN O'CONNOR JOHNSON KINDNESS PLLC

(57) ABSTRACT

Compositions and methods relating to paraoxonase fusion polypeptides are disclosed. In some aspects, the fusions are bispecific molecules that include a first biologically active polypeptide linked amino-terminal to a biologically active paraoxonase, wherein the first biologically active polypeptide is a DNase, an RNase, a SOD1, a CTLA-4 extracellular domain, a CD40 extracellular domain, or a polypeptide that specifically binds and neutralizes an inflammatory cytokine. Bispecific fusions may further include a second biologically active polypeptide (e.g., a dimerizing or FcRn-binding domain) linked carboxyl-terminal to the first biologically active polypeptide and amino-terminal to the paraoxonase. In other aspects, a fusion polypeptide includes a biologically active paraoxonase linked carboxyl-terminal or amino-terminal to a dimerizing or FcRn-binding domain. Also disclosed are dimeric proteins comprising first and second paraoxonase fusion polypeptides as disclosed herein. The fusion polypeptides and dimeric proteins are useful in methods for therapy.

22 Claims, 19 Drawing Sheets
Specification includes a Sequence Listing.

(56) References Cited

OTHER PUBLICATIONS

Fellner, R.C., et al., "Inhaled protein/peptide-based therapies for respiratory disease," Mol. Cell. Pediatr. 3:16, pp. 1-5, 2016, DOI:10.1186/s40348-016-0044-8.
Fessler, M.B., et al., "A New Frontier in Immunometabolism: Cholesterol in Lung Health and Disease," Ann. Am. Thorac. Soc. 14:S399-S405, Nov. 2017.
Gaidudkov, L., et al., "In vivo administration of BL-3050: highly stable engineered PON1-HDL complexes," BMC Clin. Pharmacol. 9:18, Nov. 17, 2009, DOI:10.1186/1472-6904-9-18.
Gallego, M., et al., "Pseudomonas aeruginosa isolates in severe chronic obstructive pulmonary disease: characterization and risk factors," BMC Pulm. Med. 14:103, pp. 1-12, 2014.
Golmanesh, L., et al., "Simple procedures for purification and stabilization of human serum paraoxonase-1," J. Biochem. Biophys. Methods 70, 1037-1042, 2008.
Golmanesh, L., et al., "Assessing the relationship of paraoxonase-1 Q192R polymorphisms and the severity of lung disease in SM-exposed patients," Immunopharmacol. Immunotoxicol. 35:419-425, 2013.
Gu, X., et al., "Identification of critical paraoxonase 1 residues involved in high density lipoprotein interaction," J. Biol. Chem. Manuscript M115.678334, Nov. 13, 2015.
Gupta, R.D., et al., "Directed evolution of hydrolases for prevention of G-type nerve agent intoxication," Nat. Chem. Biol. 7:120-125, Jan. 9, 2010, DOI:10.1038/NCHEMBIO.510.
Harel, M., et al., "Structure and evolution of the serum paraoxonase family of detoxifying and anti-atherosclerotic enzymes," Nat. Struct. Mol. Biol. 11:412-419, May 2004.
Hraiech, S., et al., "Inhaled Lactonase Reduces Pseudomonas aeruginosa Quorum Sensing and Mortality in Rat Pneumonia," 9:e107125, pp. 1-8, Oct. 2014.
Huang, Y., et al., "Myeloperoxidase, paraoxonase-1, and HDL form a functional ternary complex," J. Clin. Invest. 123:3815-3828, Sep. 2013.
Ivanisevic, J., et al., "Association of serum amyloid A and oxidative stress with paraoxonase 1 in sarcoidosis patients," Eur. J. Clin. Invest. 46:418-424, 2016.
Litvinov, D., et al., "Antioxidant and Anti Inflammatory Role of Paraoxonase 1: Implication in Arteriosclerosis Diseases," N. Am. J. Med. Sci. 4:523-532, Nov. 2012.
Mulcahy, L.R., et al., "Pseudomonas aeruginosa biofilms in disease," Microb. Ecol. 68:1-12, Jul. 2014, DOI:10.1007/s00248-013-0297-x.
Murugayah, S.A., and Gerth, M.L., "Engineering quorum quenching enzymes: progress and perspectives" Biochem. Soc. Trans. 47:793-800, 2019.
Okur, H.K., et al., "Lipid peroxidation and paraoxonase activity in nocturnal cyclic and sustained intermittent hypoxia," Sleep Breath. 17:365-371, 2013, DOI:10.1007/s11325-012-0703-5.
Rahman, I., et al., "Antioxidant therapies in COPD," Int. J. Chron. Obstruct. Pulmon. Dis. 1(1):15-29, 2006.
Rahman, I., et al., "Pharmacological Antioxidant Strategies as Therapeutic Interventions for COPD," Biochim. Biophys. Acta 1822:714-728, May 2012.
Rajkovic, M.G., "PON1 gene polymorphisms in patients with chronic obstructive pulmonary disease," J. Clin. Pathol. 71:963-970, 2018, DOI:10.1136/jclinpath-2018-205194 963.
Rosenblat, M., et al., "Paraoxonase 1 (PON1) inhibits monocyte-to-macrophage differentiation," Atherosclerosis 219:49-56, 2011.
Rumora, L., et al., "Paraoxonase 1 Activity in Patients with Chronic Obstructive Pulmonary Disease," COPD, 11:539-545, 2014.
Sahiner, U.M., et al., "Oxidative Stress in Asthma," World Allergy Organ. J. 4:151-158, 2011.
Sarioglu, N., et al., "Paraoxonase 1 Phenotype and Paraoxonase Activity in Asthmatic Patients," Iran J. Allergy Asthma Immunol. 14:60-66, Feb. 2015.
Szczeklik, K., et al., "Correlation of Paraoxonase-1 with the Severity of Crohn's Disease," Molecules 23:2603, pp. 1-15, 2018.
Tang, K., et al., "MomL, a Novel Marine-Derived N-Acyl Homoserine Lactonase from Muricauda olearia," Appl. Environ. Microbiol. 81:774-782, Jan. 2015.
Tolgyesi, G., et al., "Gene expression profiling of experimental asthma reveals a possible role of paraoxonase-1 in the disease," Int. Immunol. 21:967-975, Jun. 25, 2009.
Uzun, H., et al., "Levels of paraoxonase, an index of antioxidant defense, in patients with active sarcoidosis," Curr. Med. Res. Opin. 24:1651-1657, 2008.
Valiyaveettil, M., et al., "Protective efficacy of catalytic bioscavenger, paraoxonase 1 against sarin and soman exposure in guinea pigs," Biochem. Pharmacol. 81:800-809, 2011.
Valiyaveettil, M., et al., "Recombinant paraoxonase 1 protects against sarin and soman toxicity following microinstillation inhalation exposure in guinea pigs," Toxicol. Lett. 202:203-208, 2011.
Adawi, A., et al., "Disruption of the CD40-CD40 Ligand System Prevents an Oxygen-Induced Respiratory Distress Syndrome," Am. J. Pathol. 152:651-657, Mar. 1998.
Adawi, A., et al., "Blockade of CD40-CD40 Ligand Interactions Protects against Radiation-Induced Pulmonary Inflammation and Fibrosis," Clin. Immunol. Immunopathol. 89:222-230, Dec. 1998.
Aybey, A., and Demirkan, E., "Inhibition of quorum sensing-controlled virulence factors in Pseudomonas aeruginosa by human serum paraoxonase," J. Med. Microbiol. 65:105-113, 2016.
Billecke, S., et al., Human Serum Paraoxonase (PON1) Isozymes Q and R Hydrolyze Lactones and Cyclic Carbonate Esters, Drug Metab. Dispos. 28:1335-1342, 2000.
Boleto, G., et al., "T-cell costimulation blockade is effective in experimental digestive and lung tissue fibrosis," Arthritis Res. Ther. 20:197, pp. 1-12, 2018.
Carreno, B.M., et al., "CTLA-4 (CD152) Can Inhibit T Cell Activation by Two Different Mechanisms Depending on Its Level of Cell Surface Expression," J. Immunol. 165:1352-1356, 2000.
Cheng, W., et al., "CXXC5 Attenuates Pulmonary Fibrosis in a Bleomycin-Induced Mouse Model and MLFs by Suppression of the CD40/CD40L Pathway," BioMed. Res. Int., vol. 2020, Article ID 7840652, pp. 1-15, 2020.
Gaidukov, L., and Tawfik, D.S., "The development of human sera tests for HDL-bound serum PON1 and its lipolactonase activity," J. Lipid Res. 48:1637-1646, 2007.
Kaufman, J., et al., "Expression of CD154 (CD40 Ligand) by Human Lung Fibroblasts: Differential Regulation by IFN-gamma and IL-13, and Implications for Fibrosis," J. Immunol. 172:1862-1871, 2004.
Kheronsky, O., and Tawfik, D.S., "Structure-Reactivity Studies of Serum Paraoxonase PON1 Suggest that Its Native Activity Is Lactonase," Biochem. 44:6371-6382, 2005.
Linsley, P.S., et al., "CTLA-4 Is a Second Receptor for the B Cell Activation Antigen B7," J. Exp. Med. 174:561-569, Sep. 1991.
Liu, Z., et al., "Prevention of Experimental Colitis in SCID Mice Reconstituted with CD45RBhigh CD4+ T Cells by Blocking the CD40-CD154 Interactions," J. Immunol. 164:6005-6014, 2000.
Martinez-Solano, L., et al., "Chronic Pseudomonas aeruginosa Infection in Chronic Obstructive Pulmonary Disease," Clin. Infect. Dis. 47:1526-1533, 2008.
Mayer-Hamblett, N., et al., "Pseudomonas aeruginosa Phenotypes Associated With Eradication Failure in Children With Cystic Fibrosis," Clin. Infect. Dis. 59:624-631, 2014.
Miller, Y.I., et al., "Context-dependent role of oxidized lipids and lipoproteins in inflammation," Trends Endocrinol. Metab. 28:143-152, Feb. 2017, DOI:10.1016/j.tem.2016.11.002.
Nolan, A., et al., "CD40 and CD80/86 Act Synergistically to Regulate Inflammation and Mortality in Polymicrobial Sepsis," Am. J. Respir. Crit. Care Med. 177:301-308, 2008.
Oran, M., et al., "Evaluation of Paraoxonase and Arylesterase activities in patients with irritable bowel syndrome," J. Pak. Med. Assoc. 64:820-822, Jul. 2014.
Ponsoye, M., et al., "Treatment with abatacept prevents experimental dermal fibrosis and induces regression of established inflammation-driven fibrosis," Ann. Rheum. Dis. 75:2142-2149, 2016.
International Search Report & Written Opinion mailed Sep. 29, 2022, issued in corresponding International Application No. PCT/US2022/016723, filed Feb. 17, 2022, 20 pages.

(56) References Cited

OTHER PUBLICATIONS

Aharoni, A., et al., "Directed evolution of mammalian paraoxonases PON1 and PON3 for bacterial expression and catalytic specialization," Proc. Natl. Acad. Sci. USA 101:482-487, Jan. 13, 2004, DOI:10.1073/pnas.2536901100.

Goldsmith, M., et al., "Evolved Stereoselective Hydrolases for Broad-Spectrum G-Type Nerve Agent Detoxification," Chemistry & Biology 19:456-466, Apr. 20, 2012.

Harel, M., et al., "3-D Structure of Serum Paraoxonase 1 Sheds Light On Its Activity, Stability, Solubility and Crystallizability," Arh. Hig. Rada. Toksikol. 58:347-353, 2007.

Sarkar, M., et al., "Solubilization and Humanization of Paraoxonase-1," J. Lipids, vol. 2012, Article ID Article ID 610937, pp. 1-13, 2012, DOI:10.1155/2012/610937.

Shiokawa, D., et al., "Identification of two functional nuclear localization signals in DNase γ and their roles in its apoptotic DNase activity," Biochem. J. 376:377-381, 2003.

Zharkova, O., et al., "A Flow Cytometry-Based Assay for High-Throughput Detection and Quantification of Neutrophil Extracellular Traps in Mixed Cell Populations," Cytometry Part A 95A:268-278, 2019.

Sorenson, R.C., et al., "Human Serum Paraoxonase/Arylesterase's Retained Hydrophobic N-Terminal Leader Sequence Associates with HDLs by Binding Phospholipids—Apolipoprotein A-I Stabilizes Activity," Arterioscler. Thromb. Vasc. Biol. 19:2214-2225, 1999.

Stoltz, D.A., et al., "*Drosophila* are protected from Pseudomonas aeruginosa lethality by transgenic expression of paraoxonase-1," J. Clin. Invest. 118:3123-3131, Sep. 2008.

Bacchetti, T., et al., "Plasma oxidation status and antioxidant capacity in psoriatic children," Arch. Dermatol. Res. 312:33-39, 2020.

Shakoei, S., et al., "The Serum Level of Oxidative Stress and Antioxidant Markers in Patients with Psoriasis: A Cross-sectional Study," J. Clin. Aesthet. Dermatol. 14:38-41, 2021.

Simonetti, O., et al., "Oxidative Stress and Alterations of Paraoxonases in Atopic Dermatitis," Antioxidants 10:697, pp. 1-11, 2021.

Boado, R.J., et al., "IgG-Paraoxonase-1 Fusion Protein for Targeted Drug Delivery Across the Human Blood-Brain Barrier," Mol. Pharm. 5:1037-1043, 2008.

Lee, S.J., et al., "PEP-1-paraoxonase 1 fusion protein prevents cytokine-induced cell destruction and impaired insulin secretion in rat insulinoma cells," BMB Rep. 51:538-543, 2018.

Kim, D.S., et al. "Pharmacogenetics of paraoxonase activity: elucidating the role of high-density lipoprotein in disease," Pharmacogenomics Author Manuscript; available in PMC Jul. 1, 2014; published in final edited form as Pharmacogenomics 14:1495-1515, Sep. 2013.

Stevens, R.C., et al., "Engineered recombinants human paraoxonase 1 (rHuPON1) purified from *Escherichia coli* protects against organophosphate poisoning," Proc. Natl. Acad. Sci. USA 105:12780-12784, Sep. 2, 2008.

Eren, E., et al., "Functionally Defective High-Density Lipoprotein and Paraoxonase: A Couple for Endothelial Dysfunction in Atherosclerosis," Cholesterol, vol. 2013, Article ID 792090, 2013 DOI:10.1155/2013/792090.

Kim, M.J., et al., "Transduced PEP-1-PON1 proteins regulate microglial activation and dopaminergic neuronal death in a Parkinson's disease model," Biomaterials 64:45-56, 2015, available online Jun. 14, 2015.

Koren-Gluzer, M., et al., "The antioxidant HDL-associated paraoxonase-1 (PON1) attenuates diabetes development and stimulates ß-cell insulin release," Atherosclerosis 219:510-518, 2011, available online Aug. 4, 2011, DOI:10.1016/j.atherosclerosis.2011.07.119.

Mackness, M., et al., "Human paraoxonase-1 (PON1): Gene structure and expression, promiscuous activities and multiple physiological roles," Gene 567:12-21, 2015, available online May 9, 2015, DOI:10.1016/j.gene.2015.04.088.

Menini, T., et al., "Paraoxonase 1 in neurological disorders," Redox Report, 19:49-58, 2014, DOI:10.1179/1351000213Y.0000000071.

Peng, W., et al., "Comparative evaluation of the protective potentials of human paraoxonase 1 and 3 against CCl4-induced liver injury," Toxicol. Lett. 193:159-166, 2010, available online Jan. 15, 2010, DOI:10.1016/j.toxlet.2010.01.003.

Rosenblat, M., et al., "Injection of paraoxonase 1 (PON1) to mice stimulates their HDL and macrophage antiatherogenicity," Biofactors 37:462-467, 2011, published online Dec. 8, 2011, DOI:10.1002/biof.188.

Ceron, J.J., et al., "Serum paraoxonase 1 (PON1) measurement: an update," BMC Vet. Res. 10:74, 2014, DOI: 10.1186/1746-6148-10-74.

Dias, C.G., et al., "Quantification of the arylesterase activity of paraoxonase-1 in human blood," Anal. Methods 6:289-294, 2014, DOI:10.1039/c3ay41527a.

Gugliucci, A., et al., "Enzymatic assessment of paraoxonase 1 activity on HDL subclasses: A practical zymogram method to assess HDL function," Clin. Chim. Acta 415:162-168, 2013; available online Oct. 30, 2012; DOI:10.1016/j.cca.2012.10.044.

Kirby, S.D., et al., "Human paraoxonase double mutants hydrolyze V and G class organophosphorus nerve agents," Chem. Biol. Interact. 203:181-185, 2013; available online Nov. 15, 2012; DOI:10.1016/j.cbi.2012.10.023.

Otto, T.C., et al., "Dramatic Differences in Organophosphorus Hydrolase Activity between Human and Chimeric Recombinant Mammalian Paraoxonase-1 Enzymes," Biochemistry 48:10416-10422, 2009, DOI:10.1021/bi901161b.

Yamashita, J., et al., Paraoxonase-1 Suppresses Experimental Colitis via the Inhibition of IFN-gamma Production from CD4 T Cells, J. Immunol. 191:949-960, 2013; prepublished Jun. 14, 2013; DOI:10.4049/jimmunol.1201828.

Bojic, S., et al., "Low Paraoxonase 1 Activity Predicts Mortality in Surgical Patients with Sepsis," Disease Markers, vol. 2014, Article ID 427378, pp. 1-8, Feb. 9, 2014, DOI:10.1155/2014/427378.

Inal, V., et al., "Paraoxonase 1 Activity and Survival in Sepsis Patients," Balkan Med. J. 32:183-8, Apr. 2015, DOI:10.5152/balkanmedj.2015.15674.

Boado, R.J., et al., "CHO Cell Expression, Long-Term Stability, and Primate Pharmacokinetics and Brain Uptake of an IgG-Paraoxonase-1 Fusion Protein," Biotechnol. Bioeng. 108:186-196, Jan. 1, 2011; published online Aug. 27, 2010, DOI:10.1002/bit.22907.

Wang, X., et al., "IgG Fc engineering to modulate antibody effector functions," Protein Cell 9:63-73, 2018, DOI:10.1007/s13238-017-0473-8.

Bitonti, A.J., et al., "Pulmonary delivery of an erythropoietin Fc fusion protein in non-human primates through an immunoglobulin transport pathway," Proc. Natl. Acad. Sci. USA 101:9763-9768, Jun. 29, 2004.

Bitonti, A.J., et al., "Pulmonary administration of therapeutic proteins using an immunoglobulin transport pathway," Adv. Drug Deliv. Rev. 58:1106-1118, 2006.

Hajri, T., "Effects of oxidized lipids and lipoproteins on cardiac function," Front. Biosci. (Landmark Ed) 23:1822-1847, Jun. 1, 2018.

Hertel, S.P., et al., "Protein stability in pulmonary drug delivery via nebulization," Adv. Drug Deliv. Rev. 93:79-94, 2015, available online Oct. 12, 2014.

Lo, M., et al., "Effector-attenuating Substitutions That Maintain Antibody Stability and Reduce Toxicity in Mice," J. Biol. Chem. 292:3900-3908, Mar. 3, 2017.

Moldogazieva, N.T., et al., "Oxidative Stress and Advanced Lipoxidation and Glycation End Products (ALEs and AGEs) in Aging and Age-Related Diseases," Oxid. Med. Cell. Longev., vol. 2019, Article ID 3085756, Aug. 14, 2019.

Padlan, E.A., "Anatomy of the Antibody Molecule," Mol. Immunol. 31:169-217, 1994.

Tam, S.H., et al., "Functional, Biophysical, and Structural Characterization of Human IgG1 and IgG4 Fc Variants with Ablated Immune Functionality," Antibodies 6:12, 2017, DOI:10.3390/antib6030012.

(56) References Cited

OTHER PUBLICATIONS

Vallee, S., et al., "Pulmonary Administration of Interferon Beta-1a-Fc Fusion Protein in Non-Human Primates Using an Immunoglobulin Transport Pathway," J. Interferon Cytokine Res. 32:178-184, 2012, DOI:10.1089/jir.2011.0048.

Bajaj, P., et al., "Characterization of human paraoxonase 1 variants suggest that His residues at 115 and 134 positions are not always needed for the lactonase/arylesterase activities of the enzyme," Protein Sci. 22:1799-1807, 2013.

Bajaj, P., et al., "Expression and purification of biologically active recombinant human paraoxonase 1 from inclusion bodies of *Escherichia coli*," Protein Expr. Purif. 115:95-101, 2015.

Aalbers, F.S., and Fraaije, M.W., "Enzyme Fusions in Biocatalysis: Coupling Reactions by Pairing Enzymes," ChemBioChem 20:20-28, 2019, DOI:10.1002/cbic.201800394.

Aviram, M., et al., "Paraoxonase Inhibits High-density Lipoprotein Oxidation and Preserves its Functions: A Possible Peroxidative Role for Paraoxonase," J. Clin. Invest. 101:1581-1590, 1998.

Bajaj, P., et al., "Refolded Recombinant Human Paraoxonase 1 Variant Exhibits Prophylactic Activity Against Organophosphate Poisoning," Appl. Biochem. Biotechnol. 180:165-176, 2016.

Bergonzi, C., et al., "The quorum-quenching lactonase from Geobacillus caldoxylosilyticus: purification, characterization, crystallization and crystallographic analysis," Acta Cryst. F72:681-686, 2016.

Bergonzi, C., et al., "Structural and Biochemical Characterization of AaL, a Quorum Quenching Lactonase with Unusual Kinetic Properties," Nature 8:11262, 2018, DOI:10.1038/s41598-018-28988-5.

Chen, X., et al., "Fusion Protein Linkers: Property, Design and Functionality," Adv. Drug Deliv. Rev. 65:1357-1369, Oct. 15, 2013, DOI:10.1016/j.addr.2012.09.039.

Propst, S.M., et al., "Proinflammatory and Th2-Derived Cytokines Modulate CD40-Mediated Expression of Inflammatory Mediators in Airway Epithelia: Implications for the Role of Epithelial CD40 in Airway Inflammation," J. Immunol. 165:2214-2221, 2000.

Rothem, L., et al., "Paraoxonases are associated with intestinal inflammatory diseases and intracellularly localized to the endoplasmic reticulum," Free Radic. Biol. Med. 43:730-739, 2007.

Seo, D., et al., "The Paraoxonase Gene Family and Atherosclerosis," Curr. Atheroscler. Rep. 11:182-187, 2009.

Sime, P.J., et al., "Fibrosis of the Lung and Other Tissues: New Concepts in Pathogenesis and Treatment," Clin. Immunol. 99:308-319, Jun. 2001.

You, Y., et al., "Effect of N-acetylcysteine on the Murine Model of Colitis Induced by Dextran Sodium Sulfate Through Up-Regulating PON1 Activity," Dig. Dis. Sci. 54:1643-1650, 2009, DOI:10.1007/s10620-008-0563-9.

Zhang, Y., et al., "CD40 Engagement Up-Regulates Cyclooxygenase-2 Expression and Prostaglandin E2 Production in Human Lung Fibroblasts," J. Immunol. 160:1053-1057, 1990.

GenBank Accession No. MF101816.1, Synthetic construct long-acting recombinant human paraoxonase 1 (G4Fc-L2-rhPON1) gene, complete cds, submitted May 15, 2017.

GenBank Accession No. MF101815.1, Synthetic construct long-acting recombinant human paraoxonase 1 (G4Fc-L1-rhPON1) gene, complete cds, submitted May 15, 2017.

GenBank Accession No. MF101814.1, Synthetic construct long-acting recombinant human paraoxonase 1 (G2Fc-L2-rhPON1) gene, complete cds, submitted May 15, 2017.

GenBank Accession No. MF101813.1, Synthetic construct long-acting recombinant human paraoxonase 1 (G2Fc-L1-rhPON1) gene, complete cds, submitted May 15, 2017.

GenBank Accession No. MF101812.1, Synthetic construct long-acting recombinant human paraoxonase 1 (rhPON1) gene, complete cds, submitted May 15, 2017.

Sequence Listing submitted with International Application No. PCT/IB2014/058461, filed Jan. 22, 2014 (published Jul. 31, 2014, as International Publication No. WO 2014/115084 A2).

\* cited by examiner

PARAOXONASE FUSION POLYPEPTIDES AND RELATED COMPOSITIONS AND METHODS

CROSS-REFERENCE TO RELATED APPLICATIONS

This application is a national phase entry of International Application No. PCT/US2022/016723, filed Feb. 17, 2022, which claims the benefit of U.S. Provisional Application Nos. 63/151,236 and 63/151,272, filed Feb. 19, 2021. Each of the foregoing applications is incorporated by reference herein in its entirety.

REFERENCE TO SEQUENCE LISTING

The instant application contains a Sequence Listing which has been submitted in ASCII format via EFS-Web and is hereby incorporated by reference in its entirety. Said ASCII Copy, created on Feb. 16, 2022, is named "TRP_0410PC_20220216_Seq_Listing_ST25" and is 552,734 bytes in size.

BACKGROUND OF THE INVENTION

Lung Disease and Fibrosis

Air pollution, primarily caused by atmospheric ozone levels, is a global health problem that is projected to increase in the future (Zhang et al., *Front. Immunol.* 10:2518, 2019). Ozone is a strong oxidant and tropospheric (ground level) ozone causes lung inflammation and damage. Ozone pollution is also linked to vascular disease and neurological disease. (Zhang et al., supra).

Lung disease is already a significant health and economic burden world-wide. Lung diseases are the third leading cause of death in the United States. Including chronic obstructive pulmonary disease (COPD) and asthma, the cost is projected to be over 80 billion dollars per year by 2020 (Foster el al., *J. COPD* 3:2011-2018, 2006; Nurmagambetov el al., *Annals of Am. Thoracic Soc.*, Center for Disease Control and Prevention, 2017). Current therapies include nebulized steroids, anticholinergics, and bronchodilators for COPD and leukotriene modulators and long acting beta agonists for asthma. Humanized antibodies, given by subcutaneous or intravenous injection, are approved as add-on therapy for hard-to-control asthma patients; these antibodies deplete IgE (Omalizumab), inhibit IL-5 (Mepolizumab and Reslizumab), or deplete eosinophils (Benralizumab). There is a need for new targets and approaches for improved therapy of lung diseases.

Lung inflammation is associated with infiltration of neutrophils, eosinophils, macrophages, and lymphocytes into the lung lumen and tissues. Extracellular DNA derived from neutrophil extracellular traps (NETS) is present in the lungs in patients with asthma, cystic fibrosis, and COPD (Liu et al., *Chinese Med. Journal* 130:730-736, 2017; Twaddell et al., *CHEST* 156:774-782, 2019; Uddin et al., *Front. Immunol.* 10:47, 2019; Yamashita et al., *J. Immunol.* 191:949-960, 2013). In addition, eosinophils contribute to extracellular traps in patients with asthma (Dworski et al., *J. Allergy Clinical Immunol.* 127:1260-1266, 2011). The traps thicken lung mucus and contain inflammatory mediators including myeloperoxidase and neutrophil elastase that promote tissue damage (Uddin et al., supra). NET-associated myeloperoxidase and elastase are increased in the sputum and bronchioalveolar lavage of cystic fibrosis patients and correlate with lung disease severity (see generally Kahn et al., *Genes* 10:183, 2019). DNase1 can digest NETS and reduce the viscosity of mucus, allowing improved lung clearance (id.).

Extracellular DNA that can be digested with DNase1 was found to be essential for silica-induced lung fibrosis (see Benmerzoug et al., *Nature Comm.* 9:5226, 2018). Silica induces cell death and release of self-DNA in the alveolar space and induces the stimulator of interferon genes (STING) inflammatory pathway leading to fibrosis (id.).

*P. aeruginosa* Infections

*P. aeruginosa* is a ubiquitous Gram-negative rod that causes severe opportunistic infections in immunocompromised individuals, burn patients, and patients with lung diseases such as COPD and cystic fibrosis (CF) (see Mulcahy et al., *Microb. Ecol.* 68:1-12, 2014). It is particularly troublesome on medical surfaces such as ventilators and is among the most common nosocomial pathogens and a frequently isolated pathogen from patients with ventilator-associated pneumonia. Because it is a major pathogen in adults with cystic fibrosis (CF) and because it is associated with increased clinical deterioration, eradication of *P. aeruginosa* would have important implications for CF therapies and other *P. aeruginosa* infections. (See. e.g., Martinez-Solano et al., *Chronic Infect. Dis.* 47:1526-1533, 2008.; Meyer-Hamblett et al., *Clin Inf. Dis.* 59:624-631, 2014; Gallego et al., *BMC Pulmonary Med.* 14:103, 2014.)

Pulmonary failure, a consequence of persistent bacterial lung infections particularly with *P. aeruginosa*, accounts for 80% of deaths in CF patients. Infection with *P. aeruginosa* in CF increases the risk of early death by almost three-fold (see McColley et al., *Pediatric Pulmonology* 52:909-915, 2017). Despite intense research being focused on easing bacterial lung infections, there is still a need for additional approaches to effective treatment in the CF lung.

Quorum sensing (QS) is an important mechanism that assists in *P. aeruginosa* persistence in the CF lung and contributes significantly to its pathogenesis. QS is mediated by small molecules produced by the bacteria that allow the coordination of communitywide activities, particularly acyl homoserine lactones (or AHLs). Acyl homoserine lactones share a basic structure, consisting of a homoserine lactone ring (HSL) and an acyl chain which can vary in length and degree of saturation. The variant side chains give specificity to the QS mechanism, enabling bacteria to recognize and respond to their specific AHLs. Almost a quarter of the expressed *P. aeruginosa* proteome is controlled by QS. In *P. aeruginosa*, QS plays an essential role in the expression and regulation of numerous virulence factors. QS also plays an important role in the formation of biofilms. Biofilms essentially envelop the bacterial community in a matrix of polysaccharides, extracellular DNA, and proteins, protecting it from the host's immune responses and external antimicrobial agents like antibiotics, facilitating survival of the *P. aeruginosa*. (Mulcahy et al., supra.)

Paraoxonase 1 (PON1)

Paraoxonase 1 (PON1) is an antioxidant enzyme that inhibits oxidation of low-density lipoprotein (LDL) and preserves its function (Aviram et al., *J. Clin. Invest.* 101: 1581-1590, 1998). PON1 has multiple substrates, including organophosphates and acyl homoserine lactones, the quorum sensing molecules made by *Pseudomonas aeruginosa*. PON1 activity is important in protection from arteriosclerosis and ischemic stroke (Litvinov et al., *N. Am. J. Med. Sci.* 4:523-532, 2012). In addition, PON1 activity is reduced in patients with intestinal inflammation including those with irritable bowel syndrome (IBS) or inflammatory bowel disease (IBD) such as Crohn's disease (Oran et al., *J. Pak. Med. Assoc.* 64:820-822, 2014; Szczelkik et al., *Molecules*

23:2603, 2018; Rothem et al., *Free Rad. Biol. Med.* 43:730-739, 2007). Studies in a mouse model for colitis have demonstrated that treatment with N-acetyl cysteine stimulates upregulation of PON1, and that increased PON1 activity is associated with amelioration of colon damage (You et al., *Dig. Dis. Sci.* 54:1643-1650, 2009).

PON1 is also deficient in multiple lung diseases. There is strong evidence that PON1 is important in protection from lung inflammation, and that low PON1 activity is associated with lung diseases. Oxidative stress is an important factor in the pathogenesis of asthma (see Sahiner et al., *WAO Journal* 4:151-158, 2011), and the antioxidant activity of PON1 is impaired in asthma patients. In children with asthma, PON1 levels were significantly lower than controls ($p<0.001$) (Emin et al., *Allergol. Immunopathol.* (Madr) 43:346-352, 2014). Additional studies have reported that PON1 activity is significantly lower in asthma patients ($p<0.024$) (Sarioglu et al., *Iran J. Asthma Immunol.* 14:60-66, 2015). Another study showed that PON1 activity is lower in asthmatic patients during active disease, but PON1 activity increases during disease remission (Tolgyesi et al., *Internal. Immunol.* 21:967-975, 2009). This study also used gene profiling in an experimental mouse asthma model to identify PON1 down-regulation as a potential target for monitoring disease activity (see id.). In addition, a mouse asthma model showed that PON1 overexpression reduced airway inflammation and remodeling, and reduced inflammatory cytokines (Chen et al., *J. Cell Biochem.* 119:793-805, 2018).

Compared to controls, patients with COPD were found to have significantly lower PON1 activity and increased oxidative stress as evidenced by lower levels of reduced thiol groups (Rumora et al., *J. COPD* 11:539-545, 2014). Another study found a polymorphism at −108 C>T in the PON1 promoter was strongly associated with COPD (Rajkovic et al., *J. Clin. Path.* 71:963-970, 2018). Both the −108 TT genotype and T allele were strongly associated ($p<0.001$), and the −108T allele could be a factor in the reduced expression of PON1 in COPD patients (id.).

PON1 activity was reported to be reduced in patients with sarcoidosis and interstitial lung disease, particularly during active disease (Ivanisevic et al., *Eur. J. Clin. Invest.* 46:418-424, 2016; Uzun et al., *Curr. Med. Res. Opin.* 24:1651-1657, 2008). Another study found lower PON1 during hypoxia (Okur et al., *Sleep Breath.* 17:365-371, 2013). PON1 activity was absent in patients with lung disease who had been exposed to sulfa mustard gas, even though the exposure was decades ago (Golmanesh et al., *Immunopharmacol. and Immunotoxicol.* 35:419-425, 2013).

PON1 and myeloperoxidase were reported to exert reciprocal control, in that an excess of PON1 inhibits myeloperoxidase, whereas an excess of myeloperoxidase inhibits PON1 (Huang et al., *J. Clin. Invest.* 123:3815-3828, 2013). Huang et al. found that both PON1 and myeloperoxidase were tightly bound to apoA-I. This provides one mechanism for the decreased PON1 activity under conditions of inflammation, where neutrophils and eosinophils produce an excess of myeloperoxidase. However, under normal conditions, PON1 is in excess and represses the activity of myeloperoxidase. (See id.)

Recombinant PON1 (rPON1) was reported to inhibit PMA-induced differentiation of monocytic cell line THP-1 (Rosenblat et al., *Atherosclerosis* 219:49-56, 2011). Mice injected IP with rPON1 had reduced differentiation of monocytes to macrophages and reduced expression of CD11b and CD36. The total cellular peroxides of peritoneal macrophages decreased by 18%. (Id.)

PON1 therapy has been studied in experimental models. One study showed that recombinant human PON1 injection was able to protect guinea pigs from sarin and soman inhalation toxicity (Valiyaveettil et al., *Biochem. Pharmacol.* 81:800-809, 2011; Valiyaveettil et al., *Toxicol. Letters* 202:203-208, 2011). Other studies showed therapy with PON1 protected from organophosphate poisoning in mice (Bajaj et al., *Appl. Biochem. Biotechnol.* 180:165, 2016; Stevens et al., *Proc. Natl. Acad. Sci. USA* 105:12780-12784, 2008). These studies used recombinant PON1 purified from bacterial inclusion bodies or made in *T. ni* larvae with a baculovirus vector. Both groups also expressed PON1 192K, a variant derived from the rabbit sequence, that helps stabilize and increase PON1 enzymatic activity. (See Bajaj et al., supra; Stevens et al., supra.)

Expression of PON1 in bacteria has also been used to select mutants that have enhanced enzymatic activity towards organophosphates and nerve agents (see Aharoni et al., *Proc. Natl. Acad. Sci. USA* 101:482-487, 2004; Goldsmith et al., *Chemistry and Biology* 19:456, 2012). Engineering of PON1 was done by directed evolution to find a variant with improved, soluble expression in bacteria. One evolved PON1 was crystallized and the PON1 structure described (see Harel et al., *Nature Struct. Mol. Biol.* 11:412-419, 2004). Another PON1 variant widely used is G3C9, a hybrid PON1 formed from shuffling mouse, rat, rabbit, and human PON1 sequences (see Aharoni et al., *Proc. Natl. Acad. Sci. USA* 101:482487, 2004). Other PON1 variants with increased organophosphatase activity but reduced esterase activity have been described (see Aharoni et al., supra). Further evolution of G3C9 to increase activity towards G-type nerve agents tabun, sarin, soman, and cyclosarin has also been reported (Gupta et al., Nat. Chem. Biol. 7:120-125, 2011. Goldsmith et al., *Chemistry and Biology* 19:456-466, 2012). When compared to human PON1, G3C9 has amino acid differences at 55 positions, and the further evolved PON1 variants have even more amino acid differences (Goldsmith et al., supra).

PON1 and the PON1 variant G3C9 have been tested in mouse models of experimental colitis (Yamashita et al., *J. Immunol.* 191:949-960, 2013). PON1 therapy was effective in TNBS-induced colitis and was equivalent to anti-TNFα therapy, currently the most effective clinically used therapeutic agent in man. However, in a chronic colitis model with CD4$^+$CD45RB$^{high}$ cell transfer, PON1 was not effective but G3C9 showed strong efficacy. Efficacy of G3C9 was equivalent to anti-TNFα in the chronic colitis model. (Id.) In another study, PON1 activity was found to correlate with severity of Crohn's disease (Sczceklik et al., *Molecules* 23:2603, 2018).

Another approach towards therapy with PON1 has been to inject HDL-like particles, formed from reconstituted apo A-I plus PON1, a therapy termed BL-3050 (Gaidukov et al., *BMC Clinical Pharmacol.* 9:18, 2009). In these studies, both G3C9 expressed in bacteria and BL-3050 complexes were protective in a mouse model of organophosphate poisoning (id.).

PON1 has been expressed as a fusion protein attached to the C-terminus of a mAb heavy chain specific for insulin receptor (see, e.g., Boado el al., *Mol. Pharm.* 5:1037, 2008). Expression of this hybrid heavy chain with an insulin receptor-specific light chain resulted in secretion of a bifunctional antibody that bound insulin receptor and had PON1 enzyme activity (id.). This hybrid molecule was expressed in mammalian cells (COS and CHO) (see id.; Boado et al., *Biotechnol. and Bioengineering,* 108:186, 2011). The hybrid molecule was also tested in nonhuman primates and was found to penetrate the blood/brain barrier; however, the molecule was rapidly cleared from the peripheral blood into the peripheral tissues, primarily the liver (Boado et al. (2011), supra). There are no reports of clinical testing of this molecule. Expression levels of the fusion protein in CHO cells were low (5-10 mg/liter) even after multiple transfections and subcloning (see id.).

PON1 has also been fused with a membrane transduction domain, termed PEP-1-PON1 (Kim et al., *Biomaterials* 64:45-56, 2015). This molecule inhibited the inflammatory response of a microglial cell line and protected against dopaminergic cell death in vivo in a mouse model of Parkinson's disease (id.).

Paraoxonase enzymes are able to hydrolyse QS molecules that are acyl homoserine lactones (AHL), including C12HSL (N-3-oxo-dodecanoyl-L-Homoresine Lactone), the primary QS molecule from *P. aeruginosa*. Studies of human PON1 indicate that it has pleiotropic enzyme activities, hydrolyzing a variety of substrates, including lactones (Billecke et al., *Drug Metabolism and Disposition* 28:1335-1342, 2000; Khersonsky and Tawfik. *Biochemistry* 44:6371-6382, 2005; Gaidukov and Tawfik, *J. Lipid Res.* 48:1637-1646, 2007; Bajaj et al., *Protein Science* 22:1799-1807, 2013). One study in *Drosophila melanogaster* demonstrated protection from *Pseudomonas aeruginosa* lethality by expression of a human PON1 transgene capable of hydrolyzing a critical quorum sensing molecule N-3-oxodecanoyl homoserine lactone (3OC12-HSL) (Stoltz et al., *J. Clin. Invest.* 118:3123-3131, 2008).

DNase1

DNase1 is a calcium and magnesium-dependent endonuclease coded by the human DNASE1 gene. DNase1 cleaves single-stranded and double-stranded DNA and chromatin. Cleavage of chromatin occurs in hypersensitive sites where chromatin is open and accessible, and is used in genomics to identify regions likely to contain active genes (Boyle et al., *Cell* 132:311-322, 2008). DNase1 helps degrade DNA during apoptosis (Samejima et al., *Nat. Rev. Mol. Cell Biol.* 6:677-688, 2008) and also degrades neutrophil extracellular traps (NETS) (Hakkim et al., *Proc. Natl. Acad. Sci. USA* 107:9813, 2010). DNase1 can digest biofilm DNA, resulting in a reduction in biofilm biomass, and increase antibiotic mediated biofilm killing (Tetz et al., *Antimicrob. Agents Chemother.* 53:1204-1209, 2009).

Accumulation of extracellular DNA from dead and dying cells was identified as a driver of disease in patients with systemic lupus erythematosus (SLE) long ago. DNase1 was administered to SLE patients at the Rockefeller starting in 1959. However, bovine DNase1 was used, and therapy was limited by its immunogenicity (see Valle et al., *Autoimmunity Rev.* 7:359, 2008). Decreased levels of DNase1 and DNase1 mutations with reduced activity have been reported in patients with SLE (see Valle et al., supra). Reduced DNase1 activity in urine was found in patients with lupus nephritis, and reduced DNase1 activity was a biomarker of disease progression (Pedersen et al., *J. Pathol. Clin. Res.* 4:193, 2018). In SLE patients, defective clearance of apoptotic debris and accumulation of chromatin contributes to breaking of tolerance and development of autoimmune disease.

Activated neutrophils extrude DNA bound with cytoplasmic and granule proteins, called neutrophil extracellular traps (NETs), to combat infectious agents, a process also known as "NETosis" (see Brinkmann, *J. Innate Immun.* 10:422-431, 2018). However, NETs are not targeted and often cause collateral tissue damage and inflammation if not effectively cleared. NETs have been implicated in driving disease progression in multiple incurable and serious diseases. Evidence for the importance of NETs in psoriasis, cystic fibrosis, SLE, RA, type I diabetes, sepsis, small vessel vasculitis, IBD, type II diabetes, and obesity was recently reviewed (Mutua and Gershwin, *Clin. Rev. Allergy Immunol.*, 2020, DOI 10.1007/s12016-020-08804-7). See also Michailidou, *Front. Immunol.* 11:619705, 2020 (reviewing involvement of neutrophils and NETs in vasculitis). NETs also play an important role in cardiovascular disease and thrombosis, and in cancer where NETs promote tumor progression and metastasis (Brinkmann, supra). In addition to their importance in cystic fibrosis, NETs also play a role in the clinicopathology of other respiratory diseases such as asthma and chronic obstructive pulmonary disease (COPD) (see Liu et al., *Chinese Med. Journal* 130:730-736, 2017; Twaddell et al., *CHEST* 156:774-782, 2019; Uddin et al., *Front. Immunol.* 10:47, 2019). Recently, NETs were found to contribute to immunothrombosis in COVID-19 acute respiratory distress syndrome (Middleton el al., *Blood* 136: 1169, 2020; Zuo et al., *JCI Insight* 5:e138999, 2020; Barnes et al., *J. Exp. Med.* 217:e20200652, 2020).

DNase1 is capable of digesting NETs and works together with another extracellular DNase called DNase1 L3 to clear NETs. Mice deficient in both DNase1 and DNase1L3 were unable to clear NETs and rapidly died of massive intravascular clot formation and organ damage after neutrophil activation (Brinkmann, supra). The contribution of NETs to thrombosis has already led to a clinical trial of wild-type DNase1 (Pulmozyme®) taken by inhalation therapy in COVID-19 patients (NCT04359654).

Recombinant wild-type human DNase1 (Pulmozyme®) was produced by Genentech and first approved for cystic fibrosis (CF) to digest DNA in the lungs and reduce congestion. High levels of DNA derived primarily from NETs are pathogenic in CF lung (Law et al., *J. Inflammation*, 14:1-8, 2017). Bacterial DNA from *Pseudomonas aeruginosa* biofilm formation is also present in many CF patients and may also be digested by DNase1 (Whitchurch el al., *Science* 295:1487, 2002).

Pulmozyme is delivered directly to the lungs by nebulization and is taken daily. Pulmozyme has been studied in patients with lung diseases other than CF, but has not been approved for alternative uses (Torbic et al., *J. Pharmacy Practice* 29:480, 2016). Pulmozyme was tested in a mouse lupus model (Verthelyi et al., *Lupus* 7:223, 1998) and in a phase I clinical trial in SLE patients (Davis et al., *Lupus* 8:68-76, 1999) without a decrease in disease measurements. Systemic administration of pulmozyme therapy may be limited because the enzyme is inhibited by globular actin that is abundant in blood and lungs (Ulmer et al., *Proc. Natl. Acad. Sci. USA* 93: 8225, 1996) and because of its short half-life.

Efforts have been made to enhance DNase1 for CF and SLE patients. A site-directed mutagenesis study of the DNA-binding interface identified 27 amino acid positions critical for enzyme activity and another 13 positions peripherally involved in DNA interactions with minimal impact on enzyme activity (see Pan et al., *Prot. Sci.* 7:628-636, 1998). This group also showed that increasing the local electrostatic attraction toward DNA by adding specific additional positively charged residues not only improved binding affinity to DNA but also improved functional activity and eliminated the inhibition by salt (Pan et al., *Biochemistry* 36:6624-6632, 1997; Pan and Lazarus, *J. Biol. Chem.* 273:11701-11708, 1998). Consistent with this observation, alanine replacement of two arginines (Arg-41 and Arg-111) that make critical contacts with DNA greatly reduced the DNA cleavage activity of human DNase1 (Pan et al., 1998, supra). Furthermore, the introduction of positively or negatively charged residues at sites distal to the DNA interface did not alter specific activity (Ulmer et al., *Proc. Natl. Acad. Sci. USA* 93:8225-8229, 1996).

The hyperactive DNase1 variants showed significant enhancement (up to 10,000-fold) under conditions of low DNA concentration and short DNA length (Pan and Lazarus, supra). Under optimal conditions for wild-type DNase1, however, the best variant showed activity only 7-fold higher and contained a single amino acid change (N74K). The N74K hyperactive variant showed reduced dependence on calcium (Pan and Lazarus, *Prot. Sci.* 8:1780-1788, 1999).

Ulmer et. al. (supra) and Pan et al. (1998, supra) showed that phenylalanine replacement of Ala-114 (A114F) eliminated inhibition of DNase1 by G-actin.

Actin-resistant and hyperactive DNase1 mutant enzymes are further described in U.S. Pat. Nos. 6,348,343 and 6,391,607.

DNASE1 is polymorphic, and alleles that encode for enzyme with reduced activity are associated with increased risk for autoimmune disease. However, a naturally occurring allele, G105R, was found to encode a DNase1 variant with a three-fold increase in activity (Yasuda et al., *Int. J. Biochem. Cell. Biol.* 42:1216-1225, 2010). This is a minor allele found in African populations and could confer resistance to autoimmune disease (id.).

There is great potential for DNase1 therapy using actin/salt-resistant and hyperactive DNase1. However, it was not possible to obtain stable CHO cells that constitutively express an enhanced DNase1 despite screening of thousands of clones (see Lam et al., *Biotech. Progress* 32: 523-533, 2017). This was thought to be due to toxicity of the enzyme during high expression in CHO cells. Lam et al. (supra) describe an inducible expression system in CHO cells as one potential solution to the problem of manufacturing an enhanced DNase1 enzyme.

Dwyer et al. (*J. Biol. Chem.* 274:9738-43, 1999) describe DNase1-Fc fusion proteins with impaired enzyme activity due to dimerization by the Fc domain. Dwyer et al. added short linkers (up to 7 aa) between the DNase1 and the Fc domain without improving activity (see id.). U.S. Pat. No. 8,841,416 to Ledbetter et al. describe a DNase1-Fc fusion with a linker of 21 amino acids and having activity at least equivalent to recombinant DNase1 control.

Although wild-type DNase1 (Pulmozyme) therapy is FDA approved in CF, there is not a CF mouse model where DNase1 is active. Pulmozyme was approved for CF therapy without testing for activity in a relevant in vivo disease model (Greene, *Hum. Exp. Toxicol.*, May: 13 Suppl 1:S1-42, 1994). More recently, wild-type DNase1 therapy has been studied in several in vivo models with encouraging results. DNase1 was found to significantly reduce airway resistance but did not reduce inflammation in an acute asthma model (da Cunha et al., *Exp. Lung Res.* 42:66, 2016). In a silica-induced lung inflammation model, DNase1 therapy prevented DNA-mediated STING activation and blocked the downstream type I IFN response (Benmerzoug et al., *Nat. Comm.* 9:5226, 2018). In a model of acute lung injury, DNase1 therapy protected mice from lung edema and lung vascular permeability. DNase1 therapy also reduced NET formation and platelet sequestration in the lung (Caudrillier et al., *J. Clin. Invest.* 122:2661, 2012).

Studies in mouse tumor models have shown that NETs promote metastasis and that injection of DNase1 or DNase1-coated nanoparticles reduced tumor metastasis (Cools-Lartigue et al., *J. Clin. Invest.* 123:3446, 2013; Park et al., *Sci. Translational Med.* 8:361ra138, 2016). Another study showed that a combination of DNase1 and proteases significantly inhibited growth of human colon cancer cells in a nude mouse model (Trejo-Becirril et al., *Integrative Cancer Therapies* 15:NP35-NP43, 2016). In cancer patients, increased concentration of citrullinated histone H3, a marker of neutrophil NET formation, strongly predicted a poor clinical outcome (Thalin et al., *PLoS ONE* 13:e0191231, 2018).

In a murine DSS colitis model (Babicova et al., *Folia Biolica (Praha)* 64:10, 2018) DNase1 therapy caused a reduction in TNFα and myeloperoxidase in the colon. Another study (Li et al., *J. Crohns Colitis* 2020, 14:240-253, 2020) found that DNase1 therapy decreased cytokine production and attenuated accelerated thrombus formation and platelet activation after DSS-induced colitis.

DNase1 therapy in a hind-limb ischemia reperfusion model caused increased perfusion, decreased infiltrating inflammatory cells, and reduced a local marker of thrombosis (Albadawi et al., *J. Vasc. Surg.* 64:484, 2016). In a rat model of ischemia-reperfusion-induced acute kidney injury, DNase1 treatment showed significant renoprotective effects. Exogenous administration of DNase1 ameliorated both functional and histologic hallmarks of acute injury in kidneys of ischemic rats (Peer et al., *Am. J. Nephrol.* 43:195, 2016).

DNase1 treatment prevented organ damage and protected from death when given 4 or 6 hours after injury in a cecal ligation and puncture sepsis model in mice (Mai et al., *Shock* 44:166, 2015). Extracellular DNA from NETs has been recognized as a scaffold for thrombus formation and infusion of DNase1 prevented thrombosis in a model of inferior vena cava stenosis (Brill et al., *J. Thrombosis Haemostasis* 10:136, 2012).

RNase

RNase 1 is a member of the RNase A superfamily consisting of RNases 1 to 8 in humans. RNase A was first isolated from bovine pancreas where it functions primarily as a digestive enzyme. In humans, RNase 1 digests single stranded and double stranded RNA and RNA/DNA hybrids. RNase 1 is produced by multiple cell types in humans, and is thought to participate primarily in vascular homeostasis. RNase 1 plays a major role in polynucleotide digestion to remove inflammatory extracellular RNA. In addition, RNase 1 has anti-viral activity.

Therapy with RNase has been studied in multiple disease models. For example, growth of the human lung tumor line A549 in athymic mice was inhibited by PEG-RNase1 (Rutkoski et al., *Translational Oncology* 6:392-397, 2013). RNase therapy also showed anti-tumor activity in a syngeneic mouse tumor model with Lewis Lung carcinoma and altered microRNA profiles (Mironova et al., *Oncotarget.* 8:78796-78810, 2017). RNase1 was reported to bind to a tumor-associated antigen, Globo H, expressed on the surface of breast adenocarcinoma cells (Eller et al., *ACS Central Sci.* 1:181-190, 2015).

In addition, RNase therapy has been found effective in animal models of heart transplantation (Kleinert et al., *J. Am. Heart Assn.* doi: 10.1021, 2016), plaque formation (Simsekyilmaz et al., *Circulation* 129: 598-606, 2014), and myocardial infarction (Steiger et al., *JAMA* 6:e004541, 2017). RNase1 therapy also reduced cerebral edema and infarction size in an acute stroke model (Walberer et al., *Curr. Neovas. Res.* 6:12-19, 2009).

RNase therapy was found to prevent postoperative cognitive decline in aged mice (Chen et al., *PLoS One* 10:e0134307, 2015).

RNase therapy has also been studied in a mouse model of systemic lupus erythematosus (SLE) (Sun et al., *J. Immunol.* 190:2536-2543, 2013). Overexpression of TLR7, an RNA sensor, causes a lupus-like disease with autoantibodies, kidney disease, and early mortality. Crossing these mice with mice that overexpress RNase A as a transgene resulted in progeny with increased survival, reduced lymphocyte activation, reduced kidney deposits of IgG and C3, and reduced hepatic inflammation and necrosis. (Id.)

RNase-Ig in which human RNase1 is fused to a mutated human IgG1 Fc domain comprising P238S and P331S mutations (see U.S. Pat. No. 8,937,157) has been tested in phase I and phase 11 clinical trials in patients with systemic lupus erythematosus (SLE) and Sjogren's syndrome.

Superoxide Dismutase (SOD)

Superoxide dismutase (SOD) is an antioxidant enzyme that converts oxygen free radicals to $H_2O_2$ and $O_2$. There are three human SOD enzymes. SOD1, also called Cu/Zn SOD, is a cytoplasmic enzyme that is a homodimer stabilized by an intrachain disulfide bond and by metal binding (Doucette et al., *J. Biol. Chem.* 279:54558-54566, 2004). SOD2 is a tetramer that is localized in the mitochondria and uses manganese in its active site. SOD3 is a tetramer that is secreted and contains copper and zinc. For a review of the roles of SODs, glutathione peroxidase, and catalase in overall protection from oxidative damage, see Ighodaro and Akinolye, *Alexandria J. Med.* 54:287-293, 2018.

SOD3 is the major extracellular antioxidant enzyme in the lungs, where it protects the extracellular matrix during lung injury. Genetic variants of SOD3 are associated with decreased lung function in adults and rapid progression of COPD (see Ganguly et al., *Physiol. Genomics* 37:260-267, 2009 for review).

SOD1 has been fused with a cell membrane transduction domain in order to deliver SOD1 to the cell cytoplasm. For example, Eum et al. (*Free Rad. Biol. Med.* 37:1656-1669, 2004) made a fusion of a 21 amino acid peptide called PEP-1 with SOD, and expressed the fusion protein in bacteria. They showed that the PEP-1-SOD molecule delivered SOD through the cell membrane and was effective after IP injection in vivo in preventing neuronal death following ischemic insult. SOD1 and variant forms of SOD1 have also been fused to an enhanced green fluorescent protein (EGFP) tag to create a fusion protein which can be detected in fluorescence based binding and chaperone assays (Ganesan et al., *Cell Death and Differentiation* 15:312-321, 2008).

Cytotoxic T Lymphocyte-Associated Molecule-4 (CTLA-4)

Cytotoxic T lymphocyte-associated molecule-4 (CTLA-4) is an immunoregulatory membrane receptor resulting in the downregulation of T-cell responses by inhibiting the costimulatory interactions of CD28-B7 (Carreno et al., *J. Immunol.* 165:1352-1356, 2000). The extracellular domain of CTLA-4 fused with a human IgG1 mutant Fc domain (abatacept, Orencia™) is approved by the FDA for therapy of RA because of its ability to suppress activation of the CD28 receptor on T cells (see Linsley et al., *J. Exp. Med.* 174:561-569, 1991; Emma Hitt, *FDA Approves Subcutaneous Abatacept for RA*, Medscape Medical News, Aug. 2, 2011). Abatacept inhibits T cell production of inflammatory cytokines and inhibits B cell class switching and IgG antibody responses.

Abatacept treatment has been shown to prevent dermal fibrosis and induce regression of established inflammation-driven fibrosis (Ponsoye et al., *Ann. Rheum. Dis.* 75:2142-2149, 2016). In addition, Abatacept significantly reduced fibrogenic marker levels, T-cell proliferation, and M1/M2 macrophage infiltration in lesioned lungs of Fra-2 mice, indicating it might be useful in treatment of lung fibrosis in humans (Bolete et al., *Arthritis Research and Therapy* 20:197, 2018). According to the Pulmonary Fibrosis Foundation, Abatacept is currently being tested in a phase 2 clinical trial in interstitial fibrosis patients (trial #NCT03215927), and is also being tested in a phase 3 clinical trial for treatment of relapsing non-severe granulomatosis with polyangiitis (Wegener's granulomatosis), (trial #NCT02108860). Costimulation inhibitors are being evaluated as promising candidates for suppressing the damage associated with lung inflammation and repair processes.

CD40-CD154

CD40 is a member of the TNFα receptor superfamily and is expressed on lymphocytes, hematopoeitic and structural cells, including fibroblasts, epithelial cells and endothelial cells (Sime and O'Reilly, *Clin. Immunol.* 99:308-319, 2001). The ligand for CD40, (CD40L or CD154), is expressed on activated T lymphocytes, activated platelets, mast cells and eosinophils. CD154 expressed by activated T cells provides an essential signal to CD40 on B cells that is needed for class switching and IgG production. However, CD40 expressed on the surface of structural cells such as endothelial cells can be stimulated by binding CD154, resulting in the production of inflammatory cytokines (id.). Activated platelets express CD154 on their surface and are also the primary source of soluble CD154 in the blood.

The CD40-CD154 signaling pathway has been implicated in lung injury and disease processes including fibrosis (Kaufman et al., *J. Immunol.* 172:1862-1871, 2004). The interaction between CD40 receptor and CD154 can trigger cellular activation, including production of proinflammatory cytokines, expression of cell adhesion molecules, and induction of cyclooxygenase 2 (COX-2), and prostaglandin E2 (PGE2) (Zhang, *J. Immunol.* 160:1053-1057, 1998). These events can in turn tip the balance between Type 1 and Type 2 cytokine responses in favor of Type 2 fibrogenic responses. Suppression of the CD40-CD154 pathway has been shown to have therapeutic benefit in animal lung disease models. For example, a monoclonal anti-murine CD40L antibody, MR1, was effective in protection of hyperoxic lung injury and radiation induced lung injury and fibrosis in mouse models (Adawi et al., *Clin. Immunol. Immunopathol.* 89:222-230, 1998; Adawi et al., *Am. J. Pathol.* 152:651-657, 1998). In addition, molecules which suppress the CD40-CD40L pathway such as the CXXC5 zinc finger protein, involved in epigenetic and transcriptional regulation, have been shown to ameliorate bleomycin induced lung fibrosis in mice (Cheng et al., *BioMed. Research Intl.* Volume 2020, Article ID 7840652, 2020; Xiong et al., *J. Cell. Mol. Med.* 23:740-749, 2018), indicating an important role for the CD40-CD40L pathway in disease progression.

Tumor Necrosis Factor α (TNFα)

The tumor necrosis factor α (TNFα) cytokine is a pleotropic pro-inflammatory mediator that is produced by a variety of cell types including macrophages and monocytes. Macrophages are the major source of TNFα in the lung; however, epithelial cells, eosinophils, and mast cells also may release TNFα upon activation (Malaviya et al., *Pharmacol. Ther.* 180:90-98, 2017; Aggarwal et al., *Blood* 119: 651-665, 2012). Increased levels of TNFα have been linked to several pulmonary inflammatory diseases including asthma, chronic obstructive pulmonary disease (COPD), acute lung injury (ALI)/acute respiratory distress syndrome (ARDS), sarcoidosis, and interstitial pulmonary fibrosis (IPF) (Malaviya et al., supra).

In addition to lung pathology, TNFα is increased and implicated in inflammatory bowel disease such as Crohn's disease (CD) and ulcerative colitis (UC). Monoclonal antibody therapy directed against tumor necrosis factor-alpha (anti-TNF) has revolutionized the care of patients with inflammatory bowel disease (IBD) (Pouillon et al., *Expert Opinion on Biological Therapy* 16:1277-1290, 2016; Peyrin-Biroulet et al., *The Lancet* 372:67-81, 2008).

Transforming Growth Factor-β (TGF-β)

The TGF-β cytokine plays an important role in immune responses and regulation (Travis and Sheppard, *Annu. Rev. Immunol.* 32:51-82, 2014). In mammals, three major isoforms of TGF-β have been identified, TGF-β1, TGF-β2, and TGF-β3 (Fernandez and Eickelberg, *Proc. Amer. Thorac. Soc.* 9:111-116, 2012). Many cell types express TGF-β, but it is expressed in a non-active form complexed to other molecules and requires activation to exert its functional effects. Latent TGF-β is activated upon cleavage from a preprotein form into a cytokine with pleiotropic activities, including chemotaxis, proliferation, and stimulation of cytokines associated with inflammation. TGF-β regulates cell proliferation, differentiation, migration, adhesion, survival, epithelial-mesenchymal transition (EMT), and collagen and extracellular matrix synthesis, and is essential for angiogenesis, wound healing and immune regulation, but also can drive cancer, metastasis, diabetes, and fibrosis disease progression (Varga and Pasche, *Curr. Opin. Rheum.* 20:720-728, 2008). TGF-β has also been shown to be critical in regulating adaptive T cell responses and recent studies implicate TGF-β as an important mediator of fibrosis in different organs, including the lung. Clinical trials using several antibodies which target TGF-β isoforms, such as fresolimumab (GC-1008), have been completed or are underway for cancer therapy (melanoma, glioma, breast cancer, and non-small lung cancer) and fibrosis. In addition, antibodies which target integrins such as αVβ6, involved or important in TGF-β activation, are also being used in phase 2 clinical trials to determine their efficacy for idiopathic pulmonary fibrosis (IPF) (Fernandez and Eickelberg, supra).

Expression of Enhanced DNase1 in Mammalian Cells

Wild-type DNase1, such as the FDA approved drug Pulmozyme®, is inhibited by G-actin in the lungs and plasma. An enhanced DNase1 was engineered by Genentech, creating DNase1 resistant to inhibition by actin and with increased enzyme activity (Pan and Lazarus, *Prot. Sci.* 8:1780-8, 1999). This enhanced DNase1, however, was toxic in mammalian cells, and no stable CHO cells could be established despite screening thousands of clones. Inducible expression in CHO cells was one potential solution that was reported (Lam et al., *Biotech. Progress* 32: 523-33, 2017).

SUMMARY OF THE INVENTION

In one aspect, the present invention provides a fusion polypeptide comprising, from an amino terminal position to a carboxyl terminal position, T-L1-X-L2-P, wherein T is a first biologically active polypeptide selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes tumor necrosis factor α (TNFα) or transforming growth factor-β(TGF-β); L1 is a first polypeptide linker, wherein L1 is optionally present; X is a immunoglobulin heavy chain constant region, wherein the immunoglobulin heavy chain constant region is capable of forming dimers and specifically binding the neonatal Fc receptor (FcRn); L2 is a second polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6. In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In another aspect, the present invention provides a fusion polypeptide comprising, from an amino terminal position to a carboxyl terminal position, T-L1-X-L2-P, wherein T is a first biologically active polypeptide selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes tumor necrosis factor α (TNFα) or transforming growth factor-β(TGF-β); L1 is a first polypeptide linker, wherein L1 is optionally present; X is a second biologically active polypeptide, wherein X is optionally present; L2 is a second polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6. In some variations, the second biologically active polypeptide is present and is selected from a dimerizing domain and a domain that specifically binds to the neonatal Fc receptor (FcRn). In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In certain embodiments of a fusion polypeptide as above comprising a DNase as the first biologically active polypeptide and in which L1 is present, the DNase has at least 90% or at least 95% identity with the amino acid sequence shown in (i) residues 21-280 of SEQ ID NO:18, (ii) residues 21-280 of SEQ ID NO:152, or (iii) residues 21-290 of SEQ ID NO:136. In some embodiments wherein the DNase has at least 90% or at least 95% identity with the amino acid sequence shown in residues 21-280 of SEQ ID NO:18 or residues 21-280 of SEQ ID NO:152, the DNase contains at least one amino acid substitution at a position corresponding to an amino acid of human wild-type DNase1 (SEQ ID NO:120) selected from N74, G105, and A114, wherein (1) the amino acid substitution at a position corresponding to N74 of human DNase1 (N74 substitution), if present, increases DNA binding relative to human DNase1, (2) the amino acid substitution at a position corresponding to G105 of human DNase1 (G105 substitution), if present, increases DNA binding relative to human DNase1, and (3) the amino acid substitution at a position corresponding to A114 of human DNase1 (A114 substitution), if present, decreases G-actin-induced inhibition of endonuclease activity relative to human DNase1. In some variations, the fusion polypeptide contains both the N74 and G105 substitutions, both the G105 and A114 substitutions, or each of the N74, G105, and A114 substitutions. Particularly suitable amino acid substitutions at these positions are lysine at the position corresponding to N74 of human DNase1, arginine at the position corresponding to G105 of human DNase1, and/or phenylalanine at the position corresponding to A114 of human DNase1. In some embodiments wherein the fusion polypeptide contains both the N74 and G105 substitutions, the fusion polypeptide does not contain the A114 substitution. In some embodiments wherein the DNase has at least 90% or at least 95% identity with amino acid residues 21-290 of SEQ ID NO:136, each of the amino acids at positions corresponding to R80, R95, and N96 of SEQ ID NO:136 is alanine or serine. In more specific variations, the DNase has the amino acid sequence shown in (i) residues 21-280 of SEQ ID NO:18, (ii) residues 21-280 of SEQ ID NO:20, (iii) residues 21-280 of SEQ ID NO:152; (iv) residues 21-290 of SEQ ID NO:138, or (v) residues 21-290 of SEQ ID NO:140. In some embodiments of a fusion polypeptide comprising a DNase as above, L1 comprises at least 15 amino acid residues or at least 26 amino acid residues (e.g., an L1 linker consisting of from 26 to 60 amino acid residues or from 26 to 36 amino acid residues). In particular variations, L1 comprises three or more (e.g., four or more) tandem repeats of the amino acid sequence of SEQ ID NO:119; in some such embodiments, L1 has the amino acid sequence shown in SEQ ID NO:12 or SEQ ID NO:14.

In some embodiments of a fusion polypeptide as above comprising an RNase as the first biologically active polypeptide, the RNase has at least 90% or at least 95% identity with the amino acid sequence shown in residues 29-156 of SEQ ID NO:22. In more specific variations, the RNase has the amino acid sequence shown in residues 29-156 of SEQ ID NO:22. In certain embodiments, L1 is present and comprises at least two amino acid residues (e.g., an L1 linker consisting of from 10 to 36 amino acid residues). In particular variations, L1 comprises two or more tandem repeats of the amino acid sequence of SEQ ID NO:119; in some such embodiments, L1 has the amino acid sequence shown in SEQ ID NO:10 or SEQ ID NO:12.

In some embodiments of a fusion polypeptide as above comprising a SOD1 as the first biologically active polypeptide, the SOD1 has at least 90% or at least 95% identity with the amino acid sequence shown in residues 2-154 of SEQ ID NO:32. In some such embodiments, the SOD1 contains at least one of the following amino acid substitutions relative to human SOD1 (SEQ ID NO:32): alanine at the position corresponding to C7 of human SOD1 (C7 substitution), and serine at the position corresponding to C112 of human SOD1 (C112 substitution). In certain variations, the fusion polypeptide contains both the C7 and C112 substitutions. In more specific variations, the SOD1 has the amino acid sequence shown in residues 23-175 of SEQ ID NO:54. In certain embodiments, L1 is present and comprises at least two amino acid residues (e.g., an L1 linker consisting of from 10 to 36 amino acid residues). In particular variations, L1 comprises two or more tandem repeats of the amino acid sequence of SEQ ID NO:119; in some such embodiments, L1 has the amino acid sequence shown in SEQ ID NO:10 or SEQ ID NO:12.

In some embodiments of a fusion polypeptide as above comprising a CTLA-4 extracellular domain as the first biologically active polypeptide, the CTLA-4 extracellular domain has at least 90% or at least 95% identity with the amino acid sequence shown in residues 21-144 of SEQ ID NO:66. In more specific variations, the CTLA-4 extracellular domain has the amino acid sequence shown in residues 21-144 of SEQ ID NO:66.

In some embodiments of a fusion polypeptide as above comprising a CD40 extracellular domain as the first biologically active polypeptide, the CD40 extracellular domain has at least 90% or at least 95% identity with the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90. In some such embodiments, the CD40 extracellular domain contains at least one amino acid substitution at a position corresponding to an amino acid of human CD40 (SEQ ID NO:68) selected from E64, K81, P85, and L121, wherein the at least one amino acid substitution increases CD40 ligand binding relative to human CD40. Particularly suitable amino acid substitutions at these positions are tyrosine at the position corresponding to E64 of human CD40, threonine, histidine, or serine at the position corresponding to K81 of human CD40, tyrosine at the position corresponding to P85 of human CD40, and/or proline at the position corresponding to L121 of human CD40. In some variations, the amino acid at the position corresponding to K81 of human CD40 is selected from threonine, histidine, and serine; the amino acid at the position corresponding to K81 of human CD40 is histidine and the amino acid at the position corresponding to L121 of human CD40 is proline; or the amino acid at the position corresponding to E64 of human CD40 is tyrosine, the amino acid at the position corresponding to K81 of human CD40 is threonine, and the amino acid at the position corresponding to P85 of human CD40 is tyrosine. In more specific variations, the CD40 extracellular domain has the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In certain embodiments of a fusion polypeptide as above, the first biologically active polypeptide is the polypeptide that specifically binds and neutralizes TNFα or TGF-β. In some such embodiments, the first biologically active polypeptide is a single-chain antibody such as, e.g., a single-chain Fv (scFv) or a single-domain antibody (sdAb).

In some embodiments of a fusion polypeptide as above comprising a single-chain antibody that specifically binds and neutralizes TNFα, the single-chain antibody comprises a VH domain comprising complementarity determining regions (CDRs) CDR-H1$_{TNF\alpha}$, CDR-H2$_{TNF\alpha}$, and CDR-H3$_{TNF\alpha}$, wherein the set of VH CDRs has three or fewer amino acid substitutions relative to a set of reference CDRs CDR-H1, CDR-H2, and CDR-H3 of the VH domain having the amino acid sequence shown in SEQ ID NO:108 (e.g., a set of VH CDRs having zero amino acid substitutions relative to CDR-H1, CDR-H2, and CDR-H3 of SEQ ID NO:108, whereby CDR-H1$_{TNF\alpha}$, CDR-H2$_{TNF\alpha}$, and CDR-H3$_{TNF\alpha}$ are, respectively, a CDR-H1, a CDR-H2, and a CDR-H3 of SEQ ID NO:108). Each VH CDR may be defined, for example, according to the Chothia definition, the Kabat definition, the AbM definition, the IMGT database definition, or the contact definition of CDR. In some variations, each VH CDR is defined according the IMGT database definition of CDR, whereby the reference CDRs CDR-H1, CDR-H2, and CDR-H3 of SEQ ID NO:108 correspond to residues 26-33, 50-59, and 97-110 of SEQ ID NO:108, respectively; in some such embodiments, CDR-H1$_{TNF\alpha}$, CDR-H2$_{TNF\alpha}$, and CDR-H3$_{TNF\alpha}$ are the VH CDRs of SEQ ID NO:108 according to the IMGT database definition, whereby CDR-H1$_{TNF\alpha}$ a has the amino acid sequence shown in residues 26-33 of SEQ ID NO:108, CDR-H2$_{TNF\alpha}$ has the amino acid sequence shown in residues 50-59 of SEQ ID NO:108, and CDR-H3$_{TNF\alpha}$ has the amino acid sequence shown in residues 97-110 of SEQ ID NO:108.

In other, non-mutually exclusive embodiments of a fusion polypeptide as above comprising a single-chain antibody that specifically binds and neutralizes TNFα, the single-chain antibody comprises a VL domain comprising complementarity determining regions (CDRs) CDR-L1$_{TNF\alpha}$, CDR-L2$_{TNF\alpha}$, and CDR-L3$_{TNF\alpha}$, wherein the set of VL CDRs has three or fewer amino acid substitutions relative to a set of reference CDRs CDR-L1, CDR-L2, and CDR-L3 of the VL domain having the amino acid sequence shown in SEQ ID NO: 110 (e.g., a set of VL CDRs having zero amino acid substitutions relative to CDR-L1, CDR-L2, and CDR-L3 of SEQ ID NO:110, whereby CDR-L1$_{TNF\alpha}$, CDR-L2$_{TNF\alpha}$, and CDR-L3$_{TNF\alpha}$ are, respectively, a CDR-L1, a CDR-L2, and a CDR-L3 of SEQ ID NO:110). Each VL CDR may be defined, for example, according to the Chothia definition, the Kabat definition, the AbM definition, the IMGT database definition, or the contact definition of CDR. In some variations, each VL CDR is defined according to the IMGT database definition of CDR, wherein the reference CDRs CDR-L1, CDR-L2, and CDR-L3 of SEQ ID NO:110 correspond to residues 27-32, 50-52, and 89-97 of SEQ ID NO:110, respectively; in some such embodiments, CDR-L1$_{TNF\alpha}$, CDR-L2$_{TNF\alpha}$, and CDR-L3$_{TNF\alpha}$ are VL CDRs of SEQ ID NO:110 according to the IMGT database definition, whereby CDR-L1$_{TNF\alpha}$ has the amino acid sequence shown in residues 27-32 of SEQ ID NO:110; CDR-L2$_{TNF\alpha}$ has the amino acid sequence shown in residues 50-52 of SEQ ID NO:110; and CDR-L3$_{TNF\alpha}$ has the amino acid sequence shown in residues 89-97 of SEQ ID NO:110.

In some embodiments of a fusion polypeptide as above comprising a single-chain antibody that specifically binds and neutralizes TNFα, the single-chain antibody comprises a VH domain having at least 90% or at least 95% identity with the amino acid sequence shown in SEQ ID NO:108, and/or the single-chain antibody comprises a VL domain having at least 90% or at least 95% identity with the amino acid sequence shown in SEQ ID NO:110. In more specific variations, the single-chain antibody comprises a VH domain having the amino acid sequence shown in SEQ ID NO:108, and/or the single-chain antibody comprises a VL domain having the amino acid sequence shown in SEQ ID NO:110.

In some embodiments of a fusion polypeptide as above comprising a single-chain antibody that specifically binds and neutralizes TGF-β, the single-chain antibody comprises a VH domain comprising complementarity determining regions (CDRs) CDR-H1$_{TGF\text{-}\beta}$, CDR-H2$_{TGF\text{-}\beta}$, AND CDR-H3$_{TGF\text{-}\beta}$, WHEREIN THE SET OF VH CDRS HAS THREE OR FEWER amino acid substitutions relative to a set of reference CDRs CDR-H1, CDR-H2, and CDR-H3 of the VH domain having the amino acid sequence shown in SEQ ID NO: 112 (e.g., a set of VH CDRs having zero amino acid substitutions relative to CDR-H1, CDR-H2, and CDR-H3 of SEQ ID NO:112, whereby CDR-H1$_{TGF\text{-}\beta}$, CDR-H2$_{TGF\text{-}\beta}$, and CDR-H3$_{TGF\text{-}\beta}$ are, respectively, a CDR-H1, a CDR-H2, and a CDR-H3 of SEQ ID NO:112). Each VH CDR may be defined, for example, according to the Chothia definition, the Kabat definition, the AbM definition, the IMGT database definition, or the contact definition of CDR. In some variations, each VH CDR is defined according the Kabat definition of CDR, whereby the reference CDRs CDR-H1, CDR-H2, and CDR-H3 of SEQ ID NO: 112 correspond to residues 31-35, 50-66, and 99-106 of SEQ ID NO: 112, respectively, in some such embodiments, CDR-H1$_{TGF\text{-}\beta}$, CDR-H2$_{TGF\text{-}\beta}$, and CDR-H3$_{TGF\text{-}\beta}$ are the VH CDRs of SEQ ID NO:112 according to the Kabat definition, whereby CDR-H1$_{TGF\text{-}\beta}$ has the amino acid sequence shown in residues 31-35 of SEQ ID NO:112, CDR-H2$_{TGF\text{-}\beta}$ has the amino acid sequence shown in residues 50-66 of SEQ ID NO:112, and CDR-H3$_{TGF\text{-}\beta}$ has the amino acid sequence shown in residues 99-106 of SEQ ID NO: 112.

In other, non-mutually exclusive embodiments of a fusion polypeptide as above comprising a single-chain antibody that specifically binds and neutralizes TGF-β, the single-chain antibody comprises a VL domain comprising complementarity determining regions (CDRs) CDR-L1$_{TGF\text{-}\beta}$, CDR-L2$_{TGF\text{-}\beta}$, and CDR-L3$_{TGF\text{-}\beta}$, wherein the set of VL CDRs has three or fewer amino acid substitutions relative to a set of reference CDRs CDR-L1, CDR-L2, and CDR-L3 of the VL domain having the amino acid sequence shown in SEQ ID NO:114 (e.g., a set of VL CDRs having zero amino acid substitutions relative to CDR-L1, CDR-L2, and CDR-L3 of SEQ ID NO:114, whereby CDR-L2$_{TGF\text{-}\beta}$, CDR-L2$_{TGF\text{-}\beta}$, and CDR-L3$_{TGF\text{-}\beta}$ are, respectively, a CDR-L1, a CDR-L2, and a CDR-L3 of SEQ ID NO:114). Each VL CDR may be defined, for example, according to the Chothia definition, the Kabat definition, the AbM definition, the IMGT database definition, or the contact definition of CDR. In some variations, each VL CDR is defined according to the Kabat definition of CDR, wherein the reference CDRs CDR-L1, CDR-L2, and CDR-L3 of SEQ ID NO: 114 correspond to residues 24-40, 56-62, and 95-102 of SEQ ID NO: 114, respectively; in some such embodiments, CDR-L2$_{TGF\text{-}\beta}$, CDR-L2$_{TGF\text{-}\beta}$, and CDR-L3$_{TGF\text{-}\beta}$ are VL CDRs of SEQ ID NO: 14 according to the Kabat definition, whereby CDR-L1$_{TGF\text{-}\beta}$ has the amino acid sequence shown in residues 24-40 of SEQ ID NO:114; CDR-L2$_{TGF\text{-}\beta}$ has the amino acid sequence shown in residues 56-62 of SEQ ID NO:114; and CDR-L3$_{TGF\text{-}\beta}$ has the amino acid sequence shown in residues 95-102 of SEQ ID NO:114.

In some embodiments of a fusion polypeptide as above comprising a single-chain antibody that specifically binds and neutralizes TGF-β, the single-chain antibody comprises a VH domain having at least 90% or at least 95% identity with the amino acid sequence shown in SEQ ID NO:112, and/or the single-chain antibody comprises a VL domain having at least 90% or at least 95% identity with the amino acid sequence shown in SEQ ID NO:114. In more specific variations, the single-chain antibody comprises a VH domain having the amino acid sequence shown in SEQ ID NO:112, and/or the single-chain antibody comprises a VL domain having the amino acid sequence shown in SEQ ID NO:114.

In some embodiments of a fusion polypeptide as above comprising a single-chain antibody that specifically binds and neutralizes TNFα or TGF-β, the single-chain antibody has at least 90% or at least 95% identity with the amino acid sequence shown in (i) residues 21-268 of SEQ ID NO:92, (ii) residues 21-268 of SEQ ID NO:96, (iii) residues 21-269 of SEQ ID NO:100, or (iv) residues 21-269 of SEQ ID NO:104. In more specific variations, the single-chain antibody has the amino acid sequence shown in (i) residues 21-268 of SEQ ID NO:92, (ii) residues 21-268 of SEQ ID NO:96, (iii) residues 21-269 of SEQ ID NO:100, or (iv) residues 21-269 of SEQ ID NO:104.

In another aspect, the present invention provides a fusion polypeptide comprising, from an amino terminal position to a carboxyl terminal position, X-L2-P, wherein X is an immunoglobulin heavy chain constant region, wherein the immunoglobulin heavy chain constant region is capable of forming dimers and specifically binding the neonatal Fc receptor (FcRn); L2 is a polypeptide linker, wherein L2 is optionally present; and P is a biologically active paraoxonase, wherein the paraoxonase has at least 80% or at least 90% identity with the amino acid sequence shown in residues 16-355 or 26-355 of SEQ ID NO:6 and does not contain an amino terminal leader sequence corresponding to residues 1-15 of SEQ ID NO:6, wherein the fusion polypeptide does not comprise a biologically active polypeptide N-terminal to the immunoglobulin heavy chain constant region. In some embodiments, the biologically active paraoxonase has at least 95% identity with the amino acid sequence shown in (i) residues 16-355 or 26-355 of SEQ ID NO:6, (ii) residues 16-355 or 26-355 of SEQ ID NO:124, or (iii) residues 16-355 or 26-355 of SEQ ID NO:126.

In some embodiments of a fusion polypeptide as above comprising the formula T-L1-X-L2-P or X-L2-P, the amino acid at a position corresponding to Q192 of the human paraoxonase 1 Q192 isoform (hPON1-Q192; SEQ ID NO:4) is lysine or arginine. In other, non-mutually exclusive variations, the amino acid at the position corresponding to H115 of hPON1-Q192 is tryptophan. In specific variations, the paraoxonase has an amino acid sequence selected from (i) residues n-355 of SEQ ID NO:6, (ii) residues n-355 of SEQ ID NO:124, and (iii) residues n-355 of SEQ ID NO:126, wherein n is an integer from 16 to 26, inclusive.

In certain embodiments of a fusion polypeptide as above comprising the formula T-L1-X-L2-P or X-L2-P, L2 is present and comprises at least eight amino acid residues. In some such embodiments, L2 consists of from 12 to 25 amino acid residues. A particularly suitable L2 linker has the amino acid sequence shown in SEQ ID NO:56.

In some embodiments of a fusion polypeptide as above having the formula T-L1-X-L2-P or X-L2-P and wherein X is an immunoglobulin heavy chain constant region, the immunoglobulin heavy chain constant region is an immunoglobulin Fc region. In some such embodiments, the Fc region is a human Fc region such as, e.g., a human Fc variant comprising one or more (e.g., from one to 10) amino acid substitutions relative to the wild-type human sequence. Particularly suitable Fc regions include human γ1 and γ4 Fc regions. In some variations, the Fc region is a human γ1 Fc variant in which Eu residue C220 is replaced by serine; in some such embodiments Eu residues C226 and C229 are each replaced by serine, and/or Eu residue P238 is replaced by serine. In further variations comprising an Fc region as above, the Fc region is a human γ1 Fc variant in which Eu residue P331 is replaced by serine. In some embodiments, the Fc region has at least 90% or at least 95% identity with the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO: 116, or (v) residues 1-232 or 1-231 of SEQ ID NO:118. In more specific variations, the Fc region has the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO:118.

In some embodiments of a fusion polypeptide as above having the formula T-L1-X-L2-P or X-L2-P and wherein X is an immunoglobulin heavy chain constant region, the immunoglobulin heavy chain constant region comprises an amino acid sequence having at least 90% or at least 95% identity with the amino acid sequence shown in (i) residues 16-232 or 16-231 of SEQ ID NO:26, (ii) residues 16-232 or 16-231 of SEQ ID NO: 116, or (iii) residues 16-232 or 16-231 of SEQ ID NO: 118. In more specific variations, the immunoglobulin heavy chain constant region comprises the amino acid sequence shown in (i) residues 16-232 or 16-231 of SEQ ID NO:26, (ii) residues 16-232 or 16-231 of SEQ ID NO:116, or (iii) residues 16-232 or 16-231 of SEQ ID NO:118.

In some embodiments of a fusion polypeptide as above having the formula T-L1-X-L2-P and wherein the first biologically active polypeptide is the DNase, the fusion polypeptide comprises an amino acid sequence having at least 90% or at least 95% identity with the amino acid sequence shown in (i) residues 21-896 of SEQ ID NO:2, (ii) residues 21-896 of SEQ ID NO:128, (iii) residues 21-896 of SEQ ID NO:130, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164; in some such embodiments, the fusion polypeptide comprises the amino acid sequence shown in (i) residues 21-896 of SEQ ID NO:2, (ii) residues 21-896 of SEQ ID NO:128, (iii) residues 21-896 of SEQ ID NO:130, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164.

In some embodiments of a fusion polypeptide as above having the formula T-L1-X-L2-P and wherein the first biologically active polypeptide is the DNase, the polypeptide region corresponding to T-L1-X ("T-L1-X region") comprises the amino acid sequence shown in SEQ ID NO:149, SEQ ID NO:150, SEQ ID NO:153, or SEQ ID NO:154. In certain variations of a T-L1-X region comprising the amino acid sequence shown in SEQ ID NO:149, SEQ ID NO:150, SEQ ID NO:153, or SEQ ID NO:154, (i) the amino acid at each of positions 315 and 316 is alanine; (ii) the amino acid at position 319 is serine; (iii) the amino acid at position 378 is alanine, glutamine, or glycine, and the amino acid at position is optionally alanine; (iv) the amino acid at position 410 is alanine, glycine, or serine; (v) the amino acid at position 412 is serine or alanine; (vi) the amino acid at position 333 is tyrosine, the amino acid at position 335 is threonine, and the amino acid at position 337 is glutamate; and/or (vii) the amino acid at position 509 is leucine, and the amino acid at position 515 is serine. In other, non-mutually exclusive variations of a T-L1-X region comprising the amino acid sequence shown in SEQ ID NO:149, SEQ ID NO:150, SEQ ID NO:153, or SEQ ID NO:154, the amino acid sequence corresponding to positions 261-296 includes a Gly-Ser tandem repeat sequence having a formula selected from the group consisting of (i) [Gly-Gly-Gly-Gly-Ser]$_n$, wherein n is an integer from 4 to 7, (ii) [Gly-Gly-Gly-Ser]$_n$, wherein n is an integer from 5 to 9, and (iii) [Gly-Gly-Ser]$_n$, wherein n is an integer from 6 to 12; in some such embodiments, the amino acid sequence corresponding to positions 261-296 includes a Gly-Ser tandem repeat sequence having a formula selected from the group consisting of (i) [Gly-Gly-Gly-Gly-Ser]$_n$, wherein n is an integer from 4 to 6, (ii) [Gly-Gly-Gly-Ser]$_n$, wherein n is an integer from 5 to 7, and (iii) [Gly-Gly-Ser]$_n$, wherein n is an integer from 6 to 10. In yet other, non-mutually exclusive variations of a T-L1-X region comprising the amino acid sequence shown in SEQ ID NO:149, SEQ ID NO:150, SEQ ID NO:153, or SEQ ID NO:154, the amino acid at position 261 is aspartate, the amino acid at position 262 is leucine, the amino acid at position 263 is serine, the amino acid at position is threonine, the amino acid at position is 295 is glycine, and/or the amino acid at position 296 is leucine. In other, non-mutually exclusive variations of a T-L1-X region comprising the amino acid sequence shown in SEQ ID NO:149 or SEQ ID NO:153, the amino acid at each of positions 74 and 105 is independently lysine or arginine. In other, non-mutually exclusive variations of a T-L1-X region comprising the amino acid sequence shown in SEQ ID NO:149, the amino acid at position 114 is phenylalanine.

In some embodiments of a fusion polypeptide as above having the formula T-L1-X-L2-P and wherein the first biologically active polypeptide is the RNase, the fusion polypeptide comprises an amino acid sequence having at least 90% or at least 95% identity with the amino acid sequence shown in (i) residues 21-764 of SEQ ID NO:40 or (ii) residues 21-740 of SEQ ID NO:48; in some such embodiments, the fusion polypeptide comprises the amino acid sequence shown in (i) residues 21-764 of SEQ ID NO:40 or (ii) residues 21-740 of SEQ ID NO:48.

In some embodiments of a fusion polypeptide as above having the formula T-L1-X-L2-P and wherein the first biologically active polypeptide is the SOD1, the fusion polypeptide comprises an amino acid sequence having at least 90% or at least 95% identity with the amino acid sequence shown in (i) residues 23-781 of SEQ ID NO:50, (ii) residues 23-781 of SEQ ID NO:52, or (iii) residues 23-791 of SEQ ID NO:54; in some such embodiments, the fusion polypeptide comprises the amino acid sequence shown in (i) residues 23-781 of SEQ ID NO:50, (ii) residues 23-781 of SEQ ID NO:52, or (iii) residues 23-791 of SEQ ID NO:54.

In some embodiments of a fusion polypeptide as above having the formula T-L1-X-L2-P and wherein the first biologically active polypeptide is the CTLA-4 extracellular domain, the fusion polypeptide comprises an amino acid sequence having at least 90% or at least 95% identity with the amino acid sequence shown in residues 21-736 of SEQ ID NO:66; in some such embodiments, the fusion polypeptide comprises the amino acid sequence shown in residues 21-736 of SEQ ID NO:66.

In some embodiments of a fusion polypeptide as above having the formula T-L1-X-L2-P and wherein the first biologically active polypeptide is the CD40 extracellular domain, the fusion polypeptide comprises an amino acid sequence having at least 90% or at least 95% identity with the amino acid sequence shown in (i) residues 21-804 of SEQ ID NO:74, (ii) residues 21-804 of SEQ ID NO:78, (iii) residues 21-804 of SEQ ID NO:82, (iv) residues 21-804 of SEQ ID NO:86, or (v) residues 21-804 of SEQ ID NO:90; in some such embodiments, the fusion polypeptide comprises the amino acid sequence shown in (i) residues 21-804 of SEQ ID NO:74, (ii) residues 21-804 of SEQ ID NO:78, (iii) residues 21-804 of SEQ ID NO:82, (iv) residues 21-804 of SEQ ID NO:86, or (v) residues 21-804 of SEQ ID NO:90.

In some embodiments of a fusion polypeptide as above having the formula T-L1-X-L2-P and wherein the first biologically active polypeptide is a single-chain antibody that specifically binds and neutralizes TNFα, the fusion polypeptide comprises an amino acid sequence having at least 90% or at least 95% identity with the amino acid sequence shown in (i) residues 21-860 of SEQ ID NO:94, or (ii) residues 21-860 of SEQ ID NO:98; in some such embodiments, the fusion polypeptide comprises the amino acid sequence shown in (i) residues 21-860 of SEQ ID NO:94, or (ii) residues 21-860 of SEQ ID NO:98.

In some embodiments of a fusion polypeptide as above having the formula T-L1-X-L2-P and wherein the first biologically active polypeptide is a single-chain antibody that specifically binds and neutralizes TGF-β, the fusion polypeptide comprises an amino acid sequence having at least 90% or at least 95% identity with the amino acid sequence shown in (i) residues 21-861 of SEQ ID NO:102, or (ii) residues 21-861 of SEQ ID NO:106; in some such embodiments, the fusion polypeptide comprises the amino acid sequence shown in (i) residues 21-861 of SEQ ID NO:102, or (ii) residues 21-861 of SEQ ID NO:106.

In some embodiments of a fusion polypeptide as above having the formula X-L2-P, the fusion polypeptide comprises an amino acid sequence having at least 90% or at least 95% identity with the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146; in some such embodiments, the fusion polypeptide comprises the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146.

In another aspect, the present invention provides a dimeric protein comprising a first fusion polypeptide and a second fusion polypeptide, wherein each of the first and second fusion polypeptides is (i) a fusion polypeptide as above having the formula T-L1-X-L2-P and wherein the X is a dimerizing domain (e.g., an immunoglobulin heavy chain constant region such as, for example, an immunoglobulin Fc region), or (ii) a fusion polypeptide as above having the formula X-L2-P.

In another aspect, the present invention provides a polynucleotide encoding a fusion polypeptide as described above.

In still another aspect, the present invention provides an expression cassette comprising a DNA segment encoding a fusion polypeptide as described above and which is operably linked to a promoter. In particular variations, the encoded fusion polypeptide is a fusion polypeptide as above having the formula T-L1-X-L2-P and wherein the first biologically active polypeptide is the DNase (i) having at least 90% or at least 95% identity with amino acid residues 21-280 of SEQ ID NO:18 or residues 21-280 of SEQ ID NO:152 and (ii) comprising at least one of the N74, G105, and A114 substitutions (e.g., a DNase having two or all three substitutions). Also provided is a cultured cell into which has been introduced an expression cassette as described above, wherein the cell expresses the DNA segment. In a related aspect, the present invention provides a stable cell line comprising, within its genomic DNA, an expression cassette as described above, wherein the stable cell line constitutively expresses the DNA segment. In some embodiments, the stable cell line is a Chinese hamster ovary (CHO) cell line.

In another aspect, the present invention provides a vector comprising an expression cassette as described above.

In another aspect, the present invention provides a method of making a fusion polypeptide. The method generally includes (i) culturing a cell into which has been introduced an expression cassette as described above, wherein the cell expresses the DNA segment and the encoded fusion polypeptide is produced, and (ii) recovering the fusion polypeptide. In some variations, the cultured cell is a stable cell line as described above.

In yet another aspect, the present invention provides a method of making a dimeric protein. The method generally includes (i) culturing a cell into which has been introduced an expression cassette as described above, wherein the cell expresses the DNA segment and the encoded fusion polypeptide is produced as a dimeric protein, and (ii) recovering the dimeric protein. In some variations, the cultured cell is a stable cell line as described above.

In another aspect, the present invention provides a composition comprising a fusion polypeptide as described above and a pharmaceutically acceptable carrier.

In another aspect, the present invention provides a composition comprising a dimeric protein as described above and a pharmaceutically acceptable carrier.

In some embodiments of a composition as described above, the composition is formulated for delivery to the lung by nebulization.

In still another aspect, the present invention provides a method for treating an inflammatory disease. The method generally includes administering to a subject having the inflammatory disease an effective amount of a fusion polypeptide or dimeric protein as described above. In some embodiments, the inflammatory disease is an inflammatory lung disease such as, for example, chronic obstructive pulmonary disease (COPD), asthma, cystic fibrosis (CF), bronchiectasis, hypoxia, acute respiratory distress syndrome (ARDS) (e.g., COVID-19-associated ARDS), and interstitial lung disease (e.g., idiopathic pulmonary fibrosis (IPF) or sarcoidosis); in some variations, the inflammatory lung disease is characterized by Pseudomonas aeruginosa infection. In other embodiments, the inflammatory disease is selected from an inflammatory bowel disease (IBD) (e.g., Crohn's disease or ulcerative colitis), systemic lupus erythematosus (SLE) (e.g., SLE with lupus nephritis), type 1 diabetes, and type 2 diabetes. In still other embodiments, the inflammatory disease is an inflammatory skin disease such as, for example, psoriasis or atopic dermatitis.

In another aspect, the present invention provides a method for treating an autoimmune disease. The method generally includes administering to a subject having the autoimmune disease an effective amount of a fusion polypeptide or dimeric protein as described above. In some embodiments, the autoimmune disease is selected from systemic lupus erythematosus (SLE) (e.g., SLE with lupus nephritis), Sjogren's syndrome, rheumatoid arthritis, psoriasis, psoriatic arthritis, antiphospholipid syndrome, type 1 diabetes, vasculitis, and systemic sclerosis.

In another aspect, the present invention provides a method for treating biofilm formation by a gram-negative bacteria. The method generally includes administering to a subject having the biofilm formation an effective amount of a fusion polypeptide or dimeric protein as described above. In some embodiments, the gram-negative bacteria is Pseudomonas aeruginosa.

In another aspect, the present invention provides a method for treating exposure to sulfur mustard gas or an organophosphate. The method generally includes administering to a subject exposed to the sulfur mustard gas or to the organophosphate an effective amount of a fusion polypeptide or dimeric protein as described above. In some embodiments, the organophosphate is an insecticide selected from parathion, malathion, chlorpyrifos, diazinon, dichlorvos, phosmet, fenitrothion, terbufos, tetrachlorvinphos, azamethiphos, and azinphos-methyl. In some embodiments the organophosphate is a nerve agent selected from tabun, sarin, soman, and cyclosarin.

In yet another aspect, the present invention provides a method for treating a neurological disease. The method generally includes administering to a subject having the neurological disease an effective amount of a fusion polypeptide or dimeric protein as described above. In some embodiments, the neurological disease is selected from Parkinson's disease and Alzheimer's disease. In some embodiments, the neurological disease is a disease characterized by dementia such as, for example, Alzheimer's disease.

In another aspect, the present invention provides a method for treating a cardiovascular disease. The method generally includes administering to a subject having the cardiovascular disease an effective amount of a fusion polypeptide or dimeric protein as described above. In some embodiments, the cardiovascular disease is a disease characterized by atherosclerosis such as, e.g., coronary heart disease or ischemic stroke. In some variations, the coronary heart disease is characterized by acute coronary syndrome.

In another aspect, the present invention provides a method for treating a chronic liver disease. The method generally includes administering to a subject having the chronic liver disease an effective amount of a fusion polypeptide or dimeric protein as describe above. In some embodiments, the chronic liver disease is selected from nonalcoholic fatty liver disease (NAFLD), alcohol-associated liver disease (ALD), portal hypertension, or a complication following liver transplantation. In some variations, the nonalcoholic fatty liver disease is nonalcoholic steatohepatitis (NASH).

In another aspect, the present invention provides a method for treating a fibrotic disease. The method generally includes administering to a subject having the fibrotic disease an effective amount of a fusion polypeptide or dimeric protein as described above. In some embodiments, the fibrotic disease is selected from the group consisting of systemic sclerosis, systemic lupus erythematosus (SLE), an inflammatory lung disease, a chronic liver disease, and a chronic kidney disease (e.g., lupus nephritis, IgA nephropathy, or membranous glomerulonephritis).

In still another aspect, the present invention provides a method for treating a disease or disorder characterized by NETosis. In some embodiments, the method generally includes administering to a subject having the disease or disorder characterized by NETosis an effective amount of a fusion polypeptide having the formula T-L1-X-L2-P as described above, or a dimeric protein formed by dimerization of the fusion polypeptide, wherein the fusion polypeptide or dimeric protein comprises the DNase as the first biologically active polypeptide.

In other embodiments of a method for treating a disease or disorder characterized by NETosis, the method is a combination therapy that generally includes administering to a subject having the disease or disorder characterized by NETosis (a) an effective amount of a fusion polypeptide having the formula X-L2-P as described above, or a dimeric protein formed by dimerization of the fusion polypeptide, and (b) an effective amount of a biologically active DNase. In certain embodiments of the combination therapy method, the DNase has at least 90% or at least 95% identity with the amino acid sequence shown in (i) residues 21-280 of SEQ ID NO:18, (ii) residues 21-280 of SEQ ID NO:152, or (iii) residues 21-290 of SEQ ID NO:136. In some embodiments wherein the DNase has at least 90% or at least 95% identity with the amino acid sequence shown in residues 21-280 of SEQ ID NO:18 or residues 21-280 of SEQ ID NO:152, the DNase contains at least one amino acid substitution at a position corresponding to an amino acid of human wild-type DNase1 (SEQ ID NO:120) selected from N74, G105, and A114, wherein (1) the amino acid substitution at a position corresponding to N74 of human DNase1 (N74 substitution), if present, increases DNA binding relative to human DNase1, (2) the amino acid substitution at a position corresponding to G105 of human DNase1 (G105 substitution), if present, increases DNA binding relative to human DNase1, and (3) the amino acid substitution at a position corresponding to A114 of human DNase1 (A114 substitution), if present, decreases G-actin-induced inhibition of endonuclease activity relative to human DNase1. In some variations, the DNase contains both the N74 and G105 substitutions, or each of the N74, G105, and A114 substitutions. Particularly suitable amino acid substitutions at these positions are lysine at the position corresponding to N74 of human DNase1, arginine at the position corresponding to G105 of human DNase1, and/or phenylalanine at the position corresponding to A114 of human DNase1. In some embodiments wherein the DNase has at least 90% or at least 95% identity with amino acid sequence shown in residues 21-290 of SEQ ID NO:136, each of the amino acids at positions corresponding to R80, R95, and N96 of SEQ ID NO:136 is alanine or serine. In more specific variations, the DNase has the amino acid sequence shown in (i) residues 21-280 of SEQ ID NO:18, (ii) residues 21-280 of SEQ ID NO:20, (iii) residues 21-280 of SEQ ID NO:152, (iv) residues 21-290 of SEQ ID NO:138, or (v) residues 21-290 of SEQ ID NO:140.

In certain embodiments of a combination therapy method for treating a disease or disorder characterized by NETosis as above, the DNase is contained within a DNase fusion polypeptide comprising, from an amino terminal position to a carboxyl terminal position, D-L1-$X_d$, wherein D is the DNase, L1 is a polypeptide linker (e.g., a linker comprising at least 15 amino acid residues or at least 26 amino acid residues), and $X_d$ is an immunoglobulin Fc region. The immunoglobulin Fc region may be an Fc region as described above for a fusion polypeptide having the formula T-L1-X-L2-P or X-L2-P. In some variations, the DNase fusion polypeptide comprises an amino acid sequence having at least 90% or at least 95% identity with the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140; in some such embodiments, the DNase fusion polypeptide comprises the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140. In certain variations, the DNase comprises the amino acid sequence shown in SEQ ID NO:149, SEQ ID NO:150, SEQ ID NO:153, or SEQ ID NO:154.

In some embodiments of a method for treating a disease or disorder characterized by NETosis, the disease or disorder is an inflammatory lung disease such as, for example, chronic obstructive pulmonary disease (COPD), asthma, cystic fibrosis (CF), bronchiectasis, hypoxia, acute respiratory distress syndrome (ARDS) (e.g., COVID-19-associated ARDS), or interstitial lung disease (e.g., idiopathic pulmonary fibrosis (IPF) or sarcoidosis). In other embodiments, the disease or disorder is an inflammatory skin disease such as, for example, psoriasis or atopic dermatitis. In other embodiments, the disease or disorder is an autoimmune disease such as, e.g., systemic lupus erythematosus (SLE) (e.g., SLE with lupus nephritis), rheumatoid arthritis (RA), psoriasis, antiphospholipid syndrome, type 1 diabetes mellitus, vasculitis, or systemic sclerosis. In other embodiments, the disease or disorder is an autoinflammatory disease such as, for example, an inflammatory bowel disease (IBD) (e.g., Crohn's disease or ulcerative colitis) or gout. In other embodiments, the disease or disorder is a neurological disease or disorder such as, for example, a chronic neurodegenerative disease (e.g., Alzheimer's disease or multiple sclerosis), a central nervous system infection (e.g., meningitis, encephalitis, or cerebral malaria), or ischemic stroke. In other embodiments, the disease or disorder is a metabolic disease such as, e.g., type 2 diabetes or obesity. In other embodiments, the disease or disorder is a cardiovascular disease such as, for example, a cardiovascular disease characterized by atherosclerosis (e.g., coronary heart disease or ischemic stroke). In still other embodiments, the disease or disorder is selected from thrombosis, sepsis, and ischemia reperfusion. In other embodiments, the disease or disorder is a chronic liver disease such as, e.g., nonalcoholic steatohepatitis (NASH). In yet other embodiments, the disease or disorder is a fibrotic disease such as, e.g., systemic sclerosis, systemic lupus erythematosus (SLE), an inflammatory lung disease, a chronic liver disease, or a chronic kidney disease (e.g., lupus nephritis, IgA nephropathy, or membranous glomerulonephritis).

In yet other embodiments of a method for treating a disease or disorder characterized by NETosis, the disease or disorder is a cancer. In certain variations, the cancer treatment is a combination therapy. In some combination therapy embodiments, the combination therapy includes an immunomodulatory therapy comprising an anti-PD-1/PD-L1 therapy, an anti-CTLA-4 therapy, a CAR T cell therapy, or a combination thereof (e.g., both an anti-PD-1/PD-L1 therapy and an anti-CTLA-4 therapy). In other combination therapy embodiments, the combination therapy includes radiation therapy or chemotherapy. In some combination therapy embodiments, the combination therapy includes a targeted therapy: in some such embodiments, the targeted therapy includes (i) a therapeutic monoclonal antibody targeting a specific cell-surface or extracellular antigen (e.g., VEGF, EGFR, CTLA-4, PD-1, or PD-L1) or (ii) a small molecule targeting an intracellular protein such as, for example, an intracellular enzyme (e.g., a proteasome, a tyrosine kinase, a cyclin-dependent kinase, serine/threonine-protein kinase B-Raf (BRAF), or a MEK kinase).

In another aspect, the present invention provides a method for reducing lipid oxidation in a subject. The method generally includes administering to the subject an effective amount of a fusion polypeptide or dimeric protein as described above. In some embodiments, the method is a combination therapy that further reduces NETosis in the subject and that generally includes administering (a) an effective amount of a fusion polypeptide having the formula X-L2-P as described above, or a dimeric protein formed by dimerization of the fusion polypeptide, and (b) an effective amount of a biologically active DNase (e.g., a DNase fusion polypeptide having the formula D-L1-$X_d$ as described above).

In another aspect, the present invention provides a method for protecting a subject from aging. The method generally includes administering to the subject an effective amount of a fusion polypeptide or dimeric protein as described above. In some embodiments, the method is a combination therapy that generally includes administering (a) an effective amount of a fusion polypeptide having the formula X-L2-P as described above, or a dimeric protein formed by dimerization of the fusion polypeptide, and (b) an effective amount of a biologically active DNase (e.g., a DNase fusion polypeptide having the formula D-L1-$X_d$ as described above).

These and other aspects of the invention will become evident upon reference to the following detailed description of the invention.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

A "polypeptide" is a polymer of amino acid residues joined by peptide bonds, whether produced naturally or synthetically. Polypeptides of less than about 50 amino acid residues may also be referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The terms "polynucleotide" and "nucleic acid" are used synonymously herein and refer to a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment that, when read from the 5' to the 3' direction, encodes the sequence of amino acids of the specified polypeptide. Also, for example, in the context of a fusion polypeptide as described herein, different components of the fusion polypeptide (e.g., a DNase, an RNase, a superoxide dismutase (SOD), linker(s), an immunoglobulin Fc region, a paraoxonase) may each be referred to as a polypeptide segment.

The term "biologically active," when used in reference to a polypeptide segment of a fusion molecule as described herein, means a polypeptide that causes a measurable or detectable physiological, biochemical, or molecular effect in a biological system. Biological activities include, for example, enzymatic activity, antigen-binding, binding to a cell-surface receptor, dimerization, activation of a signaling pathway in a eukaryotic cell, induction of cell proliferation, induction of cell differentiation, and the like. When used in specific reference to a polypeptide segment that is a DNase, RNase, paraoxonase (PON), or superoxide dismutase (SOD), "biologically active" means that the polypeptide exhibits the same type of enzymatic activity as a corresponding, naturally occurring enzyme (e.g., the same type of enzymatic activity as a full-length, wild-type human DNase1/DNase1 L3, RNase1, PON1, or SOD1, respectively), allowing for differences in degree of activity, enzyme kinetics, and the like. An immunoglobulin Fc region, as referenced herein, is understood to be "biologically active" at least by virtue of its dimerizing and FcRn-binding activities.

Unless the context clearly indicates otherwise, reference herein to "paraoxonase" (e.g., "paraoxonase 1" or "PON1"), "DNase" (e.g., "DNase1" or "DNase1 L3"), "RNase" (e.g., "RNase 1"), "superoxide dismutase" (e.g., "superoxide dismutase 1" or "SOD1"), "CTLA-4 extracellular domain," and "CD40 extracellular domain" is understood to include naturally occurring polypeptides of any of the foregoing, as well as functional variants and functional fragments thereof.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "enhanced DNase1" as used herein denotes a hyperactive and/or actin-resistant variant of a naturally occurring DNase1 (e.g., human DNase1), the variant having (a) at least one amino acid substitution that decreases G-actin-induced inhibition of endonuclease activity relative to the naturally occurring DNase1, and/or (b) at least one amino acid substitution that increases DNA binding relative to the naturally occurring DNase1. In some embodiments, the enhanced DNase1 comprises the at least one amino acid substitution that decreases G-actin-induced inhibition of endonuclease activity. In some embodiments, the enhanced DNase1 comprises both the at least one amino acid substitution that decreases G-actin-induced inhibition of endonuclease activity and the at least one amino acid substitution that increases DNA binding. In some preferred embodiments, an enhanced DNase1 is a hyperactive variant of wild-type human DNase1 (mature amino acid sequence shown in SEQ ID NO:120).

The term "linker" or "polypeptide linker" is used herein to indicate two or more amino acids joined by peptide bond(s) and linking two discrete, separate polypeptide regions. The linker is typically designed to allow the separate polypeptide regions (such as, e.g., a DNase or paraoxonase polypeptide linked to an Fc region) to perform their separate functions. The linker can be a portion of a native sequence, a variant thereof, or a synthetic sequence. Linkers are also referred to herein using the abbreviation "L." The use of a numerical identifier (e.g., "1" or "2") with "L" is used herein to differentiate among linkers joining different fusion components: "L1" refers to a linker joining the C-terminus of a first biologically active polypeptide that is not a paraoxonase (e.g., a DNase, an RNase, or a SOD1) to the N-terminus of another polypeptide segment such, e.g., an immunoglobulin Fc region, and "L2" refers to a linker joining the N-terminus of a biologically active paraoxonase (e.g., a PON1) to the C-terminus of another polypeptide segment such as, e.g., an immunoglobulin Fc region. In the context of a polypeptide chain containing both L1 and L2 linkers, the linkers may be the same or different with respect to amino acid sequence. In some variations in which the carboxyl-terminus of the first biologically active polypeptide is linked directly to the amino-terminus of a biologically active paraoxonase via a single polypeptide linker (i.e., with no intervening biologically active polypeptide), such polypeptide linker may be referred to as either L1 or L2.

The term "expression cassette" is used to denote a DNA construct that comprises a segment encoding a polypeptide of interest operably linked to additional segments that provide for its transcription in an appropriate host cell. Such additional sequences include a promoter and, typically, a transcription terminator, and may also include one or more selectable markers, an enhancer, a polyadenylation signal, etc.

The term "vector" is used to denote a polynucleotide produced by recombinant DNA techniques for delivering genetic material into a cell, where it can be replicated. As is well-known in the art, it may refer, e.g., to a plasmid, a cosmid, a viral vector, an artificial chromosome, a cloning vector, or an expression vector. The term "expression vector" is used to denote a vector comprising an expression cassette.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "recombinant" when used with reference, e.g., to a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all. By the term "recombinant nucleic acid" herein is meant nucleic acid, originally formed in vitro, in general, by the manipulation of nucleic acid using, e.g., polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein. Similarly, a "recombinant protein" is a protein made using recombinant techniques, i.e., through the expression of a recombinant nucleic acid as depicted above.

The term "heterologous," when used with reference to portions of a nucleic acid, indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, "heterologous," when used in reference to portions of a protein, indicates that the protein comprises two or more subsequences that are not found in the same relationship to each other in nature (e.g., two or more segments of a fusion polypeptide).

As used herein, the term "immunoglobulin" refers to a protein consisting of one or more polypeptides substantially encoded by immunoglobulin gene(s). One form of immunoglobulin constitutes the basic structural unit of an intact, native antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. Immunoglobulins typically function as antibodies in a vertebrate organism. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA*

1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

The term "antibody," as used herein, refers to an immunoglobulin molecule, or a fragment and/or engineered variant thereof, which has the ability to specifically bind to an antigen. The term "antibody" includes intact monoclonal antibodies and antigen-binding antibody fragments such as, e.g., F(ab')2 and Fab fragments. Genetically engineered intact antibodies and fragments, such as chimeric antibodies, humanized antibodies, single-chain Fv fragments, single-chain antibodies, diabodies, minibodies, and the like are also included. Thus, the term "antibody" is used expansively to include any protein that comprises an antigen-binding site and is capable of binding to its antigen.

The term "genetically engineered antibodies" means antibodies wherein the amino acid sequence has been varied from that of a native (i.e., naturally occurring) antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with cells and other effector functions. Typically, changes in the variable region will be made in order to improve the antigen binding characteristics, improve variable region stability, or reduce the risk of immunogenicity.

An "antigen-binding site" is that portion of an antibody that is sufficient to bind to its antigen. The minimum such region is typically an immunoglobulin variable domain or fragment thereof, or a genetically engineered variant of an immunoglobulin variable domain or fragment thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362:367-369, 1993; Qiu et al., *Nature Biotechnol.* 25:921-929, 2007).

Full-length immunoglobulin "light chains" (about 25 Kd or 214 amino acids) are encoded by a variable region gene at the N-terminus (encoding about 110 amino acids) and by a kappa or lambda constant region gene at the C-terminus. Full-length immunoglobulin "heavy chains" (about 50 Kd or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region consists of a framework region interrupted by three hypervariable regions. The term "hypervariable region," also referred to herein as "complementarity determining region" ("CDR"), refers to the amino acid residues of an antibody that are responsible for antigen binding. A CDR may be defined according to any of several known methods of analysis. Examples of such methods include, e.g., the Kabat definition, the Chothia definition, the AbM definition, the IMGT database definition, and the contact definition. The Kabat definition is a standard for numbering the residues in an antibody and is typically used to identify CDR regions (see. e.g., Johnson & Wu, *Nucleic Acids Res.* 28:214-8, 2000). The Chothia definition is similar to the Kabat definition, but the Chothia definition takes into account positions of certain structural loop regions (see, e.g., Chothia et al., *J. Mol. Biol.* 196:901-17, 1986; Chothia et al., *Nature* 342:877-83, 1989). The AbM definition uses an integrated suite of computer programs produced by Oxford Molecular Group that model antibody structure (see, e.g., Martin et al., 1989, *Proc. Natl. Acad. Sci. USA* 86:9268-9272, 1989; "AbM™. A Computer Program for Modeling Variable Regions of Antibodies," Oxford, UK; Oxford Molecular, Ltd.). The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in *PROTEINS, Structure, Function and Genetics Suppl.* 3:194-198, 1999. The IMGT database definition takes into account and combines the definition of the framework (FR) and complementarity determining regions (CDRs), structural data from X-ray deffraction studies, and characterization of hypervariable loops to number the variable regions/structures (see LeFranc, *Immunol. Today* 18:509, 1997). The contact definition is based on an analysis of the available complex crystal structures (see. e.g., MacCallum et al., *J. Mol. Biol.* 5:732-45, 1996). CDRs L1, L2, and L3 of a VL domain are also referred to herein, respectively, as CDR-L1. CDR-L2, and CDR-L3; CDRs H1, H2, and H3 of a VH domain are also referred to herein, respectively, as CDR-H1, CDR-H2, and CDR-H3.

"Framework region" are those variable domain residues other than the hypervariable region residues (e.g., other than the residues of CDRs as defined by the Kabat definition, the Chothia definition, the AbM definition, the IMGT database definition, or the contact definition of CDR). The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs.

An "immunoglobulin hinge" is that portion of an immunoglobulin heavy chain connecting the CH1 and CH2 domains. The hinge region of human γ1 corresponds approximately to Eu residues 216-230.

The terms "Fc fragment," "Fc region," or "Fc domain," as used herein, are synonymous and refer to the portion of an immunoglobulin that is responsible for binding to antibody receptors on cells and the C1q component of complement (in the absence of any amino acid changes, relative to the naturally occurring sequence, to remove such binding activity). Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. As used herein, the term also refers to a single chain consisting of CH3, CH2, and at least a portion of the hinge sufficient to form a disulfide-linked dimer with a second such chain. As used herein, the term Fc region further includes variants of naturally occurring hinge-CH2-CH3 sequences, wherein the variants are capable of forming dimers at least through dimerization of the CH3 domain and including such variants that have increased or decreased Fc receptor-binding or complement-binding activity while retaining at least sufficient binding to the neonatal Fc receptor (FcRn) to confer improved half-life to a fusion partner in vivo (relative to the fusion partner in the absence of the Fc region). The abbreviated term "Fc" may also be used herein to denote "Fc region" when referring to a fusion polypeptide by its general amino- to carboxyl-terminal structure (e.g., "DNase1-L1-Fc-L2-PON1").

As used herein, the term "single-chain antibody" refers to an antibody having an antigen-binding site contained within a single polypeptide chain (e.g., the variable regions from both heavy and light chains within a single polypeptide chain). The term "single-chain Fv" refers to a single-chain antibody that comprises the variable regions from both heavy and light chains but lacks constant regions. In general, a single-chain Fv further comprises a polypeptide linker between the VH and VL domains, which enables it to form the desired structure that allows for antigen binding. Single-chain antibodies are discussed in detail by, for example, Pluckthun in *The Pharmacology of Monoclonal Antibodies*, vol. 113 (Rosenburg and Moore eds., Springer-Verlag, New York, 1994), pp. 269-315. (See also International PCT Publication No. WO 88/01649; U.S. Pat. Nos. 4,946,778 and 5,260,203; Bird et al., *Science* 242:423-426, 1988.) Single-chain antibodies can also be bi-specific and/or humanized.

The term "alternative scaffold protein" refers to a non-antibody protein in which one or more regions may be diversified to produce one or more binding domains that specifically bind to a target molecule (e.g., an inflammatory cytokine such as TNFα or TGF-β). In some embodiments, the binding domain binds the target molecule with specificity and affinity similar to that of an antibody. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), protein A (e.g., Affibody®), ankyrin repeats (e.g., DARPins), gamma-B-crystallin/ubiquitin (e.g., Affilins), CTLD₃ (e.g., Tetranectins), Fynomers, and Avimers. Additional information on alternative scaffolds is provided in Binz et al., *Nat. Biotechnol.* 23:1257-1268, 2005; Skerra, *Current Opin. in Biotech.* 18:295-304, 2007; and Silacci et al., *J. Biol. Chem.* 289:14392-14398, 2014.

The term "antiTNFα" or "antiTGFβ," as used herein when referring to a fusion polypeptide by its general amino- to carboxyl-terminal structure (e.g., "antiTNFα-L1-Fc-L2-PON1" or "antiTGFβ-L1-Fc-L2-PON1"), refers to a polypeptide (e.g., single-chain antibody) that specifically binds and neutralizes TNFα or TGFβ, respectively.

"Dimerizing domain," as used herein, refers to a polypeptide having affinity for a second polypeptide, such that the two polypeptides associate under physiological conditions to form a dimer. Typically, the second polypeptide is the same polypeptide, although in some variations the second polypeptide is different. The polypeptides may interact with each other through covalent and/or non-covalent association(s). Examples of dimerizing domains include an Fc region; a hinge region; a CH3 domain; a CH4 domain; a CH1 or CL domain; a leucine zipper domain (e.g., a jun/fos leucine zipper domain, see, e.g., Kostelney et al., *J. Immunol.*, 148:1547-1553, 1992; or a yeast GCN4 leucine zipper domain); an isoleucine zipper domain; a dimerizing region of a dimerizing cell-surface receptor (e.g., interleukin-8 receptor (IL-8R); or an integrin heterodimer such as LFA-1 or GPIIIb/IIIa); a dimerizing region of a secreted, dimerizing ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al., *J. Biol. Chem.* 269:27833-27839, 1994, and Radziejewski et al., *Biochem.* 32:1350, 1993); and a polypeptide comprising at least one cysteine residue (e.g., from about one, two, or three to about ten cysteine residues) such that disulfide bond(s) can form between the polypeptide and a second polypeptide comprising at least one cysteine residue (hereinafter "a synthetic hinge"). A preferred dimerizing domain in accordance with the present invention is an Fc region.

The term "dimer" or "dimeric protein" as used herein, refers to a multimer of two ("first" and "second") fusion polypeptides as disclosed herein linked together via a dimerizing domain. Unless the context clearly indicates otherwise, a "dimer" or "dimeric protein" includes reference to dimerized first and second fusion polypeptides in the context of higher order multimers that may be created by inclusion of an additional dimerizing domain in a first or second fusion polypeptide (e.g., a first fusion polypeptide comprising an immunoglobulin light chain and a second fusion polypeptide comprising an immunoglobulin heavy chain can heterodimerize via the interaction between the CH1 and CL domains, and two such heterodimers may further dimerize via the Fc region of the immunoglobulin heavy chain, thereby forming a tetramer).

The term "domain that specifically binds to the neonatal Fc receptor (FcRn)" or "FcRn-binding domain," as used herein, means a polypeptide that (i) binds to FcRn with a high affinity at pH 5.8, typically with a binding affinity ($K_a$) of $10^6$ $M^{-1}$ or greater (e.g., $10^7$ $M^{-1}$ or greater, $10^8$ $M^{-1}$ or greater, or 109 $M^{-1}$ or greater), and (ii) does not have affinity for FcRn at physiological pH (e.g., pH 7.4). The binding affinity of a polypeptide for FcRn can be readily determined by one of ordinary skill in the art, for example, by Scatchard analysis (Scatchard, *Ann. NY Acad. Sci.* 51:660, 1949). Typically, a FcRn-binding domain does not significantly cross-react with polypeptides related to FcRn. A polypeptide does not significantly cross-react with a polypeptide related to FcRn if, for example, it detects FcRn, but not presently known FcRn-related polypeptides, using a molecular binding assay such as, e.g., a multiwell plate assay (e.g., ELISA), a filter assay, or a surface plasmon resonance assay. Examples of known related polypeptides include known members of the major histocompatibility complex (MHC) class I protein family. An FcRn-binding domain is not mutually exclusive of a dimerizing domain, i.e., a dimerizing domain can also be an FcRn-binding domain. Examples of FcRn-binding domains that are also dimerizing domains include Fc regions that retain FcRn-binding activity.

Fusion polypeptides of the present disclosure may be referred to herein by formulae such as, for example, "DNase1-L1-Fc," "DNase1 L3-L1-Fc," "DNase1-L1-Fc-L2-PON1," "DNase1L3-L1-Fc-L2-PON1," "RNase1-L1-Fc-L2-PON1," "SOD1-L1-Fc-L2-PON1," "anti-TNFα-L1-Fc-L2-PON1," or "anti-TGFβ-L1-Fc-L2-PON1." In each such case, unless the context clearly dictates otherwise, a term referring to a particular segment of a fusion polypeptide (e.g., "DNase1," "DNase1 L3," "PON1," "RNase1," "SOD1," "L1" or "L2" (for first or second polypeptide linkers, respectively), "Fc" (for "Fc region"), etc.) is understood to have the meaning ascribed to such term herein and is inclusive of the various embodiments as described herein.

The term "disease or disorder characterized by NETosis," as used herein, means a disease or disorder in which NETosis—the process wherein activated neutrophils extrude DNA bound with cytoplasmic and granule proteins, called neutrophil extracellular traps (NETs)—plays at least some part of the clinicopathology.

The term "effective amount," in the context of treatment of a disease by administration of a soluble fusion polypeptide or dimeric protein to a subject as described herein, refers to an amount of such molecule that is sufficient to inhibit the occurrence or ameliorate one or more symptoms of the disease. For example, in the specific context of treatment of an inflammatory lung disease by administration of a fusion protein to a subject as described herein, the term "effective amount" refers to an amount of such molecule that is sufficient to modulate an inflammatory response in the subject so as to inhibit the occurrence or ameliorate one or more symptoms of the inflammatory lung disease. An effective amount of an agent is administered according to the methods of the present invention in an "effective regime." The term "effective regime" refers to a combination of amount of the agent being administered and dosage frequency adequate to accomplish treatment or prevention of the disease.

The term "patient" or "subject," in the context of treating a disease or disorder as described herein, includes mammals such as, for example, humans and other primates. The term also includes domesticated animals such as, e.g., cows, hogs, sheep, horses, dogs, and cats.

The term "combination therapy" refers to a therapeutic regimen that involves the provision of at least two distinct therapies to achieve an indicated therapeutic effect. For example, a combination therapy may involve the administration of two or more chemically distinct active ingredients, or agents, for example, a soluble PON1 fusion polypeptide or dimeric protein according to the present invention and another agent such as, e.g., another anti-inflammatory or immunomodulatory agent. Alternatively, a combination therapy may involve the administration of a soluble PON1 fusion polypeptide or dimeric protein according to the present invention, alone or in conjunction with another agent, as well as the delivery of another therapy (e.g., radiation therapy). The distinct therapies constituting a combination therapy may be delivered, e.g., as simultaneous, overlapping, or sequential dosing regimens. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires and as determined by the attending physician.

The term "targeted therapy," in the context of treating cancer, refers to a type of treatment that uses a therapeutic agent to identify and attack a specific type of cancer cell, typically with less harm to normal cells. In some embodiments, a targeted therapy blocks the action of an enzyme or other molecule involved in the growth and spread of cancer cells. In other embodiments, a targeted therapy either helps the immune system to attack cancer cells or delivers a toxic substance directly to cancer cells. In certain variations, a targeted therapy uses a small molecule drug or a monoclonal antibody as a therapeutic agent.

The phrase "protect from aging," as used herein, refers to inhibition or mitigation of any of broad aspects of aging, including, for example, age-related changes in systemic inflammation or disease risk, as indicated by accepted biomarkers. Protection from aging may also include treatment of an age-related disease where the disease is present in a subject, such as, for example, a chronic inflammatory, autoimmune, neurodegenerative, cardiovascular, or fibrotic disease.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison. Wisconsin). Other methods for comparing amino acid sequences by determining optimal alignment are well-known to those of skill in the art. (See, e.g., Peruski and Peruski, *The Internet and the New Biology: Tools for Genomic and Molecular Research* (ASM Press, Inc. 1997). Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 90%, or at least 95% sequence identity relative to each other.

Percent sequence identity is determined by conventional methods. (See, e.g., Altschul et al., *Bull. Math. Bio.* 48:603, 1986, and Henikoff and Henikoff, *Proc. Natl. Acad. Sci. USA* 89:10915, 1992.) For example, two amino acid sequences can be aligned to optimize the alignment scores using a gap opening penalty of 10, a gap extension penalty of 1, and the "BLOSUM62" scoring matrix of Henikoff and Henikoff, supra. The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and a second amino acid sequence. The FASTA algorithm is described by Pearson and Lipman, *Proc. Nat'l Acad. Sci. USA* 85:2444, 1988, and by Pearson, *Meth. Enzymol.* 183:63, 1990. Briefly, FastA first characterizes sequence similarity by identifying regions shared by the query sequence (e.g., residues 16-355 or 26-355 of SEQ ID NO:6) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=blosum62. These parameters can be introduced into a FASTA program by modifying the scoring matrix file ("SMATRIX"), as explained in Appendix 2 of Pearson, *Meth. Enzymol.* 183:63, 1990.

The term "corresponding to," when applied to positions of amino acid residues in a reference sequence to describe positions within a subject sequence, means corresponding positions in the subject sequence when the reference and subject sequences are optimally aligned.

When such a value is expressed as "about" X or "approximately" X, the stated value of X will be understood to be accurate to ±10%.

Where aspects or embodiments of the present invention are described in terms of a Markush group or other grouping of alternatives, the present invention encompasses not only the entire group listed as a whole, but each member of the group individually and all possible subgroups of the main group. The present invention also envisages the explicit exclusion of one or more of any of the group members as embodiments.

DESCRIPTION OF THE INVENTION

I. Overview

Figure 1:
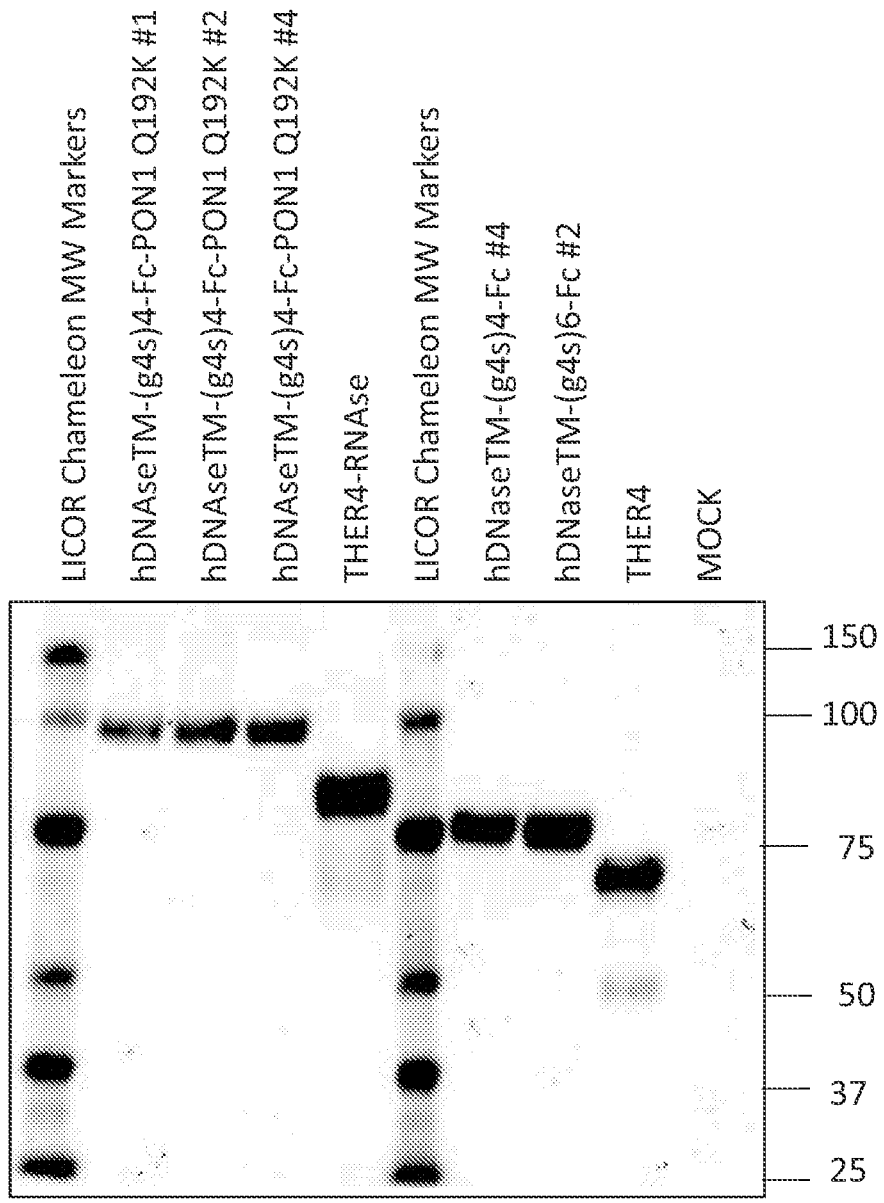
FIG. 1 shows a Western blot of culture supernatants (serum free) from transiently transfected HEK293 cells expressing DNase1-Fc and DNase1-Fc-PON1 fusion proteins. Transfections and Western blot analysis were performed as described in Example 1, infra. From left to right: Lane 1—LICOR Chameleon™ molecular weight markers; Lane 2, Lane 3, Lane 4—transfection supernatants from three different individual clones (#1, #2, #4) of hDNase™-(g4s)4-Fc-PON1-Q192K; Lane 5—THER4-RNase (control); Lane 6—LICOR Chameleon MW Markers; Lane 7—hDNase™-(g4s)4-Fc #4; Lane 8—hDNase™-(g4s)6-Fc #2; Lane 9—THER4 (control); Lane 10—mock transfection.

The present invention provides compositions and methods relating to paraoxonase fusion polypeptides. In certain aspects, a fusion polypeptide comprises a first biologically active polypeptide linked amino-terminal to a biologically active paraoxonase, wherein the first biologically active polypeptide is selected from a DNase, an RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes an inflammatory cytokine (e.g., a polypeptide that specifically binds and neutralizes tumor necrosis factor α (TNFα) or transforming growth factor-β (TGFβ)). In some aspects, the fusion polypeptide further includes a second biologically active polypeptide linked carboxyl-terminal to the first biologically active polypeptide and amino-terminal to the paraoxonase. The second biologically active polypeptide may be, for example, a dimerizing domain or a domain that specifically binds to the neonatal Fc receptor (FcRn). A particularly suitable second biologically active polypeptide is a dimerizing and FcRn-binding immunoglobulin heavy chain constant region such as, e.g., an immunoglobulin Fc region.

In other aspects, a fusion polypeptide comprises a biologically active paraoxonase linked carboxyl-terminal to a dimerizing domain or domain that specifically binds to FcRn (for example, a dimerizing and FcRn-binding immunoglobulin heavy chain constant region such as, e.g., an immunoglobulin Fc region), wherein the fusion polypeptide does not comprise a biologically active polypeptide amino-terminal to the dimerizing or FcRn-binding domain.

In other aspects, a fusion polypeptide comprises a biologically active paraoxonase linked amino-terminal to a dimerizing domain or domain that specifically binds to FcRn (for example, a dimerizing and FcRn-binding immunoglobulin heavy chain constant region such as, e.g., an immunoglobulin Fc region).

A preferred paraoxonase in fusion polypeptides of the present disclosure is a paraoxonase 1 (PON1) polypeptide. Particularly suitable PON1 polypeptides lack an amino-terminal leader sequence corresponding to the naturally occurring, non-cleaved leader sequence of PON1 (generally corresponding to residues 1-15 of human PON1 (SEQ ID NO:4)). The association of PON1 with high density lipoprotein (HDL) in serum is primarily dependent on the direct binding of the hydrophobic, non-cleaved leader to phospholipids (see Sorenson et al., *Arterioscler. Thromb. Vasc. Biol.* 19:2214-2225, 1999). The removal of this leader sequence removes PON1 from HDL binding and facilitates the retargeting of PON1 to other sites for therapeutic benefit in accordance with the present disclosure. For example, in the context of a fusion polypeptide comprising a DNase or RNase as described herein, retargeting PON1 to DNA or RNA directs the molecule to inflammatory NETs and sites of cellular death. In addition to targeting DNA or RNA at these sites, DNase-PON1 or RNase-PON1 fusion molecules as described herein can help to direct a PON1 enzyme to myeloperoxidase, another important inflammatory NET target. Also, a fusion polypeptide comprising a superoxide dismutase 1 (SOD1) as described herein provides a molecule in which PON1 can digest the hydrogen peroxide ($H_2O_2$) produced by the action of SOD1 on superoxide, thereby providing, e.g., an improved antioxidant for lung therapy. Further, fusion molecules comprising other biologically active polypeptides in accordance with the present invention (e.g., a CTLA-4 extracellular domain, a CD40 extracellular domain, or a polypeptide that specifically binds and neutralizes an inflammatory cytokine) can target PON1 to other sites of proinflammatory and/or immune cell activation for therapeutic benefit such as described herein.

Paraoxonase fusion molecules of the present invention may be used for the treatment of various diseases or disorders through its antioxidant, anti-inflammatory, atheroprotective, and/or neuroprotective properties, including, e.g., treatment of an autoimmune or inflammatory disease. For example, studies support use of a paraoxonase for treatment of autoimmune disease such as systemic lupus erythematosus (SLE). The autoantibody titer in many patients with systemic lupus erythematosus (SLE) is correlated with loss of activity of PON1 (see Batukla et al., *Ann. NY Acad. Sci.* 1108:137-146, 2007), and SLE-disease activity assessed by SLEDAI and SLE disease related organ damage assessed by SLICC/ACR damage index are negatively correlated with PON1 activity (see Ahmed et al., *EXCLI Journal* 12:719-732, 2013). Other studies support use of a paraoxonase for treatment of inflammatory disease such as inflammatory lung diseases. Studies strongly suggest, for example, that PON1 is important in protection from lung inflammation, and further show that low PON1 activity is associated with lung diseases such as, e.g., asthma, chronic obstructive pulmonary disease (COPD), and interstitial lung disease (e.g., idiopathic pulmonary fibrosis (IPF) or sarcoidosis) (see, e.g., Sahiner et al., *WAO Journal* 4:151-158, 2011; Emin et al., *Allergol. Immunopathol.* (Madr) 43:346-352, 2014; Sarioglu et al., *Iran J. Asthma Immunol.* 14:60-66, 2015; Tolgyesi et al., *Internat. Immunol.* 21:967-975, 2009; Chen et al., *J. Cell Biochem.* 119:793-805, 2018; Rumora et al., *J. COPD* 11:539-545, 2014; Rajkovic et al., *J. Clin. Path.* 71:963-970, 2018; Ivanisevic et al., *Eur. J. Clin. Invest.* 46:418-424, 2016; Uzun et al., *Curr. Med. Res. Opin.* 24:1651-1657, 2008; Okur et al., *Sleep Breath.* 17:365-371, 2013; Golmanesh et al., *Immunopharmacol. And Immunotoxicol.* 35:419-425, 2013). Another study showed that low PON1 activity is correlated with the severity of Crohn's disease (Sczceklik et al., *Molecules* 23:2603, 2018). In addition, recombinant PON1 therapy has shown efficacy in animal models of organophosphate poisoning and colitis (see, e.g., Valiyaveettil et al., *Biochem. Pharmacol.* 81:800-809, 2011; Valiyaveettil et al., *Toxicol. Letters* 202:203-208, 2011; Bajaj et al., *Appl. Biochem. Biotechnol.* 180:165, 2016; Stevens et al., *Proc. Natl. Acad. Sci. USA* 105:12780-12784, 2008; Yamashita et al., *J. Immunol.* 191:949-960, 2013).

Paraoxonase fusion molecules as described herein may also be used, e.g., for treatment of a neurological disease. For example, PON1 is protective in the brain because of its antioxidant properties. A neuroprotective role of PON1 is supported by studies showing that PON1 activity is decreased in patients with Alzheimer's disease and other dementias (see, e.g., Menini et al., *Redox Rep.* 19:49-58, 2014). In addition, a study using a PON1 fusion containing a protein transduction domain to transduce PON1 into cells and tissues showed that PON1 transduction protected microglial cells in vitro from oxidative stress-induced inflammatory responses and protected against dopaminergic neuronal cell death in a Parkinson's disease model (see Kim et al., *Biomaterials* 64:45-56, 2015).

Bispecific fusions further comprising a DNase provide additional therapeutic benefit for the treatment of diseases amenable to PON-mediated therapy, including, for example, in treatment of diseases or disorders characterized by NETosis. NETs, which cause tissue damage by themselves or by increasing the pro-inflammatory response (see Mutua and Gershwin, *Clin. Rev. Allergy Immunol.*, 2020), are implicated in a variety of serious diseases and conditions. For example, NETs can play a role in enhancement of inflammation seen in autoimmune disease, including, e.g., systemic lupus erythematosus (SLE) (e.g., SLE with lupus nephritis), rheumatoid arthritis, and psoriasis, and are also associated with autoinflammatory diseases such as, for example, inflammatory bowel disease (IBD) (see id.). NETs also play a role in sepsis, metabolic diseases (e.g., type 2 diabetes and obesity), neurological diseases (e.g., Alzheimer's disease, multiple sclerosis, meningitis, cerebral malaria, and ischemic stroke), infectious disease, cardiovascular disease and thrombosis, tumor progression and metastasis, liver disease (e.g., alcohol-associated liver disease (ALD), portal hypertension, nonalcoholic fatty liver disease (NAFLD) such as nonalcoholic steatohepatitis (NASH), and complications following liver transplantation), and various inflammatory lung diseases, including, e.g., cystic fibrosis, asthma, chronic obstructive pulmonary disease (COPD), and COVID-19-associated acute respiratory distress syndrome (ARDS) (see, e.g., id.; Brinkmann, *J. Innate Immun.* 10:422-431, 2018; Liu et al., *Chinese Med. Journal* 130:730-736, 2017; Twaddell et al., *CHEST* 156:774-782, 2019; Uddin et al., *Front. Immunol.* 10:47, 2019; Middleton et al., *Blood* 136:1169, 2020; Zuo et al., *JCI Insight* 5:e138999, 2020; Barnes et al., *J. Exp. Med.* 217:e20200652, 2020; Hilscher and Shah, *Semin. Liver Dis.* 40:171-179, 2020). The use of DNase for the treatment of diseases or disorders characterized by NETosis is further supported, for example, by the use of recombinant wild-type DNase (Pulmozyme®) for treatment of cystic fibrosis, a current clinical trial of Pulmozyme in COVID-19 patients (NCT04359654), and several animal model studies, including, e.g., models of acute asthma, silica-induced lung inflammation, acute lung injury, cancer, colitis, ischemia reperfusion, sepsis, and thrombosis (see, e.g., da Cunha et al., *Exp. Lung Res.* 42:66, 2016; Benmerzoug et al., *Nat. Comm.* 9:5226, 2018; Caudrillier et al., *J. Clin. Invest.* 122:2661, 2012; Cools-Lartigue et al., *J. Clin. Invest.* 123:3446, 2013; Park et al., *Sci. Translational Med.* 8:361ra138, 2016; Trejo-Becirril et al., *Integrative Cancer Therapies* 15:NP35-NP43, 2016; Thalin et al., *PloS ONE* 13:e0191231, 2018; Babicova et al., *Folia Biolica (Praha)* 64:10, 2018; Li et al., *J. Crohns Colitis* 2020, 14:240-253, 2020; Albadawi et al., *J. Vasc. Surg.* 64:484, 2016; Peer et al., *Am. J. Nephrol.* 43:195, 2016; Mai et al., *Shock* 44:166, 2015; Brill et al., *J. Thrombosis Haemostasis* 10:136, 2012; Manda-Handzlik and Demkow, *Cells* 8:1477, 2019; Delgado-Rizo et al., *Front. Immunol.* 8:81, 2017).

Bispecific fusions further comprising a DNase as described herein are also useful in treatment of antiphospholipid syndrome (APLS). Antiphospholipid syndrome is an autoimmune disease characterized by antibodies to phospholipids that cause a hypercoagulable state. Thrombosis occurs in both arteries and veins and causes pregnancy complications including miscarriage and stillbirths. Antiphospholipid syndrome can be primary (occurring in the absence of any other related disease) or secondary (occurring with another autoimmune disease such as, e.g., SLE). In rare cases, APLS leads to rapid organ failure due to generalized thrombosis; this is termed catastrophic antiphospholipid syndrome (CAPS or Asherson syndrome) and is associated with a high risk of death. Patients with acute respiratory distress associated with COVID-19 have antiphospholipid antibodies that promote thrombosis in vitro and in mouse thrombosis models (Zuo et al., *JCI Insight* 5:e138999, 2020; Zuo et al., *Sci. Trans. Med.* 12:eabd3876, 2020). The antiphospholipid antibodies stimulate neutrophil NET formation, providing a scaffold for thrombus formation. Digestion of NETs by DNase fusions as described herein can prevent thrombus formation and can help dissolve existing clots to restore blood flow. DNase fusion molecules of the present invention may also be used together with thrombolytics including, e.g., tPA, urokinase, and streptokinase.

Paraoxonase fusion molecules as described herein, including embodiments further comprising, e.g., a DNase, may also be used for treatment of an inflammatory skin disease. Many studies have reported the involvement of reactive oxygen species and lipid peroxidation in the pathogenesis of inflammatory skin diseases (see, e.g., Simonetti et al., *Antioxidants* 10:697, 2021). For example, significantly lower levels of paraoxonase 1 (PON1) and a significantly higher levels of myeloperoxidase (MPO) and lipid peroxides have been found in atopic dermatitis (see id.), and increased MPO and decreased PON1 activity have also been described in psoriatic children (see Bacchetti et al., *Archives of Dermatological Research* 312:33-39). In psoriasis and atopic dermatitis, neutrophil activation during inflammation leads to extruded NETs with attached MPO, causing the oxidation of lipids and damaging PON1 enzyme, which normally protects lipids from oxidation by digesting lipid peroxides. The digestion of NETs with DNase1 releases the attached MPO, allowing its clearance and removing a primary driver of oxidation, and therapy with PON1 restores protection from oxidative damage and rebalances the redox potential in patients. Thus, PON1 and DNase therapies are particularly effective as a combination.

Paraoxonase fusion molecules as described herein, including embodiments further comprising a DNase, may also be used to protect from aging. Oxidative stress is known to be a primary cause of aging. In particular, oxidized lipids are a key target for aging because of their promotion of inflammation through uptake by macrophage scavenger receptors and their damage to vascular endothelial cells. See, e.g., Moldogazieva et al. (*Oxidative Medicine and Cellular Longevity*, Volume 2019, Article ID 3085756) and Barrera et al. (*Antioxidants* 7:102, 2018) for discussions on the link between lipid oxidation and aging. See also Hajri (*Frontiers In Bioscience, Landmark* 23:1822-1847, 2018), which describes the toxic effects of oxidized lipids on inflammation and cardiac function. PON1 is known to protect lipids from oxidation by digestion of lipid peroxides. Thus, there is a direct link between increasing PON1 enzyme levels and slowing of aging. In addition, PON1 enzyme activity is known to be deficient in multiple age-related diseases including cardiovascular disease, autoimmune disease, and pulmonary disease, showing that there is a clinical need for increased PON1. In addition, embodiments further comprising a DNase are particularly useful for slowing aging because of the ability of DNase to digest NETs. NETs are a primary driver of inflammation and oxidative stress because they provide the scaffold for myeloperoxidase (MPO) and elastase produced by neutrophils and other cells. Digestion of the NETs by DNase allows the release and clearance of the inflammatory enzymes. DNase also eliminates inflammatory activation through other DNA sensing pathways (e.g., STING, TLR9).

Bispecific fusions further comprising an RNase as described herein have anti-inflammatory properties by digesting extracellular RNA derived from dead and dying cells, including, e.g., extracellular RNA associated with NETs. Extracellular RNA synergizes, for example, with TLR2 agonists to potentiate a macrophage inflammatory response and digestion of this RNA prevents inflammation through TLR2 (see Noll et al., *PloS ONE* 12:e0190002, 2017).

RNase-containing fusions provide additional therapeutic benefit for treatment of various diseases, including, e.g., autoimmune disease, inflammatory disease (e.g., inflammatory lung disease), type 2 diabetes, infectious disease, cardiovascular disease (e.g., coronary artery disease, stroke), neurodegenerative disease (e.g., Alzheimer's disease), and cancer. For example, several studies support use of an RNase for treatment of an inflammatory lung disease. One study has shown that TLR3, an RNA sensor, has a major role in the development of ARDS-like pathology in the absence of a viral pathogen (see Murray et al., *Am. J. Respir. Crit. Care Med.* 178:1227-1237, 2008). Oxygen therapy is a major therapeutic intervention in ARDS, but contributes to further lung damage and susceptibility to viral infection. Oxygen therapy was a major stimulus for increased TLR3 expression and activation in cultured human epithelial cells, and absence or blockade of TLR3 protected mice from lung injury and inflammation after exposure to hyperoxic conditions (see Murray et al., supra). Another study has shown that TLR3 activation by extracellular RNA occurs in response to acute hypoxia, and that therapy in mice with RnaseA diminished lung inflammation after acute hypoxia (see Biswas et al., *Eur. J. Immunol.* 45: 3158-3173, 2015).

Other studies support use of an RNase for treatment of an autoimmune disease such as, for example, systemic lupus erythematosus (SLE). Studies show, for example, a role of RNA immune complexes and RNA receptors, including TLR7, in SLE disease pathogenesis, as well as a protective effect of RNase overexpression in mouse models of SLE (see, e.g., Sun et al., *J. Immunol.* 190:2536-2543, 2013).

RNase-containing fusion molecules as described herein can digest RNA contained in exosomes. For a review of exosomes in lung disease, see Hough et al., *Allergy* 72:534-544, 2017. RNase1 can translocate through cellular membranes into the cytosol because of its basic charge (see Chao et al., *Biochem.* 50:8374-8382, 201.1; Haigas et al., *J. Cell Sci.* 116:313-324, 2003; Johnson et al., *Biochem.* 46:10308-10316, 2007). Cytoplasmic inhibitor binds to RNase1 with very high affinity and protects intact cells from RNase toxicity. However, extracellular RNA including RNA in extracellular vesicles, is not protected by cytoplasmic inhibitor (see Mironova et al., *Oncotarget* 8: 78796-78810, 2017).

Fusion molecules comprising an RNase as described herein can further target microRNA (miRNA), small, extracellular noncoding RNAs involved in posttranscriptional gene regulation. miRNA dysregulations are linked to a wide spectrum of diseases, including lung disease, proliferative vascular disease, cardiac disorders, kidney diseases, diabetes mellitus, fibrosis and cancer (see Rajasekaran et al., *Front. Pharmacol.* 6:254, 2015; Thum et al., *Nature* 456:980-984, 2008; Kato et al., *Clin. J. Am. Soc. Nephrol.* 4:1255-1266, 2009; Lee and Dutta, *Annu. Rev. Pathol.* 4:199-227, 2009; Kumar et al., *Protein Cell.* 3:726-738, 2012; Noetel et al., *Front. Physiol.* 3:49, 2012; Zampetaki and Mayr, *Circ. Res.* 110:508-522, 2012). For example, microRNA-33 is overexpressed in granulomatous lung tissue in murine models and in BAL fluid of patients with sarcoidosis (Barna et al., *Am. J. Respir. Cell Mol. Biol.* 54:865-871, 2016). microRNA-33 downregulates cholesterol transporters ABCA1 and ABCG1, promoting cholesterol accumulation in alveolar macrophages and foam cell formation. Another target is microRNA-466, which has been shown to be secreted in exosomes in a mouse model of acute respiratory distress syndrome (ARDS) where it activated the NLRP3 inflammasome (Shikano et al., *BMC Pulmonary Med.* 19:110, 2019).

Other targets of RNase-containing fusions as described herein include viral RNAs such as, e.g., proviral microRNAs released in the lung during influenza virus infection (see Scheller et al., *J. Inf. Dis.* 219:540-543, 2019) or HIV single-stranded RNA that was reported to stimulate macrophage foam cell formation through TLR8 binding (see Bernard et al., *PloS ONE* 9:e104039, 2014). Other viral RNA targets include coronavirus RNA (e.g., SARS-CoV-2 RNA).

Studies also support use of RNase for treatment of, e.g., cancer, ischemia/reperfusion injury, graft rejection, atherosclerotic plaque formation, myocardial infarction, acute stroke, and postoperative cognitive decline (see, e.g., Rutkoski et al., *Translational Oncology* 6:392-397, 2013; Mironova et al., *Oncotarget.* 8:78796-78810, 2017; Eller et al., *ACS Central Sci.* 1:181-190, 2015; Kleinert et al., *J. Am. Heart Assn.* doi: 10.1021, 2016; Simsekyilmaz et al., *Circulation* 129: 598-606, 2014; Steiger et al., *JAMA* 6:e004541, 2017; Walberer et al., *Curr. Neovas.* Res. 6:12-19, 2009; Chen et al., *PloS One* 10:e0134307, 2015).

A bispecific paraoxonase fusion molecule comprising a superoxide dismutase (SOD1) as described herein provides additional therapeutic benefit in protection from oxidative stress. The role of SOD1 in protection from oxidative damage is reviewed, e.g., by Ighodaro and Akinolye, *Alexandria J. Med.* 54:287-293, 2018. In its native form, SOD1 is an intracellular enzyme (see id.). In accordance with the present disclosure, a SOD1 polypeptide segment is used as an extracellular enzyme that works in conjunction with the paraoxonase segment of the fusion molecule to provide an improved antioxidant for therapy. For example, paraoxonase can digest hydrogen peroxide ($H_2O_2$), a product of the SOD1 enzymatic reaction. In addition, digestion of $H_2O_2$ will suppress the activity of myeloperoxidase that is associated with NETs. The coordinated activity of SOD1 and paraoxonase will improve the activity in protection from tissue damage and inflammation in patients with diseases associated with NET production. SOD1-PON molecules according to the present invention are particularly useful, for example, in treatment of inflammatory lung diseases such as, e.g., asthma, chronic obstructive pulmonary disease (COPD), sarcoidosis, and interstitial lung disease. In some preferred embodiments, the SOD1-PON fusion further includes a dimerizing domain such as, e.g., an immunoglobulin Fc region; such variations are particularly compatible with SOD1, which, in its native form, is a dimer stabilized by a disulfide bond.

A bispecific paraoxonase fusion molecule comprising a CTLA-4 extracellular domain as described herein is particularly useful for treatment of inflammatory and autoimmune disease, including, e.g., rheumatoid arthritis (RA) and inflammatory lung disease. Oxidized cholesterol activates inflammatory responses in macrophages and endothelial cells (see Miller and Shyy, *Trends Endocrinol. Metabol.* 28:143-152, 2017), and PON1 can suppress this inflammation by protecting lipoproteins from oxidation. The immunosuppressive properties of a soluble CTLA-4 (e.g., Abatacept or other CTLA4-Fc) are compatible with paraoxonase enzyme activity so that a CTLA4-PON molecule will retain the activity of both components and have improved activity in fibrotic lung disease and autoimmune/inflammatory disease. A CTLA4-PON1 molecule, for example, will bind to CD80 and CD86 that are expressed on activated antigen presenting cells, including monocytes and dendritic cells, where the PON1 enzyme will remain active. This molecule is effective in inhibiting activation of T cells, macrophages, and dendritic cells, and will also reduce oxidative stress in tissues such as, e.g., inflamed lungs.

A bispecific paraoxonase fusion molecule comprising a CD40 extracellular domain as described herein provides additional therapeutic benefit by suppressing the proinflammatory activation events associated with the CD40-CD154 signaling pathway. The CD40-CD154 pathway has been implicated, for example, in fibrotic disease, including fibrosis in inflammatory lung disease and injury (see. e.g., Kaufman et al., *J. Immunol.* 172:1862-1871, 2004), and studies support the use of molecules that suppress this pathway for treatment of fibrotic and inflammatory lung disease (see, e.g., Adawi et al., *Clin. Immunol. Immunopathol.* 89:222-230, 1998; Adawi et al., *Am. J. Pathol.* 152: 651-657, 1998; Cheng et al., *BioMed. Research Intl. Volume* 2020, Article ID 7840652, 2020; Xiong et al., *J. Cell. Mol. Med.* 23:740-749, 2018). CD40-PON fusions of the present invention provide molecules that inhibit both inflammation and adaptive immunity, including e.g., molecules with improved activity in lung disease and autoimmune/inflammatory disease. For example, a CD40-PON1 fusion may provide improved activity in lung diseases where CD40 activation exacerbates inflammatory processes, and where paraoxonase levels are low or absent, including asthma, COPD, hypoxia, and interstitial lung disease (e.g., idiopathic pulmonary fibrosis (IPF) or sarcoidosis). CDO40-PON1 fusions are also beneficial, for example, for treatment of liver disease (e.g., chronic liver disease such as, for example, alcohol-associated liver disease (ALD), portal hypertension, nonalcoholic steatohepatitis (NASH), or complications following liver transplantation) and kidney disease (e.g., chronic kidney disease such as, for example, lupus nephritis, IgA nephropathy, or membranous glomerulonephritis).

In some embodiments, a paraoxonase fusion molecule of the present invention comprises a variant CD40 extracellular domain having increased binding to CD154. For example, one or more single amino acid substitutions can be made at specific residues to improve binding to CD40 ligand (see, e.g., US Patent Application Publication No. 2014/0120091, incorporated by reference herein). Such CD40 extracellular domain variants may be fused to a human IgG1 (γ1) Fc variant with impaired FcR binding to provide CD40-Fc variants that do not induce platelet activation or aggregation in vitro, avoiding toxicity from simultaneous binding to CD40 and FcγRIIa on human platelets. Activation of platelets and thrombosis has been shown to occur due to cross-linking of FcR on platelets with antigens on the platelet surface such as VEGF, CD40, and CD40L (see Taylor et al., *Blood* 96:4254, 2020; Meyer el al., *J. Thromb. Haemost.* 7:151, 2009).

Bispecific fusion molecules comprising a polypeptide that specifically binds and neutralizes TNFα or TGF-β as described herein provide additional therapeutic benefit through inhibition of inflammatory, immune, and/or other cellular responses mediated by these cytokines. A paraoxonase fusion comprising an anti-TNFα component may be used, for example, to treat an inflammatory disease or autoimmune disease such as, e.g., rheumatoid arthritis (RA), an inflammatory lung disease (e.g., asthma, chronic obstructive pulmonary disease (COPD), acute lung injury (ALI), acute respiratory distress syndrome (ARDS), or interstitial lung disease (e.g., idiopathic pulmonary fibrosis or sarcoidosis)), an inflammatory bowel disease (IBD) (e.g., Crohn's disease or ulcerative colitis), or an inflammatory skin disease (e.g., psoriasis or atopic dermatitis). A paraoxonase fusion comprising an anti-TGF-β component may be used, for example, to treat an inflammatory disease, a fibrotic disease, or type 1 diabetes. In some embodiments, an inflammatory or fibrotic disease for treatment using an antiTGFβ-PON fusion of the present invention is an inflammatory lung disease such as, for example, asthma, chronic obstructive pulmonary disease (COPD), acute lung injury (ALI), acute respiratory distress syndrome (ARDS), or interstitial lung disease (e.g., idiopathic pulmonary fibrosis (IPF) or sarcoidosis). In some variations for treatment of an inflammatory lung disease, a fusion molecule comprising an anti-TNFα or anti-TGF-β polypeptide as describe herein is delivered by nebulization directly to the lungs rather than systemically, which may achieve efficient therapeutic activity with fewer unwanted side effects that may arise due to the pleiotropic activity of these cytokines.

In some aspects, the present invention provides compositions and methods for producing fusion polypeptides and dimeric proteins as described herein, including such compositions and methods for the constitutive expression of DNase-PON fusions in stable cells lines such as CHO. Previous efforts to obtain stable CHO cells that constitutively express an actin/salt-resistant and hyperactive DNase1 were unsuccessful despite screening thousands of clones (see Lam et al., *Biotech. Progress* 32: 523-533, 2017). In certain embodiments, DNase-PON fusions comprising an enhanced DNase1 as described herein are readily expressed in stable lines with minimal screening, thereby overcoming this problem in the art. The ability to readily generate stable cell lines expressing certain enhanced DNase1-PON molecules of the present disclosure indicate that these molecules have advantages in feasibility and cost of industrial scale biologic drug manufacturing.

II. Fusion Polypeptides and Dimeric Proteins

In one aspect, the present invention provides a fusion polypeptide comprising, from an amino-terminal position to a carboxyl-terminal position, T-L1-X-L2-P, wherein T, L1, X, L2, and P are defined as follows: T is a first biologically active polypeptide selected from a DNase, an RNase, a superoxide dismutase 1 (SOD1), a cytotoxic T-lymphocyte associated molecule-4 (CLTA-4) extracellular domain, a CD40 extracellular domain, and a polypeptide that specifically binds and neutralizes an inflammatory cytokine; L1 is a first polypeptide linker that is optionally present; X is a second biologically active polypeptide that is optionally present; L2 is a second polypeptide linker that is optionally present; and P is a biologically active paraoxonase. In some embodiments of a fusion polypeptide as above wherein X is present, X is selected from a dimerizing domain and a domain that specifically binds to the neonatal Fc receptor (FcRn). Typically, the biologically active paraoxonase is a naturally occurring paraoxonase 1 (PON1) polypeptide or a functional variant or fragment thereof. In variations comprising a DNase, an RNase, a SOD1, a CLTA-4 extracellular domain, or a CD40 extracellular domain, any of the foregoing biologically active polypeptides may be selected from a naturally occurring polypeptide as specified or a functional variant or fragment thereof. In certain variations comprising a polypeptide that specifically binds and neutralizes an inflammatory cytokine (e.g., TNFα or TGF-β), the anti-cytokine polypeptide is a single-chain antibody or alternative scaffold binding protein.

In another aspect, the present invention provides a fusion polypeptide comprising, from an amino-terminal position to a carboxyl-terminal position, X-L2-P, wherein X is biologically active polypeptide selected from a dimerizing domain and a domain that specifically binds to the neonatal Fc receptor (FcRn), L2 is a polypeptide linker that is optionally present, and P is a biologically active paraoxonase, wherein the fusion polypeptide does not contain a biologically active polypeptide amino-terminal to X. Typically, the biologically active paraoxonase is a naturally occurring paraoxonase 1 (PON1) polypeptide or a functional variant or fragment thereof.

In yet another aspect, the present invention provides a fusion polypeptide comprising, from an amino-terminal position to a carboxyl-terminal position, P-L1-X, wherein P is a biologically active paraoxonase, L1 is a polypeptide linker, and X is biologically active polypeptide selected from a dimerizing domain and a domain that specifically binds to the neonatal Fc receptor (FcRn). Typically, the biologically active paraoxonase is a naturally occurring paraoxonase 1 (PON1) polypeptide or a functional variant or fragment thereof.

Functional variants of a naturally occurring paraoxonase or other biologically active polypeptides specified above can be readily identified using routine assays for assessing the variant for the corresponding biological activity. For example, paraoxonase 1 (PON1) variants may be assayed for phosphotriesterase activity using diethyl p-nitrophenol phosphate (paraoxon) as a substrate, or for arylesterase activity using phenyl acetate as a substrate (see, e.g., Graves and Scott, *Curr Chem Genomics* 2:51-61, 2008; see also Example 3, infra). In addition, DNase1 and DNase1L3 variants, including hyperactive DNase1 variants, may be assayed for nuclease activity using (i) a DNA-methyl green assay, which measures the decrease of A260 as the methyl green dye is released from hydrolyzed DNA (see. e.g., Sinicropi et al., *Anal. Biochem.* 222:351-358; Pan and Lazarus, *J. Biol. Chem.* 273:11701-11708, 1998), (ii) a Kunitz hyperchromicity assay, in which the A260, due to the DNA absorption, increases as a function of degradation (see, e.g., Kunitz, J. *Gen. Physiol.* 33:349-362, 1950: Pan and Lazarus, supra); (iii) a plasmid digestion assay, which uses either supercoiled or linear plasmid DNA as a substrate and measures the disappearance of substrate and/or appearance of digestion products (e.g., appearance of linear or relaxed products from supercoiled DNA) (see, e.g., Pan and Lazarus, supra), or (iv) a SYTOX™ Green fluorescence assay, which measures the decrease in fluorescence as DNA labeled with SYTOX Green dye is hydrolyzed (see Example 2, infra). DNase1 variants may also be assayed for G-actin-induced inhibition of nuclease activity using DNase preincubated with G-actin prior to addition of substrate DNA (see, e.g., Pan el al., *J. Biol. Chem.* 273:18374-18381, 1998). In the case of RNase such as human RNase1, variants may be assayed for their ability to digest single or double-stranded RNA in known assays to assess ribonuclease activity (see, e.g., Libonati and Sorrentino, *Methods Enzymol.* 341:234-248, 2001).

SOD1 variants may be assayed using a commercially available superoxide dismutase colorimetric activity kit (ThermoFisher™ Catalog number: EIASODC). This kit is designed to measure all types of superoxide dismutase activity in a variety of sample types, including Cu/Zn, Mn, and Fc superoxide dismutase activities. Reactive oxygen species including superoxide, hydroxyl radical, and hydrogen peroxide, are produced during normal cellular aerobic metabolism, and free radicals are eliminated or converted to other products by several pathways, including the SOD enzymes. This assay should quantitatively measure SOD activity and uses a bovine erythrocyte SOD standard to generate a standard curve. A similar spectrophotometric kit is also available from Cayman Chemicals (Item number 706002), and SOD activity assays using this kit are described in Mason et al., *Free Radic. Biol. Med.* 77:130-138, 2014.

Soluble CLTA-4 and CD40 variants, as well as anti-inflammatory-cytokine polypeptides (e.g., single chain antibodies), may be assessed for desired binding activity against their respective targets (e.g., against CD80/CD86 in the case of CTLA-4, or against gp139 in the case of CD40) using any of various known assays. For example, one assay system employs a commercially available biosensor instrument (BIAcore™, Pharmacia Biosensor, Piscataway, NJ), wherein a candidate binding polypeptide (e.g., a candidate CTLA-4-Fc, CD40-Fc, or anti-cytokine antibody) is covalently attached, using amine or sulfhydryl chemistry, to dextran fibers that are attached to gold film within the flow cell. A test sample containing a soluble target molecule (e.g., CD80-Fc, CD86-Fc, CD40L-Fc (gp139-Fc), or soluble cytokine) is passed through the cell. If the immobilized protein has affinity for the target molecule, it will bind to the target causing a change in the refractive index of the medium, which is detected as a change in surface plasmon resonance of the gold film. This system allows the determination of on- and off-rates, from which binding affinity can be calculated, and assessment of stoichiometry of binding. Use of this instrument is disclosed, e.g., by Karlsson (*J. Immunol. Methods* 145:229-240, 1991) and Cunningham and Wells (J. Mol. Biol. 234:554-563, 1993). Binding activity of candidate polypeptides can also be assessed with other assay systems known in the art. Such systems include Scatchard analysis for determination of binding affinity (see Scatchard, *Ann. NY Acad Sci.* 51: 660-672, 1949) and calorimetric assays (see Cunningham et al., *Science* 253:545-548, 1991; Cunningham et al., *Science* 254:821-825, 1991).

Activity of soluble CTLA-4 and CD40 variants can also be assessed for function in appropriate in vitro cellular assays. For example, soluble CTLA-4 will inhibit T cell responses to stimulation by CD80- or CD86-expressing cells, such as B cells, dendritic cells, or CD80$^+$ or CD86$^+$ CHO cells (see, e.g., U.S. Pat. No. 5,434,131; Linsley et al., *J. Exp. Med.* 174:561-569, 1991). Soluble CD40 will block stimulation of CD40 positive cells by CD154 (CD40L, gp39). CD40-responsive cells can be B cells, monocytes, or dendritic cells. The response can vary depending on the cell type, and may include proliferation, suppression of antibody production, or inflammatory cytokine production (see, e.g., Noelle et al., *Proc. Natl. Acad. Sci. USA* 89:6550-6554, 1992; Grammer et al., *J. Immunol.* 154:4996-5010, 1995). A CD40L reporter cell line is also available from Invivogen (San Diego, CA). This reporter system uses HEK293 cells transfected with human CD40 and an NF-kB response element fused to secreted embryonic alkaline phosphatase (SEAP). Binding of the CD40 receptor by its ligand or antibodies leads to NF-kB activation and inducible expression of the SEAP. (See Jerome et al., *Anal. Biochem.* 585:113402, 2019.)

Neutralizing activity of inflammatory-cytokine-binding polypeptides can also be assessed using cellular assays known in the art. For example, anti-TNFα-binding proteins can be assayed for neutralizing activity using commercially available TNFα reporter cell lines available from Invivogen (San Diego, CA). These cell lines are transfected HEK-293 cells with a secreted embryonic alkaline phosphatase (SEAP) reporter gene attached to TNFα-responsive promoters. (Gregory et al., *Nature* 488(7412):508-511, 2012; Idress et al., *Molecules* 25:922, 2020.) In addition, anti-TGFβ-binding proteins can be assessed for neutralizing activity using similar reporter cell lines available from Invivogen (San Diego, CA), that contain TGF-β-responsive elements to drive expression of SEAP. Use of this reporter system has been described by van Noort et al. (*Cancer Res.* 74:5690-5699, 2014). Similar reporter gene assays have been reported for TNFα antagonists by Lallemand et al. (*J. Immunol. Methods* 373:229-239, 2011). The study utilized human erythroleukemic K562 cells transfected with a reporter construct incorporating TNFα response elements attached to the firefly luciferase gene. TNFα was premixed with potential antagonists for 30 minutes prior to incubation with the reporter cell line. Residual TNFα activity was quantified relative to a standard curve of TNFα alone.

Naturally occurring polypeptide segments for use in accordance with the present disclosure (e.g., a naturally occurring paraoxonase, DNase, RNase, or SOD1) include naturally occurring variants such as, for example, allelic variants and interspecies homologs consistent with the disclosure.

Functional variants of a particular reference polypeptide (e.g., a wild-type human paraoxonase 1 (PON1) as shown in residues 16-355 or 26-355 of SEQ ID NO:4, a wild-type DNase1 as shown in residues 23-282 of SEQ ID NO:16, or an enhanced DNase1 as shown in residues 21-280 of SEQ ID NO:18) are generally characterized as having one or more amino acid substitutions, deletions, or additions relative to the reference polypeptide. These changes are preferably of a minor nature, that is conservative amino acid substitutions (see, e.g., Table 1, infra, which lists some exemplary conservative amino acid substitutions) and other substitutions that do not significantly affect the folding or activity of the protein or polypeptide; small deletions, typically of one to about 30 amino acids; and small amino- or carboxyl-terminal extensions. Conservative substitutions may also be selected from the following: 1) Alanine, Glycine; 2) Aspartate, Glutamate; 3) Asparagine, Glutamine; 4) Arginine, Lysine; 5) Isoleucine, Leucine, Methionine, Valine; 6) Phenylalanine, Tyrosine, Tryptophan; 7) Serine, Threonine; and 8) Cysteine, Methionine (see, e.g., Creighton, Proteins (1984)).

TABLE 1

Conservative amino acid substitutions

| Basic | Acidic | Polar | Hydrophobic | Aromatic | Small |
|---|---|---|---|---|---|
| Arginine | Glutamate | Glutamine | Leucine | Phenylalanine | Glycine |
| Lysine | Aspartate | Asparagine | Isoleucine | Tryptophan | Alanine |
| Histidine | | | Valine | Tyrosine | Serine |
| | | | Methionine | | Threonine |
| | | | | | Methionine |

Essential amino acids in a naturally occurring polypeptide can be identified according to procedures known in the art, such as site-directed mutagenesis or alanine-scanning mutagenesis (Cunningham and Wells, Science 244:1081-1085, 1989; Bass et al., Proc. Natl. Acad. Sci. USA 88:4498-4502, 1991). In the latter technique, single alanine mutations are introduced at every residue in the molecule, and the resultant mutant molecules are tested for biological activity (e.g., phosphotriesterase or arylesterase activity for PON1 variants, or nuclease activity for DNase1 variants) to identify amino acid residues that are critical to the activity of the molecule. In addition, sites of relevant protein interactions can be determined by analysis of crystal structure as determined by such techniques as nuclear magnetic resonance, crystallography or photoaffinity labeling. The identities of essential amino acids can also be inferred from analysis of homologies with related proteins (e.g., species orthologs retaining the same protein function).

Multiple amino acid substitutions can be made and tested using known methods of mutagenesis and screening, such as those disclosed by Reidhaar-Olson and Sauer Science 241: 53-57, 1988 or Bowie and Sauer Proc. Natl. Acad. Sci. USA 86:2152-2156, 1989. Briefly, these authors disclose methods for simultaneously randomizing two or more positions in a polypeptide, selecting for functional polypeptide, and then sequencing the mutagenized polypeptides to determine the spectrum of allowable substitutions at each position. Another method that can be used is region-directed mutagenesis (Derbyshire et al., Gene 46:145, 1986; Ner et al., DNA 7:127, 1988).

Variant nucleotide and polypeptide sequences can also be generated through DNA shuffling. (See, e.g., Stemmer, Nature 370:389, 1994; Stemmer, Proc. Nat'l Acad. Sci. USA 91:10747, 1994; International PCT Publication No. WO 97/20078.) Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

As previously discussed, a polypeptide fusion in accordance with the present invention can include a polypeptide segment corresponding to a "functional fragment" of a particular polypeptide. Routine deletion analyses of nucleic acid molecules can be performed to obtain functional fragments of a nucleic acid molecule encoding a given polypeptide. As an illustration, PON1-encoding DNA molecules having the nucleotide sequence of residues 46-1099 can be digested with Bal31 nuclease to obtain a series of nested deletions. The fragments are then inserted into expression vectors in proper reading frame, and the expressed polypeptides are isolated and tested for nuclease activity. One alternative to exonuclease digestion is to use oligonucleotide-directed mutagenesis to introduce deletions or stop codons to specify production of a desired fragment. Alternatively, particular fragments of a gene encoding a polypeptide can be synthesized using the polymerase chain reaction.

Accordingly, using methods such as discussed above, one of ordinary skill in the art can prepare a variety of polypeptides that (i) are substantially identical to a reference polypeptide (e.g., a PON1 as shown in residues 16-355 or 26-355 of SEQ ID NO:6, a human wild-type DNase1 as shown in residues 23-282 of SEQ ID NO:16, or an enhanced DNase1 as shown in residues 21-280 of SEQ ID NO:18) and (ii) retains the desired functional properties of the reference polypeptide.

Polypeptide segments used within the present invention (e.g., polypeptide segments corresponding to a paraoxonase, DNase, RNase, or dimerizing or FcRn-binding domain such as, e.g., an Fc fragment) may be obtained from a variety of species. If the protein is to be used therapeutically in humans, it is preferred that human polypeptide sequences be employed. However, non-human sequences can be used, as can variant sequences. For other uses, including in vitro diagnostic uses and veterinary uses, polypeptide sequences from humans or non-human animals can be employed, although sequences from the same species as the patient may be preferred for in vivo veterinary use or for in vitro uses where species specificity of intermolecular reactions is present. Thus, polypeptide segments for use within the present invention can be, without limitation, human, non-human primate, rodent, canine, feline, equine, bovine, ovine, porcine, lagomorph, and avian polypeptides, as well as variants thereof.

In some embodiments, the paraoxonase segment is a human paraoxonase 1 (PON1) or a functional variant or fragment thereof. For example, in some embodiments, the paraoxonase (a) has at least 80%, at least 85%, at least 90%, or at least 95% identity with amino acid residues 16-355 or 26-355 of SEQ ID NO:6, SEQ ID NO:8, or SEQ ID NO:4 and (b) does not contain an amino-terminal leader sequence corresponding to residues 1-15 of SEQ ID NO:6 (also shown as residues 1-15 of SEQ ID NO:8 or SEQ ID NO:4). In some such embodiments, the biologically active paraoxonase has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:6, SEQ ID NO:8, or SEQ ID NO:4.

In some variations of a PON1 or functional variant or fragment thereof as above, the amino acid at a position corresponding to Q192 of the human paraoxonase 1 Q192 isoform (PON1-Q192; SEQ ID NO:4) is lysine or arginine. In other, non-mutually exclusive variations, the paraoxonase contains at least one of the following amino acid substitutions relative to hPON1-Q192: (i) aspartate at the position corresponding to 18R; (ii) arginine or glycine at the position corresponding to N19; (iii) glutamine at the position corresponding to H20; (iv) lysine at the position corresponding to Q21; (v) glutamate or phenylalanine at the position corresponding to Y24; (vi) phenylalanine at the amino acid corresponding to L28; (vii) valine at the position corresponding to A30; (viii) histidine at the position corresponding to L31; (ix) threonine at the position corresponding to Q35; (x) valine at the position corresponding to 148; (xi) aspartate at the position corresponding to E49; (xii) asparagine at the position corresponding to T50; (xiii) leucine or isoleucine at the position corresponding to M55; (xiv) valine at the position corresponding to L69; (xv) methionine at the position corresponding to K75; (xvi) aspartate at the position corresponding to N78; (xvii) aspartate at the position corresponding to N80; (xviii) lysine at the position corresponding to S81; (xix) serine at the position corresponding to P82; (xx) valine at the position corresponding to T96; (xxi) serine at the position corresponding to L98; (xxii) glutamate at the position corresponding to G101; (xxiii) asparagine at the position corresponding to S105; (xxiv) threonine at the position corresponding to K106; (xxv) leucine at the position corresponding to F107; (xxvi) isoleucine at the position corresponding to V109; (xxvii) threonine at the position corresponding to S111; (xxviii) tryptophan or alanine at the position corresponding to H115; (xxix) threonine at the position corresponding to A126; (xxx) valine at the position corresponding to M127; (xxxi) arginine at the position corresponding to H134; (xxxii) glutamine at the position corresponding to D136; (xxxiii) serine at the position corresponding to A137; (xxxiv) serine at the position corresponding to K138; (xxxv) valine at the position corresponding to L143; (xxxvi) serine at the position corresponding to N166; (xxxvii) valine at the position corresponding to L167; (xxxviii) alanine at the position corresponding to G180; (xxxix) glutamate at the position corresponding to Y185; (xl) glutamine at the position corresponding to F186; (xli) lysine or alanine at the position corresponding to L187; (xlii) lysine at the position corresponding to Y190; (xxiii) glutamine at the position corresponding to L191; (xliv) lysine at the position corresponding to Q192; (xlv) lysine at the position corresponding to W194; (xlvi) histidine at the position corresponding to Y197; (xlvii) glutamate at the position corresponding to L198; (xlviii) glutamine at the position corresponding to L200; (xlix) lysine at the position corresponding to W202; (l) phenylalanine at the position corresponding to Y204; (li) threonine at the position corresponding to V206; (lii) asparagine at the position corresponding to S211; (liii) aspartate at the position corresponding to E212; (liv) serine or methionine at the position corresponding to F222; (lv) aspartate at the position corresponding to N265; (lvi) valine at the position corresponding to E276; (lvii) glutamine at the position corresponding to M289; (lviii) leucine at the position corresponding to I291; (lix) glutamate or tyrosine at the position corresponding to F293; (lx) proline at the position corresponding to S296; (lxi) lysine at the position corresponding to E297; (lxii) glycine tha the position corresponding to A301; (lxiii) aspartate at the position corresponding to N309; (lxiv) serine at the position corresponding to T312; (lxv) valine at the position corresponding to Q319; (lxvi) serine at the position corresponding to T332; and alanine at the position corresponding to S335.

In some variations, the paraoxonase is a variant of human PON1 identified as G3C9 (Aharoni et al., *Proc. Natl. Acad. Sci. USA* 101:482-487, 2004; Harel et al., Nat. Struct. Mol. Biol. 11:412-419, 2004; Mukherjee and Gupta, J. Toxicol. 2020:1-16, 2020; Goldsmit et al., *Chemistry and Biology* 19:456-466, 2012), or a functional variant or fragment thereof. GC39 includes 55 amino acid substitutions from the human isoform, improving the catalytic activity against nerve agents and improving soluble expression in bacteria. The full length form of this paraoxonase sequence variant is listed in SEQ ID NO:123 (nucleotide) and SEQ ID NO:124 (amino acid). In some embodiments, a GC39 paraoxonase or functional variant thereof for use in accordance with the present invention has at least 90% or at least 95% identity with amino acid residues 16-355 or 26-355 of SEQ ID NO:124; in some such embodiments, the GC39 paraoxonase or functional variant thereof has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:124. PON1 fusions comprising G3C9 or an active variant thereof (e.g., M-IIG1 discussed below) may be particularly useful in some short term therapy applications such as, e.g., treatment of exposure to sulfur mustard gas or exposure to an organophosphate.

In some embodiments of a fusion polypeptide as above, the paraoxonase is a modified or further variant form of GC39 identified as IIG1 (also referred to as M-IIG1 herein; see Goldsmith et al., *Chemistry & Biology* 19, 456-466, 2012), or a functional variant or fragment thereof. The full length sequence of M-IIG1 is shown in SEQ ID NO:125 (nucleotide) and SEQ ID NO:126 (amino acid). In some embodiments, a M-IIG1 paraoxonase or functional variant thereof for use in accordance with the present invention has at least 90% or at least 95% identity with amino acid residues 16-355 or 26-355 of SEQ ID NO:126; in some such embodiments, the M-IIG1 paraoxonase or functional variant thereof has at least 96%, at least 97%, at least 98%, or at least 99% identity with amino acid residues 16-355, 17-355, 18-355, 19-355, 20-355, 21-355, 22-355, 23-355, 24-355, 25-355, or 26-355 of SEQ ID NO:126.

In more specific variations, the paraoxonase has an amino acid sequence selected from (i) residues 16-355 of SEQ ID NO:6, (ii) residues 17-355 of SEQ ID NO:6, (iii) residues 18-355 of SEQ ID NO:6, (iv) residues 19-355 of SEQ ID NO:6, (v) residues 20-355 of SEQ ID NO:6, (vi) residues 21-355 of SEQ ID NO:6, (vii) residues 22-355 of SEQ ID NO:6, (viii) residues 23-355 of SEQ ID NO:6, (ix) residues 24-355 of SEQ ID NO:6, (x) residues 25-355 of SEQ ID NO:6, and (xi) residues 26-355 of SEQ ID NO:6 (i.e., an amino acid sequence selected from residues n-355 of SEQ ID NO:6, wherein n is an integer from 16 to 26, inclusive). In other variations, the paraoxonase has an amino acid sequence selected from (i) residues 16-355 of SEQ ID NO:8, (ii) residues 17-355 of SEQ ID NO:8, (iii) residues 18-355 of SEQ ID NO:8, (iv) residues 19-355 of SEQ ID NO:8, (v) residues 20-355 of SEQ ID NO:8, (vi) residues 21-355 of SEQ ID NO:8, (vii) residues 22-355 of SEQ ID NO:8, (viii) residues 23-355 of SEQ ID NO:8, (ix) residues 24-355 of SEQ ID NO:8, (x) residues 25-355 of SEQ ID NO:8, and (xi) residues 26-355 of SEQ ID NO:8 (i.e., an amino acid sequence selected from residues n-355 of SEQ ID NO:8, wherein n is an integer from 16 to 26, inclusive). In still other variations, the paraoxonase has an amino acid sequence selected from (i) residues 16-355 of SEQ ID NO:4, (ii) residues 17-355 of SEQ ID NO:4, (iii) residues 18-355 of SEQ ID NO:4, (iv) residues 19-355 of SEQ ID NO:4, (v) residues 20-355 of SEQ ID NO:4, (vi) residues 21-355 of SEQ ID NO:4, (vii) residues 22-355 of SEQ ID NO:4, (viii) residues 23-355 of SEQ ID NO:4, (ix) residues 24-355 of SEQ ID NO:4. (x) residues 25-355 of SEQ ID NO:4, and (xi) residues 26-355 of SEQ ID NO:4 (i.e., an amino acid sequence selected from residues n-355 of SEQ ID NO:4, wherein n is an integer from 16 to 26, inclusive). In still other variations, the paraoxonase has an amino acid sequence selected from (i) residues 16-355 of SEQ ID NO:124, (ii) residues 17-355 of SEQ ID NO:124, (iii) residues 18-355 of SEQ ID NO:124, (iv) residues 19-355 of SEQ ID NO:124, (v) residues 20-355 of SEQ ID NO: 124, (vi) residues 21-355 of SEQ ID NO:124, (vii) residues 22-355 of SEQ ID NO:124, (viii) residues 23-355 of SEQ ID NO:124, (ix) residues 24-355 of SEQ ID NO:124, (x) residues 25-355 of SEQ ID NO:124, and (xi) residues 26-355 of SEQ ID NO:124 (i.e., an amino acid sequence selected from residues n-355 of SEQ ID NO:124, wherein n is an integer from 16 to 26, inclusive). In yet other variations, the paraoxonase has an amino acid sequence selected from (i) residues 16-355 of SEQ ID NO:126, (ii) residues 17-355 of SEQ ID NO:126, (iii) residues 18-355 of SEQ ID NO:126, (iv) residues 19-355 of SEQ ID NO:126, (v) residues 20-355 of SEQ ID NO:126, (vi) residues 21-355 of SEQ ID NO:126, (vii) residues 22-355 of SEQ ID NO:126, (viii) residues 23-355 of SEQ ID NO:126 (ix) residues 24-355 of SEQ ID NO:126, (x) residues 25-355 of SEQ ID NO:126, and (xi) residues 26-355 of SEQ ID NO:126 (i.e., an amino acid sequence selected from residues n-355 of SEQ ID NO:126, wherein n is an integer from 16 to 26, inclusive).

In some embodiments of a fusion polypeptide comprising a DNase as the first biologically active polypeptide, the DNase is a human wild-type DNase1 or a functional variant or fragment thereof. For example, in some embodiments, the DNase comprises an amino acid sequence having at least 80%, at least 85%, at least 90%, or at least 95% identity with (i) amino acid residues 23-282 of SEQ ID NO:16, (ii) amino acid residues 21-280 of SEQ ID NO:18, (iii) amino acid residues 21-280 of SEQ ID NO:20, or (iv) amino acid residues 21-280 of SEQ ID NO:152. In more particular embodiments, the DNase comprises an amino acid sequence having at least 96%, at least 97%, at least 98%, at least 99%, or 100% sequence identity with (i) amino acid residues 23-282 of SEQ ID NO:16, (ii) amino acid residues 21-280 of SEQ ID NO:18, (iii) amino acid residues 21-280 of SEQ ID NO:20, or (iv) amino acid residues 21-280 of SEQ ID NO:152.

In certain preferred embodiments, the DNase segment is a hyperactive and/or actin-resistant variant of a naturally occurring DNase1 (an "enhanced DNase1") such as, e.g., an enhanced human DNase1 variant. For example, in some variations, the DNase contains at least one amino acid substitution at a position corresponding to an amino acid of mature wild-type human DNase1 (SEQ ID NO:120) selected from N74, G105, and A114, wherein (1) the amino acid substitution at the position corresponding to N74 of human DNase1 (N74 substitution), if present, increases DNA binding of the DNase relative to human DNase1, (2) the amino acid substitution at the position corresponding to G105 of human DNase1 (G105 substitution), if present, increases DNA binding of the DNase relative to human DNase1, and (3) the amino acid substitution at the position corresponding to A114 of human DNase1 (A114 substitution), if present, decreases G-actin-induced inhibition of endonuclease activity of the DNase relative to human DNase1. Suitable amino acids for substitution at these positions include lysine at the position corresponding to N74 of human DNase1, arginine at the position corresponding to G105 of human DNase1, and/or phenylalanine at the positions corresponding to A114 of human DNase1. In some variations, an enhanced human DNase1 variant as above contains at least two of the N74, G105, and A114 substitutions (e.g., substitutions at at least the positions corresponding to both N74 and G105 or both G105 and A114 of human DNase1). In some embodiments, the enhanced human DNase1 contains each of the N74, G105, and A114 substitutions. In other variations, the enhanced human DNase1 contains the N74 and G105 substitutions but does not contain the A114 substitution. In certain embodiments, the enhanced DNase1 comprises an amino acid sequence having at least 80%, at least 85%, at least 90%, at least 95%, at least 96%, at least 97%, at least 98%, at least 99%, or 100% identity with (i) amino acid residues 21-280 of SEQ ID NO:18, (ii) amino acid residues 21-280 of SEQ ID NO:20, or (iii) residues 21-280 of SEQ ID NO:152. In some variations, the enhanced DNase1 comprises an amino acid sequence having at least 90%, at least 95%, at least 96%, at least 97%, at least 98%, or at least 99% identity with amino acid residues 21-280 of SEQ ID NO:18, wherein the enhanced DNase1 contains each of the N74, G105, and A114 substitutions but does not contain any other amino acid substitution that increases DNA binding of the DNase relative to human DNase1, and/or does not contain any other amino acid substitution that decreases G-actin-induced inhibition of endonuclease activity of the DNase relative to human DNase1. In other variations, the enhanced DNase1 comprises an amino acid sequence having at least 90%, at least 95%, at least 96%, at least 97%, at least 98%, or at least 99% identity with amino acid residues 21-280 of SEQ ID NO:152, wherein the enhanced DNase1 contains each of the N74 and G105 substitutions but does not contain any other amino acid substitution that increases DNA binding of the DNase relative to human DNase1, and/or does not contain the A114 substitution or any other amino acid substitution that decreases G-actin-induced inhibition of endonuclease activity of the DNase relative to human DNase1. Fusions comprising an enhanced DNase that lacks actin resistance are particularly beneficial for decreasing toxicity to host cells (e.g., CHO) to enable higher expression of the fusion molecule.

In other embodiments of a fusion polypeptide comprising a DNase as the first biologically active polypeptide, the DNase is a truncated form of human wild-type DNase1 L3 in which the carboxyl-terminal nuclear localization signal (referred to herein as NLS2, corresponding to amino acid residues 291-305 of SEQ ID NO:136) is deleted, or a functional variant or fragment of such truncated form of human DNase1 L3. For example, in some embodiments, the DNase comprises an amino acid sequence having at least 80%, at least 85%, at least 90%, or at least 95% identity with (i) amino acid residues 21-290 of SEQ ID NO:136, (ii) amino acid residues 21-290 of SEQ ID NO:138, or (iii) amino acid residues 21-290 of SEQ ID NO:140. In more particular embodiments, the DNase comprises an amino acid sequence having at least 96%, at least 97%, at least 98%, at least 99%, or 100% sequence identity with (i) amino acid residues 21-290 of SEQ ID NO:136, (ii) amino acid residues 21-290 of SEQ ID NO:138, or (iii) amino acid residues 21-290 of SEQ ID NO:140. In certain preferred embodiments comprising a truncated form of human DNase1 L3 or functional variant thereof, the DNase is a variant DNase1L3 containing one or more amino acid substitutions relative to wild-type human DNase1L3 (SEQ ID NO:136) that inactivate the nuclear localization signal in the N-terminal half of the molecule (referred to herein as NLS1, corresponding to amino acid residues 80-96 of SEQ ID NO:136); in some such embodiments, each of the amino acids at positions corresponding to R80, R95, and N96 of SEQ ID NO:136 is alanine or serine (e.g., each of R80, R95, and N96 is alanine, or each of R80, R95, and N96 is serine). In more specific embodiments of a variant, truncated form of DNase1 L3 as above in which the wild-type NLS1 consensus sequence is removed, the DNase has the amino acid sequence shown in (i) amino acid residues 21-290 of SEQ ID NO:138 or (ii) amino acid residues 21-290 of SEQ ID NO:140.

In some embodiments of a fusion polypeptide comprising an RNase as the first biologically active polypeptide, the RNase is a human wild-type RNase1 or a functional variant or fragment thereof. For example, in some embodiments, the RNase comprises an amino acid sequence having at least 80%, at least 85%, at least 90%, or at least 95% identity with amino acid residues 29-156 of SEQ ID NO:22. In more particular variations, the RNase comprises an amino acid sequence having at least 96%, at least 97%, at least 98%, at least 99%, or 100% identity with amino acid residues 29-156 of SEQ ID NO:22.

In some embodiments of a fusion polypeptide comprising a superoxide dismutase 1 (SOD1) as the first biologically active polypeptide, the SOD1 is a human wild-type SOD1 or a functional variant or fragment thereof. For example, in some embodiments, the SOD1 comprises an amino acid sequence having at least 80%, at least 85%, at least 90%, or at least 95% identity with amino acid residues 2-154 of SEQ ID NO:32. In more particular variations, the SOD1 comprises an amino acid sequence having at least 96%, at least 97%, at least 98%, at least 99%, or 100% identity with amino acid residues 2-154 of SEQ ID NO:32. In certain variations, the amino acid at a position corresponding to C7 of human SOD1 (SEQ ID NO:32) is not cysteine, and/or the amino acid a position corresponding to C112 of human SOD1 is not cysteine; in some such embodiments, the amino acid at a position corresponding to C7 of human SOD1 is alanine, and/or the amino acid a position corresponding to C112 of human SOD1 is serine. In more specific variations, the SOD1 comprises the amino acid sequence shown in residues 2-154 of SEQ ID NO:32 wherein the amino acid at position C7 is changed to alanine and the amino acid at position C112 is serine (also shown as residues 23-175 of SEQ ID NO:52 or residues 23-175 of SEQ ID NO:54).

In some embodiments of a fusion polypeptide comprising a CTLA-4 extracellular domain as the first biologically active polypeptide, the extracellular domain is a human wild-type CTLA-4 extracellular domain or a functional variant or fragment thereof. For example, in some embodiments, the CTLA-4 extracellular domain comprises an amino acid sequence having at least 80%, at least 85%, at least 90%, or at least 95% identity with amino acid residues 21-144 of SEQ ID NO:66. In more particular variations, the CTLA-4 extracellular domain comprises an amino acid sequence having at least 96%, at least 97%, at least 98%, at least 99%, or 100% identity with amino acid residues 21-144 of SEQ ID NO:66.

In some embodiments of a fusion polypeptide comprising a CD40 extracellular domain as the first biologically active polypeptide, the extracellular domain is a human wild-type CD40 extracellular domain or a functional variant or fragment thereof. For example, in some embodiments, the CD40 extracellular domain comprises an amino acid sequence having at least 80%, at least 85%, at least 90%, or at least 95% identity with (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90. In more particular embodiments, the CD40 extracellular domain comprises an amino acid sequence having at least 96%, at least 97%, at least 98%, or at least 99% identity with (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In certain preferred embodiments, the CD40 extracellular domain contains at least one amino acid substitution at a position corresponding to an amino acid of wild-type human CD40 (SEQ ID NO:68) selected from E64, K81, P85, and L121, wherein the at least one amino acid substitution increases CD40 ligand binding relative to human CD40. Particularly suitable amino acid substitutions at these positions are tyrosine at the position corresponding to E64 of human CD40, threonine, histidine, or serine at the position corresponding to K81 of human CD40, tyrosine at the position corresponding to P85 of human CD40, and/or proline at the position corresponding to L121 of human CD40. In some variations, the CD40 extracellular domain contains at least two of the positions corresponding to E64, K81, P85, and L121 of human CD40 (e.g., substitutions at at least the positions corresponding to K81 and L121 of human CD40, or substitutions at at least the positions corresponding to E64, K81, and P85 of human CD40). In some embodiments, the amino acid at the position corresponding to K81 of human CD40 is selected from threonine, histidine, and serine. In other embodiments, the amino acid at the position corresponding to K81 of human CD40 is histidine and the amino acid the position corresponding to L121 of human CD40 is proline. In yet other embodiments, the amino acid at the position corresponding to E64 of human CD40 is tyrosine, the amino acid at the position corresponding to K81 of human CD40 is threonine, and the amino acid at the position corresponding to P85 of human CD40 is tyrosine. In specific variations, the CD40 extracellular domain comprises the amino acid sequence shown in (i) residues 21-188 of SEQ ID NO:74, (ii) residues 21-188 of SEQ ID NO:78, (iii) residues 21-188 of SEQ ID NO:82, (iv) residues 21-188 of SEQ ID NO:86, or (v) residues 21-188 of SEQ ID NO:90.

In some embodiments of a fusion polypeptide comprising a polypeptide that specifically binds and neutralizes an inflammatory cytokine as the first biologically active polypeptide, the inflammatory cytokine is a member of the tumor necrosis factor (TNF) superfamily, a member of the transforming growth factor (TGF) superfamily, an interleukin, a chemokine, a colony-stimulating factor (CSF), or an interferon. In more particular embodiments, the inflammatory cytokine is selected from the group consisting of tumor necrosis factor α (TNFα), transforming growth factor-β (TGFβ), interleukin-4 (IL-4), interleukin-5 (IL-5), interleukin-6 (IL-6), interleukin-8 (IL-8), interleukin-10 (IL-10), interleukin-11 (IL-11), interleukin-12 (IL-12), interleukin- 13 (IL-13), interleukin-17A (IL-17A), interleukin-17F (IL-17F), interleukin-1α (IL-1α), interleukin-1β (IL-1β), interleukin-18 (IL-18), interleukin-21 (IL-21), interleukin-31 (IL-31), interleukin-33 (IL-33), interleukin-36α (IL-36α), interleukin-36β (IL-36β), interleukin IL-36γ (IL-36γ), granulocyte-macrophage colony-stimulating factor (GM-CSF), and interferon γ (IFNγ). In some variations, a polypeptide that specifically binds and neutralizes an inflammatory cytokine is an antibody. In some alternative variations, a polypeptide that specifically binds and neutralizes an inflammatory cytokine is an alternative scaffold protein.

In certain embodiments of a fusion polypeptide comprising a polypeptide that specifically binds and neutralizes TNFα("anti-TNFα polypeptide"), the anti-TNFα polypeptide competes for binding to TNFα with an antibody having the same heavy and light chain variable domains (VH and VL) as anti-TNFα monoclonal antibody adalimumab. The amino acid sequences of adalimumab VH and VL are shown herein as SEQ ID NO:108 and SEQ ID NO:110, respectively (see also GenBank Accession Nos. LQ961187 and LQ961186 for the heavy and light chain variable regions, respectively; International PCT Publication No. WO 2014/159579).

In certain embodiments of a fusion polypeptide comprising a polypeptide that specifically binds and neutralizes TGF-β("anti-TGF-β polypeptide"), the anti-TGF-β polypeptide competes for binding to TGF-β with an antibody having the same heavy and light chain variable domains (VH and VL) as anti-TGF-β monoclonal antibody fresolimumab. The amino acid sequences of fresolimumab VH and VL are shown herein as SEQ ID NO:112 and SEQ ID NO: 114, respectively (see also GenBank Accession Nos. JC232803.1 and JC232805 for the heavy and light chain variable regions, respectively; International PCT Publication No. WO 2013/065869).

The ability of a binding protein to compete for binding to TNFα or TGF-β with an antibody having the VH and VL domains of adalimumab or fresolimumab, respectively, may be determined by an assay in which a test TNFα-binding protein (e.g., an antibody), or a functional binding fragment thereof, prevents or inhibits specific binding to TNFα of a reference antibody having the VH and VL domains of adalimumab (i.e., having VH and VL domains of SEQ ID NO:108 and SEQ ID NO:110, respectively), or in which a test TNF-β-binding protein (e.g., an antibody), or a functional binding fragment thereof, prevents or inhibits specific binding to TNF-β of a reference antibody having the VH and VL domains of fresolimumab (i.e., having VH and VL domains of SEQ ID NO:112 and SEQ ID NO: 114, respectively). Typically, such an assay involves the use of purified target protein bound to a solid surface or cells bearing the target protein, an unlabeled test protein (i.e., a TNFα-binding or TGFβ i-binding protein or candidate TNFα-binding or TGF-β-binding protein), and a labeled reference antibody. Competitive inhibition is measured by determining the amount of label bound to the solid surface or cells in the presence of the test protein. Usually the test protein is present in excess and/or allowed to bind first. Soluble TNFα-binding or TGFβ-binding proteins identified by competition assay ("competing TNFα-binding or TGFβ-binding proteins") include proteins binding to the same epitope bound by the reference antibody, proteins binding to an epitope overlapping with the epitope bound by the reference antibody, and proteins binding to an epitope sufficiently proximal to the epitope bound by the reference antibody for steric hindrance to occur. Usually, when a competing TNFα-binding or TGFβ-binding protein (e.g., a competing anti-TNFα or anti-TGF-β antibody) is present in excess, it will inhibit specific binding of a reference antibody to TNFα or TGF-β target protein by at least 30%, at least 40%, at least 45%, at least 50%, at least 55%, at least 60%, at least 65%, at least 70%, or at least 75%; in some instances, binding is inhibited by at least 80%, at least 85%, at least 90%, at least 95%, at least 97%, or more. Conversely, when the reference antibody is bound, it will preferably inhibit binding of a subsequently added competing TNFα-binding or TGFβ-binding protein (e.g., a competing anti-TNFα or anti-TGF-β antibody) by at least 30%, at least 40%, at least 45%, at least 50%, at least 55%, at least 60%, at least 65%, at least 70%, or at least 75%; in some instances, binding is inhibited by at least 80%, at least 85%, at least 90%, at least 95%, at least 97%, or more.

In certain preferred embodiments, a polypeptide that specifically binds and neutralizes an inflammatory cytokine for use in accordance with the present invention is a single-chain antibody. Particularly suitable single-chain antibodies include single-chain Fvs (scFvs) and single-domain antibodies (sdAbs). A single-chain antibody may be, e.g., derived from an identified intact, native monoclonal antibody or antibody fragment having the desired specificity. Methods for preparing and isolating monoclonal antibodies and antigen-binding antibody fragments thereof are well-known in the art. See, e.g., *Current Protocols in Immunology*, (Cooligan et al. eds., John Wiley and Sons, Inc. 2006); Sambrook et al., *Molecular Cloning: A Laboratory Manual* (Cold Spring Harbor, NY, 2nd ed. 1989); and *Monoclonal Hybridoma Antibodies: Techniques and Applications* (Hurrell ed., CRC Press, Inc., Boca Raton, F L, 1982). Antigen-binding fragments, including scFv, can be prepared using, e.g., phage display libraries according to methods known in the art. As will be evident to persons of ordinary skill in the art, these methods are equally applicable to production of antibodies against an inflammatory cytokine for use in accordance with the present invention.

The amino acid sequence of native antibody variable regions can be varied through the application of recombinant DNA techniques. Thus, antibodies can be redesigned to obtain desired characteristics. Typically, changes in the variable region will be made in order to improve the antigen-binding characteristics, improve variable region stability, or reduce the risk of immunogenicity. Phage display techniques can also be employed. See, e.g., Huse et al., *Science* 246:1275-1281, 1989; Ladner et al., U.S. Pat. No. 5,571,698.

For therapeutic antibodies for use in humans, it is usually desirable to humanize non-human regions of an antibody according to known procedures. Methods of making humanized antibodies are disclosed, for example, in U.S. Pat. Nos. 5,530.101; 5,821,337; 5,585,089; 5,693,762; and 6,180,370. Methods of making humanized antibodies are also disclosed in, e.g., U.S. Pat. No. 7,732,578. Typically, a humanized anti-inflammatory-cytokine antibody comprises the complementarity determining regions (CDRs) of a murine donor immunoglobulin and heavy chain and light chain frameworks of a human acceptor immunoglobulin. Often, framework residues in the human framework regions will be substituted with the corresponding residue from the donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., *Nature* 332:323, 1988.

The present invention also encompasses use of fully human antibodies such as, for example, those selected from human antibody expression libraries (e.g., phage display libraries); those made in non-human animals (e.g., mice) transgenic for a human heavy chain locus and a human light chain locus with the corresponding endogenous immunoglobulin loci inactivated; or those prepared by immortalizing human B lymphocytes producing an antibody against an inflammatory cytokine target antigen.

Antibodies for use in accordance with the present invention have binding affinities that include a dissociation constant ($K_d$) that is, e.g., less than $10^{-4}$ M, less than $10^{-4}$ M, less than $5 \times 10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M.

Antibodies for use in accordance with the present invention include variants having one or more amino acid substitutions, deletions, or additions relative to a reference antibody such that the variant retains one or more biological properties of the reference antibody. In certain embodiments, an antibody is a variant having one or more amino acid substitutions, deletions, or additions relative to a reference anti-TNFα neutralizing antibody having VH and/or VL sequences as shown in SEQ ID NO:108 and SEQ ID NO:110, respectively, such that the antibody retains the ability of the reference antibody to specifically bind TNFα and neutralize TNFα activity. In other embodiments, an antibody is a variant having one or more amino acid substitutions, deletions, or additions relative to a reference anti-TNF-β neutralizing antibody having VH and/or VL sequences as shown in SEQ ID NO:112 and SEQ ID NO:114, respectively, such that the antibody retains the ability of the reference antibody to specifically bind TNF-β and neutralize TNF-β activity. A skilled person can readily produce variants having one or more amino acid substitutions, deletions, or additions relative to a reference antibody. The techniques for obtaining these variants, including genetic (suppressions, deletions, mutations, etc.), chemical, and enzymatic techniques, are known to the person having ordinary skill in the art.

In some embodiments of a fusion polypeptide as above comprising a single-chain antibody that specifically binds and neutralizes TNFα("anti-TNFα single-chain antibody"), the anti-TNFα single-chain antibody comprises one or more CDRs of anti-TNFα monoclonal antibody adalimumab. Thus, in certain variations, an anti-TNFα single-chain antibody comprises a heavy chain CDR (at least one of the CDR-H1, CDR-H2, and CDR-H3 regions) of the adalimumab VH domain (SEQ ID NO:108) and/or a light chain CDR (at least one of CDR-L1, CDR-L2, and CDR-L3 regions) of the adalimumab VL domain (SEQ ID NO:110). In typical embodiments, the anti-TNFα single-chain antibody has two or three CDRs of the adalimumab VH domain (SEQ ID NO:108) and/or two or three CDRs of the adalimumab VL domain (SEQ ID NO:110). In some variations, where an anti-TNFα single-chain antibody has at least one CDR of the adalimumab VH domain, the antibody further comprises at least one CDR of the adalimumab VL domain; in some such embodiments, an antibody has all three heavy chain CDRs and all three light chain CDRs of adalimumab (i.e., CDR-H1, CDR-H2, and CDR-H3 of SEQ ID NO:108 and CDR-L1, CDR-L2, and CDR-L3 of SEQ ID NO:110). The one or more CDRs may be defined, for example, according to the Chothia definition, the Kabat definition, the AbM definition, the IMGT database definition, or the contact definition of CDR. Under the IMGT database definition of CDR, CDR-H1, CDR-H2, and CDR-H3 of adalimumab correspond, respectively, to residues 26-33, 50-59, and 97-110 of SEQ ID NO:108, and CDR-L1, CDR-L2, and CDR-L3 of adalimumab correspond, respectively, to residues 27-32, 50-52, and 89-97 of SEQ ID NO:110. Under the Kabat definition of CDR, CDR-H1, CDR-H2, and CDR-H3 of adalimumab correspond, respectively, to residues 31-35, 50-66, and 99-110 of SEQ ID NO:108, and CDR-L1, CDR-L2, and CDR-L3 of adalimumab correspond, respectively, to residues 24-34, 50-56, and 89-97 of SEQ ID NO:110. In particular variations of an anti-TNFα single-chain antibody as above, the single-chain antibody comprises an VH domain and/or a VL domain having a human immunoglobulin framework region, or a variant thereof having at least 85%, at least 90%, or at least 95% amino acid sequence identity to the human immunoglobulin framework region.

In some embodiments, an anti-TNFα single-chain antibody includes (a) a heavy chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:108, and/or (b) a light chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:110.

In some embodiments, an anti-TNFα single-chain antibody for use in accordance with the present invention comprises heavy chain CDRs CDR-H1$_{TNF\alpha}$, CDR-H2$_{TNF\alpha}$, and CDR-H3$_{TNF\alpha}$, wherein the set of VH CDRs has 10 or fewer amino acid substitutions relative to a set of reference CDRs CDR-H1, CDR-H2, and CDR-H3 of the adalimumab VH domain (SEQ ID NO:108). In other, non-mutually exclusive embodiments, the anti-TNFα single-chain comprises light chain CDRs CDR-L1$_{TNF\alpha}$, CDR-L2$_{TNF\alpha}$, and CDR-L3$_{TNF\alpha}$, wherein the set of VL CDRs has 10 or fewer amino acid substitutions relative to a set of reference CDRs CDR-L1, CDR-L2, and CDR-L3 of the adalimumab VL domain (SEQ ID NO:110). In certain embodiments, an anti-TNFα single-chain antibody comprises both sets of heavy chain and light chain CDRs as above. Particularly suitable anti-TNFα single-chain antibodies comprise a heavy chain variable domain comprising CDRs CDR-H1$_{TNF\alpha}$, CDR-H2$_{TNF\alpha}$, and CDR-H3$_{TNF\alpha}$ and a light chain variable domain comprising CDRs CDR-L1$_{TNF\alpha}$, CDR-L2$_{TNF\alpha}$, and CDR-L3$_{TNF\alpha}$, wherein the set of heavy chain CDRs has six or fewer, typically five or fewer, more typically four or fewer, an most typically three or fewer amino acid substitutions relative to CDR-H1, CDR-H2, and CDR-H3 of adalimumab, and wherein the set of light chain CDRs has six or fewer, typically five or fewer, more typically four or fewer, an most typically three or fewer amino acid substitutions relative to CDR-L1, CDR-L2, and CDR-L3 of adalimumab. The CDRs as above may be defined, for example, according to the Chothia definition, the Kabat definition, the AbM definition, the IMGT database definition, or the contact definition of CDR. In particular variations of an anti-TNFα antibody as above, each of the VH and VL domains has a human immunoglobulin framework region, or a variant thereof having at least 85%, at least 90%, or at least 95% amino acid sequence identity to the human immunoglobulin framework region.

In some embodiments of a fusion polypeptide as above comprising a single-chain antibody that specifically binds and neutralizes TGF-β ("anti-TGF-β single-chain antibody"), the anti-TGF-β single-chain antibody comprises one or more CDRs of anti-TGF-β monoclonal antibody fresolimumab. Thus, in certain variations, an anti-TGF-0 single-chain antibody comprises a heavy chain CDR (at least one of the CDR-H1, CDR-H2, and CDR-H3 regions) of the fresolimumab VH domain (SEQ ID NO:112) and/or a light chain CDR (at least one of CDR-L1, CDR-L2, and CDR-L3 regions) of the fresolimumab VL domain (SEQ ID NO:114). In typical embodiments, the anti-TGF-β single-chain antibody has two or three CDRs of the fresolimumab VH domain (SEQ ID NO:112) and/or two or three CDRs of the fresolimumab VL domain (SEQ ID NO:114). In some variations, where an anti-TGF-β single-chain antibody has at least one CDR of the fresolimumab VH domain, the antibody further comprises at least one CDR of the fresolimumab VL domain; in some such embodiments, an antibody has all three heavy chain CDRs and all three light chain CDRs of fresolimumab (i.e., CDR-H1, CDR-H2, and CDR-H3 of SEQ ID NO:112 and CDR-L1, CDR-L2, and CDR-L3 of SEQ ID NO: 114). The one or more CDRs may be defined, for example, according to the Chothia definition, the Kabat definition, the AbM definition, the IMGT database definition, or the contact definition of CDR. Under the Kabat definition of CDR, CDR-H1, CDR-H2, and CDR-H3 of fresolimumab correspond, respectively, to residues 31-35, 50-66, and 99-106 of SEQ ID NO: 112, and CDR-L1, CDR-L2, and CDR-L3 of fresolimumab correspond, respectively, to residues 24-40, 56-62, and 95-102 of SEQ ID NO:114. In particular variations of an anti-TGF-β single-chain antibody as above, the single-chain antibody comprises an VH domain and/or a VL domain having a human immunoglobulin framework region, or a variant thereof having at least 85%, at least 90%, or at least 95% amino acid sequence identity to the human immunoglobulin framework region.

In some embodiments, an anti-TGF-β single-chain antibody includes (a) a heavy chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO:112, and/or (b) a light chain variable domain that is at least 60%, at least 65%, at least 70%, at least 75%, at least 80%, at least 85%, at least 90%, at least 95%, at least 96%, at least 97%, at least 98%, at least 99%, or 100% identical to the amino acid sequence of SEQ ID NO: 114.

In some embodiments, an anti-TGF-β single-chain antibody for use in accordance with the present invention comprises heavy chain CDRs CDR-H1$_{TNF\alpha}$, CDR-H2$_{TNF\alpha}$, and CDR-H3$_{TNF\alpha}$, wherein the set of VH CDRs has 10 or fewer amino acid substitutions relative to a set of reference CDRs CDR-H1, CDR-H2, and CDR-H3 of the fresolimumab VH domain (SEQ ID NO:112). In other, non-mutually exclusive embodiments, the anti-TGF-β single-chain comprises light chain CDRs CDR-H1$_{TGF\beta}$, CDR-H2$_{TGF\beta}$, and CDR-H3$_{TGF\beta}$, wherein the set of VL CDRs has 10 or fewer amino acid substitutions relative to a set of reference CDRs CDR-L1, CDR-L2, and CDR-L3 of the fresolimumab VL domain (SEQ ID NO:114). In certain embodiments, an anti-TGF-β single-chain antibody comprises both sets of heavy chain and light chain CDRs as above. Particularly suitable anti-TGF-β single-chain antibodies comprise a heavy chain variable domain comprising CDRs CDR-H1$_{TGF\beta}$, CDR-H2$_{TGF\beta}$, and CDR-H3$_{TGF\beta}$ and a light chain variable domain comprising CDRs CDR-L1$_{TGF\beta}$, CDR-L2$_{TGF\beta}$, and CDR-L3$_{TGF\beta}$, wherein the set of heavy chain CDRs has six or fewer, typically five or fewer, more typically four or fewer, and most typically three or fewer amino acid substitutions relative to CDR-H1. CDR-H2, and CDR-H3 of fresolimumab, and wherein the set of light chain CDRs has six or fewer, typically five or fewer, more typically four or fewer, and most typically three or fewer amino acid substitutions relative to CDR-L1, CDR-L2, and CDR-L3 of fresolimumab. The CDRs as above may be defined, for example, according to the Chothia definition, the Kabat definition, the AbM definition, the IMGT database definition, or the contact definition of CDR. In particular variations of an anti-TGF-β antibody as above, the each of the VH and VL domains has a human immunoglobulin framework region, or a variant thereof having at least 85%, at least 90%, or at least 95% amino acid sequence identity to the human immunoglobulin framework region.

Anti-inflammatory-cytokine antibodies for use in accordance with the present invention include affinity matured embodiments. Affinity matured antibodies can be produced by procedures known in the art (see, e.g., Marks et al., *Bio/Technology* 10:779-783, 1992; Barbas et al., *Proc Nat. Acad. Sci. USA* 91:3809-3813, 1994; Schier et al., *Gene* 169:147-155, 1995; Yelton et al., *J. Immunol.* 155:1994-2004, 1995; Jackson et al., *J. Immunol.* 154:3310-9, 1995; Hawkins et al., *J. Mol. Biol.* 226:889-896, 1992; and PCT Publication No. WO 2004/058184). One method for adjusting the affinity of an antibody is termed "library scanning mutagenesis." Generally, library scanning mutagenesis is carried out as follows. One or more amino acid positions in at least one CDR (e.g., in two, three, four, five, or six CDRs) are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Binding affinity may be determined, e.g., using Biacore™ surface plasmon resonance analysis, which detects differences in binding affinity of about 2-fold or greater. Biacore™ is particularly useful when the starting antibody already binds with a relatively high affinity, for example a $K_D$ of about 10 nM or lower.

In some embodiments of a fusion polypeptide comprising an anti-TNFα single-chain antibody as the first biologically active polypeptide, the anti-TNFα single-chain antibody comprises an amino acid sequence having at least 80%, at least 85%, at least 90%, or at least 95% identity with (i) amino acid residues 21-268 of SEQ ID NO:92 or (ii) amino acid residues 21-268 of SEQ ID NO:96. In more particular variations, the anti-TNFα single-chain antibody comprises an amino acid sequence having at least 96%, at least 97%, at least 98%, at least 99%, or 100% identity with (i) amino acid residues 21-268 of SEQ ID NO:92 or (ii) amino acid residues 21-268 of SEQ ID NO:96.

In some embodiments of a fusion polypeptide comprising an anti-TGF-β single-chain antibody as the first biologically active polypeptide, the anti-TGF-β single-chain antibody comprises an amino acid sequence having at least 80%, at least 85%, at least 90%, or at least 95% identity with (i) amino acid residues 21-269 of SEQ ID NO:100 or (ii) amino acid residues 21-269 of SEQ ID NO:104. In more particular variations, the anti-TGF-β single-chain antibody comprises an amino acid sequence having at least 96%, at least 97%, at least 98%, at least 99%, or 100% identity with (i) amino acid residues 21-269 of SEQ ID NO:100 or (ii) amino acid residues 21-269 of SEQ ID NO:104.

Polypeptide linkers for use in accordance with the present invention can be naturally occurring, synthetic, or a combination of both. The linker joins two separate polypeptide regions (e.g., an Fc region and a paraoxonase, or an Fc region and a DNase) and maintains the linked polypeptide regions as separate and discrete domains of a longer polypeptide. The linker can allow the separate, discrete domains to cooperate yet maintain separate properties (e.g., in the case of an Fc region linked to a paraoxonase or DNase, Fc receptor (e.g., FcRn) binding may be maintained for the Fc region, while functional properties of the paraoxonase (e.g., organophosphatase or arylesterase activity) or DNase (e.g., DNA binding and nuclease activity) will be maintained. For examples of the use of naturally occurring as well as artificial peptide linkers to connect heterologous polypeptides, see. e.g., Hallewell et al., *J. Biol. Chem.* 264, 5260-5268, 1989; Alfthan et al., *Protein Eng.* 8, 725-731, 1995; Robinson and Sauer, *Biochemistry* 35, 109-116, 1996; Khandekar et al., *J. Biol. Chem.* 272, 32190-32197, 1997; Fares et al., *Endocrinology* 139, 2459-2464, 1998; Smallshaw et al., *Protein Eng.* 12, 623-630, 1999; U.S. Pat. No. 5,856,456.

Typically, residues within the linker polypeptide are selected to provide an overall hydrophilic character and to be non-immunogenic and flexible. As used herein, a "flexible" linker is one that lacks a substantially stable higher-order conformation in solution, although regions of local stability are permissible. In general, small, polar, and hydrophilic residues are preferred, and bulky and hydrophobic residues are undesirable. Areas of local charge are to be avoided; if the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr, and the most preferred residues are Gly and Ser. In general, Phe, Tyr, Trp, Pro, Leu, Ile, Lys, and Arg residues will be avoided (unless present within an immunoglobulin hinge region of the linker), Pro residues due to their hydrophobicity and lack of flexibility, and Lys and Arg residues due to potential immunogenicity. The sequence of the linker will also be designed to avoid unwanted proteolysis.

In certain embodiments, linker L1 comprises at least two or at least three amino acid residues (e.g., at least five, at least 10, at least 16, at least 26, or at least 36 amino acid residues). In particular variations, L1 consists of from two to 60 amino acid residues, from three to 60 amino acid residues, from five to 40 amino acid residues, or from 15 to 40 amino acid residues. In other variations, L1 consists of from two to 50, from two to 40, from two to 36, from two to 35, from two to 30, from two to 26, from three to 50, from three to 40, from three to 36, from three to 35, from three to 30, from three to 26, from five to 60, from five to 50, from five to 40, from five to 36, from five to 35, from five to 30, from five to 26, from 10 to 60, from 10 to 50, from 10 to 40, from 10 to 36, from 10 to 35, from 10 to 30, from 10 to 26, from 15 to 60, from 15 to 50, from 15 to 36, from 15 to 35, from 15 to 30, or from 15 to 26 amino acid residues. In other variations, L1 consists of from 16 to 60, from 16 to 50, from 16 to 40, or from 16 to 36 amino acid residues. In yet other variations, L1 consists of from 20 to 60, from 20 to 50, from 20 to 40, from 20 to 36, from 25 to 60, from 25 to 50, from 25 to 40, or from 25 to 36 amino acid residues. In still other variations, L1 consists of from 26 to 60, from 26 to 50, from 26 to 40, or from 26 to 36 amino acid residues. In more specific variations, L1 consists of 16 amino acid residues, 21 amino acid residues, 26 amino acid residues, 31 amino acid residues, or 36 amino acid residues. In some embodiments, L1 comprises or consists of the amino acid sequence shown in residues SEQ ID NO:10, residues 268-288 of SEQ ID NO:12, or SEQ ID NO:14.

In typical variations of a fusion polypeptide comprising a DNase as the first biologically active polypeptide, L1 is present and comprises at least 15 amino acid residues. For example, an L1 linker joining the carboxyl-terminus of a DNase to the amino-terminus of another fusion component (e.g., an immunoglobulin Fc region) may comprise at least 20, at least 21, at least 22, at least 23, at least 24, at least 25, or at least 26 amino acid residues. In more particular variations, L1 consists of from 15 to 60 amino acid residues, from 15 to 51 amino acid residues, from 15 to 50 amino acid residues, from 15 to 46 amino acid residues, from 15 to 45 amino acid residues, from 15 to 41 amino acid residues, from 15 to 40 amino acid residues, from 15 to 36 amino acid residues, from 26 to 60 amino acid residues, from 26 to 51 amino acid residues, from 26 to 50 amino acid residues, from 26 to 46 amino acid residues, from 26 to 45 amino acid residues, from 26 to 41 amino acid residues, from 26 to 40 amino acid residues, or from 26 to 36 amino acid residues. In still more specific variations, L1 linking a DNase consists of 26 amino acid residues, 27 amino acid residues, 28 amino acid residues, 29 amino acid residues, 30 amino acid residues, 31 amino acid residues, 32 amino acid residues, 33 amino acid residues, 34 amino acid residues, 35 amino acid residues, or 36 amino acid residues. In some embodiments, L1 linking a DNase comprises or consists of the amino acid sequence shown in SEQ ID NO:12 or SEQ ID NO:14.

In some variations of a fusion polypeptide comprising an RNase or a SOD1 as the first biologically active polypeptide, L1 is present and comprises at least two amino acid residues. For example, an L1 linker joining the carboxyl-terminus of an RNase or a SOD1 to the amino-terminus of another fusion component (e.g., an immunoglobulin Fc region) may comprise at least three, at least five, or at least 10 amino acid residues. In more particular variations, L1 linking an RNase or a SOD1 consists of from two to 60 amino acid residues, from two to 51 amino acid residues, from two to 50 amino acid residues, from two to 46 amino acid residues, from two to 45 amino acid residues, from two to 41 amino acid residues, from two to 40 amino acid residues, from two to 36 amino acid residues, from 10 to 60 amino acid residues, from 10 to 51 amino acid residues, from 10 to 50 amino acid residues, from 10 to 46 amino acid residues, from 10 to 45 amino acid residues, from 10 to 41 amino acid residues, from 10 to 40 amino acid residues, or from 10 to 36 amino acid residues. In more specific variations, L1 linking an RNase or SOD1 consists of 16 or 26 amino acid residues. In some embodiments, L1 linking an RNase or a SOD1 comprises or consists of the amino acid sequence shown in SEQ ID NO:10 or SEQ ID NO:12.

In some variations of a fusion polypeptide comprising the formula P-L1-X as described herein, L1 comprises at least 20 amino acid residues. For example, an L1 linker joining the carboxyl-terminus of a paraoxonase to the amino-terminus of another fusion component (e.g., an immunoglobulin Fc region) may comprise at least 25, at least 26, at least 27, at least 28, at least 29, at least 30, at least 31, at least 32, at least 33, at least 34, at least 35, or at least 36 amino acid residues. In certain variations, L1 consists of from 20 to 60 amino acid residues, from 20 to 50 amino acid residues, from 20 to 45 amino acid residues, from 20 to 40 amino acid residues, from 20 to 36 amino acid residues, from 26 to 60 amino acid residues, from 26 to 50 amino acid residues, from 26 to 45 amino acid residues, from 26 to 40 amino acid residues, from 26 to 36 amino acid residues, from 36 to 60 amino acid residues, from 36 to 50 amino acid residues, from 36 to 45 amino acid residues, or from 36 to amino acid residues. In some embodiments, L1 linking the carboxyl-terminus of a paraoxonase comprises or consists of the amino acid sequence shown in SEQ ID NO:12 or SEQ ID NO:14.

Exemplary L2 linkers comprise at least three amino acid residues and are typically up to 60 amino acid residues. In certain variations, L2 linkers comprise at least four, at least five, at least six, at least seven, at least eight, at least 9, or at least 10 amino acid residues. In more specific variations, L2 consists of from six to 30, from six to 25, from six to 20, from seven to 30, from seven to 25, from seven to 20, from eight to 30, from eight to 25, from eight to 20, from nine to 30, from nine to 25, from nine to 20, from 10 to 30, from to 25, from 10 to 20, from 11 to 30, from 11 to 25, from 11 to 20, from 12 to 30, from 12 to 25, or from 12 to 20 amino acid residues. In some embodiments, L2 comprises or consists of the amino acid sequence shown in SEQ ID NO:56.

In certain embodiments, a polypeptide linker comprises a plurality of glycine residues. For example, in some embodiments, a polypeptide linker (e.g., L1) comprises a plurality of glycine residues and optionally at least one serine residue. In particular variations, a polypeptide linker (e.g., L1) comprises the sequence Gly-Gly-Gly-Gly-Ser (SEQ ID NO:29), such as, e.g., two or more tandem repeats of the amino acid sequence of SEQ ID NO:29. In some embodiments, a linker comprises the sequence [Gly-Gly-Gly-Gly-Ser]$_n$ ([SEQ ID NO:29]n), where n is a positive integer such as, for example, an integer from 2 to 8, from 2 to 7, from 2 to 6, from 3 to 8, from 3 to 7, from 3 to 6, from 4 to 8, from 4 to 7, or from 4 to 6. In a specific variation of a polypeptide linker comprising the formula [Gly-Gly-Gly-Gly-Ser]$_n$, n is 4. In another specific variation of a polypeptide linker comprising the formula [Gly-Gly-Gly-Gly-Ser]$_n$, n is 6. In yet another specific variation of a polypeptide linker comprising the formula [Gly-Gly-Gly-Gly-Ser]$_n$, n is 5. In certain embodiments, a polypeptide linker comprises a series of glycine and serine residues (e.g., [Gly-Gly-Gly-Gly-Ser]n, where n is defined as above) inserted between two other sequences of the polypeptide linker (e.g., inserted between Asp-Leu-Ser at the N-terminal end of the linker and Thr-Gly-Leu at the C-terminal end of the linker). In other embodiments, a polypeptide linker includes glycine and serine residues (e.g., [Gly-Gly-Gly-Gly-Ser]$_n$, where n is defined as above) attached at one or both ends of another sequence of the polypeptide linker.

In some embodiments of a fusion polypeptide as above wherein X is present, X is a dimerizing domain. Various dimerization domains are suitable for use in accordance with certain fusion polypeptide embodiments and dimeric fusion proteins as described herein. In certain embodiments of a fusion polypeptide comprising a dimerizing domain, the dimerizing domain is an immunoglobulin heavy chain constant region. The immunoglobulin heavy chain constant region may be a native sequence constant region or a variant constant region. In typical variations, an immunoglobulin heavy chain constant region is capable of binding to the neonatal Fc receptor (FcRn) with sufficient affinity to confer improved half-life to the fusion polypeptide in vivo. A particularly suitable immunoglobulin heavy chain constant region for use in accordance with the present invention is an immunoglobulin Fc region. In some embodiments, the heavy chain constant region lacks one or more effector functions (e.g., one or both of ADCC and CDC effector functions).

In some embodiments of a fusion polypeptide comprising an immunoglobulin Fc region, the immunoglobulin Fc region is a human IgG Fc region having, relative to the wild-type human IgG sequence, an amino acid substitution in the CH2 region so that the molecule is not glycosylated, including but not limited to an amino acid substitution at N297 (Eu numbering for human IgG heavy chain constant region) (corresponding to amino acid position 82 of SEQ ID NO:26, SEQ ID NO:28, SEQ ID NO: 116, or SEQ ID NO: 118). In another embodiment, the Fc region is human IgG1 (γ1) with the three cysteines of the hinge region (C220, C226, C229) each changed to a non-cysteine residue (e.g., serine) and, optionally, the proline at position 238 of the CH2 domain changed to a non-proline residue (e.g., serine or aspartate). In another embodiment, the Fc region is human γ1 with cysteine C220 changed to a non-cysteine residue (e.g., serine) and, optionally, the proline at position of the CH2 domain changed to a non-proline residue (e.g., serine or aspartate). In another embodiment, the Fc region is human γ1 with N297 changed to a non-asparagine residue (e.g., alanine, glutamine, or glycine). In another embodiment, the Fc region is human γ1 with one or more amino acid substitutions between Eu positions 292 and 300. In another embodiment, the Fc region is human γ1 with one or more amino acid additions or deletions at any position between residues 292 and 300. In another embodiment, the Fc region is human γ1 with an SCC hinge (i.e., with cysteine C220 changed to serine and with a cysteine at each of Eu positions 226 and 229) or an SSS hinge (i.e., each of the three cysteines at Eu positions 220, 226, and 229 changed to serine). In further embodiments, the Fc region is human γ1 with an SCC hinge and an amino acid substitution at P238. In another embodiment, the Fc domain is human γ1 with amino acid substitutions that alter binding by Fc gamma receptors (I, II, III) without affecting FcRn binding important for half-life. In further embodiments, an Fc region is as disclosed in Ehrhardt and Cooper, *Curr. Top. Microbiol. Immunol.* 2010 Aug. 3 (Immunoregulatory Roles for Fc Receptor-Like Molecules); Davis et al., *Ann. Rev. Immunol.* 25:525-60, 2007 (Fc receptor-like molecules); or Swainson et al., *J. Immunol.* 184:3639-47, 2010.

In some embodiments, the Fc region comprises an amino acid substitution that alters the antigen-independent effector functions of the fusion protein. In some such embodiments, the Fc region includes an amino acid substitution that alters the circulating half-life of the resulting molecule. Such Fc variants exhibit either increased or decreased binding to FcRn when compared to an Fc region lacking these substitutions and, therefore, confer increased or decreased half-life, respectively, of the resulting molecule in serum. Fc variants with improved affinity for FcRn are anticipated to have longer serum half-lives, and such Fc variants have useful applications in methods of treating mammals where long half-life of the administered Fc fusion is desired and where increased transport through the lungs to the circulation is desired. In contrast, Fc variants with decreased FcRn binding affinity are expected to have shorter half-lives, and such variants are also useful, for example, for administration to a mammal where a shortened circulation time may be advantageous (e.g., where the fusion protein has toxic side effects when present in the circulation for prolonged periods). For treatment of conditions characterized by NETosis, fine tuning of the half-life of a DNase-Fc fusion protein through altering FcRn binding may be useful since NETs, while contributing to pathogenesis, are also beneficial in certain settings; digestion of pathogenic NETs may not require as long a half life, so more rapid clearance of the DNase may allow neutrophils to form NETs in their protective anti-microbial function. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization to the brain, kidney, and/or liver is desired. In one exemplary embodiment, the fusion molecules of the invention exhibit reduced transport across the epithelium of kidney glomeruli from the vasculature. In another embodiment, the fusion molecules of the invention exhibit reduced transport across the blood brain barrier (BBB) from the brain, into the vascular space. In one embodiment, a fusion molecule with altered FcRn binding comprises an Fc region having one or more amino acid substitutions within the "FcRn binding loop" of the Fc domain. Exemplary amino acid substitutions that alter FcRn binding activity are disclosed in International PCT Publication No. WO 05/047327, which is incorporated by reference herein. Exemplary amino acid substitutions that increase FcRn binding activity are also described, e.g., by Wang et al., *Protein Cell* 9:63-73, 2018 (see, e.g., Table 1). In some embodiments, an Fc variant with increased FcRn binding activity has an amino acid substitution at each of Eu positions 252, 254, and 256 (e.g., M252Y, S254T, and T256E). In other variations, an Fc variant with increased FcRn binding activity has an amino acid substitution at each of Eu positions 428 and 434 (e.g., M428L and N434S).

In other embodiments, a fusion polypeptide of the present invention comprises an Fc variant comprising an amino acid substitution that alters one or more antigen-dependent effector functions of the polypeptide, in particular antibody-dependent cellular cytotoxicity (ADCC) or complement activation, e.g., as compared to a wild type Fc region. In an exemplary embodiment, such fusion polypeptides exhibit altered binding to an Fc gamma receptor (FcγR, e.g., CD16). Such fusion polypeptides exhibit either increased or decreased binding to Fcγ when compared to wild-type polypeptides and, therefore, mediate enhanced or reduced effector function, respectively. Fc variants with improved affinity for FcγR are anticipated to enhance effector function, and such variants have useful applications in methods of treating mammals where target molecule destruction is desired. In contrast, Fc variants with decreased FcγR binding affinity are expected to reduce effector function, and such fusion proteins are also useful, for example, for treatment of conditions in which target cell destruction is undesirable, e.g., where normal cells may express target molecules, or where chronic administration of the fusion molecule might result in unwanted immune system activation. In one embodiment, the fusion polypeptide comprising an Fc region exhibits at least one altered antigen-dependent effector function selected from the group consisting of opsonization, phagocytosis, complement dependent cytotoxicity (CDC), antibody-dependent cellular cytotoxicity (ADCC), or effector cell modulation as compared to a polypeptide comprising a wild-type Fc region. In typical embodiments of a DNase fusion molecule comprising an Fc variant with altered antigen-dependent effector function, the Fc variant has one or more reduced effector functions relative to the corresponding wild-type Fc region.

In one embodiment, a fusion polypeptide comprising an Fc region exhibits altered binding to an activating FcγR (e.g., FcγI, FcγIIa, or FcγRIIIa). In another embodiment, the fusion protein exhibits altered binding affinity to an inhibitory FcγR (e.g., FcγRIIb). Exemplary amino acid substitutions which alter FcR or complement binding activity are disclosed in International PCT Publication No. WO 05/063815, which is incorporated by reference herein. Exemplary Fc variants with reduced effector function are also described, e.g., by Tam et al., *Antibodies* 6:12, 2017 (describing variants of human IgG1 (γ1) and IgG4(γ4)); Wang et al., *Protein Cell* 9:63-73, 2018 (see, e.g., Table 1); Lo et al., *J. Biol. Chem.* 292:3900-3908, 2017; Idusogie et al., *J. Immunol.* 164:4178-4184, 2000 (each of which is incorporated by reference herein). Suitable Fc variants that reduce antigen-dependent effector function include, for example, variants having an amino acid substitution at Eu position 238 and/or position 331 (e.g., P238S and/or P331S or P331A). In addition, amino acid substitutions at Eu positions 234 and 235 of human Fc (e.g., L234A/L235A in IgG1, or F234A/L235A in IgG4) reduce FcγR binding and have been shown to reduce cytokine storm when introduced into anti-CD3 mAb (see, e.g., Wang et al., supra), and an amino acid substitution at Eu position 329 (e.g., P329A) is highly effective at reducing C1q binding (see, e.g., Lo et al., supra). Other exemplary approaches to removing ADCC and CDC effector functions is to make hybrid Fc domains derived from human IgG2 (Eu positions 118-260) and IgG4 (Eu positions 261-447), or to modify human IgG2 to contain selected amino acid substitutions from IgG4. See Wang et al., supra.

A fusion polypeptide comprising an Fc region may also comprise an amino acid substitution that alters the glycosylation of the Fc region. For example, the Fc domain of the fusion protein may have a mutation leading to reduced glycosylation (e.g., N- or O-linked glycosylation) or may comprise an altered glycoform of the wild-type Fc domain (e.g., a low fucose or fucose-free glycan). In another embodiment, the molecule has an amino acid substitution near or within a glycosylation motif, for example, an N-linked glycosylation motif that contains the amino acid sequence NXT or NXS. Exemplary amino acid substitutions which reduce or alter glycosylation are disclosed in International PCT Publication No. WO 05/018572 and US Patent Application Publication No. 2007/0111281, which are incorporated by reference herein.

Particularly suitable amino acid substitutions to reduce glycosylation and which also reduce ADCC and CDC effector functions of Fc include amino acid substitutions at Eu position 297 (e.g., N297A, N297Q, or N297G). See, e.g., Wang et al., supra. N297 substitutions may also be paired with substitutions at position 265 (e.g., D265A) to further reduce CDC. See, e.g., Lo et al., supra.

It will be understood by those of skill in the art that various embodiments of Fc variants as described herein can be combined in the fusion polypeptides of the present invention, unless the context clearly indicates otherwise.

In some embodiments, an immunoglobulin Fc region comprises an amino acid sequence having at least 80%, at least 85%, at least 90%, or at least 95% identity with an amino acid sequence selected from sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO: 116, or (v) residues 1-232 or 1-231 of SEQ ID NO:118. In yet other embodiments, the Fc region comprises an amino acid sequence having at least 96%, at least 97%, at least 98%, at least 99%, or 100% identity with the amino acid sequence shown in (i) residues 1-232 or 1-231 of SEQ ID NO:26, (ii) residues 1-232 or 1-231 of SEQ ID NO:28, (iii) residues 159-390 or 159-389 of SEQ ID NO:42, (iv) residues 1-232 or 1-231 of SEQ ID NO:116, or (v) residues 1-232 or 1-231 of SEQ ID NO: 118.

In some embodiments, an immunoglobulin heavy chain constant region comprises an amino acid sequence having at least 80%, at least 85%, at least 90%, or at least 95% identity with an amino acid sequence selected from sequence shown in (i) residues 16-232 or 16-231 of SEQ ID NO:26, (ii) residues 16-232 or 16-231 of SEQ ID NO: 116, or (iii) residues 16-232 or 16-231 of SEQ ID NO: 118. In yet other embodiments, the immunoglobulin heavy chain constant region comprises an amino acid sequence having at least 96%, at least 97%, at least 98%, at least 99%, or 100% identity with the amino acid sequence shown in (i) residues 16-232 or 16-231 of SEQ ID NO:26, (ii) residues 16-232 or 16-231 of SEQ ID NO: 116, or (iii) residues 16-232 or 16-231 of SEQ ID NO:118.

In some variations of a fusion polypeptide as above wherein X is present, X is an FcRn-binding domain. Particularly suitable FcRn-binding domains include immunoglobulin heavy chain constant regions that retain FcRn-binding activity such as, e.g., an immunoglobulin Fc region; in some such variations, the Fc region is an Fc region as described herein (e.g., as described above in the context of a dimerizing domain). In other embodiments, an FcRn-binding domain is an albumin (e.g., human albumin). Yet other suitable FcRn-binding domains include single-chain antibodies (e.g., scFvs), peptide aptamers, or alternative scaffold proteins having binding affinity for FcRn; such alternative FcRn-binding molecules are readily created using, for example, display technologies that allow for selection of binding agents through screening of large expression libraries (e.g., libraries of immunoglobulin domains, randomized peptides, or other protein structures). Such display technologies are generally well-known in the art and include, for example, phage display. See, e.g., *Antibody Engineering: A Practical Approach*, McCafferty, Hoogenboom, and Chiswell Eds., IRL Press 1996. Alternative scaffold proteins for generating FcRn-binding domains include, e.g., avimers, ankyrin repeats, and adnectins, as well as other proteins with domains that can be evolved to generate specific affinity for a desired molecular target (see, e.g., Silverman et al., *Nature Biotechnology* 23:1556-1561, 2005; Zahnd et al., *J. Mol. Biol.* 369:1015-1028, 2007; U.S. Pat. No. 7,115,396 to Lipovsek et al.).

In some embodiments of a paraoxonase fusion polypeptide comprising a DNase as described above, the fusion polypeptide comprises an amino acid sequence having at least 80%, at least 85%, at least 90%, or at least 95% identity with the amino acid sequence shown in (i) residues 21-896 or 1-896 of SEQ ID NO:2, (ii) residues 21-896 or 1-896 of SEQ ID NO:128, (iii) residues 21-896 or 1-896 of SEQ ID NO:130, (iv) residues 21-906 or 1-906 of SEQ ID NO:148, (v) residues 21-896 or 1-896 of SEQ ID NO:158, (vi) residues 21-906 or 1-906 of SEQ ID NO:160, (vii) residues 21-906 or 1-906 of SEQ ID NO:162, or (viii) residues 21-906 or 1-906 of SEQ ID NO:164. In yet other embodiments, the fusion polypeptide comprises an amino acid sequence having at least 96%, at least 97%, at least 98%, at least 99%, or 100% sequence identity with the amino acid sequence shown in (i) residues 21-896 or 1-896 of SEQ ID NO:2, (ii) residues 21-896 or 1-896 of SEQ ID NO:128, (iii) residues 21-896 or 1-896 of SEQ ID NO:130, (iv) residues 21-906 or 1-906 of SEQ ID NO:148, (v) residues 21-896 or 1-896 of SEQ ID NO:158, (vi) residues 21-906 or 1-906 of SEQ ID NO:160, (vii) residues 21-906 or 1-906 of SEQ ID NO:162, or (viii) residues 21-906 or 1-906 of SEQ ID NO:164.

In some embodiments of a paraoxonase fusion polypeptide comprising an RNase as described above, the fusion polypeptide comprises an amino acid sequence having at least 80%, at least 85%, at least 90%, or at least 95% identity with an amino acid sequence selected from the sequence shown in (i) residues 21-764 or 1-764 of SEQ ID NO:40 or (ii) residues 21-740 or 1-740 of SEQ ID NO:48. In yet other embodiments, the fusion polypeptide comprises an amino acid sequence having at least 96%, at least 97%, at least 98%, at least 99%, or 100% sequence identity with the amino acid sequence shown in (i) residues 21-764 or 1-764 of SEQ ID NO:40 or (ii) residues 21-740 or 1-740 of SEQ ID NO:48.

In some embodiments of a paraoxonase fusion polypeptide comprising a superoxide dismutase 1 (SOD1) as described above, the fusion polypeptide comprises an amino acid sequence having at least 80%, at least 85%, at least 90%, or at least 95% identity with an amino acid sequence selected from the sequence shown in (i) residues 23-781 or 1-781 of SEQ ID NO:50, (ii) residues 23-781 or 1-781 of SEQ ID NO:52, or (iii) residues 23-791 or 1-791 of SEQ ID NO:54. In yet other embodiments, the fusion polypeptide comprises an amino acid sequence having at least 96%, at least 97%, at least 98%, at least 99%, or 100% sequence identity with the amino acid sequence shown in (i) residues 23-781 or 1-781 of SEQ ID NO:50, (ii) residues 23-781 or 1-781 of SEQ ID NO:52, or (iii) residues 23-791 or 1-791 of SEQ ID NO:54.

In some embodiments of a paraoxonase fusion polypeptide comprising a CTLA-4 extracellular domain as described above, the fusion polypeptide comprises an amino acid sequence having at least 80%, at least 85%, at least 90%, or at least 95% identity with an amino acid sequence selected from the sequence shown in residues 21-736 or 1-736 of SEQ ID NO:66. In yet other embodiments, the fusion polypeptide comprises an amino acid sequence having at least 96%, at least 97%, at least 98%, at least 99%, or 100% sequence identity with the amino acid sequence shown in residues 21-736 or 1-736 of SEQ ID NO:66.

In some embodiments of a paraoxonase fusion polypeptide comprising a CD40 extracellular domain as described above, the fusion polypeptide comprises an amino acid sequence having at least 80%, at least 85%, at least 90%, or at least 95% identity with an amino acid sequence selected from the sequence shown in (i) residues 21-804 or 1-804 of SEQ ID NO:74, (ii) residues 21-804 or 1-804 of SEQ ID NO:78, (iii) residues 21-804 or 1-804 of SEQ ID NO:82, (iv) residues 21-804 or 1-804 of SEQ ID NO:86, or (v) residues 21-804 or 1-804 of SEQ ID NO:90. In yet other embodiments, the fusion polypeptide comprises an amino acid sequence having at least 96%, at least 97%, at least 98%, at least 99%, or 100% sequence identity with the amino acid sequence shown in (i) residues 21-804 of SEQ ID NO:74 or 1-804, (ii) residues 21-804 or 1-804 of SEQ ID NO:78, (iii)

residues 21-804 or 1-804 of SEQ ID NO:82, (iv) residues 21-804 or 1-804 of SEQ ID NO:86, or (v) residues 21-804 or 1-804 of SEQ ID NO:90.

In some embodiments of a paraoxonase fusion polypeptide comprising a polypeptide that specifically binds and neutralizes TNFα as described above, the fusion polypeptide comprises an amino acid sequence having at least 80%, at least 85%, at least 90%, or at least 95% identity with an amino acid sequence selected from the sequence shown in (i) residues 21-860 or 1-860 of SEQ ID NO:94 or (ii) residues 21-860 or 1-860 of SEQ ID NO:98. In yet other embodiments, the fusion polypeptide comprises an amino acid sequence having at least 96%, at least 97%, at least 98%, at least 99%, or 100% sequence identity with the amino acid sequence shown in (i) residues 21-860 or 1-860 of SEQ ID NO:94 or (ii) residues 21-860 or 1-860 of SEQ ID NO:98.

In some embodiments of a paraoxonase fusion polypeptide comprising a polypeptide that specifically binds and neutralizes TGF-β as described above, the fusion polypeptide comprises an amino acid sequence having at least 80%, at least 85%, at least 90%, or at least 95% identity with an amino acid sequence selected from the sequence shown in (i) residues 21-861 or 1-861 of SEQ ID NO:102 or (ii) residues 21-861 or 1-861 of SEQ ID NO:106. In yet other embodiments, the fusion polypeptide comprises an amino acid sequence having at least 96%, at least 97%, at least 98%, at least 99%, or 100% sequence identity with the amino acid sequence shown in (i) residues 21-861 or 1-861 of SEQ ID NO:102 or (ii) residues 21-861 or 1-861 of SEQ ID NO:106.

In some embodiments of a paraoxonase fusion polypeptide comprising the formula X-L2-P as described herein, the fusion polypeptide comprises an amino acid sequence having at least 80%, at least 85%, at least 90%, or at least 95% identity with the amino acid sequence shown in (i) residues 21-613 or 1-613 of SEQ ID NO:122, (ii) residues 21-613 or 1-613 of SEQ ID NO:132, (iii) 21-613 or 1-613 of SEQ ID NO:134, (iv) residues 21-610 or 1-610 of SEQ ID NO:142, (v) residues 21-610 or 1-610 of SEQ ID NO:144, or (vi) residues 21-610 or 1-610 of SEQ ID NO:146. In yet other embodiments, the fusion polypeptide comprises an amino acid sequence having at least 96%, at least 97%, at least 98%, at least 99%, or 100% sequence identity with the amino acid sequence shown in (i) residues 21-613 or 1-613 of SEQ ID NO:122, (ii) residues 21-613 or 1-613 of SEQ ID NO:132, (iii) 21-613 or 1-613 of SEQ ID NO:134, (iv) residues 21-610 or 1-610 of SEQ ID NO:142, (v) residues 21-610 or 1-610 of SEQ ID NO:144, or (vi) residues 21-610 or 1-610 of SEQ ID NO:146.

The present invention also provides dimeric proteins comprising first and second polypeptide fusions, each of the polypeptide fusions comprising a dimerizing domain, as described above. Accordingly, in another aspect, the present invention provides a dimeric protein comprising a first fusion polypeptide and a second fusion polypeptide, wherein each of the first and second fusion polypeptides comprises, from an amino-terminal position to a carboxyl-terminal position, T-L1-X-L2-P, wherein T is a first biologically active polypeptide is selected from a DNase, and RNase, a superoxide dismutase 1 (SOD1), a cytotoxic T-lymphocyte associated molecule-4 (CTLA-4) extracellular domain, a CD40 extracellular domain, and a polypeptide that specifically binds and neutralizes an inflammatory cytokine (e.g., a polypeptide that specifically binds and neutralizes tumor necrosis factor α (TNFα) or transforming growth factor-β (TGFβ)); L1 is a first polypeptide linker that is optionally present; X is a dimerizing domain; L2 is a second polypeptide linker that is optionally present; and P is a biologically active paraoxonase. In another aspect, the present invention provides a dimeric protein comprising a first fusion polypeptide and a second fusion polypeptide, wherein each of the first and second fusion polypeptides comprises, from an amino-terminal position to a carboxyl-terminal position, X-L2-P, wherein X is a dimerizing domain, L2 is a polypeptide linker that is optionally present, and P is a biologically active paraoxonase. In another aspect, the present invention provides a dimeric protein comprising a first fusion polypeptide and a second fusion polypeptide, wherein each of the first and second fusion polypeptides comprises, from an amino-terminal position to a carboxyl-terminal position, P-L1-X, wherein P is a biologically active paraoxonase, L1 is a polypeptide linker, and X is a dimerizing domain.

III. Materials and Methods for Making Polypeptide Fusions and Dimeric Proteins

The present invention also provides polynucleotide molecules, including DNA and RNA molecules, that encode the fusion polypeptides disclosed above. The polynucleotides of the present invention include both single-stranded and double-stranded molecules. Polynucleotides encoding various segments of a fusion polypeptide (e.g., an Fc fragment; DNase and P polypeptide segments) can be generated and linked together to form a polynucleotide encoding a fusion polypeptide as described herein using known methods for recombinant manipulation of nucleic acids.

DNA sequences encoding fusion components in accordance with the present disclosure (for example, DNases (e.g., DNase1), paraoxonases (e.g., PON1), RNases (e.g., RNase1), superoxide dismutase 1 (SOD1), CTLA-4 and CD40 extracellular domains, and immunoglobulin Fc regions) are generally known in the art. Exemplary DNA sequences are disclosed herein (see Sequence Listing). Additional DNA sequences encoding any of these polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide. DNA and RNA encoding functional variants and fragments of such polypeptides can also be obtained using known recombinant methods to introduce variation into a polynucleotide sequence, followed by expression of the encoded polypeptide and determination of functional activity (e.g., nuclease activity) using an appropriate screening assay.

Methods for preparing DNA and RNA are well known in the art. For example, complementary DNA (cDNA) clones can be prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly (A)$_+$ RNA is prepared from total RNA using the method of Aviv and Leder (*Proc. Natl. Acad. Sci. USA* 69:1408-1412, 1972). Complementary DNA is prepared from poly(A)$_+$ RNA using known methods. In the alternative, genomic DNA can be isolated. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR," Mullis, U.S. Pat. No. 4,683,202). Expression libraries can be probed with antibodies to the polypeptide of interest, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See generally Glick and Pasternak, *Molecular Biotechnology, Principles & Applications of Recombinant DNA*, ASM Press, Washington, D.C., 1994; Itakura et al., *Ann. Rev. Biochem.* 53:323-356, 1984; and Climie et al., *Proc. Natl. Acad. Sci. USA* 87:633-637, 1990.

In another aspect, materials and methods are provided for producing the polypeptide fusions of the present invention, including dimeric proteins comprising the fusion polypeptides. The fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N Y, 1989, and Ausubel et al., eds., *Current Protocols in Molecular Biology*, Green and Wiley and Sons, N Y, 1993.

In general, for production of a fusion polypeptide in a host cell, a DNA sequence encoding the fusion polypeptide is operably linked to other genetic elements required for its expression, typically including a transcription promoter and terminator, within an expression cassette. Typically, the expression cassette is contained within an expression vector for delivery into a host cell. The vector will also commonly contain one or more selectable markers and one or more origins of replication, although those skilled in the art will recognize that within certain systems selectable markers may be provided on separate vectors, and replication of the exogenous DNA may be provided by integration of an expression cassette into the host cell genome such as, e.g., in the generation of stable cell lines. Selection of promoters, terminators, selectable markers, vectors and other elements is a matter of routine design within the level of ordinary skill in the art. Many such elements are described in the literature and are available through commercial suppliers.

To direct a DNase fusion polypeptide into the secretory pathway of a host cell, a secretory signal sequence is provided in the expression cassette. The encoded secretory peptide may be that of a corresponding native protein (e.g., a native DNase secretory peptide as shown in amino acid residues 1-22 of SEQ ID NO:16, a native RNase secretory peptide as shown in amino acid residues 1-28 of SEQ ID NO:38, or a native CD40 secretory peptide as shown in amino acid residues 1-20 of SEQ ID NO:68), or may be derived from another secreted protein (e.g., t-PA; see U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Secretory signal sequences suitable for use in accordance with the present invention include, for example, polynucleotides encoding the human VK3 leader peptide (SEQ ID NO:58).

Expression of fusion polypeptides comprising a dimerizing domain as described herein, via a host cell secretory pathway, is expected to result in the production of dimeric proteins. Accordingly, in another aspect, the present invention provides dimeric proteins comprising first and second fusion polypeptides as described above (e.g., a dimeric protein comprising a first fusion polypeptide and a second fusion polypeptide, wherein each of the first and second fusion polypeptides comprises, from an amino-terminal position to a carboxyl-terminal position, T-L1-X-L2-P, X-L2-P, or P-L1-X as described herein). Dimers may also be assembled in vitro upon incubation of component polypeptides under suitable conditions. In general, In vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann el al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter el al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g., CHO-K1, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Virginia. Strong transcription promoters can be used, such as promoters from SV-40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny—by virtue of integration of the expression cassette into its genomic DNA—are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

In some aspects, the present invention provides a stable cell line containing, within its genomic DNA, an expression cassette encoding a paraoxonase fusion polypeptide as described herein, wherein the stable cell line constitutively expresses the encoded paraoxonase fusion. Stable cell lines can be generated by methods generally known in the art, which generally include the identification of single stable cell clones from a polyclonal colony of stable transfectants by limited dilution and expansion. Protein expression of selected clones can then be assessed to identify high-expressing clones for expansion. In some embodiments, the stable cell line is a mammalian cell line such as, e.g., a Chinese hamster ovary (CHO) cell line. In some preferred embodiments of a stable cell line constitutively expressing a DNase-PON fusion polypeptide in accordance with the present disclosure, the DNase is an enhanced DNase1 as described herein; in some such embodiments, the DNase-PON fusion polypeptide is an enhanced DNase1-Fc-PON1 fusion polypeptide comprising an amino acid sequence having at least 90%, at least 95%, at least 96%, at least 97%, at least 98%, at least 99%, or 100% identity with the amino acid sequence shown in (i) residues 21-896 or 1-896 of SEQ ID NO:2, (ii) residues 21-906 or 1-906 of SEQ ID NO:148, (iii) residues 21-896 or 1-896 of SEQ ID NO:158, or (iv) residues 21-906 or 1-906 of SEQ ID NO:160. In some variations, the stable cell line is a mammalian cell line (e.g., CHO) capable of producing the fusion polypeptide (e.g., a DNase1-Fc-PON1 fusion polypeptide) at a concentration of at least 25 mg/L, at least 50 mg/L, at least 100 mg/L, at least 200 mg/L, or at least 500 mg/L of the cell culture. Typically, a DNase1-Fc fusion polypeptide as described herein can be expressed at levels of approximately 25-100 mg/L from initial isolated clones. Recloning of the initial cultures can often stabilize and increase expression by 2-3 fold. Amplification of the expression level can also be achieved by further plating of cells at low density in increasing levels of methotrexate from an initial concentration of 50 nM up to as much as 1 µM. Once cells have adapted, further rounds of limiting dilution cloning are required to maintain high expression levels.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and International PCT Publication No. WO 94/06463.

Insect cells can be infected with recombinant baculovirus, commonly derived from *Autographa californica* nuclear polyhedrosis virus (AcNPV) (see King and Possee, *The Baculovirus Expression System: A Laboratory Guide*, Chapman & Hall, London; O'Reilly et al., *Baculovirus Expression Vectors: A Laboratory Manual*, Oxford University Press., New York, 1994; and Richardson, Ed., *Baculovirus Expression Protocols. Methods in Molecular Biology*, Humana Press, Totowa, N J, 1995). Recombinant baculovirus can also be produced through the use of a transposon-based system described by Luckow et al. (J. Virol. 67:4566-4579, 1993). This system, which utilizes transfer vectors, is commercially available in kit form (BAC-TO-BAC kit; Life Technologies, Gaithersburg, MD). The transfer vector (e.g., PFASTBAC1; Life Technologies) contains a Tn7 transposon to move the DNA encoding the protein of interest into a baculovirus genome maintained in *E. coli* as a large plasmid called a "bacmid" (see Hill-Perkins and Possee, *J. Gen. Virol.* 71:971-976, 1990; Bonning et al., *J. Gen. Virol.* 75:1551-1556, 1994; Chazenbalk and Rapoport, *J. Biol. Chem.* 270:1543-1549, 1995). Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, CA) (see generally Glick and Pasternak, supra; see also U.S. Pat. No. 5,300,435). Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (e.g., King and Possee, supra; O'Reilly et al., supra.; Richardson, supra).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guilliermondii*, and *Candida maltosa* are known in the art. See, e.g., Gleeson et al., J. Gen. Microbiol. 132:3459-3465, 1986; Cregg, U.S. Pat. No. 4,882,279; and Raymond et al., Yeast 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well-known in the art (see, e.g., Sambrook et al., supra). When expressing a fusion polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, e.g., Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

In some variations, for production of an actin-resistant DNase1-PON fusion polypeptide as described herein (e.g., an actin-resistant DNase1-L1-Fc-L2-PON1 fusion polypeptide comprising an amino acid sequence having at least 90%, at least 95%, at least 96%, at least 97%, at least 98%, at least 99%, or 100% identity with the amino acid sequence shown in (i) residues 21-896 or 1-896 of SEQ ID NO:2 or (ii) residues 21-906 or 1-906 of SEQ ID NO:148), host cells are cultured in the presence of a DNase1 inhibitor to reduce toxicity of the enhanced DNase during its expression. DNase1 inhibitors are generally known in the art and include, for example, the inhibitor rutin (see, e.g., Kolarevic el al., *Chem. Biodiversity* 16:e1900060, 2019). In certain embodiments, the host cells cultured in the presence of a DNase1 inhibitor are mammalian cells such as, e.g., CHO.

Proteins of the present invention are purified by conventional protein purification methods, typically by a combination of chromatographic techniques. See generally *Affinity Chromatography: Principles & Methods*, Pharmacia LKB Biotechnology, Uppsala, Sweden. 1988; and Scopes, *Protein Purification: Principles and Practice*, Springer-Verlag, New York, 1994. Proteins comprising an immunoglobulin Fc region can be purified by affinity chromatography on immobilized protein A. Additional purification steps, such as gel filtration, can be used to obtain the desired level of purity or to provide for desalting, buffer exchange, and the like.

For example, fractionation and/or conventional purification methods can be used to obtain fusion polypeptides and dimeric proteins of the present invention purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, PA), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well-known and widely used in the art, and are available from commercial suppliers. Selection of a particular method for polypeptide isolation and purification is a matter of routine design and is determined in part by the properties of the chosen support. See, e.g., *Affinity Chromatography: Principles & Methods* (Pharmacia LKB Biotechnology 1988); Doonan, *Protein Purification Protocols* (The Humana Press 1996).

Additional variations in protein isolation and purification can be devised by those of skill in the art. For example, antibodies that specifically bind a fusion polypeptide or dimeric protein as described herein (e.g., an antibody that specifically binds a polypeptide segment corresponding to a DNase) can be used to isolate large quantities of protein by immunoaffinity purification.

The proteins of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (see, e.g., M. Deutscher, (ed.), *Meth. Enzymol.* 182:529, 1990). Within additional embodiments of the invention, a fusion of the polypeptide of interest and an affinity tag (e.g., maltose-binding protein) may be constructed to facilitate purification. Moreover, receptor- or ligand-binding properties of a fusion polypeptide or dimer thereof can be exploited for purification.

In some variations, a DNase1-PON fusion molecule comprising an enhanced but non-actin-resistant DNase1 as described herein (i.e., a DNase that does not contain any amino acid substitution, relative to human DNase1, that decreases G-actin-induced inhibition of endonuclease activity of the DNase relative to human DNase1) is treated with ethylenediamine (EDA) following purification in order to reduce the molecule's actin binging, thereby providing a DNase-Fc fusion molecule that is resistant to actin. The EDA-treated DNase1-PON fusion molecule is then further treated to remove EDA using methods generally known in the art (see, e.g., U.S. Pat. No. 11,225,648). Such embodiments are advantageous for achieving higher expression of the DNase1-PON fusion for pharmaceutical use, since expression of the non-actin-resistant form of enhanced DNase1 would be less toxic to host cells (e.g., CHO). In particular embodiments, the purified DNase1-PON to be treated with EDA comprises an amino acid sequence having at least 90%, at least 95%, at least 96%, at least 97%, at least 98%, at least 99%, or 100% identity with the amino acid sequence shown in (i) residues 21-896 of SEQ ID NO:158 or (ii) residues 21-906 of SEQ ID NO:160.

The polypeptides of the present invention are typically purified to at least about 80% purity, more typically to at least about 90% purity and preferably to at least about 95%, at least about 96%, at least about 97%, at least about 98%, or at least about 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

IV. Methods of Use and Pharmaceutical Compositions

The fusion polypeptides and dimeric proteins of the present invention can be used to provide therapy for the treatment of various diseases or disorders. The paraoxonase fusion polypeptides are particularly useful, e.g., for treatment of inflammatory, autoimmune, neurological, cardiovascular, and/or fibrotic diseases and disorders. In aspects relating to bispecific fusions further comprising a first biologically active polypeptide as described herein (e.g., a DNase, RNase, or SOD1), the fusion polypeptides and dimeric proteins may further provide one or more additional biological activities for treatment. For example, paraoxonase fusion polypeptides comprising a DNase or an RNase are particularly useful, e.g., for treatment of diseases and disorders characterized by NETosis. In addition, paraoxonase fusion polypeptides comprising a CTLA-4 or CD40 extracellular domain are particularly useful, e.g., for treatment of diseases or disorders characterized by an aberrant adaptive immune response. As yet another example, paraoxonase fusion polypeptides comprising a CD40 extracellular domain or a polypeptide that specifically binds and neutralizes TGF-β are particularly useful, e.g., for treatment of diseases and disorders characterized by a fibrotic inflammatory response.

In some aspects, the present invention provides methods for treating a disease or disorder selected from an inflammatory disease, an autoimmune disease, a neurological disease, an infectious disease, a metabolic disease, a cardiovascular disease, a liver disease, a fibrotic disease, thrombosis, sepsis, ischemia repurfusion, biofilm formation by a gram-negative bacteria, exposure to sulfur mustard gas, exposure to an organophosphate, and cancer. The methods generally include administering to a subject having the disease or disorder an effective amount of a fusion polypeptide or dimeric protein as described herein.

Inflammatory diseases amenable to treatment in accordance with the present invention include, for example, inflammatory lung diseases such as, for example, asthma, cystic fibrosis (CF), chronic obstructive pulmonary disease (COPD), bronchiectasis, hypoxia, interstitial lung disease (e.g., idiopathic pulmonary fibrosis (IPF) or sarcoidosis), and acute respiratory distress syndrome (ARDS). In particular embodiments comprising treatment of ARDS, the ARDS is associated with COVID-19. In some embodiments, the inflammatory lung disease is characterized by *Pseudomonas aeruginosa* infection. In some variations, a patient having the inflammatory lung disease is a patient that has been exposed to sulfur mustard gas (SM). In other variations, a patient having the inflammatory lung disease is a patient that has been exposed to an organophosphate, such as an insecticide (e.g., parathion, malathion, chlorpyrifos, diazinon, dichlorvos, phosmet, fenitrothion, terbufos, tetrachlorvinphos, azamethiphos, or azinphos-methyl) or other neurotoxin (e.g., tabun, sarin, soman, or cyclosarin).

Other inflammatory diseases amenable to treatment in accordance with the present invention include autoinflammatory diseases (i.e., innate immune system activation disorders characterized by seemingly unprovoked episodes of inflammation and a relative lack of obvious autoimmune pathology). Exemplary autoinflammatory diseases include inflammatory bowel disease (IBD) (e.g., Crohn's disease, ulcerative colitis), Behcet's disease, systemic onset juvenile idiopathic arthritis (JIA), gout, pseudogout, storage (Gaucher's) disorders, hereditary angioedema (HAE), atypical hemolytic uremic syndrome, familial Mediterranean fever (FMF), TNF-receptor associated periodic fever syndrome (TRAPS), cryopyrin-associated periodic syndromes (CAPS)), NOD2-associated autoinflammatory disease (NAID), and Blau syndrome.

In yet other embodiments, an inflammatory disease or disorder for treatment in accordance with the present invention is selected from rheumatoid arthritis, systemic lupus erythematosus, multiple sclerosis, type 1 diabetes, type 2 diabetes, hepatitis (e.g., nonalcoholic steatohepatitis (NASH)), ankylosing spondylitis, psoriasis, psoriatic arthritis, dermatitis (e.g., atopic dermatitis), diverticulitis, irritable bowel syndrome, and nephritis. In still other variations, the inflammatory disease or disorder is an inflammatory skin disease such as, e.g., psoriasis or atopic dermatitis.

In more particular embodiments of a method for treating an inflammatory disease, a fusion molecule for the inflammatory disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fe-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating an autoinflammatory disease, the fusion molecule is a polypeptide having the structure DNase1-L1-Fc-L2-PON1, DNase1L3-L1-Fc-L2-PON1, RNase1-L1-Fc-L2-PON1, or RNase1-Fc-L2-PON1, or a dimeric protein formed by dimerization of any of the foregoing fusion polypeptides. In some embodiments of a method for treating rheumatoid arthritis, psoriatic arthritis, or juvenile idiopathic arthritis, the fusion molecule is a polypeptide having the structure CTLA4-L1-Fc-L2-PON1 or CTLA4-Fc-L2-PON1, or a dimeric protein formed by dimerization of either of the foregoing fusion polypeptides. In some embodiments of a method for treating an inflammatory bowel disease (IBD) (e.g., Crohn's disease or ulcerative colitis), the fusion molecule is a polypeptide having the structure DNase1-L1-Fc-L2-PON1, DNase1L3-L1-Fc-L2-PON1, antiTNFα-L1-Fc-L2-PON1, or antiTNFα-Fc-L2-PON1, or a dimeric protein formed by dimerization of any of the foregoing fusion polypeptides. In some embodiments of a method for treating an inflammatory skin disease (e.g., psoriasis or atopic dermatitis), the fusion molecule molecule is a polypeptide having the structure DNase1-L1-Fc-L2-PON1, DNase1L3-L1-Fc-L2-PON1, antiTNFα-L1-Fc-L2-PON1, antiTNFα-Fc-L2-PON1, Fc-L2-PON1, or PON1-L1-Fc, or a dimeric protein formed by dimerization of any of the foregoing fusion polypeptides.

Autoimmune diseases amenable to treatment in accordance with the present invention include, for example, rheumatoid arthritis, systemic lupus erythematosus, psoriasis, multiple sclerosis, type 1 diabetes, vasculitis, and systemic sclerosis (also known as scleroderma). In other embodiments, the autoimmune disease is selected from coeliac disease, neuritis, polymyositis, juvenile rheumatoid arthritis, psoriatic arthritis, vitiligo, Sjogren's syndrome, autoimmune pancreatitis, autoimmune hepatitis, glomerulonephritis, lupus nephritis, scleroderma, antiphospholipid syndrome, autoimmune vasculitis, sarcoidosis, autoimmune thyroid diseases, Hashimoto's thyroiditis, Graves disease, Wegener's granulomatosis, myasthenia gravis, Addison's disease, autoimmune uveoretinitis, pemphigus vulgaris, primary biliary cirrhosis, pernicious anemia, sympathetic opthalmia, uveitis, autoimmune hemolytic anemia, pulmonary fibrosis, chronic beryllium disease, and idiopathic pulmonary fibrosis. In some variations comprising treatment of vasculitis, the vasculitis is selected from small vessel vasculitis and medium vessel vasculitis; in other variations, the vasculitis is large vessel vasculitis.

In more particular embodiments of a method for treating an autoimmune disease, a fusion molecule for the autoimmune disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 1-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating systemic lupus erythematosus, rheumatoid arthritis, psoriasis, type 1 diabetes, or small vessel vasculitis, the fusion molecule is a fusion polypeptide having the structure DNase1-L1-Fc-L2-PON1 or DNase1 L3-L1-Fc-L2-PON1, or a dimeric protein formed by dimerization thereof. In some embodiments of a method for treating systemic lupus erythematosus, Sjogren's syndrome, or type 1 diabetes, the fusion molecule is a polypeptide having the structure RNase1-L1-Fc-L2-PON1 or RNase1-Fc-L2-PON1, or a dimeric protein formed by dimerization of either of the foregoing fusion polypeptides. In some embodiments of a method for treating rheumatoid arthritis or psoriatic arthritis, the fusion molecule is a polypeptide having the structure CLTA4-L1-Fc-L2-PON1 or CTLA4-Fc-L2-PON1, or a dimeric protein formed by dimerization of either of the foregoing fusion polypeptides.

Neurological diseases amenable to treatment in accordance with the present invention include, for example, neurodegenerative diseases characterized by inflammation in the CNS such as, e.g., multiple sclerosis, Alzheimer's disease, Parkinson's disease, or amyotrophic lateral sclerosis (ALS). In some embodiments, the neurological disease is a neurodegenerative disease characterized by dementia such as, e.g., Alzheimer's disease. In more specific variations of a method for treating multiple sclerosis (MS), the MS is spino-optical MS, primary progressive MS (PPMS), or relapsing remitting MS (RRMS). In other embodiments, a neurological disease for treatment in accordance with the present invention is a CNS infection such as, e.g., meningitis, encephalitis, or cerebral malaria. In more particular variations of a method for treating meningitis, the meningitis is a bacterial meningitis; in some such embodiments, the CNS infection is an *S. pneumoniae, N. meningitis, S. aureus, E. coli, A. baumanii, S. oralis, S. capitis*, or *S. epidermidis* infection. Other neurological diseases or disorders amenable to treatment with fusion molecules as described herein include, for example, acute brain injury such as, e.g., ischemic stroke. In still other embodiments, the neurological disease is a brain cancer such as, e.g., an intracranial tumor selected from astrocytoma, anaplastic astrocytoma, glioblastoma, oligodendroglioma, anaplastic oligodendroglioma, ependymoma, primary CNS lymphoma, medulloblastoma, germ cell tumor, pineal gland neoplasm, meningioma, pituitary tumor, tumor of the nerve sheath (e.g., schwannoma), chordoma, craniopharyngioma, and a choroid plexus tumor (e.g., choroid plexus carcinoma).

In more particular embodiments of a method for treating a neurological disease, a fusion molecule for the neurological disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-736 of SEQ ID NO:66, (viii) residues 21-804 of SEQ ID NO:74, (ix) residues 21-804 of SEQ ID NO:78, (x) residues 21-804 of SEQ ID NO:82, (xi) residues 21-804 of SEQ ID NO:86, (xii) residues 21-804 of SEQ ID NO:90, (xiii) residues 21-860 of SEQ ID NO:94, (xiv) residues 21-860 of SEQ ID NO:98, (xv) residues 21-861 of SEQ ID NO:102, (xvi) residues 21-861 of SEQ ID NO:106, (xvii) residues 21-613 of SEQ ID NO:122, (xviii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164. In some embodiments of a method for treating a neurodegenerative disease characterized by dementia (e.g., Alzheimer's disease), acute brain injury (e.g., ischemic stroke), or a brain cancer, the fusion molecule is a polypeptide having the structure DNase-L1-Fc-L2-PON1, DNase1L3-L1-Fc-L2-PON1, RNase1-L1-Fc-L2-PON1, or RNase1-Fc-L2-PON1, or a dimeric protein formed by dimerization of any of the foregoing fusion polypeptides. In some embodiments of a method for treating multiple sclerosis, Alzheimer's disease, Parkinson's disease, amylotrophic lateral sclerosis, or a CNS infection, the fusion molecule is a polypeptide having the structure DNase1-L1-Fc-L2-PON1 or DNase L3-L1-Fc-L2-PON1, or a dimeric protein formed by dimerization thereof.

Infectious diseases amenable to treatment in accordance with the present invention include, for example, bacterial infections, viral infections, fungal infections, and parasitic infections. In some embodiments comprising treatment of a parasitic infection, the infection is a *Trypanosoma brucei, Leishmania, Plasmodium falciparum*, or *Toxoplasma gondii* infection. In some embodiments comprising treatment of a bacterial infection, the infection is a *Staphylococcus aureus, Streptococcus pneumoniae*, or *Mycobacterium tuberculosis* infection. In other embodiments, the bacterial infection is a *Pseudomonas aeruginosa* infection. In yet other embodiments, the bacterial infection is a *Borrelia burgdorferi* infection (Lyme disease). In some embodiments comprising treatment of a viral infection, the infection is an influenza virus (e.g., influenza A virus) or respiratory syncytial virus (RSV) infection. In still other embodiments, the infection is a CNS infection such as, for example, meningitis (e.g., a bacterial meningitis), encephalitis, or cerebral malaria.

Paraoxonase fusion molecules for treating an infectious disease typically comprise a DNase, RNase, SOD1, or anti-TGF-β neutralizing polypeptide as the first biologically active polypeptide, or may be a monospecific paraoxonase fusion molecule. In more particular variations, a fusion molecule for infectious disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1, SOD1-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides. In some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 23-781 of SEQ ID NO:50, (v) residues 23-781 of SEQ ID NO:52, (vi) residues 23-791 of SEQ ID NO:54, (vii) residues 21-860 of SEQ ID NO:94, (viii) residues 21-860 of SEQ ID NO:98, (ix) residues 21-861 of SEQ ID NO:102, (x) residues 21-861 of SEQ ID NO:106, (xi) residues 21-613 of SEQ ID NO:122, (xii) residues 21-610 of SEQ ID NO:142, (xiii) residues 21-906 of SEQ ID NO:148, (xiv) residues 21-896 of SEQ ID NO:158, (xv) residues 21-906 of SEQ ID NO:160, (xvi) residues 21-906 of SEQ ID NO:162, or (xvii) residues 21-906 of SEQ ID NO:164.

In some embodiments of a method for treating biofilm formation by a gram negative bacteria, the gram negative bacteria is *Pseudomonas aeruginosa*. In particular variations for treating biofilm formation by a gram negative bacteria, a fusion molecule for the biofilm formation treatment is a polypeptide having the structure DNase1-L1-Fc-L2-PON1, DNase1 L3-L1-Fc-L2-PON1, Fc-L2-PON1, or PON1-L1-Fc, or a dimeric protein formed by dimerization of either of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-613 of SEQ ID NO:122, (iii) residues 21-610 of SEQ ID NO:142, (xix) residues 21-906 of SEQ ID NO:148, (xx) residues 21-896 of SEQ ID NO:158, (xxi) residues 21-906 of SEQ ID NO:160, (xxii) residues 21-906 of SEQ ID NO:162, or (xxiii) residues 21-906 of SEQ ID NO:164.

Metabolic diseases that may be treated in accordance with the present invention include, for example, type 2 diabetes and obesity. In particular variations of a method for treating a metabolic disease, a fusion molecule for the metabolic disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-613 of SEQ ID NO:122, (v) residues 21-610 of SEQ ID NO:142, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

Cardiovascular diseases that may be treated in accordance with the present invention include, for example, cardiovascular diseases characterized by atherosclerosis. In some embodiments, the cardiovascular disease characterized by atherosclerosis is coronary heart disease or ischemic stroke. In more particular variations comprising treatment of coronary heart disease, the coronary heart disease is characterized by acute coronary syndrome. In certain variations of a method for treating a cardiovascular disease, a fusion molecule for the cardiovascular disease treatment is a polypeptide having the structure DNase1-L1-Fc-L2-PON1, DNase1L3-L1-Fc-L2-PON1, RNase1-L1-Fc-L2-PON1, RNase1-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-613 of SEQ ID NO:122, (v) residues 21-610 of SEQ ID NO:142, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

In some embodiments of a method for treating thrombosis, sepsis, or ischemia reperfusion, a fusion molecule for such treatment is a polypeptide having the structure DNase1-L1-Fc-L2-PON1, DNase1L3-L1-Fc-L2-PON1, RNase1-L1-Fc-L2-PON1, or RNase1-Fc-L2-PON1, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (iv) residues 21-906 of SEQ ID NO:148, (v) residues 21-896 of SEQ ID NO:158, (vi) residues 21-906 of SEQ ID NO:160, (vii) residues 21-906 of SEQ ID NO:162, or (viii) residues 21-906 of SEQ ID NO:164.

In some embodiments of a method for treating antiphospholipid syndrome, thrombosis, or ischemic stroke, a DNase-containing fusion molecule as described herein is administered to a patient as one of the distinct therapies of a combination therapy comprising a thrombolytic agent. In some such embodiments, the thrombolytic agent is selected from anistreplase, reteplase, streptokinase, t-PA, tenecteplase, and rokinase.

In some embodiments of a method for treating exposure to sulfur mustard gas (SM) or exposure to an organophosphate (e.g., tabun, sarin, soman, or cyclosarin), a fusion molecule for such exposure treatment is a polypeptide having the structure DNase1-L1-Fc-L2-PON1, DNase1L3-L1-Fc-L2-PON1, RNase1-L1-Fc-L2-PON1, RNase1-Fc-L2-PON1, SOD1-L1-Fc-L2-PON1. SOD1-Fc-L2-PON1, CTLA4-L1-Fc-L2-PON1, CTLA4-Fc-L2-PON1, CD40-L1-Fc-L2-PON1, CD40-Fc-L2-PON1, antiTNFα-L1-Fc-L2-PON1, antiTNFα-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-896 of SEQ ID NO:128, (iii) residues 21-896 of SEQ ID NO:130, (iv) residues 21-764 of SEQ ID NO:40, (v) residues 21-740 of SEQ ID NO:48, (vi) residues 23-781 of SEQ ID NO:50, (vii) residues 23-781 of SEQ ID NO:52, (viii) residues 23-791 of SEQ ID NO:54, (ix) residues 21-736 of SEQ ID NO:66, (x) residues 21-804 of SEQ ID NO:74, (xi) residues 21-804 of SEQ ID NO:78, (xii) residues 21-804 of SEQ ID NO:82, (xiii) residues 21-804 of SEQ ID NO:86, (xiv) residues 21-804 of SEQ ID NO:90, (xv) residues 21-860 of SEQ ID NO:94, (xvi) residues 21-860 of SEQ ID NO:98, (xvii) residues 21-861 of SEQ ID NO:102, (xviii) residues 21-861 of SEQ ID NO:106, (xix) residues 21-613 of SEQ ID NO:122, (xx) residues 21-613 of SEQ ID NO:132, (xxi) residues 21-613 of SEQ ID NO:134, (xxii) residues 21-610 of SEQ ID NO:142, (xxiii) residues 21-610 of SEQ ID NO:144, (xxiv) residues 21-610 of SEQ ID NO:146, (xxv) residues 21-906 of SEQ ID NO:148, (xxvi) residues 21-896 of SEQ ID NO:158, (xxvii) residues 21-906 of SEQ ID NO:160, (xxviii) residues 21-906 of SEQ ID NO:162, or (xxix) residues 21-906 of SEQ ID NO:164.

Liver diseases or disorders that may be treated in accordance with the present invention include chronic liver diseases such as, e.g., nonalcoholic fatty liver disease (NAFLD), alcohol-associated liver disease (ALD), portal hypertension, and complications following liver transplantation. In some variations comprising treatment of nonalcoholic fatty liver disease (NAFLD), the NAFLD is nonalcoholic steatohepatitis (NASH). In particular variations of a method for treating a liver disease, a fusion molecule for the liver disease treatment is a polypeptide having the structure DNase1-L1-Fc-L2-PON1, DNase1L3-L1-Fc-L2-PON1, CD40-L1-Fc-L2-PON1, CD40-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-804 of SEQ ID NO:74, (iii) residues 21-804 of SEQ ID NO:78, (iv) residues 21-804 of SEQ ID NO:82, (v) residues 21-804 of SEQ ID NO:86, (vi) residues 21-804 of SEQ ID NO:90, (vii) residues 21-861 of SEQ ID NO:102, (viii) residues 21-861 of SEQ ID NO:106, (ix) residues 21-613 of SEQ ID NO:122, (x) residues 21-610 of SEQ ID NO:142, (xi) residues 21-906 of SEQ ID NO:148, (xii) residues 21-896 of SEQ ID NO:158, (xiii) residues 21-906 of SEQ ID NO:160, (xiv) residues 21-906 of SEQ ID NO:162, or (xv) residues 21-906 of SEQ ID NO:164.

Fibrotic diseases or disorders amenable to treatment in accordance with the present invention include systemic sclerosis, systemic lupus erythematosus, inflammatory lung diseases, chronic liver diseases, and chronic kidney diseases. In some variations comprising treatment of an inflammatory lung disease, the fibrotic disease is cystic fibrosis, chronic obstructive pulmonary disease, interstitial lung disease (e.g., idiopathic pulmonary fibrosis or sarcoidosis), acute respiratory distress syndrome, or asthma. In some variations comprising treatment of a chronic liver disease, the fibrotic disease is nonalcoholic steatohepatitis, alcohol-associated liver disease, portal hypertension, or a complication following liver transplantation. In some variations comprising treatment of a chronic kidney disease, the fibrotic disease is lupus nephritis, IgA nephropathy, or membranous glomerulonephritis. In particular variations of a method for treating a liver disease, a fusion molecule for the liver disease treatment is a polypeptide having the structure DNase1-L1-Fc-L2-PON1, DNase1L3-L1-Fc-L2-PON1, CD40-L1-Fc-L2-PON1, CD40-Fc-L2-PON1, antiTGFβ-L1-Fc-L2-PON1, antiTGFβ-Fc-L2-PON1, Fc-L2-PON1, or PON1-L1-Fc, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-804 of SEQ ID NO:74, (iii) residues 21-804 of SEQ ID NO:78, (iv) residues 21-804 of SEQ ID NO:82, (v) residues 21-804 of SEQ ID NO:86, (vi) residues 21-804 of SEQ ID NO:90, (vii) residues 21-861 of SEQ ID NO:102, (viii) residues 21-861 of SEQ ID NO:106, (ix) residues 21-613 of SEQ ID NO:122, (x) residues 21-610 of SEQ ID NO:142, (xi) residues 21-906 of SEQ ID NO:148, (xii) residues 21-896 of SEQ ID NO:158, (xiii) residues 21-906 of SEQ ID NO:160, (xiv) residues 21-906 of SEQ ID NO:162, or (xv) residues 21-906 of SEQ ID NO:164.

Paraoxonase fusion molecules for treating cancer typically comprise a DNase, RNase, or anti-TGF-β neutralizing polypeptide as the first biologically active polypeptide. In more particular variations, a fusion molecule for cancer treatment is a polypeptide having the structure DNase1-L1-Fc-L2-PON1, DNase1L3-L1-Fc-L2-PON1, RNase1-L1-Fc-L2-PON1, RNase1-Fc-L2-PON1, antiTGFβ-L1-Fc-L2-PON1, or antiTGFβ-Fc-L2-PON1, or a dimeric protein formed by dimerization of any of the foregoing fusion polypeptides; in some such embodiments, the fusion polypeptide comprises or consists of an amino acid sequence having at least 90%, at least 95%, or 100% identity with the amino acid sequence shown in (i) residues 21-896 of SEQ ID NO:2, (ii) residues 21-764 of SEQ ID NO:40, (iii) residues 21-740 of SEQ ID NO:48, (ix) residues 21-861 of SEQ ID NO:102, (v) residues 21-861 of SEQ ID NO:106, (vi) residues 21-906 of SEQ ID NO:148, (vii) residues 21-896 of SEQ ID NO:158, (viii) residues 21-906 of SEQ ID NO:160, (ix) residues 21-906 of SEQ ID NO:162, or (x) residues 21-906 of SEQ ID NO:164.

Cancers that may be treated in accordance with the present invention include, for example, the following: a cancer of the head and neck (e.g., a cancer of the oral cavity, oropharynx, nasopharynx, hypopharynx, nasal cavity or paranasal sinuses, larynx, lip, or salivary gland); a lung cancer (e.g., non-small cell lung cancer, small cell carcinoma, or mesothelioma); a gastrointestinal tract cancer (e.g., colorectal cancer, gastric cancer, esophageal cancer, or anal cancer); gastrointestinal stromal tumor (GIST); pancreatic adenocarcinoma; pancreatic acinar cell carcinoma; a cancer of the small intestine; a cancer of the liver or biliary tree (e.g., liver cell adenoma, hepatocellular carcinoma, hemangiosarcoma, extrahepatic or intrahepatic cholangiosarcoma, cancer of the ampulla of vater, or gallbladder cancer); a breast cancer (e.g., metastatic breast cancer or inflammatory breast cancer); a gynecologic cancer (e.g., cervical cancer, ovarian cancer, fallopian tube cancer, peritoneal carcinoma, vaginal cancer, vulvar cancer, gestational trophoblastic neoplasia, or uterine cancer, including endometrial cancer or uterine sarcoma); a cancer of the urinary tract (e.g., prostate cancer; bladder cancer; penile cancer; urethral cancer, or kidney cancer such as, for example, renal cell carcinoma or transitional cell carcinoma, including renal pelvis and ureter); testicular cancer; a cancer of the central nervous system (CNS) such as an intracranial tumor (e.g., astrocytoma, anaplastic astrocytoma, glioblastoma, oligodendroglioma, anaplastic oligodendroglioma, ependymoma, primary CNS lymphoma, medulloblastoma, germ cell tumor, pineal gland neoplasm, meningioma, pituitary tumor, tumor of the nerve sheath (e.g., schwannoma), chordoma, craniopharyngioma, a chloroid plexus tumor (e.g., chloroid plexus carcinoma), or other intracranial tumor of neuronal or glial origin) or a tumor of the spinal cord (e.g., schwannoma, meningioma); an endocrine neoplasm (e.g., thyroid cancer such as, for example, thyroid carcinoma, medullary cancer, or thyroid lymphoma; a pancreatic endocrine tumor such as, for example, an insulinoma or glucagonoma; an adrenal carcinoma such as, for example, pheochromocytoma; a carcinoid tumor; or a parathyroid carcinoma); a skin cancer (e.g., squamous cell carcinoma; basal cell carcinoma; Kaposi's sarcoma; or a malignant melanoma such as, for example, an intraocular melanoma); a bone cancer (e.g., a bone sarcoma such as, for example, osteosarcoma, osteochondroma, or Ewing's sarcoma); multiple myeloma; a chloroma; a soft tissue sarcoma (e.g., a fibrous tumor or fibrohistiocytic tumor); a tumor of the smooth muscle or skeletal muscle; a blood or lymph vessel perivascular tumor (e.g., Kaposi's sarcoma); a synovial tumor; a mesothelial tumor; a neural tumor; a paraganglionic tumor; an extraskeletal cartilaginous or osseous tumor; and a pluripotential mesenchymal tumor. In some such embodiments, a paraoxonase fusion molecule as described herein is administered to a cancer patient as one of the distinct therapies of a combination therapy such as, for example, a combination therapy comprising an immunomodulatory therapy (e.g., a CAR T cell therapy (see, e.g., June et al., Science 359:1361-1365, 2018) or a therapy comprising an immune checkpoint inhibitor), a radiation therapy, or a chemotherapy.

In certain embodiments, a combination cancer therapy comprises a DNase-PON, RNase-PON, or antiTGFβ-PON fusion molecule as described herein and a targeted therapy such as, e.g., a therapeutic monoclonal antibody targeting a specific cell-surface or extracellular antigen, or a small molecule targeting an intracellular protein (e.g., an intracellular enzyme). Exemplary antibody targeted therapies include anti-VEGF (e.g., bevacizumab), anti-EGFR (e.g., cetuximab), anti-CTLA-4 (e.g., ipilimumab), anti-PD-1 (e.g., nivolumab), and anti-PD-L1 (e.g., pembrolizumab). Exemplary small molecule targeted therapies include proteasome inhibitors (e.g., bortezomib), tyrosine kinase inhibitors (e.g., imatinib), cyclin-dependent kinase inhibitors (e.g., seliciclib); BRAF inhibitors (e.g., vemurafenib or dabrafenib); and MEK kinase inhibitors (e.g., trametnib).

In some cancer combination therapy variations comprising an immune checkpoint inhibitor, the combination therapy includes an anti-PD-1/PD-L1 therapy, an anti-CTLA-4 therapy, or both. In certain aspects, a DNase-PON, RNase-PON, or antiTGFβ-PON fusion molecule as described herein can increase the response rate to either anti-CTLA-4 or anti-PD-1/PD-L1 therapy, as well as the response rate to the combination of anti-CTLA-4 plus anti-PD-1/PD-L1 therapy. Fusion molecules of the invention may also be useful for reducing the toxicity associated with anti-CTLA-4, anti-PD-1/PD-L1, or the combination thereof.

In certain variations, a cancer treated in accordance with the present invention is selected from malignant melanoma, renal cell carcinoma, non-small cell lung cancer, bladder cancer, and head and neck cancer. These cancers have shown responses to immune checkpoint inhibitors anti-PD-1/PD-L1 and anti-CTLA-4. See Grimaldi et al., *Expert Opin. Biol. Ther.* 16:433-41, 2016; Gunturi et al., *Curr. Treat. Options Oncol.* 15:137-46, 2014; Topalian et al., *Nat. Rev. Cancer* 16:275-87, 2016. Thus, in some more specific variations, any of these cancers is treated with a DNase-PON, RNase-PON, or antiTGFβ-PON fusion molecule as described herein in combination with an anti-PD-1/PD-L1 therapy, an anti-CTLA-4 therapy, or both.

In other aspects, the present invention provides methods for reducing lipid oxidation in a subject. The method generally includes administering to the subject an effective amount of a fusion polypeptide or dimeric protein as described herein, wherein one or more oxidized lipids in the subject are reduced. In some embodiments, the method reduces one or more oxidized lipids associated with the presence of a disease or disorder in the subject (e.g., a disease or disorder discussed above). In other embodiments, the one or more oxidized lipids are associated with a risk of developing such a disease or disorder; in particular variations, treatment with the fusion molecule reduces the risk of developing the disease or disorder in the subject.

In another aspect, the present invention provides a method for protecting a subject from aging. The method generally includes administering to the subject an effective amount of a fusion polypeptide of a fusion polypeptide or dimeric protein as described herein. In some embodiments, the subject has an age-related disease or disorder (e.g., an inflammatory disease, an autoimmune disease, a neurodegenerative disease, a cardiovascular disease, or a fibrotic disease). In other embodiments, the subject is at risk of developing such an age-related disease or disorder, and treatment with the fusion molecule reduces the risk of the disease or disorder in the subject.

In some embodiments of a method for treating a disease or disorder, reducing lipid oxidation, or protecting from aging as above, the method is a combination therapy comprising administering to the patient (a) an effective amount of a paraoxonase fusion polypeptide having the formula X-L2-P or P-L1-X as described above, or a dimeric protein formed by dimerization of the fusion polypeptide, and (b) an effective amount of a biologically active DNase. Such embodiments are particularly useful, e.g., for treatment of diseases and disorder characterized by NETosis. In some variations, the method comprises administration of a paraoxonase fusion polypeptide having the structure Fc-L2-PON1 or PON1-L1-Fc, or a dimeric protein formed by dimerization thereof; in some such embodiments, the paraoxonase fusion polypeptide has the structure Fc-L2-PON1 and comprises or consists of an amino acid sequence having at least 90%, at least 95%, or 100% identity with the amino acid sequence shown in (i) residues 21-613 of SEQ ID NO:122, (ii) residues 21-613 of SEQ ID NO:132, (iii) residues 21-613 of SEQ ID NO:134, (iv) residues 21-610 of SEQ ID NO:142, (v) residues 21-610 of SEQ ID NO:144, or (vi) residues 21-610 of SEQ ID NO:146. The biologically active DNase may be, for example, a DNase1 or DNase1 L3 polypeptide as described herein (e.g., a polypeptide corresponding to the DNase component of a DNase-containing paraoxonase fusion as described herein such as, for example, an enhanced DNase1 polypeptide comprising or consisting of an amino acid sequence having at least 90%, at least 95%, or 100% identity with the amino acid sequence shown in residues 21-280 of SEQ ID NO:18, residues 21-280 of SEQ ID NO:20, or residues 21-280 of SEQ ID NO:152. In some embodiments, the DNase is contained within a fusion polypeptide comprising, from an amino terminal position to a carboxyl terminal position, D-L1-$X_d$, wherein D is the DNase, L1 is a polypeptide linker (e.g., an L1 linker as described herein for a DNase-containing paraoxonase fusion molecule), and $X_d$ is an immunoglobulin Fc region as described herein (or contained with a dimeric protein formed by dimerization of the fusion polypeptide); in some such embodiments, the DNase fusion polypeptide comprises or consists of an amino acid sequence having at least 90%, at least 95%, or 100% identity with the amino acid sequence shown in (i) residues 21-538 or 21-537 of SEQ ID NO:60, (ii) residues 21-548 or 21-547 of SEQ ID NO:62, (iii) residues 21-538 or 21-537 of SEQ ID NO:155, (iv) residues 21-548 or 21-547 of SEQ ID NO:156, (v) residues 21-548 or 21-547 of SEQ ID NO:138, or (vi) residues 21-548 or 21-547 of SEQ ID NO:140.

In some embodiments of a combination therapy comprising administration of a paraoxonase fusion molecule and a DNase as described above, the DNase is contained within a DNase1-L1-Fc fusion polypeptide comprising the amino acid sequence shown in SEQ ID NO:149, SEQ ID NO:150, SEQ ID NO:153, or SEQ ID NO:154. In certain variations of the combination therapy method wherein DNase fusion polypeptide comprises the amino acid sequence shown in SEQ ID NO:149, SEQ ID NO:150, SEQ ID NO:153, or SEQ ID NO:154, (i) the amino acid at each of positions 315 and 316 is alanine; (ii) the amino acid at position 319 is serine; (iii) the amino acid at position 378 is alanine, glutamine, or glycine, and the amino acid at position 346 is optionally alanine; (iv) the amino acid at position 410 is alanine, glycine, or serine; (v) the amino acid at position 412 is serine or alanine; (vi) the amino acid at position 333 is tyrosine, the amino acid at position 335 is threonine, and the amino acid at position 337 is glutamate; and/or (vii) the amino acid at position 509 is leucine, and the amino acid at position 515 is serine. In other, non-mutually exclusive variations of the combination therapy method wherein the DNase fusion polypeptide comprises the amino acid sequence shown in SEQ ID NO:149, SEQ ID NO:150, SEQ ID NO:153, or SEQ ID NO154, the amino acid sequence corresponding to positions 261-296 includes a Gly-Ser tandem repeat sequence having a formula selected from the group consisting of (i) [Gly-Gly-Gly-Gly-Ser]$_n$, wherein n is an integer from 4 to 7, (ii) [Gly-Gly-Gly-Ser]$_n$, wherein n is an integer from 5 to 9, and (iii) [Gly-Gly-Ser]$_n$, wherein n is an integer from 6 to 12; in some such embodiments, the amino acid sequence corresponding to positions 261-296 includes a Gly-Ser tandem repeat sequence having a formula selected from the group consisting of (i) [Gly-Gly-Gly-Gly-Ser]$_n$, wherein n is an integer from 4 to 6, (ii) [Gly-Gly-Gly-Ser]$_n$, wherein n is an integer from 5 to 7, and (iii) [Gly-Gly-Ser]$_n$, wherein n is an integer from 6 to 10. In yet other, non-mutually exclusive variations of the combination therapy method wherein the DNase fusion polypeptide comprises the amino acid sequence shown in SEQ ID NO:149, SEQ ID NO:150, SEQ ID NO:153, or SEQ ID NO:154, the amino acid at position 261 is aspartate, the amino acid at position 262 is leucine, the amino acid at position 263 is serine, the amino acid at position 294 is threonine, the amino acid at position is 295 is glycine, and/or the amino acid at position 296 is leucine. In other, non-mutually exclusive variations of the combination therapy method where the DNase fusion polypeptide comprises the amino acid sequence shown in SEQ ID NO:149 or SEQ ID NO:153, (i) the amino acid at each of positions 74 and 105 is independently lysine or arginine, and/or (ii) the amino acid at position 114 is phenylalanine.

In some embodiments of a method for treating a disease or disorder, reducing lipid oxidation, or protecting from aging as above, the method is a combination therapy comprising administering to the patient (a) an effective amount of a paraoxonase fusion polypeptide having the formula X-L2-P or P-L1-X as described above, or a dimeric protein formed by dimerization of the fusion polypeptide, and (b) an effective amount of a biologically active apolipoprotein A-1 (ApoA1) (e.g., an ApoA1-Fc fusion polypeptide as described in International PCT Publication No. WO 2017/044424, or a dimeric protein formed by dimerization of the fusion polypeptide).

For therapeutic use, a fusion polypeptide or dimeric protein as described herein is delivered in a manner consistent with conventional methodologies associated with management of the disease or disorder for which treatment is sought. In accordance with the disclosure herein, an effective amount of the fusion polypeptide or dimeric protein is administered to a subject in need of such treatment for a time and under conditions sufficient to prevent or treat the disease or disorder.

Subjects for administration of fusion polypeptides or dimeric proteins as described herein include patients at high risk for developing a particular disease or disorder as well as patients presenting with an existing disease or disorder. In certain embodiments, the subject has been diagnosed as having the disease or disorder for which treatment is sought. Further, subjects can be monitored during the course of treatment for any change in the disease or disorder (e.g., for an increase or decrease in clinical symptoms of the disease or disorder). Also, in some variations, the subject does not suffer from another disease or disorder requiring treatment that involves administration of a protein selected from a paraoxonase, a DNase, an RNase, a SOD1, a CTLA-4 extracellular domain, a CD40 extracellular domain, or a polypeptide (e.g, antibody) that specifically binds and neutralizes TNFα or TGFβ.

In prophylactic applications, pharmaceutical compositions or medicants are administered to a patient susceptible to, or otherwise at risk of, a particular disease in an amount sufficient to eliminate or reduce the risk or delay the onset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is referred to as a therapeutically or pharmaceutically effective dose or amount. In both prophylactic and therapeutic regimes, agents are usually administered in several dosages until a sufficient response (e.g., enhanced alveolar fluid clearance in inflammatory lung disease) has been achieved. Typically, the response is monitored and repeated dosages are given if the desired response starts to fade.

To identify subject patients for treatment according to the methods of the invention, accepted screening methods may be employed to determine risk factors associated with a specific disease or to determine the status of an existing disease identified in a subject. Such methods can include, for example, determining whether an individual has relatives who have been diagnosed with a particular disease. Screening methods can also include, for example, conventional work-ups to determine familial status for a particular disease known to have a heritable component. Toward this end, nucleotide probes can be routinely employed to identify individuals carrying genetic markers associated with a particular disease of interest. In addition, a wide variety of immunological methods are known in the art that are useful to identify markers for specific diseases. Screening may be implemented as indicated by known patient symptomology, age factors, related risk factors, etc. These methods allow the clinician to routinely select patients in need of the methods described herein for treatment. In accordance with these methods, treatment using a fusion polypeptide or dimeric protein of the present invention may be implemented as an independent treatment program or as a follow-up, adjunct, or coordinate treatment regimen to other treatments.

For treatment of a disease or disorder characterized by NETosis, subject patients likely to benefit from NET-targeted therapy may be identified, for example, by measuring NETs in candidate patients. There are multiple ways to measure NETs in vivo (for a review, see, e.g., Masuda et al., *Clin. Chim. Acta* 459:89-93, 2016). One method uses flow cytometry to measure cell-associated DNA by staining with a non-cell permeable DNA dye (Zharkova et al., *Cytometry A* 95:268-278, 2019). Other methods include measuring myeloperoxidase activity associated with DNA or measuring citrullinated histone H3 (see, e.g., Matsuda et al., supra). Yet another method measures NETosis by incubating blood neutrophils with autologous plasma (Abrams et al., *Am. J. Resp. Crit. Care Med.* 200:869, 2019). This method was able to predict disseminated intravascular coagulation in critically ill patients (id.).

For administration, a fusion polypeptide or dimeric protein in accordance with the present invention is formulated as a pharmaceutical composition. A pharmaceutical composition comprising a fusion polypeptide or dimeric protein as described herein can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, e.g., Gennaro (ed.), *Remington's Pharmaceutical Sciences* (Mack Publishing Company, 19th ed. 1995). Formulations may further include one or more excipients, preservatives, solubilizers, buffering agents, albumin to prevent protein loss on vial surfaces, etc.

A pharmaceutical composition comprising a fusion polypeptide or dimeric protein of the present invention is administered to a subject in an effective amount. The fusion polypeptide or dimeric protein may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the fusion polypeptide or dimeric protein may be administered to a subject in a single bolus delivery, via continuous delivery (e.g., continuous transdermal delivery) over an extended time period, or in a repeated administration protocol (e.g., on an hourly, daily, or weekly basis).

In some embodiments, a pharmaceutical composition comprising a fusion molecule or dimeric protein of the present invention is formulated for delivery to the lung by nebulization. Previous studies of pulmonary delivery of Fc fusion proteins, including erythropoietin-Fc, interferon Beta1a-Fc, and FSH-Fc, have shown that the immunoglobulin transport FcRn pathway is active in the lungs and provides 20% to 50% bioavailability (see Bitonti et al., *Proc. Natl. Acad. Sci. USA* 101:9763-9768, 2004; Bitonti and Dumont, *Adv. Drug Deliv. Rev.* 58:1106, 2006; Valle et al., *J. Interferon Cytokine Res.* 32:178-184, 2012). Pulmonary delivery of FcRn-binding paraoxonase fusion molecules as described herein (e.g., paraoxonase fusion molecules containing an Fc region) could act both locally and in circulation and peripheral organs. In certain embodiments wherein the treatment is a combination therapy with a paraoxonase fusion molecule and a DNase as described herein, both the paraoxonase fusion molecule (e.g., an Fc-L2-PON1 fusion as described herein) and the DNase (e.g., a DNase-Fc fusion as described herein) are delivered by a nebulizer. In some variations comprising delivery to the lung by a nebulizer, the disease or disorder to the treated is selected from an inflammatory lung disease (e.g., cystic fibrosis, interstitial lung disease (e.g., idiopathic pulmonary fibrosis or sarcoidosis), acute respiratory distress syndrome (ARDS), chronic obstructive pulmonary disease (COPD), asthma, exposure to sulfur mustard gas, or exposure to an organophosphate), biofilm formation by a gram-negative bacteria (e.g., *Pseudomonas aeruginosa*), and sepsis. In other, non-mutually exclusive variations, an FcRn-binding fusion molecule for delivery to the lung by nebulization (e.g., an Fc-L2-PON1 fusion as described herein) comprises an Fc variant with increased FcRn-binding affinity relative to the corresponding wild-type Fc, thereby increasing fusion molecule half-life and increasing concentration in the blood after inhalation with a nebulizer.

Multiple biologics have been successfully formulated to retain biologic activity after nebulization (see, e.g., Hertel et al., *Adv. Drug Deliv. Rev.* 93:79-94, 2015). Formulations for delivery of a paraoxonase fusion molecule of the present invention may include an excipient suitable for pulmonary delivery such as, e.g., Polysorbate 80 (PS80) or Polysorbate 20 (PS20), surfactants that are included in many biopharmaceutical formulations. Such stabilizing excipients protect proteins from degradation at the air-liquid interface when applied above their critical micelle concentration (for example, PS80 above 0.01% was effective in stabilizing G-CSF, LDH, rhConIFN, and t-Pa; and PS20 applied at 0.04% was effective for protection of Fc-gamma RIIb). Another suitable stabilizing excipient is HP-beta-cyclodextrin (HP-beta-CD) applied at, e.g., 0.35% or above (see Hertel et al., supra). In some variations, a stabilizing excipient is not required for nebulized delivery of a paraoxonase fusion molecule (e.g., DNase1-Fc-PON1) as described herein (for example, wild-type human DNase1 (Pulmozyme®) has been shown to not aggregate and remain stable after nebulization with either jet or vibrating mesh (VM) nebulizers without requiring excipients, see Cipolla et al., *Pharm. Res.* 11:491-498, 1994; Scherer et al., *J. Pharm. Sci.* 100:98-109, 2011).

Determination of effective dosages is typically based on animal model studies followed up by human clinical trials and is guided by determining effective dosages and administration protocols that significantly reduce the occurrence or severity of the subject disease or disorder in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects (e.g., in the case of treatment of inflammatory lung disease, where any undesired collateral effects are outweighed by any beneficial effects such as, for example, improved alveolar fluid clearance, improved lung physiology and function, etc.). For administration of a fusion polypeptide or dimeric protein of the present invention, a dosage typically ranges from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of clinical symptoms of the disease or disorder and/or monitoring of disease biomarkers or other disease correlates.

In some specific embodiments comprising delivery by inhalation with a nebulizer (for example, for treatment of an inflammatory lung disease such as, e.g., cystic fibrosis or interstitial lung disease), a fusion polypeptide or dimeric protein of the present invention is administered to the lung by a nebulizer at a dose of from about 1 mg to about 5 mg or from about 2 mg to about 4 mg per day. In other specific embodiments comprising systemic administration (for example, for treatment of systemic lupus erythematosus, lupus nephritis, rheumatoid arthritis, or inflammatory bowel disease), a fusion polypeptide or dimeric protein of the present invention is administered (e.g., by intravenous or subcutaneous injection) at a dose of from about 50 mg to about 1,000 mg, from about 50 mg to about 800 mg, from about 50 mg to about 500 mg, from about 100 mg to about 500 mg, from about 100 mg to about 400 mg, from about 100 mg to about 300 mg, from about 150 mg to about 250 mg, or about 200 mg every month to six weeks. For combination therapy with a paraoxonase fusion molecule and a DNase as described herein, each of the paraoxonase fusion molecule (e.g., an Fc-L2-PON1 fusion as described herein) and the DNase (e.g., a DNase-Fc fusion as described herein) may be administered at these doses.

Particularly suitable animal models for evaluating efficacy of a paraoxonase fusion composition of the present invention for treatment of inflammatory lung disease include, for example, a murine ovalbumin-induced acute asthma model as described by da Cunha et al. (*Exp. Lung Res.* 42:66, 2016) (showing significantly reduced airway resistance with wild-type (wt) DNase1 treatment), a murine silica-induced lung inflammation model as described by Benmerzoug et al. (Nat. Comm. 9:5226, 2018) (showing prevention of DNA-mediated STING activation and blockade of the downstream type I IFN response with wt DNase1 treatment), and a murine model of transfusion-related acute lung injury as described by Caudrillier et al. (*J. Clin. Invest.* 122:2661, 2012) (showing protection from lung edema and lung vascular permeability as well as reduced NET formation and platelet sequestration in the lung with wt DNase1 treatment).

Suitable animal models for evaluating efficacy of a paraoxonase fusion composition as described herein for treatment of exposure to exposure to sulfur mustard gas or an organophosphate include, for example, a guinea pig model as describe by Valiyaveettil et al. (*Biochem. Pharmocol.* 81:800-809, 2011; *Toxicol. Letters* 202:203-208, 2011) (showing protection from sarin and soman inhalation toxicity with recombinant human PON1 injection) and mouse models as described by Bajaj et al. (*Appl. Biochem. Biotechnol.* 180:165-176, 2016) and Stevens et al. (*Proc. Natl. Acad. Sci. USA* 105:12780-12784, 2008) (showing protection from organophosphate poisoning using a recombinant Q192K variant of PON1).

Particularly suitable animal models for evaluating efficacy of a paraoxonase composition as described herein for treatment of an inflammatory bowel disease include a TNBS-induced colitis model and a chronic colitis model with $CD4^+CD45RB^{high}$ cell transfer in mice. See, e.g., Yamashita et al., *J. Immunol.* 191:949-960, 2013 (showing efficacy of PON1 therapy in the TNBS-induced colitis model and a PON1 variant (G3C9) in the chronic colitis model). Another suitable model is a dextran sulfate sodium (DSS)-induced colitis model in mice. See, e.g., Babicova et al., *Folia Biolica (Praha)* 64:10, 2018 (showing reduction in $TNF\alpha$ and myeloperoxidase in the colon with wt DNase1 treatment of DSS-induced colitis); Li et al., *J. Crohns Colitis* 2020, 14:240-253, 2020 (showing decreased cytokine production and attenuated accelerated thrombus formation and platelet activation with DNase1 treatment of DSS-induced colitis).

Also known is the collagen-induced arthritis (CIA) model for rheumatoid arthritis (RA) (see, e.g., Brand et al., *Nat. Protoc.* 2:1269-1275, 2007). CIA shares similar immunological and pathological features with RA, making it an ideal model for evaluating efficacy of DNase compositions. Another suitable model for RA is PG-PS (proteoglycan-polysaccharide)-induced arthritis in Lewis rats (see, e.g., Esser et al., *Arthritis and Rheumatism* 28:1402-1411, 1985; Brooks et al., *Proc. Intl. Soc. Mag. Reason. Med.* 11:1526, 2003).

Suitable animal models for multiple sclerosis (MS) include, for example, experimental allergic encephalomyelitis (EAE) models that rely on the induction of an autoimmune response in the CNS by immunization with a CNS antigen (also referred to as an "encephalitogen" in the context of EAE), which leads to inflammation, demyelination, and weakness (see, e.g., Constantinescu et al., *British Journal of Pharmacology* 164:1079-1106, 2011).

Other known animal models for evaluating efficacy of paraoxonase fusion molecules of the present invention include, e.g., a hind-limb ischemia reperfusion model as described by Albadawi et al. (*J. Vasc. Surg.* 64:484, 2016) (showing increased perfusion, decreased infiltrating inflammatory cells, and reduction of a local thrombosis marker with wt DNase1 therapy), a rat model of ischemia-reperfusion-induced acute kidney injury as described by Peer et al. (*Am. J. Nephrol.* 43:195, 2016) (showing renoprotective effects with wt DNase1 therapy), a cecal ligation and puncture sepsis model in mice as described by Mai et al. (*Shock* 44:166, 2015) (showing prevention of organ damage and protection from death with wt DNase1 therapy), and a model of inferior vena cava stenosis as described by Brill et al. (*J. Thrombosis Haemostasis* 10:136, 2012) (showing prevention of thrombosis with wt DNase1 therapy). Still other exemplary animal models include models of heart transplantation rejection, plaque formation, and myocardial infarction used to show efficacy of RNase therapy (see. e.g., Kleinert et al., *J. Am. Heart Assn.* doi:10.1021, 2016; Simsekyilmaz et al., *Circulation* 129:598-606, 2014; Steiger et al., *JAMA* 6:e004541, 2017) as well as an acute stroke model as described by Walberer et al. (*Curr. Neovas. Res.* 6:12-19, 2009) (showing reduced cerebral edema and infarction size with RNase1 therapy).

Fusion molecules of the present invention can also be evaluated for anti-tumor activity in animal tumor models. For example, efficacy of DNase-PON treatment in reducing tumor metastasis associated with NET formation can be evaluated in mouse models as described by, e.g., Cools-Lartigue et al. (*J. Clin. Invest.* 123:3446, 2013) (showing reduction in metastasis of injected tumor (lung carcinoma) cells with systemic administration of wt DNase1 in a model of severe postoperative infection) and Park et al. (*Sci. Translational Med.* 8:361ra138, 2016) (showing reduction in metastasis of breast cancer cells to the lung with systemic administration of wt DNase1-coated nanoparticles). Also known is a model utilizing nude mice subcutaneously grafted with the human colon cancer cell line SW480 as described, e.g., by Trejo-Becirril et al. (*Integrative Cancer Therapies* 15:NP35-NP43, 2016) (showing inhibition of tumor growth with a combination of DNase1 and proteases). Other suitable models include a human lung tumor xenograft model described by Rutkoski et al. (*Translational Oncology* 6:392-397, 2013) (showing inhibition of tumor growth in mice using PEG-RNase1) and a syngeneic mouse tumor model with Lewis lung carcinoma described by Mironova et al., *Oncotarget* 8:78796-78810, 2017 (showing anti-tumor activity with RNase therapy).

Another known animal tumor model is B16 melanoma, a poorly immunogenic tumor. Multiple models of tumor immunotherapy have been studied. See Ngiow et al., *Adv. Immunol.* 130:1-24, 2016. The B16 melanoma model has been studied extensively with checkpoint inhibitors anti-CTLA-4, anti-PD-1, and the combination thereof. Anti-CTLA-4 alone has a potent therapeutic effect in this model only when combined with GM-CSF transduced tumor vaccine, or combined with anti-PD-1. See Weber, *Semin. Oncol.* 37:430-439, 2010. Ai et al., *Cancer Immunol. Immunother.* 64:885-92, 2015; Haanen et al., *Prog. Tumor Res.* 42:55-66, 2015. Efficacy of a DNase-PON, RNase-PON, or antiTGFβ-PON fusion molecule for treatment of malignant melanoma is shown, for example, by slowed tumor growth following administration to B16 melanoma mice that have formed palpable subcutaneous tumor nodules. Efficacy of a paraoxonase fusion molecule can be evaluated in B16 melanoma mice either alone or, alternatively, in combination with another anti-cancer therapy (e.g., anti-CTLA-4, with or without tumor vaccine or with or without anti-PD-1/PD-L1). For example, tumor rejection in B16 melanoma mice using a combination of a DNase-PON, RNase-PON, or antiTGFβ-PON fusion molecule as described herein and anti-CTLA-4, in the absence of tumor vaccine, demonstrates an enhanced response to anti-CTLA-4 using the paraoxonase fusion therapy. In exemplary studies to evaluate paraoxonase fusion molecules comprising human protein sequences, which are functionally active in mice but are expected to be immunogenic in these models (and thereby likely to result in formation of neutralizing antibodies after 7-10 days), mice may be administered a fusion molecule of the present invention for a short period (for example, one week, administered in, e.g., two doses of about 40 mg/kg three days apart), and tumor growth then monitored, typically for two to three weeks after injection with the fusion molecule.

Dosage of the pharmaceutical composition may be varied by the attending clinician to maintain a desired concentration at a target site. For example, if an intravenous mode of delivery is selected, local concentration of the agent in the bloodstream at the target tissue may be between about 1-50 nanomoles of the composition per liter, sometimes between about 1.0 nanomole per liter and 10, 15, or 25 nanomoles per liter depending on the subject's status and projected measured response. Higher or lower concentrations may be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of nanomolar. Dosing may also vary, e.g., depending on the activity of the fusion molecule being administered. For example, in the context of a DNase1-PON fusion molecule in which the DNase1 is not actin-resistant (i.e., in which the DNase1 does not contain any amino acid substitution, relative to human DNase1, that decreases G-actin-induced inhibition of endonuclease activity of the DNase relative to human DNase1), inhibition by actin may be overcome by increasing the dose relative to a dose that is effective for a similar but actin-resistant DNase1-PON fusion molecule.

A pharmaceutical composition comprising a fusion polypeptide or dimeric protein as described herein can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants. See, e.g., Bremer et al., *Pharm. Biotechnol.* 10:239, 1997; Ranade, "Implants in Drug Delivery," in *Drug Delivery Systems* 95-123 (Ranade and Hollinger, eds., CRC Press 1995); Bremer et al., "Protein Delivery with Infusion Pumps," in *Protein Delivery: Physical Systems* 239-254 (Sanders and Hendren, eds., Plenum Press 1997); Yewey et al., "Delivery of Proteins from a Controlled Release Injectable Implant," in *Protein Delivery: Physical Systems* 93-117 (Sanders and Hendren, eds., Plenum Press 1997). Other solid forms include creams, pastes, other topological applications, and the like.

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer. See, e.g., Gombotz and Pettit, *Bioconjugate Chem.* 6:332, 1995; Ranade, "Role of Polymers in Drug Delivery," in *Drug Delivery Systems* 51-93 (Ranade and Hollinger, eds., CRC Press 1995); Roskos and Maskiewicz, "Degradable Controlled Release Systems Useful for Protein Delivery," in *Protein Delivery: Physical Systems* 45-92 (Sanders and Hendren, eds., Plenum Press 1997); Bartus et al., *Science* 281:1161, 1998; Putney and Burke, *Nature Biotechnology* 16:153, 1998; Putney, *Curr. Opin. Chem. Biol.* 2:548, 1998. Polyethylene glycol (PEG)-coated nanospheres can also provide carriers for intravenous administration of therapeutic proteins. See, e.g., Gref et al., *Pharm. Biotechnol.* 10:167, 1997.

Other dosage forms can be devised by those skilled in the art, as shown by, e.g., Ansel and Popovich, *Pharmaceutical Dosage Forms and Drug Delivery Systems* (Lea & Febiger, 5th ed. 1990); Gennaro (ed.), *Remington's Pharmaceutical Sciences* (Mack Publishing Company, 19th ed. 1995), and Ranade and Hollinger, *Drug Delivery Systems* (CRC Press 1996).

In some embodiments comprising systemic administration of a fusion polypeptide or dimeric protein as described herein, the fusion molecule is formulated in a buffered saline (for example, saline buffered with 2 mM carbonate, pH 7.5, plus 1 mM calcium chloride).

Pharmaceutical compositions as described herein may also be used in the context of combination therapy. For example, for a combination therapy comprising administration of a paraoxonase fusion molecule and a DNase as described herein, each of the paraoxonase fusion molecule and the DNase (e.g., a DNase-Fc fusion as described herein) may be formulated in a buffered saline (for example, saline buffered with 2 mM carbonate, pH 7.5, plus 1 mM calcium chloride), either separately or as a mixture.

Pharmaceutical compositions may be supplied as a kit comprising a container that comprises a fusion polypeptide or dimeric protein as described herein. A therapeutic molecule can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a therapeutic protein. Such a kit may further comprise written information on indications and usage of the pharmaceutical composition.

The invention is further illustrated by the following non-limiting examples.

Example 1: Construction and Expression of DNase1-Fc and DNase1-Fc-PON1 Fusion Proteins Constructs were designed and synthesized and cassettes with the correct sequences were combined to generate synthetic fusion genes encoding unique DNase1 fusion molecules. Each construct included a variant of wild-type human DNase1 (nucleotide and encoded amino acid sequences as shown in SEQ ID NOs:15 and 16; see also GenBank accession number NM_005223). The DNase1 variant contained amino acid substitutions, relative to the mature wild-type human sequence (SEQ ID NO:120), at positions N74 (N74K), G105 (G105R), and A114 (A114F); the variant DNase1 nucleotide and encoded amino acid sequences corresponding to the mature protein are shown in residues 61-840 of SEQ ID NO:17 and residues 21-280 of SEQ ID NO:18, respectively). The signal peptide sequence utilized was the human VK3 leader peptide (nucleotide and amino acid sequences as shown in SEQ ID NO:57 and SEQ ID NO:58), an efficient heterologous leader peptide that drives high level expression and secretion of fusion proteins. The DNase1 cassette was fused to the N-terminus of a human IgG1 Fc variant (SSS hinge, P238S, P331S) using a peptide linker, either a $(Gly_4Ser)_4$ linker ((g4s)4; nucleotide and amino acid sequences as shown in SEQ ID NO: 11 and SEQ ID NO:12) or a $(Gly_4Ser)_6$ linker ((g4s)6; nucleotide and amino acid sequences as shown in SEQ ID NO:13 and SEQ ID NO:14). The Fc variant nucleotide and amino acid sequences are shown in SEQ ID NO:27 and SEQ ID NO:28. The completed DNase1-Fc constructs generated are as follows:

- [hVK3LP]-[hDNase1 N74K-G105R-A114F]-(g4s)4-[SSShinge-P238S-P331S Fc] (also referred to hereinbelow as hDNase™-(g4s)4-Fc; nucleotide and amino acid sequences as shown in SEQ ID NO:59 and SEQ ID NO:60); and
- [hVK3LP]-[hDNase1 N74K-G105R-A114F]-(g4s)6-[SSShinge-P238S-P331S Fc](also referred to hereinbelow as hDNase™-(g4s)6-Fc; nucleotide and amino acid sequences as shown in SEQ ID NO:61 and SEQ ID NO:62).

Bispecific constructs further comprising a functional PON1 enzyme were also generated by fusing the carboxyl end of hDNase™-(g4s)4-Fc or hDNase™-(gs)6-Fc to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide were deleted. The completed DNase-Fc-PON1 constructs are as follows:

- [Human VK3LP]-[hDNase1 N974K-G105R-A114F]-(g4s)4-[SSShinge-P238S-P331S Fc]-NGS-[PON1 Q192K], (nucleotide and amino acid sequences as shown in SEQ ID NO:1 and SEQ ID NO:2) (also referred to hereinbelow as hDNase™-(g4s)4-Fc-PON1-Q192K, hDNase™-(g4s)4-Fe-PON1-K, or DNase™-(g4s)4-Fc-P1-K); and
- [Human VK3LP]-[hDNase1 N974K-G105R-A114F]-(g4s)6-[SSShinge-P238S-P331S Fc]-NGS-[PON1 Q192K], (nucleotide and amino acid sequences as shown in SEQ ID NO:147 and SEQ ID NO:148) (also referred to hereinbelow as DNase™-(g4s)6-Fc-P1-K).

Transient Expression of DNase1-Fc and DNase1-Fc-PON1 Fusion Proteins

All fusion genes were assembled in a pUC based vector, then inserted into a multiple cloning site of the mammalian expression vector pDG, a pcDNA3 plasmid derivative containing a CMV promoter to drive expression of the fusion gene. Plasmid DNA was prepared using QIAGEN (Germantown, MD) mini or maxiprep plasmid DNA kits. Purified plasmid DNA was transfected into HEK293 cells plated at approximately 50-75% confluence, using Polyfect (QIAGEN, Germantown, MD) transfection reagent according to the manufacturer's instructions. Culture media was changed to DMEM Fluorobrite™ (Life Technologies, Carlsbad, CA) serum free media on the day after transfections, and transfected cells incubated for an additional 48 hours prior to harvest of culture supernatants.

FIG. 1 shows the results of Western blot analysis of fusion protein expression from a representative set of HEK293 transient transfections. Culture supernatants were loaded directly for gel electrophoresis as follows: supernatants were collected, % sample volume 4× reducing LDS sample buffer added (Life Technologies, Carlsbad, CA), samples heated for 10 minutes at 72° C., the samples centrifuged for 1 minute at 3000 rpm in a microfuge, and 30 μl sample in loading buffer (one half) from each sample was loaded onto 4-12% Bis-Tris NuPAGE gels (Life Technologies, Carlsbad, CA). Protein molecular weight markers were included on each gel (Chameleon® DUO molecular weight markers; L1-COR Biosciences, Lincoln, NE). SDS-PAGE gels were run in NuPAGE MOPS running buffer (Life Technologies, Carlsbad, CA) under reducing conditions at 185 volts for approximately 1-1.5 hours. Gels were blotted to nitrocellulose membranes using the XCell blot module (Life Technologies, Carlsbad, CA) and NUPAGE-MOPS (Life Technologies, Carlsbad, CA) transfer buffer containing 10% methanol. Blots were blocked in L1-COR Odyssey Intercept™ blocking buffer, followed by incubation with diluted goat anti-human IgG (Fc specific) secondary antibodies (Jackson Immunoresearch, West Grove, PA). Secondary antibody was conjugated with Alexafluor 790 near IR dye (L1-COR Odyssey detection) and diluted in blocking buffer 1:25,000 at 4° C. and rocked overnight. Blots were washed four times with Tris buffered saline (TBS) containing 0.1% Tween 20. Blots were then rinsed in TBS buffer and scanned with a LICOR Odyssey™ scanner. Transfection samples were loaded as follows: Lane 1—LICOR Chameleon™ molecular weight markers; Lane 2, Lane 3, Lane 4—transfection supernatants from three different individual clones (#1, #2, #4) of hDNase™-(g4s)4-Fc-PON1-Q192K; Lane 5—THER4-RNase (control; apoA1-(g4s)4-SSShinge-P238S-P331S-Fc-NGS-RNase1; see US Patent Application Publication No. 2018/0201664); Lane 6—LICOR Chameleon MW Markers; Lane 7—hDNase™-(g4s)4-Fc #4; Lane 8—hDNase™-(g4s)6-Fc #2; Lane 9—THER4 (control; apoA1-(g4s)4-SSShinge-P238S-P331S-Fc; see International PCT Publication No. WO 2017/044424); Lane 10—mock transfection. The approximate molecular weight (kDa) of each marker band is indicated on the right side of the Western blot.

Stable Expression of DNase1-Fc and DNase1-Fc-PON1 Fusion Proteins

Stable production of the DNase1 fusion proteins was achieved by electroporation of a selectable, amplifiable plasmid, pDG, containing the DNase1 fusion molecule cDNAs under the control of the CMV promoter, into Chinese Hamster Ovary (CHO) DG44 cells. The pDG vector is a modified version of pcDNA3 encoding the DHFR selectable marker with an attenuated promoter to increase selection pressure for the plasmid. Plasmid DNA (200 μg) was prepared using QIAGEN HISPEED maxiprep kits. Purified plasmid was linearized at a unique Asci site (New England Biolabs, Ipswich, MA Catalog #R0558), purified by phenol extraction (Sigma-Aldrich, St Louis, MO), ethanol precipitated, washed, and resuspended in tissue culture media, Excell 302 (Catalog #14324, SAFC/Sigma Aldrich, St Louis, MO). Salmon sperm DNA (Sigma-Aldrich, St. Louis, MO) was added as carrier DNA just prior to phenol extraction and ethanol precipitation. Plasmid and carrier DNA were coprecipitated, and the 400 μg was used to transfect $2 \times 10^7$ CHO DG44 cells by electroporation.

For electroporation, cells were grown to logarithmic phase in Excell 302 media (Catalog #13424C, SAFC Biosciences/Sigma-Aldrich, St. Louis, MO) containing glutamine (4 mM), pyruvate, recombinant insulin (1 μg/ml), penicillin-streptomycin, and 2×DMEM nonessential amino acids (all from Life Technologies, Grand Island, NY), hereinafter referred to as "Excell 302 complete" media. Media for untransfected cells and cells to be transfected also contained HT (diluted from a 100× solution of hypoxanthine and thymidine) (Invitrogen/Life Technologies, Grand Island, NY). Electroporations were performed at 280 volts, 950 microFarads, using a BioRad (Hercules, CA) GenePulser electroporation unit with capacitance extender. Electroporation was performed in 0.4 cm gap sterile, disposable cuvettes. Electroporated cells were incubated for 5 minutes after electroporation prior to transfer of the treated cells to non-selective Excell 302 complete media in T75 flasks. Transfected cells were incubated overnight at 37° C., 5% C02 in non-selective media to permit recovery, prior to selective plating in 96-well flat-bottom plates (Costar) at varying serial dilutions ranging from 250 cells/well (2500 cells/ml) to 2000 cells/well (20,000 cells/ml). Culture media for cell cloning was Excell 302 complete containing 50 nM methotrexate. Transfection plates were fed at five-day intervals with 80 µl fresh media. After the first couple of feedings, 100 µl media was removed and replaced with fresh media. Plates were monitored and individual wells with clones were fed until clonal outgrowth became close to confluent, after which clones were expanded into 24-well dishes containing 1 ml media/well. Aliquots of the culture supernatants from the original 96-well plate were harvested to a second 96-well plate prior to transfer and expansion of the cells in the 24-well plates. This second plate was frozen until performing dilutions for ELISA analysis to estimate IgG concentrations.

Screening Culture Supernatants for Production Levels of Recombinant Fusion Proteins: Once clonal outgrowth of initial transfectants was sufficient, serial dilutions of culture supernatants from master wells were thawed and the dilutions screened for expression of DNase1 fusion protein by use of an -IgG sandwich ELISA. Briefly, NUNC Maxisorp plates were coated overnight at 4° C. with 2 microgram/ml F(ab'2) goat anti-human IgG (Jackson Immunoresearch, West Grove, PA; Catalog #109-006-098) in PBS. Plates were blocked in PBS/3% BSA, and serial dilutions of culture supernatants incubated at room temperature for 2-3 hours or overnight at 4° C. Plates were washed three times in PBS/0.05% Tween 20, and incubated with horseradish-peroxidase-conjugated F(ab'2) goat anti-human IgG (Jackson Immunoresearch, West Grove, PA, Catalog #109-036-098) at 1:7500-1:10,000 in PBS/0.5% BSA, for 1-2 hours at room temperature. Plates were washed five times in PBS/0.05% Tween 20, and binding detected with SureBlue Reserve™ TMB substrate (KPL Labs/SeraCare, Gaithersburg, MD; catalog #53-00-02). Reactions were stopped by addition of equal volume of 1N HCl, and absorbance per well on each plate was read at 450 nM on a VarioSkan LUX plate reader (ThermoFisher Scientific, Waltham, MA). Concentrations were estimated by comparing the OD450 of the dilutions of culture supernatants to a standard curve generated using serial dilutions of a known standard, a protein-A-purified human -IgG fusion protein with the identical -Ig tail to clones described in this disclosure, typically THER4 (apoA1-(g4s)4-SSShinge-P238S-P331S Fc; see International PCT Publication No. WO 2017/044424) or an scFv-Fc targeted to human CD180 (G28-8). Data was collected and analyzed using platereader software and Microsoft Office Excel or GraphPad Prism 8.4.3 (San Diego, CA). The best expressing DNase-Ink-Fc clones expressed in the range of 25-55 µg/ml, while the best expressing DNase-Ink-Fc-PON1-K clones expressed at approximately 10-30 µg/ml.

Protein A purification supernatants were collected from spent CHO cell cultures expressing the fusion proteins, filtered through 0.2 µm PES express filters (Nalgene, Rochester, NY) and subjected to affinity chromatography using slow rotation of culture supernatants with Protein A-agarose (IPA 300 crosslinked agarose) slurry in 50 ml sterile, conical centrifuge tubes at 4° C. (Repligen, Waltham, MA). Fusion protein bound to protein A agarose was recovered by centrifugation, and culture supernatants removed, replaced, and the incubation process repeated until the desired volume of supernatant was processed. The final protein A agarose slurry was then loaded into sterile, acid-washed econocolumns (BioRad, Hercules, CA) to wash the resin. Columns were then washed with several column volumes of column wash buffer (Gentle Ag-Ab binding buffer, Pierce/ThermoFisher, Waltham, MA) to remove any residual culture supernatant, prior to elution. Bound protein was then eluted from the resin using gentle Ag/Ab elution buffer (Pierce/ThermoFisher, Waltham, MA). Fractions (0.8-1.0 ml) were collected and protein concentration of aliquots (2 µl) from each fraction were determined at 280 nM using a Nanodrop (Wilmington DE) microsample spectrophotometer, with blank determination using elution buffer alone. Fractions containing fusion protein were pooled, and buffer exchange was performed by dialysis using Spectrum Laboratories G2 (Ranch Dominguez, CA, Catalog #G235057, Fisher Scientific catalog #08-607-007) float-a-lyzer units (MWCO 20 kDa) against [0.9% sodium chloride, 5 mM sodium bicarbonate, 1 mM HEPES buffer, 1 mM calcium chloride, pH 7.5]. Dialysis was performed in sterile, 2.2-liter Corning roller bottles at 4° C. overnight. After dialysis, protein was filtered using 0.2 µM filter units, and aliquots tested for endotoxin contamination using Pyrotell LAL gel clot system single test vials (STV) (Catalog #G2006, Associates of Cape Cod, East Falmouth, MA).

Figure 2:
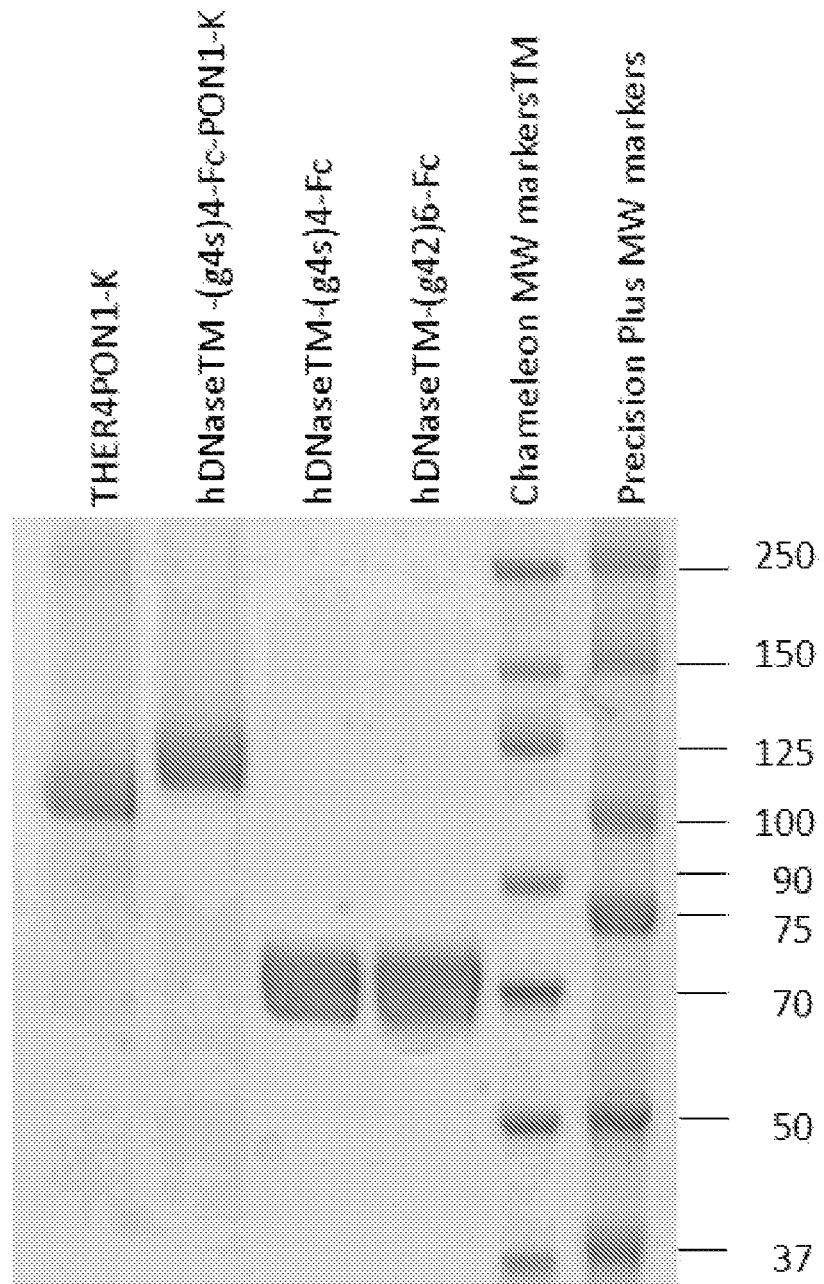
FIG. 2 shows reducing SDS-PAGE analysis of DNase1-Fc and DNase1-Fc-PON1 fusion proteins purified from CHO clone spent culture supernatants. Stable CHO cell generation. Protein A purification of fusion proteins, and SDS-PAGE were performed as described in Example 1, infra. From left to right: Lane 1—THER4PON1-K (control); Lane 2—hDNase™-(g4s)4-Fc-PON1-K; Lane 3—hDNase™-(g4s)4-Fc; Lane 4—hDNase™-(g4s)6-Fc; Lane 5—L1-COR Chameleon® MW markers; Lane 6—BioRad Precision Plus Kaleidoscope MW markers.

FIG. 2 shows purified proteins from stable CHO transfections after SDS-PAGE electrophoresis and staining with Imperial Protein Stain (Pierce/ThermoFisher, Waltham, MA/Rockville, MD. Catalog #24615). Five micrograms each protein-A-purified fusion protein was incubated in 1×LDS reducing sample buffer at 72° C. for 10 minutes followed by loading onto 4-12% Bis-Tris NuPAGE gels (Life Technologies, Carlsbad, CA). Protein molecular weight markers were included on each gel (Chameleon® DUO molecular weight markers (L1-COR Biosciences, Lincoln, NE) and Precision Plus molecular weight markers (BioRad, Hercules, CA)). SDS-PAGE gels were run in NuPAGE MOPS running buffer (Life Technologies, Carlsbad, CA) under reducing conditions at 175 volts for approximately 2 hours. Gels were washed three times in 100 ml distilled water, then stained in 30 ml Imperial Stain (Pierce/ThermoFisher, Waltham, MA) at room temperature with rocking for 2.5 hours. Gels were destained by washing 4 times in 100-200 ml distilled water and placed in a plastic sleeve prior to photographing/scanning of the stained gel. Lanes were loaded as follows: Lane 1—THER4PON1-K (apoA1-(g4s)4-SSShinge-P238S-P331S-Fc-NGS-PON1-K; see International PCT Publication No. WO 2017/044424); Lane 2—hDNase™-(g4s)4-Fc-PON1-K; Lane 3—hDNase™-(g4s)4-Fc; Lane 4—hDNase™-(g4s)6-Fc; Lane 5—L1-COR Chameleon® MW markers; Lane 6—BioRad Precision Plus Kaleidoscope MW markers. The approximate molecular weight (kDa) of each marker band is indicated on the right side of the stained gel.

Example 2: DNase Activity of DNase1—Fc and DNase1-Fc-PON1 Fusion Proteins

Nuclease activity of DNase1 fusion proteins was assessed using a modified SYTOX™ Green fluorescence assay. SYTOX Green dye (5 mM solution in DMSO, Catalog #S7020) was obtained from Molecular Probes/Invitrogen (ThermoFisher Scientific, Waltham, MA). Salmon sperm DNA was also obtained from ThermoFisher Scientific (UltraPure, sheared, phenol purified, Catalog #15632011). Enzyme activity assays were performed either by titrating the substrate concentration with a fixed enzyme concentration, or by titrating the enzyme concentration with a fixed substrate concentration. For substrate titration experiments, salmon sperm DNA was mixed with SYTOX Green stain at a ratio of 14 µM sytox green to 400 µM (140 µg/ml) salmon sperm DNA in 1× DNase reaction buffer (10 mM Tris, pH 7.5, 5 mM MgCl$_2$, 1 mM CaCl$_2$), and the mixture was incubated at 37° C. for approximately 2 hours to label and equilibrate. Appropriate dilutions of the stock labeled DNA were made for enzyme activity assays. One-third fold serial dilutions of SYTOX Green labeled DNA were prepared in a separate plate and 50 µl of each dilution was transferred to the assay plate to generate the following substrate concentrations in the final reactions: 1) 220 µM salmon sperm DNA (SS DNA) and 10 µM SYTOX Green; 2) 147 µM SS DNA and 6.7 µM SYTOX Green; 3) 98.78 µM SS DNA and 4.4 µM SYTOX Green; 4) µM SS DNA and 3.01 µM SYTOX Green; and 5) 44 µM SS DNA and 2.05 µM SYTOX Green.

Each fusion protein or recombinant DNase1 enzyme was prepared at two times the desired final concentration (9 nM initial, or 4.5 nM final concentration) to be assessed in 1×DNase reaction buffer. Fifty microliters of each fusion protein or recombinant enzyme were added to each well of the assay plate containing the labeled substrate. Plates were immediately transferred to the plate reader, and fluorescence was measured using 485 nm excitation and 528 nm emission wavelengths. Sample fluorescence was monitored using a kinetic assay on a VarioSkan LUX fluorescent plate reader (Thermo Scientific, Waltham, MA) with readings every 45 seconds for a total of 40 minutes. RFU (Relative Fluorescence Units) were plotted as a function of time for each well. The fluorescence signal in each well decreased more rapidly with increasing nuclease activity.

Figure 3A:
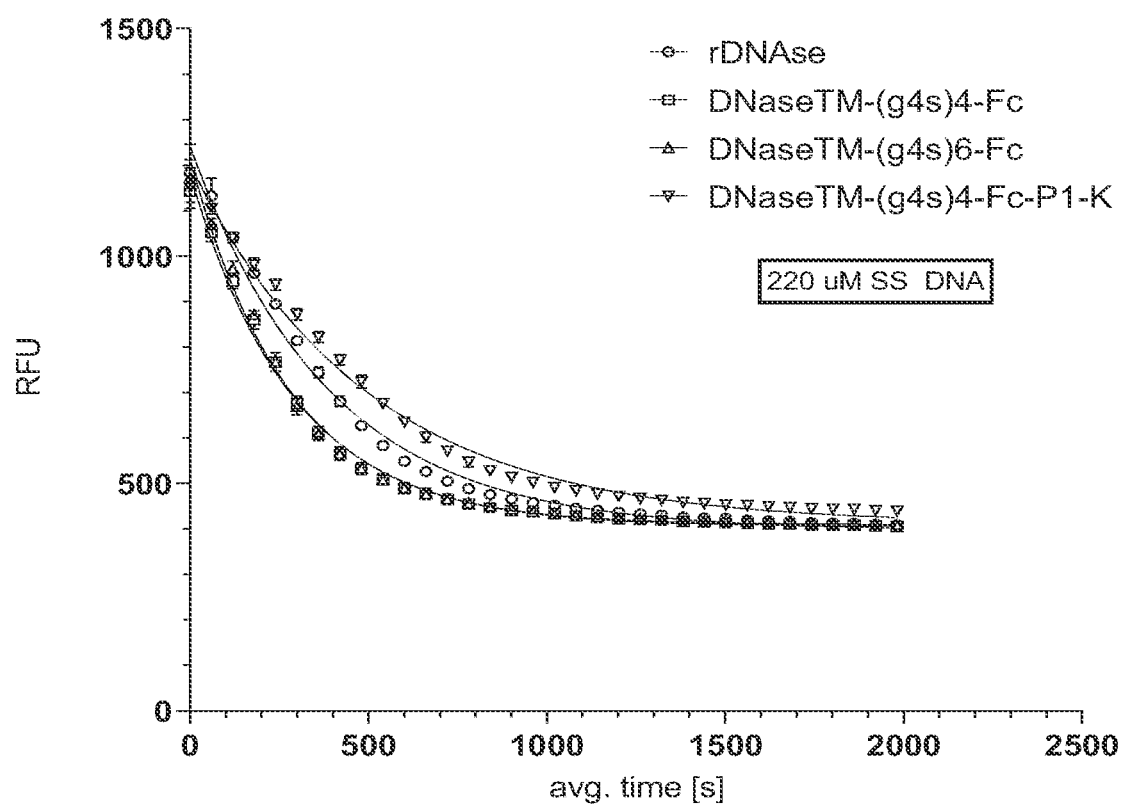
FIGS. 3A and 3B show raw data from a modified SYTOX™ Green fluorescence assay assessing nuclease activity of DNase1 fusion proteins at two different substrate concentrations, 220 μM or 66 μM salmon sperm DNA (see Example 2, infra).
Figure 3B:
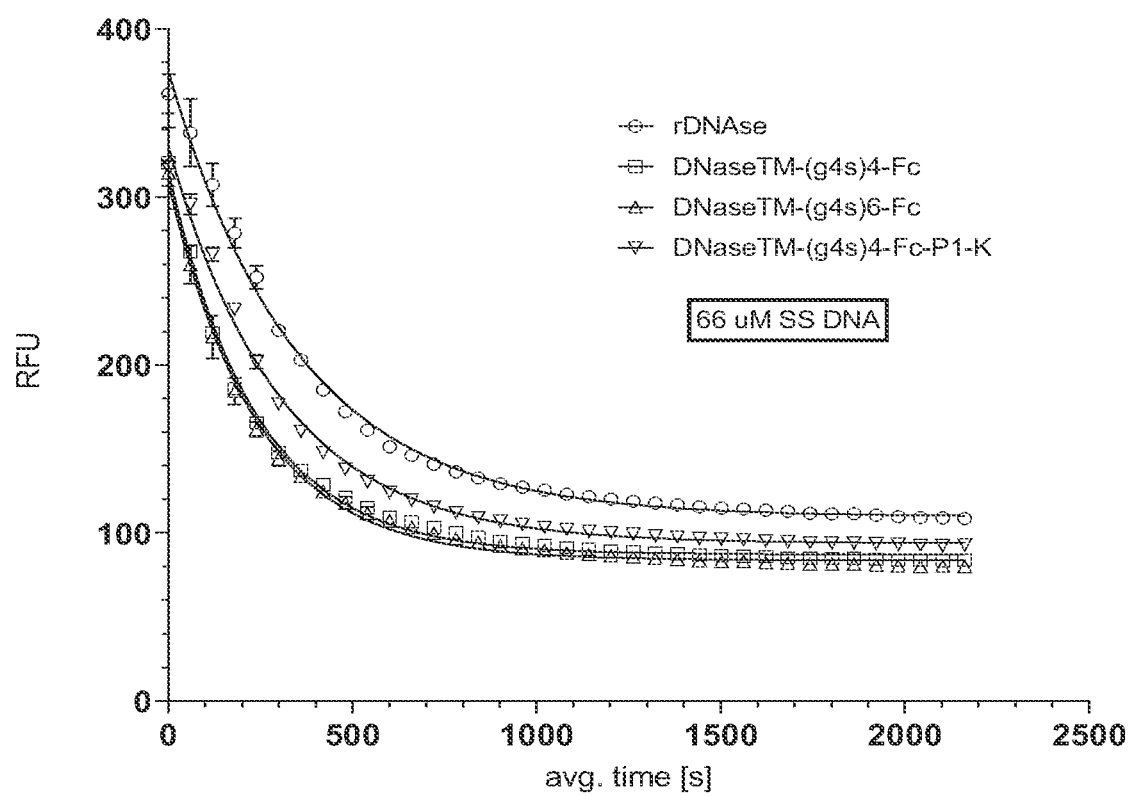

FIG. 3 shows a graphical representation of the raw data analyzing the relative fluorescence units (RFU) as a function of time at two different substrate concentrations, 220 µM or 66 µM salmon sperm DNA. For these experiments, the enzyme concentration used was fixed at 4.5 nM. The specific activity of the DNase1™-(g4s)4-Fc and DNase1TM-(g4s)6-Fc fusion proteins was higher than the recombinant wild-type human DNase1 at all substrate concentrations. At lower concentrations of substrate (the more physiologically relevant levels), the bispecific fusion protein (DNase1 ™-(g4s)4-Fc-P1-K) showed higher activity than the recombinant wild-type DNase1, while at higher concentrations of DNA substrate, the wild-type DNase1 had higher activity than the bispecific fusion protein.

Figure 4A:
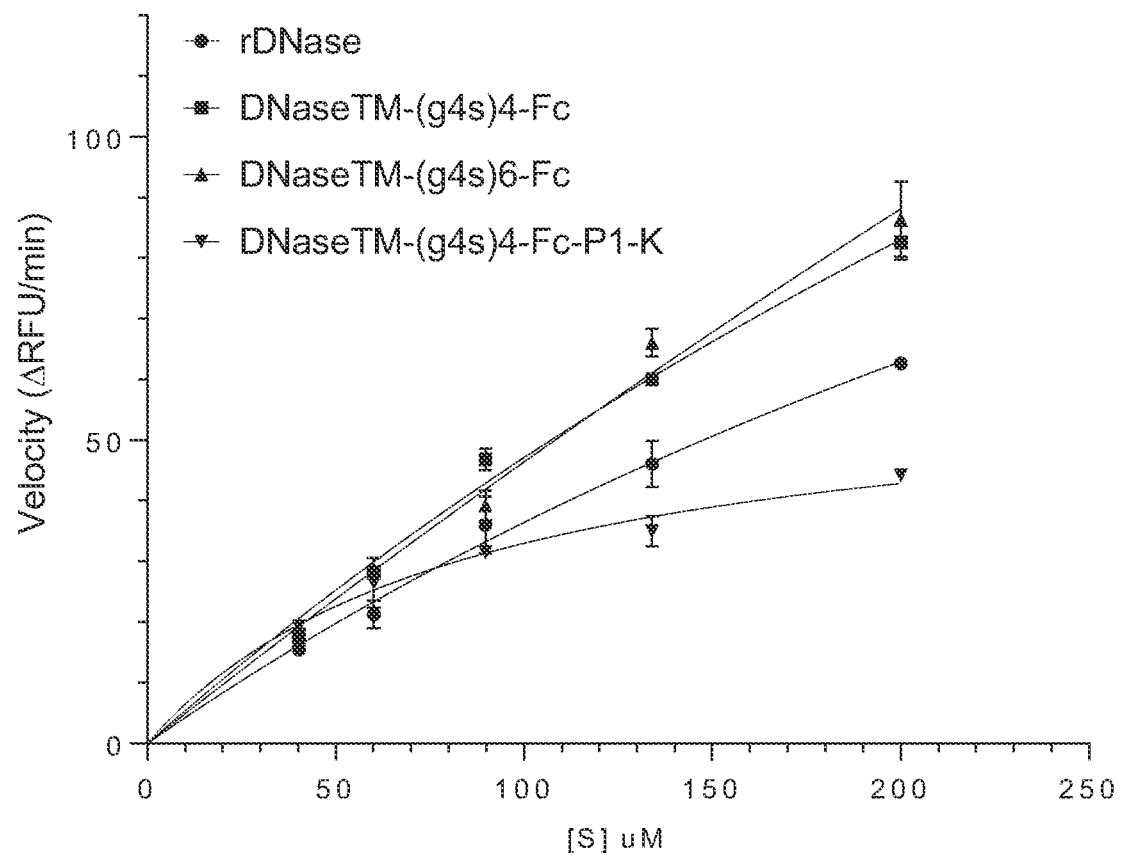
FIGS. 4A and 4B show Michaelis-Menten plots of data from two different DNase activity experiments using a modified SYTOX™ Green fluorescence assay (see Example 2, infra).
Figure 4B:
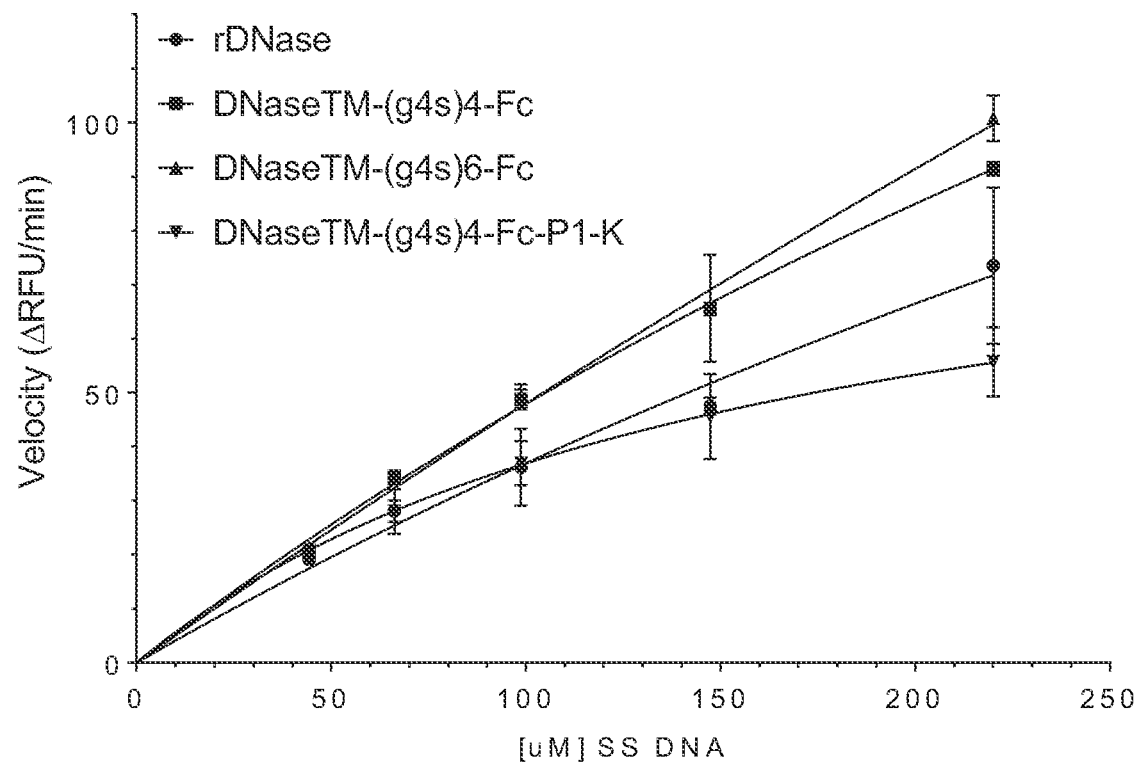

FIGS. 4A and 4B show Michaelis Menten plots of the data from two different DNase activity experiments ("Experiment #1" and "Experiment #2") using these conditions. The estimated Km and Vmax for each fusion protein in Experiment #1 and Experiment #2 are shown below in Table 2, with the tabulated data for each experiment listed. The units for the Vmax or maximal velocity are in pmoles SYTOX-labeled salmon DNA digested/min, and the units for the Km are in pmoles labeled salmon sperm DNA. Raw data was analyzed using the SkanIt™ software for the VarioSkan LUX plate reader (Thermo Scientific, Waltham, MA), then the data further analyzed using Microsoft Excel (Redmond, WA) and GraphPad Prism 8.4.3 (San Diego CA).

TABLE 2

Tabulated Michaelis Menten Data for DNase Fusion Proteins at 4.5 nM

|  | rDNase | DNaseTM-(g4s)4-Fc | DNaseTM-(g4s)6-Fc | DNaseTM-(g4s)4Fc-P1-K |
|---|---|---|---|---|
| Experiment #1 |  |  |  |  |
| Vmax | 332.5 | 374.7 | 968.9 | 95.91 |
| Km | 533.6 | 681.9 | 1919 | 159.7 |
| Experiment #2 |  |  |  |  |
| Vmax | 230.8 | 349,4 | 874.3 | 61.13 |
| Km | 533.6 | 641.6 | 1785 | 85.29 |

Vmax: µmol salmon sperm DNA digested/min
Km: µmol salmon sperm DNA

Enzyme activity assays were also performed in the presence or absence of actin to assess whether the DNase fusion proteins were sensitive to actin inhibition. These assays were performed either by titrating the substrate concentration with a fixed enzyme concentration, or by titrating the enzyme concentration with a fixed substrate concentration. For substrate titration experiments, salmon sperm DNA was mixed with SYTOX Green stain at a ratio of 14 µM sytox green to 400 µM (140 µg/ml) salmon sperm DNA in 1× DNase reaction buffer (10 mM Tris, pH 7.5, 5 mM MgCl$_2$, 1 mM CaCl$_2$)), and the mixture was incubated at 37° C. for approximately 2 hours to label and equilibrate.

Figure 5A:
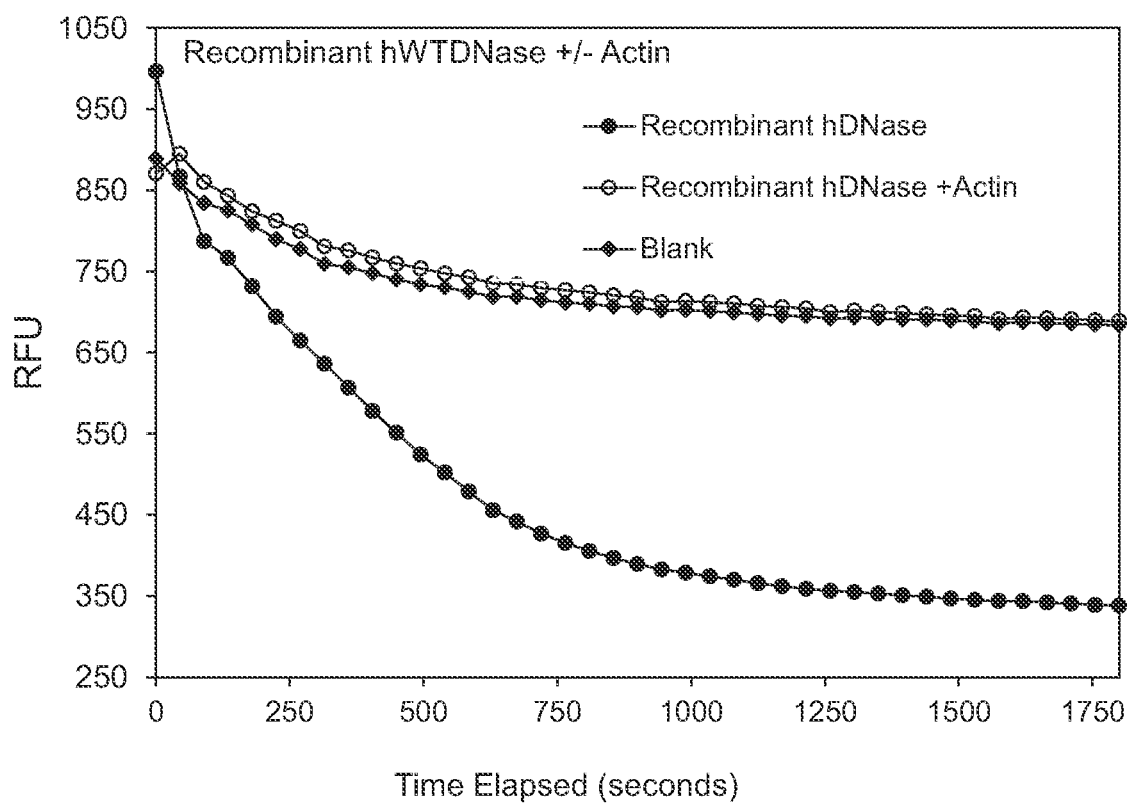
FIGS. 5A and 5B show results from a SYTOX™ Green fluorescence assay comparing relative actin-induced inhibition of DNase activity of recombinant human DNase1 and a DNase1-Fc fusion protein (see Example 2, infra).
Figure 5B:
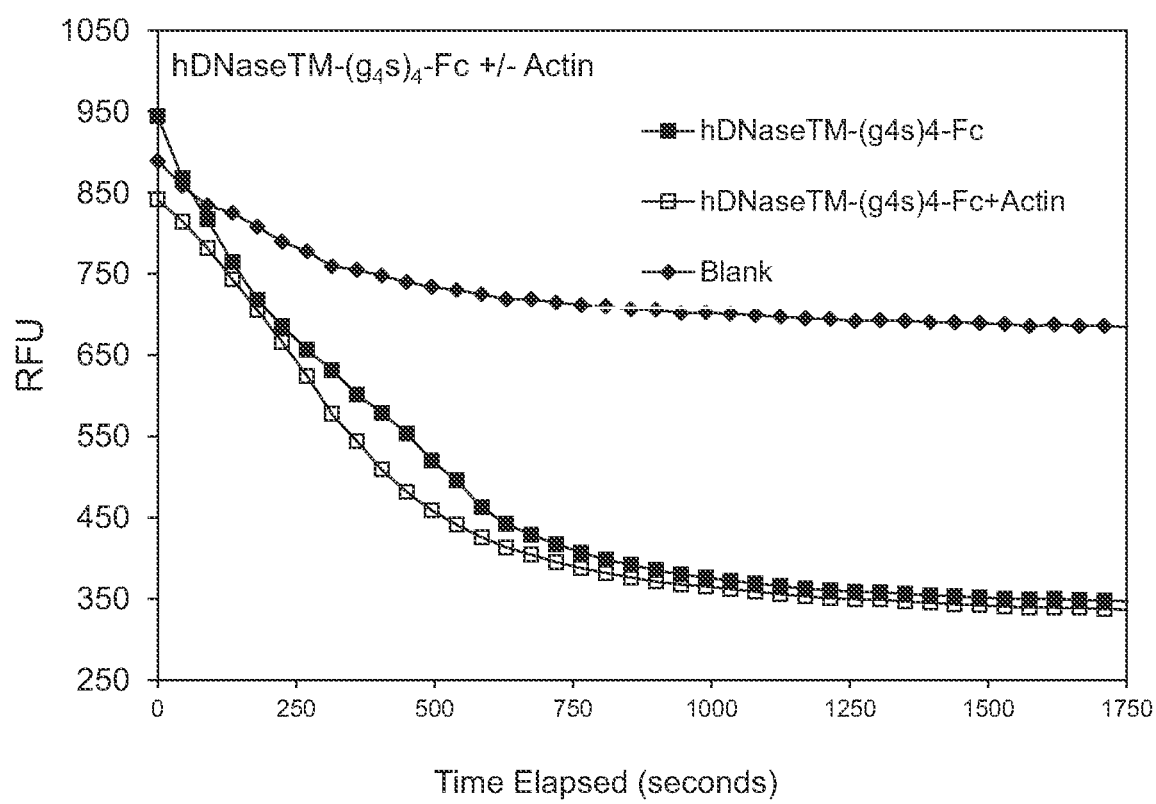

Each fusion protein or recombinant DNase1 enzyme was prepared at four times the desired final concentration (18 nM initial, or 4.5 nM final concentration) to be assessed in 1× DNase reaction buffer. Each 4× sample was then mixed 1:1 with a solution containing rabbit skeletal muscle actin protein (Cytoskeleton, Denver, CO., Catalog #AKL99-A) at 4×=160 µg/ml, or a final concentration in the nuclease reaction of 40 µg/ml; or reaction buffer containing no actin. Samples containing 9 nM fusion protein with 80 µg/ml actin were incubated at 37° C. for 45-60 minutes prior to addition of the labeled SYTOX green substrate. Sytox green substrate was prepared by adding 160 µg/ml salmon sperm DNA to 14 µM Sytox green dye in 1× DNase reaction buffer and equilibrating at 37° C. for 60-120 minutes. Fifty microliters of each actin-treated fusion protein or recombinant enzyme were added to each well of the assay plate containing 50 µl of the labeled substrate. Plates were immediately transferred to the plate reader, and fluorescence was measured using nm excitation and 528 nm emission wavelengths. Sample fluorescence was monitored using a kinetic assay on a VarioSkan LUX fluorescent plate reader (Thermo Scientific, Waltham, MA) with readings every 45 seconds for a total of 40 minutes. RFU (Relative Fluorescence Units) were plotted as a function of time for each well. The fluorescence signal in each well decreased more rapidly with increasing nuclease activity. FIGS. 5A and 5B show graphs plotting the RFU as a function of time for the DNase™-(g4s)4-Fc molecule and for the recombinant human DNase. The nuclease activity of the recombinant human DNase1 was inhibited by actin, while the fusion protein variants were not inhibited under these conditions.

Example 3: Paraoxonase Activity of DNase1-Fc-PON1 Fusion Protein Arylesterase Activity Phenyl acetate was used as a substrate to assess arylesterase activity of the DNase1TM-(g4s)4-Fc-PON1-Q192K fusion protein. Enzyme activity assays were performed either by titrating the substrate concentration with a fixed enzyme concentration, or by titrating the enzyme concentration with a fixed substrate concentration. For the phenyl acetate activity assays, reaction buffer contained 20 mM Tris-HCl, pH 8.0, 1 mM $CaCl_2$). Substrate solution contained reaction butter and 10 mM phenyl acetate, while enzyme solution contained reaction buffer and enzyme(s) at the appropriate concentrations. Substrate solution was diluted 1:1 with enzyme solutions for a final concentration of 5 mM phenyl acetate substrate in the reactions. Fusion protein (enzyme) concentration was present in the assays titrated in 1/3 serial dilutions from 40 µg/ml (40, 26.8, 17.96, 12.05, 8.06, 5.4, 3.62, and 2.4 µg/ml). Sample absorption was monitored using a kinetic assay on a VarioSkan LUX fluorescent plate reader, with readings every 45 seconds for a total of 10 minutes. Molar absorptivity at 270 nm serves as a measure of phenol formed as a function of time. The change in absorption was converted into a reaction rate using the molar extinction coefficient of 1310 $M^{-1}$ $cm^1$ for phenol.

Figure 6A:
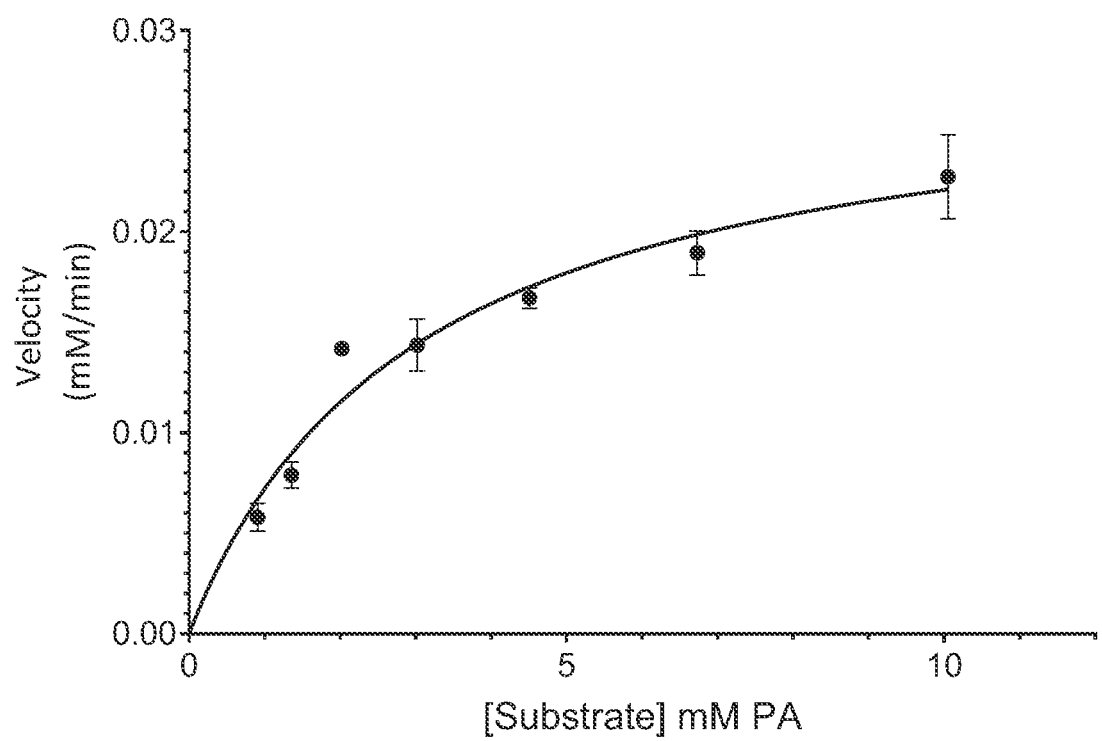
FIGS. 6A and 6B show Michaelis-Menten and Lineweaver-Burk plots, respectively, for a representative experiment measuring the arylesterase activity of a DNase1-Fc-PON1 fusion protein (see Example 3, infra).
Figure 6B:
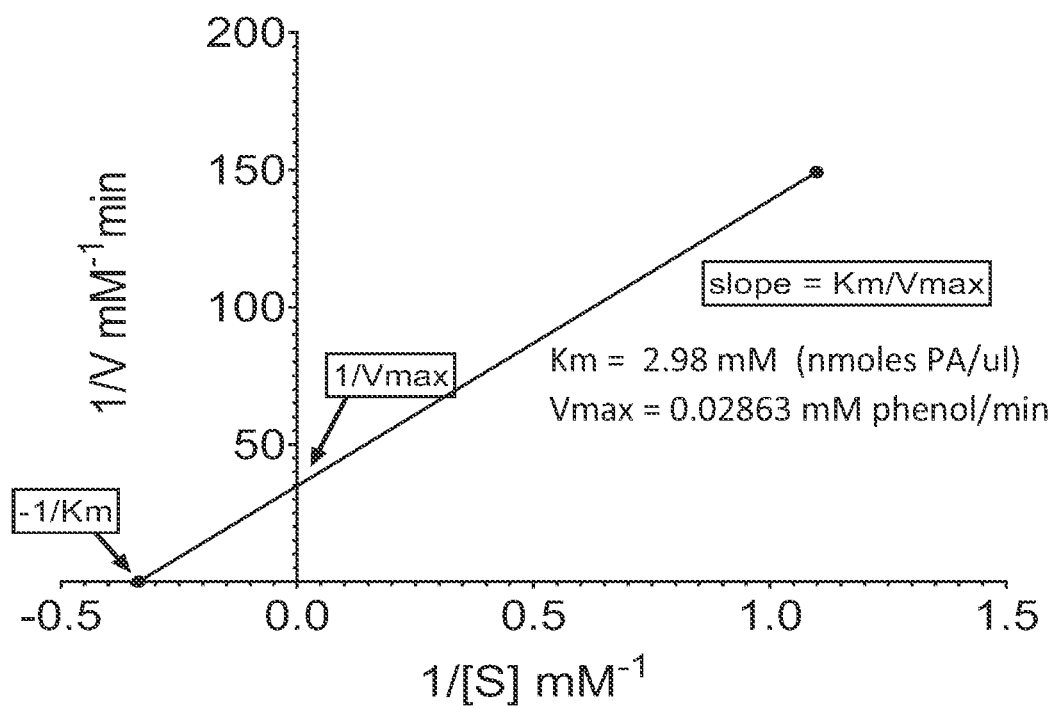

In addition, arylesterase activity assays were performed titrating the amount of phenyl acetate substrate present in 1/3-fold serial increments as follows: 15 mM, 10.05 mM, 6.73 mM, 4.51 mM, 3.02 mM, 2.03 mM, 1.36 mM, and 0.91 mM substrate. In each case, the amount of fusion protein (enzyme) present was 7.5 µg/ml. For the DNase1TM-(g4s)4-Fc-PON1-Q192K molecules, this concentration corresponds to 75 nM. FIGS. 6A and 6B show Michaelis Menten analysis and Lineweaver Burk plots for a representative experiment measuring the arylesterase activity of the DNase™-(g4s)4-Fc-PON1-Q192K fusion protein. When multiple experiments were compared, the Vmax average was approximately 0.027 mM phenol/min (mmoles/liter=nmoles/µl) and the Km was approximately 2.7 mM phenyl acetate (mmoles/liter=nmoles phenyl acetate/µl).

Organophosphatase Activity

Figure 7:
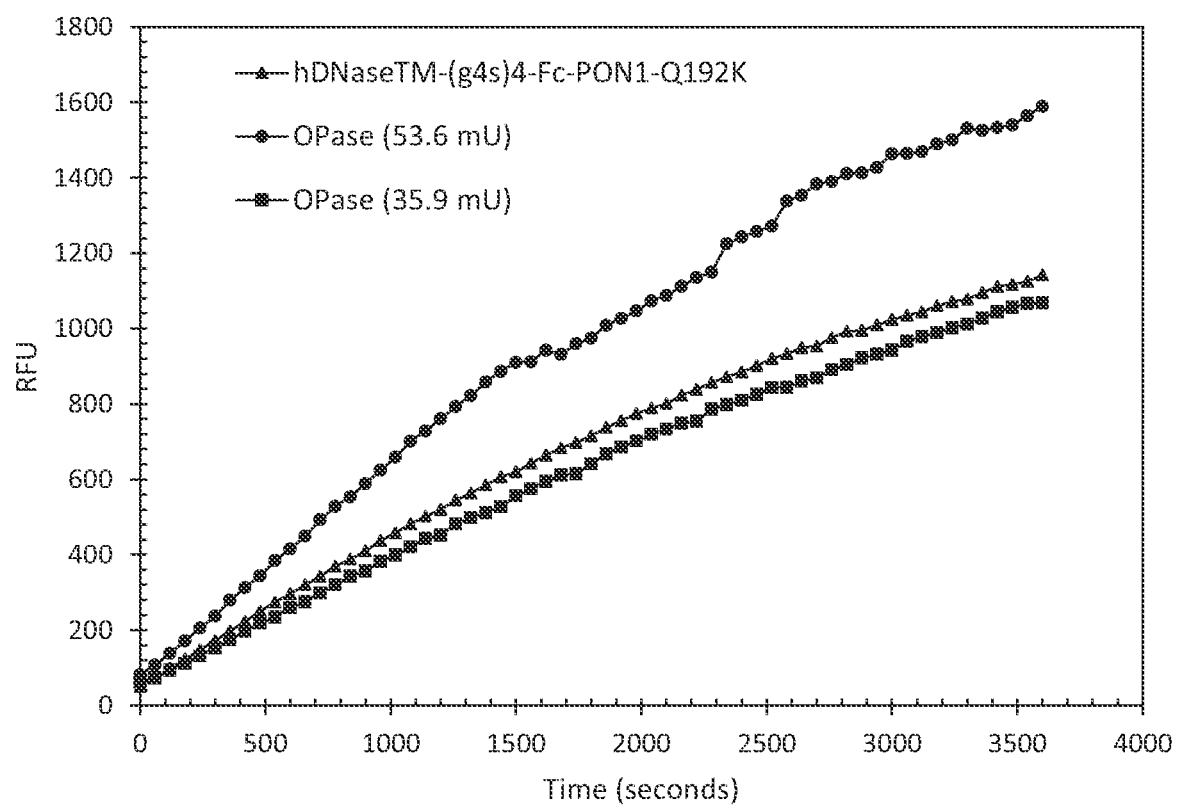
FIG. 7 shows the results of a fluorometric assay measuring the organophosphatase activity of a DNase1-Fc-PON1 fusion protein and an organophosphatase positive control enzyme (see Example 3, infra).

The Enzcheck paraoxonase activity assay (Catalog #E33702, ThermoFisher Scientific, Waltham, MA) was used to assess organophosphatase activity of the DNase1TM-(g4s)4-Fc-PON1-Q192K fusion protein. This assay is a very sensitive fluorometric assay for the organophosphatase activity of paraoxonase that uses excitation/emission maxima of 360/450 nm to measure the conversion of a fluorogenic organophosphate analog provided with the kit. The assay can either be set up as a kinetic assay or terminated after a particular period of time for an endpoint assay. The change in relative fluorescence units (RFU) per unit time is converted to the units of paraoxonase in the sample using the standard curve generated from the fluorescent standard and the conversion factor that 1 U unit of paraoxonase generates 1 nmol of fluorescent product per minute at 37° C. The amount of paraoxonase present in the fusion protein samples can be compared to the paraoxonase positive control provided with the kit. FIG. 7 shows a graphical representation of the organophosphatase activity of the DNase1TM-(g4s)4-Fc-PON1-Q192K fusion protein compared to the RFU curves generated by two different dilutions of the organophosphatase positive control in the average to above average activity range for human serum sample comparisons. The fusion protein tested had been kept at 4° C. for 11 months, but still had activity above average in the PON1 assay.

Similar activity assays to the arylesterase and organophosphatase can be performed for the PON1 enzyme activities present in fusion proteins as described herein, such as, e.g., peroxidase activity assays (Amplex Red peroxide/peroxidase assay, ThermoFisher Scientific, Waltham MA, Catalog number: A22188) or a general phosphatase assay (ENzChek phosphatase assay, ThermoFisher Scientific, Waltham MA, Catalog number: 12020).

Example 4: Assays to Assess Inhibition of Biofilm Formation by DNase-Fc and DNase-Fc-PON1 Fusion Proteins DNase-Fc and DNase-Fc-PON1 fusion proteins are characterized in biofilm formation assays to evaluate inhibition of *Pseudomonas aeruginosa* biofilm formation. *Pseudomonas aeruginosa* cultures are grown from an isolated bacterial colony by inoculation into rich media such as 2×YT or LB media. Overnight cultures are diluted 1:100 in tryptic soy broth/0.5% glucose (Teknova, Hollister, CA), and the diluted cultures used to inoculate 100 µl/well into a 96 well tissue culture plate. Wells are precoated with each fusion protein of interest at different concentrations, prior to inoculation with the diluted bacterial culture. Alternatively, fusion proteins are added directly to diluted bacterial cultures to assess inhibition activity in solution. Plates are incubated at 37° C. for 4-8 hours prior to assay. All conditions are performed in replicates of 6-8 in order to control for well-to-well variation. After the incubation, cultures are removed by aspiration or turning the plate over and shaking out the liquid. The plate is then washed with PBS to remove unattached cells and media. After washing, 125 µl of 0.1% solution crystal violet is added to each well, and the plate is incubated for 15 minutes at room temperature. Plates are rinsed 3-4 times with water or PBS using a plate washer. After the final wash, microtiter plates are inverted and left to dry for a few hours or overnight. To quantify biofilms, 125 µl 30% acetic acid is added to each dried well in order to solubilize the crystal violet. Plates are incubated at room temperature for 15 minutes, and the 125 µl of crystal violet is transferred to a new flat bottom microtiter dish. Well absorbance is then measured at 550 nm in a Varioskan plate reader using 30% acetic acid as a blank solution. Percent biofilm inhibition is estimated by subtracting the ratio of [fusion protein treated absorbance average/untreated absorbance average] from 1 and multiplying by 100.

A commercially available biofilm formation kit is also available from Dojindo (Donjindo Laboratories, Kumamoto, Japan) that uses pegged microtiter plates for biofilm formation, simplifying washing steps.

Example 5: Construction of SOD1-Fc-PON1 Fusion Proteins

The sequence for wild-type human SOD1 (see GenBank Accession Nos. NM_000454.5, CR450355.1, and CR4541742.1) is obtained from the NCBI sequence database and is designed and synthesized as an expression cassette for insertion into a molecule already containing a partial fusion gene encoding a $(Gly_4Ser)_2$ linker ((g4s)2; nucleotide and amino acid sequences as shown in SEQ ID NO:9 and SEQ ID NO:10) attached to the N-terminus of a human IgG1 Fc variant (SSS hinge, P238S, P331S Fc; nucleotide and amino acid sequences as shown in SEQ ID NO:27 and SEQ ID NO:28). The carboxyl end of the human Fc variant is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The predicted amino acid sequence of SOD1 does not contain a signal peptide for secretion, so a modified version of the human VK3 signal sequence is designed with additional amino acids at the junction site with SOD1 in order to achieve cleavage of the heterologous signal peptide at the correct location. The amino terminal methionine for SOD1 is absent in the mature secreted version of this modified SOD1, so that the predicted N-terminal amino acid after cleavage of the modified signal peptide is alanine. The encoded, modified VK3 leader and N-terminal SOD1 sequence is MET-PAQLLFLLLLWLPDTTGMA/ATKAVCVL (residues 1-30 of SEQ ID NO:50), where the slash mark indicates the junction between the VK3 leader peptide (VK3LP) and SOD1. The completed SOD1 fusion construct is [Human VK3LP]-[hSOD1]-(g4s)2-[SSShinge-P238S-P331S Fc]-NGS-[PON1 Q192K](nucleotide and amino acid sequences as shown in SEQ ID NO:49 and SEQ ID NO:50).

Additional SOD1 fusion genes containing a sequence variant of SOD1 are also constructed. The variant substitutes alternative amino acids for cysteines at positions 7 and of human SOD1 (amino acid numbering according to the full-length immature SOD1 sequence of SEQ ID NO:32), creating a C7A and C112S double mutant form of the predicted amino acid sequence. This sequence was originally described by Parge et al. (*Proc. Natl. Acad. Sci. USA* 89:6109-6113, 1992) as a thermostable mutant of SOD1 with improved solubility and stability. The SOD1 double mutant variant is fused to the N-terminus of the human Fc variant (SSS hinge, P238S, P331S Fc; see above) using either the $(Gly_4Ser)_2$ linker (see above) or a $(Gly_4Ser)_4$ linker ((g4s)4; nucleotide and amino acid sequences as shown in SEQ ID NO:11 and SEQ ID NO:12). The carboxyl end of the Fc is fused to the NGS linker followed by the PON1 Q192K variant as described above for the wild-type SOD1 fusion. The completed double mutant SOD1 fusion constructs are [Human VK3LP]-[hSOD1 C7A C112S]-(g4s)2-[SSShinge-P238S-P331S Fc]-NGS-[PON1 Q192K] (nucleotide and amino acid sequences as shown in SEQ ID NO:51 and SEQ ID NO:52) and [Human VK3LP]-[hSOD1 C7A C112S]-(g4s)4-[SSShinge-P238S-P331S Fc]-NGS-[PON1 Q192K](also referred to hereinbelow as SOD1-P1-K: nucleotide and amino acid sequences as shown in SEQ ID NO:53 and SEQ ID NO:54).

Superoxide dismutase activity of the SOD1-Fc-PON1 fusion proteins is measured using a commercially available kit such as the SOD colorimetric activity kit (ThermoFisher Scientific, Waltham MA, Catalog number: EIASODC) or a similar kit available from Cayman Chemical, (Cayman Chemical, Ann Arbor, MI; Catalog number: 706002).

Example 6: Construction of RNase1-Fc-PON1 Fusion Proteins

The sequence for wild-type human RNase 1 (see GenBank Accession Nos. NM_198235.3, NM_198234.3, NM_198232.3, and NM_002933.5) is obtained from the NCBI sequence database and is designed and synthesized as an expression cassette encoding wild-type RNase 1 with its native leader sequence (nucleotide and amino acid sequences as shown in SEQ ID NO:21 and SEQ ID NO:22) or RNase 1 attached to the human VK3 leader peptide (VK3LP) sequence (nucleotide and amino acid sequences as shown in SEQ ID NO:23 and SEQ ID NO:24). These RNase1-encoding cassettes are then fused to a human IgG1 Fc variant with C220S, C226S, C229S, and P238S amino acid substitutions, but wild-type CH2 and CH3 domains (SSS hinge, P238S Fc; nucleotide and amino acid sequences as shown in residues 475-1170 of SEQ ID NO:41 and residues 159-390 of SEQ ID NO:42). The nucleotide and amino acid sequences for the wild-type RNase1-Fc construct (with the native leader) are shown in SEQ ID NO:41 and SEQ ID NO:42, and the nucleotide and amino acid sequences for the VK3LP-RNase1-Fc construct are shown in SEQ ID NO:43 and SEQ ID NO:44. These constructs contain two heterologous, restriction-site-encoded amino acids (Asp-Leu; residues 157-158 of SEQ ID NO:42 or residues 149-150 of SEQ ID NO:44) linking the carboxyl end of RNase1 to the N-terminus of the Fc.

The RNase1-encoding cassettes are also fused to the SSS hinge, P238S Fc variant via a $(Gly_4Ser)_4$ linker peptide ((g4s)4; nucleotide and amino acid sequences as shown in SEQ ID NO:11 and SEQ ID NO:12). The resulting RNase1-(g4s)4-Fc nucleotide and predicted amino acid sequences are shown in SEQ ID NO:33 and SEQ ID NO:34 (for the wild-type RNase1 with the native leader) and SEQ ID NO:35 and SEQ ID NO:36 (for the mature wild-type RNase1 fused to the human VK3 leader).

The carboxyl end of the human Fc variant in each of the RNase1-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed RNase1-Fc-PON1 constructs generated are as follows:
  hRNase1-[SSShinge-P238S Fc]-NGS-[PON1 Q192K] (nucleotide and amino acid sequences as shown in SEQ ID NO:45 and SEQ ID NO:46);
  hVK3LP-hRNase1-[SSShinge-P238S Fc]-NGS-[PON1 Q192K](nucleotide and amino acid sequences as shown in SEQ ID NO:47 and SEQ ID NO:48);
  hRNase1-(g4s)4-[SSShinge-P238S Fc]-NGS-[PON1 Q192K](nucleotide and amino acid sequences as shown in SEQ ID NO:37 and SEQ ID NO:38); and
  hVK3LP-hRNase1-(g4s)4-[SSShinge-P238S Fc]-NGS-[PON1 Q192K](nucleotide and amino acid sequences as shown in SEQ ID NO:39 and SEQ ID NO:40).

Example 7: Construction of CTLA4-Fc-PON1 Fusion Proteins

The sequence for wild-type, full length, human CTLA-4 (see GenBank Accession Nos. AF414120.1 and L15006.1) is obtained from the NCBI sequence database and is used in the design and synthesis of an expression cassette encoding the human CTLA-extracellular domain attached to the human VK3 leader peptide (VK3LP) sequence (nucleotide and amino acid sequences as shown in SEQ ID NO: 57 and SEQ ID NO: 58). These CTLA-4-encoding cassettes are then fused to a human IgG1 Fc variant with C220S, C226S, C229S, P238S and P331S amino acid substitutions in the Fc domain (SSS hinge, P238S, P331S Fe; nucleotide and amino acid sequences as shown in SEQ ID NO:27 and SEQ ID NO:28). The nucleotide and amino acid sequences for the VK3LP-CTLA4-Fc construct are shown in SEQ ID NO:63 and SEQ ID NO:64. These constructs contain two heterologous, restriction-site-encoded amino acids (Asp-Leu or DL; residues 433-438 of SEQ ID NO:63 or residues 145-146 of SEQ ID NO:64) linking the carboxyl end of CTLA-4 to the N-terminus of the Fc region.

The carboxyl end of the human Fc variant in each of the CTLA4-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q92K; nucleotide and amino acid sequences as shown in SEQ ID NO:5 and SEQ ID NO:6) in which the first 15 amino acids of the uncleaved leader peptide are deleted. The nucleotide and amino acid sequences of the completed CTLA4-Fc-PON1 construct generated (hVK3LP-[hCTLA-4EC]-[SSShinge-P238S-P331S Fc]-NGS-[PON1 Q192K]; also referred to hereinbelow as CTLA4-Fc-P1-K) are listed in SEQ ID NO:65 and SEQ ID NO:66.

Example 8: Construction of CD40-Fc-PON1 Fusion Proteins

The sequence for wild-type, full length, human CD40 (nucleotide and amino acid sequences shown in SEQ ID NO:67 and SEQ ID NO:68; see GenBank Accession No. NM_001250) is obtained from the NCBI sequence database and is used in the design and synthesis of an expression cassette encoding the human CD40 extracellular domain with its native leader sequence or the human CD40 extracellular domain attached to the human VK3 leader peptide (VK3LP) sequence (nucleotide and amino acid sequences as shown in SEQ ID NO:57 and SEQ ID NO:58). These CD40-encoding cassettes are then fused to a $(Gly_4Ser)_4$ peptide linker (nucleotide and amino acid sequences as shown in SEQ ID NO:11 and SEQ ID NO:12, including flanking restriction sites and encoded amino acids) and a human IgG1 Fc variant with C220S, C226S, C229S, P238S and P331S amino acid substitutions in the Fc domain (SSS hinge, P238S, P331S Fc; nucleotide and amino acid sequences as shown in SEQ ID NO:27 and SEQ ID NO:28). The nucleotide and amino acid sequences for the wild-type CD40-Fc construct with the native leader ([hCD40 EC]-(g4s)4-[SSShinge-P238S Fc]) are shown in SEQ ID NO:69 and SEQ ID NO:70, and the nucleotide and amino acid sequences for the CD40-Fc construct with the VK3LP leader (hVK3LP-[hCD40 EC]-(g4s)4-[SSShinge-P238S Fc]) are shown in SEQ ID NO:71 and SEQ ID NO:72.

In addition to the wild-type form of CD40, several variants were generated which show improved binding avidity for the CD40 ligand (CD154 or gp39). Using the amino acid numbering according to the wild-type, full-length human CD40 (SEQ ID NO:68), the amino acid substitution(s) for each of these CD40 variants relative to the wild-type sequence are (i) K81T, (ii) K81H, L121P, (iii) K81S, and (iv) E64Y, K81T, P85Y. The variant CD40-Fc constructs are as follows:

hVK3LP-[hCD40 EC K81T]-(g4s)4-[SSShinge-P238S Fc](nucleotide and amino acid sequences as shown in SEQ ID NO:75 and SEQ ID NO:76);

hVK3LP-[hCD40 EC K81H-L121P]-(g4s)4-[SSShinge-P238S Fc](nucleotide and amino acid sequences as shown in SEQ ID NO:79 and SEQ ID NO:80);

hVK3LP-[hCD40 EC K81S]-(g4s)4-[SSShinge-P238S Fc](nucleotide and amino acid sequences as shown in SEQ ID NO:83 and SEQ ID NO:84); and hVK3LP-[hCD40 EC E64Y-K81T-P85Y]-(g4s)4-[SSShinge-P238S Fc](nucleotide and amino acid sequences as shown in SEQ ID NO:87 and SEQ ID NO:88).

The carboxyl end of the human Fc variant in each of the CD40-Fc constructs described above is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed CD40-Fc-PON1 constructs generated are as follows:

hVK3LP-[hCD40 EC]-(g4s)4-[SSShinge-P238S Fc]-NGS-[PON1 Q192K](nucleotide and amino acid sequences as shown in SEQ ID NO:73 and SEQ ID NO:74);

hVK3LP-[hCD40 EC K81T]-(g4s)4-[SSShinge-P238S Fc]-NGS-[PON1 Q192K](nucleotide and amino acid sequences as shown in SEQ ID NO:77 and SEQ ID NO:78);

hVK3LP-[hCD40 EC K81H-L121P]-(g4s)4-[SSShinge-P238S Fc]-NGS-[PON1 Q192K](nucleotide and amino acid sequences as shown in SEQ ID NO:81 and SEQ ID NO:82);

hVK3LP-[hCD40 EC K81S]-(g4s)4-[SSShinge-P238S Fc]-NGS-[PON1 Q192K](nucleotide and amino acid sequences as shown in SEQ ID NO:85 and SEQ ID NO:86); and hVK3LP-[hCD40EC E64Y-K81T-P85Y]-(g4s)4-[SSShinge-P238S Fc]-NGS-[PON1 Q192K] (nucleotide and amino acid sequences as shown in SEQ ID NO:89 and SEQ ID NO:90) (also referred to hereinbelow as CD40TM-Fc-P1-K).

Example 9: Construction of Anti-TNF-α scFv-Fc-PON1 Fusion Proteins

The sequence for Humira™ or the adalimumab antibody targeted to human TNF-α is obtained from the IMGT database INN number 7860, chain numbers INN 7860_H and INN 7860_L. The GenBank Accession numbers for the adalimumab anti-TNF-α antibody sequences are LQ961187 for the heavy chain variable region and LQ961186 for the light chain variable region. See also International PCT Publication No. WO 2014/159579. The sequences are used to design and synthesize an expression cassette encoding an scFv including the heavy and light chain V regions for the adalimumab antibody attached to the human VK3 leader peptide (VK3LP) sequence (nucleotide and amino acid sequences as shown in SEQ ID NO:57 and SEQ ID NO:58). The V region sequences are joined by a (gly4ser)4 linker segment to construct the scFv. The anti-TNF-α scFv is constructed in both the VL-VH and VH-VL orientations. The nucleotide and amino acid sequences for the human VK3LP anti-TNF-α VL-VH scFv are shown in SEQ ID NO:91 and SEQ ID NO:92, and the nucleotide and amino acid sequences for the human VK3LP anti-TNF-α VH-VL scFv are shown in SEQ ID NO:95 and SEQ ID NO:96.

These TNF-α scFv-encoding cassettes are then linked at the carboxyl end of the scFv to the N-terminus of the Fc domain using two heterologous, restriction-site-encoded amino acids (Asp-Leu; residues 816-822 of SEQ ID NO:93 and SEQ ID NO:97 or residues 269-270 of SEQ ID NO:94 and SEQ ID NO:98). The Fc domain encodes a human IgG1 Fc variant with C220S, C226S, C229S, and P238S amino acid substitutions, but wild-type for the remaining residues of the CH2 and CH3 domains (SSS hinge, P238S Fc; nucleotide and amino acid sequences as shown in residues 475-1170 of SEQ ID NO:41 and residues 159-390 of SEQ ID NO:42). The carboxyl end of the human Fc variant in each of the scFv-Fc constructs is fused to a peptide linker containing an N-linked glycosylation site (NGS; nucleotide and amino acid sequences as shown in SEQ ID NO:55 and SEQ ID NO:56) followed by a variant of human PON1

(PON1 Q192K; nucleotide and amino acid sequences as shown in SEQ ID NO:5 and SEQ ID NO:6) in which the first 15 amino acids of the uncleaved leader peptide are deleted. The completed anti-TNF-α scFv-Fc-PON1 constructs generated are as follows:

hVK3LP-[VL-VH anti-TNFalpha scFv]-[SSShinge-P238S-P331S Fc]-NGS-[PON1 Q192K](nucleotide and amino acid sequences as shown in SEQ ID NO:93 and SEQ ID NO:94) (also referred to hereinbelow as Adalimumab scFv-Fc-P1-K); and hVK3LP-[VH-VL anti-TNFalpha scFv]-[SSShinge-P238S-P331S Fc]-NGS-[PON1 Q192K](nucleotide and amino acid sequences as shown in SEQ ID NO:97 and SEQ ID NO:98).

Example 10: Construction of Anti-TGF-β scFv-Fc-PON1 Fusion Proteins

The sequence for humanized fresolimumab antibody (GC1008) targeted to human TGF-β cytokine isoforms is obtained from the IMGT sequence database. The chain ID designations are INN 9158_H and INN 9158_L. The GenBank Accession numbers for the fresolimumab anti-TGF-β antibody sequences are JC 232803.1 for the heavy chain and JC for the light chain. The sequences for the antibody are also listed in U.S. Pat. No. 7,723,486 and International PCT Publication No. WO 2013/065869. The sequences are used to design and synthesize an expression cassette encoding an scFv including the heavy and light chain V regions for the GC1008/fresolimumab antibody attached to the human VK3 leader peptide (VK3LP) sequence (nucleotide and amino acid sequences as shown in SEQ ID NO:57 and SEQ ID NO:58). The V region sequences are joined by a (gly4ser)4 linker segment to construct the scFv. The anti-TGF-β scFv is constructed in both the VL-VH and VH-VL orientations. The nucleotide and amino acid sequences for the human VK3LP anti-TGF-β VH-VL scFv are shown in SEQ ID NO:99 and SEQ ID NO:100, and the nucleotide and amino acid sequences for the human VK3LP anti-TGF-β VL-VH scFv are shown in SEQ ID NO:103 and SEQ ID NO:104.

These TGF-β scFv-encoding cassettes are then fused at the carboxyl end of the scFv to the N-terminus of the Fc domain using two heterologous, restriction-site-encoded amino acids (Asp-Leu; residues 819-825 of SEQ ID NO:101 and SEQ ID NO:105 or residues 270-271 of SEQ ID NO:102 and SEQ ID NO:106). The Fc domain encodes a human IgG1 Fc variant with C220S, C226S, C229S, and P238S amino acid substitutions, but wild-type for the remaining residues of the CH2 and CH3 domains (SSS hinge, P238S Fc; nucleotide and amino acid sequences as shown in residues 475-1170 of SEQ ID NO:41 and residues 159-390 of SEQ ID NO:42). The carboxyl end of the human Fc variant in each of the scFc-Fc constructs is fused to a peptide linker containing an N-linked glycosylation site (NGS; nucleotide and amino acid sequences as shown in SEQ ID NO:55 and SEQ ID NO:56) followed by a variant of human PON1 (PON1 Q192K; nucleotide and amino acid sequences as shown in SEQ ID NO:5 and SEQ ID NO:6) in which the first 15 amino acids of the uncleaved leader peptide are deleted. The completed anti-TGF-β scFv-Fc-PON1 constructs generated are as follows:

hVK3LP-[anti-hTGFbeta VH-VL scFv]-SSShinge-P238S-P331S Fc]-NGS-PON1 Q192K](nucleotide and amino acid sequences as shown in SEQ ID NO:101 and SEQ ID NO:102); and hVK3LP-[anti-hTGFbeta VL-VH scFv]-SSShinge-P238S-P331S Fc]-NGS-PON1 Q192K](nucleotide and amino acid sequences as shown in SEQ ID NO:105 and SEQ ID NO:106).

Example 11: Construction of DNase1 L3-Fc and DNase1L3-Fc-PON1 Fusion Proteins

Constructs were designed and synthesized and cassettes with the correct sequences are combined to generate two synthetic fusion genes encoding unique DNase1 L3 fusion molecules. Each construct includes a variant of wild-type human DNase1 L3 (nucleotide and encoded amino acid sequences as shown in SEQ ID NOs:135 and 136). Each DNase1 L3 sequence is modified to remove amino acid residues 291-305 of the wild-type sequence, corresponding to the C-terminal nuclear localization signal (NLS2). Each DNase1 L3 variant also contains amino acid substitutions, relative to the wild-type human sequence (SEQ ID NO:136), at positions R80, R95, and N96 (either all three positions changed to alanine or all three changed to serine) to inactivate a nuclear localization signal (NLS1) located in the N-terminal half of the molecule. The nucleotide and encoded amino acid sequences corresponding to the mature DNase1 L3 variant containing the R80A/R95A/N96A mutations are shown in residues 61-870 of SEQ ID NO:137 and residues 21-290 of SEQ ID NO:138, respectively; the nucleotide and encoded amino acid sequences corresponding to the mature DNase1L3 variant containing the R80S/R95S/N96S mutations are shown in residues 61-870 of SEQ ID NO:139 and residues 21-290 of SEQ ID NO:140, respectively. The signal peptide sequence utilized was the human VK3 leader peptide (nucleotide and amino acid sequences as shown in SEQ ID NO:57 and SEQ ID NO:58). The DNase1 cassette was fused to the N-terminus of a human IgG1 Fc variant (SSS hinge, P238S, P331S) using a (Gly$_4$Ser)$_4$ peptide linker ((g4s)4; nucleotide and amino acid sequences as shown in SEQ ID NO:11 and SEQ ID NO:12). The Fc variant nucleotide and amino acid sequences are shown in SEQ ID NO:27 and SEQ ID NO:28. The completed DNase1 L3-Fc constructs generated are as follows:

hVK3LP-[hDNase1 L3 R80A-R95A-N96A NLS2delta]-(g4s)4-[SSShinge-P238S-P331S Fc](nucleotide and amino acid sequences as shown in SEQ ID NO:137 and SEQ ID NO:138); and hVK3LP-[hDNase1L3 R80S-R95S-N96S NLS2delta]-(g4s)4-[SSShinge-P238S-P331S Fc](nucleotide and amino acid sequences as shown in SEQ ID NO:139 and SEQ ID NO:140).

Bispecific constructs further comprising a functional PON1 enzyme are also generated by fusing the carboxyl end of each variant DNase1 L3-Fc sequence above to a peptide linker containing an N-linked glycosylation site (NGS; nucleotide and amino acid sequences as shown in SEQ ID NO:55 and SEQ ID NO:56) followed by a variant of human PON](PON1 Q192K; nucleotide and amino acid sequences as shown in SEQ ID NO:5 and SEQ ID NO:6) in which the first 15 amino acids of the uncleaved leader peptide are deleted. The completed DNase1 L3-Fc-PON1 constructs are as follows:

hVK3LP-[hDNase1L3 R80A-R95A-N96A NLS2delta]-(g4s)4-[SSShinge-P238S-P331S Fc]-NGS-[PON1 Q192K](nucleotide and amino acid sequences as shown in SEQ ID NO:161 and SEQ ID NO:162); and hVK3LP-[hDNase1L3 R80S-R95S-N96S NLS2delta]-(g4s)4-[SSShinge-P238S-P331S Fc]-NGS-[PON1 Q192K](nucleotide and amino acid sequences as shown in SEQ ID NO:163 and SEQ ID NO:164) (also referred to hereinbelow as DNase1 L3-Fc-P1-K).

Example 12: Construction and Expression of Bispecific and Monospecific PON1 Fusion Proteins Various Fc fusion genes as described in Examples 1, 5, 7-9, and 11 were assembled in a pUC based vector, and assembled genes screened by DNA sequencing prior to further manipulations. Assembled genes included both a monospecific (T-L1-Fc) and a bispecific PON1 (T-L1-Fc-L2-PON1) form for each of the DNase1, SOD1, CTLA-4, CD40, anti-TNFα scFv, and DNase1 L3 "T" region fusion partners. The assembled PON1 fusion constructs included the following: DNase™-(g4s)6-Fc-P1-K, SOD1-Fc-P1-K, CTLA4-Fc-P1-K, CD40TM-Fc-P1-K, Adalimumab scFv-Fc-P1-K, and DNase1 L3-Fc-P1-K. In addition, a monospecific Fc-PON1 fusion construct was assembled (nucleotide and amino acid sequences as shown in SEQ ID NO:121 and SEQ ID NO:122; also referred to hereinbelow as Fc-PON1-K or Fc-P1-K). Also assembled were two ApoA1-Fc-PON1 fusions: THER4-P1-K (nucleotide and amino acid sequences shown in SEQ ID NO:45 and SEQ ID NO:46 of PCT Publication No. WO 2017/044424) and THER6-P1-K (identical to THER4-P1-K but with six repeats of (Gly$_4$Ser) in the linker sequence instead of four (Gly$_4$Ser) repeats). Fusion gene cassettes containing the desired sequences were then inserted into a multiple cloning site of the mammalian expression vector pDG, a pcDNA3 plasmid derivative containing a CMV promoter to drive expression of the fusion gene. Plasmid DNA was prepared using QIAGEN (Germantown, MD) mini or maxiprep plasmid DNA kits. Purified plasmid DNA was transfected into HEK293 cells plated at approximately 50-75% confluence, using Polyfect (QIAGEN, Germantown, MD) transfection reagent according to the manufacturer's instructions. Culture media was changed to DMEM Fluorobrite™ (Life Technologies, Carlsbad, CA) serum free media on the day after transfections, and transfected cells incubated for an additional 48 hours prior to harvest of culture supernatants. Culture supernatants were filtered through 0.2 μm PES syringe filters prior to analysis.

Figure 8:
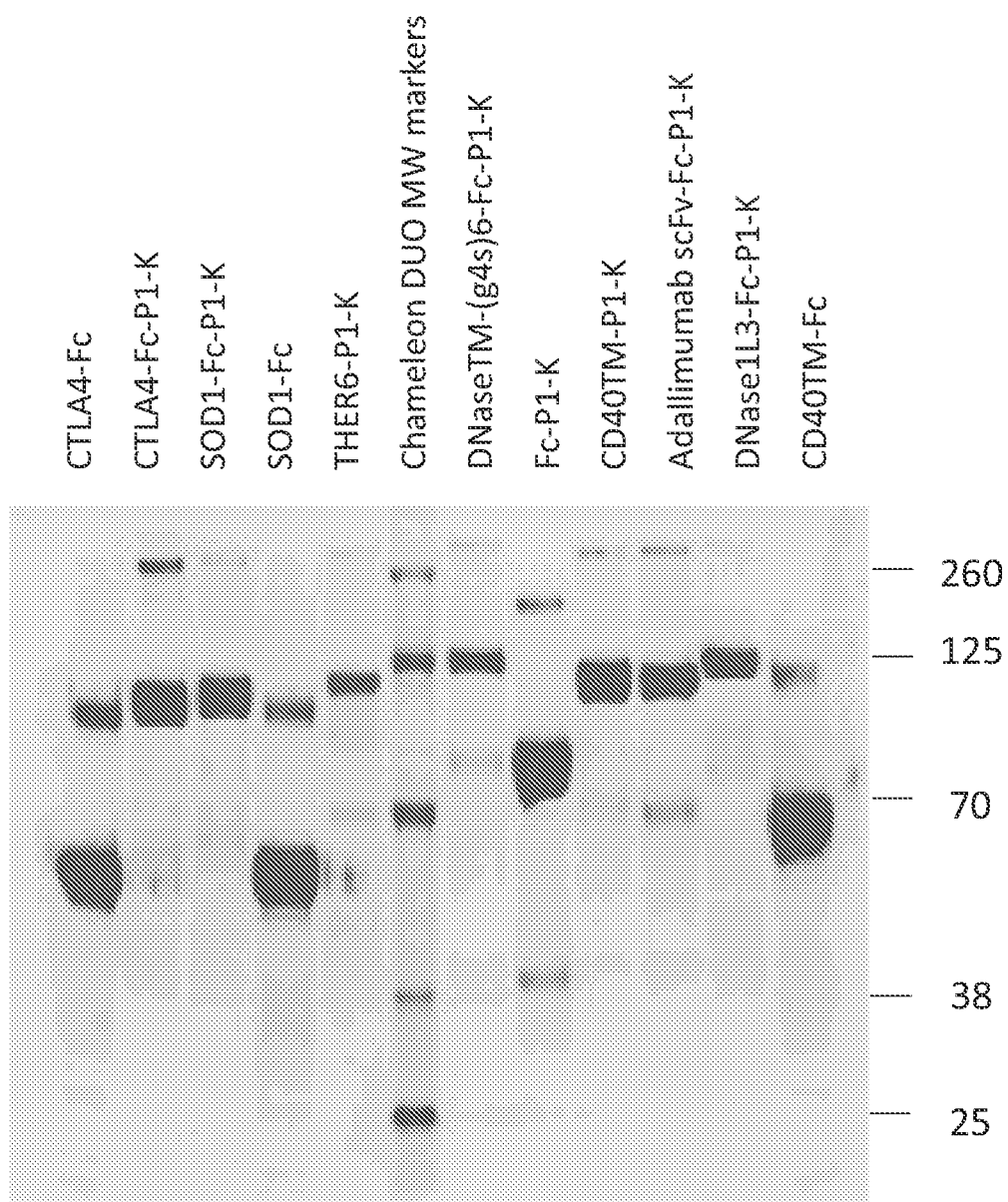
FIGS. 8 and 9 show Western blot analysis of PON1 fusion proteins immunoprecipitated from HEK293 transfection supernatants. Transfections, Protein A immunoprecipitation, and Western blot analysis were performed as described in Example 12, infra.
Figure 9:
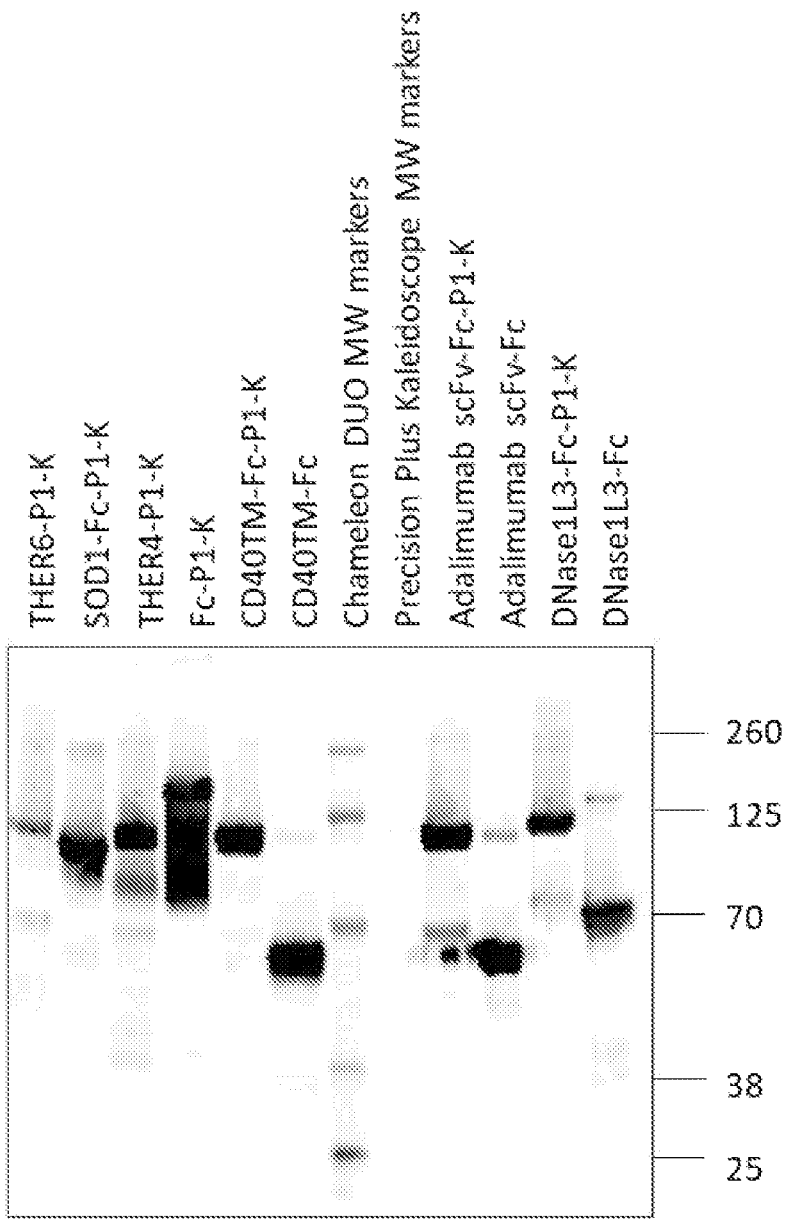

FIG. 8 and FIG. 9 show the results of Western blot analysis of fusion protein expression from a representative set of HEK293 transient transfections. Culture supernatants were immunoprecipitated with 60 μl protein A agarose (Repligen, Waltham MA) washed in gentle antigen-antibody binding buffer pH 8.0, (Pierce/Life Technologies, Carlsbad, CA) and 0.5 ml 293 transfection supernatants in Fluorobrite DMEM added to each microfuge tube. Immunoprecipitates were rotated overnight at 4° C., centrifuged at 3000 rpm, and washed in Binding Buffer pH 8.0, prior to addition of 60 μl 2×LDS sample buffer (Life Technologies, Carlsbad, CA), samples heated for 10 minutes at 72° C., the samples centrifuged for 1 minute at 3000 rpm in a microfuge, and 15 μl sample in loading buffer (one fourth) from each sample was loaded onto 4-12% Bis-Tris NuPAGE gels (Life Technologies, Carlsbad, CA). Protein molecular weight markers were included on each gel (Chameleon® DUO molecular weight markers; L1-COR Biosciences, Lincoln, NE and/or Precision Plus Kaleidoscope MW markers; BIORAD, Hercules, CA). SDS-PAGE gels were run in NuPAGE MOPS running buffer (Life Technologies, Carlsbad, CA) under reducing conditions at 185 volts for approximately 1-1.5 hours. Gels were blotted to nitrocellulose membranes using the XCell blot module (Life Technologies, Carlsbad, CA) and NUPAGE-MOPS (Life Technologies, Carlsbad, CA) transfer buffer containing 10% methanol. Blots were blocked in L1-COR Odyssey Intercept™ blocking buffer, followed by incubation with diluted goat anti-human IgG (Fc specific) secondary antibodies (Jackson Immunoresearch, West Grove, PA). Secondary antibody was conjugated with Alexafluor 790 near IR dye (L1-COR Odyssey detection) and diluted in blocking buffer 1:35,000 at 4° C. and rocked overnight. Blots were washed four times with Tris buffered saline (TBS) containing 0.1% Tween 20. Blots were then rinsed in TBS buffer and scanned with a LICOR Odyssey™ scanner. For the Western Blot shown in FIG. 8, transfection samples were loaded as follows: Lane 1-CTLA4-Fc, Lane 2-CTLA4-Fc-P1-K, Lane 3-SOD1-Fc-P1-K, Lane 4-SOD1-Fc, Lane 5—THER6-P1-K, Lane 6—LICOR Chameleon DUO MW Markers, Lane 7—DNase™-(g4s)6-Fc-P1-K, Lane 8-Fc-P1-K, Lane 9—CD40TM-Fc-P1-K; Lane 10—Adalimumab scFv-Fc-P1-K, Lane 11-DNase1 L3-Fc-P1-K, Lane 12—CD40TM-Fc. The approximate molecular weight (kDa) of each marker band is indicated on the right side of the Western blot. For the Western Blot shown in FIG. 9, transfection samples were loaded as follows: Lane 1—THER6-P1-K, Lane 2—SOD1-Fc-P1-K, Lane 3—THER4-P1-K, Lane 4—Fc-P1-K, Lane 5—CD40TM-Fc-P1-K; Lane 6—CD40TM-Fc, Lane 7-LICOR Chameleon DUO MW Markers, Lane 8—BIORAD Precision Plus Kaleidoscope MW markers, Lane 9—Adalimumab scFv-Fc-P1-K, Lane 10—Adalimumab scFv-Fe, Lane 11—DNase1L3-Fc-P1-K, Lane 12—DNase1 L3-Fc. The approximate molecular weight (kDa) of each marker band is indicated on the right side of the Western blot.

Figure 10:
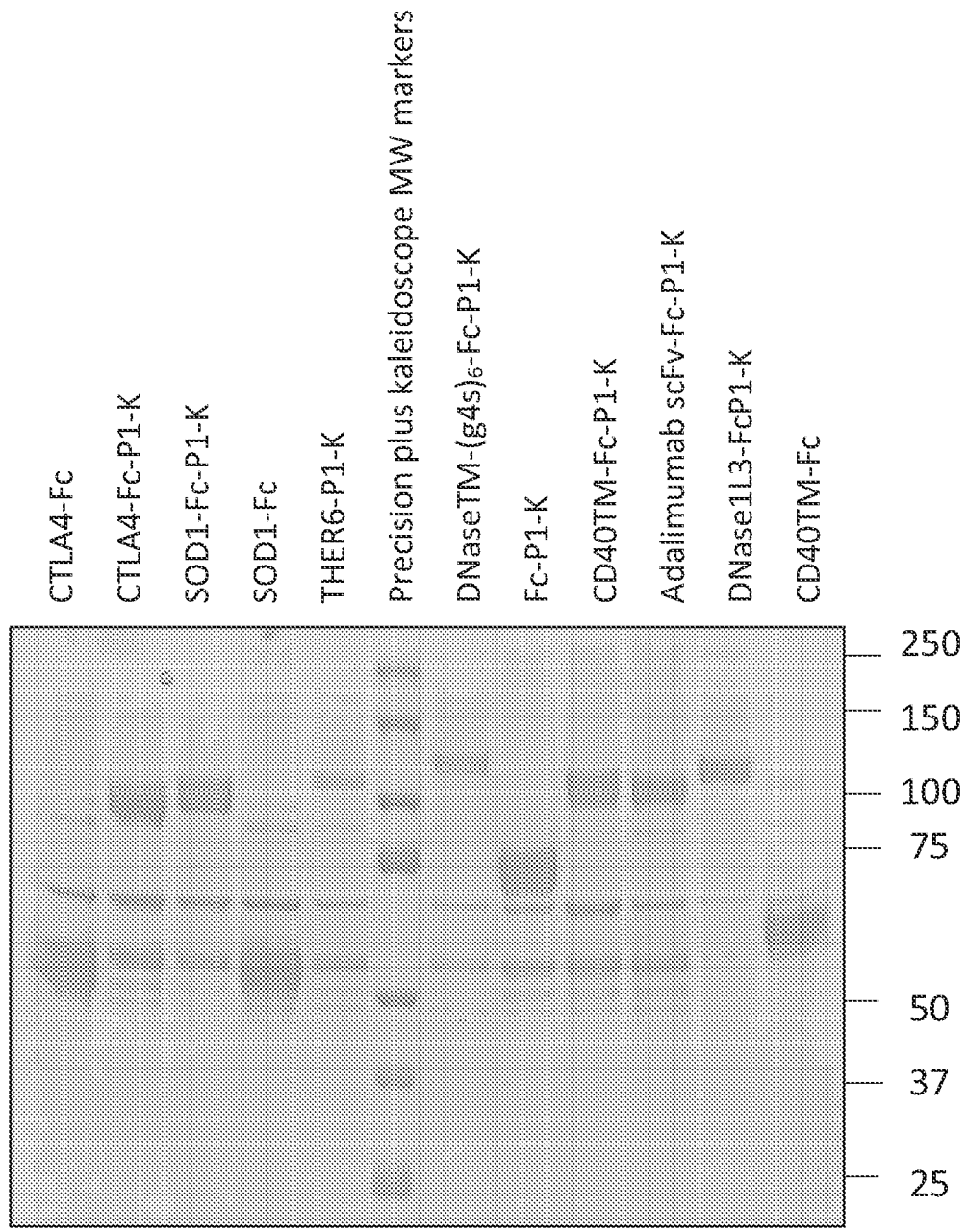
FIG. 10 shows reducing SDS-PAGE analysis of PON1 fusion proteins immunoprecipitated from HEK293 transfection supernatants. Transfections, Protein A immunoprecipitation, and SDS-PAGE were performed as described in Example 12, infra.

FIG. 10 shows the results of SDS-PAGE analysis of immunoprecipitated protein from HEK293 transfection supernatants. Culture supernatants were immunoprecipitated with 60 μl protein A agarose (Repligen, Waltham, MA), washed in gentle antigen-antibody binding buffer pH 8.0, (Pierce/Life Technologies, Carlsbad, CA) and 0.5 ml 293 transfection supernatants in Fluorobrite DMEM (ThermoFisher Scientific, Waltham, MA) added to each microfuge tube. Immunoprecipitates were rotated overnight at 4° C., centrifuged at 3000 rpm, and washed in Binding Buffer pH 8.0, prior to addition of 60 μl 2×LDS sample buffer (Life Technologies, Carlsbad, CA), samples heated for 10 minutes at 72° C., the samples centrifuged for 1 minute at 3000 rpm in a microfuge, and 15 μl sample in loading buffer (one fourth) from each sample was loaded onto 4-12% Bis-Tris NuPAGE gels (Life Technologies, Carlsbad, CA). SDS-PAGE gels were run in NuPAGE MOPS running buffer (Life Technologies, Carlsbad, CA) under reducing conditions at 185 volts for approximately 1-1.5 hours. After electrophoresis, gels were washed in distilled water several times, then incubated for 2 hours in Imperial Protein Stain (Pierce/ThermoFisher Scientific, Waltham MA). Gels were destained by washing several times in distilled water to remove nonspecific stain. Gels were then scanned using a Canon PIXMA MG8220 scanner to visualize the bands. Lanes were loaded as follows: Lane 1—CTLA4-Fc, Lane 2—CTLA4-Fc-P1-K, Lane 3—SOD1-Fc-P1-K, Lane 4—SOD1-Fc, Lane 5—THER6-P1-K, Lane 6—BIORAD Precision Plus Kaleidoscope molecular weight markers, Lane 7—DNase™-(g4s)6-Fc-P1-K, Lane 8—Fc-P1-K, Lane 9—CD40TM-Fc-P1-K; Lane 10—Adalimumab scFv-Fc-P1-K, Lane 11—DNase1 L3-Fc-P1-K, Lane 12—CD40TM-Fc. The approximate molecular weight (kDa) of each marker band is indicated on the right side of the gel image.

Example 13: In Vitro Assessment of PON1 Fusion Proteins for Functional Activity Functional activity of the PON1 fusion proteins was assessed with a series of in vitro assays. For several of the assays, protein activity was often analyzed directly from culture supernatants of transiently transfected HEK 293 cells. For other in vitro assays, fusion proteins were first purified from culture supernatants (either HEK 293 or CHO DG44 transfected cells) prior to assessment of functional activity. Fusion proteins were purified from culture supernatants by protein A affinity chromatography. Culture supernatants were filtered through 0.2 µm PES express filters (Nalgene, Rochester, NY) and subjected to affinity chromatography using slow rotation of culture supernatants with Protein A-agarose (IPA 300 crosslinked agarose) slurry in 50 ml sterile, conical centrifuge tubes at 4° C. (Repligen, Waltham, MA). Fusion protein bound to protein A agarose was recovered by centrifugation, and culture supernatants removed, replaced, and the incubation process repeated until the desired volume of supernatant was processed. The final protein A agarose slurry was then loaded into sterile, acid-washed econocolumns (BioRad, Hercules, CA) to wash the resin. Columns were then washed with several column volumes of column wash buffer (Gentle Ag-Ab binding buffer, Pierce/ThermoFisher, Waltham, MA) to remove any residual culture supernatant, prior to elution. Bound protein was then eluted from the resin using gentle Ag/Ab elution buffer (Pierce/ThermoFisher, Waltham, MA). Fractions (0.8-1.0 ml) were collected and protein concentration of aliquots (2 µl) from each fraction were determined at 280 nM using a Nanodrop (Wilmington DE) microsample spectrophotometer, with blank determination using elution buffer alone. Fractions containing fusion protein were pooled, and buffer exchange was performed by dialysis using Spectrum Laboratories G2 (Ranch Dominguez, CA, Catalog #G235057, Fisher Scientific catalog #08-607-007) float-a-lyzer units (MWCO 20 kDa) against [0.9% sodium chloride, 5 mM sodium bicarbonate, 1 mM HEPES buffer, 1 mM calcium chloride, pH 7.5]. Dialysis was performed in sterile, 2.2-liter Corning roller bottles at 4° C. overnight. After dialysis, protein was filtered using 0.2 µM filter units, and aliquots tested for endotoxin contamination using Pyrotell LAL gel clot system single test vials (STV) (Catalog #G2006, Associates of Cape Cod, East Falmouth, MA).

Figure 11:
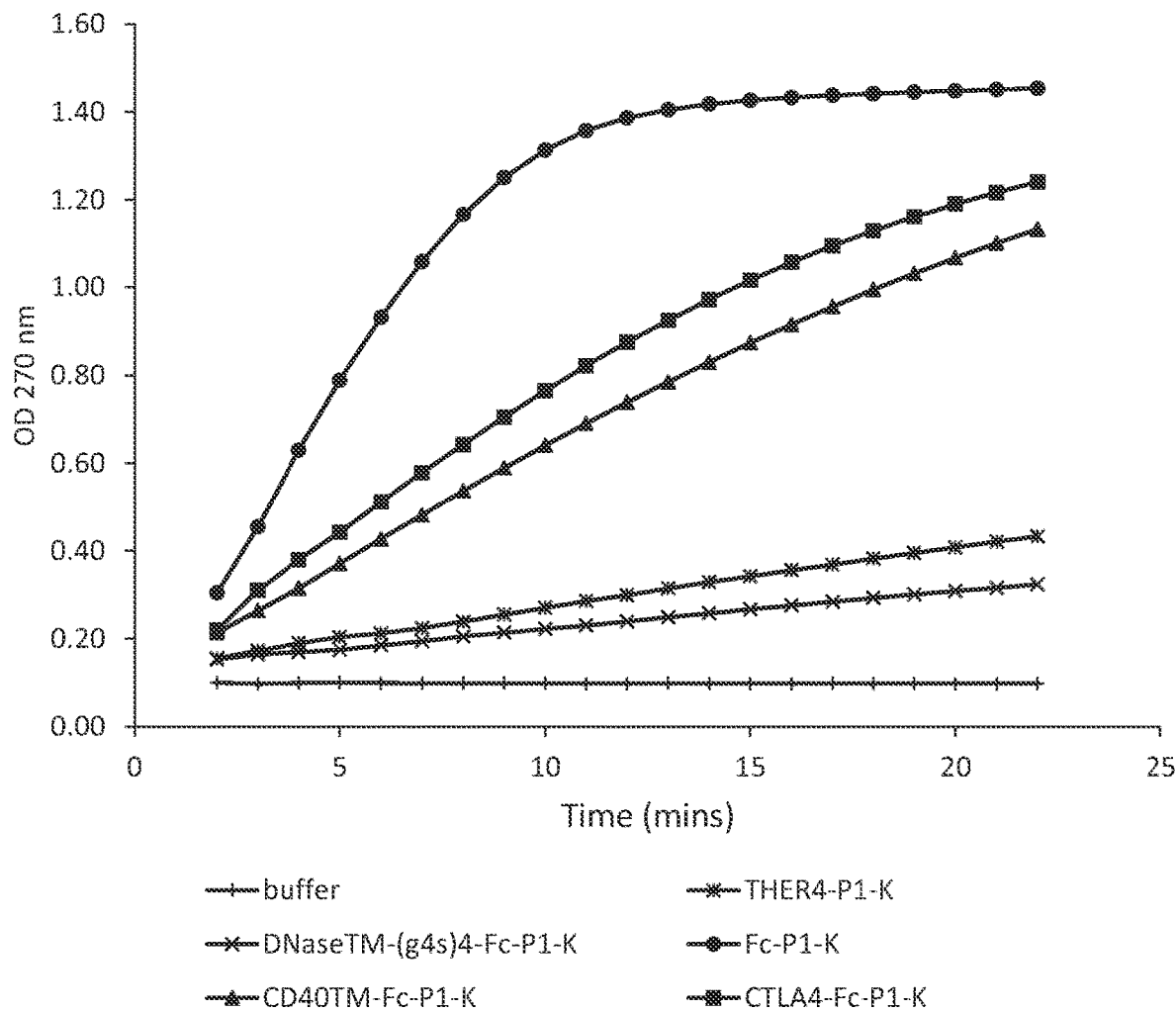
FIGS. 11-13 show arylesterase activity (FIG. 11), organophosphatase activity (FIG. 12), and lactonase activity (FIG. 13) of PON1 fusion proteins assayed directly from HEK293 culture supernatants (see Example 13, infra).

FIG. 11 shows the results from a representative assay of the PON1 arylesterase activity directly from HEK 293 culture supernatants. For this assay, culture supernatants were harvested in Fluorobrite DMEM (serum free) 72 hours after transfection, and sterile filtered with 0.2 µm syringe filters prior to use. Supernatants were diluted with reaction buffer for the assay to two times the final desired dilution. Diluted supernatants were aliquoted to individual wells of a UV transparent, 96 well flat bottom microtiter plate (ThermoFisher Scientific, Waltham, MA). Reactions were performed at 25° C. Just prior to measurement, appropriate dilutions of the arylesterase substrate phenyl acetate were added to each well with a multichannel pipettor. For the data shown in the graph, culture supernatants were diluted 1:8 and 50 µl added to each well. The substrate was then added in 50 µl/well to begin the assay. For most assays, 6-10 mM phenyl acetate was used, so that the final concentration of substrate was 3-5 mM. To monitor conversion of phenyl acetate to phenol, the absorbance change at 270 nm was monitored in a kinetic assay, with readings taken every seconds for 22.5 minutes (30 measurements/well). The absorbance at each time point was then plotted as a function of time.

Figure 12:
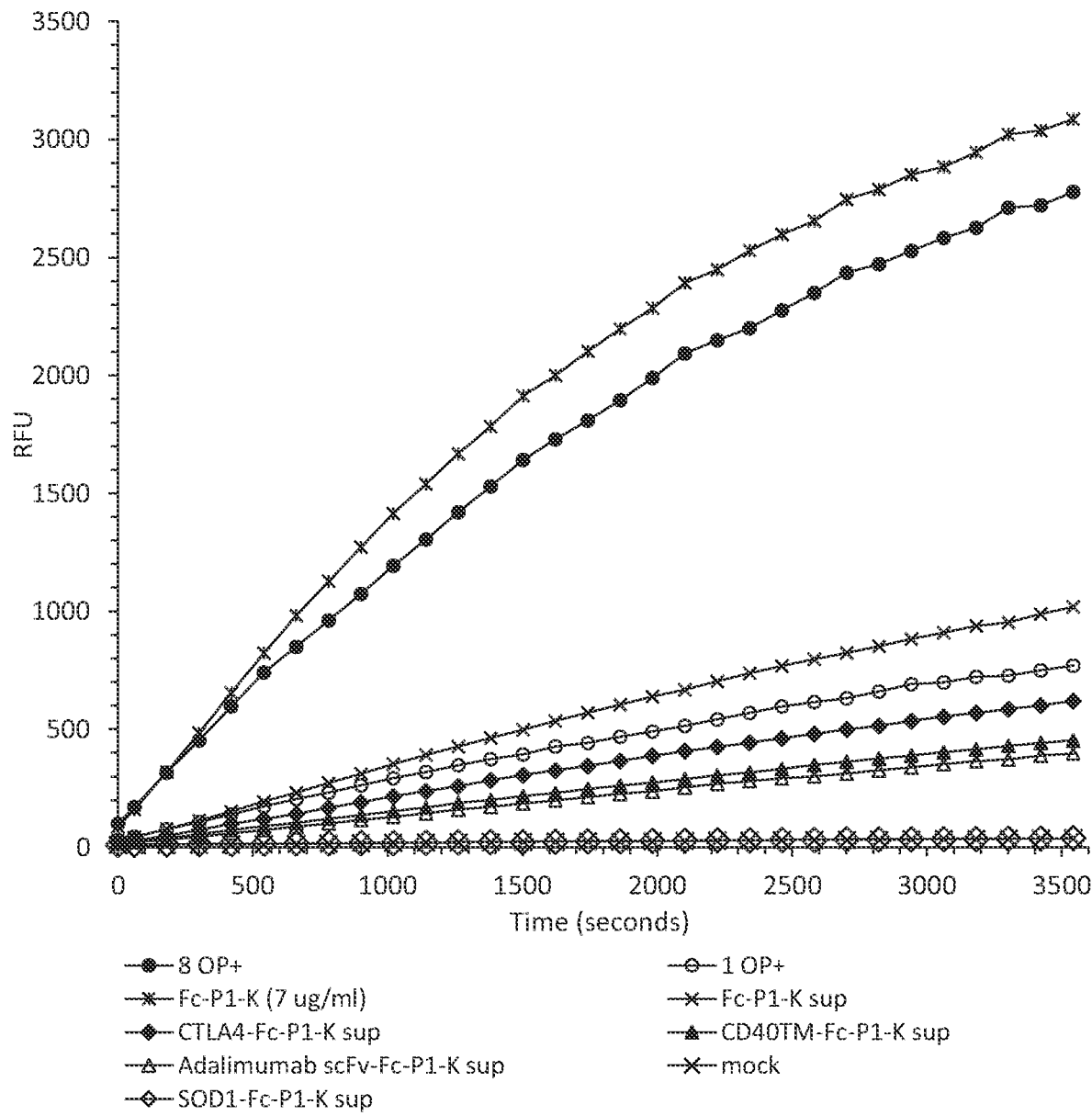

FIG. 12 shows a similar assessment measuring organophosphatase activity of the PON1 moiety in bispecific and monospecific PON1 fusion proteins. In these assays, the substrate used was a proprietary organophosphatase substrate contained in the EnzCHEK paraoxonase assay kit (Molecular Probes/ThermoFisher Scientific, Waltham, MA). This assay is a very sensitive fluorometric assay for the organophosphatase activity of paraoxonase that uses excitation/emission maxima of 360/450 nm to measure the conversion of a fluorogenic organophosphate analog provided with the kit. The assay can either be set up as a kinetic assay or terminated after a particular period of time for an endpoint assay. The change in relative fluorescence units (RFU) per unit time is converted to the units of paraoxonase in the sample using the standard curve generated from the fluorescent standard and the conversion factor that 1 U unit of paraoxonase generates 1 nmol of fluorescent product per minute at 37° C. The amount of paraoxonase present in the fusion protein samples can be compared to the paraoxonase positive control provided with the kit. FIG. 12 shows a graphical representation of the organophosphatase activity present in serial dilutions of culture supernatant from several of the SOD1-Fc-P1-K, CTLA4-Fc-P1-K, and CD40TM-Fc-P1-K fusion proteins expressed in HEK 293 transient transfections and from a purified batch of the Fc-PON1-K (Fc-P1-K) fusion protein. The organophosphatase activity is compared to the RFU curves generated by two different dilutions of the organophosphatase positive control in the average to above average activity range for human serum sample comparisons. Fc-PON1-K purified fusion protein showed high activity in this assay, and calculations relative to the fluorescent standard curve indicate that the PON1 organophosphatase activity is 700 mU/µg, or 40 U/umole, Fc-P1-K. Culture supernatants from HEK293 transfections were also included in the assay. Although they are not shown on the graph, the supernatant from the Adalimumab scFv-Fc-P1-K transfections mirrored the activity profile observed for the CD40TM-Fc-P1-K transfection. Similarly, the supernatant from the DNase1L3-Fc-P1-K transfection mirrored the negligible activity level observed for the SOD1-Fc-P1-K transfection shown on the graph.

Figure 13:
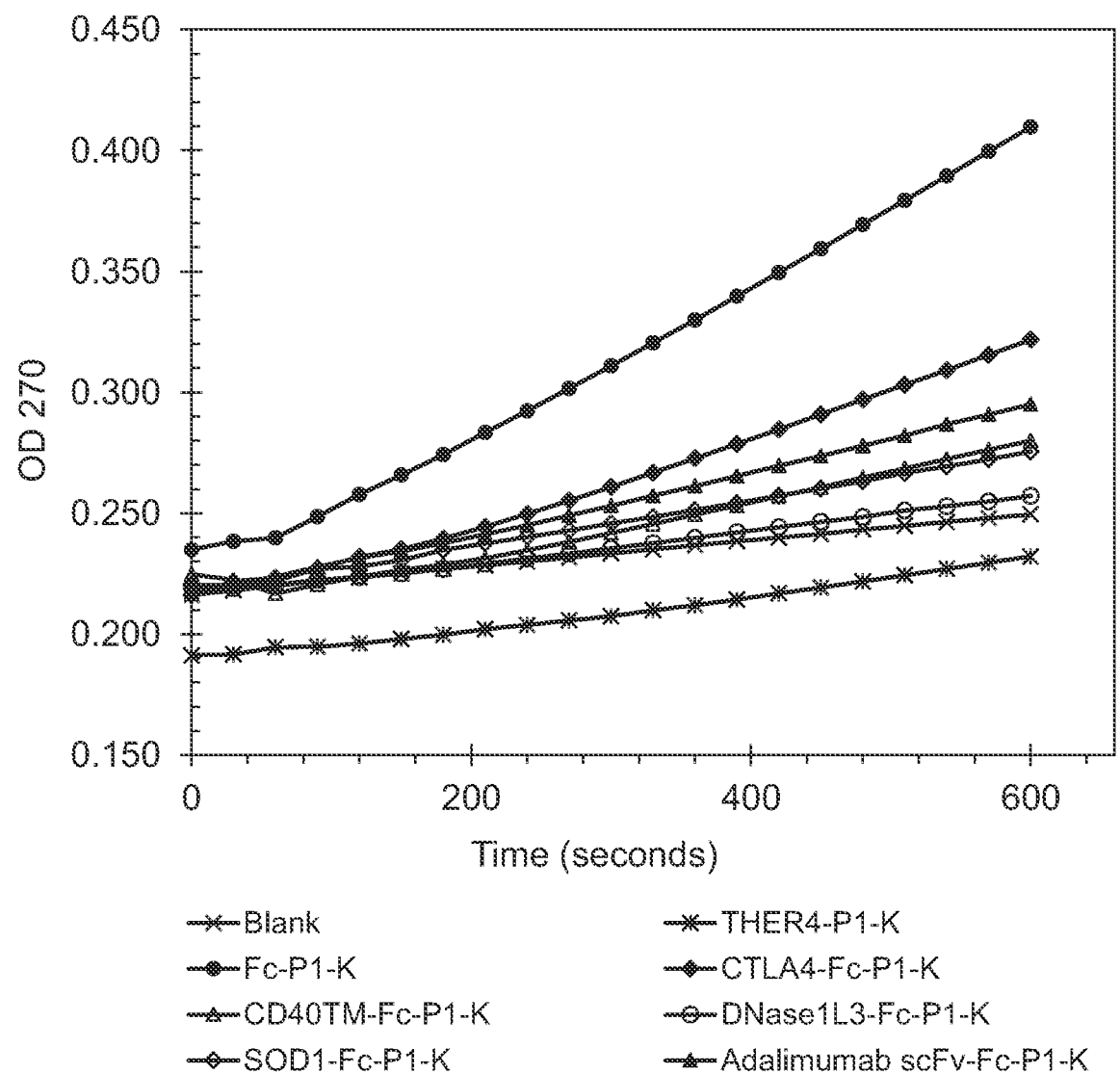

FIG. 13 shows results of an assay measuring lactonase activity of the PON1 moiety in bispecific and monospecific PON1 fusion proteins. In these assays, the substrate used was dihydrocoumarin (DHC) (Millipore-Sigma, St. Louis, MO) at a final concentration of 1 mM in 1× reaction buffer. Reaction buffer for the DHC assays was 50 mM Tris HCl (pH 7.4), 1 mM $CaCl_2$). HEK293 culture supernatants were diluted 1:4 in reaction buffer and 25 µl added to individual wells of a 96 well UV STAR (Greiner BioOne, Thomas Scientific) microtiter plate. Substrate dihydrocoumarin (DHC) solution in reaction buffer was added to each well (75 µl) to generate a final volume of 100 µl. Hydrolysis of the substrate was monitored at OD 270 for 15 minutes. Hydrolysis of DHC by the fusion proteins was monitored as the change in OD270 as a function of time.

Figure 14:
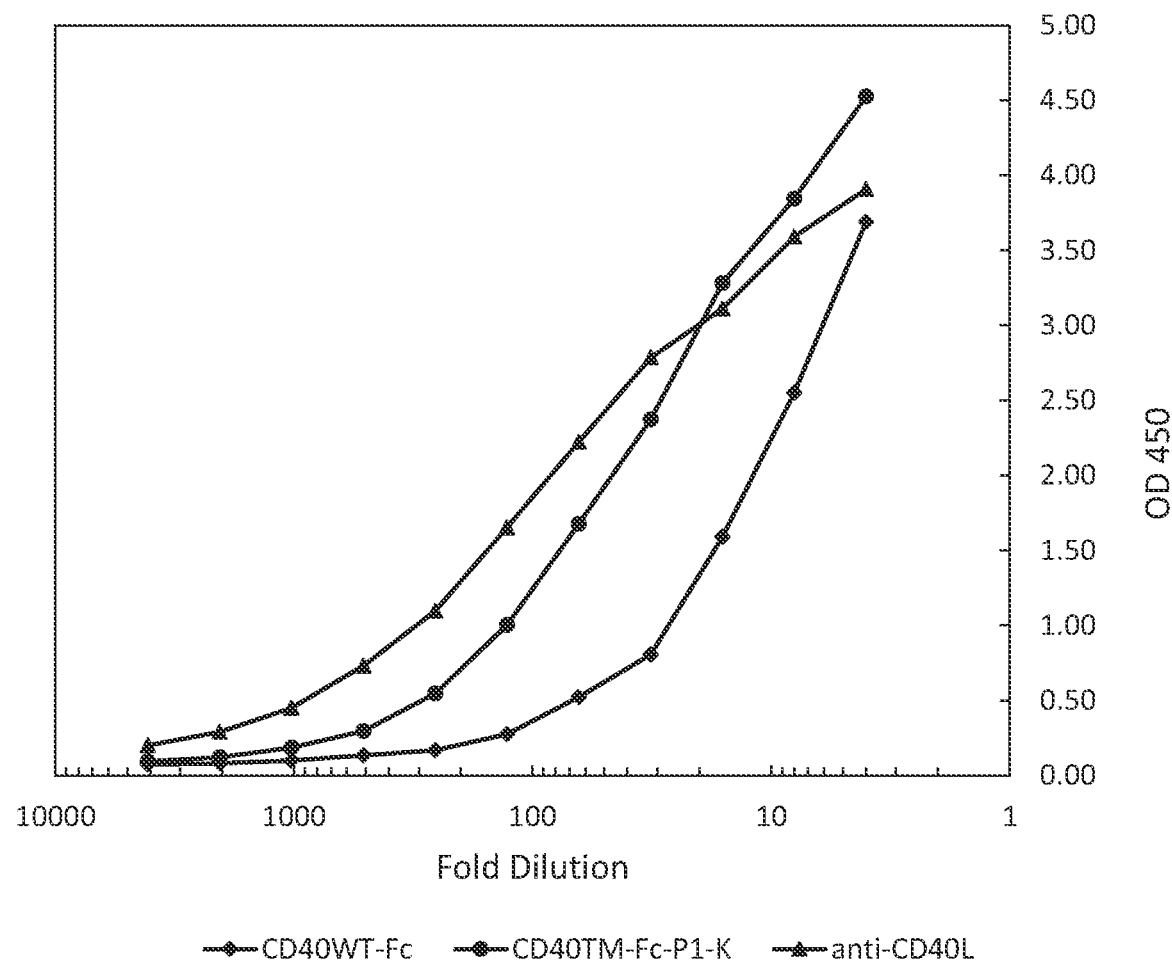
FIG. 14 shows high affinity binding of immobilized CD40 ligand to CD40-Fc-PON1 fusion protein present in HEK293 transfection supernatant (see Example 14, infra).

In addition to the paraoxonase enzyme activity, the functional properties of the different "T" domains positioned at the amino terminus of the T-L1-X-L2-P fusion proteins were also assessed. Depending on the identity of the "T" domain, binding to a target antigen or enzyme activity was monitored. FIG. 14 shows the results of an antigen binding assay to CD40 ligand for the human CD40 receptor extracellular domain triple mutant in the CD40TM-Fc-P1-K fusion proteins. The antigen binding ELISA assay was performed as follows: Human CD40 ligand was obtained from BioLegend (San Diego, CA). The human CD40 ligand was diluted in 0.1 M carbonate buffer (pH 9.0) to a concentration of 2 µg/ml and 100 µl/well aliquoted to each well to be used in the assay in a 96 well NUNC immulon II MaxiSorp plate (ThermoFisher Scientific, Waltham, MA). Plates were incubated overnight at 4° C., prior to blocking in 200 µl/well PBS/ 2.0% BSA, overnight at 4° C. Plates were washed in wash buffer (PBS, 0.5% Tween-20, 0.005% Kathon), and serial dilutions of the HEK 293 transfection supernatants added to wells of the plate. As a positive control for antigen binding, a mouse antibody targeted to the CD40 ligand was also serially diluted on the plate Plates were incubated with supernatant or antibody dilutions at 4° C., overnight. Plates were washed four times in wash buffer, then incubated with horseradish peroxidase conjugated goat anti-human IgG Fc specific, or goat anti-mouse IgG1 at a dilution of 1:10,000 (Jackson Immunoresearch, West Grove, PA). FIG. 14 shows the CD40 ligand binding curves for the CD40WT-Fc, the CD40TM-Fc-P1-K transfection supernatants, and the CD40L specific antibody dilutions by plotting the absorbance at 450 nm as a function of dilution. The CD40 mutant form shows improved binding activity to CD40 ligand when compared to the wild type CD40Fc containing supernatants.

Figure 15:
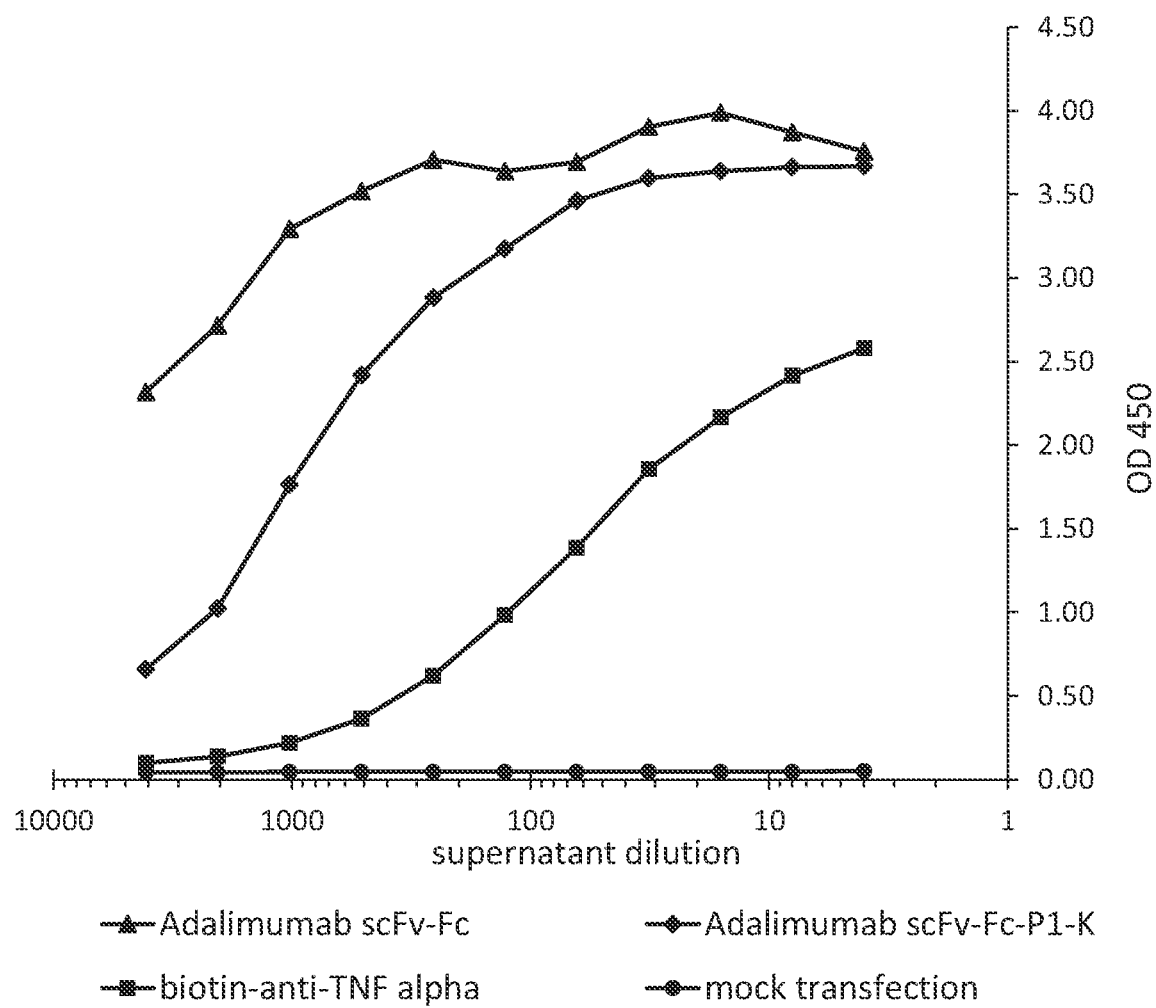
FIG. 15 shows high affinity binding of immobilized TNFα to anti-TNF-α scFv-Fc-PON1 fusion protein present in HEK293 transfection supernatant (see Example 14, infra).

FIG. 15 shows binding data for the Humira™ (adalimumab) scFv containing fusion protein supernatants to TNF-alpha (TNF-α) in an antigen binding ELISA with immobilized TNF-α. The antigen binding ELISA assay was performed as follows: Human TNF-α was obtained from BioLegend (San Diego, CA). The TNF-α protein was diluted in 0.1 M carbonate buffer (pH 9.0) to a concentration of 1 µg/ml and 100 µl/well aliquoted to each well to be used in the assay in a 96 well NUNC immulon II MaxiSorp plate (ThermoFisher Scientific, Waltham, MA). Plates were incubated overnight at 4° C., prior to blocking in 200 µl/well blocking buffer (PBS/2.0% BSA), overnight at 4° C. Plates were washed in wash buffer (PBS, 0.5% Tween-20, 0.005% Kathon), and serial dilutions of either the HEK293 transfection supernatants or mouse anti-human TNF antibody (BioLegend, San Diego, CA) added to wells of the plate. Plates were incubated with supernatant or antibody dilutions at 4° C., overnight. Plates were washed four times in wash buffer, then incubated with horseradish peroxidase conjugated goat anti-human IgG Fc specific, or goat anti-mouse IgG1 at a dilution of 1:10,000 (Jackson Immunoresearch, West Grove, PA). FIG. 15 shows the TNF-α binding curves for the adalimumab scFv-Fc transfection supernatant, the adalimumab scFv-Fc-P1-K transfection supernatant, or the TNF-α specific antibody, in which the absorbance at 450 nm was plotted as a function of dilution. The adalimumab scFv-containing fusion proteins expressed in HEK293 transient transfections bind to human TNF-α immobilized on the plate(s).

Example 15: Treatment of Lung Fibrosis by Administration of PON1 Fusion Proteins Effects of different PON1 fusion proteins on lung fibrosis are assessed using in vivo mouse models of disease. One such model involves in vivo assessment of the efficacy of the purified fusion proteins for treatment of pulmonary fibrosis in a bleomycin induced lung fibrosis mouse model. Bleomycin (BLM)-induced pulmonary fibrosis is the most well-established disease model for IPF and is widely used to investigate the efficacy and mechanism of therapeutic candidates. In the model, alveolar injury and interstitial inflammation/fibrosis are induced by intratracheal BLM administration. The aim of this study is to examine the effect of PON1 fusion test compounds on lung inflammation and fibrosis in BLM-induced pulmonary fibrosis model and compare responses to a control preparation of nintedanib. At day 0, mice are induced to develop pulmonary fibrosis by a single intratracheal administration of bleomycin hydrochloride in saline at a dose of 3.0 mg/kg, in a volume of 50 Id per animal using Microsprayer. Mice are divided into groups of 12 mice based on the body weight changes on the day before the start of treatments with the test compounds on day 7. Mice are intranasally/intravenously/intraperitoneally administered test compounds (depending on the test group). Compounds are administered daily from Day 7 to 20, animals sacrificed on Day 21 and samples analyzed for fibrotic markers.

At study termination, whole blood samples without anticoagulant are obtained via abdominal vena cava under a mixture of medetomidine, midazolam and butorphanol anesthesia. The supernatants from separated blood are collected and stored at −80° C. until further processing. Lungs are harvested from the mice and two lobes left unfixed, one lobe is frozen and another harvested for biochemical assays such as measurements of hydroxyproline or inflammatory markers. Remaining lung lobes are fixed in 10% neutral buffered formalin, paraffin embedded for Masson's trichrome staining and histology. For quantitative analysis of lung fibrosis area, bright field images of Masson's Trichrome-stained sections are randomly captured using a digital camera at 100-fold magnification, and the subpleural regions in 20 fields/mouse are evaluated according to the criteria for grading lung fibrosis (Ashcroft, T., et al., *J Clin Pathol,* 1988; 41:467-70), to generate an Ashcroft score. All sections are blindly analyzed by an experimenter. Statistics are performed on each treatment group, calculating an average Aschroft score, and comparing the scores in the different treatment groups to the Vehicle group.

Alternative methods of fusion protein delivery may be utilized. As an example, rather than intranasal spray delivery which is confined to the upper airways, nebulization of the fusion proteins may improve delivery of the fusion molecules deeper into the lungs, thereby more effectively targeting all areas of the lung. Fusion proteins can be nebulized with or without excipients and tested for protein recovery, aggregation, and enzyme activity. A vibrating mesh (VM) nebulizer (PARI eFlow. Omron NE-U100, Lake Forest, IL) can be used since other proteins have been successfully nebulized using this apparatus and because VM nebulizers are small and portable. Nebulized proteins (500 µl) at 1 mg/ml in saline plus 1 mM $CaCl_2$ (Pulmozyme® buffer) are collected on a sterile 60 mm low protein binding tissue culture dish. Recovered fusion proteins are analyzed by SDS gels, size exclusion HPLC (SEC), and for protein concentration and enzyme activity before and after nebulization to evaluate the effects of the excipients and the effects of nebulization on the protein.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A fusion polypeptide comprising, from an amino terminal position to a carboxyl terminal position, T-L1-X-L2-P, wherein:

T is a first biologically active polypeptide selected from the group consisting of
a cytotoxic T-lymphocyte associated molecule-4 (CTLA-4) extracellular domain, and
a CD40 extracellular domain;

L1 is a first polypeptide linker, wherein L1 is optionally present;

X is an immunoglobulin heavy chain constant region, wherein the immunoglobulin heavy chain constant region is capable of forming dimers and specifically binding the neonatal Fc receptor (FcRn);

L2 is a second polypeptide linker comprising at least eight amino acid residues; and P is a biologically active paraoxonase, wherein the paraoxonase has at least 95% identity with the amino acid sequence shown in residues 16-355 or 26-355 of SEQ ID NO:6, and wherein the paraoxonase does not contain an amino terminal leader sequence corresponding to residues 1-15 of SEQ ID NO:6;

wherein the fusion polypeptide comprises an amino acid sequence having at least 95% identity with the amino acid sequence shown in
(i) residues 21-736 of SEQ ID NO:66,
(ii) residues 21-804 of SEQ ID NO:74,
(iii) residues 21-804 of SEQ ID NO:78,
(iv) residues 21-804 of SEQ ID NO:82,
(v) residues 21-804 of SEQ ID NO:86, or
(vi) residues 21-804 of SEQ ID NO:90.

2. The fusion polypeptide of claim 1, wherein the immunoglobulin heavy chain constant region is a human immunoglobulin Fc region.

3. The fusion polypeptide of claim 2, wherein the human Fc region is an Fc variant comprising one or more amino acid substitutions relative to the wild-type human sequence.

4. The fusion polypeptide of claim 3, wherein the Fc region is a human γ1 Fc region or a human γ4 Fc region.

5. The fusion polypeptide of claim 3, wherein the Fc region is a human γ1 Fc variant in which
Eu residue C220 is replaced by serine,
Eu residue P238 is replaced by serine, and/or
Eu residue P331 is replaced by serine.

6. The fusion polypeptide of claim 2, wherein the Fc region has the amino acid sequence shown in
(i) residues 1-232 or 1-231 of SEQ ID NO:26,
(ii) residues 1-232 or 1-231 of SEQ ID NO:116, or
(iii) residues 1-232 or 1-231 of SEQ ID NO:118.

7. The fusion polypeptide of claim 1, wherein the fusion polypeptide comprises the amino acid sequence shown in
(i) residues 21-736 of SEQ ID NO:66,
(ii) residues 21-804 of SEQ ID NO:74,
(iii) residues 21-804 of SEQ ID NO:78,
(iv) residues 21-804 of SEQ ID NO:82,
(v) residues 21-804 of SEQ ID NO:86, or
(vi) residues 21-804 of SEQ ID NO:90.

8. A dimeric protein comprising a first fusion polypeptide and a second fusion polypeptide, wherein each of the first and second fusion polypeptides is a fusion polypeptide as defined in claim 1.

9. A composition comprising:
a dimeric protein of claim 8; and
a pharmaceutically acceptable carrier.

10. The fusion polypeptide of claim 1, wherein the first biologically active polypeptide is the CTLA-4 extracellular domain.

11. The fusion polypeptide of claim 10, wherein the CTLA-4 extracellular domain has at least 95% identity with the amino acid sequence shown in residues 21-144 of SEQ ID NO:66.

12. The fusion polypeptide of claim 11, wherein the CTLA-4 extracellular domain has the amino acid sequence shown in residues 21-144 of SEQ ID NO:66.

13. The fusion polypeptide of claim 1, wherein the first biologically active polypeptide is the CD40 extracellular domain.

14. The fusion polypeptide of claim 13, wherein the CD40 extracellular domain has at least 95% identity with the amino acid sequence shown in
(i) residues 21-188 of SEQ ID NO:74,
(ii) residues 21-188 of SEQ ID NO:78,
(iii) residues 21-188 of SEQ ID NO:82,
(iv) residues 21-188 of SEQ ID NO:86, or
(v) residues 21-188 of SEQ ID NO:90.

15. The fusion polypeptide of claim 14, wherein the CD40 extracellular domain contains at least one amino acid substitution at a position corresponding to an amino acid of human CD40 (SEQ ID NO:68) selected from the group consisting of E64, K81, P85, and L121, wherein the at least one amino acid substitution increases CD40 ligand binding relative to human CD40.

16. The fusion polypeptide of claim 15, wherein
the amino acid at the position corresponding to K81 of human CD40 is selected from the group consisting of threonine, histidine, and serine;
the amino acid at the position corresponding to K81 of human CD40 is histidine and the amino acid the position corresponding to L121 of human CD40 is proline; or
the amino acid at the position corresponding to E64 of human CD40 is tyrosine, the amino acid at the position corresponding to K81 of human CD40 is threonine, and the amino acid at the position corresponding to P85 of human CD40 is tyrosine.

17. The fusion polypeptide of claim 14, wherein the CD40 extracellular domain has the amino acid sequence shown in
(i) residues 21-188 of SEQ ID NO:74,
(ii) residues 21-188 of SEQ ID NO:78,
(iii) residues 21-188 of SEQ ID NO:82,
(iv) residues 21-188 of SEQ ID NO:86, or
(v) residues 21-188 of SEQ ID NO:90.

18. A fusion polypeptide comprising, from an amino terminal position to a carboxyl terminal position, T-L1-X-L2-P, wherein:
T is a single-chain antibody that specifically binds and neutralizes tumor necrosis factor α (TNFα), wherein the single-chain antibody is a single-chain Fv (scFv);
L1 is a first polypeptide linker, wherein L1 is optionally present;
X is an immunoglobulin heavy chain constant region, wherein the immunoglobulin heavy chain constant region is capable of forming dimers and specifically binding the neonatal Fc receptor (FcRn);
L2 is a second polypeptide linker comprising at least eight amino acid residues; and
P is a biologically active paraoxonase, wherein the paraoxonase has at least 95% identity with the amino acid sequence shown in residues 16-355 or 26-355 of SEQ ID NO:6, and wherein the paraoxonase does not contain an amino terminal leader sequence corresponding to residues 1-15 of SEQ ID NO:6;
wherein the single-chain antibody comprises a VH domain comprising complementarity determining regions (CDRs) CDR-H1$_{TNF\alpha}$, CDR-H2$_{TNF\alpha}$, and CDR-H3$_{TNF\alpha}$, wherein CDR-H1$_{TNF\alpha}$, CDR-H2$_{TNF\alpha}$, and CDR-H3$_{TNF}$α are VH CDRs of SEQ ID NO:108;
wherein the single-chain antibody comprises a VL domain comprising complementarity determining regions (CDRs) CDR-L1$_{TNF\alpha}$, CDR-L2$_{TNF\alpha}$, and CDR-L3$_{TNF\alpha}$, wherein CDR-L1$_{TNF\alpha}$, CDR-L2$_{TNF\alpha}$, and CDR-L3$_{TNF\alpha}$ are VL CDRs of SEQ ID NO:110; and
wherein the fusion polypeptide comprises an amino acid sequence having at least 95% identity with the amino acid sequence shown in
(i) residues 21-860 of SEQ ID NO:94, or
(ii) residues 21-860 of SEQ ID NO:98.

19. The fusion polypeptide of claim 18, wherein the single-chain Fv (scFv) comprises a VH domain having at least 95% identity with the amino acid sequence shown in SEQ ID NO:108, and/or wherein the single-chain antibody comprises a VL domain having at least 95% identity with the amino acid sequence shown in SEQ ID NO: 110.

20. The fusion polypeptide of claim 18, wherein the single-chain Fv (scFV) has at least 95% identity with the amino acid sequence shown in
   (i) residues 21-268 of SEQ ID NO:92, or
   (ii) residues 21-268 of SEQ ID NO:96.

21. The fusion polypeptide of claim 20, wherein the single-chain Fv (scFV) has the amino acid sequence shown in
   (i) residues 21-268 of SEQ ID NO:92, or
   (ii) residues 21-268 of SEQ ID NO:96.

22. The fusion polypeptide of claim 18, wherein the fusion polypeptide comprises the amino acid sequence shown in
   (i) residues 21-860 of SEQ ID NO:94, or
   (ii) residues 21-860 of SEQ ID NO:98.

\* \* \* \* \*

SEQUENCE LISTING

<160> NUMBER OF SEQ ID NOS: 164

<210> SEQ ID NO 1
<211> LENGTH: 2688
<212> TYPE: DNA
<213> ORGANISM: Artificial Sequence
<220> FEATURE:
<223> OTHER INFORMATION: hVK3LP-[hDNase1 N74K-G105R-A114F]-(g4s)4-
      [SSShinge-P238S-P331S Fc]-NGS-[PON1 Q192K] DNA
<220> FEATURE:
<221> NAME/KEY: sig_peptide
<222> LOCATION: (1)..(60)
<223> OTHER INFORMATION: human VK3 leader peptide
<220> FEATURE:
<221> NAME/KEY: misc_feature
<222> LOCATION: (61)..(840)
<223> OTHER INFORMATION: human DNase 1 (N74K, G105R, A114F) without
      leader peptide
<220> FEATURE:
<221> NAME/KEY: misc_feature
<222> LOCATION: (280)..(283)
<223> OTHER INFORMATION: human DNase 1 N74K substitution
<220> FEATURE:
<221> NAME/KEY: misc_feature
<222> LOCATION: (373)..(375)
<223> OTHER INFORMATION: human DNase 1 G105R substitution
<220> FEATURE:
<221> NAME/KEY: misc_feature
<222> LOCATION: (399)..(401)
<223> OTHER INFORMATION: human DNase 1 A114F substitution
<220> FEATURE:
<221> NAME/KEY: misc_feature
<222> LOCATION: (841)..(918)
<223> OTHER INFORMATION: (gly4ser)4 linker peptide sequence with
      additional restriction site amino acids
<220> FEATURE:
<221> NAME/KEY: misc_feature
<222> LOCATION: (919)..(1614)
<223> OTHER INFORMATION: human IgG1 variant Fc (SSS hinge, P238S, P331S)
<220> FEATURE:
<221> NAME/KEY: misc_feature
<222> LOCATION: (931)..(933)
<223> OTHER INFORMATION: human IgG1 hinge C220S substitution
<220> FEATURE:
<221> NAME/KEY: misc_feature
<222> LOCATION: (949)..(951)
<223> OTHER INFORMATION: human IgG1 hinge C226S substitution
<220> FEATURE:
<221> NAME/KEY: misc_feature
<222> LOCATION: (958)..(960)
<223> OTHER INFORMATION: human IgG1 hinge C229S substitution
<220> FEATURE:
<221> NAME/KEY: misc_feature
<222> LOCATION: (985)..(987)
<223> OTHER INFORMATION: human IgG1 lower hinge-CH2 P238S substitution
<220> FEATURE:
<221> NAME/KEY: misc_feature
<222> LOCATION: (1264)..(1266)
<223> OTHER INFORMATION: human IgG1 Fc P331S substitution
<220> FEATURE:
<221> NAME/KEY: misc_feature
<222> LOCATION: (1615)..(1672)
<223> OTHER INFORMATION: peptide linker containing N-linked
      glycosylation site
<220> FEATURE:
<221> NAME/KEY: misc_feature
<222> LOCATION: (1673)..(2688)
<223> OTHER INFORMATION: human PON1 Q192K without uncleaved leader
      peptide
<220> FEATURE:
<221> NAME/KEY: misc_feature
<222> LOCATION: (2197)..(2199)
<223> OTHER INFORMATION: PON1 Q192K substitution

<400> SEQUENCE: 1
atggaaaccc cagcgcagct tctcttcctc ctgctactct ggctcccaga taccaccggt    60

```
ctgaagatcg cagccttcaa catccagaca tttggggaga ccaagatgtc caatgccacc    120
ctcgtcagct acattgtgca gatcctgagc cgctatgaca tcgccctggt ccaggaggtc    180
agagacagcc acctgactgc cgtggggaag ctgctggaca acctcaatca ggatgcacca    240
gacacctatc actacgtggt cagtgagcca ctgggacgga agagctataa ggagcgctac    300
ctgttcgtgt acaggcctga ccaggtgtct gcggtggaca gctactacta cgatgatggc    360
tgcgagccct gcaggaacga caccttcaac cgagagccat tcattgtcag gttcttctcc    420
cggttcacag aggtcaggga gtttgccatt gttccctgc atgcggcccc ggggacgca     480 gtagccgaga tcgacgctct ctatgacgtc tacctggatg tccaagagaa atggggcttg    540
gaggacgtca tgttgatggg cgacttcaat gcgggctgca gctatgtgag accctcccag    600
tggtcatcca tccgcctgtg acaagcccc accttccagt ggctgatccc cgacagcgct    660
gacaccacag ctacacccac gcactgtgcc tatgacagga tcgtggttgc agggatgctg    720
ctccgaggcg ccgttgttcc cgactcggct cttccctta acttccaggc tgcctatggc    780
ctgagtgacc aactggccca agccatcagt gaccactatc agtggaggt gatgctgaaa    840 gatctctccg gaggaggtgg ctcaggtggt ggaggatctg gaggaggtgg gagtggtgga    900
ggtggttcta ccggtctcga gcccaaatct tctgacaaaa ctcacacatc tccaccgtcc    960
ccagcacctg aactcctggg aggatcgtca gtcttcctct tccccccaaa acccaaggac   1020
accctcatga tctcccggac ccctgaggtc acatgcgtgg tggtggacgt gagccacgaa   1080
gaccctgagg tcaagttcaa ctggtacgtg gacggcgtgg aggtgcataa tgccaagaca   1140
aagccgcggg aggagcagta caacagcacg taccgtgtgg tcagcgtcct caccgtcctg   1200
caccaggact ggctgaatgg caaggagtac aagtgcaagg tctccaacaa agccctccca   1260
gcctccatcg agaaaaccat ctccaaagcc aagggcagc cccgagaacc acaggtgtac   1320
accctgcccc catcccggga tgagctgacc aagaaccagg tcagcctgac ctgcctggtc   1380
aaaggcttct atcccagcga catcgccgtg gagtgggaga gcaatgggca gccggagaac   1440
aactacaaga ccacgcctcc cgtgctggac tccgacggct ccttcttcct ctacagcaag   1500
ctcaccgtgg acaagagcag gtggcagcag gggaacgtct tctcatgctc cgtgatgcat   1560
gaggctctgc acaaccacta cacgcagaag agcctctctc tctctccggg taaagtcgac   1620
ggagctagca gccccgtgaa cgtgagcagc cccagcgtgc aggatatcct cttcaggaac   1680
caccagtctt cttaccaaac acgacttaat gctctccgag aggtacaacc cgtagaactt   1740
cctaactgta atttagttaa aggaatcgaa actggctctg aagacttgga gatactgcct   1800
aatggactgg cttcattag ctctggatta aagtatcctg gaataaagag cttcaacccc   1860
aacagtcctg gaaaaatact tctgatggac ctgaatgaag aagatccaac agtgttggaa   1920
ttggggatca ctggaagtaa atttgatgta tcttcattta accctcatgg gattagcaca   1980
ttcacagatg aagataatgc catgtacctc ctggtggtga accatccaga tgccaagtcc   2040
acagtggagt tgtttaaatt tcaagaagaa gaaaaatcgc ttttgcatct aaaaaccatc   2100
agacataaac ttctgcctaa tttgaatgat attgttgctg tgggacctga gcactttttat  2160 ggcacaaatg atcactattt tcttgacccc tacttaaaat cctgggagat gtatttgggt   2220
ttagcgtggt cgtatgttgt ctactatagt ccaagtgaag ttcgagtggt ggcagaagga   2280
tttgattttg ctaatggaat caacatttca cccgatggca gtatgtcta tatagctgag   2340 ttgctggctc ataagattca tgtgtatgaa aagcatgcta attggacttt aactccattg   2400
aagtcccttg actttaatac cctcgtggat aacatatctg tggatcctga cacaggagac   2460
```

```
ctttggggttg gatgccatcc caatggcatg aaaatcttct tctatgactc agagaatcct    2520
cctgcatcag aggtgcttcg aatccagaac attctaacag aagaacctaa agtgacacag    2580
gtttatgcag aaaatggcac agtgttgcaa ggcagtacag ttgcctctgt gtacaaaggg    2640
aaactgctga ttggcacagt gtttcacaaa gctctttact gtgagctc                 2688
```

```
<210> SEQ ID NO 2
<211> LENGTH: 896
<212> TYPE: PRT
<213> ORGANISM: Artificial Sequence
<220> FEATURE:
<223> OTHER INFORMATION: hVK3LP-[hDNase1 N74K-G105R-A114F]-(g4s)4-
      [SSShinge-P238S-P331S Fc]-NGS-[PON1 Q192K]
<220> FEATURE:
<221> NAME/KEY: SIGNAL
<222> LOCATION: (1)..(20)
<223> OTHER INFORMATION: human VK3 leader peptide
<220> FEATURE:
<221> NAME/KEY: MISC_FEATURE
<222> LOCATION: (21)..(280)
<223> OTHER INFORMATION: human DNase 1 (N74K, G105R, A114F) without
      leader peptide
<220> FEATURE:
<221> NAME/KEY: MISC_FEATURE
<222> LOCATION: (94)..(94)
<223> OTHER INFORMATION: human DNase 1 N74K substitution
<220> FEATURE:
<221> NAME/KEY: MISC_FEATURE
<222> LOCATION: (125)..(125)
<223> OTHER INFORMATION: human DNase 1 G105R substitution
<220> FEATURE:
<221> NAME/KEY: MISC_FEATURE
<222> LOCATION: (134)..(134)
<223> OTHER INFORMATION: human DNase 1 A114F substitution
<220> FEATURE:
<221> NAME/KEY: MISC_FEATURE
<222> LOCATION: (281)..(306)
<223> OTHER INFORMATION: (gly4ser)4 linker peptide with restriction site
      amino acids
<220> FEATURE:
<221> NAME/KEY: MISC_FEATURE
<222> LOCATION: (307)..(538)
<223> OTHER INFORMATION: human IgG1 variant Fc (SSS hinge, P238S, P331S)
<220> FEATURE:
<221> NAME/KEY: MISC_FEATURE
<222> LOCATION: (311)..(311)
<223> OTHER INFORMATION: human IgG1 C220S substitution
<220> FEATURE:
<221> NAME/KEY: MISC_FEATURE
<222> LOCATION: (317)..(317)
<223> OTHER INFORMATION: human IgG1 C226S substitution
<220> FEATURE:
<221> NAME/KEY: MISC_FEATURE
<222> LOCATION: (320)..(320)
<223> OTHER INFORMATION: human IgG1 C229S substitution
<220> FEATURE:
<221> NAME/KEY: MISC_FEATURE
<222> LOCATION: (329)..(329)
<223> OTHER INFORMATION: P238S lower hinge-CH2 mutation
<220> FEATURE:
<221> NAME/KEY: MISC_FEATURE
<222> LOCATION: (422)..(422)
<223> OTHER INFORMATION: human IgG1 P331S substitution
<220> FEATURE:
<221> NAME/KEY: MISC_FEATURE
<222> LOCATION: (539)..(557)
<223> OTHER INFORMATION: peptide linker containing N-linked
      glycosylation site
<220> FEATURE:
<221> NAME/KEY: MISC_FEATURE
<222> LOCATION: (558)..(896)
<223> OTHER INFORMATION: human PON1 Q192K without uncleaved leader
      peptide
<220> FEATURE:
<221> NAME/KEY: MISC_FEATURE
```

<222> LOCATION: (733)..(733)
<223> OTHER INFORMATION: PON1 Q192K substitution

<400> SEQUENCE: 2

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Gly Ser
        275                 280                 285

Gly Gly Gly Gly Ser Gly Gly Gly Ser Gly Gly Gly Ser Thr
    290                 295                 300

Gly Leu Glu Pro Lys Ser Ser Asp Lys Thr His Thr Ser Pro Pro Ser
305                 310                 315                 320

Pro Ala Pro Glu Leu Leu Gly Gly Ser Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400
```

-continued

His Gln Asp Trp Leu Asn Gly Lys Glu Tyr Lys Cys Lys Val Ser Asn
                405                 410                 415

Lys Ala Leu Pro Ala Ser Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Leu Phe Arg Asn
545                 550                 555                 560

His Gln Ser Ser Tyr Gln Thr Arg Leu Asn Ala Leu Arg Glu Val Gln
                565                 570                 575

Pro Val Glu Leu Pro Asn Cys Asn Leu Val Lys Gly Ile Glu Thr Gly
            580                 585                 590

Ser Glu Asp Leu Glu Ile Leu Pro Asn Gly Leu Ala Phe Ile Ser Ser
        595                 600                 605

Gly Leu Lys Tyr Pro Gly Ile Lys Ser Phe Asn Pro Asn Ser Pro Gly
    610                 615                 620

Lys Ile Leu Leu Met Asp Leu Asn Glu Glu Asp Pro Thr Val Leu Glu
625                 630                 635                 640

Leu Gly Ile Thr Gly Ser Lys Phe Asp Val Ser Ser Phe Asn Pro His
                645                 650                 655

Gly Ile Ser Thr Phe Thr Asp Glu Asp Asn Ala Met Tyr Leu Leu Val
            660                 665                 670

Val Asn His Pro Asp Ala Lys Ser Thr Val Glu Leu Phe Lys Phe Gln
        675                 680                 685

Glu Glu Glu Lys Ser Leu Leu His Leu Lys Thr Ile Arg His Lys Leu
    690                 695                 700

Leu Pro Asn Leu Asn Asp Ile Val Ala Val Gly Pro Glu His Phe Tyr
705                 710                 715                 720

Gly Thr Asn Asp His Tyr Phe Leu Asp Pro Tyr Leu Lys Ser Trp Glu
                725                 730                 735

Met Tyr Leu Gly Leu Ala Trp Ser Tyr Val Val Tyr Tyr Ser Pro Ser
            740                 745                 750

Glu Val Arg Val Val Ala Glu Gly Phe Asp Phe Ala Asn Gly Ile Asn
        755                 760                 765

Ile Ser Pro Asp Gly Lys Tyr Val Tyr Ile Ala Glu Leu Leu Ala His
    770                 775                 780

Lys Ile His Val Tyr Glu Lys His Ala Asn Trp Thr Leu Thr Pro Leu
785                 790                 795                 800

Lys Ser Leu Asp Phe Asn Thr Leu Val Asp Asn Ile Ser Val Asp Pro
                805                 810                 815

```
Glu Thr Gly Asp Leu Trp Val Gly Cys His Pro Asn Gly Met Lys Ile
                820                 825                 830
Phe Phe Tyr Asp Ser Glu Asn Pro Pro Ala Ser Glu Val Leu Arg Ile
                835                 840                 845
Gln Asn Ile Leu Thr Glu Glu Pro Lys Val Thr Gln Val Tyr Ala Glu
                850                 855                 860
Asn Gly Thr Val Leu Gln Gly Ser Thr Val Ala Ser Val Tyr Lys Gly
865                 870                 875                 880
Lys Leu Leu Ile Gly Thr Val Phe His Lys Ala Leu Tyr Cys Glu Leu
                885                 890                 895

<210> SEQ ID NO 3
<211> LENGTH: 1065
<212> TYPE: DNA
<213> ORGANISM: Homo sapiens

<400> SEQUENCE: 3
atggcgaagc tgattgcgct caccctcttg gggatgggac tggcactctt caggaaccac      60
cagtcttctt accaaacacg acttaatgct ctccgagagg tacaacccgt agaacttcct     120
aactgtaatt tagttaaagg aatcgaaact ggctctgaag acttggagat actgcctaat     180
ggactggctt tcattagctc tggattaaag tatcctggaa taaagagctt caaccccaac     240
agtcctggaa aaatacttct gatggacctg aatgaagaag atccaacagt gttggaattg     300
gggatcactg gaagtaaatt tgatgtatct tcatttaacc ctcatgggat tagcacattc     360
acagatgaag ataatgccat gtacctcctg gtggtgaacc atccagatgc caagtccaca     420
gtggagttgt ttaaatttca agaagaagaa aaatcgcttt tgcatctaaa aaccatcaga     480
cataaacttc tgcctaattt gaatgatatt gttgctgtgg acctgagcac tttttatggc     540
acaaatgatc actattttct tgacccctac ttacaatcct gggagatgta tttgggttta     600
gcgtggtcgt atgttgtcta ctatagtcca agtgaagttc gagtggtggc agaaggattt     660
gattttgcta atggaatcaa catttcaccc gatggcaagt atgtctatat agctgagttg     720
ctggctcata gagttcatgt gtatgaaaag catgctaatt ggactttaac tccattgaag     780
tcccttgact ttaataccct cgtggataac atatctgtgg atcctgagac aggagacctt     840
tgggttggat gccatcccaa tggcatgaaa atcttcttct atgactcaga gaatcctcct     900
gcatcagagg tgcttcgaat ccagaacatt ctaacagaag aacctaaagt gacacaggtt     960
tatgcagaaa atggcacagt gttgcaaggc agtacagttg cctctgtgta caagggaaaa    1020
ctgctgattg gcacagtgtt tcacaaagct ctttactgtg agctc                   1065

<210> SEQ ID NO 4
<211> LENGTH: 355
<212> TYPE: PRT
<213> ORGANISM: Homo sapiens
<220> FEATURE:
<221> NAME/KEY: SIGNAL
<222> LOCATION: (1)..(16)
<223> OTHER INFORMATION: PON1 noncleaved signal peptide
<220> FEATURE:
<221> NAME/KEY: mat_peptide
<222> LOCATION: (1)..(355)
<223> OTHER INFORMATION: PON1 coding sequence
<220> FEATURE:
<221> NAME/KEY: MISC_FEATURE
<222> LOCATION: (17)..(355)
<223> OTHER INFORMATION: PON1 sequence without uncleaved leader sequence
<220> FEATURE:
<221> NAME/KEY: MISC_FEATURE
<222> LOCATION: (192)..(192)
```

<223> OTHER INFORMATION: PON1 sequence variant Q192

<400> SEQUENCE: 4

```
Met Ala Lys Leu Ile Ala Leu Thr Leu Leu Gly Met Gly Leu Ala Leu
1               5                   10                  15
Phe Arg Asn His Gln Ser Ser Tyr Gln Thr Arg Leu Asn Ala Leu Arg
            20                  25                  30
Glu Val Gln Pro Val Glu Leu Pro Asn Cys Asn Leu Val Lys Gly Ile
        35                  40                  45
Glu Thr Gly Ser Glu Asp Leu Glu Ile Leu Pro Asn Gly Leu Ala Phe
    50                  55                  60
Ile Ser Ser Gly Leu Lys Tyr Pro Gly Ile Lys Ser Phe Asn Pro Asn
65                  70                  75                  80
Ser Pro Gly Lys Ile Leu Leu Met Asp Leu Asn Glu Glu Asp Pro Thr
                85                  90                  95
Val Leu Glu Leu Gly Ile Thr Gly Ser Lys Phe Asp Val Ser Ser Phe
            100                 105                 110
Asn Pro His Gly Ile Ser Thr Phe Thr Asp Glu Asp Asn Ala Met Tyr
        115                 120                 125
Leu Leu Val Val Asn His Pro Asp Ala Lys Ser Thr Val Glu Leu Phe
    130                 135                 140
Lys Phe Gln Glu Glu Glu Lys Ser Leu Leu His Leu Lys Thr Ile Arg
145                 150                 155                 160
His Lys Leu Leu Pro Asn Leu Asn Asp Ile Val Ala Val Gly Pro Glu
                165                 170                 175
His Phe Tyr Gly Thr Asn Asp His Tyr Phe Leu Asp Pro Tyr Leu Gln
            180                 185                 190
Ser Trp Glu Met Tyr Leu Gly Leu Ala Trp Ser Tyr Val Val Tyr Tyr
        195                 200                 205
Ser Pro Ser Glu Val Arg Val Val Ala Glu Gly Phe Asp Phe Ala Asn
    210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                245                 250                 255
Thr Pro Leu Lys Ser Leu Asp Phe Asn Thr Leu Val Asp Asn Ile Ser
            260                 265                 270
Val Asp Pro Glu Thr Gly Asp Leu Trp Val Gly Cys His Pro Asn Gly
        275                 280                 285
Met Lys Ile Phe Phe Tyr Asp Ser Glu Asn Pro Pro Ala Ser Glu Val
    290                 295                 300
Leu Arg Ile Gln Asn Ile Leu Thr Glu Glu Pro Lys Val Thr Gln Val
305                 310                 315                 320
Tyr Ala Glu Asn Gly Thr Val Leu Gln Gly Ser Thr Val Ala Ser Val
                325                 330                 335
Tyr Lys Gly Lys Leu Leu Ile Gly Thr Val Phe His Lys Ala Leu Tyr
            340                 345                 350
Cys Glu Leu
        355
```

<210> SEQ ID NO 5
<211> LENGTH: 1065
<212> TYPE: DNA
<213> ORGANISM: Artificial Sequence
<220> FEATURE:

<223> OTHER INFORMATION: Human PON1 Q192K DNA

<400> SEQUENCE: 5

```
atggcgaagc tgattgcgct caccctcttg gggatgggac tggcactctt caggaaccac      60
cagtcttctt accaaacacg acttaatgct ctccgagagg tacaacccgt agaacttcct     120
aactgtaatt tagttaaagg aatcgaaact ggctctgaag acttggagat actgcctaat     180
ggactggctt tcattagctc tggattaaag tatcctggaa taaagagctt caaccccaac     240
agtcctggaa aaatacttct gatggacctg aatgaagaag atccaacagt gttggaattg     300
gggatcactg gaagtaaatt tgatgtatct tcatttaacc ctcatgggat tagcacattc     360
acagatgaag ataatgccat gtacctcctg gtggtgaacc atccagatgc caagtccaca     420
gtggagttgt ttaaatttca agaagaagaa aaatcgcttt tgcatctaaa aaccatcaga     480
cataaacttc tgcctaattt gaatgatatt gttgctgtgg acctgagcaa cttttatggc     540
acaaatgatc actattttct tgacccctac ttaaaatcct gggagatgta tttgggttta     600
gcgtggtcgt atgttgtcta ctatagtcca agtgaagttc gagtggtggc agaaggattt     660
gattttgcta tggaatcaa catttcaccc gatggcaagt atgtctatat agctgagttg    720
ctggctcata gattcatgt gtatgaaaag catgctaatt ggactttaac tccattgaag     780
tcccttgact ttaataccct cgtggataac atatctgtgg atcctgagac aggagacctt     840
tgggttggat gccatcccaa tggcatgaaa atcttcttct atgactcaga gaatcctcct     900
gcatcagagg tgcttcgaat ccagaacatt ctaacagaag aacctaaagt gacacaggtt     960
tatgcagaaa atggcacagt gttgcaaggc agtacagttg cctctgtgta caagggaaa    1020
ctgctgattg gcacagtgtt tcacaaagct ctttactgtg agctc                    1065
```

<210> SEQ ID NO 6
<211> LENGTH: 355
<212> TYPE: PRT
<213> ORGANISM: Artificial Sequence
<220> FEATURE:
<223> OTHER INFORMATION: Human PON1 Q192K
<220> FEATURE:
<221> NAME/KEY: SIGNAL
<222> LOCATION: (1)..(16)
<223> OTHER INFORMATION: PON1 uncleaved leader sequence
<220> FEATURE:
<221> NAME/KEY: mat_peptide
<222> LOCATION: (1)..(355)
<223> OTHER INFORMATION: PON1 mature polypeptide with uncleaved leader
<220> FEATURE:
<221> NAME/KEY: MISC_FEATURE
<222> LOCATION: (17)..(355)
<223> OTHER INFORMATION: PON1 sequence without uncleaved signal peptide
<220> FEATURE:
<221> NAME/KEY: MISC_FEATURE
<222> LOCATION: (192)..(192)
<223> OTHER INFORMATION: PON1 mutant Q192K

<400> SEQUENCE: 6

Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn

```
                65                  70                  75                  80
Ser Pro Gly Lys Ile Leu Leu Met Asp Leu Asn Glu Glu Asp Pro Thr
                    85                  90                  95
Val Leu Glu Leu Gly Ile Thr Gly Ser Lys Phe Asp Val Ser Ser Phe
                    100                 105                 110
Asn Pro His Gly Ile Ser Thr Phe Thr Asp Glu Asp Asn Ala Met Tyr
                    115                 120                 125
Leu Leu Val Val Asn His Pro Asp Ala Lys Ser Thr Val Glu Leu Phe
130                 135                 140
Lys Phe Gln Glu Glu Lys Ser Leu Leu His Leu Lys Thr Ile Arg
145                 150                 155                 160
His Lys Leu Leu Pro Asn Leu Asn Asp Ile Val Ala Val Gly Pro Glu
                    165                 170                 175
His Phe Tyr Gly Thr Asn Asp His Tyr Phe Leu Asp Pro Tyr Leu Lys
                    180                 185                 190
Ser Trp Glu Met Tyr Leu Gly Leu Ala Trp Ser Tyr Val Val Tyr Tyr
                    195                 200                 205
Ser Pro Ser Glu Val Arg Val Val Ala Glu Gly Phe Asp Phe Ala Asn
210                 215                 220
Gly Ile Asn Ile Ser Pro Asp Gly Lys Tyr Val Tyr Ile Ala Glu Leu
225                 230                 235                 240
Leu Ala His Lys Ile His Val Tyr Glu Lys His Ala Asn Trp Thr Leu
                    245                 250                 255
Thr Pro Leu Lys Ser Leu Asp Phe Asn Thr Leu Val Asp Asn Ile Ser
                    260                 265                 270
Val Asp Pro Glu Thr Gly Asp Leu Trp Val Gly Cys His Pro Asn Gly
                    275                 280                 285
Met Lys Ile Phe Phe Tyr Asp Ser Glu Asn Pro Ala Ser Glu Val
                    290                 295                 300
Leu Arg Ile Gln Asn Ile Leu Thr Glu Glu Pro Lys Val Thr Gln Val
305                 310                 315                 320
Tyr Ala Glu Asn Gly Thr Val Leu Gln Gly Ser Thr Val Ala Ser Val
                    325                 330                 335
Tyr Lys Gly Lys Leu Leu Ile Gly Thr Val Phe His Lys Ala Leu Tyr
                    340                 345                 350
Cys Glu Leu
        355

<210> SEQ ID NO 7
<211> LENGTH: 1065
<212> TYPE: DNA
<213> ORGANISM: Homo sapiens

<400> SEQUENCE: 7
atggcgaagc tgattgcgct caccctcttg gggatgggac tggcactctt caggaaccac    60
cagtcttctt accaaacacg acttaatgct ctccgagagg tacaacccgt agaacttcct   120
aactgtaatt tagttaaagg aatcgaaact ggctctgaag acttggagat actgcctaat   180
ggactggctt tcattagctc tggattaaag tatcctggaa taaagagctt caaccccaac   240
agtcctggaa aaatacttct gatggacctg aatgaagaag atccaacagt gttggaattg   300
gggatcactg gaagtaaatt tgatgtatct tcatttaacc ctcatgggat tagcacattc   360
acagatgaag ataatgccat gtacctcctg gtggtgaacc atccagatgc caagtccaca   420
gtggagttgt ttaaatttca agaagaagaa aaatcgcttt tgcatctaaa aaccatcaga   480
```

```
cataaacttc tgcctaattt gaatgatatt gttgctgtgg gacctgagca ctttttatggc    540 acaaatgatc actattttct tgaccccta c ttaagatcct gggagatgta tttgggttta    600
gcgtggtcgt atgttgtcta ctatagtcca agtgaagttc gagtggtggc agaaggattt    660
gattttgcta atggaatcaa catttcaccc gatggcaagt atgtctatat agctgagttg    720
ctggctcata agattcatgt gtatgaaaag catgctaatt ggactttaac tccattgaag    780
tcccttgact ttaatacccc t cgtggataac atatctgtgg atcctgagac aggagacctt    840
tgggttggat gccatcccaa tggcatgaaa atcttcttct atgactcaga gaatcctcct    900
gcatcagagg tgcttcgaat ccagaacatt ctaacagaag aacctaaagt gacacaggtt    960
tatgcagaaa atggcacagt gttgcaaggc agtacagttg cctctgtgta caagggaaa    1020 ctgctgattg gcacagtgtt tcacaaagct ctttactgtg agctc                    1065
```

<210> SEQ ID NO 8
<211> LENGTH: 355
<212> TYPE: PRT
<213> ORGANISM: Homo sapiens
<220> FEATURE:
<221> NAME/KEY: SIGNAL
<222> LOCATION: (1)..(16)
<223> OTHER INFORMATION: PON1 uncleaved signal peptide

<400> SEQUENCE: 8

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Leu Glu Ile Leu Pro Asn Gly Leu Ala Phe
    50                  55                  60

Ile Ser Ser Gly Leu Lys Tyr Pro Gly Ile Lys Ser Phe Asn Pro Asn
65                  70                  75                  80

Ser Pro Gly Lys Ile Leu Leu Met Asp Leu Asn Glu Glu Asp Pro Thr
                85                  90                  95

Val Leu Glu Leu Gly Ile Thr Gly Ser Lys Phe Asp Val Ser Ser Phe
            100                 105                 110

Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
    130                 135                 140

Lys Phe Gln Glu Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Tyr Phe Leu Asp Pro Tyr Leu Arg
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
```

```
                245                 250                 255
Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
    290                 295                 300

Leu Arg Ile Gln Asn Ile Leu Thr Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
                340                 345                 350

Cys Glu Leu
        355

<210> SEQ ID NO 9
<211> LENGTH: 52
<212> TYPE: DNA
<213> ORGANISM: Artificial Sequence
<220> FEATURE:
<223> OTHER INFORMATION: (gly4ser)2 linker DNA

<400> SEQUENCE: 9
agatctctcc ggaggaggtg gctcaggtgg tggaggatct accggtctcg ag            52

<210> SEQ ID NO 10
<211> LENGTH: 16
<212> TYPE: PRT
<213> ORGANISM: Artificial Sequence
<220> FEATURE:
<223> OTHER INFORMATION: (gly4ser)2 linker

<400> SEQUENCE: 10

Asp Leu Ser Gly Gly Gly Gly Ser Gly Gly Gly Gly Ser Thr Gly Leu
1               5                   10                  15

<210> SEQ ID NO 11
<211> LENGTH: 82
<212> TYPE: DNA
<213> ORGANISM: Artificial Sequence
<220> FEATURE:
<223> OTHER INFORMATION: (gly4ser)4 linker DNA

<400> SEQUENCE: 11
agatctctcc ggaggaggtg gctcaggtgg tggaggatct ggaggaggtg ggagtggtgg    60
aggtggttct accggtctcg ag                                            82

<210> SEQ ID NO 12
<211> LENGTH: 26
<212> TYPE: PRT
<213> ORGANISM: Artificial Sequence
<220> FEATURE:
<223> OTHER INFORMATION: (gly4ser)4 linker

<400> SEQUENCE: 12

Asp Leu Ser Gly Gly Gly Gly Ser Gly Gly Gly Gly Ser Gly Gly Gly
1               5                   10                  15

Gly Ser Gly Gly Gly Gly Ser Thr Gly Leu
                20                  25
```

<210> SEQ ID NO 13
<211> LENGTH: 112
<212> TYPE: DNA
<213> ORGANISM: Artificial Sequence
<220> FEATURE:
<223> OTHER INFORMATION: (gly4ser)6 linker DNA

<400> SEQUENCE: 13
agatctctcc ggaggaggtg gctcaggtgg tggaggatct ggaggaggtg ggagtggtgg    60
aggtggttct ggaggaggtg gtagtggagg tggaggttct accggtctcg ag          112

<210> SEQ ID NO 14
<211> LENGTH: 36
<212> TYPE: PRT
<213> ORGANISM: Artificial Sequence
<220> FEATURE:
<223> OTHER INFORMATION: (gly4ser)6 linker

<400> SEQUENCE: 14

Asp Leu Ser Gly Gly Gly Gly Ser Gly Gly Gly Gly Ser Gly Gly Gly
1               5                  10                  15

Gly Ser Gly Gly Gly Gly Ser Gly Gly Gly Gly Ser Gly Gly Gly Gly
            20                  25                  30

Ser Thr Gly Leu
        35

<210> SEQ ID NO 15
<211> LENGTH: 846
<212> TYPE: DNA
<213> ORGANISM: Homo sapiens

<400> SEQUENCE: 15
atgaggggca tgaagctgct gggggcgctg ctggcactgg cggccctact gcaggggcc    60 gtgtccctga agatcgcagc cttcaacatc agacatttg gggagaccaa gatgtccaat   120
gccaccctcg tcagctacat tgtgcagatc ctgagccgct atgacatcgc cctggtccag   180
gaggtcagag acagccacct gactgccgtg gggaagctgc tggacaacct caatcaggat   240
gcaccagaca cctatcacta cgtggtcagt gagccactgg acggaacag ctataaggag   300 cgctacctgt tcgtgtacag gcctgaccag gtgtctgcgg tggacagcta ctactacgat   360
gatggctgcg agccctgcgg gaacgacacc ttcaaccgag agccagccat tgtcaggttc   420
ttctcccggt tcacagaggt cagggagttt gccattgttc ccctgcatgc gggccccggg   480
gacgcagtag ccgagatcga cgctctctat gacgtctacc tggatgtcca agagaaatgg   540
ggcttggagg acgtcatgtt gatgggcgac ttcaatgcgg gctgcagcta tgtgagaccc   600
tcccagtggt catccatccg cctgtggaca agccccacct tccagtggct gatccccgac   660
agcgctgaca ccacagctac acccacgcac tgtgcctatg acaggatcgt ggttgcaggg   720
atgctgctcc gaggcgccgt tgttcccgac tcggctcttc cctttaactt ccaggctgcc   780
tatggcctga gtgaccaact ggcccaagcc atcagtgacc actatccagt ggaggtgatg   840
ctgaag                                                             846

<210> SEQ ID NO 16
<211> LENGTH: 282
<212> TYPE: PRT
<213> ORGANISM: Homo sapiens
<220> FEATURE:
<221> NAME/KEY: SIGNAL
<222> LOCATION: (1)..(22)
<223> OTHER INFORMATION: human DNase 1 signal peptide

<220> FEATURE:
<221> NAME/KEY: SIGNAL
<222> LOCATION: (1)..(22)

<400> SEQUENCE: 16

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
        35                  40                  45

Gln Ile Leu Ser Arg Tyr Asp Ile Ala Leu Val Gln Glu Val Arg Asp
50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
        275                 280

<210> SEQ ID NO 17
<211> LENGTH: 840
<212> TYPE: DNA
<213> ORGANISM: Artificial Sequence
<220> FEATURE:
<223> OTHER INFORMATION: hVK3LP-[hDNase1 N74K-G105R-A114F] DNA

<400> SEQUENCE: 17
atggaaaccc cagcgcagct tctcttcctc ctgctactct ggctcccaga taccaccggt      60
ctgaagatcg cagccttcaa catccagaca tttggggaga ccaagatgtc aatgccacc     120 ctcgtcagct acattgtgca gatcctgagc cgctatgaca tcgccctggt ccaggaggtc     180
agagacagcc acctgactgc cgtggggaag ctgctggaca acctcaatca ggatgcacca     240
gacacctatc actacgtggt cagtgagcca ctgggacgga agagctataa ggagcgctac     300

```
ctgttcgtgt acaggcctga ccaggtgtct gcggtggaca gctactacta cgatgatggc    360
tgcgagccct gcaggaacga caccttcaac cgagagccat tcattgtcag gttcttctcc    420
cggttcacag aggtcaggga gtttgccatt gttcccctgc atgcggcccc ggggacgca     480 gtagccgaga tcgacgctct ctatgacgtc tacctggatg tccaagagaa atggggcttg    540
gaggacgtca tgttgatggg cgacttcaat gcgggctgca gctatgtgag accctcccag    600
tggtcatcca tccgcctgtg acaagcccc accttccagt ggctgatccc cgacagcgct    660
gacaccacag ctacacccac gcactgtgcc tatgacagga tcgtggttgc agggatgctg    720
ctccgaggcg ccgttgttcc cgactcggct cttcccttta acttccaggc tgcctatggc    780
ctgagtgacc aactggccca agccatcagt gaccactatc cagtggaggt gatgctgaaa    840
```

<210> SEQ ID NO 18
<211> LENGTH: 280
<212> TYPE: PRT
<213> ORGANISM: Artificial Sequence
<220> FEATURE:
<223> OTHER INFORMATION: hVK3LP-[hDNase1 N74K-G105R-A114F]
<220> FEATURE:
<221> NAME/KEY: SIGNAL
<222> LOCATION: (1)..(20)
<223> OTHER INFORMATION: human VK3 leader peptide
<220> FEATURE:
<221> NAME/KEY: MISC_FEATURE
<222> LOCATION: (94)..(94)
<223> OTHER INFORMATION: N74K substitution
<220> FEATURE:
<221> NAME/KEY: MISC_FEATURE
<222> LOCATION: (125)..(125)
<223> OTHER INFORMATION: G105R substitution
<220> FEATURE:
<221> NAME/KEY: MISC_FEATURE
<222> LOCATION: (134)..(134)
<223> OTHER INFORMATION: A114F substitution

<400> SEQUENCE: 18

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
```

```
             180                 185                 190
Cys Ser Tyr Val Arg Pro Ser Gln Trp Ser Ser Ile Arg Leu Trp Thr
            195                 200                 205

Ser Pro Thr Phe Gln Trp Leu Ile Pro Asp Ser Ala Asp Thr Thr Ala
            210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
                260                 265                 270

Tyr Pro Val Glu Val Met Leu Lys
            275                 280

<210> SEQ ID NO 19
<211> LENGTH: 840
<212> TYPE: DNA
<213> ORGANISM: Artificial Sequence
<220> FEATURE:
<223> OTHER INFORMATION: hVK3LP-[hDNase1 G105R-A114F] DNA

<400> SEQUENCE: 19
atggaaaccc cagcgcagct tctcttcctc ctgctactct ggctcccaga taccaccggt      60
ctgaagatcg cagccttcaa catccagaca tttggggaga ccaagatgtc caatgccacc     120
ctcgtcagct acattgtgca gatcctgagc cgctatgaca tcgccctggt ccaggaggtc     180
agagacagcc acctgactgc cgtggggaag ctgctggaca acctcaatca ggatgcacca     240
gacacctatc actacgtggt cagtgagcca ctgggacgga cagctataa ggagcgctac     300 ctgttcgtgt acaggcctga ccaggtgtct gcggtggaca gctactacta cgatgatggc     360
tgcgagccct gcaggaacga caccttcaac cgagagccat tcattgtcag gttcttctcc     420
cggttcacag aggtcaggga gtttgccatt gttcccctgc atgcggcccc gggggacgca     480
gtagccgaga tcgacgctct ctatgacgtc tacctggatg tccaagagaa atggggcttg     540
gaggacgtca tgttgatggg cgacttcaat gcgggctgca gctatgtgag accctcccag     600
tggtcatcca tccgcctgtg gacaagcccc accttccagt ggctgatccc cgacagcgct     660
gacaccacag ctacacccac gcactgtgcc tatgacagga tcgtggttgc agggatgctg     720
ctccgaggcg ccgttgttcc cgactcggct cttcccttta acttccaggc tgcctatggc     780
ctgagtgacc aactggccca agccatcagt gaccactatc cagtggaggt gatgctgaaa     840

<210> SEQ ID NO 20
<211> LENGTH: 280
<212> TYPE: PRT
<213> ORGANISM: Artificial Sequence
<220> FEATURE:
<223> OTHER INFORMATION: hVK3LP-[hDNase1 G105R-A114F]
<220> FEATURE:
<221> NAME/KEY: SIGNAL
<222> LOCATION: (1)..(20)
<223> OTHER INFORMATION: human VK3 leader peptide
<220> FEATURE:
<221> NAME/KEY: MISC_FEATURE
<222> LOCATION: (125)..(125)
<223> OTHER INFORMATION: G105R substitution
<220> FEATURE:
<221> NAME/KEY: MISC_FEATURE
<222> LOCATION: (134)..(134)
<223> OTHER INFORMATION: A114F substitution

<400> SEQUENCE: 20
```

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Asn Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
    115                 120                 125

Phe Asn Arg Glu Pro Phe Ile Val Arg Phe Phe Ser Arg Phe Thr Glu
130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
    195                 200                 205

Ser Pro Thr Phe Gln Trp Leu Ile Pro Asp Ser Ala Asp Thr Thr Ala
210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys
    275                 280

<210> SEQ ID NO 21
<211> LENGTH: 468
<212> TYPE: DNA
<213> ORGANISM: Homo sapiens

<400> SEQUENCE: 21
atggctctgg agaagtctct tgtccggctc cttctgcttg tcctgatact gctggtgctg      60
ggctgggtcc agccttccct gggcaaggaa tcccgggcca agaaattcca gcggcagcat     120
atggactcag acagttcccc cagcagcagc tccacctact gtaaccaaat gatgaggcgc     180
cggaatatga cacaggggcg gtgcaaacca gtgaacacct tgtgcacga gcccctggta      240 gatgtccaga atgtctgttt ccaggaaaag gtcacctgca gaacgggca gggcaactgc     300 tacaagagca actccagcat gcacatcaca gactgccgcc tgacaaacgg ctccaggtac     360
cccaactgtg cataccggac cagcccgaag gagagacaca tcattgtggc ctgtgaaggg     420
agcccatatg tgccagtcca ctttgatgct tctgtggagg actctacc                  468
```

<210> SEQ ID NO 22
<211> LENGTH: 156
<212> TYPE: PRT
<213> ORGANISM: Homo sapiens
<220> FEATURE:
<221> NAME/KEY: SIGNAL
<222> LOCATION: (1)..(28)
<223> OTHER INFORMATION: human RNase signal peptide

<400> SEQUENCE: 22

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155

<210> SEQ ID NO 23
<211> LENGTH: 444
<212> TYPE: DNA
<213> ORGANISM: Artificial Sequence
<220> FEATURE:
<223> OTHER INFORMATION: hVK3LP-RNase1 DNA

<400> SEQUENCE: 23
atggaaaccc cagcgcagct tctcttcctc ctgctactct ggctcccaga taccaccggt      60
aaggaatccc gggccaagaa attccagcgg cagcatatgg actcagacag ttcccccagc     120
agcagctcca cctactgtaa ccaaatgatg aggcgccgga atatgacaca ggggcggtgc     180
aaaccagtga acacctttgt gcacgagccc ctggtagatg tccagaatgt ctgtttccag     240
gaaaaggtca cctgcaagaa cgggcagggc aactgctaca agagcaactc cagcatgcac     300
atcacagact gccgcctgac aaacgactcc aggtacccca ctgtgcata ccggaccagc      360 ccgaaggaga gacacatcat tgtggcctgt gaagggagcc catatgtgcc agtccacttt     420
gatgcttctg tggaggactc taca                                            444

<210> SEQ ID NO 24
<211> LENGTH: 148
<212> TYPE: PRT
<213> ORGANISM: Artificial Sequence
<220> FEATURE:
<223> OTHER INFORMATION: hVK3LP-RNase1
<220> FEATURE:
<221> NAME/KEY: SIGNAL
<222> LOCATION: (1)..(20)
<223> OTHER INFORMATION: human VK3 leader peptide

<400> SEQUENCE: 24

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Ser Thr Tyr Cys Asn Gln
        35                  40                  45

Met Met Arg Arg Arg Asn Met Thr Gln Gly Arg Cys Lys Pro Val Asn
50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
                100                 105                 110

Pro Asn Cys Ala Tyr Arg Thr Ser Pro Lys Glu Arg His Ile Ile Val
            115                 120                 125

Ala Cys Glu Gly Ser Pro Tyr Val Pro Val His Phe Asp Ala Ser Val
130                 135                 140

Glu Asp Ser Thr
145
```

<210> SEQ ID NO 25
<211> LENGTH: 696
<212> TYPE: DNA
<213> ORGANISM: Artificial Sequence
<220> FEATURE:
<223> OTHER INFORMATION: Human IgG1 variant Fc DNA (SCC hinge, wild-type CH2 and CH3)

<400> SEQUENCE: 25

```
gagcccaaat cttctgacaa aactcacaca tgtccaccgt gcccagcacc tgaactcctg      60
gggggaccgt cagtcttcct cttccccccca aaacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaagggcag ccccgagaa ccacaggtgt acaccctgcc cccatcccgg     420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc tctgtctccg ggtaaa                               696
```

<210> SEQ ID NO 26
<211> LENGTH: 232
<212> TYPE: PRT
<213> ORGANISM: Artificial Sequence
<220> FEATURE:
<223> OTHER INFORMATION: Human IgG1 variant Fc (SCC hinge, wild-type CH2 and CH3)

<400> SEQUENCE: 26

-continued

```
Glu Pro Lys Ser Ser Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230
```

```
<210> SEQ ID NO 27
<211> LENGTH: 696
<212> TYPE: DNA
<213> ORGANISM: Artificial Sequence
<220> FEATURE:
<223> OTHER INFORMATION: Human IgG1 variant Fc DNA (SSS hinge, P238S,
      P331S)

<400> SEQUENCE: 27
gagcccaaat cttctgacaa aactcacaca tctccaccgt ccccagcacc tgaactcctg      60
ggaggatcgt cagtcttcct cttcccccca aacccaagg acaccctcat gatctcccgg     120
accctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcctccat cgagaaaacc     360
atctccaaag ccaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga gagcctctc tctctctccg ggtaaa                               696
```

```
<210> SEQ ID NO 28
<211> LENGTH: 232
<212> TYPE: PRT
<213> ORGANISM: Artificial Sequence
<220> FEATURE:
<223> OTHER INFORMATION: Human IgG1 variant Fc (SSS hinge, P238S, P331S)
<220> FEATURE:
<221> NAME/KEY: MISC_FEATURE
<222> LOCATION: (5)..(5)
<223> OTHER INFORMATION: IgG1 hinge C220S substitution
<220> FEATURE:
<221> NAME/KEY: MISC_FEATURE
<222> LOCATION: (11)..(11)
<223> OTHER INFORMATION: IgG1 hinge C226S substitution
<220> FEATURE:
<221> NAME/KEY: MISC_FEATURE
<222> LOCATION: (14)..(14)
<223> OTHER INFORMATION: IgG1 hinge C229S substitution
<220> FEATURE:
<221> NAME/KEY: MISC_FEATURE
<222> LOCATION: (23)..(23)
<223> OTHER INFORMATION: IgG1 lower hinge-CH2 P238S substitution
<220> FEATURE:
<221> NAME/KEY: MISC_FEATURE
<222> LOCATION: (116)..(116)
<223> OTHER INFORMATION: IgG1 Fc P331S substitution

<400> SEQUENCE: 28

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 29
<211> LENGTH: 774
```

```
<212> TYPE: DNA
<213> ORGANISM: Artificial Sequence
<220> FEATURE:
<223> OTHER INFORMATION: (g4s)4-[SSShinge-P238S-P331S Fc] DNA

<400> SEQUENCE: 29
gatctctccg gaggaggtgg ctcaggtggt ggaggatctg gaggaggtgg gagtggtgga      60
ggtggttcta ccggtctcga gcccaaatct tctgacaaaa ctcacacatc tccaccgtcc     120
ccagcacctg aactcctggg aggatcgtca gtcttcctct cccccccaaa acccaaggac     180
accctcatga tctcccggac ccctgaggtc acatgcgtgg tggtggacgt gagccacgaa     240
gaccctgagg tcaagttcaa ctggtacgtg acggcgtgg aggtgcataa tgccaagaca     300
aagccgcggg aggagcagta caacagcacg taccgtgtgg tcagcgtcct caccgtcctg     360
caccaggact ggctgaatgg caaggagtac aagtgcaagg tctccaacaa agccctccca     420
gcctccatcg agaaaaccat ctccaaagcc aaagggcagc ccgagaacc acaggtgtac     480
accctgcccc catcccggga tgagctgacc aagaaccagg tcagcctgac ctgcctggtc     540
aaaggcttct atcccagcga catcgccgtg gagtgggaga gcaatgggca gccggagaac     600
aactacaaga ccacgcctcc cgtgctggac tccgacggct ccttcttcct ctacagcaag     660
ctcaccgtgg acaagagcag gtggcagcag gggaacgtct tctcatgctc cgtgatgcat     720
gaggctctgc acaaccacta cacgcagaag agcctctctc tctctccggg taaa            774

<210> SEQ ID NO 30
<211> LENGTH: 258
<212> TYPE: PRT
<213> ORGANISM: Artificial Sequence
<220> FEATURE:
<223> OTHER INFORMATION: (g4s)4-[SSShinge-P238S-P331S Fc]
<220> FEATURE:
<221> NAME/KEY: MISC_FEATURE
<222> LOCATION: (1)..(26)
<223> OTHER INFORMATION: (Gly4Ser)4 linker (including additional
      restriction site amino acids)
<220> FEATURE:
<221> NAME/KEY: MISC_FEATURE
<222> LOCATION: (27)..(258)
<223> OTHER INFORMATION: human IgG1 hinge-CH2-CH3 with substituted amino
      acids
<220> FEATURE:
<221> NAME/KEY: MISC_FEATURE
<222> LOCATION: (31)..(31)
<223> OTHER INFORMATION: human IgG1 hinge C220S substitution
<220> FEATURE:
<221> NAME/KEY: MISC_FEATURE
<222> LOCATION: (37)..(37)
<223> OTHER INFORMATION: human IgG1 hinge C226S substitution
<220> FEATURE:
<221> NAME/KEY: MISC_FEATURE
<222> LOCATION: (40)..(40)
<223> OTHER INFORMATION: human IgG1 hinge C229S substitution
<220> FEATURE:
<221> NAME/KEY: MISC_FEATURE
<222> LOCATION: (49)..(49)
<223> OTHER INFORMATION: human IgG1 lower hinge-CH2 P238S substitution
<220> FEATURE:
<221> NAME/KEY: MISC_FEATURE
<222> LOCATION: (142)..(142)
<223> OTHER INFORMATION: human IgG1 P331S substitution

<400> SEQUENCE: 30

Asp Leu Ser Gly Gly Gly Gly Ser Gly Gly Gly Gly Ser Gly Gly Gly
1               5                   10                  15

Gly Ser Gly Gly Gly Gly Ser Thr Gly Leu Glu Pro Lys Ser Ser Asp
            20                  25                  30
```

```
Lys Thr His Thr Ser Pro Pro Ser Pro Ala Pro Glu Leu Leu Gly Gly
             35                  40                  45

Ser Ser Val Phe Leu Phe Pro Pro Lys Pro Lys Asp Thr Leu Met Ile
 50                  55                  60

Ser Arg Thr Pro Glu Val Thr Cys Val Val Val Asp Val Ser His Glu
 65                  70                  75                  80

Asp Pro Glu Val Lys Phe Asn Trp Tyr Val Asp Gly Val Glu Val His
                 85                  90                  95

Asn Ala Lys Thr Lys Pro Arg Glu Glu Gln Tyr Asn Ser Thr Tyr Arg
                100                 105                 110

Val Val Ser Val Leu Thr Val Leu His Gln Asp Trp Leu Asn Gly Lys
            115                 120                 125

Glu Tyr Lys Cys Lys Val Ser Asn Lys Ala Leu Pro Ala Ser Ile Glu
130                 135                 140

Lys Thr Ile Ser Lys Ala Lys Gly Gln Pro Arg Glu Pro Gln Val Tyr
145                 150                 155                 160

Thr Leu Pro Pro Ser Arg Asp Glu Leu Thr Lys Asn Gln Val Ser Leu
                165                 170                 175

Thr Cys Leu Val Lys Gly Phe Tyr Pro Ser Asp Ile Ala Val Glu Trp
            180                 185                 190

Glu Ser Asn Gly Gln Pro Glu Asn Asn Tyr Lys Thr Thr Pro Pro Val
        195                 200                 205

Leu Asp Ser Asp Gly Ser Phe Phe Leu Tyr Ser Lys Leu Thr Val Asp
    210                 215                 220

Lys Ser Arg Trp Gln Gln Gly Asn Val Phe Ser Cys Ser Val Met His
225                 230                 235                 240

Glu Ala Leu His Asn His Tyr Thr Gln Lys Ser Leu Ser Leu Ser Pro
                245                 250                 255

Gly Lys

<210> SEQ ID NO 31
<211> LENGTH: 462
<212> TYPE: DNA
<213> ORGANISM: Homo sapiens

<400> SEQUENCE: 31
atggcgacga aggccgtgtg cgtgctgaag ggcgacggcc cagtgcaggg catcatcaat      60
ttcgagcaga aggaaagtaa tggaccagtg aaggtgtggg gaagcattaa aggactgact     120
gaaggcctgc atggattcca tgttcatgag tttggagata tacagcagg ctgtaccagt      180 gcaggtcctc actttaatcc tctatccaga aaacacggtg ggccaaagga tgaagagagg     240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aa                        462

<210> SEQ ID NO 32
<211> LENGTH: 154
<212> TYPE: PRT
<213> ORGANISM: Homo sapiens
<220> FEATURE:
<221> NAME/KEY: mat_peptide
<222> LOCATION: (1)..(154)
<223> OTHER INFORMATION: human SOD1 wild type sequence
<300> PUBLICATION INFORMATION:
<308> DATABASE ACCESSION NUMBER: NM_000454.5
```

<309> DATABASE ENTRY DATE: 2020-06-07
<313> RELEVANT RESIDUES IN SEQ ID NO: (1)..(154)
<300> PUBLICATION INFORMATION:
<308> DATABASE ACCESSION NUMBER: CR450355.1
<309> DATABASE ENTRY DATE: 2016-07-26
<313> RELEVANT RESIDUES IN SEQ ID NO: (1)..(154)
<300> PUBLICATION INFORMATION:
<308> DATABASE ACCESSION NUMBER: CR541742.1
<309> DATABASE ENTRY DATE: 2008-10-16
<313> RELEVANT RESIDUES IN SEQ ID NO: (1)..(154)

<400> SEQUENCE: 32

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

<210> SEQ ID NO 33
<211> LENGTH: 1242
<212> TYPE: DNA
<213> ORGANISM: Artificial Sequence
<220> FEATURE:
<223> OTHER INFORMATION: hRNase1-(g4s)4-[SSShinge-P238S Fc] DNA

<400> SEQUENCE: 33

```
atggctctgg agaagtctct tgtccggctc cttctgcttg tcctgatact gctggtgctg      60
ggctgggtcc agccttccct gggcaaggaa tcccgggcca agaaattcca gcggcagcat     120
atggactcag acagttcccc cagcagcagc tccacctact gtaaccaaat gatgaggcgc     180
cggaatatga cacaggggcg gtgcaaacca gtgaacacct tgtgcacga gccctggta      240 gatgtccaga atgtctgttt ccaggaaaag gtcacctgca gaacgggca gggcaactgc     300 tacaagagca actccagcat gcacatcaca gactgccgcc tgacaaacgg ctccaggtac     360
cccaactgtg cataccggac cagcccgaag gagagacaca tcattgtggc ctgtgaaggg     420
agcccatatg tgccagtcca ctttgatgct tctgtggagg actctacaga tctctccgga     480
ggaggtggct caggtggtgg aggatctgga ggaggtggga gtggtggagg tggttctacc     540
ggtctcgagc ccaaatcttc tgacaaaact cacacatctc caccgtcccc agcacctgaa     600
ctcctggggg gatcgtcagt cttcctcttc ccccaaaac ccaaggacac cctcatgatc      660
tcccggaccc ctgaggtcac atgcgtggtg gtggacgtga gccacgaaga ccctgaggtc     720
aagttcaact ggtacgtgga cggcgtggag gtgcataatg ccaagacaaa gccgcgggag     780
```

-continued

```
gagcagtaca acagcacgta ccgtgtggtc agcgtcctca ccgtcctgca ccaggactgg      840
ctgaatggca aggagtacaa gtgcaaggtc tccaacaaag ccctcccagc ccccatcgag      900
aaaaccatct ccaaagccaa agggcagccc cgagaaccac aggtgtacac cctgccccca      960
tcccgggatg agctgaccaa gaaccaggtc agcctgacct gcctggtcaa aggcttctat     1020
cccagcgaca tcgccgtgga gtgggagagc aatgggcagc cggagaacaa ctacaagacc     1080
acgcctcccg tgctggactc cgacggctcc ttcttcctct acagcaagct caccgtggac     1140
aagagcaggt ggcagcaggg gaacgtcttc tcatgctccg tgatgcatga ggctctgcac     1200
aaccactaca cgcagaagag cctctctctg tctccgggta aa                        1242
```

<210> SEQ ID NO 34
<211> LENGTH: 414
<212> TYPE: PRT
<213> ORGANISM: Artificial Sequence
<220> FEATURE:
<223> OTHER INFORMATION: hRNase1-(g4s)4-[SSShinge-P238S Fc]
<220> FEATURE:
<221> NAME/KEY: SIGNAL
<222> LOCATION: (1)..(28)
<223> OTHER INFORMATION: human RNase signal sequence
<220> FEATURE:
<221> NAME/KEY: MISC_FEATURE
<222> LOCATION: (29)..(166)
<223> OTHER INFORMATION: human RNase1 mature polypeptide
<220> FEATURE:
<221> NAME/KEY: MISC_FEATURE
<222> LOCATION: (167)..(182)
<223> OTHER INFORMATION: human (gly4ser)4 linker peptide with additional
      restriction site amino acids
<220> FEATURE:
<221> NAME/KEY: MISC_FEATURE
<222> LOCATION: (183)..(414)
<223> OTHER INFORMATION: human IgG1 variant Fc (SSS hinge, P238S)
<220> FEATURE:
<221> NAME/KEY: MISC_FEATURE
<222> LOCATION: (187)..(187)
<223> OTHER INFORMATION: human IgG1 hinge C220S substitution
<220> FEATURE:
<221> NAME/KEY: MISC_FEATURE
<222> LOCATION: (193)..(193)
<223> OTHER INFORMATION: human IgG1 hinge C226S substitution
<220> FEATURE:
<221> NAME/KEY: MISC_FEATURE
<222> LOCATION: (196)..(196)
<223> OTHER INFORMATION: human IgG1 hinge C229S substitution
<220> FEATURE:
<221> NAME/KEY: MISC_FEATURE
<222> LOCATION: (205)..(205)
<223> OTHER INFORMATION: human IgG1lower hinge-CH2 P238S substitution

<400> SEQUENCE: 34

```
Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110
```

```
Arg Leu Thr Asn Gly Ser Arg Tyr Pro Asn Cys Ala Tyr Arg Thr Ser
            115                 120                 125
Pro Lys Glu Arg His Ile Ile Val Ala Cys Glu Gly Ser Pro Tyr Val
    130                 135                 140
Pro Val His Phe Asp Ala Ser Val Glu Asp Ser Thr Asp Leu Ser Gly
145                 150                 155                 160
Gly Gly Gly Ser Gly Gly Gly Ser Gly Gly Gly Ser Gly Gly
                165                 170                 175
Gly Gly Ser Thr Gly Leu Glu Pro Lys Ser Ser Asp Lys Thr His Thr
            180                 185                 190
Ser Pro Pro Ser Pro Ala Pro Glu Leu Leu Gly Gly Ser Ser Val Phe
        195                 200                 205
Leu Phe Pro Pro Lys Pro Lys Asp Thr Leu Met Ile Ser Arg Thr Pro
    210                 215                 220
Glu Val Thr Cys Val Val Val Asp Val Ser His Glu Asp Pro Glu Val
225                 230                 235                 240
Lys Phe Asn Trp Tyr Val Asp Gly Val Glu Val His Asn Ala Lys Thr
                245                 250                 255
Lys Pro Arg Glu Glu Gln Tyr Asn Ser Thr Tyr Arg Val Val Ser Val
            260                 265                 270
Leu Thr Val Leu His Gln Asp Trp Leu Asn Gly Lys Glu Tyr Lys Cys
        275                 280                 285
Lys Val Ser Asn Lys Ala Leu Pro Ala Pro Ile Glu Lys Thr Ile Ser
    290                 295                 300
Lys Ala Lys Gly Gln Pro Arg Glu Pro Gln Val Tyr Thr Leu Pro Pro
305                 310                 315                 320
Ser Arg Asp Glu Leu Thr Lys Asn Gln Val Ser Leu Thr Cys Leu Val
                325                 330                 335
Lys Gly Phe Tyr Pro Ser Asp Ile Ala Val Glu Trp Glu Ser Asn Gly
            340                 345                 350
Gln Pro Glu Asn Asn Tyr Lys Thr Thr Pro Pro Val Leu Asp Ser Asp
        355                 360                 365
Gly Ser Phe Phe Leu Tyr Ser Lys Leu Thr Val Asp Lys Ser Arg Trp
    370                 375                 380
Gln Gln Gly Asn Val Phe Ser Cys Ser Val Met His Glu Ala Leu His
385                 390                 395                 400
Asn His Tyr Thr Gln Lys Ser Leu Ser Leu Ser Pro Gly Lys
                405                 410

<210> SEQ ID NO 35
<211> LENGTH: 1218
<212> TYPE: DNA
<213> ORGANISM: Artificial Sequence
<220> FEATURE:
<223> OTHER INFORMATION: hVK3LP-hRNase1-(g4s)4-[SSHinge-P238S Fc] DNA

<400> SEQUENCE: 35
atggaaaccc cagcgcagct tctcttcctc ctgctactct ggctcccaga taccaccggt      60
aaggaatccc gggccaagaa attccagcgg cagcatatgg actcagacag ttccccagc     120 agcagctcca cctactgtaa ccaaatgatg aggcgccgga atatgacaca ggggcggtgc    180
aaaccagtga acacctttgt gcacgagccc ctggtagatg tccagaatgt ctgtttccag    240
gaaaaggtca cctgcaagaa cgggcagggc aactgctaca agagcaactc cagcatgcac    300
atcacagact gccgcctgac aaacgactcc aggtacccca ctgtgcata ccggaccagc    360
```

-continued

```
ccgaaggaga gacacatcat tgtggcctgt gaagggagcc catatgtgcc agtccacttt      420
gatgcttctg tggaggactc tacagatctc tccggaggag gtggctcagg tggtggagga      480
tctggaggag gtgggagtgg tggaggtggt tctaccggtc tcgagcccaa atcttctgac      540
aaaactcaca catctccacc gtccccagca cctgaactcc tggggggatc gtcagtcttc      600
ctcttccccc caaaacccaa ggacaccctc atgatctccc ggacccctga ggtcacatgc      660
gtggtggtgg acgtgagcca cgaagaccct gaggtcaagt tcaactggta cgtggacggc      720
gtggaggtgc ataatgccaa gacaaagccg cgggaggagc agtacaacag cacgtaccgt      780
gtggtcagcg tcctcaccgt cctgcaccag gactggctga atggcaagga gtacaagtgc      840
aaggtctcca acaaagccct cccagccccc atcgagaaaa ccatctccaa agccaaaggg      900
cagccccgag aaccacaggt gtacaccctg cccccatccc gggatgagct gaccaagaac      960
caggtcagcc tgacctgcct ggtcaaaggc ttctatccca gcgacatcgc cgtggagtgg     1020
gagagcaatg ggcagccgga gaacaactac aagaccacgc ctcccgtgct ggactccgac     1080
ggctccttct tcctctacag caagctcacc gtggacaaga gcaggtggca gcaggggaac     1140
gtcttctcat gctccgtgat gcatgaggct ctgcacaacc actacacgca gaagagcctc     1200
tctctgtctc cgggtaaa                                                   1218
```

<210> SEQ ID NO 36
<211> LENGTH: 406
<212> TYPE: PRT
<213> ORGANISM: Artificial Sequence
<220> FEATURE:
<223> OTHER INFORMATION: hVK3LP-hRNase1-(g4s)4-[SSShinge-P238S Fc]
<220> FEATURE:
<221> NAME/KEY: SIGNAL
<222> LOCATION: (1)..(20)
<223> OTHER INFORMATION: human VK3 signal peptide
<220> FEATURE:
<221> NAME/KEY: MISC_FEATURE
<222> LOCATION: (21)..(158)
<223> OTHER INFORMATION: human RNase 1 mature polypeptide
<220> FEATURE:
<221> NAME/KEY: MISC_FEATURE
<222> LOCATION: (159)..(174)
<223> OTHER INFORMATION: (gly4ser)4 linker peptide with additional
      restriction site amino acids
<220> FEATURE:
<221> NAME/KEY: MISC_FEATURE
<222> LOCATION: (175)..(406)
<223> OTHER INFORMATION: human IgG1 variant Fc (SSS hinge, P238S)
<220> FEATURE:
<221> NAME/KEY: MISC_FEATURE
<222> LOCATION: (179)..(179)
<223> OTHER INFORMATION: human IgG1 hinge C220S substitution
<220> FEATURE:
<221> NAME/KEY: MISC_FEATURE
<222> LOCATION: (185)..(185)
<223> OTHER INFORMATION: human IgG1 hinge C226S substitution
<220> FEATURE:
<221> NAME/KEY: MISC_FEATURE
<222> LOCATION: (188)..(188)
<223> OTHER INFORMATION: human IgG1 hinge C229S substitution
<220> FEATURE:
<221> NAME/KEY: MISC_FEATURE
<222> LOCATION: (197)..(197)
<223> OTHER INFORMATION: human IgG1 lower hinge-CH2 P238S substitution

<400> SEQUENCE: 36

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30
```

```
Met Asp Ser Asp Ser Pro Ser Ser Ser Thr Tyr Cys Asn Gln
         35                  40                  45

Met Met Arg Arg Arg Asn Met Thr Gln Gly Arg Cys Lys Pro Val Asn
 50                  55                  60

Thr Phe Val His Glu Pro Leu Val Asp Val Gln Asn Val Cys Phe Gln
 65                  70                  75                  80

Glu Lys Val Thr Cys Lys Asn Gly Gln Gly Asn Cys Tyr Lys Ser Asn
                 85                  90                  95

Ser Ser Met His Ile Thr Asp Cys Arg Leu Thr Asn Asp Ser Arg Tyr
             100                 105                 110

Pro Asn Cys Ala Tyr Arg Thr Ser Pro Lys Glu Arg His Ile Ile Val
         115                 120                 125

Ala Cys Glu Gly Ser Pro Tyr Val Pro Val His Phe Asp Ala Ser Val
130                 135                 140

Glu Asp Ser Thr Asp Leu Ser Gly Gly Gly Ser Gly Gly Gly Gly
145                 150                 155                 160

Ser Gly Gly Gly Gly Ser Gly Gly Gly Gly Ser Thr Gly Leu Glu Pro
                165                 170                 175

Lys Ser Ser Asp Lys Thr His Thr Ser Pro Pro Ser Pro Ala Pro Glu
             180                 185                 190

Leu Leu Gly Gly Ser Ser Val Phe Leu Phe Pro Pro Lys Pro Lys Asp
         195                 200                 205

Thr Leu Met Ile Ser Arg Thr Pro Glu Val Thr Cys Val Val Val Asp
210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
             260                 265                 270

Leu Asn Gly Lys Glu Tyr Lys Cys Lys Val Ser Asn Lys Ala Leu Pro
         275                 280                 285

Ala Pro Ile Glu Lys Thr Ile Ser Lys Ala Lys Gly Gln Pro Arg Glu
290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
             340                 345                 350

Thr Pro Pro Val Leu Asp Ser Asp Gly Ser Phe Phe Leu Tyr Ser Lys
         355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 37
<211> LENGTH: 2316
<212> TYPE: DNA
<213> ORGANISM: Artificial Sequence
<220> FEATURE:
```

<223> OTHER INFORMATION: hRNase1-(g4s)4-[SSSH-P238S Fc]-NGS-[PON1 Q192K] DNA

<400> SEQUENCE: 37

| | | | | |
|---|---|---|---|---|
| atggctctgg | agaagtctct | tgtccggctc | cttctgcttg | tcctgatact | gctggtgctg | 60 |
| ggctgggtcc | agccttccct | gggcaaggaa | tcccgggcca | agaaattcca | gcggcagcat | 120 |
| atggactcag | acagttcccc | cagcagcagc | tccacctact | gtaaccaaat | gatgaggcgc | 180 |
| cggaatatga | cacaggggcg | tgcaaaacca | gtgaacacct | tgtgcacga | gcccctggta | 240 |
| gatgtccaga | atgtctgttt | ccaggaaaag | gtcacctgca | gaacgggca | gggcaactgc | 300 |
| tacaagagca | actccagcat | gcacatcaca | gactgccgcc | tgacaaacgg | ctccaggtac | 360 |
| cccaactgtg | cataccggac | cagcccgaag | agagacaca | tcattgtggc | ctgtgaaggg | 420 |
| agcccatatg | tgccagtcca | ctttgatgct | tctgtggagg | actctacaga | tctctccgga | 480 |
| ggaggtggct | caggtggtgg | aggatctgga | ggaggtggga | gtggtggagg | tggttctacc | 540 |
| ggtctcgagc | ccaaatcttc | tgacaaaact | cacacatctc | caccgtcccc | agcacctgaa | 600 |
| ctcctgggag | gatcgtcagt | cttcctcttc | cccccaaaac | ccaaggacac | cctcatgatc | 660 |
| tcccggaccc | ctgaggtcac | atgcgtggtg | gtggacgtga | gccacgaaga | ccctgaggtc | 720 |
| aagttcaact | ggtacgtgga | cggcgtggag | gtgcataatg | ccaagacaaa | gccgcgggag | 780 |
| gagcagtaca | acagcacgta | ccgtgtggtc | agcgtcctca | ccgtcctgca | ccaggactgg | 840 |
| ctgaatggca | aggagtacaa | gtgcaaggtc | tccaacaaag | ccctcccagc | ccccatcgag | 900 |
| aaaaccatct | ccaaagccaa | agggcagccc | cgagaaccac | aggtgtacac | cctgccccca | 960 |
| tcccgggatg | agctgaccaa | gaaccaggtc | agcctgacct | gcctggtcaa | aggcttctat | 1020 |
| cccagcgaca | tcgccgtgga | gtgggagagc | aatgggcagc | cggagaacaa | ctacaagacc | 1080 |
| acgcctcccg | tgctggactc | cgacggctcc | ttcttcctct | acagcaagct | caccgtggac | 1140 |
| aagagcaggt | ggcagcaggg | gaacgtcttc | tcatgctccg | tgatgcatga | ggctctgcac | 1200 |
| aaccactaca | cgcagaagag | cctctctctc | tctccgggta | aagtcgacgg | agctagcagc | 1260 |
| cccgtgaacg | tgagcagccc | cagcgtgcag | gatatcctct | tcaggaacca | ccagtcttct | 1320 |
| taccaaacac | gacttaatgc | tctccgagag | gtacaacccg | tagaacttcc | taactgtaat | 1380 |
| ttagttaaag | gaatcgaaac | tggctctgaa | gacttggaga | tactgcctaa | tggactggct | 1440 |
| ttcattagct | ctgattaaa | gtatcctgga | ataaagagct | tcaaccccaa | cagtcctgga | 1500 |
| aaaatacttc | tgatggacct | gaatgaagaa | gatccaacag | tgttggaatt | ggggatcact | 1560 |
| ggaagtaaat | ttgatgtatc | ttcatttaac | cctcatggga | ttagcacatt | cacagatgaa | 1620 |
| gataatgcca | tgtacctcct | ggtggtgaac | catccagatg | ccaagtccac | agtggagttg | 1680 |
| tttaaattc | aagaagaaga | aaaatcgctt | ttgcatctaa | aaaccatcag | acataaactt | 1740 |
| ctgcctaatt | tgaatgatat | tgttgctgtg | ggacctgagc | acttttatgg | cacaaatgat | 1800 |
| cactatttc | ttgaccccta | cttaaaatcc | tgggagatgt | atttgggttt | agcgtggtcg | 1860 |
| tatgttgtct | actatagtcc | aagtgaagtt | cgagtggtgg | cagaaggatt | tgattttgct | 1920 |
| aatggaatca | acatttcacc | cgatggcaag | tatgtctata | tagctgagtt | gctggctcat | 1980 |
| aagattcatg | tgtatgaaaa | gcatgctaat | tggacttta | ctccattgaa | gtcccttgac | 2040 |
| tttaatacc | tcgtggataa | catatctgtg | gatcctgaga | caggagacct | ttgggttgga | 2100 |
| tgccatccca | atggcatgaa | aatcttcttc | tatgactcag | agaatcctcc | tgcatcagag | 2160 |
| gtgcttcgaa | tccagaacat | tctaacagaa | gaacctaaag | tgcacaggt | ttatgcagaa | 2220 |

-continued

```
aatggcacag tgttgcaagg cagtacagtt gcctctgtgt acaaagggaa actgctgatt    2280
ggcacagtgt ttcacaaagc tctttactgt gagctc                              2316
```

<210> SEQ ID NO 38
<211> LENGTH: 772
<212> TYPE: PRT
<213> ORGANISM: Artificial Sequence
<220> FEATURE:
<223> OTHER INFORMATION: hRNase1-(g4s)4-[SSSH-P238S Fc]-NGS-[PON1 Q192K]
<220> FEATURE:
<221> NAME/KEY: SIGNAL
<222> LOCATION: (1)..(28)
<223> OTHER INFORMATION: human RNase 1 signal peptide
<220> FEATURE:
<221> NAME/KEY: MISC_FEATURE
<222> LOCATION: (29)..(156)
<223> OTHER INFORMATION: human RNase 1 mature polypeptide
<220> FEATURE:
<221> NAME/KEY: MISC_FEATURE
<222> LOCATION: (157)..(182)
<223> OTHER INFORMATION: (gly4ser)4 linker peptide with additional
      restriction site amino acids
<220> FEATURE:
<221> NAME/KEY: MISC_FEATURE
<222> LOCATION: (183)..(414)
<223> OTHER INFORMATION: human IgG1 variant Fc (SSS hinge, P238S)
<220> FEATURE:
<221> NAME/KEY: MISC_FEATURE
<222> LOCATION: (187)..(187)
<223> OTHER INFORMATION: Human IgG1 hinge C220S substitution
<220> FEATURE:
<221> NAME/KEY: MISC_FEATURE
<222> LOCATION: (193)..(193)
<223> OTHER INFORMATION: Human IgG1 hinge C226S substitution
<220> FEATURE:
<221> NAME/KEY: MISC_FEATURE
<222> LOCATION: (196)..(196)
<223> OTHER INFORMATION: Human IgG1 hinge C229S substitution
<220> FEATURE:
<221> NAME/KEY: MISC_FEATURE
<222> LOCATION: (205)..(205)
<223> OTHER INFORMATION: Human IgG1 lower hinge-CH2 P238S substitution
<220> FEATURE:
<221> NAME/KEY: MISC_FEATURE
<222> LOCATION: (415)..(433)
<223> OTHER INFORMATION: peptide linker containing N-linked
      glyscosylation site
<220> FEATURE:
<221> NAME/KEY: MISC_FEATURE
<222> LOCATION: (434)..(772)
<223> OTHER INFORMATION: human PON1 Q192K without uncleaved leader
      peptide
<220> FEATURE:
<221> NAME/KEY: MISC_FEATURE
<222> LOCATION: (609)..(609)
<223> OTHER INFORMATION: PON1 Q192K amino acid substitution

<400> SEQUENCE: 38

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

```
Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr Asp Leu Ser Gly
145                 150                 155                 160

Gly Gly Gly Ser Gly Gly Gly Ser Gly Gly Gly Ser Gly Gly
                165                 170                 175

Gly Gly Ser Thr Gly Leu Glu Pro Lys Ser Ser Asp Lys Thr His Thr
            180                 185                 190

Ser Pro Pro Ser Pro Ala Pro Glu Leu Leu Gly Gly Ser Ser Val Phe
        195                 200                 205

Leu Phe Pro Pro Lys Pro Lys Asp Thr Leu Met Ile Ser Arg Thr Pro
    210                 215                 220

Glu Val Thr Cys Val Val Val Asp Val Ser His Glu Asp Pro Glu Val
225                 230                 235                 240

Lys Phe Asn Trp Tyr Val Asp Gly Val Glu Val His Asn Ala Lys Thr
            245                 250                 255

Lys Pro Arg Glu Glu Gln Tyr Asn Ser Thr Tyr Arg Val Val Ser Val
        260                 265                 270

Leu Thr Val Leu His Gln Asp Trp Leu Asn Gly Lys Glu Tyr Lys Cys
    275                 280                 285

Lys Val Ser Asn Lys Ala Leu Pro Ala Pro Ile Glu Lys Thr Ile Ser
290                 295                 300

Lys Ala Lys Gly Gln Pro Arg Glu Pro Gln Val Tyr Thr Leu Pro Pro
305                 310                 315                 320

Ser Arg Asp Glu Leu Thr Lys Asn Gln Val Ser Leu Thr Cys Leu Val
            325                 330                 335

Lys Gly Phe Tyr Pro Ser Asp Ile Ala Val Glu Trp Glu Ser Asn Gly
        340                 345                 350

Gln Pro Glu Asn Asn Tyr Lys Thr Thr Pro Pro Val Leu Asp Ser Asp
    355                 360                 365

Gly Ser Phe Phe Leu Tyr Ser Lys Leu Thr Val Asp Lys Ser Arg Trp
370                 375                 380

Gln Gln Gly Asn Val Phe Ser Cys Ser Val Met His Glu Ala Leu His
385                 390                 395                 400

Asn His Tyr Thr Gln Lys Ser Leu Ser Leu Ser Pro Gly Lys Val Asp
            405                 410                 415

Gly Ala Ser Ser Pro Val Asn Val Ser Ser Pro Ser Val Gln Asp Ile
        420                 425                 430

Leu Phe Arg Asn His Gln Ser Ser Tyr Gln Thr Arg Leu Asn Ala Leu
    435                 440                 445

Arg Glu Val Gln Pro Val Glu Leu Pro Asn Cys Asn Leu Val Lys Gly
450                 455                 460

Ile Glu Thr Gly Ser Glu Asp Leu Glu Ile Leu Pro Asn Gly Leu Ala
465                 470                 475                 480

Phe Ile Ser Ser Gly Leu Lys Tyr Pro Gly Ile Lys Ser Phe Asn Pro
            485                 490                 495

Asn Ser Pro Gly Lys Ile Leu Leu Met Asp Leu Asn Glu Glu Asp Pro
        500                 505                 510

Thr Val Leu Glu Leu Gly Ile Thr Gly Ser Lys Phe Asp Val Ser Ser
```

```
                515                 520                 525
Phe Asn Pro His Gly Ile Ser Thr Phe Thr Asp Glu Asp Asn Ala Met
    530                 535                 540

Tyr Leu Leu Val Val Asn His Pro Asp Ala Lys Ser Thr Val Glu Leu
545                 550                 555                 560

Phe Lys Phe Gln Glu Glu Lys Ser Leu Leu His Leu Lys Thr Ile
                565                 570                 575

Arg His Lys Leu Leu Pro Asn Leu Asn Asp Ile Val Ala Val Gly Pro
            580                 585                 590

Glu His Phe Tyr Gly Thr Asn Asp His Tyr Phe Leu Asp Pro Tyr Leu
        595                 600                 605

Lys Ser Trp Glu Met Tyr Leu Gly Leu Ala Trp Ser Tyr Val Val Tyr
    610                 615                 620

Tyr Ser Pro Ser Glu Val Arg Val Val Ala Glu Gly Phe Asp Phe Ala
625                 630                 635                 640

Asn Gly Ile Asn Ile Ser Pro Asp Gly Lys Tyr Val Tyr Ile Ala Glu
                645                 650                 655

Leu Leu Ala His Lys Ile His Val Tyr Glu Lys His Ala Asn Trp Thr
            660                 665                 670

Leu Thr Pro Leu Lys Ser Leu Asp Phe Asn Thr Leu Val Asp Asn Ile
        675                 680                 685

Ser Val Asp Pro Glu Thr Gly Asp Leu Trp Val Gly Cys His Pro Asn
    690                 695                 700

Gly Met Lys Ile Phe Phe Tyr Asp Ser Glu Asn Pro Pro Ala Ser Glu
705                 710                 715                 720

Val Leu Arg Ile Gln Asn Ile Leu Thr Glu Glu Pro Lys Val Thr Gln
                725                 730                 735

Val Tyr Ala Glu Asn Gly Thr Val Leu Gln Gly Ser Thr Val Ala Ser
            740                 745                 750

Val Tyr Lys Gly Lys Leu Leu Ile Gly Thr Val Phe His Lys Ala Leu
        755                 760                 765

Tyr Cys Glu Leu
    770

<210> SEQ ID NO 39
<211> LENGTH: 2292
<212> TYPE: DNA
<213> ORGANISM: Artificial Sequence
<220> FEATURE:
<223> OTHER INFORMATION: hVK3LP-hRNase1-(g4s)4-[SSHinge-P238S Fc]-NGS-
      [PON1 Q192K] DNA

<400> SEQUENCE: 39
atggaaaccc cagcgcagct tctcttcctc ctgctactct ggctcccaga taccaccggt      60
aaggaatccc gggccaagaa attccagcgg cagcatatgg actcagacag ttcccccagc     120
agcagctcca cctactgtaa ccaaatgatg aggcgccgga atatgacaca ggggcgtgc      180 aaaccagtga acacctttgt gcacgagccc ctggtagatg tccagaatgt ctgtttccag     240
gaaaaggtca cctgcaagaa cgggcagggc aactgctaca agagcaactc cagcatgcac     300
atcacagact gccgcctgac aaacggctcc aggtacccca ctgtgcata ccggaccagc     360 ccgaaggaga gacacatcat tgtggcctgt gaagggagcc catatgtgcc agtccacttt     420
gatgcttctg tggaggactc tacagatctc tccggaggag gtggctcagg tggtggagga     480
tctggaggag gtgggagtgg tggaggtggt tctaccggtc tcgagcccaa atcttctgac     540
```

```
aaaactcaca catctccacc gtccccagca cctgaactcc tgggaggatc gtcagtcttc    600
ctcttccccc caaacccaa ggacaccctc atgatctccc ggaccctga ggtcacatgc      660 gtggtggtgg acgtgagcca cgaagaccct gaggtcaagt tcaactggta cgtggacggc    720
gtggaggtgc ataatgccaa gacaaagccg cgggaggagc agtacaacag cacgtaccgt    780
gtggtcagcg tcctcaccgt cctgcaccag gactggctga atggcaagga gtacaagtgc    840
aaggtctcca acaaagccct cccagccccc atcgagaaaa ccatctccaa agccaaaggg    900
cagccccgag aaccacaggt gtacaccctg cccccatccc gggatgagct gaccaagaac    960
caggtcagcc tgacctgcct ggtcaaaggc ttctatccca gcgacatcgc cgtggagtgg   1020
gagagcaatg ggcagccgga gaacaactac aagaccacgc ctcccgtgct ggactccgac   1080
ggctccttct cctctacag caagctcacc gtggacaaga gcaggtggca gcaggggaac   1140
gtcttctcat gctccgtgat gcatgaggct ctgcacaacc actacacgca gaagagcctc   1200
tctctctctc cgggtaaagt cgacggagct agcagcccg tgaacgtgag cagccccagc    1260
gtgcaggata tcctcttcag gaaccaccag tcttcttacc aaacacgact taatgctctc   1320
cgagaggtac aacccgtaga acttcctaac tgtaatttag ttaaaggaat cgaaactggc    1380
tctgaagact tggagatact gcctaatgga ctggctttca ttagctctgg attaaagtat    1440
cctggaataa agagcttcaa ccccaacagt cctggaaaaa tacttctgat ggacctgaat    1500
gaagaagatc aacagtgttt ggaattgggg atcactggaa gtaaatttga tgtatcttca    1560
tttaaccctc atgggattag cacattcaca gatgaagata atgccatgta cctcctggtg    1620
gtgaaccatc cagatgccaa gtccacagtg gagttgttta atttcaaga agaagaaaaa    1680 tcgcttttgc atctaaaaac catcagacat aaacttctgc ctaatttgaa tgatattgtt    1740
gctgtgggac ctgagcactt ttatggcaca atgatcact attttcttga ccctactta    1800 aaatcctggg agatgtattt gggtttagcg tggtcgtatg ttgtctacta tagtccaagt    1860
gaagttcgag tggtggcaga aggatttgat tttgctaatg gaatcaacat ttcacccgat    1920
ggcaagtatg tctatatagc tgagttgctg gctcataaga ttcatgtgta tgaaaagcat    1980
gctaattgga ctttaactcc attgaagtcc cttgactta taccctcgt ggataacata    2040 tctgtggatc ctgagacagg agacctttgg gttggatgcc atcccaatgg catgaaaatc    2100
ttcttctatg actcagagaa tcctcctgca tcagaggtgc ttcgaatcca gaacattcta    2160
acagaagaac ctaaagtgac acaggtttat gcagaaaatg gcacagtgtt gcaaggcagt    2220
acagttgcct ctgtgtacaa agggaaactg ctgattggca cagtgtttca caaagctctt    2280
tactgtgagc tc                                                       2292

<210> SEQ ID NO 40
<211> LENGTH: 764
<212> TYPE: PRT
<213> ORGANISM: Artificial Sequence
<220> FEATURE:
<223> OTHER INFORMATION: hVK3LP-hRNase1-(g4s)4-[SSShinge-P238S Fc]-NGS-
      [PON1 Q192K]
<220> FEATURE:
<221> NAME/KEY: SIGNAL
<222> LOCATION: (1)..(20)
<223> OTHER INFORMATION: human VK3 signal peptide
<220> FEATURE:
<221> NAME/KEY: MISC_FEATURE
<222> LOCATION: (21)..(148)
<223> OTHER INFORMATION: human RNase1 mature polypeptide
<220> FEATURE:
<221> NAME/KEY: MISC_FEATURE
<222> LOCATION: (149)..(174)
```

```
<223> OTHER INFORMATION: (gly4ser)4 linker peptide with addtional
      restriction site amino acids
<220> FEATURE:
<221> NAME/KEY: MISC_FEATURE
<222> LOCATION: (175)..(406)
<223> OTHER INFORMATION: human IgG1 variant Fc (SSS hinge, P238S)
<220> FEATURE:
<221> NAME/KEY: MISC_FEATURE
<222> LOCATION: (179)..(179)
<223> OTHER INFORMATION: human IgG1 hinge C220S amino acid substitution
<220> FEATURE:
<221> NAME/KEY: MISC_FEATURE
<222> LOCATION: (185)..(185)
<223> OTHER INFORMATION: human IgG1 hinge C226S amino acid substitution
<220> FEATURE:
<221> NAME/KEY: MISC_FEATURE
<222> LOCATION: (188)..(188)
<223> OTHER INFORMATION: human IgG1 hinge C229S amino acid substitution
<220> FEATURE:
<221> NAME/KEY: MISC_FEATURE
<222> LOCATION: (197)..(197)
<223> OTHER INFORMATION: human IgG1 lower hinge-CH2 P238S amino acid
      substitution
<220> FEATURE:
<221> NAME/KEY: MISC_FEATURE
<222> LOCATION: (407)..(425)
<223> OTHER INFORMATION: peptide linker containing N linked
      glyscosylation site
<220> FEATURE:
<221> NAME/KEY: MISC_FEATURE
<222> LOCATION: (426)..(764)
<223> OTHER INFORMATION: human PON1 Q192K without uncleaved leader
      peptide
<220> FEATURE:
<221> NAME/KEY: MISC_FEATURE
<222> LOCATION: (601)..(601)
<223> OTHER INFORMATION: PON1 Q192K amino acid substitution

<400> SEQUENCE: 40

Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Gly Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Asp Leu Ser Gly Gly Gly Ser Gly Gly Gly Gly
145                 150                 155                 160

Ser Gly Gly Gly Gly Ser Gly Gly Gly Gly Ser Thr Gly Leu Glu Pro
                165                 170                 175

Lys Ser Ser Asp Lys Thr His Thr Ser Pro Pro Ser Pro Ala Pro Glu
            180                 185                 190

Leu Leu Gly Gly Ser Ser Val Phe Leu Phe Pro Pro Lys Pro Lys Asp
        195                 200                 205
```

```
Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
                260                 265                 270

Leu Asn Gly Lys Glu Tyr Lys Cys Lys Val Ser Asn Lys Ala Leu Pro
            275                 280                 285

Ala Pro Ile Glu Lys Thr Ile Ser Lys Ala Lys Gly Gln Pro Arg Glu
290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
                340                 345                 350

Thr Pro Pro Val Leu Asp Ser Asp Gly Ser Phe Phe Leu Tyr Ser Lys
            355                 360                 365

Leu Thr Val Asp Lys Ser Arg Trp Gln Gln Gly Asn Val Phe Ser Cys
370                 375                 380

Ser Val Met His Glu Ala Leu His Asn His Tyr Thr Gln Lys Ser Leu
385                 390                 395                 400

Ser Leu Ser Pro Gly Lys Val Asp Gly Ala Ser Ser Pro Val Asn Val
                405                 410                 415

Ser Ser Pro Ser Val Gln Asp Ile Leu Phe Arg Asn His Gln Ser Ser
                420                 425                 430

Tyr Gln Thr Arg Leu Asn Ala Leu Arg Glu Val Gln Pro Val Glu Leu
            435                 440                 445

Pro Asn Cys Asn Leu Val Lys Gly Ile Glu Thr Gly Ser Glu Asp Leu
450                 455                 460

Glu Ile Leu Pro Asn Gly Leu Ala Phe Ile Ser Ser Gly Leu Lys Tyr
465                 470                 475                 480

Pro Gly Ile Lys Ser Phe Asn Pro Asn Ser Pro Gly Lys Ile Leu Leu
                485                 490                 495

Met Asp Leu Asn Glu Glu Asp Pro Thr Val Leu Glu Leu Gly Ile Thr
                500                 505                 510

Gly Ser Lys Phe Asp Val Ser Ser Phe Asn Pro His Gly Ile Ser Thr
            515                 520                 525

Phe Thr Asp Glu Asp Asn Ala Met Tyr Leu Leu Val Val Asn His Pro
530                 535                 540

Asp Ala Lys Ser Thr Val Glu Leu Phe Lys Phe Gln Glu Glu Glu Lys
545                 550                 555                 560

Ser Leu Leu His Leu Lys Thr Ile Arg His Lys Leu Leu Pro Asn Leu
                565                 570                 575

Asn Asp Ile Val Ala Val Gly Pro Glu His Phe Tyr Gly Thr Asn Asp
                580                 585                 590

His Tyr Phe Leu Asp Pro Tyr Leu Lys Ser Trp Glu Met Tyr Leu Gly
            595                 600                 605

Leu Ala Trp Ser Tyr Val Val Tyr Tyr Ser Pro Ser Glu Val Arg Val
610                 615                 620

Val Ala Glu Gly Phe Asp Phe Ala Asn Gly Ile Asn Ile Ser Pro Asp
```

| | | | | | | | | | | | | | |
|---|---|---|---|---|---|---|---|---|---|---|---|---|---|
| | 625 | | | 630 | | | 635 | | | 640 | | | |
| Gly | Lys | Tyr | Val | Tyr | Ile | Ala | Glu | Leu | Leu | Ala | His | Lys | Ile His Val |
| | | | 645 | | | | 650 | | | | 655 | | |

Tyr Glu Lys His Ala Asn Trp Thr Leu Thr Pro Leu Lys Ser Leu Asp
              660                 665                 670

Phe Asn Thr Leu Val Asp Asn Ile Ser Val Asp Pro Glu Thr Gly Asp
              675                 680                 685

Leu Trp Val Gly Cys His Pro Asn Gly Met Lys Ile Phe Phe Tyr Asp
      690                 695                 700

Ser Glu Asn Pro Pro Ala Ser Glu Val Leu Arg Ile Gln Asn Ile Leu
705                 710                 715                 720

Thr Glu Glu Pro Lys Val Thr Gln Val Tyr Ala Glu Asn Gly Thr Val
                    725                 730                 735

Leu Gln Gly Ser Thr Val Ala Ser Val Tyr Lys Gly Lys Leu Leu Ile
              740                 745                 750

Gly Thr Val Phe His Lys Ala Leu Tyr Cys Glu Leu
              755                 760

<210> SEQ ID NO 41
<211> LENGTH: 1170
<212> TYPE: DNA
<213> ORGANISM: Artificial Sequence
<220> FEATURE:
<223> OTHER INFORMATION: hRNase1-[SSShinge-P238S Fc] DNA

<400> SEQUENCE: 41

```
atggctctgg agaagtctct tgtccggctc cttctgcttg tcctgatact gctggtgctg      60
ggctgggtcc agccttccct gggcaaggaa tcccgggcca agaaattcca gcggcagcat     120
atggactcag acagttcccc cagcagcagc tccacctact gtaaccaaat gatgaggcgc     180
cggaatatga cacagggggcg gtgcaaacca gtgaacacct tgtgcacga gccctggta     240
gatgtccaga atgtctgttt ccaggaaaag gtcacctgca gaacgggca gggcaactgc     300
tacaagagca actccagcat gcacatcaca gactgccgcc tgacaaacgg ctccaggtac     360
cccaactgtg cataccggac cagcccgaag gagagacaca tcattgtggc ctgtgaaggg     420
agcccatatg tgccagtcca cttttgatgct tctgtggagg actctacaga tctcgagccc     480
aaatcttctg acaaaactca cacatctcca ccgtccccag cacctgaact cctgggggga     540
tcgtcagtct tcctcttccc cccaaaaccc aaggacaccc tcatgatctc ccggacccct     600
gaggtcacat gcgtggtggt ggacgtgagc cacgaagacc ctgaggtcaa gttcaactgg     660
tacgtggacg gcgtggaggt gcataatgcc aagacaaagc cgcgggagga gcagtacaac     720
agcacgtacc gtgtggtcag cgtcctcacc gtcctgcacc aggactggct gaatggcaag     780
gagtacaagt gcaaggtctc caacaaagcc ctcccagccc catcgagaa aaccatctcc     840
aaagccaaag gcagccccg agaaccacag gtgtacaccc tgcccccatc ccgggatgag     900
ctgaccaaga accaggtcag cctgacctgc ctggtcaaag gcttctatcc cagcgacatc     960
gccgtggagt gggagagcaa tgggcagccg gagaacaact acaagaccac gcctcccgtg    1020
ctggactccg acggctcctt cttcctctac agcaagctca ccgtggacaa gagcaggtgg    1080
cagcagggga acgtcttctc atgctccgtg atgcatgagg ctctgcacaa ccactacacg    1140
cagaagagcc tctctctgtc tccgggtaaa                                      1170
```

<210> SEQ ID NO 42
<211> LENGTH: 390

```
<212> TYPE: PRT
<213> ORGANISM: Artificial Sequence
<220> FEATURE:
<223> OTHER INFORMATION: hRNase1-[SSShinge-P238S Fc]
<220> FEATURE:
<221> NAME/KEY: SIGNAL
<222> LOCATION: (1)..(28)
<223> OTHER INFORMATION: human RNase1 signal peptide
<220> FEATURE:
<221> NAME/KEY: MISC_FEATURE
<222> LOCATION: (29)..(156)
<223> OTHER INFORMATION: human RNase1 mature polypeptide
<220> FEATURE:
<221> NAME/KEY: MISC_FEATURE
<222> LOCATION: (157)..(158)
<223> OTHER INFORMATION: restriction site amino acids
<220> FEATURE:
<221> NAME/KEY: MISC_FEATURE
<222> LOCATION: (159)..(390)
<223> OTHER INFORMATION: human IgG1 variant Fc (SSS hinge, P238S)
<220> FEATURE:
<221> NAME/KEY: MISC_FEATURE
<222> LOCATION: (163)..(163)
<223> OTHER INFORMATION: human IgG1 hinge domain C220S substitution
<220> FEATURE:
<221> NAME/KEY: MISC_FEATURE
<222> LOCATION: (169)..(169)
<223> OTHER INFORMATION: human IgG1 hinge domain C226S substitution
<220> FEATURE:
<221> NAME/KEY: MISC_FEATURE
<222> LOCATION: (172)..(172)
<223> OTHER INFORMATION: human IgG1 hinge domain C229S substitution
<220> FEATURE:
<221> NAME/KEY: MISC_FEATURE
<222> LOCATION: (181)..(181)
<223> OTHER INFORMATION: human IgG1 lower hinge-CH2 domain P238S
      substitution

<400> SEQUENCE: 42

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr Asp Leu Glu Pro
145                 150                 155                 160

Lys Ser Ser Asp Lys Thr His Thr Ser Pro Pro Ser Pro Ala Pro Glu
                165                 170                 175

Leu Leu Gly Gly Ser Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205
```

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390

<210> SEQ ID NO 43
<211> LENGTH: 1146
<212> TYPE: DNA
<213> ORGANISM: Artificial Sequence
<220> FEATURE:
<223> OTHER INFORMATION: hVK3LP-hRNase1-[SSShinge-P238S Fc] DNA

<400> SEQUENCE: 43

```
atggaaaccc cagcgcagct tctcttcctc ctgctactct ggctcccaga taccaccggt      60
aaggaatccc gggccaagaa attccagcgg cagcatatgg actcagacag ttcccccagc     120
agcagctcca cctactgtaa ccaaatgatg aggcgccgga atatgacaca ggggcggtgc     180
aaaccagtga acaccttttgt gcacgagccc ctggtagatg tccagaatgt ctgtttccag     240
gaaaaggtca cctgcaagaa cgggcagggc aactgctaca agagcaactc cagcatgcac     300
atcacagact gccgcctgac aaacgactcc aggtacccca actgtgcata ccggaccagc     360
ccgaaggaga gacacatcat tgtggcctgt gaagggagcc catatgtgcc agtccacttt     420
gatgcttctg tggaggactc tacagatctc gagcccaaat cttctgacaa aactcacaca     480
tctccaccgt ccccagcacc tgaactcctg gggggatcgt cagtcttcct cttccccca      540
aaacccaagg acaccctcat gatctcccgg acccctgagg tcacatgcgt ggtggtggac     600
gtgagccacg aagaccctga ggtcaagttc aactggtacg tggacggcgt ggaggtgcat     660
aatgccaaga caaagccgcg ggaggagcag tacaacagca cgtaccgtgt ggtcagcgtc     720
ctcaccgtcc tgcaccagga ctggctgaat ggcaaggagt acaagtgcaa ggtctccaac     780
aaagccctcc cagcccccat cgagaaaacc atctccaaag ccaagggca gccccgagaa     840
ccacaggtgt acaccctgcc cccatcccgg gatgagctga ccaagaacca ggtcagcctg     900
acctgcctgg tcaaaggctt ctatcccagc gacatcgccg tggagtggga gagcaatggg     960
cagccggaga acaactacaa gaccacgcct cccgtgctgg actccgacgg ctccttcttc    1020
```

```
ctctacagca agctcaccgt ggacaagagc aggtggcagc aggggaacgt cttctcatgc   1080
tccgtgatgc atgaggctct gcacaaccac tacacgcaga gagcctctc tctgtctccg   1140 ggtaaa                                                              1146
```

<210> SEQ ID NO 44
<211> LENGTH: 382
<212> TYPE: PRT
<213> ORGANISM: Artificial Sequence
<220> FEATURE:
<223> OTHER INFORMATION: hVK3LP-hRNase1-[SSShinge-P238S Fc]
<220> FEATURE:
<221> NAME/KEY: SIGNAL
<222> LOCATION: (1)..(20)
<223> OTHER INFORMATION: Human VK3 leader peptide
<220> FEATURE:
<221> NAME/KEY: MISC_FEATURE
<222> LOCATION: (21)..(148)
<223> OTHER INFORMATION: human RNase 1 mature polytpeptide
<220> FEATURE:
<221> NAME/KEY: MISC_FEATURE
<222> LOCATION: (149)..(150)
<223> OTHER INFORMATION: restriction site amino acids
<220> FEATURE:
<221> NAME/KEY: MISC_FEATURE
<222> LOCATION: (151)..(382)
<223> OTHER INFORMATION: human IgG1 variant Fc (SSS hinge, P238S)
<220> FEATURE:
<221> NAME/KEY: MISC_FEATURE
<222> LOCATION: (155)..(155)
<223> OTHER INFORMATION: human IgG1 hinge C220S amino acid substitution
<220> FEATURE:
<221> NAME/KEY: MISC_FEATURE
<222> LOCATION: (161)..(161)
<223> OTHER INFORMATION: human IgG1 hinge C226S amino acid substitution
<220> FEATURE:
<221> NAME/KEY: MISC_FEATURE
<222> LOCATION: (164)..(164)
<223> OTHER INFORMATION: human IgG1 hinge C229S amino acid substitution
<220> FEATURE:
<221> NAME/KEY: MISC_FEATURE
<222> LOCATION: (173)..(173)
<223> OTHER INFORMATION: human IgG1 lower hinge-CH2 P238S amino acid
      substitution

<400> SEQUENCE: 44

```
Met Glu Thr Pro Ala Gln Leu Leu Phe Leu Leu Leu Leu Trp Leu Pro
1               5                   10                  15

Asp Thr Thr Gly Lys Glu Ser Arg Ala Lys Lys Phe Gln Arg Gln His
            20                  25                  30

Met Asp Ser Asp Ser Ser Pro Ser Ser Ser Thr Tyr Cys Asn Gln
        35                  40                  45

Met Met Arg Arg Arg Asn Met Thr Gln Gly Arg Cys Lys Pro Val Asn
    50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                85                  90                  95

Ser Ser Met His Ile Thr Asp Cys Arg Leu Thr Asn Asp Ser Arg Tyr
            100                 105                 110

Pro Asn Cys Ala Tyr Arg Thr Ser Pro Lys Glu Arg His Ile Ile Val
        115                 120                 125

Ala Cys Glu Gly Ser Pro Tyr Val Pro Val His Phe Asp Ala Ser Val
    130                 135                 140

Glu Asp Ser Thr Asp Leu Glu Pro Lys Ser Ser Asp Lys Thr His Thr
145                 150                 155                 160
```

Ser Pro Pro Ser Pro Ala Pro Glu Leu Leu Gly Gly Ser Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Asp Glu Leu Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 45
<211> LENGTH: 2244
<212> TYPE: DNA
<213> ORGANISM: Artificial Sequence
<220> FEATURE:
<223> OTHER INFORMATION: hRNase1-[SSShinge-P238S Fc]-NGS-[PON1 Q192K]
      DNA

<400> SEQUENCE: 45

```
atggctctgg agaagtctct tgtccggctc cttctgcttg cctgatact gctggtgctg      60 ggctgggtcc agccttccct gggcaaggaa tcccgggcca agaaattcca gcggcagcat    120
atggactcag acagttcccc cagcagcagc tccacctact gtaaccaaat gatgaggcgc    180
cggaatatga cacaggggcg gtgcaaacca gtgaacacct tgtgcacga gcccctggta    240 gatgtccaga atgtctgttt ccaggaaaag gtcacctgca gaacgggca gggcaactgc    300 tacaagagca actccagcat gcacatcaca gactgccgcc tgacaaacgg ctccaggtac    360
cccaactgtg cataccggac cagcccgaag gagagacaca tcattgtggc ctgtgaaggg    420
agcccatatg tgccagtcca ctttgatgct tctgtggagg actctacaga tctcgagccc    480
aaatcttctg acaaaactca cacatctcca ccgtccccag cacctgaact cctgggagga    540
tcgtcagtct tcctcttccc cccaaaaccc aaggacaccc tcatgatctc ccggacccct    600
gaggtcacat gcgtggtggt ggacgtgagc cacgaagacc ctgaggtcaa gttcaactgg    660
tacgtggacg gcgtggaggt gcataatgcc aagacaaagc cgcgggagga gcagtacaac    720
agcacgtacc gtgtggtcag cgtcctcacc gtcctgcacc aggactggct gaatggcaag    780
```

-continued

```
gagtacaagt gcaaggtctc caacaaagcc ctcccagccc ccatcgagaa aaccatctcc    840
aaagccaaag gcagccccg agaaccacag gtgtacaccc tgcccccatc ccgggatgag    900
ctgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ctggactccg acggctcctt cttcctctac agcaagctca ccgtggacaa gagcaggtgg   1080
cagcagggga acgtcttctc atgctccgtg atgcatgagg ctctgcacaa ccactacacg   1140
cagaagagcc tctctctctc tccgggtaaa gtcgacggag ctagcagccc cgtgaacgtg   1200
agcagcccca gcgtgcagga tatcctcttc aggaaccacc agtcttctta ccaaacacga   1260
cttaatgctc tccgagaggt acaacccgta gaacttccta actgtaattt agttaaagga   1320
atcgaaactg ctctgaaga cttgagata ctgcctaatg gactggcttt cattagctct    1380
ggattaaagt atcctggaat aaagagcttc aaccccaaca gtcctggaaa atacttctg    1440 atggacctga tgaagaaga tccaacagtg ttggaattgg ggatcactgg aagtaaattt   1500
gatgtatctt catttaaccc tcatgggatt agcacattca cagatgaaga taatgccatg   1560
tacctcctgg tggtgaacca tccagatgcc aagtccacag tggagttgtt taaatttcaa   1620
gaagaagaaa atcgcttttt gcatctaaaa accatcagac ataaacttct gcctaatttg   1680
aatgatattg ttgctgtggg acctgagcac ttttatggca caaatgatca ctattttctt   1740 gaccccact taaaatcctg ggagatgtat ttgggtttag cgtggtcgta tgttgtctac   1800
tatagtccaa gtgaagttcg agtggtggca gaaggatttg atttgctaa tggaatcaac   1860 atttcacccg atggcaagta tgtctatata gctgagttgc tggctcataa gattcatgtg   1920
tatgaaaagc atgctaattg gactttaact ccattgaagt cccttgactt taataccctc   1980
gtggataaca tatctgtgga tcctgagaca ggagacctt gggttggatg ccatcccaat   2040
ggcatgaaaa tcttcttcta tgactcagag aatcctcctg catcagaggt gcttcgaatc   2100
cagaacattc taacagaaga acctaaagtg acacaggttt atgcagaaaa tggcacagtg   2160
ttgcaaggca gtacagttgc ctctgtgtac aaagggaaac tgctgattgg cacagtgttt   2220
cacaaagctc tttactgtga gctc                                          2244
```

```
<210> SEQ ID NO 46
<211> LENGTH: 748
<212> TYPE: PRT
<213> ORGANISM: Artificial Sequence
<220> FEATURE:
<223> OTHER INFORMATION: hRNase1-[SSShinge-P238S Fc]-NGS-[PON1 Q192K]
<220> FEATURE:
<221> NAME/KEY: SIGNAL
<222> LOCATION: (1)..(28)
<223> OTHER INFORMATION: human RNase 1 signal peptide
<220> FEATURE:
<221> NAME/KEY: MISC_FEATURE
<222> LOCATION: (29)..(156)
<223> OTHER INFORMATION: human RNase 1 mature polypeptide
<220> FEATURE:
<221> NAME/KEY: MISC_FEATURE
<222> LOCATION: (157)..(158)
<223> OTHER INFORMATION: restriction site amino acids
<220> FEATURE:
<221> NAME/KEY: MISC_FEATURE
<222> LOCATION: (159)..(390)
<223> OTHER INFORMATION: human IgG1 variant Fc (SSS hinge, P238S)
<220> FEATURE:
<221> NAME/KEY: MISC_FEATURE
<222> LOCATION: (163)..(163)
<223> OTHER INFORMATION: human IgG1 hinge C220S amino acid substitution
<220> FEATURE:
```

```
<221> NAME/KEY: MISC_FEATURE
<222> LOCATION: (169)..(169)
<223> OTHER INFORMATION: human IgG1 hinge C226S amino acid substitution
<220> FEATURE:
<221> NAME/KEY: MISC_FEATURE
<222> LOCATION: (172)..(172)
<223> OTHER INFORMATION: human IgG1 hinge C229S amino acid substitution
<220> FEATURE:
<221> NAME/KEY: MISC_FEATURE
<222> LOCATION: (182)..(182)
<223> OTHER INFORMATION: human IgG1lower hinge-CH2 P238S amino acid
      substitution
<220> FEATURE:
<221> NAME/KEY: MISC_FEATURE
<222> LOCATION: (391)..(409)
<223> OTHER INFORMATION: peptide linker containing N-linked
      glycosylation site
<220> FEATURE:
<221> NAME/KEY: MISC_FEATURE
<222> LOCATION: (410)..(748)
<223> OTHER INFORMATION: human PON1 Q192K without uncleaved leader
      peptide
<220> FEATURE:
<221> NAME/KEY: MISC_FEATURE
<222> LOCATION: (585)..(585)
<223> OTHER INFORMATION: human PON1 Q192K amino acid substitution

<400> SEQUENCE: 46

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr Asp Leu Glu Pro
145                 150                 155                 160

Lys Ser Ser Asp Lys Thr His Thr Ser Pro Pro Ser Pro Ala Pro Glu
                165                 170                 175

Leu Leu Gly Gly Ser Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270
```

```
Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
        290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
            325                 330                 335

Thr Pro Pro Val Leu Asp Ser Asp Gly Ser Phe Phe Leu Tyr Ser Lys
                340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
        370                 375                 380

Ser Leu Ser Pro Gly Lys Val Asp Gly Ala Ser Ser Pro Val Asn Val
385                 390                 395                 400

Ser Ser Pro Ser Val Gln Asp Ile Leu Phe Arg Asn His Gln Ser Ser
                405                 410                 415

Tyr Gln Thr Arg Leu Asn Ala Leu Arg Glu Val Gln Pro Val Glu Leu
                420                 425                 430

Pro Asn Cys Asn Leu Val Lys Gly Ile Glu Thr Gly Ser Glu Asp Leu
        435                 440                 445

Glu Ile Leu Pro Asn Gly Leu Ala Phe Ile Ser Ser Gly Leu Lys Tyr
        450                 455                 460

Pro Gly Ile Lys Ser Phe Asn Pro Asn Ser Pro Gly Lys Ile Leu Leu
465                 470                 475                 480

Met Asp Leu Asn Glu Glu Asp Pro Thr Val Leu Glu Leu Gly Ile Thr
            485                 490                 495

Gly Ser Lys Phe Asp Val Ser Ser Phe Asn Pro His Gly Ile Ser Thr
                500                 505                 510

Phe Thr Asp Glu Asp Asn Ala Met Tyr Leu Leu Val Asn His Pro
        515                 520                 525

Asp Ala Lys Ser Thr Val Glu Leu Phe Lys Phe Gln Glu Glu Glu Lys
        530                 535                 540

Ser Leu Leu His Leu Lys Thr Ile Arg His Lys Leu Leu Pro Asn Leu
545                 550                 555                 560

Asn Asp Ile Val Ala Val Gly Pro Glu His Phe Tyr Gly Thr Asn Asp
            565                 570                 575

His Tyr Phe Leu Asp Pro Tyr Leu Lys Ser Trp Glu Met Tyr Leu Gly
                580                 585                 590

Leu Ala Trp Ser Tyr Val Val Tyr Tyr Ser Pro Ser Glu Val Arg Val
        595                 600                 605

Val Ala Glu Gly Phe Asp Phe Ala Asn Gly Ile Asn Ile Ser Pro Asp
        610                 615                 620

Gly Lys Tyr Val Tyr Ile Ala Glu Leu Leu Ala His Lys Ile His Val
625                 630                 635                 640

Tyr Glu Lys His Ala Asn Trp Thr Leu Thr Pro Leu Lys Ser Leu Asp
            645                 650                 655

Phe Asn Thr Leu Val Asp Asn Ile Ser Val Asp Pro Glu Thr Gly Asp
                660                 665                 670

Leu Trp Val Gly Cys His Pro Asn Gly Met Lys Ile Phe Phe Tyr Asp
        675                 680                 685
```

```
Ser Glu Asn Pro Pro Ala Ser Glu Val Leu Arg Ile Gln Asn Ile Leu
    690                 695                 700

Thr Glu Glu Pro Lys Val Thr Gln Val Tyr Ala Glu Asn Gly Thr Val
705                 710                 715                 720

Leu Gln Gly Ser Thr Val Ala Ser Val Tyr Lys Gly Lys Leu Leu Ile
                725                 730                 735

Gly Thr Val Phe His Lys Ala Leu Tyr Cys Glu Leu
                740                 745
```

<210> SEQ ID NO 47
<211> LENGTH: 2220
<212> TYPE: DNA
<213> ORGANISM: Artificial Sequence
<220> FEATURE:
<223> OTHER INFORMATION: hVK3LP-hRNase1-[SSShinge-P238S Fc]-NGS-[PON1 Q192K] DNA

<400> SEQUENCE: 47

| | |
|---|---|
| atggaaaccc cagcgcagct tctcttcctc ctgctactct ggctcccaga taccaccggt | 60 |
| aaggaatccc gggccaagaa attccagcgg cagcatatgg actcagacag ttcccccagc | 120 |
| agcagctcca cctactgtaa ccaaatgatg aggcgccgga atatgacaca ggggcggtgc | 180 |
| aaaccagtga cacctttgt gcacgagccc ctggtagatg tccagaatgt ctgtttccag | 240 |
| gaaaaggtca cctgcaagaa cgggcagggc aactgctaca agagcaactc cagcatgcac | 300 |
| atcacagact gccgcctgac aaacggctcc aggtacccca ctgtgcata ccggaccagc | 360 |
| ccgaaggaga gacacatcat tgtggcctgt gaagggagcc catatgtgcc agtccacttt | 420 |
| gatgcttctg tggaggactc tacagatctc gagcccaaat cttctgacaa aactcacaca | 480 |
| tctccaccgt ccccagcacc tgaactcctg ggaggatcgt cagtcttcct cttccccca | 540 |
| aaacccaagg acaccctcat gatctcccgg acccctgagg tcacatgcgt ggtggtggac | 600 |
| gtgagccacg aagaccctga ggtcaagttc aactggtacg tggacggcgt ggaggtgcat | 660 |
| aatgccaaga caaagccgcg ggaggagcag tacaacagca cgtaccgtgt ggtcagcgtc | 720 |
| ctcaccgtcc tgcaccagga ctggctgaat ggcaaggagt acaagtgcaa ggtctccaac | 780 |
| aaagccctcc cagcccccat cgagaaaacc atctccaaag ccaaagggca gccccgagaa | 840 |
| ccacaggtgt acaccctgcc cccatcccgg gatgagctga ccaagaacca ggtcagcctg | 900 |
| acctgcctgg tcaaaggctt ctatcccagc gacatcgccg tggagtggga gagcaatggg | 960 |
| cagccggaga caactacaa gaccacgcct cccgtgctgg actccgacgg ctccttcttc | 1020 |
| ctctacagca agctcaccgt ggacaagagc aggtggcagc aggggaacgt cttctcatgc | 1080 |
| tccgtgatgc atgaggctct gcacaaccac tacacgcaga agagcctctc tctctctccg | 1140 |
| ggtaaagtcg acggagctag cagccccgtg aacgtgagca gccccagcgt gcaggatatc | 1200 |
| ctcttcagga ccaccagtc ttcttaccaa acacgactta atgctctccg agaggtacaa | 1260 |
| cccgtagaac ttcctaactg taattagtt aaaggaatcg aaactggctc tgaagacttg | 1320 |
| gagatactgc taatggact ggctttcatt agctctggat taaagtatcc tggaataaag | 1380 |
| agcttcaacc ccaacagtcc tggaaaaata cttctgatgg acctgaatga agaagatcca | 1440 |
| acagtgttgg aattggggat cactggaagt aaatttgatg tatcttcatt taaccctcat | 1500 |
| gggattagca cattcacaga tgaagataat gccatgtacc tcctggtggt gaaccatcca | 1560 |
| gatgccaagt ccacagtgga gttgtttaaa tttcaagaag aagaaaaatc gcttttgcat | 1620 |
| ctaaaaacca tcagacataa acttctgcct aatttgaatg atattgttgc tgtgggacct | 1680 |

```
gagcactttt atggcacaaa tgatcactat tttcttgacc cctacttaaa atcctgggag  1740
atgtatttgg gtttagcgtg gtcgtatgtt gtctactata gtccaagtga agttcgagtg  1800
gtggcagaag gatttgattt tgctaatgga atcaacattt cacccgatgg caagtatgtc  1860
tatatagctg agttgctggc tcataagatt catgtgtatg aaaagcatgc taattggact  1920
ttaactccat tgaagtccct tgactttaat accctcgtgg ataacatatc tgtggatcct  1980
gagacaggag accttltgggt tggatgccat cccaatggca tgaaaatctt cttctatgac  2040
tcagagaatc ctcctgcatc agaggtgctt cgaatccaga acattctaac agaagaacct  2100
aaagtgacac aggtttatgc agaaaatggc acagtgttgc aaggcagtac agttgcctct  2160
gtgtacaaag ggaaactgct gattggcaca gtgtttcaca agctctttta ctgtgagctc  2220
```

<210> SEQ ID NO 48
<211> LENGTH: 740
<212> TYPE: PRT
<213> ORGANISM: Artificial Sequence
<220> FEATURE:
<223> OTHER INFORMATION: hVK3LP-hRNase1-[SSShinge-P238S Fc]-NGS-[PON1 Q192K]
<220> FEATURE:
<221> NAME/KEY: SIGNAL
<222> LOCATION: (1)..(20)
<223> OTHER INFORMATION: human VK3 leader peptide
<220> FEATURE:
<221> NAME/KEY: MISC_FEATURE
<222> LOCATION: (21)..(148)
<223> OTHER INFORMATION: human RNase 1 mature polypeptide
<220> FEATURE:
<221> NAME/KEY: MISC_FEATURE
<222> LOCATION: (149)..(150)
<223> OTHER INFORMATION: restriction site amino acids
<220> FEATURE:
<221> NAME/KEY: MISC_FEATURE
<222> LOCATION: (151)..(382)
<223> OTHER INFORMATION: human IgG1 variant Fc (SSS hinge, P238S)
<220> FEATURE:
<221> NAME/KEY: MISC_FEATURE
<222> LOCATION: (155)..(155)
<223> OTHER INFORMATION: human IgG1 hinge C220S amino acid substitution
<220> FEATURE:
<221> NAME/KEY: MISC_FEATURE
<222> LOCATION: (161)..(161)
<223> OTHER INFORMATION: human IgG1 hinge C226S amino acid substitution
<220> FEATURE:
<221> NAME/KEY: MISC_FEATURE
<222> LOCATION: (164)..(164)
<223> OTHER INFORMATION: human IgG1 hinge C229S amino acid substitution
<220> FEATURE:
<221> NAME/KEY: MISC_FEATURE
<222> LOCATION: (173)..(173)
<223> OTHER INFORMATION: human IgG1 lower hinge-CH2 P238S amino acid substitution
<220> FEATURE:
<221> NAME/KEY: MISC_FEATURE
<222> LOCATION: (383)..(401)
<223> OTHER INFORMATION: peptide linker containing N-linked glycosylation site
<220> FEATURE:
<221> NAME/KEY: MISC_FEATURE
<222> LOCATION: (402)..(740)
<223> OTHER INFORMATION: human PON1 Q192K without uncleaved leader peptide
<220> FEATURE:
<221> NAME/KEY: MISC_FEATURE
<222> LOCATION: (577)..(577)
<223> OTHER INFORMATION: human PON1 Q192K amino acid substitution

<400> SEQUENCE: 48

Met Glu Thr Pro Ala Gln Leu Leu Phe Leu Leu Leu Leu Trp Leu Pro
1               5                   10                  15

```
Asp Thr Thr Gly Lys Glu Ser Arg Ala Lys Lys Phe Gln Arg Gln His
             20                  25                  30

Met Asp Ser Asp Ser Ser Pro Ser Ser Ser Thr Tyr Cys Asn Gln
         35                  40                  45

Met Met Arg Arg Arg Asn Met Thr Gln Gly Arg Cys Lys Pro Val Asn
50                  55                  60

Thr Phe Val His Glu Pro Leu Val Asp Val Gln Asn Val Cys Phe Gln
65                  70                  75                  80

Glu Lys Val Thr Cys Lys Asn Gly Gln Gly Asn Cys Tyr Lys Ser Asn
                 85                  90                  95

Ser Ser Met His Ile Thr Asp Cys Arg Leu Thr Asn Gly Ser Arg Tyr
             100                 105                 110

Pro Asn Cys Ala Tyr Arg Thr Ser Pro Lys Glu Arg His Ile Ile Val
         115                 120                 125

Ala Cys Glu Gly Ser Pro Tyr Val Pro Val His Phe Asp Ala Ser Val
130                 135                 140

Glu Asp Ser Thr Asp Leu Glu Pro Lys Ser Ser Asp Lys Thr His Thr
145                 150                 155                 160

Ser Pro Pro Ser Pro Ala Pro Glu Leu Leu Gly Gly Ser Ser Val Phe
                 165                 170                 175

Leu Phe Pro Pro Lys Pro Lys Asp Thr Leu Met Ile Ser Arg Thr Pro
             180                 185                 190

Glu Val Thr Cys Val Val Val Asp Val Ser His Glu Asp Pro Glu Val
         195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                 245                 250                 255

Lys Val Ser Asn Lys Ala Leu Pro Ala Pro Ile Glu Lys Thr Ile Ser
             260                 265                 270

Lys Ala Lys Gly Gln Pro Arg Glu Pro Gln Val Tyr Thr Leu Pro Pro
         275                 280                 285

Ser Arg Asp Glu Leu Thr Lys Asn Gln Val Ser Leu Thr Cys Leu Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                 325                 330                 335

Gly Ser Phe Phe Leu Tyr Ser Lys Leu Thr Val Asp Lys Ser Arg Trp
             340                 345                 350

Gln Gln Gly Asn Val Phe Ser Cys Ser Val Met His Glu Ala Leu His
         355                 360                 365

Asn His Tyr Thr Gln Lys Ser Leu Ser Leu Ser Pro Gly Lys Val Asp
370                 375                 380

Gly Ala Ser Ser Pro Val Asn Val Ser Ser Pro Ser Val Gln Asp Ile
385                 390                 395                 400

Leu Phe Arg Asn His Gln Ser Ser Tyr Gln Thr Arg Leu Asn Ala Leu
                 405                 410                 415

Arg Glu Val Gln Pro Val Glu Leu Pro Asn Cys Asn Leu Val Lys Gly
             420                 425                 430

Ile Glu Thr Gly Ser Glu Asp Leu Glu Ile Leu Pro Asn Gly Leu Ala
```

```
                435             440             445
Phe Ile Ser Ser Gly Leu Lys Tyr Pro Gly Ile Lys Ser Phe Asn Pro
    450                 455                 460
Asn Ser Pro Gly Lys Ile Leu Leu Met Asp Leu Asn Glu Glu Asp Pro
465                 470                 475                 480
Thr Val Leu Glu Leu Gly Ile Thr Gly Ser Lys Phe Asp Val Ser Ser
                485                 490                 495
Phe Asn Pro His Gly Ile Ser Thr Phe Thr Asp Glu Asp Asn Ala Met
            500                 505                 510
Tyr Leu Leu Val Val Asn His Pro Asp Ala Lys Ser Thr Val Glu Leu
            515                 520                 525
Phe Lys Phe Gln Glu Glu Glu Lys Ser Leu Leu His Leu Lys Thr Ile
    530                 535                 540
Arg His Lys Leu Leu Pro Asn Leu Asn Asp Ile Val Ala Val Gly Pro
545                 550                 555                 560
Glu His Phe Tyr Gly Thr Asn Asp His Tyr Phe Leu Asp Pro Tyr Leu
                565                 570                 575
Lys Ser Trp Glu Met Tyr Leu Gly Leu Ala Trp Ser Tyr Val Val Tyr
            580                 585                 590
Tyr Ser Pro Ser Glu Val Arg Val Val Ala Glu Gly Phe Asp Phe Ala
    595                 600                 605
Asn Gly Ile Asn Ile Ser Pro Asp Gly Lys Tyr Val Tyr Ile Ala Glu
610                 615                 620
Leu Leu Ala His Lys Ile His Val Tyr Glu Lys His Ala Asn Trp Thr
625                 630                 635                 640
Leu Thr Pro Leu Lys Ser Leu Asp Phe Asn Thr Leu Val Asp Asn Ile
                645                 650                 655
Ser Val Asp Pro Glu Thr Gly Asp Leu Trp Val Gly Cys His Pro Asn
            660                 665                 670
Gly Met Lys Ile Phe Phe Tyr Asp Ser Glu Asn Pro Pro Ala Ser Glu
        675                 680                 685
Val Leu Arg Ile Gln Asn Ile Leu Thr Glu Glu Pro Lys Val Thr Gln
    690                 695                 700
Val Tyr Ala Glu Asn Gly Thr Val Leu Gln Gly Ser Thr Val Ala Ser
705                 710                 715                 720
Val Tyr Lys Gly Lys Leu Leu Ile Gly Thr Val Phe His Lys Ala Leu
                725                 730                 735
Tyr Cys Glu Leu
            740

<210> SEQ ID NO 49
<211> LENGTH: 2343
<212> TYPE: DNA
<213> ORGANISM: Artificial Sequence
<220> FEATURE:
<223> OTHER INFORMATION: hVK3LP-hSOD1-(g4s)2-[SSShinge-P238S-P331S Fc]-
      NGS-[PON1 Q192K] DNA

<400> SEQUENCE: 49
atggaaaccc cagcgcagct tctcttcctc ctgctactct ggctcccaga taccaccggt      60
atggcggcaa cgaaggccgt gtgcgtgctg aagggcgacg cccagtgcag ggcatcatc     120 aatttcgagc agaaggaaag taatggacca gtgaaggtgt ggggaagcat taaggactg     180 actgaaggcc tgcatggatt ccatgttcat gagtttggag ataatacagc aggctgtacc     240
agtgcaggtc ctcactttaa tcctctatcc agaaaacacg gtgggccaaa ggatgaagag     300
```

```
aggcatgttg gagacttggg caatgtgact gctgacaaag atggtgtggc cgatgtgtct      360
attgaagatt ctgtgatctc actctcagga gaccattgca tcattggccg cacactggtg      420
gtccatgaaa aagcagatga cttgggcaaa ggtggaaatg aagaaagtac aaagacagga      480
aacgctggaa gtcgtttggc ttgtggtgta attgggatcg cccaagatct ctccggagga      540
ggtggctcag gtggtggagg atctaccggt ctcgagccca atcttctga caaaactcac       600
acatctccac cgtccccagc acctgaactc ctgggaggat cgtcagtctt cctcttcccc      660
ccaaaaccca aggacaccct catgatctcc cggacccctg aggtcacatg cgtggtggtg      720
gacgtgagcc acgaagaccc tgaggtcaag ttcaactggt acgtggacgg cgtggaggtg      780
cataatgcca agacaaagcc gcgggaggag cagtacaaca gcacgtaccg tgtggtcagc      840
gtcctcaccg tcctgcacca ggactggctg aatggcaagg agtacaagtg caaggtctcc      900
aacaaagccc tcccagcctc catcgagaaa accatctcca aagccaaagg gcagcccga       960
gaaccacagg tgtacaccct gcccccatcc cgggatgagc tgaccaagaa ccaggtcagc     1020
ctgacctgcc tggtcaaagg cttctatccc agcgacatcg ccgtggagtg ggagagcaat     1080
gggcagccgg agaacaacta caagaccacg cctcccgtgc tggactccga cggctccttc     1140
ttcctctaca gcaagctcac cgtggacaag agcaggtggc agcaggggaa cgtcttctca     1200
tgctccgtga tgcatgaggc tctgcacaac cactacacgc agaagagcct ctctctctct     1260
ccgggtaaag tcgacggagc tagcagcccc gtgaacgtga gcagcccag cgtgcaggat      1320
atcctcttca ggaaccacca gtcttcttac aaaacgac ttaatgctct ccgagaggta      1380
caacccgtag aacttcctaa ctgtaattta gttaaaggaa tcgaaactgg ctctgaagac     1440
ttggagatac tgcctaatgg actggctttc attagctctg gattaaagta tcctggaata     1500
aagagcttca accccaacag tcctggaaaa atacttctga tggacctgaa tgaagaagat     1560
ccaacagtgt tggaatttgg gatcactgga agtaaatttg atgtatcttc atttaaccct     1620
catgggatta gcacattcac agatgaagat aatgccatgt acctcctggt ggtgaaccat     1680
ccagatgcca gtccacagt ggagttgttt aaatttcaag aagaagaaaa atcgcttttg      1740
catctaaaaa ccatcagaca taaacttctg cctaatttga atgatattgt tgctgtggga     1800
cctgagcact tttatggcac aaatgatcac tatttcttg accctactt aaaatcctgg       1860
gagatgtatt tgggtttagc gtggtcgtat gttgtctact atagtccaag tgaagttcga     1920
gtggtggcag aaggatttga ttttgctaat ggaatcaaca tttcacccga tggcaagtat     1980
gtctatatag ctgagttgct ggctcataag attcatgtgt atgaaaagca tgctaattgg     2040
actttaactc cattgaagtc ccttgacttt aatacccctcg tggataacat atctgtggat     2100
cctgagacag gagaccttg ggttggatgc catcccaatg catgaaaat cttcttctat      2160
gactcagaga atcctcctgc atcagaggtg cttcgaatcc agaacattct aacagaagaa     2220
cctaaagtga cacaggttta tgcagaaaat ggcacagtgt gcaaggcag tacagttgcc      2280
tctgtgtaca aagggaaact gctgattggc acagtgtttc acaaagctct ttactgtgag     2340
ctc                                                                   2343
```

<210> SEQ ID NO 50
<211> LENGTH: 781
<212> TYPE: PRT
<213> ORGANISM: Artificial Sequence
<220> FEATURE:
<223> OTHER INFORMATION: hVK3LP-hSOD1-(g4s)2-[SSShinge-P238S-P331S Fc]-
    NGS-[PON1 Q192K]

-continued

```
<220> FEATURE:
<221> NAME/KEY: SIGNAL
<222> LOCATION: (1)..(22)
<223> OTHER INFORMATION: human VK3 leader peptide with 2 additional
      amino acids to drive correct cleavage
<220> FEATURE:
<221> NAME/KEY: MISC_FEATURE
<222> LOCATION: (23)..(175)
<223> OTHER INFORMATION: human SOD 1 without N-terminal methionine
<220> FEATURE:
<221> NAME/KEY: MISC_FEATURE
<222> LOCATION: (176)..(191)
<223> OTHER INFORMATION: (gly4ser)2 linker peptide with additional
      restriction site amino acids
<220> FEATURE:
<221> NAME/KEY: MISC_FEATURE
<222> LOCATION: (192)..(483)
<223> OTHER INFORMATION: human IgG1 variant Fc (SSS hinge, P238S, P331S)
<220> FEATURE:
<221> NAME/KEY: MISC_FEATURE
<222> LOCATION: (196)..(196)
<223> OTHER INFORMATION: human IgG1 hinge C220S amino acid substitution
<220> FEATURE:
<221> NAME/KEY: MISC_FEATURE
<222> LOCATION: (202)..(202)
<223> OTHER INFORMATION: human IgG1 hinge C226S amino acid substitution
<220> FEATURE:
<221> NAME/KEY: MISC_FEATURE
<222> LOCATION: (205)..(205)
<223> OTHER INFORMATION: human IgG1 hinge C229S amino acid substitution
<220> FEATURE:
<221> NAME/KEY: MISC_FEATURE
<222> LOCATION: (224)..(224)
<223> OTHER INFORMATION: human IgG1 lower hinge-CH2 P238S amino acid
      substitution
<220> FEATURE:
<221> NAME/KEY: MISC_FEATURE
<222> LOCATION: (307)..(307)
<223> OTHER INFORMATION: human IgG1 Fc P331S amino acid substitution
<220> FEATURE:
<221> NAME/KEY: MISC_FEATURE
<222> LOCATION: (424)..(442)
<223> OTHER INFORMATION: peptide linker containing N-linked
      glycosylation site
<220> FEATURE:
<221> NAME/KEY: MISC_FEATURE
<222> LOCATION: (443)..(781)
<223> OTHER INFORMATION: human PON1 Q192K without uncleaved leader
      peptide
<220> FEATURE:
<221> NAME/KEY: MISC_FEATURE
<222> LOCATION: (618)..(618)
<223> OTHER INFORMATION: human PON1 Q192K amino acid substitution

<400> SEQUENCE: 50

Met Glu Thr Pro Ala Gln Leu Leu Phe Leu Leu Leu Trp Leu Pro
1               5                   10                  15

Asp Thr Thr Gly Met Ala Ala Thr Lys Ala Val Cys Val Leu Lys Gly
            20                  25                  30

Asp Gly Pro Val Gln Gly Ile Ile Asn Phe Glu Gln Lys Glu Ser Asn
        35                  40                  45

Gly Pro Val Lys Val Trp Gly Ser Ile Lys Gly Leu Thr Glu Gly Leu
    50                  55                  60

His Gly Phe His Val His Glu Phe Gly Asp Asn Thr Ala Gly Cys Thr
65                  70                  75                  80

Ser Ala Gly Pro His Phe Asn Pro Leu Ser Arg Lys His Gly Gly Pro
                85                  90                  95

Lys Asp Glu Glu Arg His Val Gly Asp Leu Gly Asn Val Thr Ala Asp
            100                 105                 110

Lys Asp Gly Val Ala Asp Val Ser Ile Glu Asp Ser Val Ile Ser Leu
        115                 120                 125
```

-continued

```
Ser Gly Asp His Cys Ile Ile Gly Arg Thr Leu Val Val His Glu Lys
            130                 135                 140

Ala Asp Asp Leu Gly Lys Gly Gly Asn Glu Glu Ser Thr Lys Thr Gly
145                 150                 155                 160

Asn Ala Gly Ser Arg Leu Ala Cys Gly Val Ile Gly Ile Ala Gln Asp
                165                 170                 175

Leu Ser Gly Gly Gly Ser Gly Gly Gly Ser Thr Gly Leu Glu
            180                 185                 190

Pro Lys Ser Ser Asp Lys Thr His Thr Ser Pro Ser Pro Ala Pro
        195                 200                 205

Glu Leu Leu Gly Gly Ser Ser Val Phe Leu Phe Pro Pro Lys Pro Lys
210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                245                 250                 255

Gly Val Glu Val His Asn Ala Lys Thr Lys Pro Arg Glu Glu Gln Tyr
            260                 265                 270

Asn Ser Thr Tyr Arg Val Val Ser Val Leu Thr Val Leu His Gln Asp
        275                 280                 285

Trp Leu Asn Gly Lys Glu Tyr Lys Cys Lys Val Ser Asn Lys Ala Leu
290                 295                 300

Pro Ala Ser Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                325                 330                 335

Asn Gln Val Ser Leu Thr Cys Leu Val Lys Gly Phe Tyr Pro Ser Asp
            340                 345                 350

Ile Ala Val Glu Trp Glu Ser Asn Gly Gln Pro Glu Asn Asn Tyr Lys
        355                 360                 365

Thr Thr Pro Pro Val Leu Asp Ser Asp Gly Ser Phe Phe Leu Tyr Ser
370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                405                 410                 415

Leu Ser Leu Ser Pro Gly Lys Val Asp Gly Ala Ser Ser Pro Val Asn
            420                 425                 430

Val Ser Ser Pro Ser Val Gln Asp Ile Leu Phe Arg Asn His Gln Ser
        435                 440                 445

Ser Tyr Gln Thr Arg Leu Asn Ala Leu Arg Glu Val Gln Pro Val Glu
450                 455                 460

Leu Pro Asn Cys Asn Leu Val Lys Gly Ile Glu Thr Gly Ser Glu Asp
465                 470                 475                 480

Leu Glu Ile Leu Pro Asn Gly Leu Ala Phe Ile Ser Ser Gly Leu Lys
                485                 490                 495

Tyr Pro Gly Ile Lys Ser Phe Asn Pro Asn Ser Pro Gly Lys Ile Leu
            500                 505                 510

Leu Met Asp Leu Asn Glu Glu Asp Pro Thr Val Leu Glu Leu Gly Ile
        515                 520                 525

Thr Gly Ser Lys Phe Asp Val Ser Ser Phe Asn Pro His Gly Ile Ser
530                 535                 540
```

```
Thr Phe Thr Asp Glu Asp Asn Ala Met Tyr Leu Leu Val Val Asn His
545                 550                 555                 560

Pro Asp Ala Lys Ser Thr Val Glu Leu Phe Lys Phe Gln Glu Glu
                565                 570                 575

Lys Ser Leu Leu His Leu Lys Thr Ile Arg His Lys Leu Leu Pro Asn
                580                 585                 590

Leu Asn Asp Ile Val Ala Val Gly Pro Glu His Phe Tyr Gly Thr Asn
                595                 600                 605

Asp His Tyr Phe Leu Asp Pro Tyr Leu Lys Ser Trp Glu Met Tyr Leu
                610                 615                 620

Gly Leu Ala Trp Ser Tyr Val Val Tyr Ser Pro Ser Glu Val Arg
625                 630                 635                 640

Val Val Ala Glu Gly Phe Asp Phe Ala Asn Gly Ile Asn Ile Ser Pro
                645                 650                 655

Asp Gly Lys Tyr Val Tyr Ile Ala Glu Leu Leu Ala His Lys Ile His
                660                 665                 670

Val Tyr Glu Lys His Ala Asn Trp Thr Leu Thr Pro Leu Lys Ser Leu
                675                 680                 685

Asp Phe Asn Thr Leu Val Asp Asn Ile Ser Val Asp Pro Glu Thr Gly
                690                 695                 700

Asp Leu Trp Val Gly Cys His Pro Asn Gly Met Lys Ile Phe Phe Tyr
705                 710                 715                 720

Asp Ser Glu Asn Pro Pro Ala Ser Glu Val Leu Arg Ile Gln Asn Ile
                725                 730                 735

Leu Thr Glu Glu Pro Lys Val Thr Gln Val Tyr Ala Glu Asn Gly Thr
                740                 745                 750

Val Leu Gln Gly Ser Thr Val Ala Ser Val Tyr Lys Gly Lys Leu Leu
                755                 760                 765

Ile Gly Thr Val Phe His Lys Ala Leu Tyr Cys Glu Leu
                770                 775                 780

<210> SEQ ID NO 51
<211> LENGTH: 2343
<212> TYPE: DNA
<213> ORGANISM: Artificial Sequence
<220> FEATURE:
<223> OTHER INFORMATION: hVK3LP-[hSOD1 C6A C111S]-(g4s)
      2-[SSShinge-P238S-P331S Fc]-NGS-[PON1 Q192K] DNA

<400> SEQUENCE: 51
atggaaaccc cagcgcagct tctcttcctc ctgctactct ggctcccaga taccaccggt    60
atggcggcaa cgaaggccgt ggctgtgctg aagggcgacg gcccagtgca gggcatcatc   120
aatttcgagc agaaggaaag taatggacca gtgaaggtgt ggggaagcat taaaggactg   180
actgaaggcc tgcatggatt ccatgttcat gagtttggag ataatacagc aggctgtacc   240
agtgcaggtc ctcactttaa tcctctatcc agaaaacacg gtgggccaaa ggatgaagag   300
aggcatgttg gagacttggg caatgtgact gctgacaaag atggtgtggc cgatgtgtct   360
attgaagatt ctgtgatctc actctcagga gaccattcaa tcattggccg cacactggtg   420
gtccatgaaa aagcagatga cttgggcaaa ggtggaaatg aagaaagtac aaagacagga   480
aacgctggaa gtcgtttggc ttgtggtgta attgggatcg cccaagatct ctccggagga   540
ggtggctcag gtggtggagg atctaccggt ctcgagccca atcttctga caaaactcac   600 acatctccac cgtccccagc acctgaactc ctggaggat cgtcagtctt cctcttcccc   660
ccaaaaccca aggacaccct catgatctcc cggacccctg aggtcacatg cgtggtggtg   720
```

-continued

```
gacgtgagcc acgaagaccc tgaggtcaag ttcaactggt acgtggacgg cgtggaggtg    780
cataatgcca agacaaagcc gcggaggag cagtacaaca gcacgtaccg tgtggtcagc    840
gtcctcaccg tcctgcacca ggactggctg aatggcaagg agtacaagtg caaggtctcc    900
aacaaagccc tcccagcctc catcgagaaa accatctcca aagccaaagg gcagccccga    960
gaaccacagg tgtacaccct gcccccatcc cgggatgagc tgaccaagaa ccaggtcagc   1020
ctgacctgcc tggtcaaagg cttctatccc agcgacatcg ccgtggagtg ggagagcaat   1080
gggcagccgg agaacaacta caagaccacg cctcccgtgc tggactccga cggctccttc   1140
ttcctctaca gcaagctcac cgtggacaag agcaggtggc agcaggggaa cgtcttctca   1200
tgctccgtga tgcatgaggc tctgcacaac cactacacgc agaagagcct ctctctctct   1260
ccgggtaaag tcgacggagc tagcagcccc gtgaacgtga gcagcccag cgtgcaggat   1320
atcctcttca ggaaccacca gtcttcttac caaacacgac ttaatgctct ccgagaggta   1380
caacccgtag aacttcctaa ctgtaattta gttaaaggaa tcgaaactgg ctctgaagac   1440
ttggagatac tgcctaatgg actggctttc attagctctg gattaaagta tcctggaata   1500
aagagcttca accccaacag tcctggaaaa atacttctga tggacctgaa tgaagaagat   1560
ccaacagtgt tggaattggg gatcactgga agtaaatttg atgtatcttc atttaacccct  1620
catgggatta gcacattcac agatgaagat aatgccatgt acctcctggt ggtgaaccat   1680
ccagatgcca agtccacagt ggagttgttt aaatttcaag aagaagaaaa atcgcttttg   1740
catctaaaaa ccatcagaca taaacttctg cctaatttga atgatattgt tgctgtggga   1800
cctgagcact tttatggcac aaatgatcac tattttcttg accctactt aaaatcctgg   1860
gagatgtatt tgggtttagc gtggtcgtat gttgtctact atagtccaag tgaagttcga   1920
gtggtggcag aaggatttga ttttgctaat ggaatcaaca tttcacccga tggcaagtat   1980
gtctatatag ctgagttgct ggctcataag attcatgtgt atgaaaagca tgctaattgg   2040
actttaactc cattgaagtc ccttgacttt aatacctcg tggataacat atctgtggat   2100
cctgagacag gagaccttg ggttggatgc catcccaatg gcatgaaaat cttcttctat   2160
gactcagaga atcctcctgc atcagaggtg cttcgaatcc agaacattct aacagaagaa   2220
cctaaagtga cacaggttta tgcagaaaat ggcacagtgt tgcaaggcag tacagttgcc   2280
tctgtgtaca aagggaaact gctgattggc acagtgtttc acaaagctct ttactgtgag   2340
ctc                                                                2343
```

<210> SEQ ID NO 52
<211> LENGTH: 781
<212> TYPE: PRT
<213> ORGANISM: Artificial Sequence
<220> FEATURE:
<223> OTHER INFORMATION: hVK3LP-[hSOD1 C6A C111S]-(g4s)
    2-[SSShinge-P238S-P331S Fc]-NGS-[PON1 Q192K]
<220> FEATURE:
<221> NAME/KEY: SIGNAL
<222> LOCATION: (1)..(22)
<223> OTHER INFORMATION: human VK3 leader peptide with 2 additional
    amino acids to drive correct cleavage
<220> FEATURE:
<221> NAME/KEY: MISC_FEATURE
<222> LOCATION: (23)..(175)
<223> OTHER INFORMATION: human SOD1 C6A-C111S without N-terminal
    methionine
<220> FEATURE:
<221> NAME/KEY: MISC_FEATURE
<222> LOCATION: (28)..(28)
<223> OTHER INFORMATION: human SOD 1 C6A amino acid substitution

```
<220> FEATURE:
<221> NAME/KEY: MISC_FEATURE
<222> LOCATION: (133)..(133)
<223> OTHER INFORMATION: human SOD 1 C111S amino acid substitution
<220> FEATURE:
<221> NAME/KEY: MISC_FEATURE
<222> LOCATION: (176)..(191)
<223> OTHER INFORMATION: (gly4ser)2 linker peptide with additional
      restriction site amino acids
<220> FEATURE:
<221> NAME/KEY: MISC_FEATURE
<222> LOCATION: (192)..(423)
<223> OTHER INFORMATION: human IgG1 variant Fc (SSS hinge, P238S, P331S)
<220> FEATURE:
<221> NAME/KEY: MISC_FEATURE
<222> LOCATION: (196)..(196)
<223> OTHER INFORMATION: human IgG1 hinge C220S amino acid substitution
<220> FEATURE:
<221> NAME/KEY: MISC_FEATURE
<222> LOCATION: (202)..(202)
<223> OTHER INFORMATION: human IgG1 hinge C226S amino acid substitution
<220> FEATURE:
<221> NAME/KEY: MISC_FEATURE
<222> LOCATION: (205)..(205)
<223> OTHER INFORMATION: human IgG1 hinge C229S amino acid substitution
<220> FEATURE:
<221> NAME/KEY: MISC_FEATURE
<222> LOCATION: (215)..(215)
<223> OTHER INFORMATION: human IgG1 lower hinge-CH2 P238S amino acid
      substitution
<220> FEATURE:
<221> NAME/KEY: MISC_FEATURE
<222> LOCATION: (307)..(307)
<223> OTHER INFORMATION: human IgG1 Fc P331S amino acid substitution
<220> FEATURE:
<221> NAME/KEY: MISC_FEATURE
<222> LOCATION: (424)..(442)
<223> OTHER INFORMATION: linker peptide containing N-linked
      glycosylation site
<220> FEATURE:
<221> NAME/KEY: MISC_FEATURE
<222> LOCATION: (443)..(781)
<223> OTHER INFORMATION: human PON1 Q192K without uncleaved leader
      peptide
<220> FEATURE:
<221> NAME/KEY: MISC_FEATURE
<222> LOCATION: (618)..(618)
<223> OTHER INFORMATION: human PON1 Q192K amino acid substitution

<400> SEQUENCE: 52

Met Glu Thr Pro Ala Gln Leu Leu Phe Leu Leu Leu Trp Leu Pro
1               5                   10                  15

Asp Thr Thr Gly Met Ala Ala Thr Lys Ala Val Ala Val Leu Lys Gly
            20                  25                  30

Asp Gly Pro Val Gln Gly Ile Ile Asn Phe Glu Gln Lys Glu Ser Asn
        35                  40                  45

Gly Pro Val Lys Val Trp Gly Ser Ile Lys Gly Leu Thr Glu Gly Leu
    50                  55                  60

His Gly Phe His Val His Glu Phe Gly Asp Asn Thr Ala Gly Cys Thr
65                  70                  75                  80

Ser Ala Gly Pro His Phe Asn Pro Leu Ser Arg Lys His Gly Gly Pro
                85                  90                  95

Lys Asp Glu Glu Arg His Val Gly Asp Leu Gly Asn Val Thr Ala Asp
            100                 105                 110

Lys Asp Gly Val Ala Asp Val Ser Ile Glu Asp Ser Val Ile Ser Leu
        115                 120                 125

Ser Gly Asp His Ser Ile Ile Gly Arg Thr Leu Val Val His Glu Lys
    130                 135                 140

Ala Asp Asp Leu Gly Lys Gly Gly Asn Glu Glu Ser Thr Lys Thr Gly
```

```
               145                 150                 155                 160
Asn Ala Gly Ser Arg Leu Ala Cys Gly Val Ile Gly Ile Ala Gln Asp
                165                 170                 175
Leu Ser Gly Gly Gly Ser Gly Gly Gly Ser Thr Gly Leu Glu
            180                 185                 190
Pro Lys Ser Ser Asp Lys Thr His Thr Ser Pro Pro Ser Pro Ala Pro
            195                 200                 205
Glu Leu Leu Gly Gly Ser Ser Val Phe Leu Phe Pro Lys Pro Lys
    210                 215                 220
Asp Thr Leu Met Ile Ser Arg Thr Pro Glu Val Thr Cys Val Val Val
225                 230                 235                 240
Asp Val Ser His Glu Asp Pro Glu Val Lys Phe Asn Trp Tyr Val Asp
                245                 250                 255
Gly Val Glu Val His Asn Ala Lys Thr Lys Pro Arg Glu Glu Gln Tyr
                260                 265                 270
Asn Ser Thr Tyr Arg Val Val Ser Val Leu Thr Val Leu His Gln Asp
                275                 280                 285
Trp Leu Asn Gly Lys Glu Tyr Lys Cys Lys Val Ser Asn Lys Ala Leu
    290                 295                 300
Pro Ala Ser Ile Glu Lys Thr Ile Ser Lys Ala Lys Gly Gln Pro Arg
305                 310                 315                 320
Glu Pro Gln Val Tyr Thr Leu Pro Pro Ser Arg Asp Glu Leu Thr Lys
                325                 330                 335
Asn Gln Val Ser Leu Thr Cys Leu Val Lys Gly Phe Tyr Pro Ser Asp
                340                 345                 350
Ile Ala Val Glu Trp Glu Ser Asn Gly Gln Pro Glu Asn Asn Tyr Lys
                355                 360                 365
Thr Thr Pro Pro Val Leu Asp Ser Asp Gly Ser Phe Phe Leu Tyr Ser
    370                 375                 380
Lys Leu Thr Val Asp Lys Ser Arg Trp Gln Gln Gly Asn Val Phe Ser
385                 390                 395                 400
Cys Ser Val Met His Glu Ala Leu His Asn His Tyr Thr Gln Lys Ser
                405                 410                 415
Leu Ser Leu Ser Pro Gly Lys Val Asp Gly Ala Ser Ser Pro Val Asn
                420                 425                 430
Val Ser Ser Pro Ser Val Gln Asp Ile Leu Phe Arg Asn His Gln Ser
                435                 440                 445
Ser Tyr Gln Thr Arg Leu Asn Ala Leu Arg Glu Val Gln Pro Val Glu
    450                 455                 460
Leu Pro Asn Cys Asn Leu Val Lys Gly Ile Glu Thr Gly Ser Glu Asp
465                 470                 475                 480
Leu Glu Ile Leu Pro Asn Gly Leu Ala Phe Ile Ser Ser Gly Leu Lys
                485                 490                 495
Tyr Pro Gly Ile Lys Ser Phe Asn Pro Asn Ser Pro Gly Lys Ile Leu
                500                 505                 510
Leu Met Asp Leu Asn Glu Glu Asp Pro Thr Val Leu Glu Leu Gly Ile
                515                 520                 525
Thr Gly Ser Lys Phe Asp Val Ser Phe Asn Pro His Gly Ile Ser
    530                 535                 540
Thr Phe Thr Asp Glu Asp Asn Ala Met Tyr Leu Leu Val Val Asn His
545                 550                 555                 560
Pro Asp Ala Lys Ser Thr Val Glu Leu Phe Lys Phe Gln Glu Glu Glu
                565                 570                 575
```

```
Lys Ser Leu Leu His Leu Lys Thr Ile Arg His Lys Leu Leu Pro Asn
            580                 585                 590
Leu Asn Asp Ile Val Ala Val Gly Pro Glu His Phe Tyr Gly Thr Asn
        595                 600                 605
Asp His Tyr Phe Leu Asp Pro Tyr Leu Lys Ser Trp Glu Met Tyr Leu
    610                 615                 620
Gly Leu Ala Trp Ser Tyr Val Val Tyr Ser Pro Ser Glu Val Arg
625                 630                 635                 640
Val Val Ala Glu Gly Phe Asp Phe Ala Asn Gly Ile Asn Ile Ser Pro
                645                 650                 655
Asp Gly Lys Tyr Val Tyr Ile Ala Glu Leu Leu Ala His Lys Ile His
            660                 665                 670
Val Tyr Glu Lys His Ala Asn Trp Thr Leu Thr Pro Leu Lys Ser Leu
        675                 680                 685
Asp Phe Asn Thr Leu Val Asp Asn Ile Ser Val Asp Pro Glu Thr Gly
    690                 695                 700
Asp Leu Trp Val Gly Cys His Pro Asn Gly Met Lys Ile Phe Phe Tyr
705                 710                 715                 720
Asp Ser Glu Asn Pro Pro Ala Ser Glu Val Leu Arg Ile Gln Asn Ile
                725                 730                 735
Leu Thr Glu Glu Pro Lys Val Thr Gln Val Tyr Ala Glu Asn Gly Thr
            740                 745                 750
Val Leu Gln Gly Ser Thr Val Ala Ser Val Tyr Lys Gly Lys Leu Leu
        755                 760                 765
Ile Gly Thr Val Phe His Lys Ala Leu Tyr Cys Glu Leu
    770                 775                 780

<210> SEQ ID NO 53
<211> LENGTH: 2373
<212> TYPE: DNA
<213> ORGANISM: Artificial Sequence
<220> FEATURE:
<223> OTHER INFORMATION: hVK3LP-[hSOD1 C6A C111S]-(g4s)
      4-[SSShinge-P238S-P331S Fc]-NGS-[PON1 Q192K] DNA

<400> SEQUENCE: 53
atggaaaccc cagcgcagct tctcttcctc ctgctactct ggctcccaga taccaccggt      60
atggcggcaa cgaaggccgt ggctgtgctg aagggcgacg gcccagtgca ggcatcatc     120
aatttcgagc agaaggaaag taatggacca gtgaaggtgt ggggaagcat taaggactg     180
actgaaggcc tgcatggatt ccatgttcat gagtttggag ataatacagc aggctgtacc    240
agtgcaggtc ctcactttaa tcctctatcc agaaaacacg gtgggccaaa ggatgaagag    300
aggcatgttg agacttggg caatgtgact gctgacaaag atggtgtggc cgatgtgtct    360
attgaagatt ctgtgatctc actctcagga gaccattcaa tcattggccg cacactggtg    420
gtccatgaaa aagcagatga cttgggcaaa ggtggaaatg aagaaagtac aaagacagga    480
aacgctggaa gtcgtttggc ttctggtgta attgggatcg cccaagatct ctccggagga    540
ggtggctcag gtggtggagg atctggagga ggtgggagtg gtggaggtgg ttctaccggt    600
ctcgagccca atcttctga caaaactcac acatctccac cgtccccagc acctgaactc     660
ctgggaggat cgtcagtctt cctcttcccc ccaaaaccca aggacaccct catgatctcc    720
cggacccctg aggtcacatg cgtggtggtg gacgtgagcc acgaagaccc tgaggtcaag    780
ttcaactggt acgtggacgg cgtggaggtg cataatgcca agacaaagcc gcgggaggag    840
```

```
cagtacaaca gcacgtaccg tgtggtcagc gtcctcaccg tcctgcacca ggactggctg    900
aatggcaagg agtacaagtg caaggtctcc aacaaagccc tcccagcctc catcgagaaa    960
accatctcca agccaaagg gcagccccga gaaccacagg tgtacaccct gcccccatcc    1020
cgggatgagc tgaccaagaa ccaggtcagc ctgacctgcc tggtcaaagg cttctatccc   1080
agcgacatcg ccgtggagtg ggagagcaat gggcagccgg agaacaacta caagaccacg   1140
cctcccgtgc tggactccga cggctccttc ttcctctaca gcaagctcac cgtggacaag   1200
agcaggtggc agcaggggaa cgtcttctca tgctccgtga tgcatgaggc tctgcacaac   1260
cactacacgc agaagagcct ctctctctct ccgggtaaag tcgacggagc tagcagcccc   1320
gtgaacgtga gcagcccag cgtgcaggat atcctcttca ggaaccacca gtcttcttac   1380
caaacacgac ttaatgctct ccgagaggta caacccgtag aacttcctaa ctgtaattta   1440
gttaaaggaa tcgaaactgg ctctgaagac ttggagatac tgcctaatgg actggctttc   1500
attagctctg gattaaagta tcctggaata aagagcttca accccaacag tcctggaaaa   1560
atacttctga tggacctgaa tgaagaagat ccaacagtgt tggaattggg gatcactgga   1620
agtaaatttg atgtatcttc atttaacccct catgggatta gcacattcac agatgaagat   1680
aatgccatgt acctcctggt ggtgaaccat ccagatgcca gtccacagt ggagttgttt   1740
aaatttcaag aagaagaaaa atcgcttttg catctaaaaa ccatcagaca taaacttctg   1800
cctaatttga atgatattgt tgctgtggga cctgagcact tttatggcac aaatgatcac   1860
tattttcttg accctactt aaaatcctgg gagatgtatt tgggtttagc gtggtcgtat   1920
gttgtctact atagtccaag tgaagttcga gtggtggcag aaggatttga ttttgctaat   1980
ggaatcaaca tttcacccga tgcaagtat gtctatatag ctgagttgct ggctcataag   2040
attcatgtgt atgaaaagca tgctaattgg actttaactc cattgaagtc ccttgacttt   2100
aataccctcg tggataacat atctgtggat cctgagacag gagacctttg ggttggatgc   2160
catcccaatg gcatgaaaat cttcttctat gactcagaga atcctcctgc atcagaggtg   2220
cttcgaatcc agaacattct aacagaagaa cctaaagtga cacaggttta tgcagaaaat   2280
ggcacagtgt tgcaaggcag tacagttgcc tctgtgtaca aagggaaact gctgattggc   2340
acagtgtttc acaaagctct ttactgtgag ctc                                2373
```

<210> SEQ ID NO 54
<211> LENGTH: 791
<212> TYPE: PRT
<213> ORGANISM: Artificial Sequence
<220> FEATURE:
<223> OTHER INFORMATION: hVK3LP-[hSOD1 C6A C111S]-(g4s)
      4-[SSHinge-P238S-P331S Fc]-NGS-[PON1 Q192K]
<220> FEATURE:
<221> NAME/KEY: SIGNAL
<222> LOCATION: (1)..(22)
<223> OTHER INFORMATION: human VK3 leader peptide with 2 additional
      amino acids to drive correct cleavage
<220> FEATURE:
<221> NAME/KEY: MISC_FEATURE
<222> LOCATION: (23)..(175)
<223> OTHER INFORMATION: human SOD1 C6A-C111S without N-terminal
      methionine
<220> FEATURE:
<221> NAME/KEY: MISC_FEATURE
<222> LOCATION: (28)..(28)
<223> OTHER INFORMATION: human SOD 1 C6A amino acid substitution
<220> FEATURE:
<221> NAME/KEY: MISC_FEATURE
<222> LOCATION: (133)..(133)
<223> OTHER INFORMATION: human SOD 1 C111S amino acid substitution
<220> FEATURE:

```
<221> NAME/KEY: MISC_FEATURE
<222> LOCATION: (176)..(201)
<223> OTHER INFORMATION: (gly4ser)4 linker peptide with additional
      restriction site amino acids
<220> FEATURE:
<221> NAME/KEY: MISC_FEATURE
<222> LOCATION: (202)..(433)
<223> OTHER INFORMATION: human IgG1 variant Fc (SSS hinge, P238S, P331S)
<220> FEATURE:
<221> NAME/KEY: MISC_FEATURE
<222> LOCATION: (206)..(206)
<223> OTHER INFORMATION: human IgG1 hinge C220S amino acid substitution
<220> FEATURE:
<221> NAME/KEY: MISC_FEATURE
<222> LOCATION: (212)..(212)
<223> OTHER INFORMATION: human IgG1 hinge C226S amino acid substitution
<220> FEATURE:
<221> NAME/KEY: MISC_FEATURE
<222> LOCATION: (215)..(215)
<223> OTHER INFORMATION: human IgG1 hinge C229S amino acid substitution
<220> FEATURE:
<221> NAME/KEY: MISC_FEATURE
<222> LOCATION: (225)..(225)
<223> OTHER INFORMATION: human IgG1 lower hinge-CH2 P238S amino acid
      substitution
<220> FEATURE:
<221> NAME/KEY: MISC_FEATURE
<222> LOCATION: (317)..(317)
<223> OTHER INFORMATION: human IgG1 Fc P331S amino acid substitution
<220> FEATURE:
<221> NAME/KEY: MISC_FEATURE
<222> LOCATION: (434)..(452)
<223> OTHER INFORMATION: peptide linker containing N-linked
      glycosylation site
<220> FEATURE:
<221> NAME/KEY: MISC_FEATURE
<222> LOCATION: (453)..(791)
<223> OTHER INFORMATION: human PON1 Q192K without uncleaved leader
      peptide
<220> FEATURE:
<221> NAME/KEY: MISC_FEATURE
<222> LOCATION: (628)..(628)
<223> OTHER INFORMATION: human PON1 Q192K amino acid substitution

<400> SEQUENCE: 54

Met Glu Thr Pro Ala Gln Leu Leu Phe Leu Leu Leu Leu Trp Leu Pro
1               5                   10                  15

Asp Thr Thr Gly Met Ala Ala Thr Lys Ala Val Ala Val Leu Lys Gly
            20                  25                  30

Asp Gly Pro Val Gln Gly Ile Ile Asn Phe Glu Gln Lys Glu Ser Asn
        35                  40                  45

Gly Pro Val Lys Val Trp Gly Ser Ile Lys Gly Leu Thr Glu Gly Leu
    50                  55                  60

His Gly Phe His Val His Glu Phe Gly Asp Asn Thr Ala Gly Cys Thr
65                  70                  75                  80

Ser Ala Gly Pro His Phe Asn Pro Leu Ser Arg Lys His Gly Gly Pro
                85                  90                  95

Lys Asp Glu Glu Arg His Val Gly Asp Leu Gly Asn Val Thr Ala Asp
            100                 105                 110

Lys Asp Gly Val Ala Asp Val Ser Ile Glu Asp Ser Val Ile Ser Leu
        115                 120                 125

Ser Gly Asp His Ser Ile Ile Gly Arg Thr Leu Val Val His Glu Lys
    130                 135                 140

Ala Asp Asp Leu Gly Lys Gly Gly Asn Glu Glu Ser Thr Lys Thr Gly
145                 150                 155                 160

Asn Ala Gly Ser Arg Leu Ala Ser Gly Val Ile Gly Ile Ala Gln Asp
                165                 170                 175
```

```
Leu Ser Gly Gly Gly Ser Gly Gly Ser Gly Gly Gly
            180                 185             190

Ser Gly Gly Gly Ser Thr Gly Leu Glu Pro Lys Ser Ser Asp Lys
        195                 200             205

Thr His Thr Ser Pro Pro Ser Pro Ala Pro Glu Leu Leu Gly Gly Ser
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Ser Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Arg Asp Glu Leu Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys Val Asp Gly Ala Ser Ser Pro Val Asn Val Ser Ser Pro Ser Val
        435                 440                 445

Gln Asp Ile Leu Phe Arg Asn His Gln Ser Ser Tyr Gln Thr Arg Leu
    450                 455                 460

Asn Ala Leu Arg Glu Val Gln Pro Val Glu Leu Pro Asn Cys Asn Leu
465                 470                 475                 480

Val Lys Gly Ile Glu Thr Gly Ser Glu Asp Leu Glu Ile Leu Pro Asn
                485                 490                 495

Gly Leu Ala Phe Ile Ser Ser Gly Leu Lys Tyr Pro Gly Ile Lys Ser
            500                 505                 510

Phe Asn Pro Asn Ser Pro Gly Lys Ile Leu Leu Met Asp Leu Asn Glu
        515                 520                 525

Glu Asp Pro Thr Val Leu Glu Leu Gly Ile Thr Gly Ser Lys Phe Asp
    530                 535                 540

Val Ser Ser Phe Asn Pro His Gly Ile Ser Thr Phe Thr Asp Glu Asp
545                 550                 555                 560

Asn Ala Met Tyr Leu Leu Val Val Asn His Pro Asp Ala Lys Ser Thr
                565                 570                 575

Val Glu Leu Phe Lys Phe Gln Glu Glu Lys Ser Leu Leu His Leu
            580                 585                 590

Lys Thr Ile Arg His Lys Leu Leu Pro Asn Leu Asn Asp Ile Val Ala
```

```
                595                 600                 605
Val Gly Pro Glu His Phe Tyr Gly Thr Asn Asp His Tyr Phe Leu Asp
        610                 615                 620

Pro Tyr Leu Lys Ser Trp Glu Met Tyr Leu Gly Leu Ala Trp Ser Tyr
625                 630                 635                 640

Val Val Tyr Tyr Ser Pro Ser Glu Val Arg Val Ala Glu Gly Phe
                645                 650                 655

Asp Phe Ala Asn Gly Ile Asn Ile Ser Pro Asp Gly Lys Tyr Val Tyr
            660                 665                 670

Ile Ala Glu Leu Leu Ala His Lys Ile His Val Tyr Glu Lys His Ala
        675                 680                 685

Asn Trp Thr Leu Thr Pro Leu Lys Ser Leu Asp Phe Asn Thr Leu Val
    690                 695                 700

Asp Asn Ile Ser Val Asp Pro Glu Thr Gly Asp Leu Trp Val Gly Cys
705                 710                 715                 720

His Pro Asn Gly Met Lys Ile Phe Phe Tyr Asp Ser Glu Asn Pro Pro
                725                 730                 735

Ala Ser Glu Val Leu Arg Ile Gln Asn Ile Leu Thr Glu Glu Pro Lys
            740                 745                 750

Val Thr Gln Val Tyr Ala Glu Asn Gly Thr Val Leu Gln Gly Ser Thr
        755                 760                 765

Val Ala Ser Val Tyr Lys Gly Lys Leu Leu Ile Gly Thr Val Phe His
    770                 775                 780

Lys Ala Leu Tyr Cys Glu Leu
785                 790

<210> SEQ ID NO 55
<211> LENGTH: 54
<212> TYPE: DNA
<213> ORGANISM: Artificial Sequence
<220> FEATURE:
<223> OTHER INFORMATION: Peptide linker containing N-linked
      glycosylation site (NGS linker) DNA

<400> SEQUENCE: 55
gtcgacggag ctagcagccc cgtgaacgtg agcagcccca gcgtgcagga tatc          54

<210> SEQ ID NO 56
<211> LENGTH: 18
<212> TYPE: PRT
<213> ORGANISM: Artificial Sequence
<220> FEATURE:
<223> OTHER INFORMATION: Peptide linker containing N-linked
      glycosylation site (NGS linker)

<400> SEQUENCE: 56

Val Asp Gly Ala Ser Ser Pro Val Asn Val Ser Ser Pro Ser Val Gln
1               5                   10                  15

Asp Ile

<210> SEQ ID NO 57
<211> LENGTH: 72
<212> TYPE: DNA
<213> ORGANISM: Homo sapiens

<400> SEQUENCE: 57
aagcttgccg ccatggaaac cccagcgcag cttctcttcc tcctgctact ctggctccca    60
gataccaccg gt                                                       72
```

<210> SEQ ID NO 58
<211> LENGTH: 20
<212> TYPE: PRT
<213> ORGANISM: Homo sapiens

<400> SEQUENCE: 58

Met Glu Thr Pro Ala Gln Leu Leu Phe Leu Leu Leu Leu Trp Leu Pro
1               5                   10                  15

Asp Thr Thr Gly
            20

<210> SEQ ID NO 59
<211> LENGTH: 1614
<212> TYPE: DNA
<213> ORGANISM: Artificial Sequence
<220> FEATURE:
<223> OTHER INFORMATION: hVK3LP-[hDNase1 N74K-G105R-A114F]-(g4s)
      4-[SSHinge-P238S-P331S Fc] DNA

<400> SEQUENCE: 59

```
atggaaaccc cagcgcagct tctcttcctc ctgctactct ggctcccaga taccaccggt    60
ctgaagatcg cagccttcaa catccagaca tttggggaga ccaagatgtc caatgccacc   120
ctcgtcagct acattgtgca gatcctgagc cgctatgaca tcgccctggt ccaggaggtc   180
agagacagcc acctgactgc cgtggggaag ctgctggaca acctcaatca ggatgcacca   240
gacacctatc actacgtggt cagtgagcca ctgggacgga gagctataa ggagcgctac   300
ctgttcgtgt acaggcctga ccaggtgtct gcggtggaca gctactacta cgatgatggc   360
tgcgagccct gcaggaacga caccttcaac cgagagccat tcattgtcag gttcttctcc   420
cggttcacag aggtcaggga gtttgccatt gttcccctgc atgcggcccc ggggacgca   480
gtagccgaga tcgacgctct ctatgacgtc tacctggatg tccaagagaa atggggcttg   540
gaggacgtca tgttgatggg cgacttcaat gcgggctgca gctatgtgag accctcccag   600
tggtcatcca tccgcctgtg gacaagcccc accttccagt ggctgatccc cgacagcgct   660
gacaccacag ctacacccac gcactgtgcc tatgacagga tcgtggttgc agggatgctg   720
ctccgaggcg ccgttgttcc cgactcggct cttccctta acttccaggc tgcctatggc   780
ctgagtgacc aactggccca agccatcagt gaccactatc cagtggaggt gatgctgaaa   840
gatctctccg gaggagtgg ctcaggtggt ggaggatctg gaggaggtgg agtggtgga   900
ggtggttcta ccggtctcga gcccaaatct tctgacaaaa ctcacacatc tccaccgtcc   960
ccagcacctg aactcctggg aggatcgtca gtcttcctct ccccccaaa acccaaggac  1020
accctcatga tctcccggac ccctgaggtc acatgcgtgg tggtggacgt gagccacgaa  1080
gaccctgagg tcaagttcaa ctggtacgtg gacggcgtgg aggtgcataa tgccaagaca  1140
aagccgcggg aggagcagta caacagcacg taccgtgtgg tcagcgtcct caccgtcctg  1200
caccaggact ggctgaatgg caaggagtac aagtgcaagg tctccaacaa agccctccca  1260
gcctccatcg agaaaaccat ctccaaagcc aagggcagc ccgagaacc acaggtgtac  1320
accctgcccc catcccggga tgagctgacc aagaaccagg tcagcctgac ctgcctggtc  1380
aaaggcttct atcccagcga catcgccgtg gagtgggaga gcaatgggca gccggagaac  1440
aactacaaga ccacgcctcc cgtgctggac tcgacggct ccttcttcct ctacagcaag  1500
ctcaccgtgg acaagagcag gtggcagcag gggaacgtct tctcatgctc cgtgatgcat  1560
gaggctctgc acaaccacta cacgcagaag agcctctctc tctctccggg taaa          1614
```

<210> SEQ ID NO 60
<211> LENGTH: 538
<212> TYPE: PRT
<213> ORGANISM: Artificial Sequence
<220> FEATURE:
<223> OTHER INFORMATION: hVK3LP-[hDNase1 N74K-G105R-A114F]-(g4s)
      4-[SSShinge-P238S-P331S Fc]

<400> SEQUENCE: 60

Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
                35                  40                  45

Leu Ser Arg Tyr Asp Ile Ala Leu Val Gln Glu Val Arg Asp Ser His
        50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
                100                 105                 110

Asp Ser Tyr Tyr Tyr Asp Asp Gly Cys Glu Pro Cys Arg Asn Asp Thr
            115                 120                 125

Phe Asn Arg Glu Pro Phe Ile Val Arg Phe Phe Ser Arg Phe Thr Glu
            130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Ser
        275                 280                 285

Gly Gly Gly Gly Ser Gly Gly Gly Ser Gly Gly Gly Ser Thr
    290                 295                 300

Gly Leu Glu Pro Lys Ser Ser Asp Lys Thr His Thr Ser Pro Pro Ser
305                 310                 315                 320

Pro Ala Pro Glu Leu Leu Gly Ser Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
            355                 360                 365

Tyr Val Asp Gly Val Glu Val His Asn Ala Lys Thr Lys Pro Arg Glu
        370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
            405                 410                 415

Lys Ala Leu Pro Ala Ser Ile Glu Lys Thr Ile Ser Lys Ala Lys Gly
            420                 425                 430

Gln Pro Arg Glu Pro Gln Val Tyr Thr Leu Pro Pro Ser Arg Asp Glu
            435                 440                 445

Leu Thr Lys Asn Gln Val Ser Leu Thr Cys Leu Val Lys Gly Phe Tyr
        450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
            485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
            515                 520                 525

Gln Lys Ser Leu Ser Leu Ser Pro Gly Lys
        530                 535

<210> SEQ ID NO 61
<211> LENGTH: 1644
<212> TYPE: DNA
<213> ORGANISM: Artificial Sequence
<220> FEATURE:
<223> OTHER INFORMATION: hVK3LP-[hDNase1 N74K-G105R-A114F]-(g4s)
      6-[SSShinge-P238S-P331S Fc] DNA

<400> SEQUENCE: 61

```
atggaaaccc cagcgcagct tctcttcctc ctgctactct ggctcccaga taccaccggt    60
ctgaagatcg cagccttcaa catccagaca tttggggaga ccaagatgtc aatgccacc    120 ctcgtcagct acattgtgca gatcctgagc cgctatgaca tcgccctggt ccaggaggtc   180
agagacagcc acctgactgc cgtggggaag ctgctggaca acctcaatca ggatgcacca   240
gacacctatc actacgtggt cagtgagcca ctggacggga gagctataa ggagcgctac    300 ctgttcgtgt acaggcctga ccaggtgtct gcggtggaca gctactacta cgatgatggc   360
tgcgagccct gcaggaacga caccttcaac cgagagccat tcattgtcag gttcttctcc   420
cggttcacag aggtcaggga gtttgccatt gttcccctgc atgcggcccc ggggacgca    480 gtagccgaga tcgacgctct ctatgacgtc tacctggatg tccaagagaa atggggcttg   540
gaggacgtca tgttgatggg cgacttcaat gcggctgca gctatgtgag accctcccag    600
tggtcatcca tccgcctgtg gacaagcccc accttccagt ggctgatccc cgacagcgct   660
gacaccacag ctacacccac gcactgtgcc tatgacagga tcgtggttgc agggatgctg   720
ctccgaggcg ccgttgttcc cgactcggct cttcccttta acttccaggc tgcctatggc   780
ctgagtgacc aactggccca agccatcagt gaccactatc agtggaggt gatgctgaaa   840 gatctctccg gaggaggtgg ctcaggtggt ggaggatctg gaggaggtgg agtggtgga    900 ggtggttctg gaggaggtgg tagtggaggt ggaggttcta ccggtctcga gcccaaatct   960
tctgacaaaa ctcacacatc tccaccgtcc ccagcacctg aactcctggg aggatcgtca  1020
```

-continued

```
gtcttcctct tcccccaaa acccaaggac accctcatga tctcccggac ccctgaggtc   1080
acatgcgtgg tggtggacgt gagccacgaa gaccctgagg tcaagttcaa ctggtacgtg   1140
gacggcgtgg aggtgcataa tgccaagaca aagccgcggg aggagcagta caacagcacg   1200
taccgtgtgg tcagcgtcct caccgtcctg caccaggact ggctgaatgg caaggagtac   1260
aagtgcaagg tctccaacaa agccctccca gcctccatcg agaaaaccat ctccaaagcc   1320
aaagggcagc cccgagaacc acaggtgtac accctgcccc catcccggga tgagctgacc   1380
aagaaccagg tcagcctgac ctgcctggtc aaaggcttct atcccagcga catcgccgtg   1440
gagtgggaga gcaatgggca gccggagaac aactacaaga ccacgcctcc cgtgctggac   1500
tccgacggct ccttcttcct ctacagcaag ctcaccgtgg acaagagcag gtggcagcag   1560
gggaacgtct tctcatgctc cgtgatgcat gaggctctgc acaaccacta cacgcagaag   1620
agcctctctc tctctccggg taaa                                           1644
```

<210> SEQ ID NO 62
<211> LENGTH: 548
<212> TYPE: PRT
<213> ORGANISM: Artificial Sequence
<220> FEATURE:
<223> OTHER INFORMATION: hVK3LP-[hDNase1 N74K-G105R-A114F]-(g4s)
    6-[SSShinge-P238S-P331S Fc]

<400> SEQUENCE: 62

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
```

```
            245                 250                 255
Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Gly Ser
            275                 280                 285

Gly Gly Gly Gly Ser Gly Gly Gly Ser Gly Gly Gly Ser Gly
            290                 295                 300

Gly Gly Gly Ser Gly Gly Gly Ser Thr Gly Leu Glu Pro Lys Ser
305                 310                 315                 320

Ser Asp Lys Thr His Thr Ser Pro Pro Ser Pro Ala Pro Glu Leu Leu
                325                 330                 335

Gly Gly Ser Ser Val Phe Leu Phe Pro Pro Lys Pro Lys Asp Thr Leu
                340                 345                 350

Met Ile Ser Arg Thr Pro Glu Val Thr Cys Val Val Val Asp Val Ser
                355                 360                 365

His Glu Asp Pro Glu Val Lys Phe Asn Trp Tyr Val Asp Gly Val Glu
            370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Ser
                420                 425                 430

Ile Glu Lys Thr Ile Ser Lys Ala Lys Gly Gln Pro Arg Glu Pro Gln
                435                 440                 445

Val Tyr Thr Leu Pro Pro Ser Arg Asp Glu Leu Thr Lys Asn Gln Val
            450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
                500                 505                 510

Val Asp Lys Ser Arg Trp Gln Gln Gly Asn Val Phe Ser Cys Ser Val
                515                 520                 525

Met His Glu Ala Leu His Asn His Tyr Thr Gln Lys Ser Leu Ser Leu
                530                 535                 540

Ser Pro Gly Lys
545

<210> SEQ ID NO 63
<211> LENGTH: 1137
<212> TYPE: DNA
<213> ORGANISM: Artificial Sequence
<220> FEATURE:
<223> OTHER INFORMATION: hVK3LP-[hCTLA-4 EC]-[SSHinge-P238S-P331S Fc]
      DNA

<400> SEQUENCE: 63
atggaaaccc cagcgcagct tctcttcctc ctgctactct ggctcccgga taccaccggt      60
gcaatgcacg tggcccagcc tgctgtggta ctggccagca gccgaggcat cgccagcttt    120
gtgtgtgagt atgcatctcc aggcaaagca actgaggtcc gggtgacagt gcttcggcag    180
gctgacagcc aggtgactga agtctgtgcg gcaacctaca tgatgggaaa tgagttgacc    240
ttcctagatg attccatctg cacgggcacc tccagtggaa atcaagtgaa cctcactatc    300
```

-continued

```
caaggactga gggccatgga cacgggactc tacatctgca aggtggagct catgtaccca    360
ccgccatact acctgggcat aggcaacgga acccagattt atgtaattga tccagaaccg    420
tgcccagatt cagatctcga gcccaaatct tctgacaaaa ctcacacatc tccaccgtcc    480
ccagcacctg aactcctggg aggatcgtca gtcttcctct tccccccaaa acccaaggac    540
accctcatga tctcccggac ccctgaggtc acatgcgtgg tggtggacgt gagccacgaa    600
gaccctgagg tcaagttcaa ctggtacgtg gacggcgtgg aggtgcataa tgccaagaca    660
aagccgcggg aggagcagta caacagcacg taccgtgtgg tcagcgtcct caccgtcctg    720
caccaggact ggctgaatgg caaggagtac aagtgcaagg tctccaacaa agccctccca    780
gcctccatcg agaaaaccat ctccaaagcc aagggcagcc ccgagaacca caggtgtac    840
accctgcccc catcccggga tgagctgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctctc tctctccggg taaataa      1137
```

<210> SEQ ID NO 64
<211> LENGTH: 378
<212> TYPE: PRT
<213> ORGANISM: Artificial Sequence
<220> FEATURE:
<223> OTHER INFORMATION: hVK3LP-[hCTLA-4 EC]-[SSShinge-P238S-P331S Fc]

<400> SEQUENCE: 64

```
Met Glu Thr Pro Ala Gln Leu Leu Phe Leu Leu Leu Leu Trp Leu Pro
1               5                   10                  15

Asp Thr Thr Gly Ala Met His Val Ala Gln Pro Ala Val Val Leu Ala
                20                  25                  30

Ser Ser Arg Gly Ile Ala Ser Phe Val Cys Glu Tyr Ala Ser Pro Gly
            35                  40                  45

Lys Ala Thr Glu Val Arg Val Thr Val Leu Arg Gln Ala Asp Ser Gln
        50                  55                  60

Val Thr Glu Val Cys Ala Ala Thr Tyr Met Met Gly Asn Glu Leu Thr
65                  70                  75                  80

Phe Leu Asp Asp Ser Ile Cys Thr Gly Thr Ser Ser Gly Asn Gln Val
                85                  90                  95

Asn Leu Thr Ile Gln Gly Leu Arg Ala Met Asp Thr Gly Leu Tyr Ile
            100                 105                 110

Cys Lys Val Glu Leu Met Tyr Pro Pro Pro Tyr Tyr Leu Gly Ile Gly
        115                 120                 125

Asn Gly Thr Gln Ile Tyr Val Ile Asp Pro Glu Pro Cys Pro Asp Ser
    130                 135                 140

Asp Leu Glu Pro Lys Ser Ser Asp Lys Thr His Thr Ser Pro Pro Ser
145                 150                 155                 160

Pro Ala Pro Glu Leu Leu Gly Gly Ser Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
```

| | | | | | | | | | | | |
|---|---|---|---|---|---|---|---|---|---|---|---|
| | | 210 | | | 215 | | | 220 | | | |
| Glu | Gln | Tyr | Asn | Ser | Thr | Tyr | Arg | Val | Val | Ser | Val Leu Thr Val Leu |
| 225 | | | | 230 | | | | 235 | | | 240 |
| His | Gln | Asp | Trp | Leu | Asn | Gly | Lys | Glu | Tyr | Lys | Cys Lys Val Ser Asn |
| | | | 245 | | | | 250 | | | | 255 |
| Lys | Ala | Leu | Pro | Ala | Ser | Ile | Glu | Lys | Thr | Ile | Ser Lys Ala Lys Gly |
| | | | 260 | | | | 265 | | | | 270 |
| Gln | Pro | Arg | Glu | Pro | Gln | Val | Tyr | Thr | Leu | Pro | Pro Ser Arg Asp Glu |
| | | 275 | | | | | 280 | | | | 285 |
| Leu | Thr | Lys | Asn | Gln | Val | Ser | Leu | Thr | Cys | Leu | Val Lys Gly Phe Tyr |
| | 290 | | | | | 295 | | | | | 300 |
| Pro | Ser | Asp | Ile | Ala | Val | Glu | Trp | Glu | Ser | Asn | Gly Gln Pro Glu Asn |
| 305 | | | | 310 | | | | 315 | | | 320 |
| Asn | Tyr | Lys | Thr | Thr | Pro | Pro | Val | Leu | Asp | Ser | Asp Gly Ser Phe Phe |
| | | | 325 | | | | 330 | | | | 335 |
| Leu | Tyr | Ser | Lys | Leu | Thr | Val | Asp | Lys | Ser | Arg | Trp Gln Gln Gly Asn |
| | | 340 | | | | | 345 | | | | 350 |
| Val | Phe | Ser | Cys | Ser | Val | Met | His | Glu | Ala | Leu | His Asn His Tyr Thr |
| | | 355 | | | | | 360 | | | | 365 |
| Gln | Lys | Ser | Leu | Ser | Leu | Ser | Pro | Gly | Lys | | |
| 370 | | | | | 375 | | | | | | |

```
<210> SEQ ID NO 65
<211> LENGTH: 2211
<212> TYPE: DNA
<213> ORGANISM: Artificial Sequence
<220> FEATURE:
<223> OTHER INFORMATION: hVK3LP-[hCTLA-4 EC]-[SSHinge-P238S-P331S Fc]-
      NGS-[PON1 Q192K] DNA

<400> SEQUENCE: 65
atggaaaccc cagcgcagct tctcttcctc ctgctactct ggctcccgga taccaccggt      60
gcaatgcacg tggcccagcc tgctgtggta ctggccagca gccgaggcat cgccagcttt     120
gtgtgtgagt atgcatctcc aggcaaagcc actgaggtcc gggtgacagt gcttcggcag     180
gctgacagcc aggtgactga agtctgtgcg caacctaca tgatggggaa tgagttgacc      240
ttcctagatg attccatctg cacgggcacc tccagtggaa atcaagtgaa cctcactatc     300
caaggactga gggccatgga cacgggactc tacatctgca aggtggagct catgtaccca     360
ccgccatact acctgggcat aggcaacgga acccagattt atgtaattga tccagaaccg     420
tgcccagatt cagatctcga gcccaaatct tctgacaaaa ctcacacatc tccaccgtcc     480
ccagcacctg aactcctggg aggatcgtca gtcttcctct tccccccaaa acccaaggac     540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta caacagcacg taccgtgtgg tcagcgtcct caccgtcctg     720
caccaggact ggctgaatgg caaggagtac aagtgcaagg tctccaacaa agccctccca     780
gcctccatcg agaaaaccat ctccaaagcc aaagggcagc ccgagaacc acaggtgtac      840 accctgcccc catcccggga tgagctgacc aagaaccagg tcagcctgac ctgcctggtc     900
aaaggcttct atcccagcga catcgccgtg gagtgggaga gcaatgggca gccggagaac     960
aactacaaga ccacgcctcc cgtgctggac tccgacggct ccttcttcct ctacagcaag    1020
ctcaccgtgg acaagagcag gtggcagcag gggaacgtct tctcatgctc cgtgatgcat    1080
```

```
gaggctctgc acaaccacta cacgcagaag agcctctctc tctctccggg taaagtcgac    1140
ggagctagca gccccgtgaa cgtgagcagc cccagcgtgc aggatatcct cttcaggaac    1200
caccagtctt cttaccaaac acgacttaat gctctccgag aggtacaacc cgtagaactt    1260
cctaactgta atttagttaa aggaatcgaa actggctctg aagacttgga gatactgcct    1320
aatggactgg ctttcattag ctctggatta agtatcctg  gaataaagag cttcaacccc    1380
aacagtcctg gaaaaatact tctgatggac ctgaatgaag aagatccaac agtgttggaa    1440
ttggggatca ctggaagtaa atttgatgta tcttcattta accctcatgg gattagcaca    1500
ttcacagatg aagataatgc catgtacctc ctggtggtga accatccaga tgccaagtcc    1560
acagtggagt tgtttaaatt tcaagaagaa gaaaaatcgc ttttgcatct aaaaaccatc    1620
agacataaac ttctgcctaa tttgaatgat attgttgctg tgggacctga gcactttat    1680 ggcacaaatg atcactattt tcttgacccc tacttaaaat cctgggagat gtatttgggt    1740
ttagcgtggt cgtatgttgt ctactatagt ccaagtgaag ttcgagtggt ggcagaagga    1800
tttgattttg ctaatggaat caacatttca cccgatggca gtatgtcta  tatagctgag    1860 ttgctggctc ataagattca tgtgtatgaa aagcatgcta attggacttt aactccattg    1920
aagtcccttg actttaatac cctcgtggat aacatatctg tggatcctga  acagggagac    1980
ctttgggttg gatgccatcc caatggcatg aaaatcttct tctatgactc agagaatcct    2040
cctgcatcag aggtgcttcg aatccagaac attctaacag aagaacctaa agtgacacag    2100
gtttatgcag aaaatggcac agtgttgcaa ggcagtacag ttgcctctgt gtacaaaggg    2160
aaactgctga ttggcacagt gtttcacaaa gctctttact gtgagctcta a             2211

<210> SEQ ID NO 66
<211> LENGTH: 736
<212> TYPE: PRT
<213> ORGANISM: Artificial Sequence
<220> FEATURE:
<223> OTHER INFORMATION: hVK3LP-[hCTLA-4 EC]-[SSHinge-P238S-P331S Fc]-
      NGS-[PON1 Q192K]

<400> SEQUENCE: 66

Met Glu Thr Pro Ala Gln Leu Leu Phe Leu Leu Leu Leu Trp Leu Pro
1               5                   10                  15

Asp Thr Thr Gly Ala Met His Val Ala Gln Pro Ala Val Val Leu Ala
            20                  25                  30

Ser Ser Arg Gly Ile Ala Ser Phe Val Cys Glu Tyr Ala Ser Pro Gly
        35                  40                  45

Lys Ala Thr Glu Val Arg Val Thr Val Leu Arg Gln Ala Asp Ser Gln
    50                  55                  60

Val Thr Glu Val Cys Ala Ala Thr Tyr Met Met Gly Asn Glu Leu Thr
65                  70                  75                  80

Phe Leu Asp Asp Ser Ile Cys Thr Gly Thr Ser Ser Gly Asn Gln Val
                85                  90                  95

Asn Leu Thr Ile Gln Gly Leu Arg Ala Met Asp Thr Gly Leu Tyr Ile
            100                 105                 110

Cys Lys Val Glu Leu Met Tyr Pro Pro Pro Tyr Tyr Leu Gly Ile Gly
        115                 120                 125

Asn Gly Thr Gln Ile Tyr Val Ile Asp Pro Glu Pro Cys Pro Asp Ser
    130                 135                 140

Asp Leu Glu Pro Lys Ser Ser Asp Lys Thr His Thr Ser Pro Pro Ser
145                 150                 155                 160
```

```
Pro Ala Pro Glu Leu Leu Gly Gly Ser Ser Val Phe Leu Phe Pro Pro
                165                 170                 175
Lys Pro Lys Asp Thr Leu Met Ile Ser Arg Thr Pro Glu Val Thr Cys
            180                 185                 190
Val Val Val Asp Val Ser His Glu Asp Pro Glu Val Lys Phe Asn Trp
        195                 200                 205
Tyr Val Asp Gly Val Glu Val His Asn Ala Lys Thr Lys Pro Arg Glu
    210                 215                 220
Glu Gln Tyr Asn Ser Thr Tyr Arg Val Val Ser Val Leu Thr Val Leu
225                 230                 235                 240
His Gln Asp Trp Leu Asn Gly Lys Glu Tyr Lys Cys Lys Val Ser Asn
                245                 250                 255
Lys Ala Leu Pro Ala Ser Ile Glu Lys Thr Ile Ser Lys Ala Lys Gly
            260                 265                 270
Gln Pro Arg Glu Pro Gln Val Tyr Thr Leu Pro Pro Ser Arg Asp Glu
        275                 280                 285
Leu Thr Lys Asn Gln Val Ser Leu Thr Cys Leu Val Lys Gly Phe Tyr
    290                 295                 300
Pro Ser Asp Ile Ala Val Glu Trp Glu Ser Asn Gly Gln Pro Glu Asn
305                 310                 315                 320
Asn Tyr Lys Thr Thr Pro Pro Val Leu Asp Ser Asp Gly Ser Phe Phe
                325                 330                 335
Leu Tyr Ser Lys Leu Thr Val Asp Lys Ser Arg Trp Gln Gln Gly Asn
            340                 345                 350
Val Phe Ser Cys Ser Val Met His Glu Ala Leu His Asn His Tyr Thr
        355                 360                 365
Gln Lys Ser Leu Ser Leu Ser Pro Gly Lys Val Asp Gly Ala Ser Ser
    370                 375                 380
Pro Val Asn Val Ser Ser Pro Ser Val Gln Asp Ile Leu Phe Arg Asn
385                 390                 395                 400
His Gln Ser Ser Tyr Gln Thr Arg Leu Asn Ala Leu Arg Glu Val Gln
                405                 410                 415
Pro Val Glu Leu Pro Asn Cys Asn Leu Val Lys Gly Ile Glu Thr Gly
            420                 425                 430
Ser Glu Asp Leu Glu Ile Leu Pro Asn Gly Leu Ala Phe Ile Ser Ser
        435                 440                 445
Gly Leu Lys Tyr Pro Gly Ile Lys Ser Phe Asn Pro Asn Ser Pro Gly
    450                 455                 460
Lys Ile Leu Leu Met Asp Leu Asn Glu Glu Asp Pro Thr Val Leu Glu
465                 470                 475                 480
Leu Gly Ile Thr Gly Ser Lys Phe Asp Val Ser Ser Phe Asn Pro His
                485                 490                 495
Gly Ile Ser Thr Phe Thr Asp Glu Asp Asn Ala Met Tyr Leu Leu Val
            500                 505                 510
Val Asn His Pro Asp Ala Lys Ser Thr Val Glu Leu Phe Lys Phe Gln
        515                 520                 525
Glu Glu Glu Lys Ser Leu Leu His Leu Lys Thr Ile Arg His Lys Leu
    530                 535                 540
Leu Pro Asn Leu Asn Asp Ile Val Ala Val Gly Pro Glu His Phe Tyr
545                 550                 555                 560
Gly Thr Asn Asp His Tyr Phe Leu Asp Pro Tyr Leu Lys Ser Trp Glu
                565                 570                 575
Met Tyr Leu Gly Leu Ala Trp Ser Tyr Val Val Tyr Tyr Ser Pro Ser
```

```
                580             585             590
Glu Val Arg Val Val Ala Glu Gly Phe Asp Phe Ala Asn Gly Ile Asn
                    595             600             605

Ile Ser Pro Asp Gly Lys Tyr Val Tyr Ile Ala Glu Leu Leu Ala His
        610             615             620

Lys Ile His Val Tyr Glu Lys His Ala Asn Trp Thr Leu Thr Pro Leu
625             630             635             640

Lys Ser Leu Asp Phe Asn Thr Leu Val Asp Asn Ile Ser Val Asp Pro
                645             650             655

Glu Thr Gly Asp Leu Trp Val Gly Cys His Pro Asn Gly Met Lys Ile
            660             665             670

Phe Phe Tyr Asp Ser Glu Asn Pro Pro Ala Ser Glu Val Leu Arg Ile
        675             680             685

Gln Asn Ile Leu Thr Glu Pro Lys Val Thr Gln Val Tyr Ala Glu
                690             695             700

Asn Gly Thr Val Leu Gln Gly Ser Thr Val Ala Ser Val Tyr Lys Gly
705             710             715             720

Lys Leu Leu Ile Gly Thr Val Phe His Lys Ala Leu Tyr Cys Glu Leu
                725             730             735

<210> SEQ ID NO 67
<211> LENGTH: 835
<212> TYPE: DNA
<213> ORGANISM: Homo sapiens

<400> SEQUENCE: 67
atggttcgtc tgcctctgca gtgcgtcctc tggggctgct tgctgaccgc tgtccatcca     60
gaaccaccca ctgcatgcag agaaaaacag tacctaataa acagtcagtg ctgttctttg    120
tgccagccag acagaaaact ggtgagtgac tgcacagagt tcactgaaac ggaatgcctt    180
ccttgcggtg aaagcgaatt cctagacacc tggaacagag agacacactg ccaccagcac    240
aaatactgcg accccaacct agggcttcgg gtccagcaga agggcacctc agaaacagac    300
accatctgca cctgtgaaga aggctggcac tgtacgagtg aggcctgtga gagctgtgtc    360
ctgcaccgct catgctcgcc cggctttggg gtcaagcaga ttgctacagg gtttctgat     420 accatctgcg agccctgccc agtcggcttc ttctccaatg tgtcatctgc tttcgaaaaa    480
tgtcacccct ggacaagctg tgagaccaaa gacctggttg tgcaacaggc aggcacaaac    540
aagactgatg ttgtctgtgg tccccaggat cggctgagag ccctggtggt gatccccatc    600
atcttcggga tcctgtttgc catcctcttg gtgctggtct ttatcaaaaa ggtggccaag    660
aagccaacca ataaggcccc ccaccccaag caggaacccc aggagatcaa ttttcccgac    720
gatcttcctg gctccaacac tgctgctcca gtgcaggaga ctttacatgg atgccaaccg    780
gtcacccagg aggatggcaa agagagtcgc atctcagtgc aggagagaca gtgag         835

<210> SEQ ID NO 68
<211> LENGTH: 277
<212> TYPE: PRT
<213> ORGANISM: Homo sapiens

<400> SEQUENCE: 68

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30
```

```
Ile Asn Ser Gln Cys Cys Ser Leu Cys Gln Pro Gly Gln Lys Leu Val
         35                  40                  45

Ser Asp Cys Thr Glu Phe Thr Glu Thr Glu Cys Leu Pro Cys Gly Glu
 50                  55                  60

Ser Glu Phe Leu Asp Thr Trp Asn Arg Glu Thr His Cys His Gln His
65                   70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 69
<211> LENGTH: 1351
<212> TYPE: DNA
<213> ORGANISM: Artificial Sequence
<220> FEATURE:
<223> OTHER INFORMATION: [hCD40 EC]-(g4s)4-[SSShinge-P238S Fc] DNA

<400> SEQUENCE: 69
atggttcgtc tgcctctgca gtgcgtcctc tggggctgct tgctgaccgc tgtccatcca      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
aaatactgcg accccaacct agggcttcgg gtccagcaga agggcacctc agaaacagac     300
accatctgca cctgtgaaga aggctggcac tgtacgagtg aggcctgtga gagctgtgtc     360
ctgcaccgct catgctcgcc cggctttggg gtcaagcaga ttgctacagg ggtttctgat     420
accatctgcg agccctgccc agtcggcttc ttctccaatg tgtcatctgc tttcgaaaaa     480
tgtcacccCt tggacaagct gtgagaccaaa gacctggttg tgcaacaggc aggcacaaac     540
aagactgatg ttgtctgtgg tccagatctc tccggaggag gtggctcagg tggtggagga     600
tctggaggag gtgggagtgg tggaggtggt tctaccggtc tcgagcccaa atcttctgac     660
```

-continued

```
aaaactcaca catctccacc gtccccagca cctgaactcc tgggaggatc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagcctcc atcgagaaaa ccatctccaa agccaaaggg     1020
cagccccgag aaccacaggt gtacaccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tctctctctc cgggtaaata ataatctaga a                                    1351
```

<210> SEQ ID NO 70
<211> LENGTH: 446
<212> TYPE: PRT
<213> ORGANISM: Artificial Sequence
<220> FEATURE:
<223> OTHER INFORMATION: [hCD40 EC]-(g4s)4-[SSHinge-P238S Fc]

<400> SEQUENCE: 70

```
Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Gly Ser Gly Gly Gly Gly Ser Gly Gly
        195                 200                 205

Gly Gly Ser Thr Gly Leu Glu Pro Lys Ser Ser Asp Lys Thr His Thr
    210                 215                 220

Ser Pro Pro Ser Pro Ala Pro Glu Leu Leu Gly Gly Ser Ser Val Phe
225                 230                 235                 240
```

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 71
<211> LENGTH: 1341
<212> TYPE: DNA
<213> ORGANISM: Artificial Sequence
<220> FEATURE:
<223> OTHER INFORMATION: hVK3LP-[hCD40 EC]-(g4s)4-[SSHinge-P238S Fc]
      DNA

<400> SEQUENCE: 71
atggaaaccc cagcgcagct tctcttcctc ctgctactct ggctcccaga taccaccggt      60
gaaccaccca ctgcatgcag agaaaaacag tacctaataa acagtcagtg ctgttctttg     120
tgccagccag acagaaaact ggtgagtgac tgcacagagt tcactgaaac ggaatgcctt     180
ccttgcggtg aaagcgaatt cctagacacc tggaacagag acacactg ccaccagcac      240 aaatactgcg accccaacct agggcttcgg gtccagcaga agggcacctc agaaacagac     300
accatctgca cctgtgaaga aggctggaca tgtacgagtg aggcctgtga gagctgtgtc     360
ctgcaccgct catgctcgcc cggctttggg gtcaagcaga ttgctacagg ggtttctgat     420
accatctgcg agcctgccc agtcggcttc ttctccaatg tgtcatctgc tttcgaaaaa      480
tgtcaccctt ggacaagctg tgagaccaaa gacctggttg caacaggc aggcacaaac       540 aagactgatg ttgtctgtgg tccagatctc tccggaggag gtggctcagg tggtggagga     600
tctggaggag gtgggagtgg tggaggtggt tctaccggtc tcgagcccaa atcttctgac     660
aaaactcaca catctccacc gtccccagca cctgaactcc tgggaggatc gtcagtcttc     720
ctcttccccc caaaacccaa ggacaccctc atgatctccc ggaccctga ggtcacatgc       780 gtggtggtgg acgtgagcca cgaagaccct gaggtcaagt tcaactggta cgtggacggc     840

```
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagcctcc atcgagaaaa ccatctccaa agccaaaggg     1020
cagccccgag aaccacaggt gtacaccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tctctctctc cgggtaaata a                                                1341
```

<210> SEQ ID NO 72
<211> LENGTH: 446
<212> TYPE: PRT
<213> ORGANISM: Artificial Sequence
<220> FEATURE:
<223> OTHER INFORMATION: hVK3LP-[hCD40 EC]-(g4s)4-[SSShinge-P238S Fc]

<400> SEQUENCE: 72

```
Met Glu Thr Pro Ala Gln Leu Leu Phe Leu Leu Leu Leu Trp Leu Pro
1               5                   10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Gly Ser Gly Gly Gly Gly Ser Gly Gly
        195                 200                 205

Gly Gly Ser Thr Gly Leu Glu Pro Lys Ser Ser Asp Lys Thr His Thr
    210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445
```

<210> SEQ ID NO 73
<211> LENGTH: 2425
<212> TYPE: DNA
<213> ORGANISM: Artificial Sequence
<220> FEATURE:
<223> OTHER INFORMATION: hVK3LP-[hCD40 EC]-(g4s)
    4-[SSShinge-P238S Fc]-NGS-[PON1 Q192K] DNA

<400> SEQUENCE: 73

```
atggaaaccc cagcgcagct tctcttcctc ctgctactct ggctcccaga taccaccggt      60
gaaccaccca ctgcatgcag agaaaaacag tacctaataa acagtcagtg ctgttctttg     120
tgccagccag acagaaaact ggtgagtgac tgcacagagt tcactgaaac ggaatgcctt     180
ccttgcggtg aaagcgaatt cctagacacc tggaacagag agacacactg ccaccagcac     240
aaatactgcg accccaacct agggcttcgg gtccagcaga agggcacctc agaaacagac     300
accatctgca cctgtgaaga aggctggaca tgtacgagtg aggcctgtga gagctgtgtc     360
ctgcaccgct catgctcgcc cggctttggg gtcaagcaga ttgctacagg ggtttctgat     420
accatctgcg agccctgccc agtcggcttc ttctccaatg tgtcatctgc tttcgaaaaa     480
tgtcacccct tggacaagct gtgagaccaa agacctggttg tgcaacaggc aggcacaaac     540
aagactgatg ttgtctgtgg tccagatctc tccggaggag gtggctcagg tggtggagga     600
tctggaggag gtgggagtgg tggaggtggt tctaccggtc tcgagcccaa atcttctgac     660
aaaactcaca catctccacc gtccccagca cctgaactcc tgggaggatc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagcctcc atcgagaaaa ccatctccaa agccaaaggg    1020
cagccccgag aaccacaggt gtacaccctg cccccatccc gggatgagct gaccaagaac    1080
```

```
caggtcagcc tgacctgcct ggtcaaaggc ttctatccca gcgacatcgc cgtggagtgg       1140
gagagcaatg ggcagccgga gaacaactac aagaccacgc ctcccgtgct ggactccgac       1200
ggctccttct tcctctacag caagctcacc gtggacaaga gcaggtggca gcaggggaac       1260
gtcttctcat gctccgtgat gcatgaggct ctgcacaacc actacacgca gaagagcctc       1320
tctctctctc cgggtaaagt cgacggagct agcagccccg tgaacgtgag cagccccagc       1380
gtgcaggata tcctcttcag gaaccaccag tcttcttacc aaacacgact taatgctctc       1440
cgagaggtac aacccgtaga acttcctaac tgtaatttag ttaaaggaat cgaaactggc       1500
tctgaagact tggagatact gcctaatgga ctggctttca ttagctctgg attaaagtat       1560
cctggaataa agagcttcaa ccccaacagt cctggaaaaa tacttctgat ggacctgaat       1620
gaagaagatc aacagtgtt  ggaattgggg atcactggaa gtaaatttga tgtatcttca       1680
tttaaccctc atgggattag cacattcaca gatgaagata atgccatgta cctcctggtg       1740
gtgaaccatc cagatgccaa gtccacagtg gagttgttta aatttcaaga agaagaaaaa       1800
tcgcttttgc atctaaaaac catcagacat aaacttctgc ctaatttgaa tgatattgtt       1860
gctgtgggac ctgagcactt ttatggcaca aatgatcact attttcttga cccctactta       1920
aaatcctggg agatgtattt gggtttagcg tggtcgtatg ttgtctacta tagtccaagt       1980
gaagttcgag tggtggcaga aggatttgat tttgctaatg gaatcaacat ttcacccgat       2040
ggcaagtatg tctatatagc tgagttgctg gctcataaga ttcatgtgta tgaaaagcat       2100
gctaattgga ctttaactcc attgaagtcc cttgacttta ataccctcgt ggataacata       2160
tctgtggatc ctgagacagg agacctttgg gttggatgcc atcccaatgg catgaaaatc       2220
ttcttctatg actcagagaa tcctcctgca tcagaggtgc ttcgaatcca gaacattcta       2280
acagaagaac ctaaagtgac acaggtttat gcagaaaatg gcacagtgtt gcaaggcagt       2340
acagttgcct ctgtgtacaa agggaaactg ctgattggca cagtgtttca caaagctctt       2400
tactgtgagc tctaataatc tagaa                                            2425
```

<210> SEQ ID NO 74
<211> LENGTH: 804
<212> TYPE: PRT
<213> ORGANISM: Artificial Sequence
<220> FEATURE:
<223> OTHER INFORMATION: hVK3LP-[hCD40 EC]-(g4s)
      4-[SSShinge-P238S Fc]-NGS-[PON1 Q192K]

<400> SEQUENCE: 74

Met Glu Thr Pro Ala Gln Leu Leu Phe Leu Leu Leu Trp Leu Pro
1               5                  10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

```
Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
            165                 170                 175

Ala Gly Thr Asn Lys Thr Asp Val Val Cys Gly Pro Asp Leu Ser Gly
            180                 185                 190

Gly Gly Gly Ser Gly Gly Gly Ser Gly Gly Gly Ser Gly Gly
            195                 200                 205

Gly Gly Ser Thr Gly Leu Glu Pro Lys Ser Ser Asp Lys Thr His Thr
            210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Val Asp
            435                 440                 445

Gly Ala Ser Ser Pro Val Asn Val Ser Ser Pro Ser Val Gln Asp Ile
            450                 455                 460

Leu Phe Arg Asn His Gln Ser Ser Tyr Gln Thr Arg Leu Asn Ala Leu
465                 470                 475                 480

Arg Glu Val Gln Pro Val Glu Leu Pro Asn Cys Asn Leu Val Lys Gly
            485                 490                 495

Ile Glu Thr Gly Ser Glu Asp Leu Glu Ile Leu Pro Asn Gly Leu Ala
            500                 505                 510

Phe Ile Ser Ser Gly Leu Lys Tyr Pro Gly Ile Lys Ser Phe Asn Pro
            515                 520                 525

Asn Ser Pro Gly Lys Ile Leu Leu Met Asp Leu Asn Glu Glu Asp Pro
```

```
                530             535             540
Thr Val Leu Glu Leu Gly Ile Thr Gly Ser Lys Phe Asp Val Ser Ser
545                 550                 555                 560

Phe Asn Pro His Gly Ile Ser Thr Phe Thr Asp Glu Asp Asn Ala Met
                565                 570                 575

Tyr Leu Leu Val Val Asn His Pro Asp Ala Lys Ser Thr Val Glu Leu
                580                 585                 590

Phe Lys Phe Gln Glu Glu Lys Ser Leu Leu His Leu Lys Thr Ile
                595                 600                 605

Arg His Lys Leu Leu Pro Asn Leu Asn Asp Ile Val Ala Val Gly Pro
610                 615                 620

Glu His Phe Tyr Gly Thr Asn Asp His Tyr Phe Leu Asp Pro Tyr Leu
625                 630                 635                 640

Lys Ser Trp Glu Met Tyr Leu Gly Leu Ala Trp Ser Tyr Val Val Tyr
                645                 650                 655

Tyr Ser Pro Ser Glu Val Arg Val Val Ala Glu Gly Phe Asp Phe Ala
                660                 665                 670

Asn Gly Ile Asn Ile Ser Pro Asp Gly Lys Tyr Val Tyr Ile Ala Glu
                675                 680                 685

Leu Leu Ala His Lys Ile His Val Tyr Glu Lys His Ala Asn Trp Thr
690                 695                 700

Leu Thr Pro Leu Lys Ser Leu Asp Phe Asn Thr Leu Val Asp Asn Ile
705                 710                 715                 720

Ser Val Asp Pro Glu Thr Gly Asp Leu Trp Val Gly Cys His Pro Asn
                725                 730                 735

Gly Met Lys Ile Phe Phe Tyr Asp Ser Glu Asn Pro Pro Ala Ser Glu
                740                 745                 750

Val Leu Arg Ile Gln Asn Ile Leu Thr Glu Glu Pro Lys Val Thr Gln
                755                 760                 765

Val Tyr Ala Glu Asn Gly Thr Val Leu Gln Gly Ser Thr Val Ala Ser
                770                 775                 780

Val Tyr Lys Gly Lys Leu Leu Ile Gly Thr Val Phe His Lys Ala Leu
785                 790                 795                 800

Tyr Cys Glu Leu

<210> SEQ ID NO 75
<211> LENGTH: 1341
<212> TYPE: DNA
<213> ORGANISM: Artificial Sequence
<220> FEATURE:
<223> OTHER INFORMATION: hVK3LP-[hCD40 K81T EC]-(g4s)4-[SSHinge-P238S
      Fc] DNA

<400> SEQUENCE: 75
atggaaaccc cagcgcagct tctcttcctc ctgctactct ggctcccaga taccaccggt      60
gaaccaccca tgcatgcag agaaaaacag tacctaataa acagtcagtg ctgttctttg     120
tgccagccag acagaaaact ggtgagtgac tgcacagagt tcactgaaac ggaatgcctt     180
ccttgcggtg aaagcgaatt cctagacacc tggaacagag agacacactg ccaccagcac     240
acatactgcg acccccaacct agggcttcgg gtccagcaga gggcacctc agaaacagac     300 accatctgca cctgtgaaga aggctggcac tgtacgagtg aggcctgtga gagctgtgtc     360
ctgcaccgct catgctcgcc cggctttggg gtcaagcaga ttgctacagg gtttctgat     420 accatctgcg agccctgccc agtcggcttc ttctccaatg tgtcatctgc tttcgaaaaa     480
```

```
tgtcacccct tggacaagctg tgagaccaaa gacctggttg tgcaacaggc aggcacaaac    540
aagactgatg ttgtctgtgg tccagatctc tccggaggag gtggctcagg tggtggagga    600
tctggaggag gtgggagtgg tggaggtggt tctaccggtc tcgagcccaa atcttctgac    660
aaaactcaca catctccacc gtccccagca cctgaactcc tgggaggatc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagcctcc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tctctctctc cgggtaaata a                                              1341
```

<210> SEQ ID NO 76
<211> LENGTH: 446
<212> TYPE: PRT
<213> ORGANISM: Artificial Sequence
<220> FEATURE:
<223> OTHER INFORMATION: hVK3LP-[hCD40 K81T EC]-(g4s)4-[SSHinge-P238S Fc]

<400> SEQUENCE: 76

```
Met Glu Thr Pro Ala Gln Leu Leu Phe Leu Leu Leu Leu Trp Leu Pro
1               5                   10                  15

Asp Thr Thr Gly Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Thr Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Gly Ser Gly Gly Gly Gly Ser Gly Gly
        195                 200                 205
```

Gly Gly Ser Thr Gly Leu Glu Pro Lys Ser Ser Asp Lys Thr His Thr
    210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 77
<211> LENGTH: 2418
<212> TYPE: DNA
<213> ORGANISM: Artificial Sequence
<220> FEATURE:
<223> OTHER INFORMATION: hVK3LP-[hCD40 K81T EC]-(g4s)4-[SSHinge-P238S
      Fc]-NGS-[PON1 Q192K] DNA

<400> SEQUENCE: 77
atggaaaccc cagcgcagct tctcttcctc ctgctactct ggctcccaga taccaccggt      60
gaaccaccca ctgcatgcag agaaaaacag tacctaataa acagtcagtg ctgttctttg     120
tgccagccag acagaaaact ggtgagtgac tgcacagagt tcactgaaac ggaatgcctt     180
ccttgcggtg aaagcgaatt cctagacacc tggaacagag agacacactg ccaccagcac     240
acatactgcg accccaacct agggcttcgg gtccagcaga agggcacctc agaaacagac     300
accatctgca cctgtgaaga aggctggaca tgtacgagtg aggcctgtga gagctgtgtc     360
ctgcaccgct catgctcgcc cggctttggg gtcaagcaga ttgctacagg gtttctgat      420 accatctgcg agccctgccc agtcggcttc ttctccaatg tgtcatctgc tttcgaaaaa     480
tgtcacccct tggacaagct gtgagaccaaa gacctggttg tgcaacaggc aggcacaaac     540
aagactgatg ttgtctgtgg tccagatctc tccggaggag gtggctcagg tggtggagga     600
tctggaggag gtgggagtgg tggaggtggt tctaccggtc tcgagcccaa atcttctgac     660

-continued

```
aaaactcaca catctccacc gtccccagca cctgaactcc tgggaggatc gtcagtcttc    720
ctcttccccc caaaacccaa ggacaccctc atgatctccc ggaccnctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagcctcc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tctctctctc cgggtaaagt cgacggagct agcagcccg tgaacgtgag cagccccagc   1380
gtgcaggata tcctcttcag gaaccaccag tcttcttacc aaacacgact taatgctctc   1440
cgagaggtac aacccgtaga acttcctaac tgtaatttag ttaaaggaat cgaaactggc   1500
tctgaagact tggagatact gcctaatgga ctggctttca ttagctctgg attaaagtat   1560
cctggaataa agagcttcaa ccccaacagt cctggaaaaa tacttctgat ggacctgaat   1620
gaagaagatc aacagtgtt ggaattgggg atcactggaa gtaaatttga tgtatcttca   1680
tttaaccctc atgggattag cacattcaca gatgaagata tgccatgta cctcctggtg   1740
gtgaaccatc cagatgccaa gtccacagtg gagttgttta aatttcaaga agaagaaaaa   1800
tcgcttttgc atctaaaaac catcagacat aaacttctgc ctaatttgaa tgatattgtt   1860
gctgtgggac ctgagcactt ttatggcaca aatgatcact attttcttga cccctactta   1920
aaatcctggg agatgtattt gggtttagcg tggtcgtatg ttgtctacta tagtccaagt   1980
gaagttcgag tggtggcaga aggatttgat tttgctaatg aatcaacat tcacccgat    2040
ggcaagtatg tctatatagc tgagttgctg gctcataaga ttcatgtgta tgaaaagcat   2100
gctaattgga ctttaactcc attgaagtcc cttgacttta taccctcgt ggataacata    2160
tctgtggatc ctgagacagg agaccttggg gttggatgcc atcccaatgg catgaaaatc   2220
ttcttctatg actcagagaa tcctcctgca tcagaggtgc ttcgaatcca gaacattcta   2280
acagaagaac ctaaagtgac acaggtttat gcagaaaatg gcacagtgtt gcaaggcagt   2340
acagttgcct ctgtgtacaa agggaaactg ctgattggca cagtgtttca caaagctctt   2400
tactgtgagc tctaataa                                                 2418
```

<210> SEQ ID NO 78
<211> LENGTH: 804
<212> TYPE: PRT
<213> ORGANISM: Artificial Sequence
<220> FEATURE:
<223> OTHER INFORMATION: hVK3LP-[hCD40 K81T EC]-(g4s)4-[SSHinge-P238S Fc]-NGS-[PON1 Q192K]

<400> SEQUENCE: 78

Met Glu Thr Pro Ala Gln Leu Leu Phe Leu Leu Leu Leu Trp Leu Pro
1               5                   10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

```
Ser Asp Cys Thr Glu Phe Thr Glu Thr Glu Cys Leu Pro Cys Gly Glu
 50                  55                  60
Ser Glu Phe Leu Asp Thr Trp Asn Arg Glu Thr His Cys His Gln His
 65                  70                  75                  80
Thr Tyr Cys Asp Pro Asn Leu Gly Leu Arg Val Gln Gln Lys Gly Thr
                 85                  90                  95
Ser Glu Thr Asp Thr Ile Cys Thr Cys Glu Glu Gly Trp His Cys Thr
                100                 105                 110
Ser Glu Ala Cys Glu Ser Cys Val Leu His Arg Ser Cys Ser Pro Gly
            115                 120                 125
Phe Gly Val Lys Gln Ile Ala Thr Gly Val Ser Asp Thr Ile Cys Glu
130                 135                 140
Pro Cys Pro Val Gly Phe Phe Ser Asn Val Ser Ser Ala Phe Glu Lys
145                 150                 155                 160
Cys His Pro Trp Thr Ser Cys Glu Thr Lys Asp Leu Val Val Gln Gln
                165                 170                 175
Ala Gly Thr Asn Lys Thr Asp Val Val Cys Gly Pro Asp Leu Ser Gly
            180                 185                 190
Gly Gly Gly Ser Gly Gly Gly Gly Ser Gly Gly Gly Gly Ser Gly Gly
            195                 200                 205
Gly Gly Ser Thr Gly Leu Glu Pro Lys Ser Ser Asp Lys Thr His Thr
210                 215                 220
Ser Pro Pro Ser Pro Ala Pro Glu Leu Leu Gly Gly Ser Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Val Asp
            435                 440                 445
Gly Ala Ser Ser Pro Val Asn Val Ser Ser Pro Ser Val Gln Asp Ile
    450                 455                 460
```

| Leu | Phe | Arg | Asn | His | Gln | Ser | Ser | Tyr | Gln | Thr | Arg | Leu | Asn | Ala | Leu |
| 465 | | | | 470 | | | | | 475 | | | | | 480 | |

| Arg | Glu | Val | Gln | Pro | Val | Glu | Leu | Pro | Asn | Cys | Asn | Leu | Val | Lys | Gly |
| | | | 485 | | | | | 490 | | | | | 495 | | |

| Ile | Glu | Thr | Gly | Ser | Glu | Asp | Leu | Glu | Ile | Leu | Pro | Asn | Gly | Leu | Ala |
| | | | 500 | | | | | 505 | | | | | 510 | | |

| Phe | Ile | Ser | Ser | Gly | Leu | Lys | Tyr | Pro | Gly | Ile | Lys | Ser | Phe | Asn | Pro |
| | | 515 | | | | | 520 | | | | | 525 | | | |

| Asn | Ser | Pro | Gly | Lys | Ile | Leu | Leu | Met | Asp | Leu | Asn | Glu | Glu | Asp | Pro |
| | 530 | | | | | 535 | | | | | 540 | | | | |

| Thr | Val | Leu | Glu | Leu | Gly | Ile | Thr | Gly | Ser | Lys | Phe | Asp | Val | Ser | Ser |
| 545 | | | | | 550 | | | | | 555 | | | | | 560 |

| Phe | Asn | Pro | His | Gly | Ile | Ser | Thr | Phe | Thr | Asp | Glu | Asp | Asn | Ala | Met |
| | | | 565 | | | | | 570 | | | | | 575 | | |

| Tyr | Leu | Leu | Val | Val | Asn | His | Pro | Asp | Ala | Lys | Ser | Thr | Val | Glu | Leu |
| | | | 580 | | | | | 585 | | | | | 590 | | |

| Phe | Lys | Phe | Gln | Glu | Glu | Lys | Ser | Leu | Leu | His | Leu | Lys | Thr | Ile | |
| | 595 | | | | | 600 | | | | | 605 | | | | |

| Arg | His | Lys | Leu | Leu | Pro | Asn | Leu | Asn | Asp | Ile | Val | Ala | Val | Gly | Pro |
| 610 | | | | | 615 | | | | | 620 | | | | | |

| Glu | His | Phe | Tyr | Gly | Thr | Asn | Asp | His | Tyr | Phe | Leu | Asp | Pro | Tyr | Leu |
| 625 | | | | 630 | | | | | 635 | | | | | 640 | |

| Lys | Ser | Trp | Glu | Met | Tyr | Leu | Gly | Leu | Ala | Trp | Ser | Tyr | Val | Val | Tyr |
| | | | | 645 | | | | | 650 | | | | | 655 | |

| Tyr | Ser | Pro | Ser | Glu | Val | Arg | Val | Val | Ala | Glu | Gly | Phe | Asp | Phe | Ala |
| | | | 660 | | | | | 665 | | | | | 670 | | |

| Asn | Gly | Ile | Asn | Ile | Ser | Pro | Asp | Gly | Lys | Tyr | Val | Tyr | Ile | Ala | Glu |
| | | | 675 | | | | | 680 | | | | | 685 | | |

| Leu | Leu | Ala | His | Lys | Ile | His | Val | Tyr | Glu | Lys | His | Ala | Asn | Trp | Thr |
| | | 690 | | | | | 695 | | | | | 700 | | | |

| Leu | Thr | Pro | Leu | Lys | Ser | Leu | Asp | Phe | Asn | Thr | Leu | Val | Asp | Asn | Ile |
| 705 | | | | | 710 | | | | | 715 | | | | | 720 |

| Ser | Val | Asp | Pro | Glu | Thr | Gly | Asp | Leu | Trp | Val | Gly | Cys | His | Pro | Asn |
| | | | | 725 | | | | | 730 | | | | | 735 | |

| Gly | Met | Lys | Ile | Phe | Phe | Tyr | Asp | Ser | Glu | Asn | Pro | Pro | Ala | Ser | Glu |
| | | | 740 | | | | | 745 | | | | | 750 | | |

| Val | Leu | Arg | Ile | Gln | Asn | Ile | Leu | Thr | Glu | Glu | Pro | Lys | Val | Thr | Gln |
| | | | 755 | | | | | 760 | | | | | 765 | | |

| Val | Tyr | Ala | Glu | Asn | Gly | Thr | Val | Leu | Gln | Gly | Ser | Thr | Val | Ala | Ser |
| | 770 | | | | | 775 | | | | | 780 | | | | |

| Val | Tyr | Lys | Gly | Lys | Leu | Leu | Ile | Gly | Thr | Val | Phe | His | Lys | Ala | Leu |
| 785 | | | | | 790 | | | | | 795 | | | | | 800 |

Tyr Cys Glu Leu

<210> SEQ ID NO 79
<211> LENGTH: 1341
<212> TYPE: DNA
<213> ORGANISM: Artificial Sequence
<220> FEATURE:
<223> OTHER INFORMATION: hVK3LP-[hCD40 K81H-L121P EC]-(g4s)
    4-[SSShinge-P238S Fc] DNA

<400> SEQUENCE: 79
atggaaaccc cagcgcagct tctcttcctc ctgctactct ggctcccagg taccaccggt    60
gaaccaccca ctgcatgcag agaaaaacag tacctaataa acagtcagtg ctgttctttg   120

```
tgccagccag acagaaact ggtgagtgac tgcacagagt tcactgaaac ggaatgcctt      180
ccttgcggtg aaagcgaatt cctagacacc tggaacagag agacacactg ccaccagcac      240
cactactgcg accccaacct agggcttcgg gtccagcaga agggcaccctc agaaacagac      300 accatctgca cctgtgaaga aggctggcac tgtacgagtg aggcctgtga gagctgtgtc      360
ccgcaccgct catgctcgcc cggctttggg gtcaagcaga ttgctacagg ggtttctgat      420
accatctgcg agccctgccc agtcggcttc ttctccaatg tgtcatctgc tttcgaaaaa      480 tgtcacccctt ggacaagctg tgagaccaaa gacctggttg tgcaacaggc aggcacaaac      540
aagactgatg ttgtctgtgg tccagatctc tccggaggag gtggctcagg tggtggagga      600
tctggaggag gtgggagtgg tggaggtggt tctaccggtc tcgagcccaa atcttctgac      660
aaaactcaca catctccacc gtccccagca cctgaactcc tgggaggatc gtcagtcttc      720
ctcttccccc caaaacccaa ggacaccctc atgatctccc ggaccctga ggtcacatgc      780 gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagcctcc atcgagaaaa ccatctccaa agccaaaggg     1020
cagccccgag aaccacaggt gtacaccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tctctctctc cgggtaaata a                                                1341
```

<210> SEQ ID NO 80
<211> LENGTH: 446
<212> TYPE: PRT
<213> ORGANISM: Artificial Sequence
<220> FEATURE:
<223> OTHER INFORMATION: hVK3LP-[hCD40 K81H-L121P EC]-(g4s)
    4-[SSShinge-P238S Fc]

<400> SEQUENCE: 80

```
Met Glu Thr Pro Ala Gln Leu Leu Phe Leu Leu Leu Leu Trp Leu Pro
1               5                   10                  15

Gly Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

His Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Pro His Arg Ser Cys Ser Pro Gly
        115                 120                 125

Phe Gly Val Lys Gln Ile Ala Thr Gly Val Ser Asp Thr Ile Cys Glu
```

```
            130                 135                 140
Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Gly Ser Gly Gly Gly Gly Ser Gly Gly
        195                 200                 205

Gly Gly Ser Thr Gly Leu Glu Pro Lys Ser Ser Asp Lys Thr His Thr
    210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 81
<211> LENGTH: 2415
<212> TYPE: DNA
<213> ORGANISM: Artificial Sequence
<220> FEATURE:
<223> OTHER INFORMATION: hVK3LP-[hCD40 K81H-L121P EC]-(g4s)
      4-[SSShinge-P238S Fc]-NGS-[PON1 Q192K] DNA

<400> SEQUENCE: 81
atggaaaccc cagcgcagct tctcttcctc ctgctactct ggctcccagg taccaccggt      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
cactactgcg accccaacct agggcttcgg gtccagcaga agggcaccct agaaacagac     300
```

```
accatctgca cctgtgaaga aggctggcac tgtacgagtg aggcctgtga gagctgtgtc    360
ccgcaccgct catgctcgcc cggctttggg gtcaagcaga ttgctacagg ggtttctgat    420
accatctgcg agccctgccc agtcggcttc ttctccaatg tgtcatctgc tttcgaaaaa    480
tgtcacccct ggacaagctg tgagaccaaa gacctggttg tgcaacaggc aggcacaaac    540
aagactgatg ttgtctgtgg tccagatctc tccggaggag gtggctcagg tggtggagga    600
tctggaggag gtgggagtgg tggaggtggt tctaccggtc tcgagcccaa atcttctgac    660
aaaactcaca catctccacc gtccccagca cctgaactcc tgggaggatc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagcctcc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct cctctacag caagctcacc gtggacaaga gcaggtggca gcaggggaac   1260
gtcttctcat gctccgtgat gcatgaggct ctgcacaacc actacacgca gaagagcctc   1320
tctctctctc cgggtaaagt cgacggagct agcagccccg tgaacgtgag cagccccagc   1380
gtgcaggata tcctcttcag gaaccaccag tcttcttacc aaacacgact taatgctctc   1440
cgagaggtac aacccgtaga acttcctaac tgtaatttag ttaaaggaat cgaaactggc   1500
tctgaagact tggagatact gcctaatgga ctggctttca ttagctctgg attaaagtat   1560
cctggaataa agagcttcaa ccccaacagt cctggaaaaa tacttctgat ggacctgaat   1620
gaagaagatc caacagtgtt ggaattgggg atcactggaa gtaaatttga tgtatcttca   1680
tttaaccctc atgggattag cacattcaca gatgaagata tgccatgta cctcctggtg   1740 gtgaaccatc cagatgccaa gtccacagtg gagttgttta aatttcaaga agaagaaaaa   1800
tcgcttttgc atctaaaaac catcagacat aaacttctgc ctaatttgaa tgatattgtt   1860
gctgtgggac ctgagcactt ttatggcaca aatgatcact attttcttga cccctactta   1920
aaatcctggg agatgtattt gggtttagcg tggtcgtatg ttgtctacta tagtccaagt   1980
gaagttcgag tggtggcaga aggatttgat tttgctaatg gaatcaacat ttcacccgat   2040
ggcaagtatg tctatatagc tgagttgctg gctcataaga ttcatgtgta tgaaaagcat   2100
gctaattgga ctttaactcc attgaagtcc cttgactta atcccctcgt ggataacata   2160
tctgtggatc ctgagacagg agacctttgg gttggatgcc atcccaatgg catgaaaatc   2220
ttcttctatg actcagagaa tcctcctgca tcagaggtgc ttcgaatcca gaacattcta   2280
acagaagaac ctaaagtgac acaggtttat gcagaaaatg gcacagtgtt gcaaggcagt   2340
acagttgcct ctgtgtacaa agggaaactg ctgattggca cagtgtttca caaagctctt   2400
tactgtgagc tctaa                                                     2415
```

<210> SEQ ID NO 82
<211> LENGTH: 804
<212> TYPE: PRT
<213> ORGANISM: Artificial Sequence
<220> FEATURE:

<223> OTHER INFORMATION: hVK3LP-[hCD40 K81H-L121P EC]-(g4s)4-[SSShinge-P238S Fc]-NGS-[PON1 Q192K]

<400> SEQUENCE: 82

```
Met Glu Thr Pro Ala Gln Leu Leu Phe Leu Leu Leu Trp Leu Pro
1               5                   10                  15

Gly Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
50                  55                  60

Ser Glu Phe Leu Asp Thr Trp Asn Arg Glu Thr His Cys His Gln His
65                  70                  75                  80

His Tyr Cys Asp Pro Asn Leu Gly Leu Arg Val Gln Gln Lys Gly Thr
                    85                  90                  95

Ser Glu Thr Asp Thr Ile Cys Thr Cys Glu Glu Gly Trp His Cys Thr
                100                 105                 110

Ser Glu Ala Cys Glu Ser Cys Val Pro His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
                180                 185                 190

Gly Gly Gly Ser Gly Gly Gly Ser Gly Gly Gly Ser Gly Gly
            195                 200                 205

Gly Gly Ser Thr Gly Leu Glu Pro Lys Ser Ser Asp Lys Thr His Thr
210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Val Asp
            435                 440                 445

Gly Ala Ser Ser Pro Val Asn Val Ser Pro Ser Val Gln Asp Ile
        450                 455                 460

Leu Phe Arg Asn His Gln Ser Ser Tyr Gln Thr Arg Leu Asn Ala Leu
465                 470                 475                 480

Arg Glu Val Gln Pro Val Glu Leu Pro Asn Cys Asn Leu Val Lys Gly
                485                 490                 495

Ile Glu Thr Gly Ser Glu Asp Leu Glu Ile Leu Pro Asn Gly Leu Ala
                500                 505                 510

Phe Ile Ser Ser Gly Leu Lys Tyr Pro Gly Ile Lys Ser Phe Asn Pro
                515                 520                 525

Asn Ser Pro Gly Lys Ile Leu Leu Met Asp Leu Asn Glu Glu Asp Pro
            530                 535                 540

Thr Val Leu Glu Leu Gly Ile Thr Gly Ser Lys Phe Asp Val Ser Ser
545                 550                 555                 560

Phe Asn Pro His Gly Ile Ser Thr Phe Thr Asp Glu Asp Asn Ala Met
                565                 570                 575

Tyr Leu Leu Val Val Asn His Pro Asp Ala Lys Ser Thr Val Glu Leu
                580                 585                 590

Phe Lys Phe Gln Glu Glu Glu Lys Ser Leu Leu His Leu Lys Thr Ile
            595                 600                 605

Arg His Lys Leu Leu Pro Asn Leu Asn Asp Ile Val Ala Val Gly Pro
610                 615                 620

Glu His Phe Tyr Gly Thr Asn Asp His Tyr Phe Leu Asp Pro Tyr Leu
625                 630                 635                 640

Lys Ser Trp Glu Met Tyr Leu Gly Leu Ala Trp Ser Tyr Val Tyr
                645                 650                 655

Tyr Ser Pro Ser Glu Val Arg Val Val Ala Glu Gly Phe Asp Phe Ala
                660                 665                 670

Asn Gly Ile Asn Ile Ser Pro Asp Gly Lys Tyr Val Tyr Ile Ala Glu
            675                 680                 685

Leu Leu Ala His Lys Ile His Val Tyr Glu Lys His Ala Asn Trp Thr
        690                 695                 700

Leu Thr Pro Leu Lys Ser Leu Asp Phe Asn Thr Leu Val Asp Asn Ile
705                 710                 715                 720

Ser Val Asp Pro Glu Thr Gly Asp Leu Trp Val Gly Cys His Pro Asn
                725                 730                 735

Gly Met Lys Ile Phe Phe Tyr Asp Ser Glu Asn Pro Ala Ser Glu
            740                 745                 750

Val Leu Arg Ile Gln Asn Ile Leu Thr Glu Pro Lys Val Thr Gln
            755                 760                 765

Val Tyr Ala Glu Asn Gly Thr Val Leu Gln Gly Ser Thr Val Ala Ser
770                 775                 780

Val Tyr Lys Gly Lys Leu Leu Ile Gly Thr Val Phe His Lys Ala Leu
785                 790                 795                 800

Tyr Cys Glu Leu
```

<210> SEQ ID NO 83
<211> LENGTH: 1341
<212> TYPE: DNA
<213> ORGANISM: Artificial Sequence
<220> FEATURE:
<223> OTHER INFORMATION: hVK3LP-[hCD40 K81S EC]-(g4s)4-[SSShinge-P238S Fc] DNA

<400> SEQUENCE: 83

```
atggaaaccc cagcgcagct tctcttcctc ctgctactct ggctcccaga taccaccggt      60
gaaccaccca ctgcatgcag agaaaaacag tacctaataa acagtcagtg ctgttctttg     120
tgccagccag gacagaaact ggtgagtgac tgcacagagt tcactgaaac ggaatgcctt     180
ccttgcggtg aaagcgaatt cctagacacc tggaacagag agacacactg ccaccagcac     240
tcctactgcg accccaacct agggcttcgg gtccagcaga agggcacctc agaaacagac     300
accatctgca cctgtgaaga aggctggaca tgtacgagtg aggcctgtga gagctgtgtc     360
ctgcaccgct catgctcgcc cggctttggg gtcaagcaga ttgctacagg ggtttctgat     420
accatctgcg agccctgccc agtcggcttc ttctccaatg tgtcatctgc tttcgaaaaa     480
tgtcacccct tggacaagct gtgagaccaa gacctggttg tgcaacaggc aggcacaaac     540
aagactgatg ttgtctgtgg tccagatctc tccggaggag gtggctcagg tggtggagga     600
tctggaggag gtgggagtgg tggaggtggt tctaccggtc tcgagcccaa atcttctgac     660
aaaactcaca catctccacc gtccccagca cctgaactcc tggaggatcg tcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagcctcc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tctctctctc cgggtaaata a                                              1341
```

<210> SEQ ID NO 84
<211> LENGTH: 446
<212> TYPE: PRT
<213> ORGANISM: Artificial Sequence
<220> FEATURE:
<223> OTHER INFORMATION: hVK3LP-[hCD40 K81S EC]-(g4s)4-[SSShinge-P238S Fc]

<400> SEQUENCE: 84

Met Glu Thr Pro Ala Gln Leu Leu Phe Leu Leu Leu Leu Trp Leu Pro
1               5                   10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

```
Ser Glu Phe Leu Asp Thr Trp Asn Arg Glu Thr His Cys His Gln His
 65                  70                  75                  80

Ser Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Ser Gly Gly Gly Ser Gly Gly
        195                 200                 205

Gly Gly Ser Thr Gly Leu Glu Pro Lys Ser Ser Asp Lys Thr His Thr
210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 85
<211> LENGTH: 2415
<212> TYPE: DNA
<213> ORGANISM: Artificial Sequence
<220> FEATURE:
<223> OTHER INFORMATION: hVK3LP-[hCD40 K81S EC]-(g4s)4-[SSShinge-P238S
```

Fc]-NGS-[PON1 Q192K] DNA

<400> SEQUENCE: 85

```
atggaaaccc cagcgcagct tctcttcctc ctgctactct ggctcccaga taccaccggt     60
gaaccaccca ctgcatgcag agaaaaacag tacctaataa acagtcagtg ctgttctttg    120
tgccagccag gacagaaact ggtgagtgac tgcacagagt tcactgaaac ggaatgcctt    180
ccttgcggtg aaagcgaatt cctagacacc tggaacagag agacacactg ccaccagcac    240
tcctactgcg accccaacct agggcttcgg gtccagcaga agggcacctc agaaacagac    300
accatctgca cctgtgaaga aggctggcac tgtacgagtg aggcctgtga gagctgtgtc    360
ctgcaccgct catgctcgcc cggctttggg gtcaagcaga ttgctacagg ggtttctgat    420
accatctgcg agccctgccc agtcggcttc ttctccaatg tgtcatctgc tttcgaaaaa    480
tgtcacccct ggacaagctg tgagaccaaa gacctggttg gcaacaggc aggcacaaac    540
aagactgatg ttgtctgtgg tccagatctc ccggaggag gtggctcagg tggtggagga    600
tctggaggag gtgggagtgg tggaggtggt tctaccggtc tcgagcccaa atcttctgac    660
aaaactcaca catctccacc gtccccagca cctgaactcc tgggaggatc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagcctcc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tctctctctc cgggtaaagt cgacggagct agcagccccg tgaacgtgag cagccccagc   1380
gtgcaggata tcctcttcag gaaccaccag tcttcttacc aaacacgact taatgctctc   1440
cgagaggtac aacccgtaga acttcctaac tgtaatttag ttaaaggaat cgaaactggc   1500
tctgaagact tggagatact gcctaatgga ctggctttca ttagctctgg attaaagtat   1560
cctggaataa agagcttcaa ccccaacagt cctggaaaaa tacttctgat ggacctgaat   1620
gaagaagatc caacagtgtt ggaattgggg atcactggaa gtaaatttga tgtatcttca   1680
tttaaccctc atgggattag cacattcaca gatgaagata tgccatgta cctcctggtg   1740
gtgaaccatc cagatgccaa gtccacagtg gagttgttta aatttcaaga agaagaaaaa   1800
tcgcttttgc atctaaaaac catcagacat aaacttctgc taatttgaa tgatattgtt   1860
gctgtgggac ctgagcactt ttatggcaca aatgatcact atttcttga cccctactta   1920
aaatcctggg agatgtattt gggtttagcg tggtcgtatg ttgtctacta tagtccaagt   1980
gaagttcgag tggtggcaga aggatttgat tttgctaatg aatcaacat ttcacccgat   2040
ggcaagtatg tctatatagc tgagttgctg gctcataaga ttcatgtgta tgaaaagcat   2100
gctaattgga cttaactcc attgaagtcc cttgacttta ataccctcgt ggataacata   2160
tctgtggatc ctgagacagg agaccttggg gttggatgcc atcccaatgg catgaaaatc   2220
ttcttctatg actcagagaa tcctcctgca tcagaggtgc ttcgaatcca gaacattcta   2280
```

-continued

```
acagaagaac ctaaagtgac acaggtttat gcagaaaatg gcacagtgtt gcaaggcagt    2340
acagttgcct ctgtgtacaa agggaaactg ctgattggca cagtgtttca caaagctctt    2400
tactgtgagc tctaa                                                     2415
```

<210> SEQ ID NO 86
<211> LENGTH: 804
<212> TYPE: PRT
<213> ORGANISM: Artificial Sequence
<220> FEATURE:
<223> OTHER INFORMATION: hVK3LP-[hCD40 K81S EC]-(g4s)4-[SSHinge-P238S
      Fc]-NGS-[PON1 Q192K]

<400> SEQUENCE: 86

```
Met Glu Thr Pro Ala Gln Leu Leu Phe Leu Leu Leu Trp Leu Pro
1               5                   10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
50                  55                  60

Ser Glu Phe Leu Asp Thr Trp Asn Arg Glu Thr His Cys His Gln His
65                  70                  75                  80

Ser Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
            180                 185                 190

Gly Gly Gly Ser Gly Gly Gly Gly Ser Gly Gly Gly Gly Ser Gly Gly
        195                 200                 205

Gly Gly Ser Thr Gly Leu Glu Pro Lys Ser Ser Asp Lys Thr His Thr
210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Val Asp
                435                 440                 445

Gly Ala Ser Ser Pro Val Asn Val Ser Ser Pro Ser Val Gln Asp Ile
        450                 455                 460

Leu Phe Arg Asn His Gln Ser Ser Tyr Gln Thr Arg Leu Asn Ala Leu
465                 470                 475                 480

Arg Glu Val Gln Pro Val Glu Leu Pro Asn Cys Asn Leu Val Lys Gly
                485                 490                 495

Ile Glu Thr Gly Ser Glu Asp Leu Glu Ile Leu Pro Asn Gly Leu Ala
                500                 505                 510

Phe Ile Ser Ser Gly Leu Lys Tyr Pro Gly Ile Lys Ser Phe Asn Pro
            515                 520                 525

Asn Ser Pro Gly Lys Ile Leu Leu Met Asp Leu Asn Glu Glu Asp Pro
        530                 535                 540

Thr Val Leu Glu Leu Gly Ile Thr Gly Ser Lys Phe Asp Val Ser Ser
545                 550                 555                 560

Phe Asn Pro His Gly Ile Ser Thr Phe Thr Asp Glu Asp Asn Ala Met
                565                 570                 575

Tyr Leu Leu Val Val Asn His Pro Asp Ala Lys Ser Thr Val Glu Leu
                580                 585                 590

Phe Lys Phe Gln Glu Glu Glu Lys Ser Leu Leu His Leu Lys Thr Ile
            595                 600                 605

Arg His Lys Leu Leu Pro Asn Leu Asn Asp Ile Val Ala Val Gly Pro
        610                 615                 620

Glu His Phe Tyr Gly Thr Asn Asp His Tyr Phe Leu Asp Pro Tyr Leu
625                 630                 635                 640

Lys Ser Trp Glu Met Tyr Leu Gly Leu Ala Trp Ser Tyr Val Val Tyr
                645                 650                 655

Tyr Ser Pro Ser Glu Val Arg Val Val Ala Glu Gly Phe Asp Phe Ala
            660                 665                 670

Asn Gly Ile Asn Ile Ser Pro Asp Gly Lys Tyr Val Tyr Ile Ala Glu
            675                 680                 685

Leu Leu Ala His Lys Ile His Val Tyr Glu Lys His Ala Asn Trp Thr
        690                 695                 700

Leu Thr Pro Leu Lys Ser Leu Asp Phe Asn Thr Leu Val Asp Asn Ile
705                 710                 715                 720

Ser Val Asp Pro Glu Thr Gly Asp Leu Trp Val Gly Cys His Pro Asn
                725                 730                 735

Gly Met Lys Ile Phe Phe Tyr Asp Ser Glu Asn Pro Pro Ala Ser Glu
            740                 745                 750
```

Val Leu Arg Ile Gln Asn Ile Leu Thr Glu Glu Pro Lys Val Thr Gln
        755                 760                 765

Val Tyr Ala Glu Asn Gly Thr Val Leu Gln Gly Ser Thr Val Ala Ser
        770                 775                 780

Val Tyr Lys Gly Lys Leu Leu Ile Gly Thr Val Phe His Lys Ala Leu
785                 790                 795                 800

Tyr Cys Glu Leu

<210> SEQ ID NO 87
<211> LENGTH: 1341
<212> TYPE: DNA
<213> ORGANISM: Artificial Sequence
<220> FEATURE:
<223> OTHER INFORMATION: hVK3LP-[hCD40 E64Y-K81T-P85Y EC]-(g4s)
      4-[SSShinge-P238S Fc] DNA

<400> SEQUENCE: 87

| | | | |
|---|---|---|---|
| atggaaaccc cagcgcagct tctcttcctc ctgctactct ggctcccaga taccaccggt | | | 60 |
| gaaccaccca ctgcatgcag agaaaaacag tacctaataa acagtcagtg ctgttctttg | | | 120 |
| tgccagccag acagaaaact ggtgagtgac tgcacagagt tcactgaaac ggaatgcctt | | | 180 |
| ccttgcggtt acagcgaatt cctagacacc tggaacagag agacacactg ccaccagcac | | | 240 |
| acatactgcg actacaacct agggcttcgg gtccagcaga agggcacctc agaaacagac | | | 300 |
| accatctgca cctgtgaaga aggctggaca tgtacgagtg aggcctgtga gagctgtgtc | | | 360 |
| ctgcaccgct catgctcgcc cggctttggg gtcaagcaga ttgctacagg ggtttctgat | | | 420 |
| accatctgcg agccctgccc agtcggcttc ttctccaatg tgtcatctgc tttcgaaaaa | | | 480 |
| tgtcacccct tggacaagct gtgagaccaa gacctggttg tgcaacaggc aggcacaaac | | | 540 |
| aagactgatg ttgtctgtgg tccagatctc tccggaggag gtggctcagg tggtggagga | | | 600 |
| tctggaggag gtgggagtgg tggaggtggt tctaccggtc tcgagcccaa atcttctgac | | | 660 |
| aaaactcaca catctccacc gtccccagca cctgaactcc tgggaggatc gtcagtcttc | | | 720 |
| ctcttccccc caaaacccaa ggacaccctc atgatctccc ggacccctga ggtcacatgc | | | 780 |
| gtggtggtgg acgtgagcca cgaagaccct gaggtcaagt tcaactggta cgtggacggc | | | 840 |
| gtggaggtgc ataatgccaa gacaaagccg cgggaggagc agtacaacag cacgtaccgt | | | 900 |
| gtggtcagcg tcctcaccgt cctgcaccag gactggctga atggcaagga gtacaagtgc | | | 960 |
| aaggtctcca acaaagccct cccagcctcc atcgagaaaa ccatctccaa agccaaaggg | | | 1020 |
| cagccccgag aaccacaggt gtacaccctg cccccatccc gggatgagct gaccaagaac | | | 1080 |
| caggtcagcc tgacctgcct ggtcaaaggc ttctatccca gcgacatcgc cgtggagtgg | | | 1140 |
| gagagcaatg ggcagccgga gaacaactac aagaccacgc ctcccgtgct ggactccgac | | | 1200 |
| ggctccttct tcctctacag caagctcacc gtggacaaga gcaggtggca gcagggaaac | | | 1260 |
| gtcttctcat gctccgtgat gcatgaggct ctgcacaacc actacacgca gaagagcctc | | | 1320 |
| tctctctctc cgggtaaata a | | | 1341 |

<210> SEQ ID NO 88
<211> LENGTH: 446
<212> TYPE: PRT
<213> ORGANISM: Artificial Sequence
<220> FEATURE:
<223> OTHER INFORMATION: hVK3LP-[hCD40 E64Y-K81T-P85Y EC]-(g4s)
      4-[SSShinge-P238S Fc]

<400> SEQUENCE: 88

-continued

```
Met Glu Thr Pro Ala Gln Leu Leu Phe Leu Leu Leu Trp Leu Pro
1               5                   10                  15

Asp Thr Thr Gly Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35              40                  45

Ser Asp Cys Thr Glu Phe Thr Glu Thr Glu Cys Leu Pro Cys Gly Tyr
50                      55                  60

Ser Glu Phe Leu Asp Thr Trp Asn Arg Glu Thr His Cys His Gln His
65                  70                  75                  80

Thr Tyr Cys Asp Tyr Asn Leu Gly Leu Arg Val Gln Gln Lys Gly Thr
            85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
                180                 185                 190

Gly Gly Gly Ser Gly Gly Gly Ser Gly Gly Gly Ser Gly Gly
                195                 200                 205

Gly Gly Ser Thr Gly Leu Glu Pro Lys Ser Ser Asp Lys Thr His Thr
    210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 89
<211> LENGTH: 2415
<212> TYPE: DNA
<213> ORGANISM: Artificial Sequence
<220> FEATURE:
<223> OTHER INFORMATION: hVK3LP-[hCD40 E64Y-K81T-P85Y EC]-(g4s)
      4-[SSHinge-P238S Fc]-NGS-[PON1 Q192K] DNA

<400> SEQUENCE: 89

| | |
|---|---|
| atggaaaccc cagcgcagct tctcttcctc ctgctactct ggctcccaga taccaccggt | 60 |
| gaaccaccca ctgcatgcag agaaaaacag tacctaataa acagtcagtg ctgttctttg | 120 |
| tgccagccag gacagaaact ggtgagtgac tgcacagagt tcactgaaac ggaatgcctt | 180 |
| ccttgcggtt acagcgaatt cctagacacc tggaacagag agacacactg ccaccagcac | 240 |
| acatactgcg actacaacct agggcttcgg gtccagcaga agggcacctc agaaacagac | 300 |
| accatctgca cctgtgaaga aggctggact gtacgagtg aggcctgtga gagctgtgtc | 360 |
| ctgcaccgct catgctcgcc cggctttggg gtcaagcaga ttgctacagg ggtttctgat | 420 |
| accatctgcg agccctgccc agtcggcttc ttctccaatg tgtcatctgc tttcgaaaaa | 480 |
| tgtcacccct tggacaagct gtgagaccaaa gacctggttg tgcaacaggc aggcacaaac | 540 |
| aagactgatt ttgtctgtgg tccagatctc tccggaggag gtggctcagg tggtggagga | 600 |
| tctggaggag gtgggagtgg tggaggtggt tctaccggtc tcgagcccaa atcttctgac | 660 |
| aaaactcaca catctccacc gtccccagca cctgaactcc tgggaggatc gtcagtcttc | 720 |
| ctcttccccc caaaacccaa ggacaccctc atgatctccc ggaccccctga ggtcacatgc | 780 |
| gtggtggtgg acgtgagcca cgaagaccct gaggtcaagt tcaactggta cgtggacggc | 840 |
| gtggaggtgc ataatgccaa gacaaagccg cgggaggagc agtacaacag cacgtaccgt | 900 |
| gtggtcagcg tcctcaccgt cctgcaccag gactggctga atggcaagga gtacaagtgc | 960 |
| aaggtctcca acaaagccct cccagcctcc atcgagaaaa ccatctccaa agccaaaggg | 1020 |
| cagccccgag aaccacaggt gtacaccctg cccccatccc gggatgagct gaccaagaac | 1080 |
| caggtcagcc tgacctgcct ggtcaaaggc ttctatccca gcgacatcgc cgtggagtgg | 1140 |
| gagagcaatg ggcagccgga gaacaactac aagaccacgc ctcccgtgct ggactccgac | 1200 |
| ggctccttct tcctctacag caagctcacc gtggacaaga gcaggtggca gcaggggaac | 1260 |
| gtcttctcat gctccgtgat gcatgaggct ctgcacaacc actacacgca gaagagcctc | 1320 |
| tctctctctc cgggtaaagt cgacggagct agcagcccg tgaacgtgag cagccccagc | 1380 |
| gtgcaggata tcctcttcag gaaccaccag tcttcttacc aaacacgact taatgctctc | 1440 |
| cgagaggtac aacccgtaga acttcctaac tgtaatttag ttaaaggaat cgaaactggc | 1500 |
| tctgaagact tggagatact gcctaatgga ctggcttttc ttagctctgg attaaagtat | 1560 |
| cctggaataa agagcttcaa ccccaacagt cctggaaaaa tacttctgat ggacctgaat | 1620 |
| gaagaagatc aacagtgtt ggaattgggg atcactggaa gtaaatttga tgtatcttca | 1680 |
| tttaaccctc atgggattag cacattcaca gatgaagata tgccatgta cctcctggtg | 1740 |
| gtgaaccatc cagatgccaa gtccacagtg gagttgttta aatttcaaga agaagaaaaa | 1800 |
| tcgcttttgc atctaaaaac catcagacat aaacttctgc taatttgaa tgatattgtt | 1860 |

-continued

```
gctgtgggac ctgagcactt ttatggcaca aatgatcact attttcttga cccctactta    1920
aaatcctggg agatgtattt gggtttagcg tggtcgtatg ttgtctacta tagtccaagt    1980
gaagttcgag tggtggcaga aggatttgat tttgctaatg gaatcaacat tcacccgat     2040 ggcaagtatg tctatatagc tgagttgctg gctcataaga ttcatgtgta tgaaaagcat    2100
gctaattgga ctttaactcc attgaagtcc cttgacttta ataccctcgt ggataacata    2160
tctgtggatc ctgagacagg agacctttgg gttggatgcc atcccaatgg catgaaaatc    2220
ttcttctatg actcagagaa tcctcctgca tcagaggtgc ttcgaatcca gaacattcta    2280
acagaagaac ctaaagtgac acaggtttat gcagaaaatg gcacagtgtt gcaaggcagt    2340
acagttgcct ctgtgtacaa agggaaactg ctgattggca cagtgtttca caaagctctt    2400
tactgtgagc tctaa                                                      2415
```

<210> SEQ ID NO 90
<211> LENGTH: 804
<212> TYPE: PRT
<213> ORGANISM: Artificial Sequence
<220> FEATURE:
<223> OTHER INFORMATION: hVK3LP-[hCD40 E64Y-K81T-P85Y EC]-(g4s)
4-[SSShinge-P238S Fc]-NGS-[PON1 Q192K]

<400> SEQUENCE: 90

```
Met Glu Thr Pro Ala Gln Leu Leu Phe Leu Leu Leu Trp Leu Pro
1               5                   10                  15

Asp Thr Thr Gly Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
                35                  40                  45

Ser Asp Cys Thr Glu Phe Thr Glu Thr Glu Cys Leu Pro Cys Gly Tyr
50                  55                  60

Ser Glu Phe Leu Asp Thr Trp Asn Arg Glu Thr His Cys His Gln His
65                  70                  75                  80

Thr Tyr Cys Asp Tyr Asn Leu Gly Leu Arg Val Gln Gln Lys Gly Thr
                85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
                115                 120                 125

Phe Gly Val Lys Gln Ile Ala Thr Gly Val Ser Asp Thr Ile Cys Glu
130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Asp Leu Ser Gly
                180                 185                 190

Gly Gly Gly Ser Gly Gly Gly Gly Ser Gly Gly Gly Ser Gly Gly
                195                 200                 205

Gly Gly Ser Thr Gly Leu Glu Pro Lys Ser Ser Asp Lys Thr His Thr
                210                 215                 220

Ser Pro Pro Ser Pro Ala Pro Glu Leu Leu Gly Gly Ser Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Val Asp
        435                 440                 445
Gly Ala Ser Ser Pro Val Asn Val Ser Ser Pro Ser Val Gln Asp Ile
    450                 455                 460
Leu Phe Arg Asn His Gln Ser Ser Tyr Gln Thr Arg Leu Asn Ala Leu
465                 470                 475                 480
Arg Glu Val Gln Pro Val Glu Leu Pro Asn Cys Asn Leu Val Lys Gly
                485                 490                 495
Ile Glu Thr Gly Ser Glu Asp Leu Glu Ile Leu Pro Asn Gly Leu Ala
            500                 505                 510
Phe Ile Ser Ser Gly Leu Lys Tyr Pro Gly Ile Lys Ser Phe Asn Pro
        515                 520                 525
Asn Ser Pro Gly Lys Ile Leu Leu Met Asp Leu Asn Glu Glu Asp Pro
    530                 535                 540
Thr Val Leu Glu Leu Gly Ile Thr Gly Ser Lys Phe Asp Val Ser Ser
545                 550                 555                 560
Phe Asn Pro His Gly Ile Ser Thr Phe Thr Asp Glu Asp Asn Ala Met
                565                 570                 575
Tyr Leu Leu Val Val Asn His Pro Asp Ala Lys Ser Thr Val Glu Leu
            580                 585                 590
Phe Lys Phe Gln Glu Glu Glu Lys Ser Leu Leu His Leu Lys Thr Ile
        595                 600                 605
Arg His Lys Leu Leu Pro Asn Leu Asn Asp Ile Val Ala Val Gly Pro
    610                 615                 620
Glu His Phe Tyr Gly Thr Asn Asp His Tyr Phe Leu Asp Pro Tyr Leu
625                 630                 635                 640
Lys Ser Trp Glu Met Tyr Leu Gly Leu Ala Trp Ser Tyr Val Val Tyr
                645                 650                 655
Tyr Ser Pro Ser Glu Val Arg Val Val Ala Glu Gly Phe Asp Phe Ala
            660                 665                 670
Asn Gly Ile Asn Ile Ser Pro Asp Gly Lys Tyr Val Tyr Ile Ala Glu
```

```
                    675                 680                 685
Leu Leu Ala His Lys Ile His Val Tyr Glu Lys His Ala Asn Trp Thr
            690                 695                 700
Leu Thr Pro Leu Lys Ser Leu Asp Phe Asn Thr Leu Val Asp Asn Ile
705                 710                 715                 720
Ser Val Asp Pro Glu Thr Gly Asp Leu Trp Val Gly Cys His Pro Asn
                        725                 730                 735
Gly Met Lys Ile Phe Phe Tyr Asp Ser Glu Asn Pro Pro Ala Ser Glu
                740                 745                 750
Val Leu Arg Ile Gln Asn Ile Leu Thr Glu Pro Lys Val Thr Gln
            755                 760                 765
Val Tyr Ala Glu Asn Gly Thr Val Leu Gln Gly Ser Thr Val Ala Ser
        770                 775                 780
Val Tyr Lys Gly Lys Leu Leu Ile Gly Thr Val Phe His Lys Ala Leu
785                 790                 795                 800
Tyr Cys Glu Leu

<210> SEQ ID NO 91
<211> LENGTH: 816
<212> TYPE: DNA
<213> ORGANISM: Artificial Sequence
<220> FEATURE:
<223> OTHER INFORMATION: hVK3LP-[VL-VH anti-TNFalpha scFv] DNA

<400> SEQUENCE: 91
aagcttgccg ccatggaaac cccagcgcag cttctcttcc tcctgctact ctggctcccg      60
gataccaccg gtgacatcca gatgacccag tctccatcct ccctgtctgc atctgtaggg     120
gacagagtca ccatcacttg tcgggcaagt cagggcatca gaaattactt agcctggtat     180
cagcaaaaac cagggaaagc ccctaagctc ctgatctatg ctgcatccac tttgcaatca     240
ggggtcccat ctcggttcag tggcagtgga tctgggacag atttcactct caccatcagc     300
agcctacagc ctgaagatgt tgcaacttat tactgtcaaa ggtataaccg tgcaccgtat     360
acttttggcc aggggaccaa ggtggaaatc aaaggaggtg gtggatctgg tggaggaggt     420
tcaggtggtg gaggatctgg gggtggaggt agtgaggtgc agctggtgga gtctggggga     480
ggcttggtac agcccggcag gtccctgaga ctctcctgtg cggcctctgg attcaccttt     540
gatgattatg ccatgcactg ggtccggcaa gctccaggga agggcctgga atgggtctca     600
gctatcactt ggaatagtgg tcacatagac tatgcggact ctgtggaggg ccgattcacc     660
atctccagag acaacgccaa gaactccctg tatctgcaaa tgaacagtct gagagctgag     720
gatacggccg tatattactg tgcgaaagtc tcgtacctta gcaccgcgtc ctcccttgac     780
tattggggcc aaggtaccct ggtcaccgtc tcgtca                                816

<210> SEQ ID NO 92
<211> LENGTH: 268
<212> TYPE: PRT
<213> ORGANISM: Artificial Sequence
<220> FEATURE:
<223> OTHER INFORMATION: hVK3LP-[VL-VH anti-TNFalpha scFv]

<400> SEQUENCE: 92

Met Glu Thr Pro Ala Gln Leu Leu Phe Leu Leu Leu Trp Leu Pro
1               5                  10                  15
Asp Thr Thr Gly Asp Ile Gln Met Thr Gln Ser Pro Ser Ser Leu Ser
            20                  25                  30
```

| | | | | | | | | | | |
|---|---|---|---|---|---|---|---|---|---|---|
|Ala|Ser|Val|Gly|Asp|Arg|Val|Thr|Ile|Thr|Cys|Arg|Ala|Ser|Gln|Gly|
| | |35| | | |40| | | |45| | | | | |

Ile Arg Asn Tyr Leu Ala Trp Tyr Gln Gln Lys Pro Gly Lys Ala Pro
  50                  55                  60

Lys Leu Leu Ile Tyr Ala Ala Ser Thr Leu Gln Ser Gly Val Pro Ser
65                70                  75                  80

Arg Phe Ser Gly Ser Gly Ser Gly Thr Asp Phe Thr Leu Thr Ile Ser
                  85                  90                  95

Ser Leu Gln Pro Glu Asp Val Ala Thr Tyr Tyr Cys Gln Arg Tyr Asn
            100              105              110

Arg Ala Pro Tyr Thr Phe Gly Gln Gly Thr Lys Val Glu Ile Lys Gly
      115                120              125

Gly Gly Gly Ser Gly Gly Gly Gly Ser Gly Gly Gly Gly Ser Gly Gly
  130                135              140

Gly Gly Ser Glu Val Gln Leu Val Glu Ser Gly Gly Gly Leu Val Gln
145               150               155              160

Pro Gly Arg Ser Leu Arg Leu Ser Cys Ala Ala Ser Gly Phe Thr Phe
            165              170              175

Asp Asp Tyr Ala Met His Trp Val Arg Gln Ala Pro Gly Lys Gly Leu
      180                185              190

Glu Trp Val Ser Ala Ile Thr Trp Asn Ser Gly His Ile Asp Tyr Ala
            195              200              205

Asp Ser Val Glu Gly Arg Phe Thr Ile Ser Arg Asp Asn Ala Lys Asn
      210              215              220

Ser Leu Tyr Leu Gln Met Asn Ser Leu Arg Ala Glu Asp Thr Ala Val
225               230               235              240

Tyr Tyr Cys Ala Lys Val Ser Tyr Leu Ser Thr Ala Ser Ser Leu Asp
            245              250              255

Tyr Trp Gly Gln Gly Thr Leu Val Thr Val Ser Ser
      260                265

<210> SEQ ID NO 93
<211> LENGTH: 2605
<212> TYPE: DNA
<213> ORGANISM: Artificial Sequence
<220> FEATURE:
<223> OTHER INFORMATION: hVK3LP-[VL-VH anti-TNFalpha scFv]-
    [SSShinge-P238S-P331S Fc]-NGS-[PON1 Q192K] DNA

<400> SEQUENCE: 93

```
aagcttgccg ccatggaaac cccagcgcag cttctcttcc tcctgctact ctggctcccg      60
gataccaccg gtgacatcca gatgacccag tctccatcct ccctgtctgc atctgtaggg     120
gacagagtca ccatcacttg tcgggcaagt cagggcatca gaaattactt agcctggtat     180
cagcaaaaac cagggaaagc ccctaagctc ctgatctatg ctgcatccac tttgcaatca     240
ggggtcccat ctcggttcag tggcagtgga tctgggacag atttcactct caccatcagc     300
agcctacagc ctgaagatgt tgcaacttat tactgtcaaa ggtataaccg tgcaccgtat     360
acttttggcc aggggaccaa ggtggaaatc aaaggaggtg gtggatctgg tggaggaggt     420
tcaggtggtg gaggatctgg gggtggaggt agtgaggtgc agctggtgga gtctggggga     480
ggcttggtac agcccggcag gtccctgaga ctctcctgtg cggcctctgg attcaccttt     540
gatgattatg ccatgcactg ggtccggcaa gctccaggga agggcctgga atgggtctca     600
gctatcactt ggaatagtgg tcacatagac tatgcggact ctgtggaggg ccgattcacc     660
atctccagag acaacgccaa gaactccctg tatctgcaaa tgaacagtct gagagctgag     720
```

```
gatacggccg tatattactg tgcgaaagtc tcgtacctta gcaccgcgtc ctcccttgac    780
tattggggcc aaggtaccct ggtcaccgtc tcgtcagatc tcgagcccaa atcttctgac    840
aaaactcaca catctccacc gtccccagca cctgaactcc tgggaggatc gtcagtcttc    900
ctcttccccc caaaacccaa ggacaccctc atgatctccc ggacccctga ggtcacatgc    960
gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca acaaagccct cccagcctcc atcgagaaaa ccatctccaa agccaaaggg   1200
cagccccgag aaccacaggt gtacaccctg cccccatccc gggatgagct gaccaagaac   1260
caggtcagcc tgacctgcct ggtcaaaggc ttctatccca gcgacatcgc cgtggagtgg   1320
gagagcaatg ggcagccgga gaacaactac aagaccacgc ctcccgtgct ggactccgac   1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tctctctctc cgggtaaagt cgacggagct agcagccccg tgaacgtgag cagccccagc   1560
gtgcaggata tcctcttcag gaaccaccag tcttcttacc aaacacgact taatgctctc   1620
cgagaggtac aacccgtaga acttcctaac tgtaatttag ttaaaggaat cgaaactggc   1680
tctgaagact ggagatact  gcctaatgga ctggctttca ttagctctgg attaaagtat   1740
cctggaataa agagcttcaa ccccaacagt cctggaaaaa tacttctgat ggacctgaat   1800
gaagaagatc aacagtgtt  ggaattgggg atcactggaa gtaaatttga tgtatcttca   1860
tttaaccctc atgggattag cacattcaca gatgaagata atgccatgta cctcctggtg   1920
gtgaaccatc cagatgccaa gtccacagtg gagttgttta aatttcaaga agaagaaaaa   1980
tcgcttttgc atctaaaaac catcagacat aaacttctgc taatttgaa  tgatattgtt   2040
gctgtgggac ctgagcactt ttatggcaca aatgatcact attttcttga ccctacttta   2100
aaatcctggg agatgtattt gggtttagcg tggtcgtatg ttgtctacta tagtccaagt   2160
gaagttcgag tggtggcaga aggatttgat tttgctaatg gaatcaacat tcacccgat    2220
ggcaagtatg tctatatagc tgagttgctg gctcataaga ttcatgtgta tgaaaagcat   2280
gctaattgga ctttaactcc attgaagtcc cttgacttta taccctcgt  ggataacata   2340
tctgtggatc ctgagacagg agacctttgg gttggatgcc atcccaatgg catgaaaatc   2400
ttcttctatg actcagagaa tcctcctgca tcagaggtgc ttcgaatcca gaacattcta   2460
acagaagaac ctaaagtgac acaggtttat gcagaaaatg gcacagtgtt gcaaggcagt   2520
acagttgcct ctgtgtacaa agggaaactg ctgattggca cagtgtttca caagctctt    2580
tactgtgagc tctaataatc tagaa                                         2605
```

<210> SEQ ID NO 94
<211> LENGTH: 860
<212> TYPE: PRT
<213> ORGANISM: Artificial Sequence
<220> FEATURE:
<223> OTHER INFORMATION: hVK3LP-[VL-VH anti-TNFalpha scFv]-
    [SSShinge-P238S-P331S Fc]-NGS-[PON1 Q192K]

<400> SEQUENCE: 94

Met Glu Thr Pro Ala Gln Leu Leu Phe Leu Leu Leu Leu Trp Leu Pro
1               5                   10                  15

```
Asp Thr Thr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Arg Asn Tyr Leu Ala Trp Tyr Gln Gln Lys Pro Gly Lys Ala Pro
 50                  55                  60

Lys Leu Leu Ile Tyr Ala Ala Ser Thr Leu Gln Ser Gly Val Pro Ser
 65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Tyr Cys Gln Arg Tyr Asn
                100                 105                 110

Arg Ala Pro Tyr Thr Phe Gly Gln Gly Thr Lys Val Glu Ile Lys Gly
            115                 120                 125

Gly Gly Gly Ser Gly Gly Gly Gly Ser Gly Gly Gly Gly Ser Gly Gly
        130                 135                 140

Gly Gly Ser Glu Val Gln Leu Val Glu Ser Gly Gly Gly Leu Val Gln
145                 150                 155                 160

Pro Gly Arg Ser Leu Arg Leu Ser Cys Ala Ala Ser Gly Phe Thr Phe
                165                 170                 175

Asp Asp Tyr Ala Met His Trp Val Arg Gln Ala Pro Gly Lys Gly Leu
                180                 185                 190

Glu Trp Val Ser Ala Ile Thr Trp Asn Ser Gly His Ile Asp Tyr Ala
            195                 200                 205

Asp Ser Val Glu Gly Arg Phe Thr Ile Ser Arg Asp Asn Ala Lys Asn
 210                 215                 220

Ser Leu Tyr Leu Gln Met Asn Ser Leu Arg Ala Glu Asp Thr Ala Val
225                 230                 235                 240

Tyr Tyr Cys Ala Lys Val Ser Tyr Leu Ser Thr Ala Ser Ser Leu Asp
            245                 250                 255

Tyr Trp Gly Gln Gly Thr Leu Val Thr Val Ser Ser Asp Leu Glu Pro
            260                 265                 270

Lys Ser Ser Asp Lys Thr His Thr Ser Pro Pro Ser Pro Ala Pro Glu
            275                 280                 285

Leu Leu Gly Gly Ser Ser Val Phe Leu Phe Pro Pro Lys Pro Lys Asp
290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Ser Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
```

```
            435                 440                 445
Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                    485                 490                 495

Ser Leu Ser Pro Gly Lys Val Asp Gly Ala Ser Ser Pro Val Asn Val
            500                 505                 510

Ser Ser Pro Ser Val Gln Asp Ile Leu Phe Arg Asn His Gln Ser Ser
            515                 520                 525

Tyr Gln Thr Arg Leu Asn Ala Leu Arg Glu Val Gln Pro Val Glu Leu
            530                 535                 540

Pro Asn Cys Asn Leu Val Lys Gly Ile Glu Thr Gly Ser Glu Asp Leu
545                 550                 555                 560

Glu Ile Leu Pro Asn Gly Leu Ala Phe Ile Ser Ser Gly Leu Lys Tyr
                    565                 570                 575

Pro Gly Ile Lys Ser Phe Asn Pro Asn Ser Pro Gly Lys Ile Leu Leu
            580                 585                 590

Met Asp Leu Asn Glu Glu Asp Pro Thr Val Leu Glu Leu Gly Ile Thr
            595                 600                 605

Gly Ser Lys Phe Asp Val Ser Ser Phe Asn Pro His Gly Ile Ser Thr
            610                 615                 620

Phe Thr Asp Glu Asp Asn Ala Met Tyr Leu Leu Val Val Asn His Pro
625                 630                 635                 640

Asp Ala Lys Ser Thr Val Glu Leu Phe Lys Phe Gln Glu Glu Glu Lys
                    645                 650                 655

Ser Leu Leu His Leu Lys Thr Ile Arg His Lys Leu Leu Pro Asn Leu
            660                 665                 670

Asn Asp Ile Val Ala Val Gly Pro Glu His Phe Tyr Gly Thr Asn Asp
            675                 680                 685

His Tyr Phe Leu Asp Pro Tyr Leu Lys Ser Trp Glu Met Tyr Leu Gly
            690                 695                 700

Leu Ala Trp Ser Tyr Val Val Tyr Tyr Ser Pro Ser Glu Val Arg Val
705                 710                 715                 720

Val Ala Glu Gly Phe Asp Phe Ala Asn Gly Ile Asn Ile Ser Pro Asp
                    725                 730                 735

Gly Lys Tyr Val Tyr Ile Ala Glu Leu Leu Ala His Lys Ile His Val
            740                 745                 750

Tyr Glu Lys His Ala Asn Trp Thr Leu Thr Pro Leu Lys Ser Leu Asp
            755                 760                 765

Phe Asn Thr Leu Val Asp Asn Ile Ser Val Asp Pro Glu Thr Gly Asp
            770                 775                 780

Leu Trp Val Gly Cys His Pro Asn Gly Met Lys Ile Phe Phe Tyr Asp
785                 790                 795                 800

Ser Glu Asn Pro Pro Ala Ser Glu Val Leu Arg Ile Gln Asn Ile Leu
                    805                 810                 815

Thr Glu Glu Pro Lys Val Thr Gln Val Tyr Ala Glu Asn Gly Thr Val
            820                 825                 830

Leu Gln Gly Ser Thr Val Ala Ser Val Tyr Lys Gly Lys Leu Leu Ile
            835                 840                 845

Gly Thr Val Phe His Lys Ala Leu Tyr Cys Glu Leu
            850                 855                 860
```

<210> SEQ ID NO 95
<211> LENGTH: 816
<212> TYPE: DNA
<213> ORGANISM: Artificial Sequence
<220> FEATURE:
<223> OTHER INFORMATION: hVK3LP-[VH-VL anti-TNFalpha scFv] DNA

<400> SEQUENCE: 95

```
aagcttgccg ccatggaaac cccagcgcag cttctcttcc tcctgctact ctggctcccg      60
gataccaccg gtgaggtgca gctggtggag tctgggggag gcttggtaca gcccggcagg     120
tccctgagac tctcctgtgc ggcctctgga ttcacctttg atgattatgc catgcactgg     180
gtccggcaag ctccagggaa gggcctggaa tgggtctcag ctatcacttg aatagtggt      240
cacatagact atgcggactc tgtggagggc cgattcacca tctccagaga caacgccaag     300
aactccctgt atctgcaaat gaacagtctg agagctgagg atacggccgt atattactgt     360
gcgaaagtct cgtaccttag caccgcgtcc tccttgact attggggcca aggtaccctg      420
gtcaccgtct cgagtggagg tggtggatct ggtggaggag gttcaggtgg tggaggatct     480
gggggtggag gtagtgacat ccagatgacc cagtctccat cctccctgtc tgcatctgta     540
ggggacagag tcaccatcac ttgtcgggca agtcagggca tcagaaatta cttagcctgg     600
tatcagcaaa aaccagggaa agcccctaag ctcctgatct atgctgcatc cactttgcaa     660
tcaggggtcc catctcggtt cagtggcagt ggatctggga cagatttcac tctcaccatc     720
agcagcctac agcctgaaga tgttgcaact tattactgtc aaaggtataa ccgtgcaccg     780
tatacttttg gccaggggac caaggtggaa atcaaa                                816
```

<210> SEQ ID NO 96
<211> LENGTH: 268
<212> TYPE: PRT
<213> ORGANISM: Artificial Sequence
<220> FEATURE:
<223> OTHER INFORMATION: hVK3LP-[VH-VL anti-TNFalpha scFv]

<400> SEQUENCE: 96

Met Glu Thr Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Lys Val Ser Tyr Leu Ser Thr Ala Ser Ser Leu
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Gly Gly Gly Gly
145                 150                 155                 160

```
Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Gly Ile Arg Asn
            180                 185                 190

Tyr Leu Ala Trp Tyr Gln Gln Lys Pro Gly Lys Ala Pro Lys Leu Leu
        195                 200                 205

Ile Tyr Ala Ala Ser Thr Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Val Ala Thr Tyr Tyr Cys Gln Arg Tyr Asn Arg Ala Pro
                245                 250                 255

Tyr Thr Phe Gly Gln Gly Thr Lys Val Glu Ile Lys
            260                 265
```

<210> SEQ ID NO 97
<211> LENGTH: 2605
<212> TYPE: DNA
<213> ORGANISM: Artificial Sequence
<220> FEATURE:
<223> OTHER INFORMATION: hVK3LP-[VH-VL anti-TNFalpha scFv]-
      [SSHinge-P238S-P331S Fc]-NGS-[PON1 Q192K] DNA

<400> SEQUENCE: 97

| | | | | | |
|---|---|---|---|---|---|
| aagcttgccg | ccatggaaac | cccagcgcag | cttctcttcc | tcctgctact | ctggctcccg | 60 |
| gataccaccg | gtgaggtgca | gctggtggag | tctgggggag | gcttggtaca | gcccggcagg | 120 |
| tccctgagac | tctcctgtgc | ggcctctgga | ttcacctttg | atgattatgc | catgcactgg | 180 |
| gtccggcaag | ctccagggaa | gggcctggaa | tgggtctcag | ctatcacttg | aatagtggt | 240 |
| cacatagact | atgcggactc | tgtgagggc | cgattcacca | tctccagaga | caacgccaag | 300 |
| aactccctgt | atctgcaaat | gaacagtctg | agagctgagg | atacggccgt | atattactgt | 360 |
| gcgaaagtct | cgtaccttag | cacccgcgtcc | tcccttgact | attggggcca | aggtaccctg | 420 |
| gtcaccgtct | cgagtggagg | tggtggatct | ggtggaggag | gttcaggtgg | tggaggatct | 480 |
| gggggtggag | gtagtgacat | ccagatgacc | cagtctccat | cctccctgtc | tgcatctgta | 540 |
| ggggacagag | tcaccatcac | ttgtcgggca | agtcagggca | tcagaaatta | cttagcctgg | 600 |
| tatcagcaaa | aaccagggaa | agcccctaag | ctcctgatct | atgctgcatc | cactttgcaa | 660 |
| tcaggggtcc | catctcggtt | cagtggcagt | ggatctggga | cagatttcac | tctcaccatc | 720 |
| agcagcctac | agcctgaaga | tgttgcaact | tattactgtc | aaaggtataa | ccgtgcaccg | 780 |
| tatacttttg | gccaggggac | caaggtggaa | atcaaagatc | tcgagcccaa | atcttctgac | 840 |
| aaaactcaca | catctccacc | gtccccagca | cctgaactcc | tgggaggatc | gtcagtcttc | 900 |
| ctcttccccc | caaaacccaa | ggacaccctc | atgatctccc | ggacccctga | ggtcacatgc | 960 |
| gtggtggtgg | acgtgagcca | cgaagaccct | gaggtcaagt | tcaactggta | cgtggacggc | 1020 |
| gtggaggtgc | ataatgccaa | gacaaagccg | cgggaggagc | agtacaacag | cacgtaccgt | 1080 |
| gtggtcagcg | tcctcaccgt | cctgcaccag | gactggctga | atggcaagga | gtacaagtgc | 1140 |
| aaggtctcca | acaaagccct | cccagcctcc | atcgagaaaa | ccatctccaa | agccaaaggg | 1200 |
| cagccccgag | aaccacaggt | gtacaccctg | cccccatccc | gggatgagct | gaccaagaac | 1260 |
| caggtcagcc | tgacctgcct | ggtcaaaggc | ttctatccca | gcgacatcgc | cgtggagtgg | 1320 |
| gagagcaatg | ggcagccgga | gaacaactac | aagaccacgc | ctcccgtgct | ggactccgac | 1380 |
| ggctccttct | tcctctacag | caagctcacc | gtggacaaga | gcaggtggca | gcaggggaac | 1440 |

```
gtcttctcat gctccgtgat gcatgaggct ctgcacaacc actacacgca gaagagcctc    1500
tctctctctc cgggtaaagt cgacggagct agcagcccg tgaacgtgag cagccccagc    1560
gtgcaggata tcctcttcag gaaccaccag tcttcttacc aaacacgact taatgctctc    1620
cgagaggtac aacccgtaga acttcctaac tgtaatttag ttaaaggaat cgaaactggc    1680
tctgaagact tggagatact gcctaatgga ctggctttca ttagctctgg attaaagtat    1740
cctggaataa agagcttcaa ccccaacagt cctggaaaaa tacttctgat ggacctgaat    1800
gaagaagatc aacagtgtt ggaattgggg atcactggaa gtaaatttga tgtatcttca    1860
tttaaccctc atgggattag cacattcaca gatgaagata tgccatgta cctcctggtg    1920 gtgaaccatc cagatgccaa gtccacagtg gagttgttta aatttcaaga agaagaaaaa    1980
tcgcttttgc atctaaaaac catcagacat aaacttctgc ctaatttgaa tgatattgtt    2040
gctgtgggac ctgagcactt ttatggcaca aatgatcact attttcttga cccctactta    2100
aaatcctggg agatgtattt gggtttagcg tggtcgtatg ttgtctacta tagtccaagt    2160
gaagttcgag tggtggcaga aggatttgat tttgctaatg gaatcaacat ttcacccgat    2220
ggcaagtatg tctatatagc tgagttgctg gctcataaga ttcatgtgta tgaaaagcat    2280
gctaattgga ctttaactcc attgaagtcc cttgactta taccctcgt ggataacata    2340 tctgtggatc ctgagacagg agacctttgg gttggatgcc atcccaatgg catgaaaatc    2400
ttcttctatg actcagagaa tcctcctgca tcagaggtgc ttcgaatcca gaacattcta    2460
acagaagaac ctaaagtgac acaggtttat gcagaaaatg gcacagtgtt gcaaggcagt    2520
acagttgcct ctgtgtacaa agggaaactg ctgattggca cagtgtttca caaagctctt    2580
tactgtgagc tctaataatc tagaa                                         2605
```

<210> SEQ ID NO 98
<211> LENGTH: 860
<212> TYPE: PRT
<213> ORGANISM: Artificial Sequence
<220> FEATURE:
<223> OTHER INFORMATION: hVK3LP-[VH-VL anti-TNFalpha scFv]-
      [SSShinge-P238S-P331S Fc]-NGS-[PON1 Q192K]

<400> SEQUENCE: 98

```
Met Glu Thr Pro Ala Gln Leu Leu Phe Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Arg Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Ala Ile Thr Trp Asn Ser Gly His Ile Asp Tyr
65                  70                  75                  80

Ala Asp Ser Val Glu Gly Arg Phe Thr Ile Ser Arg Asp Asn Ala Lys
                85                  90                  95

Asn Ser Leu Tyr Leu Gln Met Asn Ser Leu Arg Ala Glu Asp Thr Ala
            100                 105                 110

Val Tyr Tyr Cys Ala Lys Val Ser Tyr Leu Ser Thr Ala Ser Ser Leu
        115                 120                 125

Asp Tyr Trp Gly Gln Gly Thr Leu Val Thr Val Ser Ser Gly Gly Gly
    130                 135                 140
```

Gly Ser Gly Gly Gly Ser Gly Gly Gly Ser Gly Gly Gly Gly
145                 150                 155                 160

Ser Asp Ile Gln Met Thr Gln Ser Pro Ser Ser Leu Ser Ala Ser Val
            165                 170                 175

Gly Asp Arg Val Thr Ile Thr Cys Arg Ala Ser Gln Gly Ile Arg Asn
                180                 185                 190

Tyr Leu Ala Trp Tyr Gln Gln Lys Pro Gly Lys Ala Pro Lys Leu Leu
        195                 200                 205

Ile Tyr Ala Ala Ser Thr Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Val Ala Thr Tyr Tyr Cys Gln Arg Tyr Asn Arg Ala Pro
                245                 250                 255

Tyr Thr Phe Gly Gln Gly Thr Lys Val Glu Ile Lys Asp Leu Glu Pro
        260                 265                 270

Lys Ser Ser Asp Lys Thr His Thr Ser Pro Ser Pro Ala Pro Glu
    275                 280                 285

Leu Leu Gly Gly Ser Ser Val Phe Leu Phe Pro Lys Pro Lys Asp
290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
        355                 360                 365

Leu Asn Gly Lys Glu Tyr Lys Cys Lys Val Ser Asn Lys Ala Leu Pro
    370                 375                 380

Ala Ser Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys Val Asp Gly Ala Ser Ser Pro Val Asn Val
            500                 505                 510

Ser Ser Pro Ser Val Gln Asp Ile Leu Phe Arg Asn His Gln Ser Ser
        515                 520                 525

Tyr Gln Thr Arg Leu Asn Ala Leu Arg Glu Val Gln Pro Val Glu Leu
    530                 535                 540

Pro Asn Cys Asn Leu Val Lys Gly Ile Glu Thr Gly Ser Glu Asp Leu
545                 550                 555                 560

Glu Ile Leu Pro Asn Gly Leu Ala Phe Ile Ser Ser Gly Leu Lys Tyr

Pro Gly Ile Lys Ser Phe Asn Pro Asn Ser Pro Gly Lys Ile Leu Leu
                565                 570                 575
            580                 585                 590

Met Asp Leu Asn Glu Glu Asp Pro Thr Val Leu Glu Leu Gly Ile Thr
            595                 600                 605

Gly Ser Lys Phe Asp Val Ser Phe Asn Pro His Gly Ile Ser Thr
            610                 615                 620

Phe Thr Asp Glu Asp Asn Ala Met Tyr Leu Leu Val Val Asn His Pro
625                 630                 635                 640

Asp Ala Lys Ser Thr Val Glu Leu Phe Lys Phe Gln Glu Glu Lys
                645                 650                 655

Ser Leu Leu His Leu Lys Thr Ile Arg His Lys Leu Leu Pro Asn Leu
                660                 665                 670

Asn Asp Ile Val Ala Val Gly Pro Glu His Phe Tyr Gly Thr Asn Asp
                675                 680                 685

His Tyr Phe Leu Asp Pro Tyr Leu Lys Ser Trp Glu Met Tyr Leu Gly
            690                 695                 700

Leu Ala Trp Ser Tyr Val Val Tyr Tyr Ser Pro Ser Glu Val Arg Val
705                 710                 715                 720

Val Ala Glu Gly Phe Asp Phe Ala Asn Gly Ile Asn Ile Ser Pro Asp
                            725                 730                 735

Gly Lys Tyr Val Tyr Ile Ala Glu Leu Leu Ala His Lys Ile His Val
                740                 745                 750

Tyr Glu Lys His Ala Asn Trp Thr Leu Thr Pro Leu Lys Ser Leu Asp
                755                 760                 765

Phe Asn Thr Leu Val Asp Asn Ile Ser Val Asp Pro Glu Thr Gly Asp
770                 775                 780

Leu Trp Val Gly Cys His Pro Asn Gly Met Lys Ile Phe Phe Tyr Asp
785                 790                 795                 800

Ser Glu Asn Pro Pro Ala Ser Glu Val Leu Arg Ile Gln Asn Ile Leu
                805                 810                 815

Thr Glu Glu Pro Lys Val Thr Gln Val Tyr Ala Glu Asn Gly Thr Val
                820                 825                 830

Leu Gln Gly Ser Thr Val Ala Ser Val Tyr Lys Gly Lys Leu Leu Ile
                835                 840                 845

Gly Thr Val Phe His Lys Ala Leu Tyr Cys Glu Leu
                850                 855                 860

<210> SEQ ID NO 99
<211> LENGTH: 819
<212> TYPE: DNA
<213> ORGANISM: Artificial Sequence
<220> FEATURE:
<223> OTHER INFORMATION: hVK3LP-[anti-hTGFbeta VH-VL scFv] DNA

<400> SEQUENCE: 99
aagcttgccg ccatggaaac cccagcgcag cttctcttcc tcctgctact ctggctcccg      60
gataccaccg gtgaagttca gctggtggag tctggcggtg gcctggtgca gccagggggc    120
tcactccgtt tgtcctgtgc agcttctggc tacgcattca ccaactatct gatcgagtgg    180
gtccgtcagg cccccgggta agggcctcga gtgggttggtg ttaacaatcc tggatccgga    240
ggctccaact ataacgagaa gttcaagggg cgcgccacta tcagtgcaga caattcgaaa    300
aacacattat acctgcagat gaacagcctg cgtgctgagg acactgccgt ctattattgt    360
gctcgatccg gaggcttcta cttcgactac tggggtcaag aaccctggt caccgtctcc    420

```
tcgggaggtg gtggatctgg tggaggaggt tcaggtggtg gaggatctgg gggtggaggt    480
agtgatatcc agatgaccca gtccccgagc tccctgtccg cctctgtggg cgatagggtc    540
accatcacct gcagagccag tcagagcgtg ctgtatagtt cgaatcagaa gaactacctg    600
gcctggtatc aacagaaacc aggaaaagct ccgaaactac tgatttactg ggctagcact    660
agagaatctg gagtcccttc tcgcttctct ggatccggtt ctgggacgga tttcactctg    720
accatcagca gtctgcagcc agaagacttc gcaacttatt actgtcacca gtatctgagc    780
tctgacacat ttggacaggg taccaaggtg gagatcaaa                           819
```

```
<210> SEQ ID NO 100
<211> LENGTH: 269
<212> TYPE: PRT
<213> ORGANISM: Artificial Sequence
<220> FEATURE:
<223> OTHER INFORMATION: hVK3LP-[anti-hTGFbeta VH-VL scFv]

<400> SEQUENCE: 100

Met Glu Thr Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Tyr Ala
        35                  40                  45

Phe Thr Asn Tyr Leu Ile Glu Trp Val Arg Gln Ala Pro Gly Lys Gly
    50                  55                  60

Leu Glu Trp Val Gly Val Asn Asn Pro Gly Ser Gly Ser Asn Tyr
65                  70                  75                  80

Asn Glu Lys Phe Lys Gly Arg Ala Thr Ile Ser Ala Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Gly Gly Phe Tyr Phe Asp Tyr Trp Gly
        115                 120                 125

Gln Gly Thr Leu Val Thr Val Ser Ser Gly Gly Gly Gly Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Val Leu Tyr Ser Ser Asn Gln
            180                 185                 190

Lys Asn Tyr Leu Ala Trp Tyr Gln Gln Lys Pro Gly Lys Ala Pro Lys
        195                 200                 205

Leu Leu Ile Tyr Trp Ala Ser Thr Arg Glu Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys His Gln Tyr Leu Ser
                245                 250                 255

Ser Asp Thr Phe Gly Gln Gly Thr Lys Val Glu Ile Lys
            260                 265

<210> SEQ ID NO 101
<211> LENGTH: 2608
```

<212> TYPE: DNA
<213> ORGANISM: Artificial Sequence
<220> FEATURE:
<223> OTHER INFORMATION: hVK3LP-[anti-hTGFbeta VH-VL scFv]-SSShinge-P238S-P331S Fc]-NGS-PON1 Q192K] DNA

<400> SEQUENCE: 101

| | |
|---|---:|
| aagcttgccg ccatggaaac cccagcgcag cttctcttcc tcctgctact ctggctcccg | 60 |
| gataccaccg gtgaagttca gctggtggag tctggcggtg gcctggtgca gccaggggc | 120 |
| tcactccgtt tgtcctgtgc agcttctggc tacgcattca ccaactatct gatcgagtgg | 180 |
| gtccgtcagg ccccgggtaa gggcctcgag tgggttggtg ttaacaatcc tggatccgga | 240 |
| ggctccaact ataacgagaa gttcaagggg cgcgccacta tcagtgcaga caattcgaaa | 300 |
| aacacattat acctgcagat gaacagcctg cgtgctgagg acactgccgt ctattattgt | 360 |
| gctcgatccg gaggcttcta cttcgactac tggggtcaag aaccctggt caccgtctcc | 420 |
| tcggaggtg gtggatctgg tggaggaggt tcaggtggtg gaggatctgg gggtggaggt | 480 |
| agtgatatcc agatgaccca gtccccgagc tccctgtccg cctctgtggg cgatagggtc | 540 |
| accatcacct gcagagccag tcagagcgtg ctgtatagtt cgaatcagaa gaactacctg | 600 |
| gcctggtatc aacagaaacc aggaaaagct ccgaaactac tgatttactg ggctagcact | 660 |
| agagaatctg gagtcccttc tcgcttctct ggatccggtt ctgggacgga tttcactctg | 720 |
| accatcagca gtctgcagcc agaagacttc gcaacttatt actgtcacca gtatctgagc | 780 |
| tctgacacat ttggacaggg taccaaggtg gagatcaaag atctcgagcc caatcttct | 840 |
| gacaaaactc acacatctcc accgtcccca gcacctgaac tcctgggagg atcgtcagtc | 900 |
| ttcctcttcc ccccaaaaacc caaggacacc ctcatgatct cccggacccc tgaggtcaca | 960 |
| tgcgtggtgg tggacgtgag ccacgaagac cctgaggtca gttcaactg gtacgtggac | 1020 |
| ggcgtggagg tgcataatgc caagacaaag ccgcgggagg agcagtacaa cagcacgtac | 1080 |
| cgtgtggtca gcgtcctcac cgtcctgcac caggactggc tgaatggcaa ggagtacaag | 1140 |
| tgcaaggtct ccaacaaagc cctcccagcc tccatcgaga aaaccatctc caaagccaaa | 1200 |
| gggcagcccc gagaaccaca ggtgtacacc ctgcccccat cccgggatga gctgaccaag | 1260 |
| aaccaggtca gcctgacctg cctggtcaaa ggcttctatc cagcgacat cgccgtggag | 1320 |
| tgggagagca atgggcagcc ggagaacaac tacaagacca cgcctcccgt gctggactcc | 1380 |
| gacggctcct tcttcctcta cagcaagctc accgtggaca agagcaggtg gcagcagggg | 1440 |
| aacgtcttct catgctccgt gatgcatgag gctctgcaca accactacac gcagaagagc | 1500 |
| ctctctctct ctccgggtaa agtcgacgga gctagcagcc ccgtgaacgt gagcagcccc | 1560 |
| agcgtgcagg atatcctctt caggaaccac cagtcttctt accaaacacg acttaatgct | 1620 |
| ctccgagagg tacaacccgt agaacttcct aactgtaatt tagttaaagg aatcgaaact | 1680 |
| ggctctgaag acttggagat actgcctaat ggactggctt tcattagctc tggattaaag | 1740 |
| tatcctggaa taaagagctt caaccccaac agtcctggaa aaatacttct gatggacctg | 1800 |
| aatgaagaag atccaacagt gttggaattg gggatcactg gaagtaaatt tgatgtatct | 1860 |
| tcatttaacc ctcatgggat tagcacattc acagatgaag ataatgccat gtacctcctg | 1920 |
| gtggtgaacc atccagatgc caagtccaca gtggagttgt ttaaatttca agaagaagaa | 1980 |
| aaatcgcttt tgcatctaaa aaccatcaga cataaacttc tgcctaattt gaatgatatt | 2040 |
| gttgctgtgg gacctgagca cttttatgc acaaatgatc actattttct tgaccccctac | 2100 |
| ttaaaatcct gggagatgta tttgggttta gcgtggtcgt atgttgtcta ctatagtcca | 2160 |

```
agtgaagttc gagtggtggc agaaggattt gattttgcta atggaatcaa catttcaccc    2220
gatggcaagt atgtctatat agctgagttg ctggctcata agattcatgt gtatgaaaag   2280
catgctaatt ggactttaac tccattgaag tcccttgact ttaataccct cgtggataac   2340
atatctgtgg atcctgagac aggagacctt tgggttggat gccatcccaa tggcatgaaa   2400
atcttcttct atgactcaga gaatcctcct gcatcagagg tgcttcgaat ccagaacatt   2460
ctaacagaag aacctaaagt gacacaggtt tatgcagaaa atggcacagt gttgcaaggc   2520
agtacagttg cctctgtgta caagggaaa ctgctgattg cacagtgtt tcacaaagct    2580 ctttactgtg agctctaata atctagaa                                       2608
```

<210> SEQ ID NO 102
<211> LENGTH: 861
<212> TYPE: PRT
<213> ORGANISM: Artificial Sequence
<220> FEATURE:
<223> OTHER INFORMATION: hVK3LP-[anti-hTGFbeta VH-VL scFv]-SSShinge-
      P238S-P331S Fc]-NGS-PON1 Q192K]

<400> SEQUENCE: 102

```
Met Glu Thr Pro Ala Gln Leu Leu Phe Leu Leu Leu Leu Trp Leu Pro
1               5                   10                  15

Asp Thr Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Tyr Ala
        35                  40                  45

Phe Thr Asn Tyr Leu Ile Glu Trp Val Arg Gln Ala Pro Gly Lys Gly
    50                  55                  60

Leu Glu Trp Val Gly Val Asn Asn Pro Gly Ser Gly Gly Ser Asn Tyr
65                  70                  75                  80

Asn Glu Lys Phe Lys Gly Arg Ala Thr Ile Ser Ala Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ser Gly Gly Phe Tyr Phe Asp Tyr Trp Gly
        115                 120                 125

Gln Gly Thr Leu Val Thr Val Ser Ser Gly Gly Gly Ser Gly Gly
    130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Val Leu Tyr Ser Ser Asn Gln
            180                 185                 190

Lys Asn Tyr Leu Ala Trp Tyr Gln Gln Lys Pro Gly Lys Ala Pro Lys
        195                 200                 205

Leu Leu Ile Tyr Trp Ala Ser Thr Arg Glu Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Tyr Cys His Gln Tyr Leu Ser
                245                 250                 255

Ser Asp Thr Phe Gly Gln Gly Thr Lys Val Glu Ile Lys Asp Leu Glu
            260                 265                 270
```

```
Pro Lys Ser Ser Asp Lys Thr His Thr Ser Pro Pro Ser Pro Ala Pro
            275                 280                 285

Glu Leu Leu Gly Gly Ser Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
                340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Lys Val Ser Asn Lys Ala Leu
        370                 375                 380

Pro Ala Ser Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys Val Asp Gly Ala Ser Ser Pro Val Asn
            500                 505                 510

Val Ser Ser Pro Ser Val Gln Asp Ile Leu Phe Arg Asn His Gln Ser
        515                 520                 525

Ser Tyr Gln Thr Arg Leu Asn Ala Leu Arg Glu Val Gln Pro Val Glu
    530                 535                 540

Leu Pro Asn Cys Asn Leu Val Lys Gly Ile Glu Thr Gly Ser Glu Asp
545                 550                 555                 560

Leu Glu Ile Leu Pro Asn Gly Leu Ala Phe Ile Ser Ser Gly Leu Lys
                565                 570                 575

Tyr Pro Gly Ile Lys Ser Phe Asn Pro Asn Ser Pro Gly Lys Ile Leu
            580                 585                 590

Leu Met Asp Leu Asn Glu Glu Asp Pro Thr Val Leu Glu Leu Gly Ile
        595                 600                 605

Thr Gly Ser Lys Phe Asp Val Ser Ser Phe Asn Pro His Gly Ile Ser
    610                 615                 620

Thr Phe Thr Asp Glu Asp Asn Ala Met Tyr Leu Leu Val Val Asn His
625                 630                 635                 640

Pro Asp Ala Lys Ser Thr Val Glu Leu Phe Lys Phe Gln Glu Glu Glu
                645                 650                 655

Lys Ser Leu Leu His Leu Lys Thr Ile Arg His Lys Leu Leu Pro Asn
            660                 665                 670

Leu Asn Asp Ile Val Ala Val Gly Pro Glu His Phe Tyr Gly Thr Asn
        675                 680                 685

Asp His Tyr Phe Leu Asp Pro Tyr Leu Lys Ser Trp Glu Met Tyr Leu
```

| | | | | | | | | | |
|---|---|---|---|---|---|---|---|---|---|
| | | 690 | | | 695 | | | 700 | |
| Gly | Leu | Ala | Trp | Ser | Tyr | Val | Tyr | Ser | Pro | Ser | Glu | Val | Arg |
| 705 | | | | 710 | | | | 715 | | | | 720 | |

Val Val Ala Glu Gly Phe Asp Phe Ala Asn Gly Ile Asn Ile Ser Pro
                725                 730                 735

Asp Gly Lys Tyr Val Tyr Ile Ala Glu Leu Leu Ala His Lys Ile His
            740                 745                 750

Val Tyr Glu Lys His Ala Asn Trp Thr Leu Thr Pro Leu Lys Ser Leu
        755                 760                 765

Asp Phe Asn Thr Leu Val Asp Asn Ile Ser Val Asp Pro Glu Thr Gly
    770                 775                 780

Asp Leu Trp Val Gly Cys His Pro Asn Gly Met Lys Ile Phe Phe Tyr
785                 790                 795                 800

Asp Ser Glu Asn Pro Pro Ala Ser Glu Val Leu Arg Ile Gln Asn Ile
                805                 810                 815

Leu Thr Glu Glu Pro Lys Val Thr Gln Val Tyr Ala Glu Asn Gly Thr
            820                 825                 830

Val Leu Gln Gly Ser Thr Val Ala Ser Val Tyr Lys Gly Lys Leu Leu
        835                 840                 845

Ile Gly Thr Val Phe His Lys Ala Leu Tyr Cys Glu Leu
    850                 855                 860

<210> SEQ ID NO 103
<211> LENGTH: 819
<212> TYPE: DNA
<213> ORGANISM: Artificial Sequence
<220> FEATURE:
<223> OTHER INFORMATION: hVK3LP-[anti-hTGFbeta VL-VH scFv] DNA

<400> SEQUENCE: 103

```
aagcttgccg ccatggaaac cccagcgcag cttctcttcc tcctgctact ctggctcccg      60
gataccaccg gtgatatcca gatgacccag tccccgagct ccctgtccgc ctctgtgggc     120
gatagggtca ccatcacctg cagagccagt cagagcgtgc tgtatagttc gaatcagaag     180
aactacctgg cctggtatca acagaaacca ggaaaagctc cgaaactact gatttactgg     240
gctagcacta gagaatctgg agtcccttct cgcttctctg gatccggttc tgggacggat     300
ttcactctga ccatcagcag tctgcagcca gaagacttcg caacttatta ctgtcaccag     360
tatctgagct ctgacacatt tggacagggt accaaggtgg agatcaaagg aggtggtgga     420
tctggtggag gaggttcagg tggtggagga tctggggggtg gaggtagtga agttcagctg     480
gtggagtctg gcggtggcct ggtgcagcca gggggctcac tccgtttgtc ctgtgcagct     540
tctggctacg cattcaccaa ctatctgatc gagtgggtcc gtcaggcccc gggtaagggc     600
ctcgagtggg ttggtgttaa caatcctgga tccggaggct ccaactataa cgagaagttc     660
aaggggcgcg ccactatcag tgcagacaat tcgaaaaaca cattataccc tgcagatgaac     720 agcctgcgtg ctgaggacac tgccgtctat tattgtgctc gatccggagg cttctacttc     780
gactactggg gtcaaggaac cctggtcacc gtctcctcg                           819
```

<210> SEQ ID NO 104
<211> LENGTH: 269
<212> TYPE: PRT
<213> ORGANISM: Artificial Sequence
<220> FEATURE:
<223> OTHER INFORMATION: hVK3LP-[anti-hTGFbeta VL-VH scFv]

<400> SEQUENCE: 104

```
Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Val Leu Tyr Ser Ser Asn Gln Lys Asn Tyr Leu Ala Trp Tyr Gln Gln
    50                  55                  60

Lys Pro Gly Lys Ala Pro Lys Leu Leu Ile Tyr Trp Ala Ser Thr Arg
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys His Gln Tyr Leu Ser Ser Asp Thr Phe Gly Gln Gly Thr Lys
        115                 120                 125

Val Glu Ile Lys Gly Gly Gly Gly Ser Gly Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ala Phe Thr Asn Tyr Leu Ile Glu Trp Val Arg Gln Ala
            180                 185                 190

Pro Gly Lys Gly Leu Glu Trp Val Gly Val Asn Pro Gly Ser Gly
        195                 200                 205

Gly Ser Asn Tyr Asn Glu Lys Phe Lys Gly Arg Ala Thr Ile Ser Ala
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Ser Gly Gly Phe Tyr Phe
                245                 250                 255

Asp Tyr Trp Gly Gln Gly Thr Leu Val Thr Val Ser Ser
        260                 265

<210> SEQ ID NO 105
<211> LENGTH: 2608
<212> TYPE: DNA
<213> ORGANISM: Artificial Sequence
<220> FEATURE:
<223> OTHER INFORMATION: hVK3LP-[anti-hTGFbeta VL-VH scFv]-SSshinge-
      P238S-P331S Fc]-NGS-PON1 Q192K] DNA

<400> SEQUENCE: 105
aagcttgccg ccatggaaac cccagcgcag cttctcttcc tcctgctact ctggctcccg      60
gataccaccg gtgatatcca gatgacccag tccccgagct ccctgtccgc ctctgtgggc    120
gatagggtca ccatcacctg cagagccagt cagagcgtgc tgtatagttc gaatcagaag    180
aactacctgg cctggtatca acagaaacca ggaaaagctc cgaaactact gatttactgg    240
gctagcacta gagaatctgg agtcccttct cgcttctctg gatccggttc tgggacggat    300
ttcactctga ccatcagcag tctgcagcca gaagacttcg caacttatta ctgtcaccag    360
tatctgagct ctgacacatt tggacagggt accaaggtgg agatcaaagg aggtggtgga    420
tctggtggag gaggttcagg tggtggagga tctggggggtg gaggtagtga agttcagctg    480
```

```
gtggagtctg gcggtggcct ggtgcagcca gggggctcac tccgtttgtc ctgtgcagct      540
tctggctacg cattcaccaa ctatctgatc gagtgggtcc gtcaggcccc gggtaagggc      600
ctcgagtggg ttggtgttaa caatcctgga tccggaggct ccaactataa cgagaagttc      660
aaggggcgcg ccactatcag tgcagacaat tcgaaaaaca cattatacct gcagatgaac      720
agcctgcgtg ctgaggacac tgccgtctat tattgtgctc gatccggagg cttctacttc      780
gactactggg gtcaaggaac cctggtcacc gtctcctcag atctcgagcc caaatcttct      840
gacaaaactc acacatctcc accgtcccca gcacctgaac tcctgggagg atcgtcagtc      900
ttcctcttcc ccccaaaacc caaggacacc ctcatgatct cccggacccc tgaggtcaca      960
tgcgtggtgg tggacgtgag ccacgaagac cctgaggtca agttcaactg gtacgtggac     1020
ggcgtggagg tgcataatgc caagacaaag ccgcggagg agcagtacaa cagcacgtac      1080
cgtgtggtca gcgtcctcac cgtcctgcac caggactggc tgaatggcaa ggagtacaag     1140
tgcaaggtct ccaacaaagc cctcccagcc tccatcgaga aaccatctc caaagccaaa      1200 gggcagcccc gagaaccaca ggtgtacacc ctgcccccat cccgggatga gctgaccaag     1260
aaccaggtca gcctgacctg cctggtcaaa ggcttctatc ccagcgacat cgccgtggag     1320
tgggagagca atgggcagcc ggagaacaac tacaagacca cgcctcccgt gctggactcc     1380
gacggctcct tcttcctcta cagcaagctc accgtggaca gagcaggtg gcagcagggg      1440 aacgtcttct catgctccgt gatgcatgag gctctgcaca accactacac gcagaagagc     1500
ctctctctct ctccgggtaa gtcgacgga gctagcagcc ccgtgaacgt gagcagcccc      1560
agcgtgcagg atatcctctt caggaaccac cagtcttctt accaaacacg acttaatgct     1620
ctccgagagg tacaacccgt agaacttcct aactgtaatt tagttaaagg aatcgaaact     1680
ggctctgaag acttggagat actgcctaat ggactggctt tcattagctc tggattaaag     1740
tatcctggaa taaagagctt caaccccaac agtcctggaa aaatacttct gatggacctg     1800
aatgaagaag atccaacagt gttggaattg gggatcactg gaagtaaatt tgatgtatct     1860
tcatttaacc ctcatgggat tagcacattc acagatgaag ataatgccat gtacctcctg     1920
gtggtgaacc atccagatgc caagtccaca gtggagttgt ttaaatttca agaagaagaa     1980
aaatcgcttt tgcatctaaa aaccatcaga cataaacttc tgcctaattt gaatgatatt     2040
gttgctgtgg gacctgagca ctttttatggc acaaatgatc actattttct tgacccctac     2100
ttaaaatcct gggagatgta tttgggttta gcgtggtcgt atgttgtcta ctatagtcca     2160
agtgaagttc gagtggtggc agaaggattt gattttgcta atggaatcaa catttcacccc    2220 gatggcaagt atgtctatat agctgagttg ctggctcata agattcatgt gtatgaaaag     2280
catgctaatt ggactttaac tccattgaag tcccttgact ttaataccct cgtggataac    2340
atatctgtgg atcctgagac aggagacctt gggttggat gccatcccaa tggcatgaaa     2400
atcttcttct atgactcaga gaatcctcct gcatcagagg tgcttcgaat ccagaacatt    2460
ctaacagaag aacctaaagt gacacaggtt tatgcagaaa atggcacagt gttgcaaggc     2520
agtacagttg cctctgtgta caaagggaaa ctgctgattg gcacagtgtt tcacaaagct     2580 cтттактgтg agctctaata atctagaa                                        2608
```

<210> SEQ ID NO 106
<211> LENGTH: 861
<212> TYPE: PRT
<213> ORGANISM: Artificial Sequence
<220> FEATURE:
<223> OTHER INFORMATION: hVK3LP-[anti-hTGFbeta VL-VH scFv]-SSHinge- P238S-P331S Fc]-NGS-PON1 Q192K]

<400> SEQUENCE: 106

```
Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Val Leu Tyr Ser Ser Asn Gln Lys Asn Tyr Leu Ala Trp Tyr Gln Gln
    50                  55                  60

Lys Pro Gly Lys Ala Pro Lys Leu Leu Ile Tyr Trp Ala Ser Thr Arg
65                  70                  75                  80

Glu Ser Gly Val Pro Ser Arg Phe Ser Gly Ser Gly Ser Gly Thr Asp
                85                  90                  95

Phe Thr Leu Thr Ile Ser Ser Leu Gln Pro Glu Asp Phe Ala Thr Tyr
            100                 105                 110

Tyr Cys His Gln Tyr Leu Ser Ser Asp Thr Phe Gly Gln Gly Thr Lys
        115                 120                 125

Val Glu Ile Lys Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ala Phe Thr Asn Tyr Leu Ile Glu Trp Val Arg Gln Ala
            180                 185                 190

Pro Gly Lys Gly Leu Glu Trp Val Gly Val Asn Asn Pro Gly Ser Gly
        195                 200                 205

Gly Ser Asn Tyr Asn Glu Lys Phe Lys Gly Arg Ala Thr Ile Ser Ala
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Ser Gly Gly Phe Tyr Phe
                245                 250                 255

Asp Tyr Trp Gly Gln Gly Thr Leu Val Thr Val Ser Ser Asp Leu Glu
            260                 265                 270

Pro Lys Ser Ser Asp Lys Thr His Thr Ser Pro Pro Ser Pro Ala Pro
        275                 280                 285

Glu Leu Leu Gly Gly Ser Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Ser Ile Glu Lys Thr Ile Ser Lys Ala Lys Gly Gln Pro Arg
385                 390                 395                 400
```

-continued

```
Glu Pro Gln Val Tyr Thr Leu Pro Pro Ser Arg Asp Glu Leu Thr Lys
                405                 410                 415
Asn Gln Val Ser Leu Thr Cys Leu Val Lys Gly Phe Tyr Pro Ser Asp
            420                 425                 430
Ile Ala Val Glu Trp Glu Ser Asn Gly Gln Pro Glu Asn Asn Tyr Lys
        435                 440                 445
Thr Thr Pro Pro Val Leu Asp Ser Asp Gly Ser Phe Phe Leu Tyr Ser
    450                 455                 460
Lys Leu Thr Val Asp Lys Ser Arg Trp Gln Gln Gly Asn Val Phe Ser
465                 470                 475                 480
Cys Ser Val Met His Glu Ala Leu His Asn His Tyr Thr Gln Lys Ser
                485                 490                 495
Leu Ser Leu Ser Pro Gly Lys Val Asp Gly Ala Ser Ser Pro Val Asn
            500                 505                 510
Val Ser Ser Pro Ser Val Gln Asp Ile Leu Phe Arg Asn His Gln Ser
        515                 520                 525
Ser Tyr Gln Thr Arg Leu Asn Ala Leu Arg Glu Val Gln Pro Val Glu
    530                 535                 540
Leu Pro Asn Cys Asn Leu Val Lys Gly Ile Glu Thr Gly Ser Glu Asp
545                 550                 555                 560
Leu Glu Ile Leu Pro Asn Gly Leu Ala Phe Ile Ser Ser Gly Leu Lys
                565                 570                 575
Tyr Pro Gly Ile Lys Ser Phe Asn Asn Ser Pro Gly Lys Ile Leu
            580                 585                 590
Leu Met Asp Leu Asn Glu Glu Asp Pro Thr Val Leu Glu Leu Gly Ile
        595                 600                 605
Thr Gly Ser Lys Phe Asp Val Ser Ser Phe Asn Pro His Gly Ile Ser
    610                 615                 620
Thr Phe Thr Asp Glu Asp Asn Ala Met Tyr Leu Leu Val Asn His
625                 630                 635                 640
Pro Asp Ala Lys Ser Thr Val Glu Leu Phe Lys Phe Gln Glu Glu Glu
                645                 650                 655
Lys Ser Leu Leu His Leu Lys Thr Ile Arg His Lys Leu Leu Pro Asn
            660                 665                 670
Leu Asn Asp Ile Val Ala Val Gly Pro Glu His Phe Tyr Gly Thr Asn
        675                 680                 685
Asp His Tyr Phe Leu Asp Pro Tyr Leu Lys Ser Trp Glu Met Tyr Leu
    690                 695                 700
Gly Leu Ala Trp Ser Tyr Val Val Tyr Ser Pro Ser Glu Val Arg
705                 710                 715                 720
Val Val Ala Glu Gly Phe Asp Phe Ala Asn Gly Ile Asn Ile Ser Pro
                725                 730                 735
Asp Gly Lys Tyr Val Tyr Ile Ala Glu Leu Leu Ala His Lys Ile His
            740                 745                 750
Val Tyr Glu Lys His Ala Asn Trp Thr Leu Thr Pro Leu Lys Ser Leu
        755                 760                 765
Asp Phe Asn Thr Leu Val Asp Asn Ile Ser Val Asp Pro Glu Thr Gly
    770                 775                 780
Asp Leu Trp Val Gly Cys His Pro Asn Gly Met Lys Ile Phe Phe Tyr
785                 790                 795                 800
Asp Ser Glu Asn Pro Pro Ala Ser Glu Val Leu Arg Ile Gln Asn Ile
                805                 810                 815
Leu Thr Glu Glu Pro Lys Val Thr Gln Val Tyr Ala Glu Asn Gly Thr
```

```
                820             825             830
Val Leu Gln Gly Ser Thr Val Ala Ser Val Tyr Lys Gly Lys Leu Leu
        835             840             845

Ile Gly Thr Val Phe His Lys Ala Leu Tyr Cys Glu Leu
    850             855             860
```

<210> SEQ ID NO 107
<211> LENGTH: 363
<212> TYPE: DNA
<213> ORGANISM: Homo sapiens

<400> SEQUENCE: 107

```
gataccaccg gtgaggtgca gctggtggag tctgggggag gcttggtaca gcccggcagg    60
tccctgagac tctcctgtgc ggcctctgga ttcacctttg atgattatgc catgcactgg   120
gtccggcaag ctccagggaa gggcctggaa tgggtctcag ctatcacttg gaatagtggt   180
cacatagact atgcggactc tgtggagggc cgattcacca tctccagaga caacgccaag   240
aactccctgt atctgcaaat gaacagtctg agagctgagg acacggccgt atattactgt   300
gcgaaagtct cgtaccttag caccgcgtcc tcccttgact attggggcca aggtaccctg   360
gtc                                                                 363
```

<210> SEQ ID NO 108
<211> LENGTH: 121
<212> TYPE: PRT
<213> ORGANISM: Homo sapiens

<400> SEQUENCE: 108

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

<210> SEQ ID NO 109
<211> LENGTH: 321
<212> TYPE: DNA
<213> ORGANISM: Homo sapiens

<400> SEQUENCE: 109

```
gataccaccg gtgacatcca gatgacccag tctccatcct ccctgtctgc atctgtaggg    60
gacagagtca ccatcacttg tcgggcaagt cagggcatca gaaattactt agcctggtat   120
cagcaaaaac cagggaaagc ccctaagctc ctgatctatg ctgcatccac tttgcaatca   180
ggggtcccat ctcggttcag tggcagtgga tctgggacag atttcactct caccatcagc   240
agcctacagc ctgaagatgt tgcaacttat tactgtcaaa ggtataaccg tgcaccgtat   300
```

```
acttttggcc aggggaccaa g                                              321
```

<210> SEQ ID NO 110
<211> LENGTH: 107
<212> TYPE: PRT
<213> ORGANISM: Homo sapiens

<400> SEQUENCE: 110

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

<210> SEQ ID NO 111
<211> LENGTH: 351
<212> TYPE: DNA
<213> ORGANISM: Artificial Sequence
<220> FEATURE:
<223> OTHER INFORMATION: Humanized anti-hTGFbeta VH DNA

<400> SEQUENCE: 111

```
gataccaccg gtgaagttca gctggtggag tctggcggtg gcctggtgca gccaggggc    60
tcactccgtt tgtcctgtgc agcttctggc tacgcattca ccaactatct gatcgagtgg  120
gtccgtcagg ccccgggtaa gggcctcgag tgggttggtg ttaacaatcc tggatccgga  180
ggctccaact ataacgagaa gttcaagggg cgcgccacta tcagtgcaga caattcgaaa  240
aacacattat acctgcagat gaacagcctg cgtgctgagg acactgccgt ctattattgt  300
gctcgatccg gaggcttcta cttcgactac tggggtcaag gaaccctggt c            351
```

<210> SEQ ID NO 112
<211> LENGTH: 117
<212> TYPE: PRT
<213> ORGANISM: Artificial Sequence
<220> FEATURE:
<223> OTHER INFORMATION: Humanized anti-hTGFbeta VH

<400> SEQUENCE: 112

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ala Phe Thr Asn Tyr
            20                  25                  30

Leu Ile Glu Trp Val Arg Gln Ala Pro Gly Lys Gly Leu Glu Trp Val
        35                  40                  45

Gly Val Asn Asn Pro Gly Ser Gly Gly Ser Asn Tyr Asn Glu Lys Phe
    50                  55                  60

Lys Gly Arg Ala Thr Ile Ser Ala Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Gly Gly Phe Tyr Phe Asp Tyr Trp Gly Gln Gly Thr Leu
            100                 105                 110

Val Thr Val Ser Ser
            115

<210> SEQ ID NO 113
<211> LENGTH: 336
<212> TYPE: DNA
<213> ORGANISM: Artificial Sequence
<220> FEATURE:
<223> OTHER INFORMATION: Humanized anti-hTGFbeta VL DNA

<400> SEQUENCE: 113
gataccaccg gtgatatcca gatgacccag tccccgagct ccctgtccgc ctctgtgggc      60
gatagggtca ccatcacctg cagagccagt cagagcgtgc tgtatagttc gaatcagaag     120
aactacctgg cctggtatca acagaaacca ggaaaagctc cgaaactact gatttactgg     180
gctagcacta gagaatctgg agtcccttct cgcttctctg gatccggttc tgggacggat     240
ttcactctga ccatcagcag tctgcagcca gaagacttcg caacttatta ctgtcaccag     300
tatctgagct ctgacacatt tggacagggt accaag                               336

<210> SEQ ID NO 114
<211> LENGTH: 112
<212> TYPE: PRT
<213> ORGANISM: Artificial Sequence
<220> FEATURE:
<223> OTHER INFORMATION: Humanized anti-hTGFbeta VL

<400> SEQUENCE: 114

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys His Gln
                85                  90                  95

Tyr Leu Ser Ser Asp Thr Phe Gly Gln Gly Thr Lys Val Glu Ile Lys
            100                 105                 110

<210> SEQ ID NO 115
<211> LENGTH: 696
<212> TYPE: DNA
<213> ORGANISM: Artificial Sequence
<220> FEATURE:
<223> OTHER INFORMATION: Human IgG1 variant Fc DNA (SCC hinge, P238S,
      P331S)

<400> SEQUENCE: 115
gagcccaaat cttctgacaa aactcacaca tgtccaccgt gcccagcacc tgaactcctg      60
ggaggatcgt cagtcttcct cttccccccc aaacccaagg acaccctcat gatctcccgg     120 accccctgagg tcacatgcgt ggtggtggac gtgagccacg aagaccctga ggtcaagttc     180
```

```
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcctccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc tctctctccg ggtaaa                              696
```

<210> SEQ ID NO 116
<211> LENGTH: 232
<212> TYPE: PRT
<213> ORGANISM: Artificial Sequence
<220> FEATURE:
<223> OTHER INFORMATION: Human IgG1 variant Fc (SCC hinge, P238S, P331S)

<400> SEQUENCE: 116

```
Glu Pro Lys Ser Ser Asp Lys Thr His Thr Cys Pro Pro Cys Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 117
<211> LENGTH: 696
<212> TYPE: DNA
<213> ORGANISM: Artificial Sequence
<220> FEATURE:

<223> OTHER INFORMATION: Human IgG1 variant Fc DNA (SCC hinge, P238S)

<400> SEQUENCE: 117

```
gagcccaaat cttctgacaa aactcacaca tgtccaccgt gcccagcacc tgaactcctg      60
ggaggatcgt cagtcttcct cttccccca  aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa  gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc tctctctccg ggtaaa                               696
```

<210> SEQ ID NO 118
<211> LENGTH: 232
<212> TYPE: PRT
<213> ORGANISM: Artificial Sequence
<220> FEATURE:
<223> OTHER INFORMATION: Human IgG1 variant Fc (SCC hinge, P238S)

<400> SEQUENCE: 118

```
Glu Pro Lys Ser Ser Asp Lys Thr His Thr Cys Pro Pro Cys Pro Ala
1               5                   10                  15
Pro Glu Leu Leu Gly Gly Ser Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
```

```
Ser Leu Ser Leu Ser Pro Gly Lys
225                 230

<210> SEQ ID NO 119
<211> LENGTH: 5
<212> TYPE: PRT
<213> ORGANISM: Artificial Sequence
<220> FEATURE:
<223> OTHER INFORMATION: (gly4ser) tandem repeat sequence

<400> SEQUENCE: 119

Gly Gly Gly Gly Ser
1               5

<210> SEQ ID NO 120
<211> LENGTH: 260
<212> TYPE: PRT
<213> ORGANISM: Homo sapiens

<400> SEQUENCE: 120

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Asn Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Gly Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys
            260

<210> SEQ ID NO 121
<211> LENGTH: 1842
```

<212> TYPE: DNA
<213> ORGANISM: Artificial Sequence
<220> FEATURE:
<223> OTHER INFORMATION: hVK3LP-[KDL-SCChinge-P238S-P331S Fc]-NGS-
    [PON1 Q192K] DNA

<400> SEQUENCE: 121

```
atggaaaccc cagcgcagct tctcttcctc ctgctactct ggctcccaga taccaccggt      60
aaagatctcg agcccaaatc ttctgacaaa actcacacat gtccaccgtg cccagcacct     120
gaactcctgg gaggatcgtc agtcttcctc ttccccccaa acccaagga caccctcatg      180
atctcccgga cccctgaggt cacatgcgtg gtggtggacg tgagccacga agaccctgag     240
gtcaagttca actggtacgt ggacggcgtg gaggtgcata atgccaagac aaagccgcgg     300
gaggagcagt acaacagcac gtaccgtgtg gtcagcgtcc tcaccgtcct gcaccaggac     360
tggctgaatg gcaaggagta caagtgcaag gtctccaaca agcccctccc agcctccatc     420
gagaaaacca tctccaaagc caaagggcag ccccgagaac cacaggtgta caccctgccc     480
ccatcccggg atgagctgac caagaaccag gtcagcctga cctgcctggt caaaggcttc     540
tatcccagcg acatcgccgt ggagtgggag agcaatgggc agccggagaa caactacaag     600
accacgcctc ccgtgctgga ctccgacggc tccttcttcc tctacagcaa gctcaccgtg     660
gacaagagca ggtggcagca ggggaacgtc ttctcatgct ccgtgatgca tgaggctctg     720
cacaaccact acacgcagaa gagcctctct ctctctccgg gtaaagtcga cggagctagc     780
agccccgtga acgtgagcag ccccagcgtg caggatatcc tcttcaggaa ccaccagtct     840
tcttaccaaa cacgacttaa tgctctccga gaggtacaac ccgtagaact tcctaactgt     900
aatttagtta aggaatcga aactggctct gaagacttgg agatactgcc taatggactg     960
gctttcatta gctctggatt aaagtatcct ggaataaaga gcttcaaccc caacagtcct    1020
ggaaaaatac ttctgatgga cctgaatgaa gagatccaa cagtgttgga attggggatc    1080
actgaagta aatttgatgt atcttcattt aaccctcatg ggattagcac attcacagat    1140
gaagataatg ccatgtacct cctggtggtg aaccatccag atgccaagtc cacagtggag    1200
ttgtttaaat tcaagaagag agaaaaatcg cttttgcatc taaaaccat cagacataaa    1260
cttctgccta atttgaatga tattgttgct gtgggacctg agcacttta tggcacaaat    1320
gatcactatt tcttgaccc ctacttaaaa tcctgggaga tgtatttggg tttagcgtgg    1380
tcgtatgttg tctactatag tccaagtgaa gttcgagtgg tggcagaagg atttgatttt    1440
gctaatggaa tcaacatttc acccgatggc aagtatgtct atatagctga ttgctggaaag   1500
cataagattc atgtgtatga aaagcatgct aattggactt taactccatt gaagtccctt    1560
gactttaata ccctcgtgga taacatatct gtggatcctg agacaggaga cctttgggtt    1620
ggatgccatc ccaatggcat gaaaatcttc ttctatgact cagagaatcc tcctgcatca    1680
gaggtgcttc gaatccagaa cattctaaca gaagaaccta agtgacaca ggtttatgca    1740
gaaaatggca cagtgttgca aggcagtaca gttgcctctg tgtacaaagg gaaactgctg    1800
attggcacag tgtttcacaa agctcttta tgtgagctct aa                       1842
```

<210> SEQ ID NO 122
<211> LENGTH: 613
<212> TYPE: PRT
<213> ORGANISM: Artificial Sequence
<220> FEATURE:
<223> OTHER INFORMATION: hVK3LP-[KDL-SCChinge-P238S-P331S Fc]-NGS-
    [PON1 Q192K]

-continued

```
<400> SEQUENCE: 122

Met Glu Thr Pro Ala Gln Leu Leu Phe Leu Leu Leu Trp Leu Pro
1               5                   10                  15

Asp Thr Thr Gly Lys Asp Leu Glu Pro Lys Ser Ser Asp Lys Thr His
            20                  25                  30

Thr Cys Pro Pro Cys Pro Ala Pro Glu Leu Leu Gly Gly Ser Ser Val
        35                  40                  45

Phe Leu Phe Pro Pro Lys Pro Lys Asp Thr Leu Met Ile Ser Arg Thr
    50                  55                  60

Pro Glu Val Thr Cys Val Val Val Asp Val Ser His Glu Asp Pro Glu
65              70                  75                  80

Val Lys Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Ser Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Val
                245                 250                 255

Asp Gly Ala Ser Ser Pro Val Asn Val Ser Ser Pro Ser Val Gln Asp
            260                 265                 270

Ile Leu Phe Arg Asn His Gln Ser Ser Tyr Gln Thr Arg Leu Asn Ala
        275                 280                 285

Leu Arg Glu Val Gln Pro Val Glu Leu Pro Asn Cys Asn Leu Val Lys
    290                 295                 300

Gly Ile Glu Thr Gly Ser Glu Asp Leu Glu Ile Leu Pro Asn Gly Leu
305                 310                 315                 320

Ala Phe Ile Ser Ser Gly Leu Lys Tyr Pro Gly Ile Lys Ser Phe Asn
                325                 330                 335

Pro Asn Ser Pro Gly Lys Ile Leu Leu Met Asp Leu Asn Glu Glu Asp
            340                 345                 350

Pro Thr Val Leu Glu Leu Gly Ile Thr Gly Ser Lys Phe Asp Val Ser
        355                 360                 365

Ser Phe Asn Pro His Gly Ile Ser Thr Phe Thr Asp Glu Asp Asn Ala
    370                 375                 380

Met Tyr Leu Leu Val Val Asn His Pro Asp Ala Lys Ser Thr Val Glu
385                 390                 395                 400

Leu Phe Lys Phe Gln Glu Glu Glu Lys Ser Leu Leu His Leu Lys Thr
                405                 410                 415
```

Ile Arg His Lys Leu Leu Pro Asn Leu Asn Asp Ile Val Ala Val Gly
        420                 425                 430

Pro Glu His Phe Tyr Gly Thr Asn Asp His Tyr Phe Leu Asp Pro Tyr
            435                 440                 445

Leu Lys Ser Trp Glu Met Tyr Leu Gly Leu Ala Trp Ser Tyr Val Val
    450                 455                 460

Tyr Tyr Ser Pro Ser Glu Val Arg Val Val Ala Glu Gly Phe Asp Phe
465                 470                 475                 480

Ala Asn Gly Ile Asn Ile Ser Pro Asp Gly Lys Tyr Val Tyr Ile Ala
                485                 490                 495

Glu Leu Leu Ala His Lys Ile His Val Tyr Glu Lys His Ala Asn Trp
                500                 505                 510

Thr Leu Thr Pro Leu Lys Ser Leu Asp Phe Asn Thr Leu Val Asp Asn
            515                 520                 525

Ile Ser Val Asp Pro Glu Thr Gly Asp Leu Trp Val Gly Cys His Pro
    530                 535                 540

Asn Gly Met Lys Ile Phe Phe Tyr Asp Ser Glu Asn Pro Pro Ala Ser
545                 550                 555                 560

Glu Val Leu Arg Ile Gln Asn Ile Leu Thr Glu Glu Pro Lys Val Thr
                565                 570                 575

Gln Val Tyr Ala Glu Asn Gly Thr Val Leu Gln Gly Ser Thr Val Ala
            580                 585                 590

Ser Val Tyr Lys Gly Lys Leu Leu Ile Gly Thr Val Phe His Lys Ala
    595                 600                 605

Leu Tyr Cys Glu Leu
    610

<210> SEQ ID NO 123
<211> LENGTH: 1065
<212> TYPE: DNA
<213> ORGANISM: Artificial Sequence
<220> FEATURE:
<223> OTHER INFORMATION: Human PON1 variant G3C9 DNA

<400> SEQUENCE: 123
atggctaaac tgacagcgct cacactcttg ggctgggat tggcactctt cgatggacag      60
aagtcttctt tccaaacacg atttaatgtt caccgtgaag taactccagt ggaacttcct     120
aactgtaatt tagttaaagg ggttgacaat ggttctgaag acttggaaat actgcccaat    180
ggactggctt tcatcagctc cggattaaag tatcctggaa taatgagctt tgaccctgat    240
aagtctggaa agatacttct aatggacctg aatgaggaag acccagtagt gttggaactg    300
ggcattactg gaaatacatt ggatatatct tcatttaacc ctcatgggat tagcacattc    360
acagatgaag ataacactgt gtacctactg gtggtaaacc atccagactc ctcgtccacc    420
gtggaggtgt ttaaatttca agaagaagaa aaatcacttt tgcatctgaa accatcaga    480 cacaagcttc tgcctagtgt gaatgacatt gtcgctgtgg acctgaaca cttttatgcc    540 acaaatgatc actattttgc tgaccttac ttaaaatcct gggaaatgca tttgggatta    600
gcgtggtcat tgttactta ttatagtccc aatgatgttc gagtagtggc agaaggattt    660
gattttgcta acggaatcaa catctcacca gacggcaagt atgtctatat agctgagttg    720
ctggctcata gatccatgt gtatgaaaag cacgctaatt ggactttaac tccattgaag    780
tccctcgact tgacaccct tgtggataac atctctgtgg atcctgtgac aggggacctc    840
tgggtgggat gccatcccaa cggaatgcga atcttctact atgacccaaa gaatcctccc    900

```
ggctcagagg tgcttcgaat ccaggacatt ttatccgaag agcccaaagt gacagtggtt      960
tatgcagaaa atggcactgt gttacagggc agcacggtgg ccgctgtgta caaagggaaa     1020
ctgctgattg gcacagtgtt tcacaaagct ctttactgtg agctg                     1065
```

<210> SEQ ID NO 124  
<211> LENGTH: 355  
<212> TYPE: PRT  
<213> ORGANISM: Artificial Sequence  
<220> FEATURE:  
<223> OTHER INFORMATION: Human PON1 variant G3C9

<400> SEQUENCE: 124

```
Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Leu Glu Ile Leu Pro Asn Gly Leu Ala Phe
    50                  55                  60

Ile Ser Ser Gly Leu Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val
                85                  90                  95

Val Leu Glu Leu Gly Ile Thr Gly Asn Thr Leu Asp Ile Ser Ser Phe
            100                 105                 110

Asn Pro His Gly Ile Ser Thr Phe Thr Asp Glu Asp Asn Thr Val Tyr
        115                 120                 125

Leu Leu Val Val Asn His Pro Asp Ser Ser Thr Val Glu Val Phe
    130                 135                 140

Lys Phe Gln Glu Glu Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175

His Phe Tyr Ala Thr Asn Asp His Tyr Phe Ala Asp Pro Tyr Leu Lys
            180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
    210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Gly Ser Glu Val
    290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Thr Val Ala Ala Val
                325                 330                 335
```

Tyr Lys Gly Lys Leu Leu Ile Gly Thr Val Phe His Lys Ala Leu Tyr
            340                 345                 350

Cys Glu Leu
        355

<210> SEQ ID NO 125
<211> LENGTH: 1065
<212> TYPE: DNA
<213> ORGANISM: Artificial Sequence
<220> FEATURE:
<223> OTHER INFORMATION: PON1 variant M-IIG1 DNA

<400> SEQUENCE: 125

```
atggctaaac tgacagcgct cacactcttg ggctgggat tggcactctt cgatggacag       60
aagtcttctt tccaaacacg atttaatgtt caccgtgaag taactccagt ggaacttcct      120
aactgtaatt tagttaaagg ggttgacaat ggttctgaag acattgaaat actgcccaat      180
ggactggctt tcatcagctc cggagttaag tatcctggaa taatgagctt tgaccctgat      240
aagtctggaa agatacttct aatggacctg aatgaggaag acccagtagt gttggaactg      300
ggcattactg gaaatacatt ggatatatct tcatttaacc ctgctgggat tagcacattc      360
acagatgaag ataacactgt gtacctactg gtggtaaacc gaccagactc ctcgtccacc      420
gtggaggtgt ttaaatttca agaagaagaa aaatcacttt tgcatctgaa accatcaga      480
cacaagcttc tgcctagtgt gaatgacatt gtcgctgtgg gacctgaaca cttttatgcc      540
acaaatgatc actattttgc tgacccttac ttaaaatcct gggaaatgca tttgggatta      600
gcgtggtcat tgttactta ttatagtccc aatgatgttc gagtagtggc agaaggattt      660
gatatggcta acggaatcaa catctcacca gacggcaagt atgtctatat agctgagttg      720
ctggctcata agatccatgt gtatgaaaag cacgctaatt ggactttaac tccattgaag      780
tccctcgact ttgacaccct tgtggataac atctctgtgg atcctgtgac aggggacctc      840
tgggtgggat gccatcccaa cggaatgcga ttattctact atgacccaaa gaatcctccc      900
ggctcagagg tgcttcgaat ccaggacatt ttatccgaag agcccaaagt gacagtggtt      960
tatgcagaaa atggcactgt gttacagggc agcagtgtgg ccgctgtgta caagggaaa     1020
ctgctgattg cacagtgttt tcacaaagct ctttactgtg agctg                    1065
```

<210> SEQ ID NO 126
<211> LENGTH: 355
<212> TYPE: PRT
<213> ORGANISM: Artificial Sequence
<220> FEATURE:
<223> OTHER INFORMATION: PON1 variant M-IIG1

<400> SEQUENCE: 126

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Val
        35                  40                  45

Asp Asn Gly Ser Glu Asp Ile Glu Ile Leu Pro Asn Gly Leu Ala Phe
    50                  55                  60

Ile Ser Ser Gly Val Lys Tyr Pro Gly Ile Met Ser Phe Asp Pro Asp
65                  70                  75                  80

Lys Ser Gly Lys Ile Leu Leu Met Asp Leu Asn Glu Glu Asp Pro Val 85                  90                  95
Val Leu Glu Leu Gly Ile Thr Gly Asn Thr Leu Asp Ile Ser Ser Phe
        100                 105                 110

Asn Pro Ala Gly Ile Ser Thr Phe Thr Asp Glu Asp Asn Thr Val Tyr
        115                 120                 125

Leu Leu Val Val Asn Arg Pro Asp Ser Ser Thr Val Glu Val Phe
130                 135                 140

Lys Phe Gln Glu Glu Lys Ser Leu His Leu Lys Thr Ile Arg
145                 150                 155                 160

His Lys Leu Leu Pro Ser Val Asn Asp Ile Ala Val Gly Pro Glu
                165                 170                 175

His Phe Tyr Ala Thr Asn Asp His Tyr Phe Ala Asp Pro Tyr Leu Lys
                180                 185                 190

Ser Trp Glu Met His Leu Gly Leu Ala Trp Ser Phe Val Thr Tyr Tyr
                195                 200                 205

Ser Pro Asn Asp Val Arg Val Val Ala Glu Gly Phe Asp Met Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asp Thr Leu Val Asp Asn Ile Ser
                260                 265                 270

Val Asp Pro Val Thr Gly Asp Leu Trp Val Gly Cys His Pro Asn Gly
        275                 280                 285

Met Arg Leu Phe Tyr Tyr Asp Pro Lys Asn Pro Pro Gly Ser Glu Val
        290                 295                 300

Leu Arg Ile Gln Asp Ile Leu Ser Glu Glu Pro Lys Val Thr Val Val
305                 310                 315                 320

Tyr Ala Glu Asn Gly Thr Val Leu Gln Gly Ser Ser Val Ala Ala Val
                325                 330                 335

Tyr Lys Gly Lys Leu Leu Ile Gly Thr Val Phe His Lys Ala Leu Tyr
                340                 345                 350

Cys Glu Leu
        355

<210> SEQ ID NO 127
<211> LENGTH: 2713
<212> TYPE: DNA
<213> ORGANISM: Artificial Sequence
<220> FEATURE:
<223> OTHER INFORMATION: hVK3LP-[hDNase1 N74K-G105R-A114F]-(g4s)4-
      [SSHinge-P238S-P331S Fc]-NGS-[G3C9 PON1] DNA

<400> SEQUENCE: 127
aagcttgccg ccatggaaac cccagcgcag cttctcttcc tcctgctact ctggctccca    60
gataccaccg gtctgaagat cgcagccttc aacatccaga catttgggga gaccaagatg   120
tccaatgcca ccctcgtcag ctacattgtg cagatcctga ccgctatga catcgccctg    180 gtccaggagg tcagagacag ccacctgact gccgtgggga agctgctgga caacctcaat   240
caggatgcac agacacccta tcactacgtg gtcagtgagc cactgggacg aagagctat    300 aaggagcgct acctgttcgt gtacaggcct gaccaggtgt ctgcggtgga cagctactac   360
tacgatgatg gctgcgagcc ctgcaggaac gacaccttca accgagagcc attcattgtc   420
aggttcttct cccggttcac agaggtcagg gagtttgcca ttgttccct gcatgcggcc   480

```
ccgggggacg cagtagccga gatcgacgct ctctatgacg tctacctgga tgtccaagag    540
aaatggggct tggaggacgt catgttgatg ggcgacttca atgcgggctg cagctatgtg    600
agaccctccc agtggtcatc catccgcctg tggacaagcc ccaccttcca gtggctgatc    660
cccgacagcg ctgacaccac agctacaccc acgcactgtg cctatgacag gatcgtggtt    720
gcagggatgc tgctccgagg cgccgttgtt cccgactcgg ctcttcccct taacttccag    780
gctgcctatg gcctgagtga ccaactggcc caagccatca gtgaccacta tccagtggag    840
gtgatgctga aagatctctc cggaggaggt ggctcaggtg gtggaggatc tggaggaggt    900
gggagtggtg gaggtggttc taccggtctc gagcccaaat cttctgacaa aactcacaca    960
tctccaccgt ccccagcacc tgaactcctg ggaggatcgt cagtcttcct cttccccca    1020 aaacccaagg acaccctcat gatctcccgg acccctgagg tcacatgcgt ggtggtggac    1080
gtgagccacg aagaccctga ggtcaagttc aactggtacg tggacggcgt ggaggtgcat    1140
aatgccaaga caaagccgcg ggaggagcag tacaacagca cgtaccgtgt ggtcagcgtc    1200
ctcaccgtcc tgcaccagga ctggctgaat ggcaaggagt acaagtgcaa ggtctccaac    1260
aaagccctcc cagcctccat cgagaaaacc atctccaaag ccaaagggca gccccgagaa    1320
ccacaggtgt acaccctgcc cccatcccgg gatgagctga ccaagaacca ggtcagcctg    1380
acctgcctgg tcaaaggctt ctatcccagc gacatcgccg tggagtggga gagcaatggg    1440
cagccggaga acaactacaa gaccacgcct cccgtgctgg actccgacgg ctccttcttc    1500
ctctacagca agctcaccgt ggacaagagc aggtggcagc aggggaacgt cttctcatgc    1560
tccgtgatgc atgaggctct gcacaaccac tacacgcaga agagcctctc tctctctccg    1620
ggtaaagtcg acgagctagc agccccgtg aacgtgagca gccccagcgt gcaggatatc    1680
ctcttcgatg gacagaagtc ttctttccaa acacgattta atgttcaccg tgaagtaact    1740
ccagtggaac ttcctaactg taatttagtt aaaggggttg acaatggttc tgaagacttg    1800
gaaatactgc ccaatggact ggctttcatc agctccggat aaagtatcc tggaataatg    1860 agctttgacc ctgataagtc tggaaagata cttctaatgg acctgaatga ggaagaccca    1920
gtagtgttgg aactgggcat tactggaaat acattggata tatcttcatt taaccctcat    1980
gggattagca cattcacaga tgaagataac actgtgtacc tactggtggt aaaccatcca    2040
gactcctcgt ccaccgtgga ggtgtttaaa tttcaagaag aagaaaaatc acttttgcat    2100
ctgaaaacca tcagacacaa gcttctgcct agtgtgaatg acattgtcgc tgtgggacct    2160
gaacactttt atgccacaaa tgatcactat tttgctgacc cttacttaaa atcctgggaa    2220
atgcatttgg gattagcgtg gtcatttgtt acttattata gtcccaatga tgttcgagta    2280
gtggcagaag gatttgattt tgctaacgga atcaacatct caccagacgg caagtatgtc    2340
tatatagctg agttgctggc tcataagatc catgtgtatg aaaagcacgc taattggact    2400
ttaactccat tgaagtccct cgactttgac acccttgtgg ataacatctc tgtggatcct    2460
gtgacagggg acctctgggt gggatgccat cccaacggaa tgcgaatctt ctactatgac    2520
ccaaagaatc ctcccggctc agaggtgctt cgaatccagg acattttatc gaagagccc    2580 aaagtgcacg tggtttatgc agaaaatggc actgtgttac agggcagcac ggtggccgct    2640
gtgtacaaag ggaaactgct gattggcaca gtgttcaca aagctcttta ctgtgagctg    2700
taataatcta gaa                                                       2713
```

<210> SEQ ID NO 128

```
<211> LENGTH: 896
<212> TYPE: PRT
<213> ORGANISM: Artificial Sequence
<220> FEATURE:
<223> OTHER INFORMATION: hVK3LP-[hDNase1 N74K-G105R-A114F]-(g4s)4-
      [SSShinge-P238S-P331S Fc]-NGS-[G3C9 PON1]

<400> SEQUENCE: 128

Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Gly Ser
        275                 280                 285

Gly Gly Gly Gly Ser Gly Gly Gly Ser Gly Gly Gly Ser Thr
    290                 295                 300

Gly Leu Glu Pro Lys Ser Ser Asp Lys Thr His Thr Ser Pro Pro Ser
305                 310                 315                 320

Pro Ala Pro Glu Leu Leu Gly Gly Ser Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
```

```
            370                 375                 380
Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Ser Ile Glu Lys Thr Ile Ser Lys Ala Lys Gly
                420                 425                 430

Gln Pro Arg Glu Pro Gln Val Tyr Thr Leu Pro Pro Ser Arg Asp Glu
            435                 440                 445

Leu Thr Lys Asn Gln Val Ser Leu Thr Cys Leu Val Lys Gly Phe Tyr
450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
                500                 505                 510

Val Phe Ser Cys Ser Val Met His Glu Ala Leu His Asn His Tyr Thr
            515                 520                 525

Gln Lys Ser Leu Ser Leu Ser Pro Gly Lys Val Asp Gly Ala Ser Ser
530                 535                 540

Pro Val Asn Val Ser Ser Pro Ser Val Gln Asp Ile Leu Phe Asp Gly
545                 550                 555                 560

Gln Lys Ser Ser Phe Gln Thr Arg Phe Asn Val His Arg Glu Val Thr
                565                 570                 575

Pro Val Glu Leu Pro Asn Cys Asn Leu Val Lys Gly Val Asp Asn Gly
            580                 585                 590

Ser Glu Asp Leu Glu Ile Leu Pro Asn Gly Leu Ala Phe Ile Ser Ser
            595                 600                 605

Gly Leu Lys Tyr Pro Gly Ile Met Ser Phe Asp Pro Asp Lys Ser Gly
            610                 615                 620

Lys Ile Leu Leu Met Asp Leu Asn Glu Glu Asp Pro Val Val Leu Glu
625                 630                 635                 640

Leu Gly Ile Thr Gly Asn Thr Leu Asp Ile Ser Ser Phe Asn Pro His
                645                 650                 655

Gly Ile Ser Thr Phe Thr Asp Glu Asp Asn Thr Val Tyr Leu Leu Val
                660                 665                 670

Val Asn His Pro Asp Ser Ser Ser Thr Val Glu Val Phe Lys Phe Gln
            675                 680                 685

Glu Glu Glu Lys Ser Leu Leu His Leu Lys Thr Ile Arg His Lys Leu
            690                 695                 700

Leu Pro Ser Val Asn Asp Ile Val Ala Val Gly Pro Glu His Phe Tyr
705                 710                 715                 720

Ala Thr Asn Asp His Tyr Phe Ala Asp Pro Tyr Leu Lys Ser Trp Glu
                725                 730                 735

Met His Leu Gly Leu Ala Trp Ser Phe Val Thr Tyr Tyr Ser Pro Asn
                740                 745                 750

Asp Val Arg Val Val Ala Glu Gly Phe Asp Phe Ala Asn Gly Ile Asn
            755                 760                 765

Ile Ser Pro Asp Gly Lys Tyr Val Tyr Ile Ala Glu Leu Leu Ala His
            770                 775                 780

Lys Ile His Val Tyr Glu Lys His Ala Asn Trp Thr Leu Thr Pro Leu
785                 790                 795                 800
```

```
Lys Ser Leu Asp Phe Asp Thr Leu Val Asp Asn Ile Ser Val Asp Pro
                805                 810                 815

Val Thr Gly Asp Leu Trp Val Gly Cys His Pro Asn Gly Met Arg Ile
            820                 825                 830

Phe Tyr Tyr Asp Pro Lys Asn Pro Pro Gly Ser Glu Val Leu Arg Ile
        835                 840                 845

Gln Asp Ile Leu Ser Glu Glu Pro Lys Val Thr Val Val Tyr Ala Glu
    850                 855                 860

Asn Gly Thr Val Leu Gln Gly Ser Thr Val Ala Ala Val Tyr Lys Gly
865                 870                 875                 880

Lys Leu Leu Ile Gly Thr Val Phe His Lys Ala Leu Tyr Cys Glu Leu
                885                 890                 895

<210> SEQ ID NO 129
<211> LENGTH: 2688
<212> TYPE: DNA
<213> ORGANISM: Artificial Sequence
<220> FEATURE:
<223> OTHER INFORMATION: hVK3LP-[hDNase1 N74K-G105R-A114F]-(g4s)4-
      [SSShinge-P238S-P331S Fc]-NGS-[M-IIG1 PON1] DNA

<400> SEQUENCE: 129
atggaaaccc cagcgcagct tctcttcctc ctgctactct ggctcccaga taccaccggt     60
ctgaagatcg cagccttcaa catccagaca tttgggagag ccaagatgtc aatgccacc    120
ctcgtcagct acattgtgca gatcctgagc cgctatgaca tcgccctggt ccaggaggtc   180
agagacagcc acctgactgc cgtggggaag ctgctggaca acctcaatca ggatgccaca   240
gacaccctat actacgtggt cagtgagcca ctgggacgga gagctataa ggagcgctac    300
ctgttcgtgt acaggcctga ccaggtgtct gcggtggaca gctactacta cgatgatggc   360
tgcgagccct gcaggaacga caccttcaac cgagagccat tcattgtcag gttcttctcc   420
cggttcacag aggtcaggga gtttgccatt gttcccctgc atgcggcccc ggggacgca    480
gtagccgaga tcgacgctct ctatgacgtc tacctggatg tccaagagaa atggggcttg   540
gaggacgtca tgttgatggg cgacttcaat gcgggctgca gctatgtgag acccctccag   600
tggtcatcca tccgcctgtg acaagcccc accttccagt ggctgatccc cgacagcgct    660
gacaccacag ctacacccac gcactgtgcc tatgacagga tcgtggttgc agggatgctg   720
ctccgaggcg ccgttgttcc cgactcggct cttccctta acttccaggc tgcctatggc    780
ctgagtgacc aactggccca agccatcagt gaccactatc cagtggaggt gatgctgaaa   840
gatctctccg gaggaggtgg ctcaggtggt ggaggatctg gaggaggtgg gagtggtgga   900
ggtggttcta ccggtctcga gcccaaatct tctgacaaaa ctcacacatc tccaccgtcc   960
ccagcacctg aactcctggg aggatcgtca gtcttcctct tccccccaaa acccaaggac  1020
accctcatga tctcccggac ccctgaggtc acatgcgtgg tggtggacgt gagccacgaa  1080
gaccctgagg tcaagttcaa ctggtacgtg gacggcgtgg aggtgcataa tgccaagaca  1140
aagccgcggg aggagcagta caacagcacg taccgtgtgg tcagcgtcct caccgtcctg  1200
caccaggact ggctgaatgg caaggagtac aagtgcaagg tctccaacaa agccctccca  1260
gcctccatcg agaaaaccat ctccaaagcc aagggcagc ccgagaacc acaggtgtac    1320
accctgcccc catcccggga tgagctgacc aagaaccagg tcagcctgac ctgcctggtc  1380
aaaggcttct atcccagcga catcgccgtg gagtgggaga gcaatgggca gccggagaac  1440
aactacaaga ccacgcctcc cgtgctggac tccgacggct ccttcttcct ctacagcaag  1500
```

```
ctcaccgtgg acaagagcag gtggcagcag gggaacgtct tctcatgctc cgtgatgcat    1560
gaggctctgc acaaccacta cacgcagaag agcctctctc tctctccggg taaagtcgac    1620
ggagctagca gccccgtgaa cgtgagcagc ccagcgtgc aggatatcct cttcgatgga    1680
cagaagtctt ctttccaaac acgatttaat gttcaccgtg aagtaactcc agtggaactt    1740
cctaactgta atttagttaa aggggttgac aatggttctg aagacattga atactgccc    1800 aatggactgg ctttcatcag ctccggagtt aagtatcctg aataatgag ctttgacect    1860 gataagtctg gaaagatact tctaatggac ctgaatgagg aagacccagt agtgttggaa    1920
ctgggcatta ctggaaatac attggatata tcttcattta ccctgctgg gattagcaca    1980 ttcacagatg aagataacac tgtgtaccta ctggtggtaa accgaccaga ctcctcgtcc    2040
accgtggagg tgtttaaatt tcaagaagaa gaaaaatcac ttttgcatct gaaaaccatc    2100
agacacaagc ttctgcctag tgtgaatgac attgtcgctg tgggacctga acacttttat    2160
gccacaaatg atcactattt tgctgaccct tacttaaaat cctgggaaat gcatttggga    2220
ttagcgtggt catttgttac ttattatagt cccaatgatg ttcgagtagt ggcagaagga    2280
tttgatatgg ctaacggaat caacatctca ccagacggca gtatgtcta tatagctgag    2340 ttgctggctc ataagatcca tgtgtatgaa aagcacgcta attggacttt aactccattg    2400
aagtccctcg actttgacac ccttgtggat aacatctctg tggatcctgt gacagggggac    2460 ctctgggtgg gatgccatcc caacggaatg cgattattct actatgaccc aaagaatcct    2520
cccggctcag aggtgcttcg aatccaggac atttttatccg aagagcccaa agtgacagtg    2580
gtttatgcag aaaatggcac tgtgttacag ggcagcagtg tggccgctgt gtacaaaggg    2640
aaactgctga ttggcacagt gtttcacaaa gctctttact gtgagctg                2688
```

<210> SEQ ID NO 130
<211> LENGTH: 896
<212> TYPE: PRT
<213> ORGANISM: Artificial Sequence
<220> FEATURE:
<223> OTHER INFORMATION: hVK3LP-[hDNase1 N74K-G105R-A114F]-(g4s)4-
      [SSShinge-P238S-P331S Fc]-NGS-[M-IIG1 PON1]

<400> SEQUENCE: 130

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
    130                 135                 140
```

```
Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Pro Asp Ser Ala Leu Pro Phe Asn Phe Gln
            245                 250                 255

Ala Ala Tyr Gly Leu Ser Asp Gln Leu Ala Gln Ala Ile Ser Asp His
        260                 265                 270

Tyr Pro Val Glu Val Met Leu Lys Asp Leu Ser Gly Gly Gly Ser
    275                 280                 285

Gly Gly Gly Gly Ser Gly Gly Gly Ser Gly Gly Gly Ser Thr
290                 295                 300

Gly Leu Glu Pro Lys Ser Ser Asp Lys Thr His Thr Ser Pro Pro Ser
305                 310                 315                 320

Pro Ala Pro Glu Leu Leu Gly Gly Ser Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Ser Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Leu Phe Asp Gly
545                 550                 555                 560

Gln Lys Ser Ser Phe Gln Thr Arg Phe Asn Val His Arg Glu Val Thr
```

565                 570                 575
Pro Val Glu Leu Pro Asn Cys Asn Leu Val Lys Gly Val Asp Asn Gly
            580                 585                 590

Ser Glu Asp Ile Glu Ile Leu Pro Asn Gly Leu Ala Phe Ile Ser Ser
            595                 600                 605

Gly Val Lys Tyr Pro Gly Ile Met Ser Phe Asp Pro Asp Lys Ser Gly
            610                 615                 620

Lys Ile Leu Leu Met Asp Leu Asn Glu Glu Asp Pro Val Val Leu Glu
625                 630                 635                 640

Leu Gly Ile Thr Gly Asn Thr Leu Asp Ile Ser Ser Phe Asn Pro Ala
                645                 650                 655

Gly Ile Ser Thr Phe Thr Asp Glu Asp Asn Thr Val Tyr Leu Leu Val
                660                 665                 670

Val Asn Arg Pro Asp Ser Ser Thr Val Glu Val Phe Lys Phe Gln
                675                 680                 685

Glu Glu Glu Lys Ser Leu Leu His Leu Lys Thr Ile Arg His Lys Leu
            690                 695                 700

Leu Pro Ser Val Asn Asp Ile Val Ala Val Gly Pro Glu His Phe Tyr
705                 710                 715                 720

Ala Thr Asn Asp His Tyr Phe Ala Asp Pro Tyr Leu Lys Ser Trp Glu
                725                 730                 735

Met His Leu Gly Leu Ala Trp Ser Phe Val Thr Tyr Tyr Ser Pro Asn
                740                 745                 750

Asp Val Arg Val Val Ala Glu Gly Phe Asp Met Ala Asn Gly Ile Asn
            755                 760                 765

Ile Ser Pro Asp Gly Lys Tyr Val Tyr Ile Ala Glu Leu Leu Ala His
770                 775                 780

Lys Ile His Val Tyr Glu Lys His Ala Asn Trp Thr Leu Thr Pro Leu
785                 790                 795                 800

Lys Ser Leu Asp Phe Asp Thr Leu Val Asp Asn Ile Ser Val Asp Pro
                805                 810                 815

Val Thr Gly Asp Leu Trp Val Gly Cys His Pro Asn Gly Met Arg Leu
            820                 825                 830

Phe Tyr Tyr Asp Pro Lys Asn Pro Pro Gly Ser Glu Val Leu Arg Ile
            835                 840                 845

Gln Asp Ile Leu Ser Glu Glu Pro Lys Val Thr Val Val Tyr Ala Glu
            850                 855                 860

Asn Gly Thr Val Leu Gln Gly Ser Ser Val Ala Val Tyr Lys Gly
865                 870                 875                 880

Lys Leu Leu Ile Gly Thr Val Phe His Lys Ala Leu Tyr Cys Glu Leu
                885                 890                 895

<210> SEQ ID NO 131
<211> LENGTH: 1839
<212> TYPE: DNA
<213> ORGANISM: Artificial Sequence
<220> FEATURE:
<223> OTHER INFORMATION: hVK3LP-[KDL-SCChinge-P238S-P331S Fc]-NGS-
      [G3C9 PON1] DNA

<400> SEQUENCE: 131
atggaaaccc cagcgcagct tctcttcctc ctgctactct ggctcccaga taccaccggt    60
aaagatctcg agcccaaatc ttctgacaaa actcacacat gtccaccgtg cccagcacct   120
gaactcctgg gaggatcgtc agtcttcctc ttccccccaa aacccaagga caccctcatg   180

-continued

| | |
|---|---|
| atctcccgga cccctgaggt cacatgcgtg gtggtggacg tgagccacga agaccctgag | 240 |
| gtcaagttca actggtacgt ggacggcgtg gaggtgcata atgccaagac aaagccgcgg | 300 |
| gaggagcagt acaacagcac gtaccgtgtg gtcagcgtcc tcaccgtcct gcaccaggac | 360 |
| tggctgaatg gcaaggagta caagtgcaag gtctccaaca aagccctccc agcctccatc | 420 |
| gagaaaacca tctccaaagc caaagggcag ccccgagaac acaggtgta caccctgccc | 480 |
| ccatcccggg atgagctgac caagaaccag gtcagcctga cctgcctggt caaaggcttc | 540 |
| tatcccagcg acatcgccgt ggagtgggag agcaatgggc agccggagaa caactacaag | 600 |
| accacgcctc ccgtgctgga ctccgacggc tccttcttcc tctacagcaa gctcaccgtg | 660 |
| gacaagagca ggtggcagca ggggaacgtc ttctcatgct ccgtgatgca tgaggctctg | 720 |
| cacaaccact acacgcagaa gagcctctct ctctctccgg gtaaagtcga cggagctagc | 780 |
| agccccgtga acgtgagcag ccccagcgtg caggatatcc tcttcgatgg acagaagtct | 840 |
| tctttccaaa cacgatttaa tgttcaccgt gaagtaactc cagtggaact tcctaactgt | 900 |
| aatttagtta aggggttgga caatggttct gaagacttgg aaatactgcc caatggactg | 960 |
| gctttcatca gctccggatt aaagtatcct ggaataatga gctttgaccc tgataagtct | 1020 |
| ggaaagatac ttctaatgga cctgaatgag gaagacccag tagtgttgga actgggcatt | 1080 |
| actggaaata cattggatat atcttcattt aaccctcatg ggattagcac attcacagat | 1140 |
| gaagataaca ctgtgtacct actggtggta aaccatccag actcctcgtc caccgtggag | 1200 |
| gtgtttaaat ttcaagaaga agaaaaatca cttttgcatc tgaaaaccat cagacacaag | 1260 |
| cttctgccta gtgtgaatga cattgtcgct gtgggacctg aacacttta tgccacaaat | 1320 |
| gatcactatt ttgctgaccc ttacttaaaa tcctgggaaa tgcatttggg attagcgtgg | 1380 |
| tcatttgtta cttattatag tcccaatgat gttcgagtag tggcagaagg atttgatttt | 1440 |
| gctaacggaa tcaacatctc accagacggc aagtatgtct atatagctga gttgctggct | 1500 |
| cataagatcc atgtgtatga aaagcacgct aattggactt taactccatt gaagtccctc | 1560 |
| gactttgaca cccttgtgga taacatctct gtggatcctg tgacagggga cctctgggtg | 1620 |
| ggatgccatc ccaacggaat gcgaatcttc tactatgacc caaagaatcc tcccggctca | 1680 |
| gaggtgcttc gaatccagga catttttatcc gaagagccca agtgacagt ggtttatgca | 1740 |
| gaaaatggca ctgtgttaca gggcagcacg gtggccgctg tgtacaaagg gaaactgctg | 1800 |
| attggcacag tgtttcacaa agctctttac tgtgagctg | 1839 |

<210> SEQ ID NO 132
<211> LENGTH: 613
<212> TYPE: PRT
<213> ORGANISM: Artificial Sequence
<220> FEATURE:
<223> OTHER INFORMATION: hVK3LP-[KDL-SCChinge-P238S-P331S Fc]-NGS-
    [G3C9 PON1]

<400> SEQUENCE: 132

Met Glu Thr Pro Ala Gln Leu Leu Phe Leu Leu Leu Leu Trp Leu Pro
1               5                   10                  15

Asp Thr Thr Gly Lys Asp Leu Glu Pro Lys Ser Ser Asp Lys Thr His
            20                  25                  30

Thr Cys Pro Pro Cys Pro Ala Pro Glu Leu Leu Gly Gly Ser Ser Val
        35                  40                  45

Phe Leu Phe Pro Pro Lys Pro Lys Asp Thr Leu Met Ile Ser Arg Thr
    50                  55                  60

```
Pro Glu Val Thr Cys Val Val Asp Val Ser His Glu Asp Pro Glu
 65                  70                  75                  80

Val Lys Phe Asn Trp Tyr Val Asp Gly Val Glu Val His Asn Ala Lys
                 85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Ser Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Val
                245                 250                 255

Asp Gly Ala Ser Ser Pro Val Asn Val Ser Ser Pro Ser Val Gln Asp
            260                 265                 270

Ile Leu Phe Asp Gly Gln Lys Ser Ser Phe Gln Thr Arg Phe Asn Val
        275                 280                 285

His Arg Glu Val Thr Pro Val Glu Leu Pro Asn Cys Asn Leu Val Lys
    290                 295                 300

Gly Val Asp Asn Gly Ser Glu Asp Leu Glu Ile Leu Pro Asn Gly Leu
305                 310                 315                 320

Ala Phe Ile Ser Ser Gly Leu Lys Tyr Pro Gly Ile Met Ser Phe Asp
                325                 330                 335

Pro Asp Lys Ser Gly Lys Ile Leu Leu Met Asp Leu Asn Glu Glu Asp
            340                 345                 350

Pro Val Val Leu Glu Leu Gly Ile Thr Gly Asn Thr Leu Asp Ile Ser
        355                 360                 365

Ser Phe Asn Pro His Gly Ile Ser Thr Phe Thr Asp Glu Asp Asn Thr
    370                 375                 380

Val Tyr Leu Leu Val Val Asn His Pro Asp Ser Ser Ser Thr Val Glu
385                 390                 395                 400

Val Phe Lys Phe Gln Glu Glu Lys Ser Leu Leu His Leu Lys Thr
                405                 410                 415

Ile Arg His Lys Leu Leu Pro Ser Val Asn Asp Ile Val Ala Val Gly
            420                 425                 430

Pro Glu His Phe Tyr Ala Thr Asn Asp His Tyr Phe Ala Asp Pro Tyr
        435                 440                 445

Leu Lys Ser Trp Glu Met His Leu Gly Leu Ala Trp Ser Phe Val Thr
    450                 455                 460

Tyr Tyr Ser Pro Asn Asp Val Arg Val Val Ala Glu Gly Phe Asp Phe
465                 470                 475                 480

Ala Asn Gly Ile Asn Ile Ser Pro Asp Gly Lys Tyr Val Tyr Ile Ala
```

```
                     485                 490                 495
Glu Leu Leu Ala His Lys Ile His Val Tyr Glu Lys His Ala Asn Trp
                500                 505                 510

Thr Leu Thr Pro Leu Lys Ser Leu Asp Phe Asp Thr Leu Val Asp Asn
            515                 520                 525

Ile Ser Val Asp Pro Val Thr Gly Asp Leu Trp Val Gly Cys His Pro
        530                 535                 540

Asn Gly Met Arg Ile Phe Tyr Tyr Asp Pro Lys Asn Pro Pro Gly Ser
545                 550                 555                 560

Glu Val Leu Arg Ile Gln Asp Ile Leu Ser Glu Pro Lys Val Thr
                565                 570                 575

Val Val Tyr Ala Glu Asn Gly Thr Val Leu Gln Gly Ser Thr Val Ala
                580                 585                 590

Ala Val Tyr Lys Gly Lys Leu Leu Ile Gly Thr Val Phe His Lys Ala
                595                 600                 605

Leu Tyr Cys Glu Leu
        610

<210> SEQ ID NO 133
<211> LENGTH: 1839
<212> TYPE: DNA
<213> ORGANISM: Artificial Sequence
<220> FEATURE:
<223> OTHER INFORMATION: hVK3LP-[KDL-SCChinge-P238S-P331S Fc]-NGS-
      [M-IIG1 PON1] DNA

<400> SEQUENCE: 133
atggaaaccc cagcgcagct tctcttcctc ctgctactct ggctcccaga taccaccggt        60
aaagatctcg agcccaaatc ttctgacaaa actcacacat gtccaccgtg cccagcacct       120
gaactcctgg gaggatcgtc agtcttcctc ttccccccaa acccaaggac acccctcatg       180
atctcccgga cccctgaggt cacatgcgtg gtggtggacg tgagccacga agaccctgag       240
gtcaagttca actggtacgt ggacggcgtg gaggtgcata atgccaagac aaagccgcgg       300
gaggagcagt acaacagcac gtaccgtgtg gtcagcgtcc tcaccgtcct gcaccaggac       360
tggctgaatg gcaaggagta caagtgcaag gtctccaaca agcccctccc agcctccatc       420
gagaaaacca tctccaaagc caaagggcag ccccgagaac cacaggtgta caccctgccc       480
ccatcccggg atgagctgac caagaaccag gtcagcctga cctgcctggt caaaggcttc       540
tatcccagcg acatcgccgt ggagtgggag agcaatgggc agccggagaa caactacaag       600
accacgcctc ccgtgctgga ctccgacggc tccttcttcc tctacagcaa gctcaccgtg       660
gacaagagca ggtggcagca ggggaacgtc ttctcatgct ccgtgatgca tgaggctctg       720
cacaaccact acacgcagaa gagcctctct ctctctccgg gtaaagtcga cggagctagc       780
agccccgtga acgtgagcag ccccagcgtg caggatatcc tcttcgatgg acagaagtct       840
tctttccaaa cacgatttaa tgttcaccgt gaagtaactc cagtgaact tcctaactgt       900 aatttagtta aggggttgaa caatggttct gaagacattg aaatactgcc caatggactg       960
gctttcatca gctccggagt taagtatcct ggaataatga gctttgaccc tgataagtct      1020
ggaaagatac ttctaatgga cctgaatgag gaagacccag tagtgttgga actgggcatt      1080
actggaaata cattggatat atcttcattt aaccctgctg ggattagcac attcacagat      1140
gaagataaca ctgtgtacct actggtggta aaccgaccag actcctcgtc caccgtggag      1200
gtgtttaaat tcaagaaga agaaaaatca cttttgcatc tgaaaaccat cagacacaag      1260
```

-continued

```
cttctgccta gtgtgaatga cattgtcgct gtgggacctg aacactttta tgccacaaat    1320
gatcactatt ttgctgaccc ttacttaaaa tcctgggaaa tgcatttggg attagcgtgg    1380
tcatttgtta cttattatag tcccaatgat gttcgagtag tggcagaagg atttgatatg    1440
gctaacggaa tcaacatctc accagacggc aagtatgtct atatagctga gttgctggct    1500
cataagatcc atgtgtatga aaagcacgct aattggactt taactccatt gaagtccctc    1560
gactttgaca cccttgtgga taacatctct gtggatcctg tgacagggga cctctgggtg    1620
ggatgccatc ccaacggaat gcgattattc tactatgacc caaagaatcc tcccggctca    1680
gaggtgcttc gaatccagga cattttatcc gaagagccca agtgacagt ggtttatgca    1740 gaaaatggca ctgtgttaca gggcagcagt gtggccgctg tgtacaaagg gaaactgctg    1800
attggcacag tgtttcacaa agctctttac tgtgagctg                           1839
```

<210> SEQ ID NO 134
<211> LENGTH: 613
<212> TYPE: PRT
<213> ORGANISM: Artificial Sequence
<220> FEATURE:
<223> OTHER INFORMATION: hVK3LP-[KDL-SCChinge-P238S-P331S Fc]-NGS-[M-IIG1 PON1]

<400> SEQUENCE: 134

```
Met Glu Thr Pro Ala Gln Leu Leu Phe Leu Leu Leu Trp Leu Pro
1               5                   10                  15

Asp Thr Thr Gly Lys Asp Leu Glu Pro Lys Ser Ser Asp Lys Thr His
            20                  25                  30

Thr Cys Pro Pro Cys Pro Ala Pro Glu Leu Leu Gly Gly Ser Ser Val
        35                  40                  45

Phe Leu Phe Pro Pro Lys Pro Lys Asp Thr Leu Met Ile Ser Arg Thr
    50                  55                  60

Pro Glu Val Thr Cys Val Val Asp Val Ser His Glu Asp Pro Glu
65                  70                  75                  80

Val Lys Phe Asn Trp Tyr Val Asp Gly Val Glu Val His Asn Ala Lys
                85                  90                  95

Thr Lys Pro Arg Glu Glu Gln Tyr Asn Ser Thr Tyr Arg Val Val Ser
            100                 105                 110

Val Leu Thr Val Leu His Gln Asp Trp Leu Asn Gly Lys Glu Tyr Lys
        115                 120                 125

Cys Lys Val Ser Asn Lys Ala Leu Pro Ala Ser Ile Glu Lys Thr Ile
    130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Val
                245                 250                 255
```

Asp Gly Ala Ser Ser Pro Val Asn Val Ser Ser Pro Val Gln Asp
                260                 265                 270

Ile Leu Phe Asp Gly Gln Lys Ser Ser Phe Gln Thr Arg Phe Asn Val
            275                 280                 285

His Arg Glu Val Thr Pro Val Glu Leu Pro Asn Cys Asn Leu Val Lys
        290                 295                 300

Gly Val Asp Asn Gly Ser Glu Asp Ile Glu Ile Leu Pro Asn Gly Leu
305                 310                 315                 320

Ala Phe Ile Ser Ser Gly Val Lys Tyr Pro Gly Ile Met Ser Phe Asp
                325                 330                 335

Pro Asp Lys Ser Gly Lys Ile Leu Leu Met Asp Leu Asn Glu Glu Asp
            340                 345                 350

Pro Val Val Leu Glu Leu Gly Ile Thr Gly Asn Thr Leu Asp Ile Ser
        355                 360                 365

Ser Phe Asn Pro Ala Gly Ile Ser Thr Phe Thr Asp Glu Asp Asn Thr
    370                 375                 380

Val Tyr Leu Leu Val Val Asn Arg Pro Asp Ser Ser Thr Val Glu
385                 390                 395                 400

Val Phe Lys Phe Gln Glu Glu Lys Ser Leu Leu His Leu Lys Thr
                405                 410                 415

Ile Arg His Lys Leu Leu Pro Ser Val Asn Asp Ile Val Ala Val Gly
            420                 425                 430

Pro Glu His Phe Tyr Ala Thr Asn Asp His Tyr Phe Ala Asp Pro Tyr
        435                 440                 445

Leu Lys Ser Trp Glu Met His Leu Gly Leu Ala Trp Ser Phe Val Thr
    450                 455                 460

Tyr Tyr Ser Pro Asn Asp Val Arg Val Val Ala Glu Gly Phe Asp Met
465                 470                 475                 480

Ala Asn Gly Ile Asn Ile Ser Pro Asp Gly Lys Tyr Val Tyr Ile Ala
                485                 490                 495

Glu Leu Leu Ala His Lys Ile His Val Tyr Glu Lys His Ala Asn Trp
            500                 505                 510

Thr Leu Thr Pro Leu Lys Ser Leu Asp Phe Asp Thr Leu Val Asp Asn
        515                 520                 525

Ile Ser Val Asp Pro Val Thr Gly Asp Leu Trp Val Gly Cys His Pro
    530                 535                 540

Asn Gly Met Arg Leu Phe Tyr Tyr Asp Pro Lys Asn Pro Pro Gly Ser
545                 550                 555                 560

Glu Val Leu Arg Ile Gln Asp Ile Leu Ser Glu Pro Lys Val Thr
                565                 570                 575

Val Val Tyr Ala Glu Asn Gly Thr Val Leu Gln Gly Ser Ser Val Ala
            580                 585                 590

Ala Val Tyr Lys Gly Lys Leu Leu Ile Gly Thr Val Phe His Lys Ala
        595                 600                 605

Leu Tyr Cys Glu Leu
    610

<210> SEQ ID NO 135
<211> LENGTH: 982
<212> TYPE: DNA
<213> ORGANISM: Homo sapiens

<400> SEQUENCE: 135
atgtcacggg agctggcccc actgctgctt ctcctcctct ccatccacag cgccctggcc    60

```
atgaggatct gctccttcaa cgtcaggtcc tttggggaaa gcaagcagga agacaagaat    120
gccatggatg tcattgtgaa ggtcatcaaa cgctgtgaca tcatactcgt gatggaaatc    180
aaggacagca acaacaggat ctgccccata ctgatggaga agctgaacag aaattcaagg    240
agaggcataa cgtacaacta tgtgattagc tctcggcttg gaagaaacac atataaagaa    300
caatatgcct ttctctacaa ggaaaagctg gtgtctgtga agaggagtta tcactaccat    360
gactatcagg atggagacgc agatgtgttt tccagggagc cctttgtggt ctggttccaa    420
tctccccaca ctgctgtcaa agacttcgtg attatccccc tgcacaccac cccagagaca    480
tccgttaagg agatcgatga gttggttgag gtctacacgg acgtgaaaca ccgctggaag    540
gcggagaatt tcattttcat gggtgacttc aatgccggct gcagctacgt ccccaagaag    600
gcctggaaga acatccgctt gaggactgac cccaggtttg tttggctgat cggggaccaa    660
gaggacacca cggtgaagaa gagcaccaac tgtgcatatg acaggattgt gcttagagga    720
caagaaatcg tcagttctgt tgttcccaag tcaaacagtg tttttgactt ccagaaagct    780
tacaagctga ctgaagagga ggccctggat gtcagcgacc actttccagt tgaatttaaa    840
ctacagtctt caagggcctt caccaacagc aaaaaatctg tcactctaag gaagaaaaca    900
aagaggaaac gctcctaccc aactttcttg tacaaagttg gcattataag aaagcattgc    960
ttatcaattt gttgcaacga ac                                             982
```

```
<210> SEQ ID NO 136
<211> LENGTH: 305
<212> TYPE: PRT
<213> ORGANISM: Homo sapiens

<400> SEQUENCE: 136
```

```
Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205
```

Thr Asp Pro Arg Phe Val Trp Leu Ile Gly Asp Gln Glu Asp Thr Thr
    210                 215                 220
Val Lys Lys Ser Thr Asn Cys Ala Tyr Asp Arg Ile Val Leu Arg Gly
225                 230                 235                 240
Gln Glu Ile Val Ser Ser Val Pro Lys Ser Asn Ser Val Phe Asp
                245                 250                 255
Phe Gln Lys Ala Tyr Lys Leu Thr Glu Glu Ala Leu Asp Val Ser
                260                 265                 270
Asp His Phe Pro Val Glu Phe Lys Leu Gln Ser Ser Arg Ala Phe Thr
            275                 280                 285
Asn Ser Lys Lys Ser Val Thr Leu Arg Lys Lys Thr Lys Arg Lys Arg
    290                 295                 300
Ser
305

<210> SEQ ID NO 137
<211> LENGTH: 1647
<212> TYPE: DNA
<213> ORGANISM: Artificial Sequence
<220> FEATURE:
<223> OTHER INFORMATION: hVK3LP-[hDNase1L3 NLS1mutAAA,
    NLS2delta]-(g4s)4-[SSShinge-P238S-P331S Fc] DNA

<400> SEQUENCE: 137

| | |
|---|---|
| atggaaaccc cagcgcagct tctcttcctc ctgctactct ggctcccaga taccaccggt | 60 |
| atgaggatct gctccttcaa cgtcaggtcc tttggggaaa gcaagcagga agacaagaat | 120 |
| gccatggatg tcattgtgaa ggtcatcaaa cgctgtgaca tcatactcgt gatggaaatc | 180 |
| aaggacagca caacaggat ctgccccata ctgatggaga agctgaacag aaattcagca | 240 |
| agaggcataa cgtacaacta tgtgattagc tctcggcttg agcagctac atataaagaa | 300 |
| caatatgcct ttctctacaa ggaaaagctg gtgtctgtga agaggagtta tcactaccat | 360 |
| gactatcagg atggagacgc agatgtgttt tccagggagc cctttgtggt ctggttccaa | 420 |
| tctcccccaca ctgctgtcaa agacttcgtg attatccccc tgcacaccac cccagagaca | 480 |
| tccgttaagg agatcgatga gttggttgag gtctacacgg acgtgaaaca ccgctggaag | 540 |
| gcggagaatt tcattttcat gggtgacttc aatgccggct gcagctacgt ccccaagaag | 600 |
| gcctggaaga catccgctt gaggactgac cccaggtttg tttggctgat cggggaccaa | 660 |
| gaggacacca cggtgaagaa gagcaccaac tgtgcatatg acaggattgt gcttagagga | 720 |
| caagaaatcg tcagttctgt tgttcccaag tcaaacagtg ttttgactt ccagaaagct | 780 |
| tacaagctga ctgaagagga ggccctggat gtcagcgacc actttccagt gaatttaaa | 840 |
| ctacagtctt caagggcctt caccaactca gatctctccg gaggaggtgg ctcaggtggt | 900 |
| ggaggatctg gaggaggtgg gagtggtgga ggtggttcta ccggtctcga gcccaaatct | 960 |
| tctgacaaaa ctcacacatc tccaccgtcc ccagcacctg aactcctggg aggatcgtca | 1020 |
| gtcttcctct tccccccaaa acccaaggac accctcatga tctcccggac ccctgaggtc | 1080 |
| acatgcgtgg tggtggacgt gagccacgaa gaccctgagg tcaagttcaa ctggtacgtg | 1140 |
| gacggcgtgg aggtgcataa tgccaagaca aagccgcggg aggagcagta acagcacg | 1200 |
| taccgtgtgg tcagcgtcct caccgtcctg caccaggact ggctgaatgg caaggagtac | 1260 |
| aagtgcaagg tctccaacaa agccctccca gcctccatcg agaaaaccat ctccaaagcc | 1320 |
| aaagggcagc cccgagaacc acaggtgtac accctgcccc catcccggga tgagctgacc | 1380 |
| aagaaccagg tcagcctgac ctgcctggtc aaaggcttct atcccagcga catcgccgtg | 1440 |

-continued

```
gagtgggaga gcaatgggca gccggagaac aactacaaga ccacgcctcc cgtgctggac    1500
tccgacggct ccttcttcct ctacagcaag ctcaccgtgg acaagagcag gtggcagcag    1560
gggaacgtct tctcatgctc cgtgatgcat gaggctctgc acaaccacta cacgcagaag    1620
agcctctctc tctctccggg taaataa                                        1647
```

<210> SEQ ID NO 138
<211> LENGTH: 548
<212> TYPE: PRT
<213> ORGANISM: Artificial Sequence
<220> FEATURE:
<223> OTHER INFORMATION: hVK3LP-[hDNase1L3 NLS1mutAAA,
   NLS2delta]-(g4s)4-[SSShinge-P238S-P331S Fc]

<400> SEQUENCE: 138

```
Met Glu Thr Pro Ala Gln Leu Leu Phe Leu Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Ala
65                  70                  75                  80

Arg Gly Ile Thr Tyr Asn Tyr Val Ile Ser Ser Arg Leu Gly Ala Ala
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Asp Leu Ser Gly Gly Gly Ser Gly Gly Gly Ser Gly
    290                 295                 300

Gly Gly Gly Ser Gly Gly Gly Gly Ser Thr Gly Leu Glu Pro Lys Ser
305                 310                 315                 320
```

Ser Asp Lys Thr His Thr Ser Pro Ser Pro Ala Pro Glu Leu Leu
              325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

His Glu Asp Pro Glu Val Lys Phe Asn Trp Tyr Val Asp Gly Val Glu
    370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Arg Asp Glu Leu Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
        515                 520                 525

Met His Glu Ala Leu His Asn His Tyr Thr Gln Lys Ser Leu Ser Leu
    530                 535                 540

Ser Pro Gly Lys
545

<210> SEQ ID NO 139
<211> LENGTH: 1647
<212> TYPE: DNA
<213> ORGANISM: Artificial Sequence
<220> FEATURE:
<223> OTHER INFORMATION: hVK3LP-[hDNase1L3 NLS1mutSSS,
      NLS2delta]-(g4s)4-[SSShinge-P238S-P331S Fc] DNA

<400> SEQUENCE: 139
atggaaaccc cagcgcagct tctcttcctc ctgctactct ggctcccaga taccaccggt      60
atgaggatct gctccttcaa cgtcaggtcc tttggggaaa gcaagcagga agacaagaat    120
gccatggatg tcattgtgaa ggtcatcaaa cgctgtgaca tcatactcgt gatggaaatc    180
aaggacagca acaacaggat ctgccccata ctgatggaga agctgaacag aaattcatca    240
agaggcataa cgtacaacta tgtgattagc tctcggcttg aagttctac atataagaa      300 caatatgcct ttctctacaa ggaaaagctg gtgtctgtga gaggagtta tcactaccat    360 gactatcagg atgagacgc agatgtgttt tccagggagc cctttgtggt ctggttccaa    420
tctccccaca ctgctgtcaa agacttcgtg attatccccc tgcacaccac cccagagaca    480
tccgttaagg agatcgatga gttggttgag gtctacacgg acgtgaaaca ccgctggaag    540
gcggagaatt tcattttcat gggtgacttc aatgccggct gcagctacgt ccccaagaag    600
gcctggaaga acatccgctt gaggactgac cccaggtttg tttggctgat cggggaccaa    660

-continued

```
gaggacacca cggtgaagaa gagcaccaac tgtgcatatg acaggattgt gcttagagga    720
caagaaatcg tcagttctgt tgttcccaag tcaaacagtg ttttt gactt ccagaaagct    780 tacaagctga ctgaagagga ggccctggat gtcagcgacc actttccagt tgaatttaaa    840
ctacagtctt caagggcctt caccaactca gatctctccg gaggaggtgg ctcaggtggt    900
ggaggatctg gaggaggtgg gagtggtgga ggtggttcta ccggtctcga gcccaaatct    960
tctgacaaaa ctcacacatc tccaccgtcc ccagcacctg aactcctggg aggatcgtca    1020
gtcttcctct tccccccaaa acccaaggac accctcatga tctcccggac ccctgaggtc    1080
acatgcgtgg tggtggacgt gagccacgaa gaccctgagg tcaagttcaa ctggtacgtg    1140
gacggcgtgg aggtgcataa tgccaagaca aagccgcggg aggagcagta caacagcacg    1200
taccgtgtgg tcagcgtcct caccgtcctg caccaggact ggctgaatgg caaggagtac    1260
aagtgcaagg tctccaacaa agccctccca gcctccatcg agaaaaccat ctccaaagcc    1320
aaagggcagc cccgagaacc acaggtgtac accctgcccc catcccggga tgagctgacc    1380
aagaaccagg tcagcctgac ctgcctggtc aaaggcttct atcccagcga catcgccgtg    1440
gagtgggaga gcaatgggca gccggagaac aactacaaga ccacgcctcc cgtgctggac    1500
tccgacggct ccttcttcct ctacagcaag ctcaccgtgg acaagagcag gtggcagcag    1560
gggaacgtct tctcatgctc cgtgatgcat gaggctctgc acaaccacta cacgcagaag    1620
agcctctctc tctctccggg taaataa                                        1647
```

<210> SEQ ID NO 140
<211> LENGTH: 548
<212> TYPE: PRT
<213> ORGANISM: Artificial Sequence
<220> FEATURE:
<223> OTHER INFORMATION: hVK3LP-[hDNase1L3 NLS1mutSSS,
 NLS2delta]-(g4s)4-[SSShinge-P238S-P331S Fc]

<400> SEQUENCE: 140

```
Met Glu Thr Pro Ala Gln Leu Leu Phe Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Ser
65                  70                  75                  80

Arg Gly Ile Thr Tyr Asn Tyr Val Ile Ser Ser Arg Leu Gly Ser Ser
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
```

```
                180             185             190
Gly Cys Ser Tyr Val Lys Lys Ala Trp Lys Asn Ile Arg Leu Arg
            195             200             205
Thr Asp Pro Arg Phe Val Trp Leu Ile Gly Asp Gln Glu Asp Thr Thr
 210             215             220
Val Lys Lys Ser Thr Asn Cys Ala Tyr Asp Arg Ile Val Leu Arg Gly
 225             230             235             240
Gln Glu Ile Val Ser Ser Val Pro Lys Ser Asn Ser Val Phe Asp
            245             250             255
Phe Gln Lys Ala Tyr Lys Leu Thr Glu Glu Glu Ala Leu Asp Val Ser
            260             265             270
Asp His Phe Pro Val Glu Phe Lys Leu Gln Ser Ser Arg Ala Phe Thr
            275             280             285
Asn Ser Asp Leu Ser Gly Gly Gly Gly Ser Gly Gly Gly Ser Gly
            290             295             300
Gly Gly Ser Gly Gly Gly Ser Thr Gly Leu Glu Pro Lys Ser
 305             310             315             320
Ser Asp Lys Thr His Thr Ser Pro Pro Ser Pro Ala Pro Glu Leu Leu
            325             330             335
Gly Gly Ser Ser Val Phe Leu Phe Pro Pro Lys Pro Lys Asp Thr Leu
            340             345             350
Met Ile Ser Arg Thr Pro Glu Val Thr Cys Val Val Val Asp Val Ser
            355             360             365
His Glu Asp Pro Glu Val Lys Phe Asn Trp Tyr Val Asp Gly Val Glu
            370             375             380
Val His Asn Ala Lys Thr Lys Pro Arg Glu Glu Gln Tyr Asn Ser Thr
 385             390             395             400
Tyr Arg Val Val Ser Val Leu Thr Val Leu His Gln Asp Trp Leu Asn
            405             410             415
Gly Lys Glu Tyr Lys Cys Lys Val Ser Asn Lys Ala Leu Pro Ala Ser
            420             425             430
Ile Glu Lys Thr Ile Ser Lys Ala Lys Gly Gln Pro Arg Glu Pro Gln
            435             440             445
Val Tyr Thr Leu Pro Pro Ser Arg Asp Glu Leu Thr Lys Asn Gln Val
 450             455             460
Ser Leu Thr Cys Leu Val Lys Gly Phe Tyr Pro Ser Asp Ile Ala Val
 465             470             475             480
Glu Trp Glu Ser Asn Gly Gln Pro Glu Asn Asn Tyr Lys Thr Thr Pro
            485             490             495
Pro Val Leu Asp Ser Asp Gly Ser Phe Phe Leu Tyr Ser Lys Leu Thr
            500             505             510
Val Asp Lys Ser Arg Trp Gln Gln Gly Asn Val Phe Ser Cys Ser Val
            515             520             525
Met His Glu Ala Leu His Asn His Tyr Thr Gln Lys Ser Leu Ser Leu
            530             535             540
Ser Pro Gly Lys
 545

<210> SEQ ID NO 141
<211> LENGTH: 1842
<212> TYPE: DNA
<213> ORGANISM: Artificial Sequence
<220> FEATURE:
<223> OTHER INFORMATION: hVK3LP-[SCChinge-P238S-P331S Fc]-NGS-
      [PON1 Q192K] DNA
```

<400> SEQUENCE: 141

```
atggaaaccc cagcgcagct tctcttcctc ctgctactct ggctcccaga taccaccggt      60
gagcccaaat cttctgacaa aactcacaca tgtccaccgt gcccagcacc tgaactcctg     120
ggaggatcgt cagtcttcct cttcccccca aaacccaagg acaccctcat gatctcccgg     180
accccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggagt acaagtgcaa ggtctccaac aaagccctcc cagcctccat cgagaaaacc     420
atctccaaag ccaaagggca gccccgagaa ccacaggtgt acaccctgcc cccatcccgg     480
gatgagctga ccaagaacca ggtcagcctg acctgcctgg tcaaaggctt ctatcccagc     540
gacatcgccg tggagtggga gagcaatggg cagccggaga caactacaa gaccacgcct     600
cccgtgctgg actccgacgg ctccttcttc ctctacagca agctcaccgt ggacaagagc     660
aggtggcagc aggggaacgt cttctcatgc tccgtgatgc atgaggctct gcacaaccac     720
tacacgcaga gagcctctc tctctctccg ggtaaagtcg acggagctag cagccccgtg     780
aacgtgagca gccccagcgt gcaggatatc ctcttcagga ccaccagtc ttcttaccaa     840
acacgactta atgctctccg agaggtacaa cccgtagaac ttcctaactg taatttagtt     900
aaaggaatcg aaactggctc tgaagacttg agatactgc ctaatggact ggctttcatt     960
agctctggat taaagtatcc tggaataaag agcttcaacc ccaacagtcc tggaaaaata    1020
cttctgatgg acctgaatga agaagatcca acagtgttgg aattggggat cactggaagt    1080
aaatttgatg tatcttcatt taaccctcat gggattagca cattcacaga tgaagataat    1140
gccatgtacc tcctggtggt gaaccatcca gatgccaagt ccacagtgga gttgtttaaa    1200
tttcaagaag aagaaaaatc gcttttgcat ctaaaaacca tcagacataa acttctgcct    1260
aatttgaatg atattgttgc tgtgggacct gagcactttt atggcacaaa tgatcactat    1320
tttcttgacc cctacttaaa atcctgggag atgtatttgg gtttagcgtg gtcgtatgtt    1380
gtctactata gtccaagtga agttcgagtg gtggcagaag gatttgattt tgctaatgga    1440
atcaacattt cacccgatgg caagtatgtc tatatagctg agttgctggc tcataagatt    1500
catgtgtatg aaaagcatgc taattggact ttaactccat tgaagtccct tgactttaat    1560
accctcgtgg ataacatatc tgtggatcct gagacaggag cctttgggt tggatgccat    1620
cccaatggca tgaaaatctt cttctatgac tcagagaatc ctcctgcatc agaggtgctt    1680
cgaatccaga acattctaac agaagaacct aaagtgacac aggtttatgc agaaaatggc    1740
acagtgttgc aaggcagtac agttgcctct gtgtacaaag gaaactgct gattggcaca    1800
gtgtttcaca agctcttta ctgtgagctc taataatcta ga                        1842
```

<210> SEQ ID NO 142
<211> LENGTH: 610
<212> TYPE: PRT
<213> ORGANISM: Artificial Sequence
<220> FEATURE:
<223> OTHER INFORMATION: hVK3LP-[SCChinge-P238S-P331S Fc]-NGS-
      [PON1 Q192K]

<400> SEQUENCE: 142

```
Met Glu Thr Pro Ala Gln Leu Leu Phe Leu Leu Leu Leu Trp Leu Pro
 1               5                  10                  15
```

-continued

Asp Thr Thr Gly Glu Pro Lys Ser Ser Asp Lys Thr His Thr Cys Pro
            20                  25                  30

Pro Cys Pro Ala Pro Glu Leu Leu Gly Gly Ser Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Ser Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Val Asp Gly Ala
                245                 250                 255

Ser Ser Pro Val Asn Val Ser Ser Pro Ser Val Gln Asp Ile Leu Phe
            260                 265                 270

Arg Asn His Gln Ser Ser Tyr Gln Thr Arg Leu Asn Ala Leu Arg Glu
        275                 280                 285

Val Gln Pro Val Glu Leu Pro Asn Cys Asn Leu Val Lys Gly Ile Glu
    290                 295                 300

Thr Gly Ser Glu Asp Leu Glu Ile Leu Pro Asn Gly Leu Ala Phe Ile
305                 310                 315                 320

Ser Ser Gly Leu Lys Tyr Pro Gly Ile Lys Ser Phe Asn Pro Asn Ser
                325                 330                 335

Pro Gly Lys Ile Leu Leu Met Asp Leu Asn Glu Glu Asp Pro Thr Val
            340                 345                 350

Leu Glu Leu Gly Ile Thr Gly Ser Lys Phe Asp Val Ser Ser Phe Asn
        355                 360                 365

Pro His Gly Ile Ser Thr Phe Thr Asp Glu Asp Asn Ala Met Tyr Leu
    370                 375                 380

Leu Val Val Asn His Pro Asp Ala Lys Ser Thr Val Glu Leu Phe Lys
385                 390                 395                 400

Phe Gln Glu Glu Glu Lys Ser Leu Leu His Leu Lys Thr Ile Arg His
                405                 410                 415

Lys Leu Leu Pro Asn Leu Asn Asp Ile Val Ala Val Gly Pro Glu His
            420                 425                 430

Phe Tyr Gly Thr Asn Asp His Tyr Phe Leu Asp Pro Tyr Leu Lys Ser

```
            435                 440                 445
Trp Glu Met Tyr Leu Gly Leu Ala Trp Ser Tyr Val Tyr Tyr Ser
    450                 455                 460

Pro Ser Glu Val Arg Val Ala Glu Gly Phe Asp Phe Ala Asn Gly
465                 470                 475                 480

Ile Asn Ile Ser Pro Asp Gly Lys Tyr Val Tyr Ile Ala Glu Leu Leu
                485                 490                 495

Ala His Lys Ile His Val Tyr Glu Lys His Ala Asn Trp Thr Leu Thr
                500                 505                 510

Pro Leu Lys Ser Leu Asp Phe Asn Thr Leu Val Asp Asn Ile Ser Val
        515                 520                 525

Asp Pro Glu Thr Gly Asp Leu Trp Val Gly Cys His Pro Asn Gly Met
530                 535                 540

Lys Ile Phe Phe Tyr Asp Ser Glu Asn Pro Ala Ser Glu Val Leu
545                 550                 555                 560

Arg Ile Gln Asn Ile Leu Thr Glu Glu Pro Lys Val Thr Gln Val Tyr
                565                 570                 575

Ala Glu Asn Gly Thr Val Leu Gln Gly Ser Thr Val Ala Ser Val Tyr
                580                 585                 590

Lys Gly Lys Leu Leu Ile Gly Thr Val Phe His Lys Ala Leu Tyr Cys
        595                 600                 605

Glu Leu
    610

<210> SEQ ID NO 143
<211> LENGTH: 1830
<212> TYPE: DNA
<213> ORGANISM: Artificial Sequence
<220> FEATURE:
<223> OTHER INFORMATION: hVK3LP-[SCChinge-P238S-P331S Fc]-NGS-
      [G3C9 PON1] DNA

<400> SEQUENCE: 143
atggaaaccc cagcgcagct tctcttcctc ctgctactct ggctcccaga taccaccggt    60
gagcccaaat cttctgacaa aactcacaca tgtccaccgt gcccagcacc tgaactcctg   120
ggaggatcgt cagtcttcct cttcccccca aaacccaagg acaccctcat gatctcccgg   180 accccctgagg tcacatgcgt ggtggtggac gtgagccacg aagaccctga ggtcaagttc   240
aactggtacg tggacggcgt ggaggtgcat aatgccaaga caaagccgcg ggaggagcag   300
tacaacagca cgtaccgtgt ggtcagcgtc ctcaccgtcc tgcaccagga ctggctgaat   360
ggcaaggagt acaagtgcaa ggtctccaac aaagccctcc cagcctccat cgagaaaacc   420
atctccaaag ccaaagggca gccccgagaa ccacaggtgt acaccctgcc cccatcccgg   480
gatgagctga ccaagaacca ggtcagcctg acctgcctgg tcaaaggctt ctatcccagc   540
gacatcgccg tggagtggga gagcaatggg cagccggaga acaactacaa gaccacgcct   600
cccgtgctgg actccgacgg ctccttcttc ctctacagca agctcaccgt ggacaagagc   660
aggtggcagc aggggaacgt cttctcatgc tccgtgatgc atgaggctct gcacaaccac   720
tacacgcaga agagcctctc tctctctccg ggtaaagtcg acggagctag cagccccgtg   780
aacgtgagca gccccagcgt gcaggatatc ctcttcgatg acagaagtc ttctttccaa   840 acacgattta atgttcaccg tgaagtaact ccagtggaac ttcctaactg taatttagtt   900
aaaggggttg acaatggttc tgaagacttg gaaatactgc ccaatggact ggctttcatc   960
agctccggat taaagtatcc tggaataatg agctttgacc ctgataagtc tggaaagata  1020
```

```
cttctaatgg acctgaatga ggaagaccca gtagtgttgg aactgggcat tactggaaat    1080
acattggata tatcttcatt taaccctcat gggattagca cattcacaga tgaagataac    1140
actgtgtacc tactggtggt aaaccatcca gactcctcgt ccaccgtgga ggtgtttaaa    1200
tttcaagaag aagaaaaatc actttttgcat ctgaaaacca tcagacacaa gcttctgcct    1260
agtgtgaatg acattgtcgc tgtgggacct gaacactttt atgccacaaa tgatcactat    1320
tttgctgacc cttacttaaa atcctgggaa atgcatttgg gattagcgtg gtcatttgtt    1380
acttattata gtcccaatga tgttcgagta gtggcagaag atttgatttt tgctaacgga    1440
atcaacatct caccagacgg caagtatgtc tatatagctg agttgctggc tcataagatc    1500
catgtgtatg aaaagcacgc taattggact ttaactccat tgaagtccct cgactttgac    1560
acccttgtgg ataacatctc tgtggatcct gtgacagggg acctctgggt gggatgccat    1620
cccaacggaa tgcgaatctt ctactatgac ccaaagaatc ctcccggctc agaggtgctt    1680
cgaatccagg acattttatc cgaagagccc aaagtgacag tggtttatgc agaaaatggc    1740
actgtgttac agggcagcac ggtggccgct gtgtacaaag ggaaactgct gattggcaca    1800
gtgtttcaca aagctcttta ctgtgagctg                                      1830
```

<210> SEQ ID NO 144
<211> LENGTH: 610
<212> TYPE: PRT
<213> ORGANISM: Artificial Sequence
<220> FEATURE:
<223> OTHER INFORMATION: hVK3LP-[SCChinge-P238S-P331S Fc]-NGS-
 [G3C9 PON1]

<400> SEQUENCE: 144

```
Met Glu Thr Pro Ala Gln Leu Leu Phe Leu Leu Leu Trp Leu Pro
1               5                   10                  15

Asp Thr Thr Gly Glu Pro Lys Ser Ser Asp Lys Thr His Thr Cys Pro
                20                  25                  30

Pro Cys Pro Ala Pro Glu Leu Leu Gly Gly Ser Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Ser Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205
```

```
Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Val Asp Gly Ala
                245                 250                 255

Ser Ser Pro Val Asn Val Ser Ser Pro Ser Val Gln Asp Ile Leu Phe
            260                 265                 270

Asp Gly Gln Lys Ser Ser Phe Gln Thr Arg Phe Asn Val His Arg Glu
        275                 280                 285

Val Thr Pro Val Glu Leu Pro Asn Cys Asn Leu Val Lys Gly Val Asp
290                 295                 300

Asn Gly Ser Glu Asp Leu Glu Ile Leu Pro Asn Gly Leu Ala Phe Ile
305                 310                 315                 320

Ser Ser Gly Leu Lys Tyr Pro Gly Ile Met Ser Phe Asp Pro Asp Lys
                325                 330                 335

Ser Gly Lys Ile Leu Leu Met Asp Leu Asn Glu Glu Asp Pro Val Val
            340                 345                 350

Leu Glu Leu Gly Ile Thr Gly Asn Thr Leu Asp Ile Ser Ser Phe Asn
        355                 360                 365

Pro His Gly Ile Ser Thr Phe Thr Asp Glu Asp Asn Thr Val Tyr Leu
    370                 375                 380

Leu Val Val Asn His Pro Asp Ser Ser Ser Thr Val Glu Val Phe Lys
385                 390                 395                 400

Phe Gln Glu Glu Glu Lys Ser Leu Leu His Leu Lys Thr Ile Arg His
                405                 410                 415

Lys Leu Leu Pro Ser Val Asn Asp Ile Val Ala Val Gly Pro Glu His
            420                 425                 430

Phe Tyr Ala Thr Asn Asp His Tyr Phe Ala Asp Pro Tyr Leu Lys Ser
        435                 440                 445

Trp Glu Met His Leu Gly Leu Ala Trp Ser Phe Val Thr Tyr Tyr Ser
    450                 455                 460

Pro Asn Asp Val Arg Val Val Ala Glu Gly Phe Asp Phe Ala Asn Gly
465                 470                 475                 480

Ile Asn Ile Ser Pro Asp Gly Lys Tyr Val Tyr Ile Ala Glu Leu Leu
                485                 490                 495

Ala His Lys Ile His Val Tyr Glu Lys His Ala Asn Trp Thr Leu Thr
            500                 505                 510

Pro Leu Lys Ser Leu Asp Phe Asp Thr Leu Val Asp Asn Ile Ser Val
        515                 520                 525

Asp Pro Val Thr Gly Asp Leu Trp Val Gly Cys His Pro Asn Gly Met
    530                 535                 540

Arg Ile Phe Tyr Tyr Asp Pro Lys Asn Pro Pro Gly Ser Glu Val Leu
545                 550                 555                 560

Arg Ile Gln Asp Ile Leu Ser Glu Glu Pro Lys Val Thr Val Val Tyr
                565                 570                 575

Ala Glu Asn Gly Thr Val Leu Gln Gly Ser Thr Val Ala Ala Val Tyr
            580                 585                 590

Lys Gly Lys Leu Leu Ile Gly Thr Val Phe His Lys Ala Leu Tyr Cys
        595                 600                 605

Glu Leu
    610
```

<210> SEQ ID NO 145
<211> LENGTH: 1830
<212> TYPE: DNA
<213> ORGANISM: Artificial Sequence
<220> FEATURE:
<223> OTHER INFORMATION: hVK3LP-[SCChinge-P238S-P331S Fc]-NGS-
      [M-IIG1 PON1] DNA

<400> SEQUENCE: 145

| | |
|---|---:|
| atggaaaccc cagcgcagct tctcttcctc ctgctactct ggctcccaga taccaccggt | 60 |
| gagcccaaat cttctgacaa aactcacaca tgtccaccgt gcccagcacc tgaactcctg | 120 |
| ggaggatcgt cagtcttcct cttccccca aaacccaagg acaccctcat gatctcccgg | 180 |
| acccctgagg tcacatgcgt ggtggtggac gtgagccacg aagaccctga ggtcaagttc | 240 |
| aactggtacg tggacggcgt ggaggtgcat aatgccaaga caaagccgcg ggaggagcag | 300 |
| tacaacagca cgtaccgtgt ggtcagcgtc ctcaccgtcc tgcaccagga ctggctgaat | 360 |
| ggcaaggagt acaagtgcaa ggtctccaac aaagccctcc cagcctccat cgagaaaacc | 420 |
| atctccaaag ccaaagggca gccccgagaa ccacaggtgt acaccctgcc cccatcccgg | 480 |
| gatgagctga ccaagaacca ggtcagcctg acctgcctgg tcaaaggctt ctatcccagc | 540 |
| gacatcgccg tggagtggga gagcaatggg cagccggaga caactacaa gaccacgcct | 600 |
| cccgtgctgg actccgacgg ctccttcttc ctctacagca agctcaccgt ggacaagagc | 660 |
| aggtggcagc aggggaacgt cttctcatgc tccgtgatgc atgaggctct gcacaaccac | 720 |
| tacacgcaga agagcctctc tctctctccg ggtaaagtcg acggagctag cagcccgtg | 780 |
| aacgtgagca gccccagcgt gcaggatatc ctcttcgatg acagaagtc ttctttccaa | 840 |
| acacgattta atgttcaccg tgaagtaact ccagtggaac ttcctaactg taatttagtt | 900 |
| aaaggggttg acaatggttc tgaagacatt gaaatactgc caatggact ggctttcatc | 960 |
| agctccggag ttaagtatcc tggaataatg agctttgacc ctgataagtc tggaaagata | 1020 |
| cttctaatgg acctgaatga ggaagaccca gtagtgttgg aactgggcat tactggaaat | 1080 |
| acattggata tatcttcatt taaccctgct gggattagca cattcacaga tgaagataac | 1140 |
| actgtgtacc tactggtggt aaaccgacca gactcctcgt ccaccgtgga ggtgtttaaa | 1200 |
| tttcaagaag aagaaaaatc acttttgcat ctgaaaacca tcagacacaa gcttctgcct | 1260 |
| agtgtgaatg acattgtcgc tgtgggacct gaacactttt atgccacaaa tgatcactat | 1320 |
| tttgctgacc ttacttaaa atcctgggaa atgcatttgg gattagcgtg gtcatttgtt | 1380 |
| acttattata gtcccaatga tgttcgagta gtggcagaag gatttgatat ggctaacgga | 1440 |
| atcaacatct caccagacgg caagtatgtc tatatagctg agttgctggc tcataagatc | 1500 |
| catgtgtatg aaaagcacgc taattggact ttaactccat gaagtccct cgactttgac | 1560 |
| acccttgtgg ataacatctc tgtggatcct gtgacagggg acctctgggt gggatgccat | 1620 |
| cccaacggaa tgcgattatt ctactatgac ccaaagaatc ctcccggctc agaggtgctt | 1680 |
| cgaatccagg acattttatc cgaagagccc aaagtgacga tggtttatgc agaaaatggc | 1740 |
| actgtgttac agggcagcag tgtggccgct gtgtacaaag ggaaactgct gattggcaca | 1800 |
| gtgtttcaca agctctttta ctgtgagctg | 1830 |

<210> SEQ ID NO 146
<211> LENGTH: 610
<212> TYPE: PRT
<213> ORGANISM: Artificial Sequence
<220> FEATURE:
<223> OTHER INFORMATION: hVK3LP-[SCChinge-P238S-P331S Fc]-NGS- -continued

[M-IIG1 PON1]

<400> SEQUENCE: 146

Met Glu Thr Pro Ala Gln Leu Leu Phe Leu Leu Leu Trp Leu Pro
1               5                   10                  15

Asp Thr Thr Gly Glu Pro Lys Ser Ser Asp Lys Thr His Thr Cys Pro
            20                  25                  30

Pro Cys Pro Ala Pro Glu Leu Leu Gly Gly Ser Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Ser Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Val Asp Gly Ala
                245                 250                 255

Ser Ser Pro Val Asn Val Ser Ser Pro Ser Val Gln Asp Ile Leu Phe
            260                 265                 270

Asp Gly Gln Lys Ser Ser Phe Gln Thr Arg Phe Asn Val His Arg Glu
        275                 280                 285

Val Thr Pro Val Glu Leu Pro Asn Cys Asn Leu Val Lys Gly Val Asp
    290                 295                 300

Asn Gly Ser Glu Asp Ile Glu Ile Leu Pro Asn Gly Leu Ala Phe Ile
305                 310                 315                 320

Ser Ser Gly Val Lys Tyr Pro Gly Ile Met Ser Phe Asp Pro Asp Lys
                325                 330                 335

Ser Gly Lys Ile Leu Leu Met Asp Leu Asn Glu Glu Asp Pro Val Val
            340                 345                 350

Leu Glu Leu Gly Ile Thr Gly Asn Thr Leu Asp Ile Ser Ser Phe Asn
        355                 360                 365

Pro Ala Gly Ile Ser Thr Phe Thr Asp Glu Asp Asn Thr Val Tyr Leu
    370                 375                 380

Leu Val Val Asn Arg Pro Asp Ser Ser Ser Thr Val Glu Val Phe Lys
385                 390                 395                 400

Phe Gln Glu Glu Glu Lys Ser Leu Leu His Leu Lys Thr Ile Arg His
                    405                 410                 415
Lys Leu Leu Pro Ser Val Asn Asp Ile Val Ala Val Gly Pro Glu His
            420                 425                 430
Phe Tyr Ala Thr Asn Asp His Tyr Phe Ala Asp Pro Tyr Leu Lys Ser
        435                 440                 445
Trp Glu Met His Leu Gly Leu Ala Trp Ser Phe Val Thr Tyr Tyr Ser
    450                 455                 460
Pro Asn Asp Val Arg Val Ala Glu Gly Phe Asp Met Ala Asn Gly
465                 470                 475                 480
Ile Asn Ile Ser Pro Asp Gly Lys Tyr Val Tyr Ile Ala Glu Leu Leu
                485                 490                 495
Ala His Lys Ile His Val Tyr Glu Lys His Ala Asn Trp Thr Leu Thr
            500                 505                 510
Pro Leu Lys Ser Leu Asp Phe Asp Thr Leu Val Asp Asn Ile Ser Val
        515                 520                 525
Asp Pro Val Thr Gly Asp Leu Trp Val Gly Cys His Pro Asn Gly Met
    530                 535                 540
Arg Leu Phe Tyr Tyr Asp Pro Lys Asn Pro Pro Gly Ser Glu Val Leu
545                 550                 555                 560
Arg Ile Gln Asp Ile Leu Ser Glu Glu Pro Lys Val Thr Val Tyr
                565                 570                 575
Ala Glu Asn Gly Thr Val Leu Gln Gly Ser Ser Val Ala Ala Val Tyr
            580                 585                 590
Lys Gly Lys Leu Leu Ile Gly Thr Val Phe His Lys Ala Leu Tyr Cys
        595                 600                 605
Glu Leu
    610

<210> SEQ ID NO 147
<211> LENGTH: 2721
<212> TYPE: DNA
<213> ORGANISM: Artificial Sequence
<220> FEATURE:
<223> OTHER INFORMATION: hVK3LP-[hDNase1 N74K-G105R-A114F]-(g4s)6-
      [SSShinge-P238S-P331S Fc]-NGS-[PON1 Q192K] DNA

<400> SEQUENCE: 147
atggaaaccc cagcgcagct tctcttcctc ctgctactct ggctcccaga taccaccggt    60
ctgaagatcg cagccttcaa catccagaca tttggggaga ccaagatgtc caatgccacc   120
ctcgtcagct acattgtgca gatcctgagc cgctatgaca tcgccctggt ccaggaggtc   180
agagacagcc acctgactgc cgtggggaag ctgctggaca acctcaatca ggatgcacca   240
gacacctatc actacgtggt cagtgagcca ctgggacgga gagctataa ggagcgctac   300 ctgttcgtgt acaggcctga ccaggtgtct gcggtggaca gctactacta cgatgatggc   360
tgcgagccct gcaggaacga cacccttcaac cgagagccat tcattgtcag gttcttctcc   420
cggttcacag aggtcaggga gtttgccatt gttcccctgc atgcggcccc ggggacgca   480 gtagccgaga tcgacgctct ctatgacgtc tacctggatg ccaagagaa atggggcttg   540 gaggacgtca tgttgatggg cgacttcaat gcgggctgca gctatgtgag acctcccag   600 tggtcatcca tccgcctgtg gacaagcccc accttccagt ggctgatccc cgacagcgct   660
gacaccacag ctacacccac gcactgtgcc tatgacagga tcgtggttgc agggatgctg   720
ctccgaggcg ccgttgttcc cgactcggct cttccctta acttccaggc tgcctatggc   780

| | |
|---|---|
| ctgagtgacc aactggccca agccatcagt gaccactatc cagtggaggt gatgctgaaa | 840 |
| gatctctccg gaggaggtgg ctcaggtggt ggaggatctg gaggaggtgg gagtggtgga | 900 |
| ggtggttctg gaggaggtgg tagtggaggt ggaggttcta ccggtctcga gcccaaatct | 960 |
| tctgacaaaa ctcacacatc tccaccgtcc ccagcacctg aactcctggg aggatcgtca | 1020 |
| gtcttcctct tccccccaaa acccaaggac accctcatga tctcccggac ccctgaggtc | 1080 |
| acatgcgtgg tggtggacgt gagccacgaa gaccctgagg tcaagttcaa ctggtacgtg | 1140 |
| gacggcgtgg aggtgcataa tgccaagaca aagccgcggg aggagcagta caacagcacg | 1200 |
| taccgtgtgg tcagcgtcct caccgtcctg caccaggact ggctgaatgg caaggagtac | 1260 |
| aagtgcaagg tctccaacaa agccctccca gcctccatcg agaaaaccat ctccaaagcc | 1320 |
| aaagggcagc cccgagaacc acaggtgtac accctgcccc catcccggga tgagctgacc | 1380 |
| aagaaccagg tcagcctgac ctgcctggtc aaaggcttct atcccagcga catcgccgtg | 1440 |
| gagtgggaga gcaatgggca gccggagaac aactacaaga ccacgcctcc cgtgctggac | 1500 |
| tccgacggct ccttcttcct ctacagcaag ctcaccgtgg acaagagcag gtggcagcag | 1560 |
| gggaacgtct tctcatgctc cgtgatgcat gaggctctgc acaaccacta cacgcagaag | 1620 |
| agcctctctc tctctccggg taaagtcgac ggagctagca gccccgtgaa cgtgagcagc | 1680 |
| cccagcgtgc aggatatcct cttcaggaac caccagtctt cttaccaaac acgacttaat | 1740 |
| gctctccgag aggtacaacc cgtagaactt cctaactgta atttagttaa aggaatcgaa | 1800 |
| actggctctg aagacttgga gatactgcct aatggactgg cttttcattag ctctggatta | 1860 |
| aagtatcctg aataaagag cttcaacccc aacagtcctg gaaaaatact tctgatggac | 1920 |
| ctgaatgaag aagatccaac agtgttggaa ttggggatca ctggaagtaa atttgatgta | 1980 |
| tcttcattta accctcatgg gattagcaca ttcacagatg aagataatgc catgtacctc | 2040 |
| ctggtggtga ccatccaga tgccaagtcc acagtggagt tgtttaaatt tcaagaagaa | 2100 |
| gaaaaatcgc ttttgcatct aaaaaccatc agacataaac ttctgcctaa tttgaatgat | 2160 |
| attgttgctg tgggacctga gcactttat ggcacaaatg atcactattt tcttgacccc | 2220 |
| tacttaaaat cctgggagat gtatttgggt ttagcgtggt cgtatgttgt ctactatagt | 2280 |
| ccaagtgaag ttcgagtggt ggcagaagga tttgattttg ctaatggaat caacatttca | 2340 |
| cccgatggca gtatgtcta tatagctgag ttgctggctc ataagattca tgtgtatgaa | 2400 |
| aagcatgcta attggacttt aactccattg aagtccttg actttaatac cctcgtggat | 2460 |
| aacatatctg tggatcctga acaggagac ctttgggttg gatgccatcc caatggcatg | 2520 |
| aaaatcttct tctatgactc agagaatcct cctgcatcag aggtgcttcg aatccagaac | 2580 |
| attctaacag aagaacctaa agtgacacag gtttatgcag aaaatggcac agtgttgcaa | 2640 |
| ggcagtacag ttgcctctgt gtacaaaggg aaactgctga ttggcacagt gtttcacaaa | 2700 |
| gctctttact gtgagctcta a | 2721 |

<210> SEQ ID NO 148
<211> LENGTH: 906
<212> TYPE: PRT
<213> ORGANISM: Artificial Sequence
<220> FEATURE:
<223> OTHER INFORMATION: hVK3LP-[hDNase1 N74K-G105R-A114F]-(g4s)6-
    [SSShinge-P238S-P331S Fc]-NGS-[PON1 Q192K]

<400> SEQUENCE: 148

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
 50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Phe Ile Val Arg Phe Phe Ser Arg Phe Thr Glu
130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Ser
        275                 280                 285

Gly Gly Gly Gly Ser Gly Gly Gly Ser Gly Gly Gly Ser Gly
            290                 295                 300

Gly Gly Gly Ser Gly Gly Gly Ser Thr Gly Leu Glu Pro Lys Ser
305                 310                 315                 320

Ser Asp Lys Thr His Thr Ser Pro Pro Ser Pro Ala Pro Glu Leu Leu
                325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

His Glu Asp Pro Glu Val Lys Phe Asn Trp Tyr Val Asp Gly Val Glu
        370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Ser
            420                 425                 430

```
Ile Glu Lys Thr Ile Ser Lys Ala Lys Gly Gln Pro Arg Glu Pro Gln
            435                 440                 445

Val Tyr Thr Leu Pro Pro Ser Arg Asp Glu Leu Thr Lys Asn Gln Val
450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
530                 535                 540

Ser Pro Gly Lys Val Asp Gly Ala Ser Ser Pro Val Asn Val Ser Ser
545                 550                 555                 560

Pro Ser Val Gln Asp Ile Leu Phe Arg Asn His Gln Ser Ser Tyr Gln
            565                 570                 575

Thr Arg Leu Asn Ala Leu Arg Glu Val Gln Pro Val Glu Leu Pro Asn
            580                 585                 590

Cys Asn Leu Val Lys Gly Ile Glu Thr Gly Ser Glu Asp Leu Glu Ile
            595                 600                 605

Leu Pro Asn Gly Leu Ala Phe Ile Ser Ser Gly Leu Lys Tyr Pro Gly
            610                 615                 620

Ile Lys Ser Phe Asn Pro Asn Ser Pro Gly Lys Ile Leu Leu Met Asp
625                 630                 635                 640

Leu Asn Glu Glu Asp Pro Thr Val Leu Glu Leu Gly Ile Thr Gly Ser
                645                 650                 655

Lys Phe Asp Val Ser Ser Phe Asn Pro His Gly Ile Ser Thr Phe Thr
            660                 665                 670

Asp Glu Asp Asn Ala Met Tyr Leu Leu Val Val Asn His Pro Asp Ala
            675                 680                 685

Lys Ser Thr Val Glu Leu Phe Lys Phe Gln Glu Glu Lys Ser Leu
            690                 695                 700

Leu His Leu Lys Thr Ile Arg His Lys Leu Leu Pro Asn Leu Asn Asp
705                 710                 715                 720

Ile Val Ala Val Gly Pro Glu His Phe Tyr Gly Thr Asn Asp His Tyr
                725                 730                 735

Phe Leu Asp Pro Tyr Leu Lys Ser Trp Glu Met Tyr Leu Gly Leu Ala
            740                 745                 750

Trp Ser Tyr Val Val Tyr Tyr Ser Pro Ser Glu Val Arg Val Val Ala
            755                 760                 765

Glu Gly Phe Asp Phe Ala Asn Gly Ile Asn Ile Ser Pro Asp Gly Lys
            770                 775                 780

Tyr Val Tyr Ile Ala Glu Leu Leu Ala His Lys Ile His Val Tyr Glu
785                 790                 795                 800

Lys His Ala Asn Trp Thr Leu Thr Pro Leu Lys Ser Leu Asp Phe Asn
                805                 810                 815

Thr Leu Val Asp Asn Ile Ser Val Asp Pro Glu Thr Gly Asp Leu Trp
            820                 825                 830

Val Gly Cys His Pro Asn Gly Met Lys Ile Phe Phe Tyr Asp Ser Glu
            835                 840                 845

Asn Pro Pro Ala Ser Glu Val Leu Arg Ile Gln Asn Ile Leu Thr Glu
```

```
                850                 855                 860
Glu Pro Lys Val Thr Gln Val Tyr Ala Glu Asn Gly Thr Val Leu Gln
865                 870                 875                 880

Gly Ser Thr Val Ala Ser Val Tyr Lys Gly Lys Leu Leu Ile Gly Thr
                885                 890                 895

Val Phe His Lys Ala Leu Tyr Cys Glu Leu
                900                 905

<210> SEQ ID NO 149
<211> LENGTH: 528
<212> TYPE: PRT
<213> ORGANISM: Artificial Sequence
<220> FEATURE:
<223> OTHER INFORMATION: [hDNase1 N74X-G105X-A114X]-[gs linker]-
      [SSShinge Fc]
<220> FEATURE:
<221> NAME/KEY: MISC_FEATURE
<222> LOCATION: (74)..(74)
<223> OTHER INFORMATION: Xaa is Lys, Arg, or His
<220> FEATURE:
<221> NAME/KEY: MISC_FEATURE
<222> LOCATION: (105)..(105)
<223> OTHER INFORMATION: Xaa is Lys, Arg, or His
<220> FEATURE:
<221> NAME/KEY: MISC_FEATURE
<222> LOCATION: (114)..(114)
<223> OTHER INFORMATION: Xaa is Phe, Glu, Met, Arg, or Tyr
<220> FEATURE:
<221> NAME/KEY: MISC_FEATURE
<222> LOCATION: (261)..(263)
<223> OTHER INFORMATION: Xaa is any naturally occurring non-cysteine
      amino acid
<220> FEATURE:
<221> NAME/KEY: MISC_FEATURE
<222> LOCATION: (264)..(283)
<223> OTHER INFORMATION: Xaa is Gly or Ser
<220> FEATURE:
<221> NAME/KEY: MISC_FEATURE
<222> LOCATION: (284)..(293)
<223> OTHER INFORMATION: Xaa is Gly or Ser or is absent
<220> FEATURE:
<221> NAME/KEY: MISC_FEATURE
<222> LOCATION: (294)..(296)
<223> OTHER INFORMATION: Xaa is any naturally occurring non-cysteine
      amino acid
<220> FEATURE:
<221> NAME/KEY: MISC_FEATURE
<222> LOCATION: (315)..(316)
<223> OTHER INFORMATION: Xaa is Leu or Ala
<220> FEATURE:
<221> NAME/KEY: MISC_FEATURE
<222> LOCATION: (319)..(319)
<223> OTHER INFORMATION: Xaa is Pro or Ser
<220> FEATURE:
<221> NAME/KEY: MISC_FEATURE
<222> LOCATION: (333)..(333)
<223> OTHER INFORMATION: Xaa is Met or Tyr
<220> FEATURE:
<221> NAME/KEY: MISC_FEATURE
<222> LOCATION: (335)..(335)
<223> OTHER INFORMATION: Xaa is Ser or Thr
<220> FEATURE:
<221> NAME/KEY: MISC_FEATURE
<222> LOCATION: (337)..(337)
<223> OTHER INFORMATION: Xaa is Thr or Glu
<220> FEATURE:
<221> NAME/KEY: MISC_FEATURE
<222> LOCATION: (346)..(346)
<223> OTHER INFORMATION: Xaa is Asp or Ala
<220> FEATURE:
<221> NAME/KEY: MISC_FEATURE
<222> LOCATION: (378)..(378)
<223> OTHER INFORMATION: Xaa is Asn, Ala, Gln, or Gly
<220> FEATURE:
<221> NAME/KEY: MISC_FEATURE
```

```
<222> LOCATION: (410)..(410)
<223> OTHER INFORMATION: Xaa is Pro, Ala, Gly, or Ser
<220> FEATURE:
<221> NAME/KEY: MISC_FEATURE
<222> LOCATION: (412)..(412)
<223> OTHER INFORMATION: Xaa is Pro, Ser, or Ala
<220> FEATURE:
<221> NAME/KEY: MISC_FEATURE
<222> LOCATION: (509)..(509)
<223> OTHER INFORMATION: Xaa is Met or Leu
<220> FEATURE:
<221> NAME/KEY: MISC_FEATURE
<222> LOCATION: (515)..(515)
<223> OTHER INFORMATION: Xaa is Asn or Ser
<220> FEATURE:
<221> NAME/KEY: MISC_FEATURE
<222> LOCATION: (528)..(528)
<223> OTHER INFORMATION: Xaa is Lys or is absent

<400> SEQUENCE: 149

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Xaa Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Xaa Asn Asp Thr Phe Asn Arg Glu
            100                 105                 110

Pro Xaa Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Glu Pro Lys Ser Ser Asp Lys Thr
    290                 295                 300

His Thr Ser Pro Pro Ser Pro Ala Pro Glu Xaa Xaa Gly Gly Xaa Ser
```

```
                305                 310                 315                 320
Val Phe Leu Phe Pro Pro Lys Pro Lys Asp Thr Leu Xaa Ile Xaa Arg
                    325                 330                 335

Xaa Pro Glu Val Thr Cys Val Val Xaa Val Ser His Glu Asp Pro
                340                 345                 350

Glu Val Lys Phe Asn Trp Tyr Val Asp Gly Val Glu Val His Asn Ala
                    355                 360                 365

Lys Thr Lys Pro Arg Glu Glu Gln Tyr Xaa Ser Thr Tyr Arg Val Val
    370                 375                 380

Ser Val Leu Thr Val Leu His Gln Asp Trp Leu Asn Gly Lys Glu Tyr
385                 390                 395                 400

Lys Cys Lys Val Ser Asn Lys Ala Leu Xaa Ala Xaa Ile Glu Lys Thr
                    405                 410                 415

Ile Ser Lys Ala Lys Gly Gln Pro Arg Glu Pro Gln Val Tyr Thr Leu
                420                 425                 430

Pro Pro Ser Arg Asp Glu Leu Thr Lys Asn Gln Val Ser Leu Thr Cys
                435                 440                 445

Leu Val Lys Gly Phe Tyr Pro Ser Asp Ile Ala Val Glu Trp Glu Ser
450                 455                 460

Asn Gly Gln Pro Glu Asn Asn Tyr Lys Thr Thr Pro Pro Val Leu Asp
465                 470                 475                 480

Ser Asp Gly Ser Phe Phe Leu Tyr Ser Lys Leu Thr Val Asp Lys Ser
                485                 490                 495

Arg Trp Gln Gln Gly Asn Val Phe Ser Cys Ser Val Xaa His Glu Ala
                    500                 505                 510

Leu His Xaa His Tyr Thr Gln Lys Ser Leu Ser Leu Ser Pro Gly Xaa
                515                 520                 525

<210> SEQ ID NO 150
<211> LENGTH: 528
<212> TYPE: PRT
<213> ORGANISM: Artificial Sequence
<220> FEATURE:
<223> OTHER INFORMATION: [hDNase1 N74K-G105R-A114F]-[gs linker]-
      [SSShinge Fc]
<220> FEATURE:
<221> NAME/KEY: MISC_FEATURE
<222> LOCATION: (261)..(263)
<223> OTHER INFORMATION: Xaa is any naturally occurring non-cysteine
      amino acid
<220> FEATURE:
<221> NAME/KEY: MISC_FEATURE
<222> LOCATION: (264)..(283)
<223> OTHER INFORMATION: Xaa is Gly or Ser
<220> FEATURE:
<221> NAME/KEY: MISC_FEATURE
<222> LOCATION: (284)..(293)
<223> OTHER INFORMATION: Xaa is Gly or Ser or is absent
<220> FEATURE:
<221> NAME/KEY: MISC_FEATURE
<222> LOCATION: (294)..(296)
<223> OTHER INFORMATION: Xaa is any naturally occurring non-cysteine
      amino acid
<220> FEATURE:
<221> NAME/KEY: MISC_FEATURE
<222> LOCATION: (315)..(316)
<223> OTHER INFORMATION: Xaa is Leu or Ala
<220> FEATURE:
<221> NAME/KEY: MISC_FEATURE
<222> LOCATION: (319)..(319)
<223> OTHER INFORMATION: Xaa is Pro or Ser
<220> FEATURE:
<221> NAME/KEY: MISC_FEATURE
<222> LOCATION: (333)..(333)
<223> OTHER INFORMATION: Xaa is Met or Tyr
```

```
<220> FEATURE:
<221> NAME/KEY: MISC_FEATURE
<222> LOCATION: (335)..(335)
<223> OTHER INFORMATION: Xaa is Ser or Thr
<220> FEATURE:
<221> NAME/KEY: MISC_FEATURE
<222> LOCATION: (337)..(337)
<223> OTHER INFORMATION: Xaa is Thr or Glu
<220> FEATURE:
<221> NAME/KEY: MISC_FEATURE
<222> LOCATION: (346)..(346)
<223> OTHER INFORMATION: Xaa is Asp or Ala
<220> FEATURE:
<221> NAME/KEY: MISC_FEATURE
<222> LOCATION: (378)..(378)
<223> OTHER INFORMATION: Xaa is Asn, Ala, Gln, or Gly
<220> FEATURE:
<221> NAME/KEY: MISC_FEATURE
<222> LOCATION: (410)..(410)
<223> OTHER INFORMATION: Xaa is Pro, Ala, Gly, or Ser
<220> FEATURE:
<221> NAME/KEY: MISC_FEATURE
<222> LOCATION: (412)..(412)
<223> OTHER INFORMATION: Xaa is Pro, Ser, or Ala
<220> FEATURE:
<221> NAME/KEY: MISC_FEATURE
<222> LOCATION: (509)..(509)
<223> OTHER INFORMATION: Xaa is Met or Leu
<220> FEATURE:
<221> NAME/KEY: MISC_FEATURE
<222> LOCATION: (515)..(515)
<223> OTHER INFORMATION: Xaa is Asn or Ser
<220> FEATURE:
<221> NAME/KEY: MISC_FEATURE
<222> LOCATION: (528)..(528)
<223> OTHER INFORMATION: Xaa is Lys or is absent

<400> SEQUENCE: 150

Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Lys Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
            100                 105                 110

Pro Phe Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
```

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
            245                 250                 255

Val Met Leu Lys Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Glu Pro Lys Ser Ser Asp Lys Thr
290                 295                 300

His Thr Ser Pro Pro Ser Pro Ala Pro Glu Xaa Xaa Gly Gly Xaa Ser
305                 310                 315                 320

Val Phe Leu Phe Pro Pro Lys Pro Lys Asp Thr Leu Xaa Ile Xaa Arg
                325                 330                 335

Xaa Pro Glu Val Thr Cys Val Val Val Xaa Val Ser His Glu Asp Pro
                340                 345                 350

Glu Val Lys Phe Asn Trp Tyr Val Asp Gly Val Glu Val His Asn Ala
            355                 360                 365

Lys Thr Lys Pro Arg Glu Glu Gln Tyr Xaa Ser Thr Tyr Arg Val Val
370                 375                 380

Ser Val Leu Thr Val Leu His Gln Asp Trp Leu Asn Gly Lys Glu Tyr
385                 390                 395                 400

Lys Cys Lys Val Ser Asn Lys Ala Leu Xaa Ala Xaa Ile Glu Lys Thr
                405                 410                 415

Ile Ser Lys Ala Lys Gly Gln Pro Arg Glu Pro Gln Val Tyr Thr Leu
            420                 425                 430

Pro Pro Ser Arg Asp Glu Leu Thr Lys Asn Gln Val Ser Leu Thr Cys
            435                 440                 445

Leu Val Lys Gly Phe Tyr Pro Ser Asp Ile Ala Val Glu Trp Glu Ser
            450                 455                 460

Asn Gly Gln Pro Glu Asn Asn Tyr Lys Thr Thr Pro Pro Val Leu Asp
465                 470                 475                 480

Ser Asp Gly Ser Phe Phe Leu Tyr Ser Lys Leu Thr Val Asp Lys Ser
                485                 490                 495

Arg Trp Gln Gln Gly Asn Val Phe Ser Cys Ser Val Xaa His Glu Ala
                500                 505                 510

Leu His Xaa His Tyr Thr Gln Lys Ser Leu Ser Leu Ser Pro Gly Xaa
        515                 520                 525

<210> SEQ ID NO 151
<211> LENGTH: 840
<212> TYPE: DNA
<213> ORGANISM: Artificial Sequence
<220> FEATURE:
<223> OTHER INFORMATION: hVK3LP-[hDNase1 N74K-G105R] DNA

<400> SEQUENCE: 151
atggaaaccc cagcgcagct tctcttcctc ctgctactct ggctcccaga taccaccggt    60
ctgaagatcg cagccttcaa catccagaca tttgggagga ccaagatgtc caatgccacc    120
ctcgtcagct acattgtgca gatcctgagc cgctatgaca tcgccctggt ccaggaggtc    180
agagacagcc acctgactgc cgtggggaag ctgctggaca acctcaatca ggatgcacca    240
gacaccctat cactacgtgg tcagtgagcc actgggacgg agagctataa ggagcgctac    300

```
ctgttcgtgt acaggcctga ccaggtgtct gcggtggaca gctactacta cgatgatggc    360
tgcgagccct gcaggaacga caccttcaac cgagagccag ccattgtcag gttcttctcc    420
cggttcacag aggtcaggga gtttgccatt gttcccctgc atgcggcccc ggggacgca     480
gtagccgaga tcgacgctct ctatgacgtc tacctggatg tccaagagaa atggggcttg    540
gaggacgtca tgttgatggg cgacttcaat gcgggctgca gctatgtgag accctcccag    600
tggtcatcca tccgcctgtg gacaagcccc accttccagt ggctgatccc cgacagcgct    660
gacaccacag ctacacccac gcactgtgcc tatgacagga tcgtggttgc agggatgctg    720
ctccgaggcg ccgttgttcc cgactcggct cttcccttta acttccaggc tgcctatggc    780
ctgagtgacc aactggccca agccatcagt gaccactatc cagtggaggt gatgctgaaa    840
```

<210> SEQ ID NO 152
<211> LENGTH: 280
<212> TYPE: PRT
<213> ORGANISM: Artificial Sequence
<220> FEATURE:
<223> OTHER INFORMATION: hVK3LP-[hDNase1 N74K-G105R]

<400> SEQUENCE: 152

Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys
            275                 280

<210> SEQ ID NO 153
<211> LENGTH: 528
<212> TYPE: PRT
<213> ORGANISM: Artificial Sequence
<220> FEATURE:
<223> OTHER INFORMATION: [hDNase1 N74X-G105X]-[gs linker]-[SSHinge Fc]
<220> FEATURE:
<221> NAME/KEY: MISC_FEATURE
<222> LOCATION: (74)..(74)
<223> OTHER INFORMATION: Xaa is Lys, Arg, or His
<220> FEATURE:
<221> NAME/KEY: MISC_FEATURE
<222> LOCATION: (105)..(105)
<223> OTHER INFORMATION: Xaa is Lys, Arg, or His
<220> FEATURE:
<221> NAME/KEY: MISC_FEATURE
<222> LOCATION: (261)..(263)
<223> OTHER INFORMATION: Xaa is any naturally occurring non-cysteine
      amino acid
<220> FEATURE:
<221> NAME/KEY: MISC_FEATURE
<222> LOCATION: (264)..(283)
<223> OTHER INFORMATION: Xaa is Gly or Ser
<220> FEATURE:
<221> NAME/KEY: MISC_FEATURE
<222> LOCATION: (284)..(293)
<223> OTHER INFORMATION: Xaa is Gly or Ser or is absent
<220> FEATURE:
<221> NAME/KEY: MISC_FEATURE
<222> LOCATION: (294)..(296)
<223> OTHER INFORMATION: Xaa is any naturally occurring non-cysteine
      amino acid
<220> FEATURE:
<221> NAME/KEY: MISC_FEATURE
<222> LOCATION: (315)..(316)
<223> OTHER INFORMATION: Xaa is Leu or Ala
<220> FEATURE:
<221> NAME/KEY: MISC_FEATURE
<222> LOCATION: (319)..(319)
<223> OTHER INFORMATION: Xaa is Pro or Ser
<220> FEATURE:
<221> NAME/KEY: MISC_FEATURE
<222> LOCATION: (333)..(333)
<223> OTHER INFORMATION: Xaa is Met or Tyr
<220> FEATURE:
<221> NAME/KEY: MISC_FEATURE
<222> LOCATION: (335)..(335)
<223> OTHER INFORMATION: Xaa is Ser or Thr
<220> FEATURE:
<221> NAME/KEY: MISC_FEATURE
<222> LOCATION: (337)..(337)
<223> OTHER INFORMATION: Xaa is Thr or Glu
<220> FEATURE:
<221> NAME/KEY: MISC_FEATURE
<222> LOCATION: (346)..(346)
<223> OTHER INFORMATION: Xaa is Asp or Ala
<220> FEATURE:
<221> NAME/KEY: MISC_FEATURE
<222> LOCATION: (378)..(378)
<223> OTHER INFORMATION: Xaa is Asn, Ala, Gln, or Gly
<220> FEATURE:
<221> NAME/KEY: MISC_FEATURE
<222> LOCATION: (410)..(410)
<223> OTHER INFORMATION: Xaa is Pro, Ala, Gly, or Ser
<220> FEATURE:
<221> NAME/KEY: MISC_FEATURE
<222> LOCATION: (412)..(412)
<223> OTHER INFORMATION: Xaa is Pro, Ser, or Ala
<220> FEATURE:
<221> NAME/KEY: MISC_FEATURE
<222> LOCATION: (509)..(509)
<223> OTHER INFORMATION: Xaa is Met or Leu
<220> FEATURE:
<221> NAME/KEY: MISC_FEATURE
<222> LOCATION: (515)..(515)

<223> OTHER INFORMATION: Xaa is Asn or Ser
<220> FEATURE:
<221> NAME/KEY: MISC_FEATURE
<222> LOCATION: (528)..(528)
<223> OTHER INFORMATION: Xaa is Lys or is absent

<400> SEQUENCE: 153

```
Leu Lys Ile Ala Ala Phe Asn Ile Gln Thr Phe Gly Glu Thr Lys Met
1               5                   10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Xaa Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Xaa Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Glu Pro Lys Ser Ser Asp Lys Thr
    290                 295                 300

His Thr Ser Pro Pro Ser Pro Ala Pro Glu Xaa Xaa Gly Gly Xaa Ser
305                 310                 315                 320

Val Phe Leu Phe Pro Pro Lys Pro Lys Asp Thr Leu Xaa Ile Xaa Arg
                325                 330                 335

Xaa Pro Glu Val Thr Cys Val Val Xaa Val Ser His Glu Asp Pro
        340                 345                 350

Glu Val Lys Phe Asn Trp Tyr Val Asp Gly Val Glu Val His Asn Ala
    355                 360                 365

Lys Thr Lys Pro Arg Glu Glu Gln Tyr Xaa Ser Thr Tyr Arg Val Val
370                 375                 380
```

-continued

```
Ser Val Leu Thr Val Leu His Gln Asp Trp Leu Asn Gly Lys Glu Tyr
385                 390                 395                 400

Lys Cys Lys Val Ser Asn Lys Ala Leu Xaa Ala Xaa Ile Glu Lys Thr
            405                 410                 415

Ile Ser Lys Ala Lys Gly Gln Pro Arg Glu Pro Gln Val Tyr Thr Leu
        420                 425                 430

Pro Pro Ser Arg Asp Glu Leu Thr Lys Asn Gln Val Ser Leu Thr Cys
        435                 440                 445

Leu Val Lys Gly Phe Tyr Pro Ser Asp Ile Ala Val Glu Trp Glu Ser
    450                 455                 460

Asn Gly Gln Pro Glu Asn Asn Tyr Lys Thr Thr Pro Pro Val Leu Asp
465                 470                 475                 480

Ser Asp Gly Ser Phe Phe Leu Tyr Ser Lys Leu Thr Val Asp Lys Ser
                485                 490                 495

Arg Trp Gln Gln Gly Asn Val Phe Ser Cys Ser Val Xaa His Glu Ala
            500                 505                 510

Leu His Xaa His Tyr Thr Gln Lys Ser Leu Ser Leu Ser Pro Gly Xaa
        515                 520                 525

<210> SEQ ID NO 154
<211> LENGTH: 528
<212> TYPE: PRT
<213> ORGANISM: Artificial Sequence
<220> FEATURE:
<223> OTHER INFORMATION: [hDNase1 N74K-G105R]-[gs linker]-[SSHinge Fc]
<220> FEATURE:
<221> NAME/KEY: MISC_FEATURE
<222> LOCATION: (261)..(263)
<223> OTHER INFORMATION: Xaa is any naturally occurring non-cysteine
      amino acid
<220> FEATURE:
<221> NAME/KEY: MISC_FEATURE
<222> LOCATION: (264)..(283)
<223> OTHER INFORMATION: Xaa is Gly or Ser
<220> FEATURE:
<221> NAME/KEY: MISC_FEATURE
<222> LOCATION: (284)..(293)
<223> OTHER INFORMATION: Xaa is Gly or Ser or is absent
<220> FEATURE:
<221> NAME/KEY: MISC_FEATURE
<222> LOCATION: (294)..(296)
<223> OTHER INFORMATION: Xaa is any naturally occurring non-cysteine
      amino acid
<220> FEATURE:
<221> NAME/KEY: MISC_FEATURE
<222> LOCATION: (315)..(316)
<223> OTHER INFORMATION: Xaa is Leu or Ala
<220> FEATURE:
<221> NAME/KEY: MISC_FEATURE
<222> LOCATION: (319)..(319)
<223> OTHER INFORMATION: Xaa is Pro or Ser
<220> FEATURE:
<221> NAME/KEY: MISC_FEATURE
<222> LOCATION: (333)..(333)
<223> OTHER INFORMATION: Xaa is Met or Tyr
<220> FEATURE:
<221> NAME/KEY: MISC_FEATURE
<222> LOCATION: (335)..(335)
<223> OTHER INFORMATION: Xaa is Ser or Thr
<220> FEATURE:
<221> NAME/KEY: MISC_FEATURE
<222> LOCATION: (337)..(337)
<223> OTHER INFORMATION: Xaa is Thr or Glu
<220> FEATURE:
<221> NAME/KEY: MISC_FEATURE
<222> LOCATION: (346)..(346)
<223> OTHER INFORMATION: Xaa is Asp or Ala
<220> FEATURE:
<221> NAME/KEY: MISC_FEATURE
```

```
<222> LOCATION: (378)..(378)
<223> OTHER INFORMATION: Xaa is Asn, Ala, Gln, or Gly
<220> FEATURE:
<221> NAME/KEY: MISC_FEATURE
<222> LOCATION: (410)..(410)
<223> OTHER INFORMATION: Xaa is Pro, Ala, Gly, or Ser
<220> FEATURE:
<221> NAME/KEY: MISC_FEATURE
<222> LOCATION: (412)..(412)
<223> OTHER INFORMATION: Xaa is Pro, Ser, or Ala
<220> FEATURE:
<221> NAME/KEY: MISC_FEATURE
<222> LOCATION: (509)..(509)
<223> OTHER INFORMATION: Xaa is Met or Leu
<220> FEATURE:
<221> NAME/KEY: MISC_FEATURE
<222> LOCATION: (515)..(515)
<223> OTHER INFORMATION: Xaa is Asn or Ser
<220> FEATURE:
<221> NAME/KEY: MISC_FEATURE
<222> LOCATION: (528)..(528)
<223> OTHER INFORMATION: Xaa is Lys or is absent

<400> SEQUENCE: 154

Leu Lys Ile Ala Ala Phe Asn Ile Gln Thr Phe Gly Glu Thr Lys Met
 1               5                  10                  15

Ser Asn Ala Thr Leu Val Ser Tyr Ile Val Gln Ile Leu Ser Arg Tyr
            20                  25                  30

Asp Ile Ala Leu Val Gln Glu Val Arg Asp Ser His Leu Thr Ala Val
        35                  40                  45

Gly Lys Leu Leu Asp Asn Leu Asn Gln Asp Ala Pro Asp Thr Tyr His
    50                  55                  60

Tyr Val Val Ser Glu Pro Leu Gly Arg Lys Ser Tyr Lys Glu Arg Tyr
65                  70                  75                  80

Leu Phe Val Tyr Arg Pro Asp Gln Val Ser Ala Val Asp Ser Tyr Tyr
                85                  90                  95

Tyr Asp Asp Gly Cys Glu Pro Cys Arg Asn Asp Thr Phe Asn Arg Glu
            100                 105                 110

Pro Ala Ile Val Arg Phe Phe Ser Arg Phe Thr Glu Val Arg Glu Phe
        115                 120                 125

Ala Ile Val Pro Leu His Ala Ala Pro Gly Asp Ala Val Ala Glu Ile
    130                 135                 140

Asp Ala Leu Tyr Asp Val Tyr Leu Asp Val Gln Glu Lys Trp Gly Leu
145                 150                 155                 160

Glu Asp Val Met Leu Met Gly Asp Phe Asn Ala Gly Cys Ser Tyr Val
                165                 170                 175

Arg Pro Ser Gln Trp Ser Ser Ile Arg Leu Trp Thr Ser Pro Thr Phe
            180                 185                 190

Gln Trp Leu Ile Pro Asp Ser Ala Asp Thr Thr Ala Thr Pro Thr His
        195                 200                 205

Cys Ala Tyr Asp Arg Ile Val Val Ala Gly Met Leu Leu Arg Gly Ala
    210                 215                 220

Val Val Pro Asp Ser Ala Leu Pro Phe Asn Phe Gln Ala Ala Tyr Gly
225                 230                 235                 240

Leu Ser Asp Gln Leu Ala Gln Ala Ile Ser Asp His Tyr Pro Val Glu
                245                 250                 255

Val Met Leu Lys Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa
        275                 280                 285
```

Xaa Xaa Xaa Xaa Xaa Xaa Xaa Glu Pro Lys Ser Ser Asp Lys Thr
    290                 295                 300

His Thr Ser Pro Pro Ser Pro Ala Pro Glu Xaa Xaa Gly Gly Xaa Ser
305                 310                 315                 320

Val Phe Leu Phe Pro Pro Lys Pro Lys Asp Thr Leu Xaa Ile Xaa Arg
                325                 330                 335

Xaa Pro Glu Val Thr Cys Val Val Xaa Val Ser His Glu Asp Pro
        340                 345                 350

Glu Val Lys Phe Asn Trp Tyr Val Asp Gly Val Glu Val His Asn Ala
                355                 360                 365

Lys Thr Lys Pro Arg Glu Glu Gln Tyr Xaa Ser Thr Tyr Arg Val Val
    370                 375                 380

Ser Val Leu Thr Val Leu His Gln Asp Trp Leu Asn Gly Lys Glu Tyr
385                 390                 395                 400

Lys Cys Lys Val Ser Asn Lys Ala Leu Xaa Ala Xaa Ile Glu Lys Thr
                405                 410                 415

Ile Ser Lys Ala Lys Gly Gln Pro Arg Glu Pro Gln Val Tyr Thr Leu
        420                 425                 430

Pro Pro Ser Arg Asp Glu Leu Thr Lys Asn Gln Val Ser Leu Thr Cys
    435                 440                 445

Leu Val Lys Gly Phe Tyr Pro Ser Asp Ile Ala Val Glu Trp Glu Ser
450                 455                 460

Asn Gly Gln Pro Glu Asn Asn Tyr Lys Thr Thr Pro Pro Val Leu Asp
465                 470                 475                 480

Ser Asp Gly Ser Phe Phe Leu Tyr Ser Lys Leu Thr Val Asp Lys Ser
                485                 490                 495

Arg Trp Gln Gln Gly Asn Val Phe Ser Cys Ser Val Xaa His Glu Ala
        500                 505                 510

Leu His Xaa His Tyr Thr Gln Lys Ser Leu Ser Leu Ser Pro Gly Xaa
    515                 520                 525

<210> SEQ ID NO 155
<211> LENGTH: 538
<212> TYPE: PRT
<213> ORGANISM: Artificial Sequence
<220> FEATURE:
<223> OTHER INFORMATION: hVK3LP-[hDNase1 N96K-G127R]-(g4s)
     4-[SSShinge-P238S-P331S Fc]

<400> SEQUENCE: 155

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
        35                  40                  45

Leu Ser Arg Tyr Asp Ile Ala Leu Val Gln Glu Val Arg Asp Ser His
    50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

```
Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Ser
        275                 280                 285

Gly Gly Gly Gly Ser Gly Gly Gly Ser Gly Gly Gly Ser Thr
290                 295                 300

Gly Leu Glu Pro Lys Ser Ser Asp Lys Thr His Thr Ser Pro Pro Ser
305                 310                 315                 320

Pro Ala Pro Glu Leu Leu Gly Ser Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Ser Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535
```

<210> SEQ ID NO 156
<211> LENGTH: 548
<212> TYPE: PRT
<213> ORGANISM: Artificial Sequence
<220> FEATURE:
<223> OTHER INFORMATION: hVK3LP-[hDNase1 N96K-G127R]-(g4s)
      6-[SSHinge-P238S-P331S Fc]

<400> SEQUENCE: 156

```
Met Glu Thr Pro Ala Gln Leu Leu Phe Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile
                35                  40                  45

Leu Ser Arg Tyr Asp Ile Ala Leu Val Gln Glu Val Arg Asp Ser His
        50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220

Thr Pro Thr His Cys Ala Tyr Asp Arg Ile Val Val Ala Gly Met Leu
225                 230                 235                 240

Leu Arg Gly Ala Val Val Pro Asp Ser Ala Leu Pro Phe Asn Phe Gln
                245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Ser
        275                 280                 285

Gly Gly Gly Gly Ser Gly Gly Gly Ser Gly Gly Gly Ser Gly
    290                 295                 300

Gly Gly Gly Ser Gly Gly Gly Ser Thr Gly Leu Glu Pro Lys Ser
305                 310                 315                 320

Ser Asp Lys Thr His Thr Ser Pro Pro Ser Ala Pro Glu Leu Leu
                325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365
```

```
His Glu Asp Pro Glu Val Lys Phe Asn Trp Tyr Val Asp Gly Val Glu
    370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Arg Asp Glu Leu Thr Lys Asn Gln Val
        450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
530                 535                 540

Ser Pro Gly Lys
545

<210> SEQ ID NO 157
<211> LENGTH: 2713
<212> TYPE: DNA
<213> ORGANISM: Artificial Sequence
<220> FEATURE:
<223> OTHER INFORMATION: hVK3LP-[hDNase1 N74K-G105R]-(g4s)
      4-[SSShinge-P238S-P331S Fc]-NGS-[PON1 Q192K] DNA

<400> SEQUENCE: 157
aagcttgccg ccatggaaac cccagcgcag cttctcttcc tcctgctact ctggctccca    60
gataccaccg gtctgaagat cgcagccttc aacatccaga catttgggga gaccaagatg   120
tccaatgcca ccctcgtcag ctacattgtg cagatcctga ccgctatgat catcgccctg   180
gtccaggagg tcagagacag ccacctgact gccgtgggga agctgctgga caacctcaat   240
caggatgcac agacaccta tcactacgtg gtcagtgagc cactgggacg aaagagctat   300
aaggagcgct acctgttcgt gtacaggcct gaccaggtgt ctgcggtgga cagctactac   360
tacgatgatg gctgcgagcc ctgcaggaac gacaccttca ccgagagcc agccattgtc   420 aggttcttct cccggttcac agaggtcagg gagtttgcca ttgttcccct gcatgcggcc   480 ccggggacg cagtagccga gatcgacgct ctctatgacg tctacctgga tgtccaagag   540
aaatggggct tggaggacgt catgttgatg ggcgacttca atgcgggctg cagctatgtg   600
agaccctccc agtggtcatc catccgcctg tggacaagcc caccttcca gtggctgatc   660 cccgacagcg ctgacaccac agctacaccc acgcactgtg cctatgacag gatcgtggtt   720
gcagggatgc tgctccgagg cgccgttgtt cccgactcgg ctcttcccctt taacttccag   780 gctgcctatg cctgagtga ccaactggcc caagccatca gtgaccacta tccagtggag   840
gtgatgctga agatctctc cggaggaggt ggctcaggtg gtggaggatc tggaggaggt   900
gggagtggtg gaggtggttc taccggtctc gagcccaaat cttctgacaa aactcacaca   960
```

-continued

```
tctccaccgt ccccagcacc tgaactcctg ggaggatcgt cagtcttcct cttccccca      1020
aaacccaagg acaccctcat gatctcccgg acccctgagg tcacatgcgt ggtggtggac      1080
gtgagccacg aagaccctga ggtcaagttc aactggtacg tggacggcgt ggaggtgcat      1140
aatgccaaga caaagccgcg ggaggagcag tacaacagca cgtaccgtgt ggtcagcgtc      1200
ctcaccgtcc tgcaccagga ctggctgaat ggcaaggagt acaagtgcaa ggtctccaac      1260
aaagccctcc cagcctccat cgagaaaacc atctccaaag ccaagggca gccccgagaa      1320
ccacaggtgt acaccctgcc cccatcccgg gatgagctga ccaagaacca ggtcagcctg      1380
acctgcctgg tcaaaggctt ctatcccagc gacatcgccg tggagtggga gagcaatggg      1440
cagccggaga caactacaa gaccacgcct cccgtgctgg actccgacgg ctccttcttc      1500
ctctacagca agctcaccgt ggacaagagc aggtggcagc aggggaacgt cttctcatgc      1560
tccgtgatgc atgaggctct gcacaaccac tacacgcaga agagcctctc tctctctccg      1620
ggtaaagtcg acggagctag cagccccgtg aacgtgagca gccccagcgt gcaggatatc      1680
ctcttcagga accaccagtc ttcttaccaa acacgactta atgctctccg agaggtacaa      1740
cccgtagaac ttcctaactg taatttagtt aaaggaatcg aaactggctc tgaagacttg      1800
gagatactgc ctaatggact ggctttcatt agctctggat aaagtatcc tggaataaag      1860
agcttcaacc ccaacagtcc tggaaaaata cttctgatgg acctgaatga agaagatcca      1920
acagtgttgg aattggggat cactggaagt aaatttgatg tatcttcatt taaccctcat      1980
gggattagca cattcacaga tgaagataat gccatgtacc tcctggtggt gaaccatcca      2040
gatgccaagt ccacagtgga gttgtttaaa tttcaagaag aagaaaaatc gcttttgcat      2100
ctaaaaacca tcagacataa acttctgcct aatttgaatg atattgttgc tgtgggacct      2160
gagcactttt atggcacaaa tgatcactat tttcttgacc cctacttaaa atcctgggag      2220
atgtatttgg gtttagcgtg gtcgtatgtt gtctactata gtccaagtga agttcgagtg      2280
gtggcagaag gatttgattt tgctaatgga atcaacattt cacccgatgg caagtatgtc      2340
tatatagctg agttgctggc tcataagatt catgtgtatg aaaagcatgc taattggact      2400
ttaactccat tgaagtccct tgactttaat accctcgtgg ataacatatc tgtggatcct      2460
gagacaggag accttggt tggatgccat cccaatggca tgaaaatctt cttctatgac      2520
tcagagaatc ctcctgcatc agaggtgctt cgaatccaga acattctaac agaagaacct      2580
aaagtgacac aggtttatgc agaaaatggc acagtgttgc aaggcagtac agttgcctct      2640
gtgtacaaag gaaactgct gattggcaca gtgtttcaca agctctttta ctgtgagctc      2700
taataatcta gaa                                                          2713
```

<210> SEQ ID NO 158
<211> LENGTH: 896
<212> TYPE: PRT
<213> ORGANISM: Artificial Sequence
<220> FEATURE:
<223> OTHER INFORMATION: hVK3LP-[hDNase1 N74K-G105R]-(g4s)
    4-[SSShinge-P238S-P331S Fc]-NGS-[PON1 Q192K]

<400> SEQUENCE: 158

Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
            20                  25                  30

Glu Thr Lys Met Ser Asn Ala Thr Leu Val Ser Tyr Ile Val Gln Ile

-continued

```
                35                  40                  45
Leu Ser Arg Tyr Asp Ile Ala Leu Val Gln Glu Val Arg Asp Ser His
            50                  55                  60
Leu Thr Ala Val Gly Lys Leu Leu Asp Asn Leu Asn Gln Asp Ala Pro
65                  70                  75                  80
Asp Thr Tyr His Tyr Val Val Ser Glu Pro Leu Gly Arg Lys Ser Tyr
                85                  90                  95
Lys Glu Arg Tyr Leu Phe Val Tyr Arg Pro Asp Gln Val Ser Ala Val
                100                 105                 110
Asp Ser Tyr Tyr Tyr Asp Asp Gly Cys Glu Pro Cys Arg Asn Asp Thr
            115                 120                 125
Phe Asn Arg Glu Pro Ala Ile Val Arg Phe Phe Ser Arg Phe Thr Glu
        130                 135                 140
Val Arg Glu Phe Ala Ile Val Pro Leu His Ala Ala Pro Gly Asp Ala
145                 150                 155                 160
Val Ala Glu Ile Asp Ala Leu Tyr Asp Val Tyr Leu Asp Val Gln Glu
                165                 170                 175
Lys Trp Gly Leu Glu Asp Val Met Leu Met Gly Asp Phe Asn Ala Gly
            180                 185                 190
Cys Ser Tyr Val Arg Pro Ser Gln Trp Ser Ser Ile Arg Leu Trp Thr
        195                 200                 205
Ser Pro Thr Phe Gln Trp Leu Ile Pro Asp Ser Ala Asp Thr Thr Ala
    210                 215                 220
Thr Pro Thr His Cys Ala Tyr Asp Arg Ile Val Val Ala Gly Met Leu
225                 230                 235                 240
Leu Arg Gly Ala Val Val Pro Asp Ser Ala Leu Pro Phe Asn Phe Gln
                245                 250                 255
Ala Ala Tyr Gly Leu Ser Asp Gln Leu Ala Gln Ala Ile Ser Asp His
            260                 265                 270
Tyr Pro Val Glu Val Met Leu Lys Asp Leu Ser Gly Gly Gly Ser
        275                 280                 285
Gly Gly Gly Gly Ser Gly Gly Gly Ser Gly Gly Gly Ser Thr
290                 295                 300
Gly Leu Glu Pro Lys Ser Ser Asp Lys Thr His Thr Ser Pro Pro Ser
305                 310                 315                 320
Pro Ala Pro Glu Leu Leu Gly Gly Ser Ser Val Phe Leu Phe Pro Pro
                325                 330                 335
Lys Pro Lys Asp Thr Leu Met Ile Ser Arg Thr Pro Glu Val Thr Cys
            340                 345                 350
Val Val Val Asp Val Ser His Glu Asp Pro Glu Val Lys Phe Asn Trp
        355                 360                 365
Tyr Val Asp Gly Val Glu Val His Asn Ala Lys Thr Lys Pro Arg Glu
    370                 375                 380
Glu Gln Tyr Asn Ser Thr Tyr Arg Val Val Ser Val Leu Thr Val Leu
385                 390                 395                 400
His Gln Asp Trp Leu Asn Gly Lys Glu Tyr Lys Cys Lys Val Ser Asn
                405                 410                 415
Lys Ala Leu Pro Ala Ser Ile Glu Lys Thr Ile Ser Lys Ala Lys Gly
            420                 425                 430
Gln Pro Arg Glu Pro Gln Val Tyr Thr Leu Pro Pro Ser Arg Asp Glu
        435                 440                 445
Leu Thr Lys Asn Gln Val Ser Leu Thr Cys Leu Val Lys Gly Phe Tyr
    450                 455                 460
```

```
Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                        485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys Val Asp Gly Ala Ser Ser
    530                 535                 540

Pro Val Asn Val Ser Ser Pro Ser Val Gln Asp Ile Leu Phe Arg Asn
545                 550                 555                 560

His Gln Ser Ser Tyr Gln Thr Arg Leu Asn Ala Leu Arg Glu Val Gln
                565                 570                 575

Pro Val Glu Leu Pro Asn Cys Asn Leu Val Lys Gly Ile Glu Thr Gly
            580                 585                 590

Ser Glu Asp Leu Glu Ile Leu Pro Asn Gly Leu Ala Phe Ile Ser Ser
        595                 600                 605

Gly Leu Lys Tyr Pro Gly Ile Lys Ser Phe Asn Pro Asn Ser Pro Gly
    610                 615                 620

Lys Ile Leu Leu Met Asp Leu Asn Glu Glu Asp Pro Thr Val Leu Glu
625                 630                 635                 640

Leu Gly Ile Thr Gly Ser Lys Phe Asp Val Ser Ser Phe Asn Pro His
                645                 650                 655

Gly Ile Ser Thr Phe Thr Asp Glu Asp Asn Ala Met Tyr Leu Leu Val
            660                 665                 670

Val Asn His Pro Asp Ala Lys Ser Thr Val Glu Leu Phe Lys Phe Gln
        675                 680                 685

Glu Glu Glu Lys Ser Leu Leu His Leu Lys Thr Ile Arg His Lys Leu
    690                 695                 700

Leu Pro Asn Leu Asn Asp Ile Val Ala Val Gly Pro Glu His Phe Tyr
705                 710                 715                 720

Gly Thr Asn Asp His Tyr Phe Leu Asp Pro Tyr Leu Lys Ser Trp Glu
                725                 730                 735

Met Tyr Leu Gly Leu Ala Trp Ser Tyr Val Val Tyr Tyr Ser Pro Ser
            740                 745                 750

Glu Val Arg Val Val Ala Glu Gly Phe Asp Phe Ala Asn Gly Ile Asn
        755                 760                 765

Ile Ser Pro Asp Gly Lys Tyr Val Tyr Ile Ala Glu Leu Leu Ala His
    770                 775                 780

Lys Ile His Val Tyr Glu Lys His Ala Asn Trp Thr Leu Thr Pro Leu
785                 790                 795                 800

Lys Ser Leu Asp Phe Asn Thr Leu Val Asp Asn Ile Ser Val Asp Pro
                805                 810                 815

Glu Thr Gly Asp Leu Trp Val Gly Cys His Pro Asn Gly Met Lys Ile
            820                 825                 830

Phe Phe Tyr Asp Ser Glu Asn Pro Pro Ala Ser Glu Val Leu Arg Ile
        835                 840                 845

Gln Asn Ile Leu Thr Glu Glu Pro Lys Val Thr Gln Val Tyr Ala Glu
    850                 855                 860

Asn Gly Thr Val Leu Gln Gly Ser Thr Val Ala Ser Val Tyr Lys Gly
865                 870                 875                 880
```

Lys Leu Leu Ile Gly Thr Val Phe His Lys Ala Leu Tyr Cys Glu Leu
           885                 890                 895

<210> SEQ ID NO 159
<211> LENGTH: 2743
<212> TYPE: DNA
<213> ORGANISM: Artificial Sequence
<220> FEATURE:
<223> OTHER INFORMATION: hVK3LP-[hDNase1 N74K-G105R]-(g4s)
      6-[SSShinge-P238S-P331S Fc]-NGS-[PON1 Q192K] DNA

<400> SEQUENCE: 159

| | | |
|---|---|---|
| aagcttgccg ccatggaaac cccagcgcag cttctcttcc tcctgctact ctggctccca | 60 |
| gataccaccg gtctgaagat cgcagccttc aacatccaga catttgggga gaccaagatg | 120 |
| tccaatgcca ccctcgtcag ctacattgtg cagatcctga ccgctatga catcgccctg | 180 |
| gtccaggagg tcagagacag ccacctgact gccgtgggga gctgctgga caacctcaat | 240 |
| caggatgcac cagacaccta tcactacgtg gtcagtgagc cactgggacg aagagctat | 300 |
| aaggagcgct acctgttcgt gtacaggcct gaccaggtgt ctgcggtgga cagctactac | 360 |
| tacgatgatg gctgcgagcc ctgcaggaac gacaccttca accgagagcc agccattgtc | 420 |
| aggttcttct cccggttcac agaggtcagg agtttgcca ttgttcccct gcatgcggcc | 480 |
| ccggggacg cagtagccga gatcgacgct ctctatgacg tctacctgga tgtccaagag | 540 |
| aaatggggct tggaggacgt catgttgatg ggcgacttca atgcgggctg cagctatgtg | 600 |
| agaccctccc agtggtcatc catccgcctg tggacaagcc ccaccttcca gtggctgatc | 660 |
| cccgacagcg ctgacaccac agctacaccc acgcactgtg cctatgacag gatcgtggtt | 720 |
| gcagggatgc tgctccgagg cgccgttgtt cccgactcgg ctcttcccct taacttccag | 780 |
| gctgcctatg gcctgagtga ccaactggcc caagccatca gtgaccacta tccagtggag | 840 |
| gtgatgctga agatctctc cggaggaggt ggctcaggtg gtggaggatc tggaggaggt | 900 |
| gggagtggtg gaggtggttc tggaggaggt ggtagtggag gtggaggttc taccggtctc | 960 |
| gagcccaaat cttctgacaa aactcacaca tctccaccgt ccccagcacc tgaactcctg | 1020 |
| ggaggatcgt cagtcttcct cttcccccca aaacccaagg acaccctcat gatctcccgg | 1080 |
| acccctgagg tcacatgcgt ggtggtggac gtgagccacg aagaccctga ggtcaagttc | 1140 |
| aactggtacg tggacggcgt ggaggtgcat aatgccaaga caaagccgcg ggaggagcag | 1200 |
| tacaacagca cgtaccgtgt ggtcagcgtc ctcaccgtcc tgcaccagga ctggctgaat | 1260 |
| ggcaaggagt acaagtgcaa ggtctccaac aaagccctcc cagcctccat cgagaaaacc | 1320 |
| atctccaaag ccaaagggca gccccgagaa ccacaggtgt acaccctgcc cccatcccgg | 1380 |
| gatgagctga ccaagaacca ggtcagcctg acctgcctgg tcaaaggctt ctatcccagc | 1440 |
| gacatcgccg tggagtggga gagcaatggg cagccggaga caactacaa gaccacgcct | 1500 |
| cccgtgctgg actccgacgg ctccttcttc ctctacagca agctcaccgt ggacaagagc | 1560 |
| aggtggcagc aggggaacgt cttctcatgc tccgtgatgc atgaggctct gcacaaccac | 1620 |
| tacacgcaga agagcctctc tctctctccg ggtaaagtcg acggagctag cagccccgtg | 1680 |
| aacgtgagca gccccagcgt gcaggatatc ctcttcagga ccaccagtc ttcttaccaa | 1740 |
| acacgactta atgctctccg agaggtacaa cccgtagaac ttcctaactg taatttagtt | 1800 |
| aaaggaatcg aaactggctc tgaagacttg agatactgc taatggact ggctttcatt | 1860 |
| agctctggat taaagtatcc tggaataaag agcttcaacc caacagtcc tggaaaaata | 1920 |
| cttctgatgg acctgaatga agaagatcca acagtgttgg aattggggat cactggaagt | 1980 |

```
aaatttgatg tatcttcatt taaccctcat gggattagca cattcacaga tgaagataat    2040
gccatgtacc tcctggtggt gaaccatcca gatgccaagt ccacagtgga gttgtttaaa    2100
tttcaagaag aagaaaaatc gcttttgcat ctaaaaacca tcagacataa acttctgcct    2160
aatttgaatg atattgttgc tgtgggacct gagcactttt atggcacaaa tgatcactat    2220
tttcttgacc cctacttaaa atcctgggag atgtatttgg gtttagcgtg gtcgtatgtt    2280
gtctactata gtccaagtga agttcgagtg gtggcagaag gatttgattt tgctaatgga    2340
atcaacattt cacccgatgg caagtatgtc tatatagctg agttgctggc tcataagatt    2400
catgtgtatg aaaagcatgc taattggact ttaactccat tgaagtccct tgactttaat    2460
accctcgtgg ataacatatc tgtggatcct gagacaggag acctttgggt tggatgccat    2520
cccaatggca tgaaaatctt cttctatgac tcagagaatc ctcctgcatc agaggtgctt    2580
cgaatccaga acattctaac agaagaacct aaagtgacac aggtttatgc agaaaatggc    2640
acagtgttgc aaggcagtac agttgcctct gtgtacaaag ggaaactgct gattggcaca    2700
gtgtttcaca agctctttta ctgtgagctc taataatcta gaa                      2743
```

<210> SEQ ID NO 160
<211> LENGTH: 906
<212> TYPE: PRT
<213> ORGANISM: Artificial Sequence
<220> FEATURE:
<223> OTHER INFORMATION: hVK3LP-[hDNase1 N74K-G105R]-(g4s)
      6-[SSShinge-P238S-P331S Fc]-NGS-[PON1 Q192K]

<400> SEQUENCE: 160

```
Met Glu Thr Pro Ala Gln Leu Leu Phe Leu Leu Leu Leu Trp Leu Pro
1               5                   10                  15

Asp Thr Thr Gly Leu Lys Ile Ala Ala Phe Asn Ile Gln Thr Phe Gly
                20                  25                  30

Glu Thr Lys Met Ser Asn Ala Thr Leu Val Ser Tyr Ile Val Gln Ile
            35                  40                  45

Leu Ser Arg Tyr Asp Ile Ala Leu Val Gln Glu Val Arg Asp Ser His
        50                  55                  60

Leu Thr Ala Val Gly Lys Leu Leu Asp Asn Leu Asn Gln Asp Ala Pro
65                  70                  75                  80

Asp Thr Tyr His Tyr Val Val Ser Glu Pro Leu Gly Arg Lys Ser Tyr
                85                  90                  95

Lys Glu Arg Tyr Leu Phe Val Tyr Arg Pro Asp Gln Val Ser Ala Val
            100                 105                 110

Asp Ser Tyr Tyr Tyr Asp Asp Gly Cys Glu Pro Cys Arg Asn Asp Thr
        115                 120                 125

Phe Asn Arg Glu Pro Ala Ile Val Arg Phe Phe Ser Arg Phe Thr Glu
    130                 135                 140

Val Arg Glu Phe Ala Ile Val Pro Leu His Ala Ala Pro Gly Asp Ala
145                 150                 155                 160

Val Ala Glu Ile Asp Ala Leu Tyr Asp Val Tyr Leu Asp Val Gln Glu
                165                 170                 175

Lys Trp Gly Leu Glu Asp Val Met Leu Met Gly Asp Phe Asn Ala Gly
            180                 185                 190

Cys Ser Tyr Val Arg Pro Ser Gln Trp Ser Ser Ile Arg Leu Trp Thr
        195                 200                 205

Ser Pro Thr Phe Gln Trp Leu Ile Pro Asp Ser Ala Asp Thr Thr Ala
    210                 215                 220
```

-continued

```
Thr Pro Thr His Cys Ala Tyr Asp Arg Ile Val Val Ala Gly Met Leu
225                 230                 235                 240

Leu Arg Gly Ala Val Pro Asp Ser Ala Leu Pro Phe Asn Phe Gln
        245                 250                 255

Ala Ala Tyr Gly Leu Ser Asp Gln Leu Ala Gln Ala Ile Ser Asp His
            260                 265                 270

Tyr Pro Val Glu Val Met Leu Lys Asp Leu Ser Gly Gly Gly Ser
        275                 280                 285

Gly Gly Gly Gly Ser Gly Gly Gly Ser Gly Gly Gly Ser Gly
        290                 295                 300

Gly Gly Gly Ser Gly Gly Gly Ser Thr Gly Leu Glu Pro Lys Ser
305                 310                 315                 320

Ser Asp Lys Thr His Thr Ser Pro Pro Ser Pro Ala Pro Glu Leu Leu
                325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

His Glu Asp Pro Glu Val Lys Phe Asn Trp Tyr Val Asp Gly Val Glu
370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Ala Leu Pro Ala Ser
            420                 425                 430

Ile Glu Lys Thr Ile Ser Lys Ala Lys Gly Gln Pro Arg Glu Pro Gln
        435                 440                 445

Val Tyr Thr Leu Pro Pro Ser Arg Asp Glu Leu Thr Lys Asn Gln Val
    450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
        515                 520                 525

Met His Glu Ala Leu His Asn His Tyr Thr Gln Lys Ser Leu Ser Leu
    530                 535                 540

Ser Pro Gly Lys Val Asp Gly Ala Ser Ser Pro Val Asn Val Ser Ser
545                 550                 555                 560

Pro Ser Val Gln Asp Ile Leu Phe Arg Asn His Gln Ser Ser Tyr Gln
                565                 570                 575

Thr Arg Leu Asn Ala Leu Arg Glu Val Gln Pro Val Glu Leu Pro Asn
            580                 585                 590

Cys Asn Leu Val Lys Gly Ile Glu Thr Gly Ser Glu Asp Leu Glu Ile
        595                 600                 605

Leu Pro Asn Gly Leu Ala Phe Ile Ser Ser Gly Leu Lys Tyr Pro Gly
    610                 615                 620

Ile Lys Ser Phe Asn Pro Asn Ser Pro Gly Lys Ile Leu Leu Met Asp
625                 630                 635                 640
```

Leu Asn Glu Glu Asp Pro Thr Val Leu Glu Leu Gly Ile Thr Gly Ser
              645                 650                 655

Lys Phe Asp Val Ser Ser Phe Asn Pro His Gly Ile Ser Thr Phe Thr
        660                 665                 670

Asp Glu Asp Asn Ala Met Tyr Leu Leu Val Val Asn His Pro Asp Ala
    675                 680                 685

Lys Ser Thr Val Glu Leu Phe Lys Phe Gln Glu Glu Lys Ser Leu
690                 695                 700

Leu His Leu Lys Thr Ile Arg His Lys Leu Leu Pro Asn Leu Asn Asp
705                 710                 715                 720

Ile Val Ala Val Gly Pro Glu His Phe Tyr Gly Thr Asn Asp His Tyr
                725                 730                 735

Phe Leu Asp Pro Tyr Leu Lys Ser Trp Glu Met Tyr Leu Gly Leu Ala
            740                 745                 750

Trp Ser Tyr Val Val Tyr Tyr Ser Pro Ser Glu Val Arg Val Val Ala
        755                 760                 765

Glu Gly Phe Asp Phe Ala Asn Gly Ile Asn Ile Ser Pro Asp Gly Lys
    770                 775                 780

Tyr Val Tyr Ile Ala Glu Leu Leu Ala His Lys Ile His Val Tyr Glu
785                 790                 795                 800

Lys His Ala Asn Trp Thr Leu Thr Pro Leu Lys Ser Leu Asp Phe Asn
                805                 810                 815

Thr Leu Val Asp Asn Ile Ser Val Asp Pro Glu Thr Gly Asp Leu Trp
            820                 825                 830

Val Gly Cys His Pro Asn Gly Met Lys Ile Phe Phe Tyr Asp Ser Glu
        835                 840                 845

Asn Pro Pro Ala Ser Glu Val Leu Arg Ile Gln Asn Ile Leu Thr Glu
    850                 855                 860

Glu Pro Lys Val Thr Gln Val Tyr Ala Glu Asn Gly Thr Val Leu Gln
865                 870                 875                 880

Gly Ser Thr Val Ala Ser Val Tyr Lys Gly Lys Leu Leu Ile Gly Thr
                885                 890                 895

Val Phe His Lys Ala Leu Tyr Cys Glu Leu
            900                 905

<210> SEQ ID NO 161
<211> LENGTH: 2721
<212> TYPE: DNA
<213> ORGANISM: Artificial Sequence
<220> FEATURE:
<223> OTHER INFORMATION: hVK3LP-[hDNase1L3 R80A-R95A-N96A
    NLS2delta]-(g4s)4-[SSShinge-P238S-P331S Fc]-NGS-[PON1 Q192K] DNA

<400> SEQUENCE: 161
atggaaaccc cagcgcagct tctcttcctc ctgctactct ggctcccaga taccaccggt      60
atgaggatct gctccttcaa cgtcaggtcc tttggggaaa gcaagcagga agacaagaat     120
gccatggatg tcattgtgaa ggtcatcaaa cgctgtgaca tcatactcgt gatggaaatc     180
aaggacagca acaacaggat ctgccccata ctgatggaga agctgaacag aaattcagca     240
agaggcataa cgtacaacta tgtgattagc tctcggcttg agcagctac atataaagaa      300 caatatgcct ttctctacaa ggaaaagctg gtgtctgtga agaggagtta tcactaccat     360
gactatcagg atgagacgc agatgtgttt ccagggagc cctttgtggg ctggttccaa       420
tctccccaca ctgctgtcaa agacttcgtg attatccccc tgcacaccac cccagagaca    480
tccgttaagg agatcgatga gttggttgag gtctacacgg acgtgaaaca ccgctggaag    540

```
gcggagaatt tcattttcat gggtgacttc aatgccggct gcagctacgt ccccaagaag    600
gcctggaaga acatccgctt gaggactgac cccaggtttg tttggctgat cggggaccaa    660
gaggacacca cggtgaagaa gagcaccaac tgtgcatatg acaggattgt gcttagagga    720
caagaaatcg tcagttctgt tgttcccaag tcaaacagtg tttttgactt ccagaaagct    780
tacaagctga ctgaagagga ggccctggat gtcagcgacc actttccagt tgaatttaaa    840
ctacagtctt caagggcctt caccaactca gatctctccg gaggaggtgg ctcaggtggt    900
ggaggatctg gaggaggtgg gagtggtgga ggtggttcta ccggtctcga gcccaaatct    960
tctgacaaaa ctcacacatc tccaccgtcc cagcacctg aactcctggg aggatcgtca   1020
gtcttcctct ccccccaaa acccaaggac accctcatga tctcccggac ccctgaggtc   1080
acatgcgtgg tggtggacgt gagccacgaa gaccctgagg tcaagttcaa ctggtacgtg   1140
gacggcgtgg aggtgcataa tgccaagaca aagccgcggg aggagcagta acagcacg   1200 taccgtgtgg tcagcgtcct caccgtcctg caccaggact ggctgaatgg caaggagtac   1260
aagtgcaagg tctccaacaa agccctccca gcctccatcg agaaaaccat ctccaaagcc   1320
aaagggcagc cccgagaacc acaggtgtac accctgcccc catcccggga tgagctgacc   1380
aagaaccagg tcagcctgac ctgcctggtc aaaggcttct atcccagcga catcgccgtg   1440
gagtgggaga gcaatgggca gccggagaac aactacaaga ccacgcctcc cgtgctggac   1500
tccgacggct ccttcttcct ctacagcaag ctcaccgtgg acaagagcag gtggcagcag   1560
gggaacgtct tctcatgctc cgtgatgcat gaggctctgc acaaccacta cacgcagaag   1620
agcctctctc tctctccggg taaagtcgac ggagctagca gccccgtgaa cgtgagcagc   1680
cccagcgtgc aggatatcct cttcaggaac caccagtctt cttaccaaac acgacttaat   1740
gctctccgag aggtacaacc cgtagaactt cctaactgta atttagttaa aggaatcgaa   1800
actggctctg aagacttgga gatactgcct aatggactgg cttcattag ctctggatta   1860 aagtatcctg gaataaagag cttcaacccc aacagtcctg gaaaaatact tctgatggac   1920
ctgaatgaag aagatccaac agtgttggaa ttggggatca ctggaagtaa atttgatgta   1980
tcttcattta accctcatgg gattagcaca ttcacagatg aagataatgc catgtacctc   2040
ctggtggtga accatccaga tgccaagtcc acagtggagt tgtttaaatt tcaagaagaa   2100
gaaaaatcgc ttttgcatct aaaaaccatc agacataaac ttctgcctaa tttgaatgat   2160
attgttgctg tgggacctga gcactttat ggcacaaatg atcactattt tcttgacccc   2220
tacttaaaat cctgggagat gtatttgggt ttagcgtggt cgtatgttgt ctactatagt   2280
ccaagtgaag ttcgagtggt ggcagaagga tttgattttg ctaatggaat caacatttca   2340
cccgatggca gtatgtcta tatagctgag ttgctggctc ataagattca tgtgtatgaa   2400
aagcatgcta attggacttt aactccattg aagtcccttg actttaatac cctcgtggat   2460
aacatatctg tggatcctga cagggagac ctttgggttg gatgccatcc caatggcatg   2520
aaaatcttct tctatgactc agagaatcct cctgcatcag aggtgcttcg aatccagaac   2580
attctaacag aagaacctaa agtgacacag gtttatgcag aaaatggcac agtgttgcaa   2640
ggcagtacag ttgcctctgt gtacaaaggg aaactgctga ttggcacagt gtttcacaaa   2700
gctctttact gtgagctcta a                                             2721
```

<210> SEQ ID NO 162
<211> LENGTH: 906
<212> TYPE: PRT

<213> ORGANISM: Artificial Sequence
<220> FEATURE:
<223> OTHER INFORMATION: hVK3LP-[hDNase1L3 R80A-R95A-N96A
NLS2delta]-(g4s)4-[SSShinge-P238S-P331S Fc]-NGS-[PON1 Q192K]

<400> SEQUENCE: 162

```
Met Glu Thr Pro Ala Gln Leu Leu Phe Leu Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Ala
65                  70                  75                  80

Arg Gly Ile Thr Tyr Asn Tyr Val Ile Ser Ser Arg Leu Gly Ala Ala
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Asp Leu Ser Gly Gly Gly Gly Ser Gly Gly Gly Ser Gly
290                 295                 300

Gly Gly Ser Gly Gly Gly Ser Thr Gly Leu Glu Pro Lys Ser
305                 310                 315                 320

Ser Asp Lys Thr His Thr Ser Pro Ser Pro Ala Pro Glu Leu Leu
                325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Val Asp Val Ser
        355                 360                 365

His Glu Asp Pro Glu Val Lys Phe Asn Trp Tyr Val Asp Gly Val Glu
370                 375                 380
```

```
Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Ala Leu Pro Ala Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Arg Asp Glu Leu Thr Lys Asn Gln Val
        450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
530                 535                 540

Ser Pro Gly Lys Val Asp Gly Ala Ser Ser Pro Val Asn Val Ser Ser
545                 550                 555                 560

Pro Ser Val Gln Asp Ile Leu Phe Arg Asn His Gln Ser Ser Tyr Gln
            565                 570                 575

Thr Arg Leu Asn Ala Leu Arg Glu Val Gln Pro Val Glu Leu Pro Asn
            580                 585                 590

Cys Asn Leu Val Lys Gly Ile Glu Thr Gly Ser Glu Asp Leu Glu Ile
            595                 600                 605

Leu Pro Asn Gly Leu Ala Phe Ile Ser Ser Gly Leu Lys Tyr Pro Gly
            610                 615                 620

Ile Lys Ser Phe Asn Pro Asn Ser Pro Gly Lys Ile Leu Leu Met Asp
625                 630                 635                 640

Leu Asn Glu Glu Asp Pro Thr Val Leu Glu Leu Gly Ile Thr Gly Ser
            645                 650                 655

Lys Phe Asp Val Ser Ser Phe Asn Pro His Gly Ile Ser Thr Phe Thr
            660                 665                 670

Asp Glu Asp Asn Ala Met Tyr Leu Leu Val Val Asn His Pro Asp Ala
            675                 680                 685

Lys Ser Thr Val Glu Leu Phe Lys Phe Gln Glu Glu Lys Ser Leu
            690                 695                 700

Leu His Leu Lys Thr Ile Arg His Lys Leu Leu Pro Asn Leu Asn Asp
705                 710                 715                 720

Ile Val Ala Val Gly Pro Glu His Phe Tyr Gly Thr Asn Asp His Tyr
                725                 730                 735

Phe Leu Asp Pro Tyr Leu Lys Ser Trp Glu Met Tyr Leu Gly Leu Ala
            740                 745                 750

Trp Ser Tyr Val Val Tyr Tyr Ser Pro Ser Glu Val Arg Val Val Ala
            755                 760                 765

Glu Gly Phe Asp Phe Ala Asn Gly Ile Asn Ile Ser Pro Asp Gly Lys
            770                 775                 780

Tyr Val Tyr Ile Ala Glu Leu Leu Ala His Lys Ile His Val Tyr Glu
785                 790                 795                 800

Lys His Ala Asn Trp Thr Leu Thr Pro Leu Lys Ser Leu Asp Phe Asn
```

```
                805                 810                 815
Thr Leu Val Asp Asn Ile Ser Val Asp Pro Glu Thr Gly Asp Leu Trp
            820                 825                 830

Val Gly Cys His Pro Asn Gly Met Lys Ile Phe Phe Tyr Asp Ser Glu
        835                 840                 845

Asn Pro Pro Ala Ser Glu Val Leu Arg Ile Gln Asn Ile Leu Thr Glu
    850                 855                 860

Glu Pro Lys Val Thr Gln Val Tyr Ala Glu Asn Gly Thr Val Leu Gln
865                 870                 875                 880

Gly Ser Thr Val Ala Ser Val Tyr Lys Gly Lys Leu Leu Ile Gly Thr
                885                 890                 895

Val Phe His Lys Ala Leu Tyr Cys Glu Leu
            900                 905

<210> SEQ ID NO 163
<211> LENGTH: 2721
<212> TYPE: DNA
<213> ORGANISM: Artificial Sequence
<220> FEATURE:
<223> OTHER INFORMATION: hVK3LP-[hDNase1L3 R80S-R95S-N96S
      NLS2delta]-(g4s)4-[SSShinge-P238S-P331S Fc]-NGS-[PON1 Q192K] DNA

<400> SEQUENCE: 163
```

| | | |
|---|---|---|
| atggaaaccc cagcgcagct tctcttcctc ctgctactct ggctcccaga taccaccggt | 60 |
| atgaggatct gctccttcaa cgtcaggtcc tttggggaaa gcaagcagga agacaagaat | 120 |
| gccatggatg tcattgtgaa ggtcatcaaa cgctgtgaca tcatactcgt gatggaaatc | 180 |
| aaggacagca caacaggat ctgccccata ctgatgagaa agctgaacag aaattcatca | 240 |
| agaggcataa cgtacaacta tgtgattagc tctcggcttg gaagttctac atataaagaa | 300 |
| caatatgcct ttctctacaa ggaaaagctg gtgtctgtga gaggagtta tcactaccat | 360 |
| gactatcagg atgagacgc agatgtgttt tccagggagc cctttgtggt ctggttccaa | 420 |
| tctcccaca ctgctgtcaa agacttcgtg attatccccc tgcacaccac cccagagaca | 480 |
| tccgttaagg atcgatga gttggttgag tctacacgg acgtgaaaca ccgctggaag | 540 |
| gcggagaatt tcattttcat gggtgacttc aatgccggct gcagctacgt ccccaagaag | 600 |
| gcctggaaga acatccgctt gaggactgac cccaggtttg tttggctgat cggggaccaa | 660 |
| gaggacacca cggtgaagaa gagcaccaac tgtgcatatg acaggattgt gcttagagga | 720 |
| caagaaatcg tcagttctgt tgttcccaag tcaaacagtg ttttgacttc ccagaaagct | 780 |
| tacaagctga ctgaagagga ggccctggat gtcagcgacc actttccagt gaatttaaa | 840 |
| ctacagtctt caagggcctt caccaactca gatctctccg gaggaggtgg ctcaggtggt | 900 |
| ggaggatctg gaggaggtgg gagtggtgga ggtggttcta ccggtctcga gcccaaatct | 960 |
| tctgacaaaa ctcacacatc tccaccgtcc ccagcacctg aactcctggg aggatcgtca | 1020 |
| gtcttcctct tccccccaaa acccaaggac accctcatga tctcccggac ccctgaggtc | 1080 |
| acatgcgtgg tggtggacgt gagccacgaa gaccctgagg tcaagttcaa ctggtacgtg | 1140 |
| gacggcgtgg aggtgcataa tgccaagaca aagccgcggg aggagcagta caacagcacg | 1200 |
| taccgtgtgt cagcgtcct caccgtcctg caccaggact ggctgaatgg caaggagtac | 1260 |
| aagtgcaagg tctccaacaa agccctccca gcctccatcg agaaaaccat ctccaaagcc | 1320 |
| aaagggcagc cccgagaacc acaggtgtac accctgcccc catcccggga tgagctgacc | 1380 |
| aagaaccagg tcagcctgac ctgcctggtc aaaggcttct atcccagcga catcgccgtg | 1440 |

```
gagtgggaga gcaatgggca gccggagaac aactacaaga ccacgcctcc cgtgctggac    1500
tccgacggct ccttcttcct ctacagcaag ctcaccgtgg acaagagcag gtggcagcag    1560
gggaacgtct tctcatgctc cgtgatgcat gaggctctgc acaaccacta cacgcagaag    1620
agcctctctc tctctccggg taaagtcgac ggagctagca gccccgtgaa cgtgagcagc    1680
cccagcgtgc aggatatcct cttcaggaac caccagtctt cttaccaaac acgacttaat    1740
gctctccgag aggtacaacc cgtagaactt cctaactgta atttagttaa aggaatcgaa    1800
actggctctg aagacttgga gatactgcct aatggactgg ctttcattag ctctggatta    1860
aagtatcctg gaataaagag cttcaacccc aacagtcctg aaaaatact tctgatggac     1920 ctgaatgaag aagatccaac agtgttggaa ttggggatca ctggaagtaa atttgatgta    1980
tcttcattta accctcatgg gattagcaca ttcacagatg aagataatgc catgtacctc    2040
ctggtggtga accatccaga tgccaagtcc acagtggagt tgtttaaatt tcaagaagaa    2100
gaaaaatcgc ttttgcatct aaaaaccatc agacataaac ttctgcctaa tttgaatgat    2160
attgttgctg tgggacctga gcactttat ggcacaaatg atcactattt tcttgacccc    2220
tacttaaaat cctgggagat gtatttgggt ttagcgtggt cgtatgttgt ctactatagt    2280
ccaagtgaag ttcgagtggt ggcagaagga tttgattttg ctaatggaat caacatttca    2340
cccgatggca gtatgtcta tatagctgag ttgctggctc ataagattca tgtgtatgaa     2400
aagcatgcta attggacttt aactccattg aagtcccttg actttaatac cctcgtggat    2460
aacatatctg tggatcctga cacggagac ctttgggttg gatgccatcc caatggcatg     2520
aaaatcttct tctatgactc agagaatcct cctgcatcag aggtgcttcg aatccagaac    2580
attctaacag aagaacctaa agtgacacag gtttatgcag aaaatggcac agtgttgcaa    2640
ggcagtacag ttgcctctgt gtacaaaggg aaactgctga ttggcacagt gtttcacaaa    2700
gctctttact gtgagctcta a                                              2721
```

<210> SEQ ID NO 164
<211> LENGTH: 906
<212> TYPE: PRT
<213> ORGANISM: Artificial Sequence
<220> FEATURE:
<223> OTHER INFORMATION: hVK3LP-[hDNase1L3 R80S-R95S-N96S
    NLS2delta]-(g4s)4-[SSShinge-P238S-P331S Fc]-NGS-[PON1 Q192K]

<400> SEQUENCE: 164

```
Met Glu Thr Pro Ala Gln Leu Leu Phe Leu Leu Leu Trp Leu Pro
1               5                   10                  15

Asp Thr Thr Gly Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Ser
65                  70                  75                  80

Arg Gly Ile Thr Tyr Asn Tyr Val Ile Ser Ser Arg Leu Gly Ser Ser
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125
```

```
Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
    275                 280                 285

Asn Ser Asp Leu Ser Gly Gly Gly Ser Gly Gly Gly Ser Gly
290                 295                 300

Gly Gly Gly Ser Gly Gly Gly Ser Thr Gly Leu Glu Pro Lys Ser
305                 310                 315                 320

Ser Asp Lys Thr His Thr Ser Pro Pro Ser Pro Ala Pro Glu Leu Leu
                325                 330                 335

Gly Gly Ser Ser Val Phe Leu Phe Pro Pro Lys Pro Lys Asp Thr Leu
            340                 345                 350

Met Ile Ser Arg Thr Pro Glu Val Thr Cys Val Val Asp Val Ser
            355                 360                 365

His Glu Asp Pro Glu Val Lys Phe Asn Trp Tyr Val Asp Gly Val Glu
    370                 375                 380

Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
                405                 410                 415

Gly Lys Glu Tyr Lys Cys Lys Val Ser Asn Lys Ala Leu Pro Ala Ser
            420                 425                 430

Ile Glu Lys Thr Ile Ser Lys Ala Lys Gly Gln Pro Arg Glu Pro Gln
            435                 440                 445

Val Tyr Thr Leu Pro Pro Ser Arg Asp Glu Leu Thr Lys Asn Gln Val
450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
                485                 490                 495

Pro Val Leu Asp Ser Asp Gly Ser Phe Phe Leu Tyr Ser Lys Leu Thr
            500                 505                 510

Val Asp Lys Ser Arg Trp Gln Gln Gly Asn Val Phe Ser Cys Ser Val
            515                 520                 525

Met His Glu Ala Leu His Asn His Tyr Thr Gln Lys Ser Leu Ser Leu
530                 535                 540

Ser Pro Gly Lys Val Asp Gly Ala Ser Ser Pro Val Asn Val Ser Ser
```

```
545              550              555              560
Pro Ser Val Gln Asp Ile Leu Phe Arg Asn His Gln Ser Ser Tyr Gln
                565              570              575
Thr Arg Leu Asn Ala Leu Arg Glu Val Gln Pro Val Glu Leu Pro Asn
                580              585              590
Cys Asn Leu Val Lys Gly Ile Glu Thr Gly Ser Glu Asp Leu Glu Ile
                595              600              605
Leu Pro Asn Gly Leu Ala Phe Ile Ser Ser Gly Leu Lys Tyr Pro Gly
            610              615              620
Ile Lys Ser Phe Asn Pro Asn Ser Pro Gly Lys Ile Leu Leu Met Asp
625              630              635              640
Leu Asn Glu Glu Asp Pro Thr Val Leu Glu Leu Gly Ile Thr Gly Ser
                645              650              655
Lys Phe Asp Val Ser Ser Phe Asn Pro His Gly Ile Ser Thr Phe Thr
                660              665              670
Asp Glu Asp Asn Ala Met Tyr Leu Leu Val Val Asn His Pro Asp Ala
                675              680              685
Lys Ser Thr Val Glu Leu Phe Lys Phe Gln Glu Glu Glu Lys Ser Leu
                690              695              700
Leu His Leu Lys Thr Ile Arg His Lys Leu Leu Pro Asn Leu Asn Asp
705              710              715              720
Ile Val Ala Val Gly Pro Glu His Phe Tyr Gly Thr Asn Asp His Tyr
                725              730              735
Phe Leu Asp Pro Tyr Leu Lys Ser Trp Glu Met Tyr Leu Gly Leu Ala
                740              745              750
Trp Ser Tyr Val Val Tyr Tyr Ser Pro Ser Glu Val Arg Val Val Ala
            755              760              765
Glu Gly Phe Asp Phe Ala Asn Gly Ile Asn Ile Ser Pro Asp Gly Lys
            770              775              780
Tyr Val Tyr Ile Ala Glu Leu Leu Ala His Lys Ile His Val Tyr Glu
785              790              795              800
Lys His Ala Asn Trp Thr Leu Thr Pro Leu Lys Ser Leu Asp Phe Asn
                805              810              815
Thr Leu Val Asp Asn Ile Ser Val Asp Pro Glu Thr Gly Asp Leu Trp
                820              825              830
Val Gly Cys His Pro Asn Gly Met Lys Ile Phe Phe Tyr Asp Ser Glu
            835              840              845
Asn Pro Pro Ala Ser Glu Val Leu Arg Ile Gln Asn Ile Leu Thr Glu
    850              855              860
Glu Pro Lys Val Thr Gln Val Tyr Ala Glu Asn Gly Thr Val Leu Gln
865              870              875              880
Gly Ser Thr Val Ala Ser Val Tyr Lys Gly Lys Leu Leu Ile Gly Thr
                885              890              895
Val Phe His Lys Ala Leu Tyr Cys Glu Leu
                900              905
```